(12) United States Patent
Weiss et al.

(10) Patent No.: US 8,685,720 B2
(45) Date of Patent: Apr. 1, 2014

(54) ENGINEERED CELLULAR PATHWAYS FOR PROGRAMMED AUTOREGULATION OF DIFFERENTIATION

(75) Inventors: Ron Weiss, Princeton, NJ (US); Ihor Lemischka, Princeton, NJ (US); Priscilla E. M. Purnick, West Windsor, NJ (US); Christoph Schaniel, New York, NY (US); Miles Miller, Indianapolis, IN (US); Patrick Guye, Rupperswil (CH)

(73) Assignee: The Trustees of Princeton University, Princeton, NJ (US)

( * ) Notice: Subject to any disclaimer, the term of this patent is extended or adjusted under 35 U.S.C. 154(b) by 907 days.

(21) Appl. No.: 12/312,197

(22) PCT Filed: Nov. 1, 2007

(86) PCT No.: PCT/US2007/023227
§ 371 (c)(1),
(2), (4) Date: Jun. 22, 2010

(87) PCT Pub. No.: WO2008/066658
PCT Pub. Date: Jun. 5, 2008

(65) Prior Publication Data
US 2010/0285584 A1    Nov. 11, 2010

Related U.S. Application Data

(60) Provisional application No. 60/856,531, filed on Nov. 3, 2006, provisional application No. 60/905,483, filed on Mar. 7, 2007.

(51) Int. Cl.
C12N 15/00    (2006.01)
C12N 15/09    (2006.01)
C12N 15/31    (2006.01)
C12N 15/63    (2006.01)

(52) U.S. Cl.
USPC ... 435/320.1; 435/69.1; 536/23.1; 536/23.72; 536/24.1; 536/24.5

(58) Field of Classification Search
None
See application file for complete search history.

(56) References Cited

U.S. PATENT DOCUMENTS

| | | | |
|---|---|---|---|
| 5,061,620 A | 10/1991 | Tsukamoto et al. | 435/7.21 |
| 5,139,941 A | 8/1992 | Muzyczka et al. | 435/456 |
| 5,166,065 A | 11/1992 | Williams et al. | 435/377 |
| 5,173,414 A | 12/1992 | Lebkowski et al. | 435/91.4 |
| 5,197,985 A | 3/1993 | Caplan et al. | 128/898 |
| 5,225,347 A | 7/1993 | Goldberg et al. | 435/320.1 |
| 5,226,914 A | 7/1993 | Caplan et al. | 435/325 |
| 5,340,740 A | 8/1994 | Petitte et al. | 435/349 |
| 5,453,357 A | 9/1995 | Hogan | 435/7.21 |
| 5,486,359 A | 1/1996 | Caplan et al. | 424/93.7 |
| 5,512,421 A | 4/1996 | Burns et al. | 435/320.1 |
| 5,523,226 A | 6/1996 | Wheeler | 435/325 |
| 5,589,376 A | 12/1996 | Anderson et al. | 435/325 |
| 5,591,625 A | 1/1997 | Gerson et al. | 435/366 |
| 5,654,183 A | 8/1997 | Anderson et al. | 435/456 |
| 5,672,499 A | 9/1997 | Anderson et al. | 435/353 |
| 5,686,120 A | 11/1997 | Mertz et al. | 435/353 |
| 5,716,827 A | 2/1998 | Tsukamoto et al. | 435/325 |
| 5,719,055 A | 2/1998 | Cooper | 135/320.1 |
| 5,750,376 A | 5/1998 | Weiss et al. | 435/69.52 |
| 5,750,397 A | 5/1998 | Tsukamoto et al. | 435/372 |
| 5,843,742 A | 12/1998 | Natsoulis et al. | 435/465 |
| 5,843,780 A | 12/1998 | Thomson | 435/363 |
| 5,849,553 A | 12/1998 | Anderson et al. | 435/467 |
| 5,914,267 A | 6/1999 | Mertz et al. | 435/320.1 |
| 5,958,775 A | 9/1999 | Wickstrom et al. | 435/455 |
| 5,965,443 A | 10/1999 | Reznikoff et al. | 435/473 |
| 5,968,785 A | 10/1999 | Devine et al. | 435/91.41 |
| 5,968,829 A | 10/1999 | Carpenter | 435/467 |
| 5,994,136 A | 11/1999 | Naldini et al. | 435/455 |
| 6,013,516 A | 1/2000 | Verma et al. | 435/325 |

(Continued)

FOREIGN PATENT DOCUMENTS

| EP | 0117058 | 9/1989 |
|---|---|---|
| WO | WO/88/05486 | 7/1988 |

(Continued)

OTHER PUBLICATIONS

Larson et al, The leukocyte integrin LFA-1 reconstituted by cDNA transfection in a nonhematopoietic cell line is functionally active and not transiently regulated, Cell Regulation, 1990, vol. 1 pp. 359-367.*

(Continued)

Primary Examiner — Maria Marvich
(74) Attorney, Agent, or Firm — Medlen & Carroll, LLP

(57) ABSTRACT

The present invention provides compositions and methods for programming mammalian cells to perform desired functions. In particular, the present invention provides compositions and methods for programming stem cells to differentiate into a desired cell type. A quorum sensing systems that regulates the expression of cell fate regulators is introduced into mammalian host cells, such as stem cells. The quorum sensing systems generally comprises vectors that express the components of a bacterial quorum sensing pathway, including proteins which catalyze the synthesis of an autoinducer and a gene encoding a regulatory partner of the autoinducer, and vectors in which genes encoding cell fate regulators are operably linked to a promoter induced by the autoinducer/regulatory partner complex. The system can also comprise vectors in which genes encoding additional cell fate regulators are operably linked to a promoter that is induced by a factor synthesized in response to a first stage of differentiation, so that a second stage of differentiation is triggered.

5 Claims, 153 Drawing Sheets

(56) References Cited

U.S. PATENT DOCUMENTS

| | | | |
|---|---|---|---|
| 6,027,722 A | 2/2000 | Hodgson | 424/93.21 |
| 6,136,597 A | 10/2000 | Hope et al. | 435/325 |
| 6,200,806 B1 | 3/2001 | Thomson | 435/325 |

FOREIGN PATENT DOCUMENTS

| | | |
|---|---|---|
| WO | WO/92/01070 | 1/1992 |
| WO | WO/92/22584 | 12/1992 |
| WO | WO/93/03143 | 2/1993 |
| WO | WO/93/03769 | 3/1993 |
| WO | WO/99/14310 | 3/1999 |

OTHER PUBLICATIONS

Princeton:Project Summary, Programmed Differentiation of Mouse Embryonic Stem Cells Using Artificial Signaling Pathways, Oct. 2006, downloaded Oct. 22, 2012, pp. 1-3.*

Weber et al, *Streptomyces*-derived quorum-sensing systems engineered for adjustable transgene expression in mammalian cells and mice, Nucleic Acids Research, 2003, vol. 31, No. 14 e71.*

Drubin et al, Designing biological systems, Genes & Development, 2007, 21:242-254.*

Agrawal, S. et al. (1988) Oligodeoxynucleoside phosphoramidates and phosphorothioates as inhibitors of human immunodeficiency virus, *Proceedings of the National Academy of Sciences* 85(19), 7079-7083.

Anderson, M. L. M. et al. (1985) Quantitative Filter Hybridization, in *Nucleic Acid Hybridisation: A Practical Approach* (Hames, B. D., et al., Eds.), pp. 73-111, Oxford University Press, USA.

Boshart, M. et al. (1985) A very strong enhancer is located upstream of an immediate early gene of human cytomegalovirus, *Cell* 41(2), 521-530.

Bosslet, K. et al. (1998) Elucidation of the Mechanism Enabling Tumor Selective Prodrug Monotherapy, *Cancer Res.* 58(6), 1195-1201.

Bradley, A. et al. (1984) Formation of germ-line chimaeras from embryo-derived teratocarcinoma cell lines, *Nature* 309(5965), 255-256.

Burns, J. C. et al. (1993) Vesicular stomatitis virus G glycoprotein pseudotyped retroviral vectors: concentration to very high titer and efficient gene transfer into mammalian and nonmammalian cells, *Proceedings of the National Academy of Sciences* 90(17), 8033-8037.

Burt, R. K. et al. (2004) Embryonic Stem Cells as an Alternate Marrow Donor Source: Engraftment without Graft-Versus-Host Disease,*The Journal of Experimental Medicine* 199(7), 895-904.

Carter, B. J. (1992) Adeno-associated virus vectors, *Current Opinion in Biotechnology* 3(5), 533-539.

Cech, T. R. et al. (1992) RNA catalysis by a group I ribozyme. Developing a model for transition state stabilization, *Journal of Biological Chemistry* 267(25), 17479-17482.

Collins, C. A. et al. (2005) Self-Renewal of the Adult Skeletal Muscle Satellite Cell, *Cell Cycle* 4(10), 1338-1341.

Couper, J. J. et al. (2003) 2: Recent advances in therapy of diabetes, *The Medical Journal of Australia* 179(8), 441-447.

Craig, N. L. (1996) Transposon Tn7, *Current Topics in Microbiology and Immunology* 204, 27-48.

de la Cruz, N. B. et al. (1993) Characterization of the Tn5 transposase and inhibitor proteins: a model for the inhibition of transposition, *J. Bacteriol.* 175(21), 6932-6938.

Dijkema, R. et al. (1985) Cloning and expression of the chromosomal immune interferon gene of the rat, *The EMBO Journal* 4(3), 761-767.

Doetschman, T. et al. (1988) Establishment of hamster blastocyst-derived embryonic stem (ES) cells, *Developmental Biology* 127(1), 224-227.

Evans, M. J. et al. (1981) Establishment in culture of pluripotential cells from mouse embryos, *Nature* 292(5819), 154-156.

Evans, M. J. et al. (1990) Derivation and preliminary characterization of pluripotent cell lines from porcine and bovine blastocysts, *Theriogenology* 33(1), 125-128.

Giles, J. et al. (1993) Pluripotency of cultured rabbit inner cell mass cells detected by isozyme analysis and eye pigmentation of fetuses following injection into blastocysts or morulae, *Molecular Reproduction and Development* 36(2), 130-138.

Gluckman, E. (2001) Hematopoietic Stem-Cell Transplants Using Umbilical-Cord Blood, *New England Journal of Medicine* 344(24), 1860-1861.

Gorman, C. M. et al. (1982) The *Rous sarcoma virus* long terminal repeat is a strong promoter when introduced into a variety of eukaryotic cells by DNA-mediated transfection, *Proceedings of the National Academy of Sciences of the United States of America* 79(22), 6777-6781.

Graham, F. L. et al. (1977) Characteristics of a Human Cell Line Transformed by DNA from Human Adenovirus Type 5, *Journal of General Virology* 36(1), 59-72.

Graves, K. et al. (1993) Derivation and characterization of putative pluripotential embryonic stem cells from preimplantation rabbit embryos, *Molecular reproduction and development* 36(4), 424-433.

Gray, G. L. et al. (1985) Periplasmic production of correctly processed human growth hormone in *Escherichia coli*: natural and bacterial signal sequences are interchangeable, *Gene* 39(2-3), 247-254.

Haller, A. A. et al. (1992) Linker scanning mutagenesis of the internal ribosome entry site of poliovirus RNA, *Journal of Virology* 66(8), 5075-5086.

Han, L. et al. (1991) Inhibition of Moloney murine leukemia virus-induced leukemia in transgenic mice expressing antisense RNA complementary to the retroviral packaging sequences, *Proceedings of the National Academy of Sciences* 88(10), 4313-4317.

Heikkila, R. et al. (1987) A c-myc antisense oligodeoxynucleotide inhibits entry into S phase but not progress from G0 to G1, *Nature* 328(6129), 445-449.

Hélène, C. et al. (1990) Specific regulation of gene expression by antisense, sense and antigene nucleic acids, *Biochimica et Biophysica Acta (BBA)—Gene Structure and Expression* 1049(2), 99-125.

Hochedlinger, K. et al. (2003) Nuclear Transplantation, Embryonic Stem Cells, and the Potential for Cell Therapy, *New England Journal of Medicine* 349(3), 275-286.

Iannaccone, P. M. et al. (1994) Pluripotent Embryonic Stem Cells from the Rat are Capable of Producing Chimeras, *Developmental Biology* 163(1), 288-292.

Jang, S. K. et al. (1988) A segment of the 5' nontranslated region of encephalomyocarditis virus RNA directs internal entry of ribosomes during in vitro translation, *Journal of Virology* 62(8), 2636-2643.

Kim, D. W. et al. (1990) Use of the human elongation factor 1α promoter as a versatile and efficient expression system, *Gene* 91(2), 217-223.

Kotin, R. M. (1994) Prospects for the Use of Adeno-Associated Virus as a Vector for Human Gene Therapy, *Human Gene Therapy* 5(7), 793-801.

Ku, H. T. et al. (2004) Committing Embryonic Stem Cells to Early Endocrine Pancreas In Vitro, *Stem Cells* 22(7), 1205-1217.

Lagasse, E. et al. (2001) Toward Regenerative Medicine, *Immunity* 14(4), 425-436.

Lebkowski, J. S. et al. (1988) Adeno-associated virus: a vector system for efficient introduction and integration of DNA into a variety of mammalian cell types, *Molecular and Cellular Biology* 8(10), 3988-3996.

Mandell, J. G. et al. (2006) Zinc Finger Tools: custom DNA-binding domains for transcription factors and nucleases, *Nucleic Acids Research* 34(suppl 2), W516-W523.

Markowitz, D. et al. (1988) A safe packaging line for gene transfer: separating viral genes on two different plasmids, *J. Virol.* 62(4), 1120-1124.

Martial, J. A. et al. (1979) Human growth hormone: complementary DNA cloning and expression in bacteria, *Science* 205(4406), 602-607.

Martin, G. R. (1981) Isolation of a pluripotent cell line from early mouse embryos cultured in medium conditioned by teratocarcinoma stem cells, *Proc. Natl. Acad. Sci. U. S. A.* 78(12), 7634-7638.

(56) References Cited

OTHER PUBLICATIONS

Mastromarino, P. et al. (1987) Characterization of Membrane Components of the Erythrocyte Involved in Vesicular Stomatitis Virus Attachment and Fusion at Acidic pH, *J. Gen. Virol.* 68(9), 2359-2369.

Mather, J. P. (1980) Establishment and Characterization of Two Distinct Mouse Testicular Epithelial Cell Lines, *Biol. Reprod.* 23(1), 243-252.

Mather, J. P. et al. (1982) Culture of Testicular Cells in Hormone-Supplemented Serum-Free Medium, *Ann. N. Y. Acad. Sci.* 383(1), 44-68.

Meyer, K. et al. (1995) Interaction of eukaryotic initiation factor eIF-4B with a picornavirus internal translation initiation site, *J. Virol.* 69(5), 2819-2824.

Miller, A. D. et al. (1986) Redesign of retrovirus packaging cell lines to avoid recombination leading to helper virus production, *Mol. Cell. Biol.* 6(8), 2895-2902.

Mizushima, S. et al. (1990) pEF-BOS, a powerful mammalian expression vector, *Nucleic Acids Res.* 18(17), 5322.

Morisato, D. et al. (1987) Tn10 transposition and circle formation in vitro, *Cell* 51(1), 101-111.

Muzyczka, N. (1992) Use of adeno-associated virus as a general transduction vector for mammalian cells, *Curr. Top. Microbiol. Immunol.* 158, 97-129.

Nagy, A. et al. (1990) Embryonic stem cells alone are able to support fetal development in the mouse, *Development* 110(3), 815-821.

Ritz-Laser, B. et al. (2005) The Zinc Finger-Containing Transcription Factor Gata-4 is Expressed in the Developing Endocrine Pancreas and Activates Glucagon Gene Expression, *Mol. Endocrinol.* 19(3), 759-770.

Sambrook, J. et al. (1989) In *Molecular Cloning: A Laboratory Manual* (Sambrook, J., et al., Eds.) 2nd ed., pp. 16.17-16.18, Cold Spring Harbor Laboratory Press, New York.

Sambrook, J. et al. (1989) In *Molecular Cloning: A Laboratory Manual* (Sambrook, J., et al., Eds.) 2nd ed., pp. 16.19-16.15, Cold Spring Harbor Laboratory Press, New York.

Scheper, G. C. et al. (1994) Binding of eukaryotic initiation factor-2 and trans-acting factors to the 5' untranslated region of encephalomyocarditis virus RNA, *Biochimie* 76(8), 801-809.

Seshagiri, P. B. et al. (1993) Non-surgical uterine flushing for the recovery of preimplantation embryos in rhesus monkeys: Lack of seasonal infertility, *Am. J. Primatol.* 29(2), 81-91.

Shapiro, A. M. J. et al. (2006) International Trial of the Edmonton Protocol for Islet Transplantation, *N. Engl. J. Med.* 355(13), 1318-1330.

Shelling, A. N. et al. (1994) Targeted integration of transfected and infected adeno-associated virus vectors containing the neomycin resistance gene, *Gene Ther.* 1(3), 165-169.

Soria, B. (2001) In-vitro differentiation of pancreatic β-cells, *Differentiation* 68(4-5), 205-219.

Sukoyan, M. A. et al. (1992) Isolation and cultivation of blastocyst-derived stem cell lines from American mink (Mustela vison), *Mol. Reprod. Dev.* 33(4), 418-431.

Sukoyan, M. A. et al. (1993) Embryonic stem cells derived from morulae, inner cell mass, and blastocysts of mink: comparisons of their pluripotencies, *Mol. Reprod. Dev.* 36(2), 148-158.

Thomson, J. A. et al. (1994) Nonsurgical uterine stage preimplantation embryo collection from the common marmoset, *J. Med. Primatol.* 23(6), 333-336.

Uetsuki, T. et al. (1989) Isolation and characterization of the human chromosomal gene for polypeptide chain elongation factor-1 alpha, *J. Biol. Chem.* 264(10), 5791-5798.

Uhlmann, E. et al. (1990) Antisense oligonucleotides: a new therapeutic principle, *Chemical Reviews* 90, 543-584.

Vincent, K. A. et al. (1990) Replication and packaging of HIV envelope genes in a novel adeno-associated virus vector system, *Vaccines (Cold Spring Harbor)* 90, 353-359.

Voss, S. D. et al. (1986) The role of enhancers in the regulation of cell-type-specific transcriptional control, *Trends Biochem. Sci.* 11(7), 287-289.

Weissman, I. L. (2000) Translating Stem and Progenitor Cell Biology to the Clinic: Barriers and Opportunities, *Science* 287(5457), 1442-1446.

Zhou, S. Z. et al. (1994) Adeno-associated virus 2-mediated high efficiency gene transfer into immature and mature subsets of hematopoietic progenitor cells in human umbilical cord blood, *The Journal of Experimental Medicine* 179(6), 1867-1875.

Zwizinski, C. et al. (1980) Purification and characterization of leader (signal) peptidase from *Escherichia coli*, *J. Biol. Chem.* 255(16), 7973-7977.

\* cited by examiner

−AHL      +AHL
MAMMALIAN RECEIVERS

MyoD (MYOBLASTS)    PPAR (ADIPOCYTES)    Nanog (SELF-RENEWAL)
mES CELL DIFFERENTIATION SEQ ID NO:01:
cggccatcgataaggatccgccctctcctccccccccctaacgttactggccgaagccgcttgg
aataaggccggtgtgcgtttgtctatatgttattttccaccatattgccgtcttttggcaatgtgag
ggcccggaaacctggccctgtcttcttgacgagcattcctaggggtctttcccctctcgccaaagga
atgcaaggtctgttgaatgtcgtgaaggaagcagttcctctggaagcttcttgaagacaaacaacgt
ctgtagcgacccttgcaggcagcggaaccccccacctggcgacaggtgcctctgcggccaaaagcc
acgtgtataagatacacctgcaaaggcggcacaaccccagtgccacgttgtgagttggatagttgtg
gaaagagtcaaatggctctcctcaagcgtattcaacaaggggctgaaggatgcccagaaggtaccc
attgtatgggatctgatctggggcctcggtgcacatgcttacatgtgtttagtcgaggttaaaaaa
acgtctaggcccccgaaccacggggacgtggttttcctttgaaaaacacgatgataatatggccac
aaccatggcctcctccgaggacgtcatcaaggagttcatgcgcttcaaggtgcgcatggagggctcc
gtgaacggccacgagttcgagatcgagggcgagggcgagggccgcccctacgagggcacccagaccg
ccaagctgaaggtgaccaagggcggccccctgcccttcgcctgggacatcctgtcccccagttcca
gtacggctccaaggtgtacgtgaagcacccgccgacatccccgactacaagaagctgtccttcccc
gagggcttcaagtgggagcgcgtgatgaacttcgaggacggcggcgtggtgaccgtgacccaggact
cctccctgcaggacggctccttcatctacaaggtgaagttcatcggcgtgaacttccctccgacgg
cccgtaatgcagaagaagactatgggctgggaggcctccaccgagcgcctgtaccccgcgacggc
gtgctgaagggcgagatccacaaggccctgaagctgaaggacggcggccactacctggtggagttca
agtccatctacatggccaagaagcccgtgcagctgcccggctactactacgtggactccaagctgga
catcacctcccacaacgaggactacaccatcgtggagcagtacgagcgcgccgagggccgccaccac
ctgttcctgtaggcggccgcaatcaacctctggattacaaaatttgtgaaagattgactggtattct
taactatgttgctccttttacgctatgtggatacgctgctttaatgcctttgtatcatgctattact
tcccgtacggctttcatttttctcctccttgtataaatcctggttgctgtctctttatgaggagttgt
ggcccgttgtcaggcaacgtggcgtggtgtgcactgtgtttgctgacgcaaccccactggttgggg
cattgccaccacctatcaactcctttcgggacttcgctttcccctcccctattgccacggcggaa
ctcattgccgcctgccttgcccgctgctggacaggggctcggctgttgggcactgacaattccgtgg
tgttgtcggggaagctgacgtcctttccatggctgctcgcctgtgttgccaactggattctgcgcgg
gacgtccttctgctacgtcccttcggccctcaatccagcggaccttccttcccgcggcctgctgccg
gttctgcggcctcttccgcgtcttcgccttcgccctcagacgagtcggatctcccctttgggccgcct
ccccgcctgcctgcaggtttgtcgagacctagaaaaacatggagcaatcacaagtagcaatacagca
gctaccaatgctgattgtgcctggctagaagcacaagaggaggaggaggtgggttttccagtcacac
ctcaggtaccttaagaccaatgacttacaaggcagctgtagatcttagccactttttaaaagaaaa
gggggactggaagggctaattcactcccaacgaagacaagatctgcttttgcttgtactgggtct
ctctggttagaccagatctgagcctgggagctctctggctaactagggaacccactgcttaagcctc
aataaagcttgccttgagtgcttcaagtagtgtgtgcccgtctgttgtgtgactctggtaactagag
atccctcagacccttttagtcagtgtggaaaatctctagcagggcccgtttaaacccgctgatcagc
ctcgactgtgccttctagttgccagccatctgttgtttgcccctcccccgtgccttccttgaccctg
gaaggtgccactcccactgtcctttcctaataaaatgaggaaattgcatcgcattgtctgagtaggt
gtcattctattctggggggtggggtggggcaggacagcaaggggggaggattgggaagacaatagcag
gcatgctggggatgcggtgggctctatggcttctgaggcggaaagaaccagctggggctctaggggg
tatccccacgcgccctgtagcggcgcattaagcgcggcgggtgtggtggttacgcgcagcgtgaccg
ctacacttgccagcgccctagcgcccgctcctttcgctttcttcccttcctttctcgccacgttcgc
cggctttccccgtcaagctctaaatcggggcatccctttagggttccgatttagtgctttacggcac
ctcgaccccaaaaaacttgattagggtgatggttcacgtagtgggccatcgccctgatagacggttt
ttcgccctttgacgttggagtccacgttctttaatagtggactcttgttccaaactggaacaacact
caaccctatctcggtctattcttttgatttataagggattttggggatttcggcctattggttaaaa
aatgagctgatttaacaaaaatttaacgcgaattaattctgtggaatgtgtgtcagttagggtgtgg
aaagtccccaggctccccaggcaggcagaagtatgcaaagcatgcatctcaattagtcagcaaccag
gtgtggaaagtccccaggctccccagcaggcagaagtatgcaaagcatgcatctcaattagtcagca
accatagtcccgcccctaactccgcccatcccgcccctaactccgcccagttccgcccattctccgc
cccatggctgactaattttttttatttatgcagaggccgaggccgcctctgcctctgagctattcca

FIG. 5A

```
gaagtagtgaggaggctttttggaggcctaggcttttgcaaaaagctcccgggagcttgtatatcc
attttcggatctgatcagcacgtgttgacaattaatcatcggcatagtatatcggcatagtataata
cgacaaggtgaggaactaaaccatggccaagttgaccagtgccgttccggtgctcaccgcgcgcgac
gtcgccggagcggtcgagttctggaccgaccggctcgggttctcccgggacttcgtggaggacgact
tcgccggtgtggtccgggacgacgtgaccctgttcatcagcgcggtccaggaccaggtggtgccgga
caacaccctggcctgggtgtgggtgcgcggcctggacgagctgtacgccgagtggtcggaggtcgtg
tccacgaacttccgggacgcctccgggccggccatgaccgagatcggcgagcagccgtggggcggg
agttcgcctgcgcgacccggccggcaactgcgtgcacttcgtggccgaggagcaggactgacacgt
gctacgagatttcgattccaccgccgccttctatgaaaggttgggcttcggaatcgttttccgggac
gccggctggatgatcctccagcgcggggatctcatgctggagttcttcgcccacccaacttgttta
ttgcagcttataatggttacaaataaagcaatagcatcacaaatttcacaaataaagcattttttc
actgcattctagttgtggtttgtccaaactcatcaatgtatcttatcatgtctgtataccgtcgacc
tctagctagagcttggcgtaatcatggtcatagctgttcctgtgtgaaattgttatccgctcacaa
ttccacacaacatacgagccggaagcataaagtgtaaagcctggggtgcctaatgagtgagctaact
cacattaattgcgttgcgctcactgcccgctttccagtcgggaaacctgtcgtgccagctgcattaa
tgaatcggccaacgcgcggggagaggcggtttgcgtattgggcgctcttccgcttcctcgctcactg
actcgctgcgctcggtcgttcggctgcggcgagcggtatcagctcactcaaaggcggtaatacggtt
atccacagaatcaggggataacgcaggaaagaacatgtgagcaaaaggccagcaaaaggccaggaac
cgtaaaaaggccgcgttgctggcgtttttccataggctccgcccccctgacgagcatcacaaaaatc
gacgctcaagtcagaggtggcgaaacccgacaggactataaagataccaggcgtttccccctggaag
ctccctcgtgcgctctcctgttccgaccctgccgcttaccggatacctgtccgcctttctcccttcg
ggaagcgtggcgctttctcaatgctcacgctgtaggtatctcagttcggtgtaggtcgttcgctcca
agctgggctgtgtgcacgaaccccccgttcagcccgaccgctgcgccttatccggtaactatcgtct
tgagtccaacccggtaagacacgacttatcgccactggcagcagccactggtaacaggattagcaga
gcgaggtatgtaggcggtgctacagagttcttgaagtggtggcctaactacggctacactagaagga
cagtatttggtatctgcgctctgctgaagccagttaccttcggaaaaagagttggtagctcttgatc
cggcaaacaaaccaccgctggtagcggtggtttttttgtttgcaagcagcagattacgcgcagaaaa
aaaggatctcaagaagatcctttgatcttttctacggggtctgacgctcagtggaacgaaaactcac
gttaagggattttggtcatgagattatcaaaaaggatcttcacctagatcctttaaattaaaaatg
aagttttaaatcaatctaaagtatatatgagtaaacttggtctgacagttaccaatgcttaatcagt
gaggcacctatctcagcgatctgtctatttcgttcatccatagttgcctgactccccgtcgtgtaga
taactacgatacgggagggcttaccatctggccccagtgctgcaatgataccgcgagacccacgctc
accggctccagatttatcagcaataaaccagccagccggaagggccgagcgcagaagtggtcctgca
actttatccgcctccatccagtctattaattgttgccgggaagctagagtaagtagttcgccagtta
atagtttgcgcaacgttgttgccattgctacaggcatcgtggtgtcacgctcgtcgtttggtatggc
ttcattcagctccggttcccaacgatcaaggcgagttacatgatcccccatgttgtgcaaaaaagcg
gttagctccttcggtcctccgatcgttgtcagaagtaagttggccgcagtgttatcactcatggtta
tggcagcactgcataattctcttactgtcatgccatccgtaagatgcttttctgtgactggtgagta
ctcaaccaagtcattctgagaatagtgtatgcggcgaccgagttgctcttgcccggcgtcaatacgg
gataataccgcgccacatagcagaactttaaaagtgctcatcattggaaaacgttcttcggggcgaa
aactctcaaggatcttaccgctgttgagatccagttcgatgtaacccactcgtgcacccaactgatc
ttcagcatcttttactttcaccagcgtttctgggtgagcaaaaacaggaaggcaaaatgccgcaaaa
aagggaataagggcgacacggaaatgttgaatactcatactcttcctttttcaatattattgaagca
tttatcagggttattgtctcatgagcggatacatatttgaatgtatttagaaaaataaacaaatagg
ggttccgcgcacatttccccgaaaagtgccacctgacgtcgacggatcgggagatctcccgatcccc
tatggtgcactctcagtacaatctgctctgatgccgcatagttaagccagtatctgctccctgcttg
tgtgttggaggtcgctgagtagtgcgcgagcaaaatttaagctacaacaaggcaaggcttgaccgac
aattgcatgaagaatctgcttagggttaggcgttttgcgctgcttcgcgatgtacgggccagatata
cgcgttgacattgattattgactagttattaatagtaatcaattacggggtcattagttcatagccc
atatatggagttccgcgttacataacttacggtaaatggcccgcctggctgaccgcccaacgaccc
cgcccattgacgtcaataatgacgtatgttcccatagtaacgccaatagggactttccattgacgtc
```

FIG. 5B aatgggtggactatttacggtaaactgcccacttggcagtacatcaagtgtatcatatgccaagtac
gcccccctattgacgtcaatgacggtaaatggcccgcctggcattatgcccagtacatgaccttatgg
gactttcctacttggcagtacatctacgtattagtcatcgctattaccatggtgatgcggttttggc
agtacatcaatgggcgtggatagcggtttgactcacggggatttccaagtctccaccccattgacgt
caatgggagtttgttttggcaccaaaatcaacggactttccaaaatgtcgtaacaactccgcccca
ttgacgcaaatgggcggtaggcgtgtacggtgggaggtctatataagcagagctctctggctaacta
gagaacccactgcttactggcttatcgaaattaatacgactcactatagggagacccaagctggttt
aaacttaagcttggtaccgagctcactagtccagtgtggtggcagatatccagcacagtggcggccg
ctcgagtctagagggcccgttttgcctgtactgggtctctctggttagaccagatctgagcctggga
gctctctggctaactagggaacccactgcttaagcctcaataaagcttgccttgagtgcttcaagta
gtgtgtgcccgtctgttgtgtgactctggtaactagagatccctcagacccttagtcagtgtgga
aaatctctagcagtggcgcccgaacagggacttgaaagcgaaagggaaaccagaggagctctctcga
cgcaggactcggcttgctgaagcgcgcacggcaagaggcgaggggcggcgactggtgagtacgccaa
aaattttgactagcggaggctagaaggagagagatgggtgcgagagcgtcagtattaagcggggag
aattagatcgcgatgggaaaaaattcggttaaggccaggggaaagaaaaaatataaattaaaacat
atagtatgggcaagcagggagctagaacgattcgcagttaatcctggcctgttagaaacatcagaag
gctgtagacaaatactgggacagctacaaccatcccttcagacaggatcagaagaacttagatcatt
atataatacagtagcaaccctctattgtgtgcatcaaaggatagagataaaagacaccaaggaagct
ttagacaagatagaggaagagcaaaacaaaagtaagaccaccgcacagcaagcggccgctgatcttc
agacctggaggaggagatatgagggacaattggagaagtgaattatataaatataaagtagtaaaaa
ttgaaccattaggagtagcacccaccaaggcaaagagaagagtggtgcagagagaaaaaagagcagt
gggaataggagctttgttccttgggttcttgggagcagcaggaagcactatgggcgcagcgtcaatg
acgctgacggtacaggccagacaattattgtctggtatagtgcagcagcagaacaatttgctgaggg
ctattgaggcgcaacagcatctgttgcaactcacagtctggggcatcaagcagctccaggcaagaat
cctggctgtggaaagatacctaaaggatcaacagctcctggggatttggggttgctctggaaaactc
atttgcaccactgctgtgccttggaatgctagttggagtaataaatctctggaacagatttggaatc
acacgacctggatggagtgggacagagaaattaacaattacacaagcttaatacactccttaattga
agaatcgcaaaaccagcaagaaaagaatgaacaagaattattggaattagataaatgggcaagtttg
tggaattggtttaacataacaaattggctgtggtatataaaattattcataatgatagtaggaggct
tggtaggtttaagaatagttttgctgtactttctatagtgaatagagttaggcagggatattcacc
attatcgtttcagacccacctcccaaccccgaggggacccgacaggcccttaattaattggctccgg
tgcccgtcagtgggcagagcgcacatcgcccacagtccccgagaagttggggggaggggtcggcaat
tgaaccggtgcctagagaaggtggcgcggggtaaactgggaaagtgatgtcgtgtactggctccgcc
ttttccccgagggtgggggagaaccgtatataagtgcagtagtcgccgtgaacgttcttttttcgcaa
cgggtttgccgccagaacacaggtaagtgccgtgtgtggttcccgcgggcctggcctctttacgggt
tatggcccttgcgtgccttgaattacttccacctggctgcagtacgtgattcttgatcccgagcttc
gggttggaagtgggtgggagagttcgaggccttgcgcttaaggagccccttcgcctcgtgcttgagt
tgaggcctggcctgggcgctggggccgccgcgtgcgaatctggtggcaccttcgcgcctgtctcgct
gctttcgataagtctctagccatttaaaattttgatgacctgctgcgacgctttttctggcaag
atagtcttgtaaatgcgggccaagatctgcacactggtatttcggttttttggggccgcgggcggcga
cggggcccgtgcgtcccagcgcacatgttcggcgaggcggggcctgcgagcgcggccaccgagaatc
ggacgggggtagtctcaagctggccggcctgctctggtgcctggcctcgcgccgcgtgtatcgccc
cgccctgggcggcaaggctggcccggtcggcaccagttgcgtgagcggaaagatggccgcttcccgg
ccctgctgcagggagctcaaaatggaggacgcggcgctcgggagagcgggcggtgagtcacccaca
caaaggaaaagggcctttccgtcctcagccgtcgcttcatgtgactccacggagtaccgggcgccgt
ccaggcacctcgattagttctcgagcttttggagtacgtcgtctttaggttgggggagggggtttta
tgcgatggagtttccccacactgagtgggtggagactgaagttaggccagcttggcacttgatgtaa
ttctccttggaatttgccctttttgagtttggatcttggttcattctcaagcctcagacagtggttc
aaagttttttcttccatttcaggtgtcgtgaggaattcggccattacggcccgccaccatgaccat
catgatcaagaagagcgacttcctggccatccccagcgaggagtacaagggcatcctgagcctgaga
taccaggtgttcaagcagaggctggagtgggacctggtggtggagaacaacctggagagcgacgagt

FIG. 5C

```
acgacaacagcaacgccgagtacatctacgcctgcgacgacaccgagaacgtgagcggctgctggcg
cctgctgcccaccaccggcgactacatgctgaagagcgtgttccccgagctgctgggccagcagagc
gccccaaggaccccaacatcgtggagctgtccaggttcgccgtgggcaagaacagcagcaagatca
acaacagcgccagcgagatcaccatgaagctgttcgaggccatctacaagcacgccgtgagccaggg
catcaccgagtacgtgaccgtgaccagcaccgccatcgagagatttctgaagaggatcaaggtgccc
tgccacaggatcggcgacaaggagatccacgtcctgggcgacaccaagagcgtggtgctgtccatgc
ccatcaacgagcagttcaaaaaggccgtgctgaactgaggccgcct
```

FIG. 5D

```
FEATURES            Location/Qualifiers
    promoter        8835..10008
                    /vntifkey="29"
                    /label=PEF1-alpha
    promoter        6547..7198
                    /vntifkey="29"
                    /label=PCMV
    promoter        7201..7220
                    /vntifkey="29"
                    /label=T7\promoter
    misc_feature    2345..2558
                    /vntifkey="21"
                    /label=BGH\PolyA
    rep_origin      2621..3033
                    /vntifkey="33"
                    /label=f1\ori
    rep_origin      3099..3424
                    /vntifkey="33"
                    /label=SV40\ori
    promoter        3440..3505
                    /vntifkey="29"
                    /label=EM7
    CDS             3507..3881
                    /vntifkey="4"
                    /label=Zeocin(r)
    rep_origin      complement(4524..5197)
                    /vntifkey="33"
                    /label=pUC\ori
    promoter        complement(6203..6300)
                    /vntifkey="29"
                    /label=bla
    CDS             complement(5342..6202)
                    /vntifkey="4"
                    /label=Amp(r)
    misc_feature    1294..1885
                    /vntifkey="21"
                    /label=WPRE
    misc_feature    20..604
                    /vntifkey="21"
                    /label=IRES
    misc_feature    7233..7335
                    /vntifkey="21"
                    /label=MCS
    misc_feature    2085..2319
                    /vntifkey="21"
                    /label=deltaU3-3'LTR
    misc_feature    7336..7516
```

FIG. 7A

```
                        /vntifkey="21"
                        /label=5'\LTR
        CDS             608..1285
                        /vntifkey="4"
                        /label=DsRED2
        RBS             602..611
                        /vntifkey="32"
                        /label=Kozak\consensus
        CDS             10043..11728
                        /vntifkey="4"
                        /label=p65H4LuxRFmNLS
        RBS             10036..10046
                        /vntifkey="32"
                        /label=Kozak\consensus
BASE COUNT       2739 a        3198 c       3147 g          2652 t
SEQ ID NO:02
       1 cggccatcga taaggatccg ccoctctccc tcccccccc ctaacgttac tggccgaagc
      61 cgcttggaat aaggccggtg tgcgtttgtc tatatgttat tttccaccat attgccgtct
     121 tttggcaatg tgagggcccg gaaacctggc cctgtcttct tgacgagcat tcctaggggt
     181 ctttcccctc tcgccaaagg aatgcaaggt ctgttgaatg tcgtgaagga agcagttcct
     241 ctggaagctt cttgaagaca acaacgtct gtagcgaccc tttgcaggca gcggaacccc
     301 ccacctggcg acaggtgcct ctgccggcaa aagccacgtg tataagatac acctgcaaag
     361 gcggcacaac cccagtgcca cgttgtgagt tggatagttg tggaaagagt caaatggctc
     421 tcctcaagcg tattcaacaa ggggctgaag gatgcccaga aggtacccca ttgtatggga
     481 tctgatctgg ggcctcggtg cacatgcttt acatgtgttt agtcgaggtt aaaaaaacgt
     541 ctaggccccc cgaaccacgg ggacgtggtt ttcctttgaa aaacacgatg ataatatggc
     601 cacaaccatg gcctcctccg aggacgtcat caaggagttc atgcgcttca aggtgcgcat
     661 ggagggctcc gtgaacggcc acgagttcga gatcgagggc gagggcgagg ccgcccccta
     721 cgagggcacc cagaccgcca agctgaaggt gaccaagggc ggccccctgc ccttcgcctg
     781 ggacatcctg tcccccagt tccagtacgg ctccaagtg tacgtgaagc accccgccga
     841 catccccgac tacaagaagc tgtccttccc cgagggcttc aagtgggagc gcgtgatgaa
     901 cttcgaggac ggcggcgtgg tgaccgtgac ccaggactcc tccctgcagg acggctcctt
     961 catctacaag gtgaagttca tcggcgtgaa cttcccctcc gacggccccg taatgcagaa
    1021 gaagactatg gctgggagg cctccaccga gcgcctgtac ccccgcgacg gcgtgctgaa
    1081 gggcgagatc cacaaggccc tgaagctgaa ggacggcggc cactacctgg tggagttcaa
    1141 gtccatctac atggccaaga agcccgtgca gctgcccggc tactactacg tggactccaa
    1201 gctggacatc acctcccaca acgaggacta caccatcgtg agcagtacg agcgcgccga
    1261 gggccgccac cacctgttcc tgtaggcggc cgcaatcaac ctctggatta caaaatttgt
    1321 gaaagattga ctggtattct taactatgtt gctcctttta cgctatgtgg atacgctgct
    1381 ttaatgcctt tgtatcatgc tattacttcc cgtacggctt tcatttctc ctccttgtat
    1441 aaatcctggt tgctgtctct ttatgaggag ttgtggcccg ttgtcaggca acgtggcgtg
    1501 gtgtgcactg tgtttgctga cgcaaccccc actggttggg gcattgccac cacctatcaa
    1561 ctcctttccg ggactttcgc tttccccctc cctattgcca cggcggaact cattgccgcc
    1621 tgccttgccc gctgctggac aggggctcgg ctgttgggca ctgacaattc cgtggtgttg
    1681 tcggggaagc tgacgtcctt tccatggctg ctcgcctgtg ttgccaactg gattctgcgc
    1741 gggacgtcct tctgctacgt cccttcggcc ctcaatccag cggaccttcc ttcccgcggc
    1801 ctgctgccgg ttctgcggcc tcttccgcgt cttcgccttc gccctcagac gagtcggatc
    1861 tcccttggg ccgcctcccc gcctgcctgc aggtttgtcg agacctagaa aaacatggag
    1921 caatcacaag tagcaataca gcagctacca atgctgattg tgcctggcta gaagcacaag
    1981 aggaggagga ggtgggtttt ccagtcacac ctcaggtacc tttaagacca atgacttaca
    2041 aggcagctgt agatcttagc cactttttaa aagaaaaggg gggactggaa gggctaattc
    2101 actcccaacg aagacaagat ctgcttttg cttgtactgg gtctctctgg ttagaccaga
    2161 tctgagcctg ggagctctct ggctaactag gaacccact gcttaagcct caataaagct
    2221 tgccttgagt gcttcaagta gtgtgtgccc gtctgttgtg tgactctggt aactagagat
```

FIG. 7B

```
2281 ccctcagacc cttttagtca gtgtggaaaa tctctagcag ggcccgttta aacccgctga
2341 tcagcctcga ctgtgccttc tagttgccag ccatctgttg tttgccsctc ccccgtgcct
2401 tccttgaccc tggaaggtgc cactcccact gtcctttcct aataaaatga ggaaattgca
2461 tcgcattgtc tgagtaggtg tcattctatt ctgggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcggggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt tggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt gggggcggga gttcgccctg cgcgaccggg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccaccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata agtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc cctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaaccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
```

FIG. 7C

```
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct cggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc gcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta gaaggagaga gatgggtgcg
7681 agagcgtcag tattaagcgg gggagaatta gatcgcgatg ggaaaaaatt cggttaaggc
7741 caggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata aaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag ggacccgac
8821 aggcccttaa ttaattggct ccggtgcccg tcagtgggca gagcgcacat cgcccacagt
8881 ccccgagaca ttgggggag ggtcggcaa ttgaaccggt gcctagaaa ggtggcgcgg
8941 ggtaaactgg gaaagtgatg tcgtgtactg gctccgcctt tttcccgagg gtggggggaga
9001 accgtatata agtgcagtag tcgccgtgaa cgttcttttt cgcaacgggt ttgccgccag
9061 aacacaggta agtgccgtgt gtggttcccg cgggcctggc ctctttacgg gttatggccc
```

FIG. 7D

```
 9121 ttgcgtgcct tgaattactt ccacctggct gcagtacgtg attcttgatc ccgagcttcg
 9181 ggttggaagt gggtgggaga gttcgaggcc ttgcgcttaa ggagcccctt cgcctcgtgc
 9241 ttgagttgag gcctggcctg ggcgctgggg ccgccgcgtg cgaatctggt ggcaccttcg
 9301 cgcctgtctc gctgctttcg ataagtctct agccatttaa aattttgat gacctgctgc
 9361 gacgcttttt ttctggcaag atagtcttgt aaatgcgggc caagatctgc acactggtat
 9421 ttcggttttt ggggccgcgg gcggcgacgg ggcccgtgcg tcccagcgca catgttcggc
 9481 gaggcggggc ctgcgagcgc ggccaccgag aatcggacgg gggtagtctc aagctggccg
 9541 gcctgctctg gtgcctggcc tcgcgccgcc gtgtatcgcc ccgccctggg cggcaaggct
 9601 ggcccggtcg gcaccagttg cgtgagcgga aagatggccg cttcccggcc ctgctgcagg
 9661 gagctcaaaa tggaggacgc ggcgctcggg agagcgggcg ggtgagtcac ccacacaaag
 9721 gaaaagggcc tttccgtcct cagccgtcgc ttcatgtgac tccacggagt accgggcgcc
 9781 gtccaggcac ctcgattagt tctcgagctt ttggagtacg tcgtctttag gttggggga
 9841 ggggttttat gcgatggagt ttccccacac tgagtgggtg gagactgaag ttaggccagc
 9901 ttggcacttg atgtaattct ccttggaatt tgccctttt gagtttggat cttggttcat
 9961 tctcaagcct cagacagtgg ttcaaagttt ttttcttcca tttcaggtgt cgtgaggaat
10021 tcggccatta cggcctgcca ccatggacca gtacctgccc gacaccgacg acaggcacag
10081 gatcgaggag aagaggaaga ggacctacga gaccttcaag agcatcatga agaagagccc
10141 cttcaacggc cccaccgagc ccagaccccc caccaggcgg atcgccgtgc cacaaggaa
10201 cagcaccagc gtgcccaagc ctgcccccca gcctacacc ttccccgcca gcctgagcac
10261 catcaacttc gacgagttca gccccatgct gctgccagc ggccagatca gcaaccaggc
10321 cctggccctg gctcctagca gcgcccctgt gctggcccag accatggtgc ccagcagcgc
10381 catggtgcct ctggcccagc ctcctgcccc tgcccccgtg ctgaccctg ccccctca
10441 gagcctgagc gcccagtgc ccaagagcac ccaggccgg gagggcacac tgagcgaggc
10501 cctgctgcac ctgcagttcg acgccgacga ggacctgggc gccctgctgg gcaacagcac
10561 cgaccccggc gtgttcaccg acctggccag cgtggacaac agcgagttcc agcagctgct
10621 gaaccagggc gtgagcatga gccacagcac cgccgagccc atgctgatgg agtaccccga
10681 ggccatcacc aggctggtga ccggcagcca gagacccccc gacctgccc ctacccctct
10741 gggcaccagc ggcctgccca acggcctgag cggcgacgag gacttcagca gcatcgccga
10801 catggacttc tccgccctgc tgtcccagat cagctccctg gagctggccg aggccgctgc
10861 caaggaggct gccgctaagg aggccgctgc taaggaggct gctgccaagg ccgctgccat
10921 gaagaacatc aacgccgacg acacctacag gatcatcaac aagatcaagg cctgcagaag
10981 caacaacgac atcaaccagt gcctgagcga catggccaag atggtgcact gcgagtacta
11041 cctgctggcc ttcatctacc cccacagcat ggtgaagagc gacatcagca tcctggacaa
11101 ctaccccaag aagtggaggc agtactacga gacgccaac ctgatcaagt acgacccat
11161 cgtggactac agcaacagca ccacagccc catcaactgg aacatcttcg agaacaacgc
11221 cgtgaacaaa aagtcccca acgtgatcaa ggaggccaag acagccggcc tgatcaccgg
11281 cttcagcttc cccatccaca ccgccaacaa cggcttcggc atgctgtcct cgcccacag
11341 cgagaaggac aactacatcg acagcctgtt tctgcacgcc tgcatgaaca tccccctgat
11401 cgtgcccagc ctggtggata actaccggaa gatcaacatc gccaacaaca gtccaacaa
11461 cgacctgacc aagcgggaga aggagtgcct ggcctgggcc tgcgagggca agagcagctg
11521 ggacatcagc aagatcctgg gctgcagcga gaggaccgtg accttccacc tgaccaacgc
11581 ccagatgaag ctgaacacca ccaacaggtg ccagagcatc agcaaggcca tcctgaccgg
11641 cgccatcgac tgccctact tcaagaacag cagcctgagg ccccccaaaa agaaaagaaa
11701 ggtgcaccac caccaccacc actgatgagg ccgcct
```

FIG. 7E

```
FEATURES          Location/Qualifiers
     misc_feature     7427..7607
                      /vntifkey="21"
                      /label=5'\LTR
     misc_feature     2176..2410
                      /vntifkey="21"
                      /label=deltaU3-3'LTR
     misc_feature     7324..7426
                      /vntifkey="21"
                      /label=MCS
     RBS              650..660
                      /vntifkey="32"
                      /label=Kozak\consensus
     CDS              657..1376
                      /vntifkey="4"
                      /label=EGFP
     misc_feature     69..653
                      /vntifkey="21"
                      /label=IRES2
     misc_feature     1385..1976
                      /vntifkey="21"
                      /label=WPRE
     CDS              complement(5433..6293)
                      /vntifkey="4"
                      /label=Amp(r)
     promoter         complement(6294..6391)
                      /vntifkey="29"
                      /label=bla
     rep_origin       complement(4615..5288)
                      /vntifkey="33"
                      /label=pUC\ori
     CDS              3598..3972
                      /vntifkey="4"
                      /label=Zeocin(r)
     promoter         3531..3596
                      /vntifkey="29"
                      /label=EM7
     rep_origin       3190..3515
                      /vntifkey="33"
                      /label=SV40\ori
     rep_origin       2712..3124
                      /vntifkey="33"
                      /label=f1\ori
     misc_feature     2436..2649
```

FIG. 9A

```
                        /vntifkey="21"
                        /label=BGH\PolyA
promoter                7292..7311
                        /vntifkey="29"
                        /label=T7\promoter
promoter                6638..7289
                        /vntifkey="29"
                        /label=PCMV
promoter                9935..10045
                        /vntifkey="29"
                        /label=pminCMV
protein_bind            9904..9923
                        /vntifkey="31"
                        /label=lux\box
protein_bind            9861..9880
                        /vntifkey="31"
                        /label=lux\box
protein_bind            9818..9837
                        /vntifkey="31"
                        /label=lux\box
protein_bind            9775..9794
                        /vntifkey="31"
                        /label=lux\box
protein_bind            9732..9751
                        /vntifkey="31"
                        /label=lux\box
protein_bind            9689..9708
                        /vntifkey="31"
                        /label=lux\box
protein_bind            9646..9665
                        /vntifkey="31"
                        /label=lux\box
BASE COUNT        2544 a       2506 c       2598 g       2402 t
ORIGIN
SEQ ID NO:03
      1 aattcggcca ttacggccgc tagcgttaac gtcgacggcc gcctcggcca tcgataagga
     61 tccggaatgc ccctctccct cccccccccc taacgttact ggccgaagcc gcttggaata
    121 aggccggtgt gcgtttgtct atatgttatt ttccaccata ttgccgtctt ttggcaatgt
    181 gagggcccgg aaacctggcc ctgtcttctt gacgagcatt cctaggggtc tttcccctct
    241 cgccaaagga atgcaaggtc tgttgaatgt cgtgaaggaa gcagttcctc tggaagcttc
    301 ttgaagacaa acaacgtctg tagcgaccct ttgcaggcag cggaaccccc cacctggcga
    361 caggtgcctc tgcggccaaa agccacgtgt ataagataca cctgcaaagg cggcacaacc
    421 ccagtgccac gttgtgagtt ggatagttgt ggaaagagtc aaatggctct cctcaagcgt
    481 attcaacaag gggctgaagg atgcccagaa ggtacccat tgtatgggat ctgatctggg
    541 gcctcggtgc acatgcttta catgtgttta gtcgaggtta aaaaaacgtc taggcccccc
    601 gaaccacggg gacgtggttt tcctttgaaa aacacgatga taatatggcc acaaccatgg
    661 tgagcaaggg cgaggagctg ttcaccgggg tggtgcccat cctggtcgag ctggacggcg
    721 acgtaaacgg ccacaagttc agcgtgtccg gcgagggcga gggcgatgcc acctacggca
    781 agctgaccct gaagttcatc tgcaccaccg gcaagctgcc cgtgccctgg cccaccctcg
    841 tgaccaccct gacctacggc gtgcagtgct tcagccgcta ccccgaccac atgaagcagc
```

FIG. 9B

```
 901 acgacttctt caagtccgcc atgcccgaag gctacgtcca ggagcgcacc atcttcttca
 961 aggacgacgg caactacaag acccgcgccg aggtgaagtt cgagggcgac accctggtga
1021 accgcatcga gctgaagggc atcgacttca aggaggacgg caacatcctg gggcacaagc
1081 tggagtacaa ctacaacagc cacaacgtct atatcatggc cgacaagcag aagaacggca
1141 tcaaggtgaa cttcaagatc cgccacaaca tcgaggacgg cagcgtgcag ctcgccgacc
1201 actaccagca gaacaccccc atcggcgacg gccccgtgct gctgcccgac aaccactacc
1261 tgagcaccca gtccgccctg agcaaagacc ccaacgagaa gcgcgatcac atggtcctgc
1321 tggagttcgt gaccgccgcc gggatcactc tcggcatgga cgagctgtac aagtaagcgg
1381 ccgcaatcaa cctctggatt acaaaatttg tgaaagattg actggtattc ttaactatgt
1441 tgctcctttt acgctatgtg gatacgctgc tttaatgcct ttgtatcatg ctattacttc
1501 ccgtacggct ttcattttct cctccttgta taaatcctgg ttgctgtctc tttatgagga
1561 gttgtggccc gttgtcaggc aacgtggcgt ggtgtgcact gtgtttgctg acgcaacccc
1621 cactggttgg ggcattgcca ccacctatca actcctttcc gggactttcg ctttcccccct
1681 ccctattgcc acggcggaac tcattgccgc ctgccttgcc cgctgctgga cagggctcg
1741 gctgttgggc actgacaatt ccgtggtgtt gtcggggaag ctgacgtcct ttccatggct
1801 gctcgcctgt gttgccaact ggattctgcg cgggacgtcc ttctgctacg tcccttcggc
1861 cctcaatcca gcggaccttc cttcccgcgg cctgctgccg gttctgcggc ctcttccgcg
1921 tcttcgcctt cgccctcaga cgagtcggat ctccctttgg gccgcctccc cgcctgcctg
1981 caggtttgtc gagacctaga aaaacatgga gcaatcacaa gtagcaatac agcagctacc
2041 aatgctgatt gtgcctggct agaagcacaa gaggaggagg aggtgggttt tccagtcaca
2101 cctcaggtac ctttaagacc aatgacttac aaggcagctg tagatcttag ccacttttta
2161 aaagaaaagg ggggactgga agggctaatt cactcccaac gaagacaaga tctgcttttt
2221 gcttgtactg ggtctctctg gttagaccag atctgagcct gggagctctc tggctaacta
2281 gggaacccac tgcttaagcc tcaataaagc ttgccttgag tgcttcaagt agtgtgtgcc
2341 cgtctgttgt gtgactctgg taactagaga tccctcagac cctttagtc agtgtggaaa
2401 atctctagca gggcccgttt aaacccgctg atcagcctcg actgtgcctt ctagttgcca
2461 gccatctgtt gtttgcccct ccccgtgcc ttccttgacc ctggaaggtg ccactcccac
2521 tgtcctttcc taataaaatg aggaaattgc atcgcattgt ctgagtaggt gtcattctat
2581 tctgggggt ggggtgggc aggacagcaa gggggaggat tgggaagaca atagcaggca
2641 tgctggggat gcggtgggct ctatgcttc tgaggcggaa agaaccagct ggggctctag
2701 ggggtatccc cacgcgccct gtagcggcgc attaagcgcg gcgggtgtgg tggttacgcg
2761 cagcgtgacc gctacacttg ccagcgccct agcgcccgct cctttcgctt tcttcccttc
2821 ctttctcgcc acgttcgccg gctttccccg tcaagctcta atcggggca tccctttagg
2881 gttccgattt agtgctttac ggcacctcga ccccaaaaaa cttgattagg gtgatggttc
2941 acgtagtggg ccatcgccct gatagacggt ttttcgccct tgacgttgg agtccacgtt
3001 ctttaatagt ggactcttgt tccaaactgg aacaacactc aaccctatct cggtctattc
3061 ttttgattta taagggattt tggggatttc ggcctattgg ttaaaaaatg agctgattta
3121 acaaaaattt aacgcgaatt aattctgtgg aatgtgtgtc agttagggtg tggaaagtcc
3181 ccaggctccc caggcaggca gaagtatgca aagcatgcat ctcaattagt cagcaaccag
3241 gtgtggaaag tccccaggct ccccagcagg cagaagtatg caaagcatgc atctcaatta
3301 gtcagcaacc atagtcccgc ccctaactcc gcccatcccg ccctaactc cgcccagttc
3361 cgcccattct ccgccccatg gctgactaat tttttttatt tatgcagagg ccgaggccgc
3421 ctctgcctct gagctattcc agaagtagtg aggaggcttt tttggaggcc taggcttttg
3481 caaaaagctc ccgggagctt gtatatccat tttcggatct gatcagcacg tgttgacaat
3541 taatcatcgg catagtatat cggcatagta taatacgaca aggtgaggaa ctaaaccatg
3601 gccaagttga ccagtgccgt tccggtgctc accgcgcgcg acgtcgccgg agcggtcgag
3661 ttctggaccg accggctcgg gttctcccgg gacttcgtgg aggacgactt cgccggtgtg
3721 gtccgggacg acgtgaccct gttcatcagc gcggtccagg accaggtggt gccggacaac
3781 accctggcct gggtgtgggt gcgcggcctg gacgagctgt acgccgagtg gtcggaggtc
3841 gtgtccacga acttccggga cgcctccggg ccggccatga ccgagatcgg cgagcagccg
3901 tggggcgggg agttcgccct gcgcgacccg gccggcaact gcgtgcactt cgtggccgag
3961 gagcaggact gacacgtgct acgagatttc gattccaccg ccgccttcta tgaaaggttg
4021 ggcttcggaa tcgttttccg gacgccggc tggatgatcc tccagcgcgg gatctcatg
4081 ctggagttct tcgcccaccc caacttgttt attgcagctt ataatggtta caaataaagc
4141 aatagcatca caaatttcac aaataaagca ttttttcac tgcattctag ttgtggtttg
4201 tccaaactca tcaatgtatc ttatcatgtc tgtataccgt cgacctctag ctagagcttg
4261 gcgtaatcat ggtcatagct gtttcctgtg tgaaattgtt atccgctcac aattccacac
```

FIG. 9C

```
4321 aacatacgag ccggaagcat aaagtgtaaa gcctggggtg cctaatgagt gagctaactc
4381 acattaattg cgttgcgctc actcccgct ttccagtcgg gaaacctgtc gtgccagctg
4441 cattaatgaa tcggccaacg cgcggggaga ggcggtttgc gtattgggcg ctcttccgct
4501 tcctcgctca ctgactcgct gcgctcggtc gttcggctgc ggcgagcggt atcagctcac
4561 tcaaaggcgg taatacggtt atccacagaa tcagggata acgcaggaaa gaacatgtga
4621 gcaaaaggcc agcaaaaggc caggaaccgt aaaaaggccg cgttgctggc gttttccat
4681 aggctccgcc cccctgacga gcatcacaaa aatcgacgct caagtcagag gtggcgaaac
4741 ccgacaggac tataaagata ccaggcgttt ccccctggaa gctccctcgt gcgctctcct
4801 gttccgaccc tgccgcttac cggatacctg tccgccttc tcccttcggg aagcgtggcg
4861 ctttctcaat gctcacgctg taggtatctc agttcggtgt aggtcgttcg ctccaagctg
4921 ggctgtgtgc acgaaccccc cgttcagccc gaccgctgcg ccttatccgg taactatcgt
4981 cttgagtcca acccggtaag cacgactta tcgccactgg cagcagccac tggtaacagg
5041 attagcagag cgaggtatgt aggcggtgct acagagttct tgaagtggtg gcctaactac
5101 ggctacacta gaaggacagt atttggtatc tgcgctctgc tgaagccagt taccttcgga
5161 aaaagagttg gtagctcttg atccggcaaa caaccaccg ctggtagcgg tggttttttt
5221 gtttgcaagc agcagattac gcgcagaaaa aaggatctc aagaagatcc tttgatcttt
5281 tctacggggt ctgacgctca gtggaacgaa aactcacgtt aagggatttt ggtcatgaga
5341 ttatcaaaaa ggatcttcac ctagatcctt ttaaattaaa aatgaagttt aaatcaatc
5401 taaagtatat atgagtaaac ttggtctgac agttaccaat gcttaatcag tgaggcacct
5461 atctcagcga tctgtctatt tcgttcatcc atagttgcct gactccccgt cgtgtagata
5521 actacgatac gggagggctt accatctggc cccagtgctg caatgatacc gcgagaccca
5581 cgctcaccgg ctccagattt atcagcaata aaccagccag ccggaagggc cgagcgcaga
5641 agtggtcctg caactttatc cgcctccatc cagtctatta attgttgccg ggaagctaga
5701 gtaagtagtt cgccagttaa tagtttgcgc aacgttgttg ccattgctac aggcatcgtg
5761 gtgtcacgct cgtcgtttgg tatggcttca ttcagctccg gttcccaacg atcaaggcga
5821 gttacatgat cccccatgtt gtgcaaaaaa gcggttagct ccttcggtcc tccgatcgtt
5881 gtcagaagta agttggccgc agtgttatca ctcatggtta tggcagcact gcataattct
5941 cttactgtca tgccatccgt aagatgcttt tctgtgactg gtgagtactc aaccaagtca
6001 ttctgagaat agtgtatgcg gcgaccgagt tgctcttgcc cggcgtcaat acgggataat
6061 accgcgccac atagcagaac tttaaaagtg ctcatcattg gaaaacgttc ttcggggcga
6121 aaactctcaa ggatcttacc gctgttgaga tccagttcga tgtaacccac tcgtgcaccc
6181 aactgatctt cagcatcttt tactttcacc agcgtttctg ggtgagcaaa aacaggaagg
6241 caaaatgccg caaaaaggg aataagggcg acacggaaat gttgaatact catactcttc
6301 cttttttcaat attattgaag catttatcag ggttattgtc tcatgagcgg atacatattt
6361 gaatgtattt agaaaaataa acaaataggg gttccgcgca catttccccg aaaagtgcca
6421 cctgacgtcg acggatcggg agatctcccg atccccctatg gtgcactctc agtacaatct
6481 gctctgatgc cgcatagtta agccagtatc tgctccctgc ttgtgtgttg gaggtcgctg
6541 agtagtgcgc gagcaaaatt taagctacaa caaggcaagg cttgaccgac aattgcatga
6601 agaatctgct tagggttagg cgttttgcgc tgcttcgcga tgtacgggcc agatatacgc
6661 gttgacattg attattgact agttattaat agtaatcaat tacggggtca ttagttcata
6721 gcccatatat ggagttccgc gttacataac ttacggtaaa tggcccgcct ggctgaccgc
6781 ccaacgaccc ccgcccattg acgtcaataa tgacgtatgt tcccatagta acgccaatag
6841 ggactttcca ttgacgtcaa tgggtggact atttacggta aactgcccac ttggcagtac
6901 atcaagtgta tcatatgcca agtacgcccc ctattgacgt caatgacggt aaatggcccg
6961 cctggcatta tgcccagtac atgaccttat gggactttcc tacttggcag tacatctacg
7021 tattagtcat cgctattacc atggtgatgc ggttttggca gtacatcaat gggcgtggat
7081 agcggtttga ctcacgggga tttccaagtc tccacccat tgacgtcaat gggagtttgt
7141 tttggcacca aaatcaacgg gactttccaa aatgtcgtaa caactccgcc ccattgacgc
7201 aaatgggcgg taggcgtgta cggtgggagg tctatataag cagagctctc tggctaacta
7261 gagaacccac tgcttactgg cttatcgaaa ttaatacgac tcactatagg gagacccaag
7321 ctggtttaaa cttaagcttg gtaccgagct cactagtcca gtgtggtggc agatatccag
7381 cacagtggcg gccgctcgag tctagagggc ccgtttgcc tgtactgggt ctctctggtt
7441 agaccagatc tgagcctggg agctctctgg ctaactaggg aacccactgc ttaagcctca
7501 ataagcttg ccttgagtgc ttcaagtagt gtgtgcccgt ctgttgtgtg actctggtaa
7561 ctagagatcc ctcagaccct tttagtcagt gtggaaaatc tctagcagtg gcgcccgaac
7621 agggacttga aagcgaaagg gaaaccagag gagctctctc gacgcaggac tcggcttgct
7681 gaagcgcgca cggcaagagg cgaggggcgg cgactggtga gtacgccaaa aattttgact
```

FIG. 9D

```
 7741 agcggaggct agaaggagag agatgggtgc gagagcgtca gtattaagcg ggggagaatt
 7801 agatcgcgat gggaaaaaat tcggttaagg ccaggggaa agaaaaaata taaattaaaa
 7861 catatagtat gggcaagcag ggagctagaa cgattcgcag ttaatcctgg cctgttagaa
 7921 acatcagaag gctgtagaca aatactggga cagctacaac catcccttca gacaggatca
 7981 gaagaactta gatcattata taatacagta gcaaccctct attgtgtgca tcaaaggata
 8041 gagataaaag acaccaagga agctttagac aagatagagg aagagcaaaa caaaagtaag
 8101 accaccgcac agcaagcggc cgctgatctt cagacctgga ggaggagata tgagggacaa
 8161 ttggagaagt gaattatata aatataaagt agtaaaaatt gaaccattag gagtagcacc
 8221 caccaaggca aagagaagag tggtgcagag agaaaaaaga gcagtgggaa taggagcttt
 8281 gttccttggg ttcttgggag cagcaggaag cactatgggc gcagcgtcaa tgacgctgac
 8341 ggtacaggcc agacaattat tgtctggtat agtgcagcag cagaacaatt tgctgagggc
 8401 tattgaggcg caacagcatc tgttgcaact cacagtctgg ggcatcaagc agctccaggc
 8461 aagaatcctg gctgtggaaa gatacctaaa ggatcaacag ctcctgggga tttggggttg
 8521 ctctggaaaa ctcatttgca ccactgctgt gccttggaat gctagttgga gtaataaatc
 8581 tctggaacag atttggaatc acacgacctg gatggagtgg gacagagaaa ttaacaatta
 8641 cacaagctta atacactcct taattgaaga atcgcaaaac cagcaagaaa agaatgaaca
 8701 agaattattg gaattagata aatgggcaag tttgtggaat tggtttaaca taacaaattg
 8761 gctgtggtat atagaaatta ttcataatga tagtaggagg cttggtaggt ttaagaatag
 8821 tttttgctgt actttctata gtgaatagag ttaggcaggg atattcacca ttatcgtttc
 8881 agacccacct cccaaccccg aggggacccg acaggcccga aggaatagaa gaagaaggtg
 8941 gagagagaga cagagacaga tccattcgat tagtgaacgg atcggcactg cgtgcgccaa
 9001 ttctgcagac aaatggcagt attcatccac aatttaaaa gaaaggggg gattgggggg
 9061 tacagtgcag gggaagaat agtagacata atagcaacag acatacaaac taaagaatta
 9121 caaaaacaaa ttacaaaaat tcaaaatttt cgggtttatt acagggacag cagagatcca
 9181 gtttggggtt gctctggaaa actcatttgc accactgctg tgccttggaa tgctagttgg
 9241 agtaataaat ctctggaaca gatttggaat cacacgacct ggatggagtg ggacagagaa
 9301 attaacaatt acacaagctt aatacactcc ttaattgaag aatcgcaaaa ccagcaagaa
 9361 aagaatgaac aagaattatt ggaattagat aaatgggcaa gtttgtggaa ttggtttaac
 9421 ataacaaatt ggctgtggta tataaaatta ttcataatga tagtaggagg cttggtaggt
 9481 ttaagaatag tttttgctgt actttctata gtgaatagag ttaggcaggg atattcacca
 9541 ttatcgtttc agacccacct cccaaccccg aggggacccg acaggccctt aattaatccc
 9601 ctgattctgt ggataaccgt attaccgcct tgagtgagc tgcacacctg taggatcgta
 9661 caggtaaagt gaaaggctac aataggacac ctgtaggatc gtacaggtgg taaactcgag
 9721 agcgcccaat aacctgtagg atcgtacagg tagcgcacta gagagcgccc aataacctgt
 9781 aggatcgtac aggtaaagtg aaaggctaca ataggacacc tgtaggatcg tacaggtggt
 9841 aaactcgaga gcgcccaata acctgtagga tcgtacaggt aaagtgaaag gctacaatag
 9901 gacacctgta ggatcgtaca ggtggtaaac tcgacctata taagcagagc tcgtttagtg
 9961 aaccgtcaga tcgcctggag acgccatcca cgctgtttg acctccatag aagacaccgg
10021 gaccgatcca gcctccgcgg ccccgaattg
```

FIG. 9E

| FEATURES | Location/Qualifiers |
|---|---|
| promoter | 8835..10008<br>/vntifkey="29"<br>/label=PEF1-alpha |
| promoter | 6547..7198<br>/vntifkey="29"<br>/label=PCMV |
| promoter | 7201..7220<br>/vntifkey="29"<br>/label=T7\promoter |
| misc_feature | 2345..2558<br>/vntifkey="21"<br>/label=BGH\PolyA |
| rep_origin | 2621..3033<br>/vntifkey="33"<br>/label=f1\ori |
| rep_origin | 3099..3424<br>/vntifkey="33"<br>/label=SV40\ori |
| promoter | 3440..3505<br>/vntifkey="29"<br>/label=EM7 |
| CDS | 3507..3881<br>/vntifkey="4"<br>/label=Zeocin(r) |
| rep_origin | complement(4524..5197)<br>/vntifkey="33"<br>/label=pUC\ori |
| promoter | complement(6203..6300)<br>/vntifkey="29"<br>/label=bla |
| CDS | complement(5342..6202)<br>/vntifkey="4"<br>/label=Amp(r) |
| misc_feature | 1294..1885<br>/vntifkey="21"<br>/label=WPRE |
| misc_feature | 20..604<br>/vntifkey="21"<br>/label=IRES |
| misc_feature | 7233..7335<br>/vntifkey="21"<br>/label=MCS |
| misc_feature | 2085..2319<br>/vntifkey="21"<br>/label=deltaU3-3'LTR |
| misc_feature | 7336..7516 |

FIG. 11A

```
                        /vntifkey="21"
                        /label=5'\LTR
        CDS             608..1285
                        /vntifkey="4"
                        /label=DsRED2
        RBS             602..611
                        /vntifkey="32"
                        /label=Kozak\consensus
        CDS             10043..10279
                        /vntifkey="4"
                        /label=ACPm
        RBS             10036..10046
                        /vntifkey="32"
                        /label=Kozak\consensus
BASE COUNT      2383 a         2649 c         2791 g         2464 t
ORIGIN
SEQ ID NO:04
     1 cggccatcga taaggatccg cccctctccc tccccccccc ctaacgttac tggccgaagc
    61 cgcttggaat aaggccggtg tgcgtttgtc tatatgttat tttccaccat attgccgtct
   121 tttggcaatg tgagggcccg gaaacctggc cctgtcttct tgacgagcat tcctaggggt
   181 ctttcccctc tcgccaaagg aatgcaaggt ctgttgaatg tcgtgaagga agcagttcct
   241 ctggaagctt cttgaagaca acaacgtct gtagcgaccc tttgcaggca gcggaacccc
   301 ccacctggcg acaggtgcct ctgcggccaa aagccacgtg tataagatac acctgcaaag
   361 gcggcacaac cccagtgcca cgttgtgagt tggatagttg tggaaagagt caaatggctc
   421 tcctcaagcg tattcaacaa ggggctgaag gatgcccaga aggtacccca ttgtatggga
   481 tctgatctgg ggcctcggtg cacatgcttt acatgtgttt agtcgaggtt aaaaaaacgt
   541 ctaggccccc cgaaccacgg ggacgtggtt ttcctttgaa aaacacgatg ataatatggc
   601 cacaaccatg gcctcctccg aggacgtcat caaggagttc atgcgcttca aggtgcgcat
   661 ggagggctcc gtgaacggcc acgagttcga gatcgagggc gagggcgagg gccgccccta
   721 cgagggcacc cagaccgcca agctgaaggt gaccaagggc ggccccctgc ccttcgcctg
   781 ggacatcctg tcccccagt tccagtacgg ctccaaggtg tacgtgaagc accccgccga
   841 catccccgac tacaagaagc tgtccttccc cgagggcttc aagtgggagc gcgtgatgaa
   901 cttcgaggac ggcggcgtgg tgaccgtgac ccaggactcc tccctgcagg acggctcctt
   961 catctacaag gtgaagttca tcggcgtgaa cttcccctcc gacggccccg taatgcagaa
  1021 gaagactatg ggctgggagg cctccaccga gcgcctgtac ccccgcgacg gcgtgctgaa
  1081 gggcgagatc cacaaggccc tgaagctgaa ggacggcggc cactacctgg tggagttcaa
  1141 gtccatctac atggccaaga agcccgtgca gctgcccggc tactactacg tggactccaa
  1201 gctggacatc acctcccaca acgaggacta caccatcgtg gagcagtacg agcgcgccga
  1261 gggccgccac caccgttcc tgtaggcggc cgcaatcaac ctctggatta caaaatttgt
  1321 gaaagattga ctggtattct taactatgtt gctcctttta cgctatgtgg atacgctgct
  1381 ttaatgcctt tgtatcatgc tattacttcc cgtacggctt tcattttctc ctccttgtat
  1441 aaatcctggt tgctgtctct ttatgaggag ttgtggcccg ttgtcaggca acgtggcgtg
  1501 gtgtgcactg tgtttgctga cgcaaccccc actggttggg gcattgccac cacctatcaa
  1561 ctcctttccg ggactttcgc tttccccctc cctattgcca cggcggaact cattgccgcc
  1621 tgccttgccc gctgctggac aggggctcgg ctgttgggca ctgacaattc cgtggtgttg
  1681 tcggggaagc tgacgtcctt tccatggctg ctcgcctgtg ttgccaactg gattctgcgc
  1741 gggacgtcct tctgctacgt cccttcggcc ctcaatccag cggaccttcc ttcccgcggc
  1801 ctgctgccgg ttctgcggcc tcttccgcgt cttcgccttc gccctcagac gagtcggatc
  1861 tccctttggg ccgcctcccc gcctgcctgc aggtttgtcg agacctagaa aaacatggag
  1921 caatcacaag tagcaataca gcagctacca atgctgattg tgcctggcta gaagcacaag
  1981 aggaggagga ggtgggtttt ccagtcacac ctcaggtacc tttaagacca atgacttaca
  2041 aggcagctgt agatcttagc cacttttaa aagaaagg gggactggaa gggctaattc
  2101 actcccaacg aagacaagat ctgcttttg cttgtactgg gtctctctgg ttagaccaga
```

```
2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgcccctc ccccgtgcct
2401 tccttgaccc tggaaggtgc cactcccact gtcctttcct aataaaatga ggaaattgca
2461 tcgcattgtc tgagtaggtg tcattctatt ctgggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcggggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt ggggcgggga gttcgccctg cgcgacccgg
3841 ccggcaactg cgtgcacttc gtggccgagg agcaggactg cacgtgctca cgagatttcg
3901 attccaccgc cgccttctat gaaaggttgg ctgagttctt cgcccacccc aacttgttta
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc cctgacgag catcacaaaa
4621 atcgacgctc aagtcagagg tggcgaaacc cgacaggact ataaagatac caggcgtttc
4681 ccctgaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaaccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc
```

FIG. 11C

```
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgcccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactcccgcc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta aaggagaga gatgggtgcg
7681 agagcgtcag tattaagcgg gggagaatta gatcgcgatg ggaaaaaatt cggttaaggc
7741 cagggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctgaacagat ttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata aaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag ggacccgac
8821 aggcccttaa ttaattggct ccggtgcccg tcagtgggca gagcgcacat cgcccacagt
8881 ccccgagaag tggggggag gggtcggcaa ttgaaccggt gcctagagaa ggtggcgcgg
8941 ggtaaactgg gaaagtgatg tcgtgtactg gctccgcctt tttcccgagg gtggggggaga
```

FIG. 11D

```
 9001 accgtatata agtgcagtag tcgccgtgaa cgttctttttt cgcaacgggt ttgccgccag
 9061 aacacaggta agtgccgtgt gtggttcccg cgggcctggc ctctttacgg gttatggccc
 9121 ttgcgtgcct tgaattactt ccacctggct gcagtacgtg attcttgatc ccgagcttcg
 9181 ggttggaagt gggtgggaga gttcgaggcc ttgcgcttaa ggagccccctt cgcctcgtgc
 9241 ttgagttgag gcctggcctg ggcgctgggg ccgccgcgtg cgaatctggt ggccacttcg
 9301 cgcctgtctc gctgctttcg ataagtctct agccatttaa aatttttgat gacctgctgc
 9361 gacgcttttt ttctggcaag atagtcttgt aaatgcgggc caagatctgc acactggtat
 9421 ttcggttttt ggggccgcgg gcggcgacgg ggcccgtgcg tcccagcgca catgttcggc
 9481 gaggcggggc ctgcgagcgc ggccaccgag aatcggacgg gggtagtctc aagctggccg
 9541 gcctgctctg gtgcctggcc tcgcgccgcc gtgtatcgcc ccgccctggg cggcaaggct
 9601 ggcccggtcg gcaccagttg cgtgagcgga aagatggccg cttcccggcc ctgctgcagg
 9661 gagctcaaaa tggaggacgc ggcgctcggg agagcgggcg ggtgagtcac ccacacaaag
 9721 gaaaagggcc tttccgtcct cagccgtcgc ttcatgtgac tccacggagt accgggcgcc
 9781 gtccaggcac ctcgattagt tctcgagctt ttggagtacg tcgtctttag gttgggggga
 9841 ggggttttat gcgatggagt ttccccacac tgagtgggtg gagactgaag ttaggccagc
 9901 ttggcacttg atgtaattct ccttggaatt tgccctttttt gagtttggat cttggttcat
 9961 tctcaagcct cagacagtgg ttcaaagttt ttttcttcca tttcaggtgt cgtgaggaat
10021 tcggccatta cggcccgcca ccatgagcac catcgaggag agggtgaaga agatcatcgg
10081 cgagcagctg ggcgtgaagc aggaggaggt caccaacaac gccagcttcg tggaggacct
10141 gggcgccgac agcctggaca ccgtggagct ggtgatggcc ctggaggagg agttcgacac
10201 cgagatcccc gacgaggagg ccgagaagat caccaccgtg caggccgcca tcgactacat
10261 caacggccac caggcctgag gccgcct
```

FIG. 11E

```
FEATURES           Location/Qualifiers
    misc_feature   7397..7577
                   /vntifkey="21"
                   /label=5'\LTR
    misc_feature   2146..2380
                   /vntifkey="21"
                   /label=deltaU3-3'LTR
    misc_feature   7294..7396
                   /vntifkey="21"
                   /label=MCS
    RBS            620..630
                   /vntifkey="32"
                   /label=Kozak\consensus
    CDS            627..1346
                   /vntifkey="4"
                   /label=EGFP
    misc_feature   39..623
                   /vntifkey="21"
                   /label=IRES
    promoter       8896..10516
                   /vntifkey="29"
                   /label=PEF1-alpha
    misc_feature   1355..1946
                   /vntifkey="21"
                   /label=WPRE
    CDS            complement(5403..6263)
                   /vntifkey="4"
                   /label=Amp(r)
    promoter       complement(6264..6361)
                   /vntifkey="29"
                   /label=bla
    rep_origin     complement(4585..5258)
                   /vntifkey="33"
                   /label=pUC\ori
    CDS            3568..3942
                   /vntifkey="4"
                   /label=Zeocin(r)
    promoter       3501..3566
                   /vntifkey="29"
                   /label=EM7
    rep_origin     3160..3485
                   /vntifkey="33"
                   /label=SV40\ori
    rep_origin     2682..3094
                   /vntifkey="33"
                   /label=f1\ori
```

FIG. 13A

```
       misc_feature    2406..2619
                       /vntifkey="21"
                       /label=BGH\PolyA
       promoter        7262..7281
                       /vntifkey="29"
                       /label=T7\promoter
       promoter        6608..7259
                       /vntifkey="29"
                       /label=PCMV
       CDS             10569..12728
                       /vntifkey="4"
                       /label=AAS
BASE COUNT        2991 a       3207 c       3449 g       3083 t
ORIGIN
SEQ ID NO:05
        1 cgcgccaagc tagcaagtta acaaatcgat ccggatccgc ccctctccct ccccccccc
       61 taacgttact ggccgaagcc gcttggaata aggccggtgt gcgtttgtct atatgttatt
      121 ttccaccata ttgccgtctt ttggcaatgt gagggcccgg aaacctggcc ctgtcttctt
      181 gacgagcatt cctaggggtc tttcccctct cgccaaagga atgcaaggtc tgttgaatgt
      241 cgtgaaggaa gcagttcctc tggaagcttc ttgaagacaa acaacgtctg tagcgaccct
      301 ttgcaggcag cggaaccccc cacctggcga caggtgcctc tgcggccaaa agccacgtgt
      361 ataagataca cctgcaaagg cggcacaacc ccagtgccac gttgtgagtt ggatagttgt
      421 ggaaagagtc aaatggctct cctcaagcgt attcaacaag gggctgaagg atgcccagaa
      481 ggtaccccat tgtatgggat ctgatctggg gcctcggtgc acatgcttta catgtgttta
      541 gtcgaggtta aaaaaacgtc taggccccc gaaccacggg gacgtggttt tcctttgaaa
      601 aacacgatga taatatggcc acaaccatgg tgagcaaggg cgaggagctg ttcaccgggg
      661 tggtgcccat cctggtcgag ctggacggcg acgtaaacgg ccacaagttc agcgtgtccg
      721 gcgagggcga gggcgatgcc acctacggca agctgaccct gaagttcatc tgcaccaccg
      781 gcaagctgcc cgtgccctgg cccaccctcg tgaccaccct gacctacggc gtgcagtgct
      841 tcagccgcta ccccgaccac atgaagcagc acgacttctt caagtccgcc atgcccgaag
      901 gctacgtcca ggagcgcacc atcttcttca aggacgacgg caactacaag acccgcgccg
      961 aggtgaagtt cgagggcgac accctggtga accgcatcga gctgaagggc atcgacttca
     1021 aggaggacgg caacatcctg ggcacaagc tggagtacaa ctacaacagc cacaacgtct
     1081 atatcatggc cgacaagcag aagaacggca tcaaggtgaa cttcaagatc cgccacaaca
     1141 tcgaggacgg cagcgtgcag ctcgccgacc actaccagca gaacaccccc atcggcgacg
     1201 gccccgtgct gctgcccgac aaccactacc tgagcaccca gtccgccctg agcaaagacc
     1261 ccaacgagaa gcgcgatcac atggtcctgc tggagttcgt gaccgccgcc gggatcactc
     1321 tcggcatgga cgagctgtac aagtaagcgg ccgcaatcaa cctctggatt acaaaatttg
     1381 tgaaagattg actggtattc ttaactatgt tgctcctttt acgctatgtg gatacgctgc
     1441 tttaatgcct ttgtatcatg ctattacttc ccgtacggct ttcatttct cctccttgta
     1501 taaatcctgg ttgctgtctc tttatgagga gttgtggccc gttgtcaggc aacgtggcgt
     1561 ggtgtgcact gtgtttgctg acgcaacccc cactggttgg ggcattgcca ccacctatca
     1621 actcctttcc gggactttcg ctttcccccct cctattgcc acggcggaac tcattgccgc
     1681 ctgccttgcc cgctgctgga caggggctcg gctgttgggc actgacaatt ccgtggtgtt
     1741 gtcggggaag ctgacgtcct ttccatgct gctgcctgtc gttgccaact ggattctgcg
     1801 cgggacgtcc ttctgctacg tcccttcggc cctcaatcca gcggaccttc cttcccgcgg
     1861 cctgctgccg gttctgcggc ctcttccgcg tcttcgcctt cgccctcaga cgagtcggat
     1921 ctccctttgg gccgcctccc cgcctgcctg caggtttgtc gagacctaga aaacatgga
     1981 gcaatcacaa gtagcaatac agcagctacc aatgctgatt gtgcctggct agaagcacaa
     2041 gaggaggagg aggtgggttt tccagtcaca cctcaggtac ctttaagacc aatgacttac
     2101 aaggcagctg tagatcttag ccactttta aagaaaagg ggggactgga agggctaatt
     2161 cactcccaac gaagacaaga tctgcttttt gcttgtactg ggtctctctg gttagaccag
     2221 atctgagcct gggagctctc tggctaacta gggaacccac tgcttaagcc tcaataaagc
     2281 ttgccttgag tgcttcaagt agtgtgtgcc cgtctgttgt gtgactctgg taactagaga
```

FIG. 13B

```
2341 tccctcagac ccttttagtc agtgtggaaa atctctagca gggcccgttt aaacccgctg
2401 atcagcctcg actgtgcctt ctagttgcca gccatctgtt gtttgcccct ccccgtgcc
2461 ttccttgacc ctggaaggtg ccactcccac tgtcctttcc taataaaatg aggaaattgc
2521 atcgcattgt ctgagtaggt gtcattctat tctgggggt ggggtggggc aggacagcaa
2581 gggggaggat tgggaagaca atagcaggca tgctggggat gcggtgggct ctatggcttc
2641 tgaggcggaa agaaccagct ggggctctag ggggtatccc cacgcgccct gtagcggcgc
2701 attaagcgcg gcgggtgtgg tggttacgcg cagcgtgacc gctacacttg ccagcgccct
2761 agcgcccgct cctttcgctt tcttcccttc ctttctcgcc acgttcgccg gctttccccg
2821 tcaagctcta aatcggggca tccctttagg gttccgattt agtgctttac ggcacctcga
2881 ccccaaaaaa cttgattagg gtgatggttc acgtagtggg ccatcgccct gatagacggt
2941 ttttcgccct ttgacgttgg agtccacgtt ctttaatagt ggactcttgt tccaaactgg
3001 aacaacactc aaccctatct cggtctattc ttttgattta tagggatttt tggggatttc
3061 ggcctattgg ttaaaaaatg agctgattta acaaaaattt aacgcgaatt aattctgtgg
3121 aatgtgtgtc agttagggtg tggaaagtcc ccaggctccc caggcaggca gaagtatgca
3181 aagcatgcat ctcaattagt cagcaaccag gtgtggaaag tccccaggct ccccagcagg
3241 cagaagtatg caaagcatgc atctcaatta gtcagcaacc atagtcccgc ccctaactcc
3301 gcccatcccg cccctaactc cgcccagttc cgcccattct ccgccccatg gctgactaat
3361 tttttttatt tatgcagagg ccgaggccgc ctctgcctct gagctattcc agaagtagtg
3421 aggaggcttt tttggaggcc taggcttttg caaaaagctc ccgggagctt gtatatccat
3481 ttcggatct gatcagcacg tgttgacaat taatcatcgg catagtatat cggcatagta
3541 taatacgaca aggtgaggaa ctaaaccatg gccaagttga ccagtgccgt tccggtgctc
3601 accgcgcgcg acgtcgccgg agcggtcgag ttctggaccg accggctcgg gttctcccgg
3661 gacttcgtgg aggacgactt cgccggtgtg gtccgggacg acgtgaccct gttcatcagc
3721 gcggtccagg accaggtggt gccggacaac accctggcct gggtgtgggt gcgcggcctg
3781 gacgagctgt acgccgagtg gtcggaggtc gtgtccacga cttccggga cgcctccggg
3841 ccggccatga ccgagatcgg cgagcagccg tggggcggg agttcgccct gcgcgacccg
3901 gccggcaact gcgtgcactt cgtggccgag gagcaggact gacacgtgct acgagatttc
3961 gattccaccg ccgccttcta tgaaaggttg ggcttcggaa tcgttttccg ggacgccggc
4021 tggatgatcc tccagcgcgg ggatctcatg ctggagttct tcgcccaccc caacttgttt
4081 attgcagctt ataatggtta caaataaagc aataacatca caaattcac aaataaagca
4141 tttttttcac tgcattctag ttgtggtttg tccaaactca tcaatgtatc ttatcatgtc
4201 tgtataccgt cgacctctag ctagagcttg gcgtaatcat ggtcatagct gtttcctgtg
4261 tgaaattgtt atccgctcac aattccacac aacatacgag ccggaagcat aaagtgtaaa
4321 gcctggggtg cctaatgagt gagctaactc acattaattg cgttgcgctc actgcccgct
4381 ttccagtcgg gaaacctgtc gtgccagctg cattaatgaa tcggccaacg cgcggggaga
4441 ggcggtttgc gtattgggcg ctcttccgct tcctcgctca ctgactcgct gcgctcggtc
4501 gttcggctgc ggcgagcggt atcagctcac tcaaaggcgg taatacggtt atccacagaa
4561 tcaggggata acgcaggaaa gaacatgtga gcaaaaggcc agcaaaaggc caggaaccgt
4621 aaaaaggccg cgttgctggc gtttttccat aggctccgcc cccctgacga gcatcacaaa
4681 aatcgacgct caagtcagag gtggcgaaac ccgacagac tataaagata ccaggcgttt
4741 cccccctggaa gctccctcgt gcgctctcct gttccgaccc tgccgcttac cggatacctg
4801 tccgcctttc tcccttcggg aagcgtggcg ctttctcaat gctcacgctg taggtatctc
4861 agttcggtgt aggtcgttcg ctccaagctg ggctgtgtgc acgaaccccc cgttcagccc
4921 gaccgctgcg ccttatccgg taactatcgt cttgagtcca acccggtaag acacgactta
4981 tcgccactgg cagcagccac tggtaacagg attagcagag cgaggtatgt aggcggtgct
5041 acagagttct tgaagtggtg gcctaactac ggctacacta aaggacagt atttggtatc
5101 tgcgctctgc tgaagccagt taccttcgga aaaagagttg gtagctcttg atccggcaaa
5161 caaaccaccg ctggtagcgg tggtttttt gtttgcaagc agcagattac gcgcagaaaa
5221 aaaggatctc aagaagatcc tttgatcttt tctacgggt ctgacgctca gtggaacgaa
5281 aactcacgtt aagggatttt ggtcatgaga ttatcaaaaa ggatcttcac ctagatcctt
5341 ttaaattaaa aatgaagttt taaatcaatc taaagtatat atgagtaaac ttggtctgac
5401 agttaccaat gcttaatcag tgaggcacct atctcagcga tctgtctatt tcgttcatcc
5461 atagttgcct gactccccgt cgtgtagata actacgatac gggagggctt accatctggc
5521 cccagtgctg caatgatacc gcgagaccca cgctcaacgg ctccagattt atcagcaata
5581 aaccagccag ccggaagggc cgagcgcaga agtggtcctg caactttatc cgcctccatc
5641 cagtctatta attgttgccg ggaagctaga gtaagtagtt cgccagttaa tagtttgcgc
5701 aacgttgttg ccattgctac aggcatcgtg gtgtcacgct cgtcgtttgg tatggcttca
```

FIG. 13C

```
5761 ttcagctccg gttcccaacg atcaaggcga gttacatgat cccccatgtt gtgcaaaaaa
5821 gcggttagct ccttcggtcc tccgatcgtt gtcagaagta agttggccgc agtgttatca
5881 ctcatggtta tggcagcact gcataattct cttactgtca tgccatccgt aagatgcttt
5941 tctgtgactg gtgagtactc aaccaagtca ttctgagaat agtgtatgcg gcgaccgagt
6001 tgctcttgcc cggcgtcaat acgggataat accgcgccac atagcagaac tttaaaagtg
6061 ctcatcattg gaaaacgttc tcggggcga aaactctcaa ggatcttacc gctgttgaga
6121 tccagttcga tgtaacccac tcgtgcaccc aactgatctt cagcatcttt tactttcacc
6181 agcgttctg ggtgagcaaa aacaggaagg caaaatgccg caaaaaggg aataagggcg
6241 acacggaaat gttgaatact catactcttc cttttcaat attattgaag catttatcag
6301 ggttattgtc tcatgagcgg atacatattt gaatgtattt agaaaaataa acaaataggg
6361 gttccgcgca catttccccg aaaagtgcca cctgacgtcg acggatcggg agatctcccg
6421 atcccctatg gtgcactctc agtacaatct gctctgatgc cgcatagtta agcagtatc
6481 tgctccctgc ttgtgtgttg gaggtcgctg agtagtgcgc gagcaaaatt taagctacaa
6541 caaggcaagg cttgaccgac aattgcatga agaatctgct tagggttagg cgttttgcgc
6601 tgcttcgcga tgtacgggcc agatatacgc gttgacattg attattgact agttattaat
6661 agtaatcaat tacggggtca ttagttcata gcccatatat ggagttccgc gttacataac
6721 ttacggtaaa tggcccgcct ggctgaccgc ccaacgaccc ccgcccattg acgtcaataa
6781 tgacgtatgt tcccatagta acgccaatag ggactttcca ttgacgtcaa tgggtggact
6841 atttacggta aactgcccac ttggcagtac atcaagtgta tcatatgcca agtacgcccc
6901 ctattgacgt caatgacggt aaatggcccg cctggcatta tgcccagtac atgaccttat
6961 gggactttcc tacttggcag tacatctacg tattagtcat cgctattacc atggtgatgc
7021 ggttttggca gtacatcaat gggcgtggat agcggtttga ctcacgggga tttccaagtc
7081 tccaccccat tgacgtcaat gggagtttgt tttggcacca aaatcaacgg gactttccaa
7141 aatgtcgtaa caactccgcc ccattgacgc aaatgggcgg taggcgtgta cggtgggagg
7201 tctatataag cagagctctc tggctaacta gagaacccac tgcttactgg cttatcgaaa
7261 ttaatacgac tcactatagg gagacccaag ctggtttaaa cttaagcttg gtaccgagct
7321 cactagtcca gtgtggtggc agatatccag cacagtggcg gccgctcgag tctagagggc
7381 ccgttttgcc tgtactgggt ctctctggtt agaccagatc tgagcctggg agctctctgg
7441 ctaactaggg aacccactgc ttaagcctca ataaagcttg ccttgagtgc ttcaagtagt
7501 gtgtgcccgt ctgttgtgtg actctggtaa ctagagatcc ctcagaccct tttagtcagt
7561 gtggaaaatc tctagcagtg gcgcccgaac agggacttga aagcgaaagg gaaaccagag
7621 gagctctctc gacgcaggac tcggcttgct gaagcgcgca cggcaagagg cgaggggcgg
7681 cgactggtga gtacgccaaa aattttgact agcggaggct agaaggagag agatgggtgc
7741 gagagcgtca gtattaagcg ggggagaatt agatcgcgat gggaaaaaat tcggttaagg
7801 ccagggggaa agaaaaaata taattaaaa catatagtat gggcaagcag ggagctagaa
7861 cgattcgcag ttaatcctgg cctgttagaa acatcagaag gctgtagaca atactggga
7921 cagctacaac catcccttca gacaggatca gaagaactta gatcattata taatacagta
7981 gcaaccctct attgtgtgca tcaaggata gagataaaag acaccaagga agctttagac
8041 aagatagagg aagagcaaaa caaaagtaag accaccgcac agcaagcggc cgctgatctt
8101 cagacctgga ggaggagata tgagggacaa ttggagaagt gaattatata aatataaagt
8161 agtaaaaatt gaaccattag gagtagcacc caccaaggca aagagaagag tggtgcagag
8221 agaaaaaaga gcagtgggaa taggagcttt gttccttggg ttcttgggag cagcaggaag
8281 cactatgggc gcagcgtcaa tgacgctgac ggtacaggcc agacaattat tgtctggtat
8341 agtgcagcag cagaacaatt gctgagggc tattgaggcg caacagcatc tgttgcaact
8401 cacagtctgg ggcatcaagc agctccaggc aagaatcctg gctgtggaaa gatacctaaa
8461 ggatcaacag ctcctgggga tttggggttg ctctggaaaa ctcatttgca ccactgctgt
8521 gccttggaat gctagttgga gtaataaatc tctggaacag atttggaatc acacgacctg
8581 gatggagtgg gacagagaaa ttaacaatta cacaagctta atacactcct taattgaaga
8641 atcgcaaaac cagcaagaaa agaatgaaca agaattattg gaattagata aatgggcaag
8701 tttgtggaat tggtttaaca taacaaattg gctgtggtat ataaaattat tcataatgat
8761 agtaggaggc ttggtaggtt taagaatagt ttttgctgta ctttctatag tgaatagagt
8821 taggcaggga tattcaccat tatcgtttca gacccacctc ccaaccccga ggggacccga
8881 caggccctta attaagctac atcatcaata atataccta ttttggattg aagccaatat
8941 gataatgagg gggtggagtt tgtgacgtgg cgcggggcgt gggaacgggg cgggtgacgt
9001 agtagtgtgg cggaagtgtg atgttgcaag tgtggcggaa cacatgtaag cgacggatgt
9061 ggcaaaagtg acgtttttgg tgtgcgccgg tgtacacagg aagtgacaat tttcgcgcgg
9121 ttttaggcgg atgttgtagt aaatttgggc gtaaccgagt aagatttggc cattttcgcg
```

FIG. 13D

```
 9181 ggaaaactga ataagaggaa gtgaaatctg aataattttg tgttactcat agcgcgtaat
 9241 atttgtctag ggagatccga gctttgcaaa gatggataaa gttttaaaca gagaggaatc
 9301 tttgcagcta atggaccttc taggtcttga aaggagtggg aattggctcc ggtgcccgtc
 9361 agtgggcaga gcgcacatcg cccacagtcc ccgagaagtt gggggagggg gtcggcaatt
 9421 gaaccggtgc ctagagaagg tggcgcgggg taaactggga aagtgatgtc gtgtactggc
 9481 tccgcctttt tcccgagggt gggggagaac cgtatataag tgcagtagtc gccgtgaacg
 9541 ttcttttcg caacgggttt gccgccagaa cacaggtaag tgccgtgtgt ggttcccgcg
 9601 ggcctggcct ctttacgggt tatggccctt gcgtgccttg aattacttcc acctggctgc
 9661 agtacgtgat tcttgatccc gagcttcggg ttggaagtgg gtgggagagt tcgaggcctt
 9721 gcgcttaagg agcccttcg cctcgtgctt gagttgaggc ctggcctggg cgctggggcc
 9781 gccgcgtgcg aatctggtgg caccttcgcg cctgtctcgc tgctttcgat aagtctctag
 9841 ccatttaaaa tttttgatga cctgctgcga cgcttttttt ctggcaagat agtcttgtaa
 9901 atgcgggcca agatctgcac actggtattt cggttttgg ggccgcgggc ggcgacgggg
 9961 cccgtgcgtc ccagcgcaca tgttcggcga ggcggggcct gcgagcgcgg ccaccgagaa
10021 tcggacgggg gtagtctcaa gctggccggc ctgctctggt gcctggcctc gcgccgccgt
10081 gtatcgcccc gccctgggcg gcaaggctgg cccggtcggc accagttgcg tgagcggaaa
10141 gatggccgct tcccggccct gctgcaggga gctcaaaatg gaggacgcgg cgctcgggag
10201 agcgggcggg tgagtcaccc acacaaagga aaagggcctt tccgtcctca gccgtcgctt
10261 catgtgactc cacggagtac cgggcgccgt ccaggcacct cgattagttc tcgagctttt
10321 ggagtacgtc gtctttaggt tgggggagg ggtttatgc gatggagttt ccccacactg
10381 agtgggtgga gactgaagtt aggccagctt ggcacttgat gtaattctcc ttggaatttg
10441 cccttttga gtttggatct tggttcattc tcaagcctca gacagtggtt caaagttttt
10501 ttcttccatt tcaggtgtcg tgaggaattc gctactagct cgagaagaat tcaaggcgcg
10561 ccgccaccat gcttttagc tttttcgaa atttgtgccg tgttttgtat cgcgttcgcg
10621 ttacgggtga cacccaggca ctgaagggcg agcgcgttct aattacgcct aatcacgtct
10681 cttttattga tggcattttg cttggactgt ttttacctgt gcgtccagtg tttgccgttt
10741 acacctcaat aagccaacag tggtatatgc gttggctgaa atcatttatc gactttgttc
10801 ctctcgaccc gacgcaacct atggctatta aacatctggt acgtctggtg aacagggcc
10861 gaccagtggt gatttttcct gaaggacgca tcaccacgac aggctcgctg atgaaaatct
10921 acgatggcgc gggttttgtc gcggcgaagt ctggtgcaac ggttattcct gtgcgtattg
10981 aaggggcgga acttacgcac ttcagccgcc tgaaaggtct ggttaaacgt cgcttgttcc
11041 cgcaaattac tctgcatatt ttgccaccaa cgcaggtggc gatgccggat gcgccgcgtg
11101 cccgtgaccg tcgcaaaatc gctggcgaaa tgctgcatca aataatgatg gaagcgcgaa
11161 tggcggtgcg cccgcgtgaa acgctgtacg aatctttact gagtgcaatg taccgcttcg
11221 gagccgggaa gaaatgtgtc gaagacgtca actttacccc agactcctat cgcaaattgc
11281 ttacgaaaac gctgtttgtt ggacgcatcc ttgaaaaata cagtgttgaa ggcgaacgca
11341 tcggcttaat gctgcccaat gcaggcatca gtgcggcagt gattttggg gccatcgccc
11401 gtcgccgcat gcccgcaatg atgaactaca ctgccggggt aaaagggctg accagtgcta
11461 ttacggcggc tgaaatcaaa accatcttca cttcccgcca gtttctcgat aaaggcaaac
11521 tctggcatct gccggagcaa cttactcagg tgcgctgggt ctatctggaa gatttaaaag
11581 cagatgtcac cactgccgac aaagtatgga tcttcgctca tttgctgatg ccgcgtctgg
11641 cacaggttaa acagcagccg gaagaagagg cgctgatcct ttttaccctcc ggttctgaag
11701 gccatccgaa aggcgtcgtc catagccata aaagcattct ggcgaatgtc gagcagatta
11761 aaacgattgc cgacttcacc accaacgatc gctttatgtc ggcgttaccg ctgtttcact
11821 cctttgggct gacggtaggc ctgttacgc cactgcttac aggtgcagaa gtgttcctttt
11881 atccaagccc gctgcattac cgcattgtgc cggagttggt gtatgaccgc agttgcaccg
11941 tgttgttcgg cacctcgact ttcctcggtc actacgcgcg tttcgccaac ccgtatgact
12001 tctatcgtct acgctatgtg gtggcaggcg cagaaaaatt acaagaaagt accaaacagc
12061 tttggcagga taaatttggc ctgcgcatcc ttgaaggcta cggcgtgacc gaatgcgcgc
12121 ctgtcgtttc tatcaacgta ccgatggcgg cgaaaccgg tacgtaggg cgtattctac
12181 caggaatgga tgcgcgcctg ttgtcggtcc ctggtatcga agagggcgga cgcctgcaac
12241 tgaaagggcc gaacataatg aacggctatc tgcgggtgga gaagccaggt gtactggaag
12301 tgcccaccgc cgagaatgtt cgcggcgaaa tggagcgcgg ctggtatgac actggcgata
12361 ttgtgcgttt tgacgagcag ggcttgtgc agattcaggg ccgcgcaaaa cgctttgcca
12421 aaattgcagg cgaaatggtg tcgctggaaa tggtggaaca actggcactt ggtgtttcgc
12481 cagataaagt ccatgccact gcgattaaga gcgatgccag caaaggcgag gcactggtgc
12541 ttttcaccac agataacgaa ctgacgcgcg ataagttgca acagtatgcc cgcgagcacg
```

FIG. 13E

```
12601 gcgtgccgga gcttgctgta ccgcgcgata ttcgctatct gaaacagatg ccattacttg
12661 gcagcggcaa acctgacttt gtcacgttga aaagctgggt agacgaagcg gaacaacacg
12721 atgagtgagg
```

FIG. 13F

| | |
|---|---|
| FEATURES | Location/Qualifiers |
| promoter | 8835..9884 |
| | /vntifkey="29" |
| | /label=alpha-fetoprotein-promoter |
| RBS | 602..611 |
| | /vntifkey="32" |
| | /label=Kozak\consensus |
| CDS | 608..1285 |
| | /vntifkey="4" |
| | /label=DsRED2 |
| misc_feature | 7336..7516 |
| | /vntifkey="21" |
| | /label=5'\LTR |
| misc_feature | 2085..2319 |
| | /vntifkey="21" |
| | /label=deltaU3-3'LTR |
| misc_feature | 7233..7335 |
| | /vntifkey="21" |
| | /label=MCS |
| misc_feature | 20..604 |
| | /vntifkey="21" |
| | /label=IRES |
| misc_feature | 1294..1885 |
| | /vntifkey="21" |
| | /label=WPRE |
| CDS | complement(5342..6202) |
| | /vntifkey="4" |
| | /label=Amp(r) |
| promoter | complement(6203..6300) |
| | /vntifkey="29" |
| | /label=bla |
| rep_origin | complement(4524..5197) |
| | /vntifkey="33" |
| | /label=pUC\ori |
| CDS | 3507..3881 |
| | /vntifkey="4" |
| | /label=Zeocin(r) |
| promoter | 3440..3505 |
| | /vntifkey="29" |
| | /label=EM7 |
| rep_origin | 3099..3424 |
| | /vntifkey="33" |
| | /label=SV40\ori |
| rep_origin | 2621..3033 |
| | /vntifkey="33" |
| | /label=f1\ori |
| misc_feature | 2345..2558 |

FIG. 15A

```
                         /vntifkey="21"
                         /label=BGH\PolyA
    promoter          7201..7220
                         /vntifkey="29"
                         /label=T7\promoter
    promoter          6547..7198
                         /vntifkey="29"
                         /label=PCMV
    CDS               9911..10765
                         /vntifkey="4"
                         /label=Pdx1
BASE COUNT        2660 a      2758 c       2769 g        2586 t
ORIGIN
SEQ ID NO:06
    1 cggccatcga taaggatccg cccctctccc tccccccccc ctaacgttac tggccgaagc
   61 cgcttggaat aaggccggtg tgcgtttgtc tatatgttat tttccaccat attgccgtct
  121 tttggcaatg tgagggcccg gaaacctggc cctgtcttct tgacgagcat tcctaggggt
  181 ctttcccctc tcgccaaagg aatgcaaggt ctgttgaatg tcgtgaagga agcagttcct
  241 ctggaagctt cttgaagaca aacaacgtct gtagcgaccc tttgcaggca gcggaacccc
  301 ccacctggcg acaggtgcct ctgcggccaa aagccacgtg tataagatac acctgcaaag
  361 gcggcacaac cccagtgcca cgttgtgagt tggatagttg tggaaagagt caaatggctc
  421 tcctcaagcg tattcaacaa ggggctgaag gatgcccaga aggtacccca ttgtatggga
  481 tctgatctgg ggcctcggtg cacatgcttt acatgtgttt agtcgaggtt aaaaaaacgt
  541 ctaggccccc cgaaccacgg ggacgtggtt ttcctttgaa aaacacgatg ataatatggc
  601 cacaaccatg gcctcctccg aggacgtcat caaggagttc atgcgcttca aggtgcgcat
  661 ggagggctcc gtgaacggcc acgagttcga gatcgagggc gagggcgagg gccgccccta
  721 cgagggcacc cagaccgcca agctgaaggt gaccaagggc ggccccctgc ccttcgcctg
  781 ggacatcctg tcccccccagt tccagtacgg ctccaaggtg tacgtgaagc accccgccga
  841 catccccgac tacaagaagc tgtccttccc cgagggcttc aagtgggagc gcgtgatgaa
  901 cttcgaggac ggcggcgtgg tgaccgtgac ccaggactcc tccctgcagg acggctcctt
  961 catctacaag gtgaagttca tcggcgtgaa cttcccctcc gacggccccg taatgcagaa
 1021 gaagactatg ggctgggagg cctccaccga gcgcctgtac ccccgcgacg gcgtgctgaa
 1081 gggcgagatc cacaaggccc tgaagctgaa ggacggcggc cactacctgg tggagttcaa
 1141 gtccatctac atggccaaga agcccgtgca gctgcccggc tactactacg tggactccaa
 1201 gctggacatc acctcccaca acgaggacta caccatcgtg gagcagtacg agcgcgccga
 1261 gggccgccac cacctgttcc tgtaggcggc cgcaatcaac ctctggatta caaaatttgt
 1321 gaaagattga ctggtattct taactatgtt gctccttta cgctatgtgg atacgctgct
 1381 ttaatgcctt tgtatcatgc tattacttcc cgtacggctt tcattttctc ctccttgtat
 1441 aaatcctggt tgctgtctct ttatgaggag ttgtggcccg ttgtcaggca acgtggcgtg
 1501 gtgtgcactg tgtttgctga cgcaacccc actggttggg gcattgccac cacctatcaa
 1561 ctcctttccg gactttcgc tttccccctc cctattgcca cggcggaact cattgccgcc
 1621 tgccttgccc gctgctggac aggggctcgg ctgttgggca ctgacaattc cgtggtgttg
 1681 tcggggaagc tgacgtcctt tccatggctg ctcgcctgtg ttgccaactg gattctgcgc
 1741 gggacgtcct tctgctacgt cccttcggcc ctcaatccag cggaccttcc ttcccgcggc
 1801 ctgctgccgg ttctgcggcc tcttccgcgt cttcgccttc gccctcagac gagtcggatc
 1861 tccctttggg ccgcctcccc gcctgctgc aggtttgtcg agacctagaa aaacatggag
 1921 caatcacaag tagcaataca gcagctacca atgctgattg tgcctggcta gaagcacaag
 1981 aggaggagga ggtgggtttt ccagtcacac ctcaggtacc tttaagacca atgacttaca
 2041 aggcagctgt agatcttagc cacttttaa agaaaaggg gggactggaa gggctaattc
 2101 actcccaacg aagacaagat ctgcttttg cttgtactgg gtctctctgg ttagaccaga
 2161 tctgagcctg ggagctctct ggctaactag ggaacccact gcttaagcct caataaagct
 2221 tgccttgagt gcttcaagta gtgtgtgccc gtctgttgtg tgactctggt aactagagat
 2281 ccctcagacc cttttagtca gtgtggaaaa tctctagcag ggcccgttta acccgctga
 2341 tcagcctcga ctgtgccttc tagttgccag ccatctgttg tttgcccctc ccccgtgcct
```

FIG. 15B

```
2401 tccttgaccc tggaaggtgc cactcccact gtcctttcct aataaaatga ggaaattgca
2461 tcgcattgtc tgagtaggtg tcattctatt ctgggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcggggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca acctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt ggggcgggaa gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata agtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg ttttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaacccccc gttcagcccg
4861 accgctgcgc cttatccggt aactatcgtc ttgagtccaa cccggtaaga cgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacgggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa tacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
```

FIG. 15C

```
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct tcggggcgaa aactctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga ataagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tccccatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat tccaagtct
7021 ccacccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagacccct ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta aaggagaga gatgggtgcg
7681 agagcgtcag tattaagcgg gggagaatta gatcgcgatg ggaaaaaatt cggttaaggc
7741 caggggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag ataccctaaag
8401 gatcaacagc tcctggggat ttggggttgc tctggaaaac tcatttgcac cactgctgtg
8461 ccttggaatg ctagttggag taataaatct ctgaacagat ttggaatca cgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaagccacc tatcctcttc agacctcttc aggaaacagc tatgcacata
8881 gcacacaggc atatgttcaa ccaaaacact gaaacacata aagaaatgt ttaaagaatg
8941 aatttaaaaa aataaaaat aaactcaact acatatgaag ccttagcaaa catgtctgga
9001 cctctagaca cacagactct gacacgccaa cgtctgagtt ctagtttcga tacgcactgg
9061 gaagttttaa aagttttcca tcaactctaa tgtgtagaga aatgaaact atcatagact
9121 ctacggcatt gagggtgaag gtatgagtga agcactctta gggtcagaag tatgtcagtg
9181 cccatttgtt gctgttagca tcatcatctt agggcttgag aggatgttgc agctgaccca
```

FIG. 15D

```
 9241 tgcacctgtg acatacatat ggaattattc tttggcacat aaaattagaa tgggagctgg
 9301 ctcatcaggt tttgtgctgt aagttttcta tgttaaacca gatgcgatac actaaataaa
 9361 ataaaatata cttgaccgat ggttttgagc gaaataataa ctggataatc aagaaatata
 9421 tccactaatg aatagcctga actactgaaa caatttgttc agtgcctagc atatggtgtg
 9481 cattttatta tttctttcaa aaagaatgta tttggagtta catagtaagt ctgctacctt
 9541 ttctttatgg ctatatctat gtcttatgtt gagatgaatg aattattctt caggggaaat
 9601 aatctatttg aacagtttag atggtgaaga acatttgcag catttgcaag attttttttcc
 9661 actctgaagt ggtctttgtc cttgaacata ggatacaagt gacccctgct ctgttaatta
 9721 ttggcaaatt gcctaacttc aacgtaagga aatagagtca tatgtttgct cactgaaggt
 9781 tactagttaa caggcatccc ttaaacagga tataaaagga cttcagcagg actgctcgaa
 9841 acatcccact tccagcactg cctgcggtga aggaaccagc agccgaattc ggccattacg
 9901 gcctgccacc atgaacagtg aggagcagta ctacgcggcc acacagctct acaaggaccc
 9961 gtgcgcattc cagaggggcc cggtgccaga gttcagcgct aacccccctg cgtgcctgta
10021 catgggccgc cagcccccac ctccgccgcc accccagttt acaagctcgc tgggatcact
10081 ggagcaggga agtcctccgg acatctcccc atacgaagtg cccccgctcg cctccgacga
10141 cccggctggc gctcacctcc accaccacct tccagctcag ctcgggctcg cccatccacc
10201 tcccggacct ttcccgaatg gaaccgagcc tgggggcctg gaagagccca accgcgtcca
10261 gctcccttc ccgtggatga aatccaccaa agctcacgcg tggaaaggcc agtgggcagg
10321 aggtgcttac acagcggaac ccgaggaaaa caagaggacc cgtactgcct cacccgggc
10381 gcagctgctg gagctggaga aggaattctt atttaacaaa tacatctccc ggccccgccg
10441 ggtggagctg gcagtgatgt tgaacttgac cgagagacac atcaaaatct ggttccaaaa
10501 ccgtcgcatg aagtgaaaaa aagaggaaga taagaaacgt agtagcggga ccccgagtgg
10561 gggcggtggg ggcgaagagc cggagcaaga ttgtgcggtg acctcgggcg aggagctgct
10621 ggcagtgcca ccgctgccac ctcccggagg tgccgtgccc ccaggcgtcc cagctgcagt
10681 ccgggagggc ctactgcctt cgggccttag cgtgtcgcca cagccctcca gcatcgcgcc
10741 actgcgaccg caggaacccc ggtgaggccg cct
```

FIG. 15E

```
FEATURES         Location/Qualifiers
    promoter     8835..9884
                 /vntifkey="29"
                 /label=alpha-fetoprotein-promoter
    RBS          602..611
                 /vntifkey="32"
                 /label=Kozak\consensus
    CDS          608..1285
                 /vntifkey="4"
                 /label=DsRED2
    misc_feature 7336..7516
                 /vntifkey="21"
                 /label=5'\LTR
    misc_feature 2085..2319
                 /vntifkey="21"
                 /label=deltaU3-3'LTR
    misc_feature 7233..7335
                 /vntifkey="21"
                 /label=MCS
    misc_feature 20..604
                 /vntifkey="21"
                 /label=IRES
    misc_feature 1294..1885
                 /vntifkey="21"
                 /label=WPRE
    CDS          complement(5342..6202)
                 /vntifkey="4"
                 /label=Amp(r)
    promoter     complement(6203..6300)
                 /vntifkey="29"
                 /label=bla
    rep_origin   complement(4524..5197)
                 /vntifkey="33"
                 /label=pUC\ori
    CDS          3507..3881
                 /vntifkey="4"
                 /label=Zeocin(r)
    promoter     3440..3505
                 /vntifkey="29"
                 /label=EM7
    rep_origin   3099..3424
                 /vntifkey="33"
                 /label=SV40\ori
    rep_origin   2621..3033
                 /vntifkey="33"
                 /label=f1\ori
    misc_feature 2345..2558
```

FIG. 17A

```
                        /vntifkey="21"
                        /label=BGH\PolyA
    promoter            7201..7220
                        /vntifkey="29"
                        /label=T7\promoter
    promoter            6547..7198
                        /vntifkey="29"
                        /label=PCMV
    RBS                 9903..9913
                        /vntifkey="32"
                        /label=Kozak\consensus
    CDS                 9910..10554
                        /vntifkey="4"
                        /label=NEUROG3
    misc_difference     10505..10505
                        /gene="NEUROG3"
                        /vntifkey="85"
                        /label=NEUROG3
                        /note="'C' in cDNA is 'T' in the human
genome; amino acid difference: 'S' in cDNA, 'F' in the human
genome. The chimpanzee genome agrees with the cDNA sequence,
suggesting that this difference is unlikely to be due to an
artifact."
BASE COUNT       2594 a        2699 c        2725 g        2544 t
ORIGIN
SEQ ID NO:07
    1 cggccatcga taaggatccg ccctctccc tccccccc ctaacgttac tggccgaagc
   61 cgcttggaat aaggccggtg tgcgtttgtc tatatgttat tttccaccat attgccgtct
  121 tttggcaatg tgagggcccg gaaacctggc cctgtcttct tgacgagcat tcctagggqt
  181 ctttcccctc tcgccaaagg aatgcaaggt ctgttgaatg tcgtgaagga agcagttcct
  241 ctggaagctt cttgaagaca aacaacgtct gtagcgaccc tttgcaggca gcggaacccc
  301 ccacctggcg acaggtgcct ctgcggccaa aagccacgtg tataagatac acctgcaaag
  361 gcggcacaac cccagtgcca cgttgtgagt tggatagttg tggaaagagt caaatggctc
  421 tcctcaagcg tattcaacaa ggggctgaag gatgcccaga aggtacccca ttgtatggga
  481 tctgatctgg ggcctcggtg cacatgcttt acatgtgttt agtcgaggtt aaaaaaacgt
  541 ctaggccccc cgaaccacgg ggacgtggtt ttcctttgaa aaacacgatg ataatatggc
  601 cacaaccatg gcctcctccg aggacgtcat caaggagttc atgcgcttca aggtgcgcat
  661 ggagggctcc gtgaacggcc acgagttcga gatcgagggc gagggcgagg gccgccccta
  721 cgagggcacc cagaccgcca agctgaaggt gaccaagggc ggccccctgc ccttcgcctg
  781 ggacatcctg tccccccagt tccagtacgg ctccaaggtg tacgtgaagc accccgccga
  841 catccccgac tacaagaagc tgtccttccc cgagggcttc aagtgggagc gcgtgatgaa
  901 cttcgaggac ggcggcgtgg tgaccgtgac ccaggactcc tccctgcagg acggctcctt
  961 catctacaag gtgaagttca tcggcgtgaa cttcccctcc gacggccccg taatgcagaa
 1021 gaagactatg ggctgggagg cctccaccga gcgcctgtac ccccgcacg gcgtgctgaa
 1081 ggcgagatc cacaaggccc tgaagctgaa ggacggcggc cactacctgg tggagttcaa
 1141 gtccatctac atggccaaga agcccgtgca gctgcccggc tactactacg tggactccaa
 1201 gctggacatc acctcccaca acgaggacta caccatcgtg gagcagtacg agcgcgccga
 1261 gggccgccac caccctgttcc tgtaggcggc cgcaatcaac ctctggatta caaaatttgt
 1321 gaaagattga ctggtattct taactatgtt gctccttta cgctatgtgg atacgctgct
 1381 ttaatgcctt tgtatcatgc tattacttcc cgtacggctt tcatttctc ctccttgtat
 1441 aaatcctggt tgctgtctct ttatgaggag ttgtggcccg ttgtcaggca acgtggcgtg
 1501 gtgtgcactg tgtttgctga cgcaacccc actggttggg gcattgccac cacctatcaa

FIG. 17B
```

```
1561 ctcctttccg ggactttcgc tttccccctc cctattgcca cggcggaact cattgccgcc
1621 tgccttgccc gctgctggac aggggctcgg ctgttgggca ctgacaattc cgtggtgttg
1681 tcggggaagc tgacgtcctt tccatggctg ctcgcctgtg ttgccaactg gattctgcgc
1741 gggacgtcct tctgctacgt cccttcggcc ctcaatccag cggaccttcc ttcccgcggc
1801 ctgctgccgg ttctgcggcc tcttccgcgt cttcgccttc gccctcagac gagtcggatc
1861 tccctttggg ccgcctcccc gcctgcctgc aggtttgtcg agacctagaa aaacatggag
1921 caatcacaag tagcaataca gcagctacca atgctgattg tgcctggcta gaagcacaag
1981 aggaggagga ggtgggtttt ccagtcacac ctcaggtacc tttaagacca atgacttaca
2041 aggcagctgt agatcttagc cacttttaa aagaaaaggg gggactggaa gggctaattc
2101 actcccaacg aagacaagat ctgcttttg cttgtactgg gtctctctgg ttagaccaga
2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgcccctc cccgtgcct
2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctgggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcggggcat cccttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg actcttgtt ccaaactgga
2941 acaacactca accctatctc ggtctattct tttgatttat aagggatttt ggggatttcg
3001 gcctattggt taaaaatga gctgatttaa caaaattta acgcgaatta attctgtgga
3061 atgtgtgtca gttagggtgt ggaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttcgggac gcctccgggc
3781 cggccatgac cgagatcggc gagcagccgt ggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata agtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcgggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg tttttccata ggctccgccc ccctgacgag catcacaaaa
4621 atcgacgctc aagtcagagg tggcgaaacc cgacaggact ataaagatac caggcgtttc
4681 ccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaaccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
```

FIG. 17C

```
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact tggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
5461 ccagtgctgc aatgatacccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact taaaagtgc
6001 tcatcattgg aaaacgttct cggggcgaaa actctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga taagggcga
6181 cacggaaatg ttgaatactc atactcttcc ttttttcaata ttattgaagc atttatcagg
6241 gttattgtct catgagcgga tacatatttg aatgtattta gaaaaataaa caaataggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccaccccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta aaggagaga gatgggtgcg
7681 agagcgtcag tattaagcgg gggagaatta gatcgcgatg ggaaaaaatt cggttaaggc
7741 caggggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
```

FIG. 17D

```
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caacccgag gggacccgac
8821 aggcccttaa ttaagccacc tatcctcttc agacctcttc aggaaacagc tatgcacata
8881 gcacacaggc atatgttcaa ccaaaacact gaaacacata aaagaaatgt ttaaagaatg
8941 aatttaaaaa aataaaaaat aaactcaact acatatgaag ccttagcaaa catgtctgga
9001 cctctagaca cacagactct gacacgccaa cgtctgagtt ctagtttcga tacgcactgg
9061 gaagttttaa aagttttcca tcaactctaa tgtgtagaga aatggaaact atcatagact
9121 ctacggcatt gagggtgaag gtatgagtga agcactctta gggtcagaag tatgtcagtg
9181 cccatttgtt gctgttagca tcatcatctt agggcttgag aggatgttgc agctgaccca
9241 tgcacctgtg acatacatat ggaattattc tttggcacat aaaattagaa tgggagctgg
9301 ctcatcaggt tttgtgctgt aagtttttcta tgttaaacca gatgcgatac actaaataaa
9361 ataaaatata cttgaccgat ggtttgagc gaaataataa ctggataatc aagaaatata
9421 tccactaatg aatagcctga actactgaaa caatttgttc agtgcctagc atatggtgtg
9481 catttatta tttctttcaa aaagaatgta tttggagtta catagtaagt ctgctacctt
9541 ttctttatgg ctatatctat gtcttatgtt gagatgaatg aattattctt caggggaaat
9601 aatctatttg aacagtttag atggtgaaga acatttgcag catttgcaag attttttttcc
9661 actctgaagt ggtctttgtc cttgaacata ggatacaagt gaccctgct ctgttaatta
9721 ttggcaaatt gcctaacttc aacgtaagga aatagagtca tatgtttgct cactgaaggt
9781 tactagttaa caggcatccc ttaaacagga tataaagga cttcagcagg actgctcgaa
9841 acatcccact tccagcactg cctgcggtga aggaaccagc agccgaattc ggccattacg
9901 gccaccacca tgacgcctca accctgaggt gcgcccactg tccaagtgac ccgtgagacg
9961 gagcggtcct tccccagagc ctcggaagac gaagtgacct gccccacgtc cgccccgccc
10021 agccccactc gcacacgggg gaactgcgca gaggcggaag agggaggctg ccgaggggcc
10081 ccgaggaagc tccgggcacg gcgcggggga cgcagccggc ctaagagcga gttggcactg
10141 agcaagcagc gacggagtcg gcgaaagaag gccaacgacc gcgagcgcaa tcgaatgcac
10201 aacctcaact cggcactgga cgccctgcgc ggtgtcctgc ccaccttccc agacgacgcg
10261 aagctcacca agatcgagac gctgcgcttc gcccacaact acatctgggc gctgactcaa
10321 acgctgcgca tagcggacca cagcttgtac gcgctggagc cgccggcgcc gcactgcggg
10381 gagctgggca gcccaggcgg ttcccccggg gactggggt ccctctactc cccagtctcc
10441 caggctggca gcctgagtcc cgccgcgtcg ctggaggagc gacccgggct gctggggcc
10501 acctcttccg cctgcttgag cccaggcagt ctggctttct cagattttct gtgaggccgc
10561 ct
```

FIG. 17E

| FEATURES | Location/Qualifiers |
|---|---|
| promoter | 8835..9884<br>/vntifkey="29"<br>/label=alpha-fetoprotein-promoter |
| RBS | 602..611<br>/vntifkey="32"<br>/label=Kozak\consensus |
| CDS | 608..1285<br>/vntifkey="4"<br>/label=DsRED2 |
| misc_feature | 7336..7516<br>/vntifkey="21"<br>/label=5'\LTR |
| misc_feature | 2085...2319<br>/vntifkey="21"<br>/label=deltaU3-3'LTR |
| misc_feature | 7233..7335<br>/vntifkey="21"<br>/label=MCS |
| misc_feature | 20..604<br>/vntifkey="21"<br>/label=IRES |
| misc_feature | 1294..1885<br>/vntifkey="21"<br>/label=WPRE |
| CDS | complement(5342..6202)<br>/vntifkey="4"<br>/label=Amp(r) |
| promoter | complement(6203..6300)<br>/vntifkey="29"<br>/label=bla |
| rep_origin | complement(4524..5197)<br>/vntifkey="33"<br>/label=pUC\ori |
| CDS | 3507..3881<br>/vntifkey="4"<br>/label=Zeocin(r) |
| promoter | 3440..3505<br>/vntifkey="29"<br>/label=EM7 |
| rep_origin | 3099..3424<br>/vntifkey="33"<br>/label=SV40\ori |
| rep_origin | 2621..3033<br>/vntifkey="33"<br>/label=f1\ori |
| misc_feature | 2345..2558 |

FIG. 19A

```
                        /vntifkey="21"
                        /label=BGH\PolyA
    promoter            7201..7220
                        /vntifkey="29"
                        /label=T7\promoter
    promoter            6547..7198
                        /vntifkey="29"
                        /label=PCMV
    RBS                 9904..9914
                        /vntifkey="32"
                        /label=Kozak\consensus
    CDS                 9911..10918
                        /vntifkey="4"
                        /label=tTR-KRAB
BASE COUNT     2787 a      2665 c      2762 g      2712 t
ORIGIN
SEQ ID NO:08
      1 cggccatcga taaggatccg cccctctccc tcccccccc ctaacgttac tggccgaagc
     61 cgcttggaat aaggccggtg tgcgtttgtc tatatgttat tttccaccat attgccgtct
    121 tttggcaatg tgagggcccg gaaacctggc cctgtcttct tgacgagcat tcctagggt
    181 ctttcccctc tcgccaaagg aatgcaaggt ctgttgaatg tcgtgaagga agcagttcct
    241 ctggaagctt cttgaagaca acaacgtct gtagcgaccc tttgcaggca gcggaacccc
    301 ccacctggcg acaggtgcct ctgcggccaa aagccacgtg tataagatac acctgcaaag
    361 gcggcacaac cccagtgcca cgttgtgagt tggatagttg tggaaagagt caaatggctc
    421 tcctcaagcg tattcaacaa ggggctgaag gatgcccaga aggtacccca ttgtatggga
    481 tctgatctgg ggcctcggtg cacatgcttt acatgtgttt agtcgaggtt aaaaaaacgt
    541 ctaggccccc cgaaccacgg ggacgtggtt ttcctttgaa aaacacgatg ataatatggc
    601 cacaaccatg gcctcctccg aggacgtcat caaggagttc atgcgcttca aggtgcgcat
    661 ggagggctcc gtgaacggcc acgagttcga gatcgagggc gagggcgagg gccgccccta
    721 cgagggcacc cagaccgcca agctgaaggt gaccaagggc ggccccctgc ccttcgcctg
    781 ggacatcctg tcccccagt tccagtacgg ctccaaggtg tacgtgaagc accccgccga
    841 catccccgac tacaagaagc tgtccttccc cgagggcttc aagtgggagc gcgtgatgaa
    901 cttcgaggac ggcggcgtgg tgaccgtgac ccaggactcc tccctgcagg acggctcctt
    961 catctacaag gtgaagttca tcggcgtgaa cttccccctc gacggccccg taatgcagaa
   1021 gaagactatg ggctgggagg cctccaccga gcgcctgtac cccgcgacg gcgtgctgaa
   1081 gggcgagatc cacaaggccc tgaagctgaa ggacggcggc cactacctgg tggagttcaa
   1141 gtccatctac atggccaaga gcccgtgca gctgcccggc tactactacg tggactccaa
   1201 gctggacatc acctcccaca acgaggacta caccatcgtg gagcagtacg agcgcgccga
   1261 gggccgccac caccttgttcc tgtaggcggc cgcaatcaac ctctggatta caaaatttgt
   1321 gaaagattga ctggtattct taactatgtt gctccttta cgctatgtgg atacgctgct
   1381 ttaatgcctt tgtatcatgc tattacttcc cgtacggctt tcatttttct ctccttgtat
   1441 aaatcctggt tgctgtctct ttatgaggag ttgtggcccg ttgtcaggca acgtggcgtg
   1501 gtgtgcactg tgtttgctga cgcaaccccc actggttggg cattgccac cacctatcaa
   1561 ctcctttccg ggactttcgc tttccccctc cctattgcca cggcggaact cattgccgcc
   1621 tgccttgccc gctgctggac aggggctcgg ctgttgggca ctgacaattc cgtggtgttg
   1681 tcggggaagc tgacgtcctt tccatggctg ctcgcctgtg ttgccaactg gattctgcgc
   1741 gggacgtcct tctgctacgt cccttcggcc ctcaatccag cggaccttcc ttcccgcggc
   1801 ctgctgccgg ttctgcggcc tcttccgcgt cttcgccttc gccctcagac gagtcggatc
   1861 tccctttggg ccgcctcccc gcctgcctgc aggttgtcg agacctagaa aaacatggag
   1921 caatcacaag tagcaataca gcagctacca atgctgattg tgcctggcta gaagcacaag
   1981 aggaggagga ggtgggtttt ccagtcacac ctcaggtacc tttaagacca atgacttaca
   2041 aggcagctgt agatcttagc cactttttaa aagaaaaggg gggactggaa gggctaattc
   2101 actcccaacg aagacaagat ctgcttttg cttgtactgg gtctctctgg ttagaccaga
```

FIG. 19B

```
2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgcccctc ccccgtgcct
2401 tccttgaccc tggaaggtgc cactcccact gtcctttcct aataaaatga ggaaattgca
2461 tcgcattgtc tgagtaggtg tcattctatt ctggggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgcccgctc ctttcgcttt cttcccttcc tttctcgcca cgttcgccgg ctttccccgt
2761 caagctctaa atcggggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt ggggatttcg
3001 gcctattggt taaaaaatga gctgatttaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 ttttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgc caagttgac cagtgccgtt ccggtgctca
3541 ccgcgcgcga cgtcgccgga gcggtcgagt tctgaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt ggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 tttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata aagtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg ttttttccata ggctccgccc cctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaaccccc gttcagcccg
4861 accgctcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggtttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact ggtctgaca
5341 gttaccaatg cttaatcagt gaggcaccta tctcagcgat ctgtctattt cgttcatcca
5401 tagttgcctg actcccgtc gtgtagataa ctacgatacg ggagggctta ccatctggcc
5461 ccagtgctgc aatgataccg cgagacccac gctcaccggc tccagattta tcagcaataa
5521 accagccagc cggaagggcc gagcgcagaa gtggtcctgc aactttatcc gcctccatcc
```

FIG. 19C

```
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct cggggcgaaa actctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga taagggcga
6181 cacggaaatg ttgaatactc atactcttcc tttttcaata ttattgaagc atttatcagg
6241 gttattgtct catgagcgga tacatatttg aatgtattta gaaaaataaa caaatagggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgccccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccacccatt gacgtcaatg ggagtttgtt ttggcaccaa aatcaacggg actttccaaa
7081 atgtcgtaac aactccgccc cattgacgca aatgggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtgca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagacccct ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta aaggagaga gatgggtgcg
7681 agagcgtcag tattaagcgg gggagaatta gatcgcgatg ggaaaaaatt cggttaaggc
7741 caggggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga agagcaaaac aaaagtaaga ccaccgcaca gcaagcggcc gctgatcttc
8041 agacctggag gaggagatat gagggacaat tggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag ataccctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag gggacccgac
8821 aggcccttaa ttaagccacc tatcctcttc agacctcttc aggaaacagc tatgcacata
8881 gcacacaggc atatgttcaa ccaaaacact gaaacacata aagaaatgt ttaaagaatg
8941 aatttaaaaa aataaaaaat aaactcaact acatatgaag ccttagcaaa catgtctgga
```

FIG. 19D

```
 9001 cctctagaca cacagactct gacacgccaa cgtctgagtt ctagtttcga tacgcactgg
 9061 gaagttttaa aagttttcca tcaactctaa tgtgtagaga aatggaaact atcatagact
 9121 ctacggcatt gagggtgaag gtatgagtga agcactctta gggtcagaag tatgtcagtg
 9181 cccatttgtt gctgttagca tcatcatctt agggcttgag aggatgttgc agctgaccca
 9241 tgcacctgtg acatacatat ggaattattc tttggcacat aaaattagaa tgggagctgg
 9301 ctcatcaggt tttgtgctgt aagttttcta tgttaaacca gatgcgatac actaaataaa
 9361 ataaaatata cttgaccgat ggttttgagc gaaataataa ctggataatc aagaaatata
 9421 tccactaatg aatagcctga actactgaaa caatttgttc agtgcctagc atatggtgtg
 9481 cattttatta tttctttcaa aaagaatgta tttggagtta catagtaagt ctgctaccct
 9541 ttctttatgg ctatatctat gtcttatgtt gagatgaatg aattattctt caggggaaat
 9601 aatctatttg aacagtttag atggtgaaga acatttgcag catttgcaag attttttttcc
 9661 actctgaagt ggtctttgtc cttgaacata ggatacaagt gacccctgct ctgttaatta
 9721 ttggcaaatt gcctaacttc aacgtaagga aatagagtca tatgtttgct cactgaaggt
 9781 tactagttaa caggcatccc ttaaacagga tataaaagga cttcagcagg actgctcgaa
 9841 acatcccact tccagcactg cctgcggtga aggaaccagc agccgaattc ggccattacg
 9901 gcccgccacc atggctagat tagataaaag taaagtgatt aacagcgcat tagagctgct
 9961 taatgaggtc ggaatcgaag gtttaacaac ccgtaaactc gcccagaagc taggtgtaga
10021 gcagcctaca ttgtattggc atgtaaaaaa taagcgggct ttgctcgacg ccttagccat
10081 tgagatgtta gataggcacc atactcactt ttgcccttta gaaggggaaa gctggcaaga
10141 ttttttacgt aataacgcta aaagttttag atgtgcttta ctaagtcatc gcgatggagc
10201 aaaagtacat ttaggtacac ggcctacaga aaaacagtat gaaactctcg aaaatcaatt
10261 agccttttta tgccaacaag ttttttcact agagaatgca ttatatgcac tcagcgctgt
10321 ggggcatttt actttaggtt gcgtattgga agatcaagag catcaagtcg ctaaagaaga
10381 aagggaaaca cctactactg atagtatgcc gccattatta cgacaagcta tcgaattatt
10441 tgatcaccaa ggtgcagagc cagccttctt attcggcctt gaattgatca tatgcggatt
10501 agaaaaacaa cttaaatgtg aaagtgggtc gccaaaaaag aagagaaagg tcgacggcgg
10561 tggtgctttg tctcctcagc actctgctgt cactcaagga agtatcatca agaacaagga
10621 gggcatggat gctaagtcac taactgcctg gtcccggaca ctggtgacct tcaaggatgt
10681 atttgtggac ttcaccaggg aggagtggaa gctgctggac actgctcagc agatcgtgta
10741 cagaaatgtg atgctggaga actataagaa cctggtttcc ttgggttatc agcttactaa
10801 gccagatgtg atcctccggt tggagaaggg agaagagccc tggctggtgg agagagaaat
10861 tcaccaagag acccatcctg attcagagac tgcatttgaa atcaaatcat cagtttaagg
10921 ccgcct
```

FIG. 19E

```
COMMENT      VNTNAME|pLV-Hef1a-rhlI-IRES-DsRed2|

FEATURES            Location/Qualifiers
    promoter        8835..10008
                    /vntifkey="29"
                    /label=PEF1-alpha
    promoter        6547..7198
                    /vntifkey="29"
                    /label=PCMV
    promoter        7201..7220
                    /vntifkey="29"
                    /label=T7\promoter
    misc_feature    2345..2558
                    /vntifkey="21"
                    /label=BGH\PolyA
    rep_origin      2621..3033
                    /vntifkey="33"
                    /label=f1\ori
    rep_origin      3099..3424
                    /vntifkey="33"
                    /label=SV40\ori
    promoter        3440..3505
                    /vntifkey="29"
                    /label=EM7
    CDS             3507..3881
                    /vntifkey="4"
                    /label=Zeocin(r)
    rep_origin      complement(4524..5197)
                    /vntifkey="33"
                    /label=pUC\ori
    promoter        complement(6203..6300)
                    /vntifkey="29"
                    /label=bla
    CDS             complement(5342..6202)
                    /vntifkey="4"
                    /label=Amp(r)
    misc_feature    1294..1885
                    /vntifkey="21"
                    /label=WPRE
    misc_feature    20..604
                    /vntifkey="21"
                    /label=IRES
    misc_feature    7233..7335
                    /vntifkey="21"
                    /label=MCS
    misc_feature    2085..2319
                    /vntifkey="21"
```

FIG. 21A

```
                        /label=deltaU3-3'LTR
     misc_feature       7336..7516
                        /vntifkey="21"
                        /label=5'\LTR
     CDS                608..1285
                        /vntifkey="4"
                        /label=DsRED2
     RBS                602..611
                        /vntifkey="32"
                        /label=Kozak\consensus
     RBS                10036..10046
                        /vntifkey="32"
                        /label=Kozak\consensus
     CDS                10043..10648
                        /vntifkey="4"
                        /label=rhlI
BASE COUNT      2424 a       2785 c       2901 g       2546 t
ORIGIN
SEQ ID NO:09
    1 cggccatcga taaggatccg cccctctccc tccccccccc ctaacgttac tggccgaagc
   61 cgcttggaat aaggccggtg tgcgtttgtc tatatgttat tttccaccat attgccgtct
  121 tttggcaatg tgagggcccg gaaacctggc cctgtcttct tgacgagcat tcctaggggt
  181 ctttcccctc tcgccaaagg aatgcaaggt ctgttgaatg tcgtgaagga agcagttcct
  241 ctggaagctt cttgaagaca acaacgtct gtagcgaccc tttgcaggca gcggaacccc
  301 ccacctggcg acaggtgcct ctgcggccaa aagccacgtg tataagatac acctgcaaag
  361 gcggcacaac cccagtgcca cgttgtgagt tggatagttg tggaaagagt caaatggctc
  421 tcctcaagcg tattcaacaa ggggctgaag gatgcccaga aggtacccca ttgtatggga
  481 tctgatctgg ggcctcggtg cacatgcttt acatgtgttt agtcgaggtt aaaaaaaacgt
  541 ctaggccccc cgaaccacgg ggacgtggtt ttcctttgaa aaacacgatg ataatatggc
  601 cacaaccatg gcctcctccg aggacgtcat caaggagttc atgcgcttca aggtgcgcat
  661 ggagggctcc gtgaacggcc acgagttcga gatcgagggc gagggcgagg ccgccccta
  721 cgagggcacc cagaccgcca agctgaaggt gaccaagggc ggccccctgc ccttcgcctg
  781 ggacatcctg tcccccagt tccagtacgg ctcaaggtg tacgtgaagc accccgccga
  841 catccccgac tacaagaagc tgtccttccc cgagggcttc aagtgggagc gcgtgatgaa
  901 cttcgaggac ggcggcgtgg tgaccgtgac ccaggactcc tccctgcagg acggctcctt
  961 catctacaag gtgaagttca tcggcgtgaa cttcccctcc gacggccccg taatgcagaa
 1021 gaagactatg ggctgggagg cctccaccga gcgcctgtac ccccgcgacg gcgtgctgaa
 1081 gggcgagatc cacaaggccc tgaagctgaa ggacggcggc cactacctgg tggagttcaa
 1141 gtccatctac atggccaaga gcccgtgca gctgccggc tactactacg tggactccaa
 1201 gctggacatc acctcccaca cgaggacta caccatcgtg gagcagtacg agcgcgccga
 1261 gggccgccac cacctgttcc tgtaggcggc cgcaatcaac ctctggatta caaaatttgt
 1321 gaaagattga ctggtattct taactatgtt gctcctttta cgctatgtgg atacgctgct
 1381 ttaatgcctt tgtatcatgc tattacttcc cgtacggctt tcattttctc ctccttgtat
 1441 aaatcctggt tgctgtctct ttatgaggag ttgtggcccg ttgtcaggca acgtggcgtg
 1501 gtgtgcactg tgtttgctga cgcaaccccc actggttggg gcattgccac cacctatcaa
 1561 ctcctttccg ggactttcgc tttcccctc cctattgcca cggcggaact cattgccgcc
 1621 tgccttgccc gctgctggac aggggctcgg ctgttgggca ctgacaattc cgtggtgttg
 1681 tcggggaagc tgacgtcctt tccatggctg ctcgcctgtg ttgccaactg gattctgcgc
 1741 gggacgtcct tctgctacgt cccttcggcc ctcaatccag cggaccttcc ttcccgcggc
 1801 ctgctgccgg ttctgcggcc tcttccgcgt cttcgccttc gccctcagac gagtcggatc
 1861 tccctttggg ccgcctcccc gcctgcctgc aggtttgtcg agacctagaa aaacatggag
 1921 caatcacaag tagcaataca gcagctacca atgctgattg tgcctggcta gaagcacaag
 1981 aggaggagga ggtgggtttt ccagtcacac ctcaggtacc tttaagacca atgacttaca
```

FIG. 21B

```
2041 aggcagctgt agatcttagc cacttttta aagaaaaggg gggactggaa gggctaattc
2101 actcccaacg aagacaagat ctgcttttg cttgtactgg gtctctctgg ttagaccaga
2161 tctgagcctg ggagctctct ggctaactag ggaacccact gcttaagcct caataaagct
2221 tgccttgagt gcttcaagta gtgtgtgccc gtctgttgtg tgactctggt aactagagat
2281 ccctcagacc cttttagtca gtgtggaaaa tctctagcag ggcccgttta aacccgctga
2341 tcagcctcga ctgtgccttc tagttgccag ccatctgttg tttgccctc ccccgtgcct
2401 tccttgaccc tggaaggtgc cactcccact gtcctttcct aataaatga ggaaattgca
2461 tcgcattgtc tgagtaggtg tcattctatt ctgggggtg gggtggggca ggacagcaag
2521 ggggaggatt gggaagacaa tagcaggcat gctggggatg cggtgggctc tatggcttct
2581 gaggcggaaa gaaccagctg gggctctagg gggtatcccc acgcgccctg tagcggcgca
2641 ttaagcgcgg cgggtgtggt ggttacgcgc agcgtgaccg ctacacttgc cagcgcccta
2701 gcgccgctc ctttcgcttt cttccctcc tttctcgcca cgttcgccgg ctttccccgt
2761 caagctctaa atcgggcat ccctttaggg ttccgattta gtgctttacg gcacctcgac
2821 cccaaaaaac ttgattaggg tgatggttca cgtagtgggc catcgccctg atagacggtt
2881 tttcgccctt tgacgttgga gtccacgttc tttaatagtg gactcttgtt ccaaactgga
2941 acaacactca accctatctc ggtctattct tttgatttat aagggatttt gggatttcg
3001 gcctattggt taaaaatga gctgattaa caaaaattta acgcgaatta attctgtgga
3061 atgtgtgtca gttagggtgt ggaaagtccc caggctcccc aggcaggcag aagtatgcaa
3121 agcatgcatc tcaattagtc agcaaccagg tgtggaaagt ccccaggctc cccagcaggc
3181 agaagtatgc aaagcatgca tctcaattag tcagcaacca tagtcccgcc cctaactccg
3241 cccatcccgc ccctaactcc gcccagttcc gcccattctc cgccccatgg ctgactaatt
3301 tttttattt atgcagaggc cgaggccgcc tctgcctctg agctattcca gaagtagtga
3361 ggaggctttt ttggaggcct aggcttttgc aaaaagctcc cgggagcttg tatatccatt
3421 ttcggatctg atcagcacgt gttgacaatt aatcatcggc atagtatatc ggcatagtat
3481 aatacgacaa ggtgaggaac taaaccatgg ccaagttgac cagtgccgtt ccggtgctca
3541 ccgcgcgcga cgtcgccgga gcggtcgagt tctggaccga ccggctcggg ttctcccggg
3601 acttcgtgga ggacgacttc gccggtgtgg tccgggacga cgtgaccctg ttcatcagcg
3661 cggtccagga ccaggtggtg ccggacaaca ccctggcctg ggtgtgggtg cgcggcctgg
3721 acgagctgta cgccgagtgg tcggaggtcg tgtccacgaa cttccgggac gcctccgggc
3781 cggccatgac cgagatcggc gagcagccgt ggggcggga gttcgccctg cgcgacccgg
3841 ccggcaactg cgtgcacttc gtggccgagg agcaggactg acacgtgcta cgagatttcg
3901 attccaccgc cgccttctat gaaaggttgg gcttcggaat cgttttccgg gacgccggct
3961 ggatgatcct ccagcgcggg gatctcatgc tggagttctt cgcccacccc aacttgttta
4021 ttgcagctta taatggttac aaataaagca atagcatcac aaatttcaca aataaagcat
4081 ttttttcact gcattctagt tgtggtttgt ccaaactcat caatgtatct tatcatgtct
4141 gtataccgtc gacctctagc tagagcttgg cgtaatcatg gtcatagctg tttcctgtgt
4201 gaaattgtta tccgctcaca attccacaca acatacgagc cggaagcata agtgtaaag
4261 cctggggtgc ctaatgagtg agctaactca cattaattgc gttgcgctca ctgcccgctt
4321 tccagtcggg aaacctgtcg tgccagctgc attaatgaat cggccaacgc gcggggagag
4381 gcggtttgcg tattgggcgc tcttccgctt cctcgctcac tgactcgctg cgctcggtcg
4441 ttcggctgcg gcgagcggta tcagctcact caaaggcggt aatacggtta tccacagaat
4501 caggggataa cgcaggaaag aacatgtgag caaaaggcca gcaaaaggcc aggaaccgta
4561 aaaaggccgc gttgctggcg ttttttccata ggctccgccc ccctgacgag catcacaaaa
4621 atcgacgctc aagtcagagg tggcgaaacc cgacaggact ataaagatac caggcgtttc
4681 cccctggaag ctccctcgtg cgctctcctg ttccgaccct gccgcttacc ggatacctgt
4741 ccgcctttct cccttcggga agcgtggcgc tttctcaatg ctcacgctgt aggtatctca
4801 gttcggtgta ggtcgttcgc tccaagctgg gctgtgtgca cgaaccccc gttcagcccg
4861 accgctgcgc cttatccggt aactatcgtc ttgagtccaa cccggtaaga cacgacttat
4921 cgccactggc agcagccact ggtaacagga ttagcagagc gaggtatgta ggcggtgcta
4981 cagagttctt gaagtggtgg cctaactacg gctacactag aaggacagta tttggtatct
5041 gcgctctgct gaagccagtt accttcggaa aaagagttgg tagctcttga tccggcaaac
5101 aaaccaccgc tggtagcggt ggttttttg tttgcaagca gcagattacg cgcagaaaaa
5161 aaggatctca agaagatcct ttgatctttt ctacggggtc tgacgctcag tggaacgaaa
5221 actcacgtta agggattttg gtcatgagat tatcaaaaag gatcttcacc tagatccttt
5281 taaattaaaa atgaagtttt aaatcaatct aaagtatata tgagtaaact ggtctgaca
5341 gttaccaatg cttaatcagt gaggcaccta tctcagcgat ctgtctattt cgttcatcca
5401 tagttgcctg actccccgtc gtgtagataa ctacgatacg ggagggctta ccatctggcc
```

FIG. 21C

```
5461 ccagtgctgc aatgataccg cgagacccac gctcaccggc tccagattta tcagcaataa
5521 accagccagc cggaagggcc gagcgcagaa gtggtcctgc aactttatcc gcctccatcc
5581 agtctattaa ttgttgccgg gaagctagag taagtagttc gccagttaat agtttgcgca
5641 acgttgttgc cattgctaca ggcatcgtgg tgtcacgctc gtcgtttggt atggcttcat
5701 tcagctccgg ttcccaacga tcaaggcgag ttacatgatc ccccatgttg tgcaaaaaag
5761 cggttagctc cttcggtcct ccgatcgttg tcagaagtaa gttggccgca gtgttatcac
5821 tcatggttat ggcagcactg cataattctc ttactgtcat gccatccgta agatgctttt
5881 ctgtgactgg tgagtactca accaagtcat tctgagaata gtgtatgcgg cgaccgagtt
5941 gctcttgccc ggcgtcaata cgggataata ccgcgccaca tagcagaact ttaaaagtgc
6001 tcatcattgg aaaacgttct cggggcgaaa actctcaag gatcttaccg ctgttgagat
6061 ccagttcgat gtaacccact cgtgcaccca actgatcttc agcatctttt actttcacca
6121 gcgtttctgg gtgagcaaaa acaggaaggc aaaatgccgc aaaaaaggga taagggcga
6181 cacggaaatg ttgaatactc atactcttcc tttttcaata ttattgaagc atttatcagg
6241 gttattgtct catgagcgga tacatatttg aatgtattta gaaaaataaa caaataggg
6301 ttccgcgcac atttccccga aaagtgccac ctgacgtcga cggatcggga gatctcccga
6361 tcccctatgg tgcactctca gtacaatctg ctctgatgcc gcatagttaa gccagtatct
6421 gctccctgct tgtgtgttgg aggtcgctga gtagtgcgcg agcaaaattt aagctacaac
6481 aaggcaaggc ttgaccgaca attgcatgaa gaatctgctt agggttaggc gttttgcgct
6541 gcttcgcgat gtacgggcca gatatacgcg ttgacattga ttattgacta gttattaata
6601 gtaatcaatt acggggtcat tagttcatag cccatatatg gagttccgcg ttacataact
6661 tacggtaaat ggcccgcctg gctgaccgcc caacgacccc cgcccattga cgtcaataat
6721 gacgtatgtt cccatagtaa cgccaatagg gactttccat tgacgtcaat gggtggacta
6781 tttacggtaa actgcccact tggcagtaca tcaagtgtat catatgccaa gtacgcccc
6841 tattgacgtc aatgacggta aatggcccgc ctggcattat gcccagtaca tgaccttatg
6901 ggactttcct acttggcagt acatctacgt attagtcatc gctattacca tggtgatgcg
6961 gttttggcag tacatcaatg ggcgtggata gcggtttgac tcacggggat ttccaagtct
7021 ccacccccatt gacgtcaatg ggagtttgtt ttggcaccaa aatcaacggg actttccaaa
7081 atgtcgtaac aactccgccc cattgacgca aatggcggt aggcgtgtac ggtgggaggt
7141 ctatataagc agagctctct ggctaactag agaacccact gcttactggc ttatcgaaat
7201 taatacgact cactataggg agacccaagc tggtttaaac ttaagcttgg taccgagctc
7261 actagtccag tgtggtggca gatatccagc acagtggcgg ccgctcgagt ctagagggcc
7321 cgttttgcct gtactgggtc tctctggtta gaccagatct gagcctggga gctctctggc
7381 taactaggga acccactgct taagcctcaa taaagcttgc cttgagtgct tcaagtagtg
7441 tgtgcccgtc tgttgtgtga ctctggtaac tagagatccc tcagaccctt ttagtcagtg
7501 tggaaaatct ctagcagtgg cgcccgaaca gggacttgaa agcgaaaggg aaaccagagg
7561 agctctctcg acgcaggact cggcttgctg aagcgcgcac ggcaagaggc gaggggcggc
7621 gactggtgag tacgccaaaa attttgacta gcggaggcta aaggagaga gatgggtgcg
7681 agagcgtcag tattaagcgg gggagaatta gatcgcgatg ggaaaaaatt cggttaaggc
7741 cagggggaaa gaaaaaatat aaattaaaac atatagtatg ggcaagcagg gagctagaac
7801 gattcgcagt taatcctggc ctgttagaaa catcagaagg ctgtagacaa atactgggac
7861 agctacaacc atcccttcag acaggatcag aagaacttag atcattatat aatacagtag
7921 caaccctcta ttgtgtgcat caaaggatag agataaaaga caccaaggaa gctttagaca
7981 agatagagga gagcaaaac aaaagtaaga ccaccgcaca gcaagcggcc gctgatcttc
8041 agacctggag gaggagatat gagggacaat ggagaagtg aattatataa atataaagta
8101 gtaaaaattg aaccattagg agtagcaccc accaaggcaa agagaagagt ggtgcagaga
8161 gaaaaaagag cagtgggaat aggagctttg ttccttgggt tcttgggagc agcaggaagc
8221 actatgggcg cagcgtcaat gacgctgacg gtacaggcca gacaattatt gtctggtata
8281 gtgcagcagc agaacaattt gctgagggct attgaggcgc aacagcatct gttgcaactc
8341 acagtctggg gcatcaagca gctccaggca agaatcctgg ctgtggaaag atacctaaag
8401 gatcaacagc tcctggggat ttggggttgc tctggaaaac tcatttgcac cactgctgtg
8461 ccttggaatg ctagttggag taataaatct ctggaacaga tttggaatca cacgacctgg
8521 atggagtggg acagagaaat taacaattac acaagcttaa tacactcctt aattgaagaa
8581 tcgcaaaacc agcaagaaaa gaatgaacaa gaattattgg aattagataa atgggcaagt
8641 ttgtggaatt ggtttaacat aacaaattgg ctgtggtata taaaattatt cataatgata
8701 gtaggaggct tggtaggttt aagaatagtt tttgctgtac tttctatagt gaatagagtt
8761 aggcagggat attcaccatt atcgtttcag acccacctcc caaccccgag ggacccgac
8821 aggcccttaa ttaattggct ccggtgcccg tcagtgggca gagcgcacat cgcccacagt
```

FIG. 21D

```
8881  ccccgagaag ttggggggag gggtcggcaa ttgaaccggt gcctagagaa ggtggcgcgg
8941  ggtaaactgg gaaagtgatg tcgtgtactg gctccgcctt ttccccgagg gtgggggaga
9001  accgtatata agtgcagtag tcgccgtgaa cgttcttttt cgcaacgggt ttgccgccag
9061  aacacaggta agtgccgtgt gtggttcccg cgggcctggc ctctttacgg gttatggccc
9121  ttgcgtgcct tgaattactt ccacctggct gcagtacgtg attcttgatc ccgagcttcg
9181  ggttggaagt gggtgggaga gttcgaggcc ttgcgcttaa ggagcccctt cgcctcgtgc
9241  ttgagttgag gcctggcctg ggcgctgggg ccgccgcgtg cgaatctggt ggcaccttcg
9301  cgcctgtctc gctgctttcg ataagtctct agccatttaa aattttttgat gacctgctgc
9361  gacgctttt ttctggcaag atagtcttgt aaatgcgggc caagatctgc acactggtat
9421  ttcggttttt ggggccgcgg gcggcgacgg ggcccgtgcg tcccagcgca catgttcggc
9481  gaggcgggggc ctgcgagcgc ggccaccgag aatcggacgg gggtagtctc aagctggccg
9541  gcctgctctg tgcctggcc tcgcccgcc gtgtatcgcc ccgccctggg cggcaaggct
9601  ggcccggtcg gcaccagttg cgtgagcgga aagatggccg cttccggcc ctgctgcagg
9661  gagctcaaaa tggaggacgc ggcgctcggg agagcgggcg ggtgagtcac ccacacaaag
9721  gaaaagggcc tttccgtcct cagccgtcgc ttcatgtgac tccacggagt accgggcgcc
9781  gtccaggcac ctcgattagt tctcgagctt ttggagtacg tcgtctttag gttggggga
9841  ggggttttat gcgatggagt tttcccacac tgagtgggtg gagactgaag ttaggccagc
9901  ttggcacttg atgtaattct ccttggaatt tgccctttttt gagtttggat cttggttcat
9961  tctcaagcct cagacagtgg ttcaaagttt ttttcttcca tttcaggtgt cgtgaggaat
10021 tcggccatta cggcccgcca ccatgatcga attgctctct gaatcgctgg aagggctttc
10081 cgccgccatg atcgccgagc tgggacgcta ccggcatcag gtcttcatcg agaagctggg
10141 ctgggacgtg gtctccacct ccagggtccg cgaccaggaa ttcgaccagt tcgaccatcc
10201 gcaaacccgc tacatcgtcg ccatgagccg ccagggcatc tgcggttgcg cccgcctgct
10261 gccgacgacc gacgcctacc tgctcaagga cgtcttcgcc tacctgtgca gcgaaacccc
10321 gccgagcgat ccgtcggtct gggagctttc gcgctacgcc gccagcgcgg cggacgatcc
10381 gcagctggcg atgaagatat tctggtccag cctgcaatgc gcctggtacc tgggcgccag
10441 ttcggtggtg gcggtgacca ccacggccat ggagcgctat ttcgttcgca acggcgtgat
10501 cctccagcgc ctcggcccgc cgcagaaggt caagggcgag acgctggtcg cgatcagctt
10561 cccggcctac caggagcgcg cctggagat gctgctgcgc taccacccgg aatggctgca
10621 gggcgtaccg ctgtcgatgg cggtgtgagg ccgcct
```

SEQ ID NO: 10 gatccgcccctctccctccccccctaacgttactggccaagccgcttgaataaggccgtgtgcgtttgtctatatgttatttccaccatattgccgtc
ttttggcaatgtgagggcccggaaacctggccctgtcttcttgacgagtcattcctagggtcttccctctcgccaaaggaatgcaaggtctgttgaatgtc
gtgaaggaagcagttcctctgtgaagcttcttgaagacaaacaacgtctgtagcgaccctttgcaggcagcggaaccccccacctggcgacaggtgcctct
gcggccaaagccacgtgtataagataccctgcaaaggcggcacaaccccagtgccacgttgtgagttggatagttgtggaaaagagtcaaatgctctc
ctcaagcgtattcaacaaggggctgaaggatgccagaaggtacccccattgtatggatctgatctgggcctggtgcacatgctttacatgtgtttagtc
gaggttaaaaaacgtctaggccccccgaaccactggttttcttgaaaaacgatgataatatggccacaaccatgtgagcaagggcg
aggagctgttcaccggggtggtgcccatcctggtcgagctggtgacggcgacgtaaaacgccacaagttcagcgtgtccggcgagggcgagggcgatgc
cacctacggcaagctgaccctgaagttcatctgcaccaccggcaagctgcccgtgccgtggcccaccctcgtgaccaccctgacctacggcgtgcagtg
cttcagccgctaccccgaccacatgaagcagcacgacttcttcaagtccgccatgcccgaaggctacgtccaggagcgcaccatcttcttcaaggacgac
ggcaactacaagacccgcgccgaggtgaagttcgagggcgacaccctggtgaaccgcatcgagctgaagggcatcgacttcaaggaggacggcaac
atcctggggcacaagctgaagtacaactacaacagccacaacgtctatatcatgccgacaagcagaagaacgcatccaagtgaacttcaagatccgc
cacaacatcgaggacggcagcgtgcagctcgccgaccactaccagcagaacacccccatcggcgacggccccgtgctgctgcccgacaaccactac
ctgagcacccagtccgccctgagcaaagaccccaacgagaagcgcgatcacatggtcctgctgagttcgtgaccgccgccgggatcactctcggcat

FIG. 23B

```
ggacgagctgtacaagtaagcggccgcaatcaacctctggattacaaaatttgtg
aaagattgactggtattcttaactatgttgctccttttacgctatgtggatacgc
tgctttaatgcctttgtatcatgctattacttcccgtacggctttcattttctcc
tccttgtataaatcctggttgctgtctctttatgaggagttgtggcccgttgtca
ggcaacgtggcgtggtgtgcactgtgtttgctgacgcaaccccactggttgggg
cattgccaccacctatcaactcctttccgggactttcgctttcccctccctatt
gccacggcggaactcattgccgcctgccttgccgctgctggacaggggctcggc
tgttgggcactgacaattccgtggtgttgtcggggaagctgacgtccttccatg
gctgctcgcctgtgttgccaactggattctgcgcgggacgtccttctgctacgtc
ccttcggccctcaatccagcggaccttccttcccgcggcctgctgccggtctgc
ggcctcttccgcgtcttcgccttcgccctcagacgagtcggatctcccttgggc
cgcctccccgcctgcctgcaggtttgtcgagacctagaaaaacatggagcaatca
caagtagcaatacagcagctaccaatgctgattgtgcctggctagaagcacaaga
ggaggaggaggtgggttttccagtcacacctcaggtacctttaagaccaatgact
tacaaggcagctgtagatcttagccacttttaaaagaaaaggggggactggaag
ggctaattcactcccaacgaagacaagatctgcttttgcttgtactgggtctct
ctggttagaccagatctgagcctgggagctctctggctaactagggaacccactg
cttaagcctcaataaagcttgccttgagtgcttcaagtagtgtgtgcccgtctgt
tgtgtgactctggtaactagagatccctcagaccctttagtcagtgtggaaaat
ctctagcagggcccgtttaaacccgctgatcagcctcgactgtgccttctagttg
ccagccatctgttgtttgcccctccccgtgccttccttgaccctggaaggtgcc
actcccactgtccttttcctaataaaatgaggaaattgcatcgcattgtctgagta
ggtgtcattctattctgggggggtggggtggggcaggacagcaaggggaggattg
ggaagacaatagcaggcatgctggggatgcggtgggctctatggcttctgaggcg
gaaagaaccagctggggctctaggggggtatccccacgcgccctgtagcggcgcat
taagcgcggcgggtgtggtggttacgcgcagcgtgaccgctacacttgccagcgc
cctagcgcccgctcctttcgctttcttcccttcctttctcgccacgttcgccggc
tttccccgtcaagctctaaatcggggcatccctttagggttccgatttagtgctt
tacggcacctcgaccccaaaaaacttgattagggtgatggttcacgtagtgggcc
atcgccctgatagacggttttcgccctttgacgttggagtccacgttctttaat
agtggactcttgttccaaactggaacaacactcaacctatctcggtctattctt
ttgatttataagggatttggggatttcggcctattggttaaaaaatgagctgat
ttaacaaaaatttaacgcgaattaattctgtggaatgtgtgtcagttagggtgtg
gaaagtccccaggctccccaggcaggcagaagtatgcaaagcatgcatctcaatt
agtcagcaaccaggtgtggaaagtccccaggctccccagcaggcagaagtatgca
aagcatgcatctcaattagtcagcaaccatagtcccgcccctaactccgcccatc
ccgcccctaactccgcccagttcgcccattctccgcccatggctgactaattt
ttttatttatgcagaggccgaggccgcctctgcctctgagctattccagaagta
gtgaggaggcttttttggaggcctaggcttttgcaaaaagctcccgggagcttgt
atatccatttcggatctgatcagcacgtgttgacaattaatcatcggcatagta
```

FIG. 23C

```
tatcggcatagtataatacgacaaggtgaggaactaaaccatggccaagttgacc
agtgccgttccggtgctcaccgcgcgacgtcgccggagcggtcgagttctgga
ccgaccggctcgggttctcccgggacttcgtggaggacgacttcgccggtgtggt
ccgggacgacgtgaccctgttcatcagcgcggtccaggaccaggtggtgccggac
aacaccctggcctgggtgtgggtgcgcggcctggacgagctgtacgccgagtggt
cggaggtcgtgtccacgaacttccgggacgcctccgggccggccatgaccgagat
cggcgagcagccgtgggggcgggagttcgccctgcgcgacccggccggcaactgc
gtgcacttcgtggccgaggagcaggactgacacgtgctacgagatttcgattcca
ccgccgccttctatgaaaggttgggcttcggaatcgttttccgggacgccggctg
gatgatcctccagcgcggggatctcatgctggagttcttcgcccaccccaacttg
tttattgcagcttataatggttacaaataaagcaatagcatcacaaatttcacaa
ataaagcattttttcactgcattctagttgtggtttgtccaaactcatcaatgt
atcttatcatgtctgtataccgtcgacctctagctagagcttggcgtaatcatgg
tcatagctgtttcctgtgtgaaattgttatccgctcacaattccacacaacatac
gagccggaagcataaagtgtaaagcctggggtgcctaatgagtgagctaactcac
attaattgcgttgcgctcactgcccgctttccagtcgggaaacctgtcgtgccag
ctgcattaatgaatcggccaacgcgcggggagaggcggtttgcgtattgggcgct
cttccgcttcctcgctcactgactcgctgcgctcggtcgttcggctgcggcgagc
ggtatcagctcactcaaaggcggtaatacggttatccacagaatcaggggataac
gcaggaaagaacatgtgagcaaaaggccagcaaaaggccaggaaccgtaaaaagg
ccgcgttgctggcgtttttccataggctccgcccccctgacgagcatcacaaaaa
tcgacgctcaagtcagaggtggcgaaacccgacaggactataaagataccaggcg
tttccccctggaagctccctcgtgcgctctcctgttccgaccctgccgcttaccg
gatacctgtccgcctttctcccttcgggaagcgtggcgctttctcaatgctcacg
ctgtaggtatctcagttcggtgtaggtcgttcgctccaagctgggctgtgtgcac
gaaccccccgttcagcccgaccgctgcgccttatccggtaactatcgtcttgagt
ccaacccggtaagacacgacttatcgccactggcagcagccactggtaacaggat
tagcagagcgaggtatgtaggcggtgctacagagttcttgaagtggtggcctaac
tacggctacactagaaggacagtatttggtatctgcgctctgctgaagccagtta
ccttcggaaaaagagttggtagctcttgatccggcaaacaaaccaccgctggtag
cggtggtttttttgtttgcaagcagcagattacgcgcagaaaaaaaggatctcaa
gaagatcctttgatcttttctacggggtctgacgctcagtggaacgaaaactcac
gttaagggattttggtcatgagattatcaaaaggatcttcacctagatcctttt
aaattaaaaatgaagttttaaatcaatctaaagtatatatgagtaaacttggtct
gacagttaccaatgcttaatcagtgaggcacctatctcagcgatctgtctatttc
gttcatccatagttgcctgactccccgtcgtgtagataactacgatacgggaggg
cttaccatctggccccagtgctgcaatgataccgcgagacccacgctcaccggct
ccagatttatcagcaataaaccagccagccggaagggccgagcgcagaagtggtc
ctgcaactttatccgcctccatccagtctattaattgttgccgggaagctagagt
aagtagttcgccagttaatagtttgcgcaacgttgttgccattgctacaggcatc
```

FIG. 23D

```
gtggtgtcacgctcgtcgtttggtatggcttcattcagctccggttcccaacgat
caaggcgagttacatgatcccccatgttgtgcaaaaaagcggttagctccttcgg
tcctccgatcgttgtcagaagtaagttggccgcagtgttatcactcatggttatg
gcagcactgcataattctcttactgtcatgccatccgtaagatgcttttctgtga
ctggtgagtactcaaccaagtcattctgagaatagtgtatgcggcgaccgagttg
ctcttgcccggcgtcaatacgggataataccgcgccacatagcagaactttaaaa
gtgctcatcattggaaaacgttcttcggggcgaaaactctcaaggatcttaccgc
tgttgagatccagttcgatgtaacccactcgtgcacccaactgatcttcagcatc
ttttactttcaccagcgtttctgggtgagcaaaaacaggaaggcaaaatgccgca
aaaagggaataagggcgacacggaaatgttgaatactcatactcttccttttc
aatattattgaagcatttatcagggttattgtctcatgagcggatacatatttga
atgtatttagaaaaataaacaatagggttccgcgcacatttccccgaaaagtg
ccacctgacgtcgacggatcgggagatctcccgatccctatggtgcactctcag
tacaatctgctctgatgccgcatagttaagccagtatctgctccctgcttgtgtg
ttggaggtcgctgagtagtgcgcgagcaaaatttaagctacaacaaggcaaggct
tgaccgacaattgcatgaagaatctgcttagggttaggcgttttgcgctgcttcg
cgatgtacgggccagatatacgcgttgacattgattattgactagttattaatag
taatcaattacggggtcattagttcatagcccatatatggagttccgcgttacat
aacttacggtaaatggcccgcctggctgaccgcccaacgaccccgcccattgac
gtcaataatgacgtatgttcccatagtaacgccaatagggactttccattgacgt
caatgggtggactatttacggtaaactgcccacttggcagtacatcaagtgtatc
atatgccaagtacgccccctattgacgtcaatgacggtaaatggcccgcctggca
ttatgcccagtacatgaccttatgggactttcctacttggcagtacatctacgta
ttagtcatcgctattaccatggtgatgcggttttggcagtacatcaatgggcgtg
gatagcggtttgactcacggggatttccaagtctccaccccattgacgtcaatgg
gagtttgttttggcaccaaaatcaacgggactttccaaaatgtcgtaacaactcc
gccccattgacgcaaatgggcggtaggcgtgtacggtgggaggtctatataagca
gagctctctggctaactagagaacccactgcttactggcttatcgaaattaatac
gactcactataggagacccaagctggtttaaacttaagcttggtaccgagctca
ctagtccagtgtggtggcagatatccagcacagtggcggccgctcgagtctagag
ggcccgtttaaacnnnngggtctctctggttagaccagatctgagcctgggagc
tctctggctaactagggaacccactgcttaagcctcaataaagcttgccttgagt
gcttcaagtagtgtgtgcccgtctgttgtgtgactctggtaactagagatccctc
agacccttttagtcagtgtggaaaatctctagcannnnnnnnnnccagcaactta
tctgtgtctgtccgattgtctagtgtctatgtttgatgttatgcgcctgcgtctg
tactagttagctaactagctctgtatctggcggacccgtggtggaactgacgagt
tctgaacacccggccgcaaccctgggagacgtcccagggactttggggccgttt
ttgtggcccgacctgaggaagggagtcgatgtggaatccgaccccgtcaggatat
gtggttctggtaggagacgagaacctaaaacagttcccgcctccgtctgaatttt
tgctttcggtttggaaccgaagccgcgcgtcttgtctgctgcagcgctgcagcat
```

FIG. 23E

```
cgttctgtgttgtctctgtctgactgtgtttctgtatttgtctgaaaattagggc
cagactgttaccactcccttaagtttgaccttaggtcactggaaagatgtcgagc
ggatcgctcacaaccagtcggtagatgtcaagaagagacgttgggttaccttctg
ctctgcagaatggccaacctttaacgtcggatggccgcgagacggcacctttaac
cgagacctcatcacccaggttaagatcaaggtcttttcacctggcccgcatggac
acccagaccaggtcccctacatcgtgacctgggaagccttggcttttgacccccc
tccctgggtcaagccctttgtacaccctaagcctccgcctcctcttcctccatcc
gccccgtctctccccttgaacctcctcgttcgacccccgcctcgatcctccctt
atccagccctcactccttctctaggcgccnnnnnggaaaagtttagtaaaacacc
atatgtatgtttcagggaaagctaggggatggttttatagacatcactatgaaag
ccctcatccaagaataagttcagaagtacacatcccactaggggatgctagattg
gtaataacaacatattggggtctgcatacaggagaaagagactggcatctgggtc
agggagtctccatagaatggaggaaaaagagatatagcacacaagtagaccctga
actagcagaccaactaattcatctgtattactttgactgtttttcagactctgct
ataagaaaggccttattaggacatatagttagccctaggtgtgaatatcaagcag
gacataacaaggtaggatctctacaatacttggcactagcagcattaataacacc
aaaaagataaagccacctttgcctagtgttacgaaactgacagaggatagatgg
aacaagccccagaagaccaagggccacagagggagccacacaatgaatggacact
agagcttttagaggagcttaagaatgaagctgttagacatttcctaggatttgg
ctccatggcttagggcaacatatctatgaaacttatggggatacttgggcaggag
tggaagccataataatgcaacaactgctgtttatccatttcagaattgggtgtcg
acatagcagaataggcgttactcaacagaggagagcaagaaatggagccagtaga
tcctagactagagccctggaagcatccaggaagtcagcctaaaactgcttgtacc
acttgctattgtaaaagtgttgctttcattgccaagtttgtttcacaacaaaag
ccttaggcatctcctatggcaggaagaagcggagacagcgacgaagacctcctca
aggcagtcagactcatcaagtttctctatcaaagcagtaagtagtacatgtaatg
caacctatacaaatagcaatagcagcattagtagtagcaataataatagcaatag
ttgtgtggtccatagtaatcatagaatataggaaaatattaagacaaagaaaaat
agacaggttaattgatagactaatnnnnnnnnggcccgaaggaatagaagaagaa
ggtggagagagagacagagacagatccattcgattagtgaacggatcggcactgc
gtgcgccaattctgcagacaaatggcagtattcatccacaattttaaaagaaaag
gggggattggggggtacagtgcagggaaagaatagtagacataatagcaacaga
catacaaactaaagaattacaaaaacaaattacaaaaattcaaaattttcgggtt
tattacagggacagcagagatccagtttggttaattaatgctgctgagccacgtg
aagccttaagccgcagggagaccctgaaaatagactgtaagcaaccttggggtgg
ggtaagcctgttgcagcgttagtgtatccatgaactccttaagatacaagctat
gtgtcattcctcatggagacgccggagagtcttgagcttacatgatggtcctgcg
gaggccttaaagtcctgtggggatgctcagggttgtccctgtgtgtcactgagac
ctccgaaagaatttaaatatcacagaaaaaaaaacataaagaagaccttaagcc
tttttaagttcccaaggagagccagaagtggtggtatatagctcaacttgggaga
```

FIG. 23F

```
ctgaggcaaaaagactgactgagtttaagaccagcctagctacaccacaaagctc
ctttctcaaaagaaaaagctcccaaggaggttggatccccagtgagaccctcagc
aaggccctctggcctcactatggtcctgaggacacccctccacactgccctgatc
ttcttacccatcctgcctgagctcttcacctgctctcctcttgcattcaaatat
cttctgctacagtaggtccactggagtctcccaggtacccagagtgtgaatgtct
gcagcactttctggggacaaggagcagagagcaagggacccacaattcgggtct
agtgtctgtaaagccttgcggagggtagagttctagttcacacaaggcaccaagt
gttttgctggttgcctaggaaacaggacagtgccaaatcaggaacagaaagagt
caaggaaccccaaccactccaagcggaggctgagaaaggttttgtagctggaat
agagcatgcactaacagatggagacagctggctttgagctctgaagcaagtatta
catatggagacttgctggccttcaggtgcttatcttgttattggatactgcagga
ggatgtaccacagggcttcagctcagctgaccccaagtgggatatggaaagaga
gatagaggaggagggaccattaagtgccttgctgcctgaattctgctttccttct
acctctgagagagagctggggactcggctgagttaagaacccagctatcaattgg
aactgtgaaacagtccaagggacaaagatactaggtccccaactgcaacttcctg
gggaatgatgtggaaaaatgctcagccaaggacaaagaaagcatcacccactctg
gaacaatgtccctgctgtgaactggttcatcaggccatcagggccccttgttaa
gactctaattaccctaggactaagtagaggtgttgacgtccaatgagcgctttct
gcagacctagcaccagggaagtgtttggaaactgcagcttcagcccctctggcca
tctgctgacctaccccacctggagcccttaatgggtcaaacagcaaagtccaggg
ggcagagaggaggtgctttggtctataaaggtagtggggacccagtaaccaccgg
cgcgccaagctagcaagttaacaaatcgatccggatcctccaccatgaaaccag
taacgttatacgatgtcgcagagtatgccggtgtctcttatcagaccgtttccg
cgtggtgaaccaggccagccacgtttctgcgaaaacgcgggaaaaagtggaagcg
gcgatggcggagctgaattacattcccaaccgcgtggcacaacaactggcgggca
aacagtcgttgctgattggcgttgccacctccagtctggccctgcacgcgccgtc
gcaaattgtcgcggcgattaaatctcgcgccgatcaactgggtgccagcgtggtg
gtgtcgatggtagaacgaagcggcgtcgaagcctgtaaagcggcggtgcacaatc
ttctcgcgcaacgcgtcagtgggctgatcattaactatccgctggatgaccagga
tgccattgctgtggaagctgcctgcactaatgttccggcgttatttcttgatgtc
tctgaccagacacccatcaacagtattattttctcccatgaagacggtacgcgac
tgggcgtggagcatctggtcgcattgggtcaccagcaaatcgcgctgttagcggg
cccattaagttctgtctcggcgcgtctgcgtctggctggctggcataaatatctc
actcgcaatcaaattcagccgatagcggaacgggaaggcgactggagtgccatgt
ccggttttcaacaaaccatgcaaatgctgaatgagggcatcgttcccactgcgat
gctggttgccaacgatcagatggcgctgggcgcaatgcgcgccattaccgagtcc
gggctgcgcgttggtgcggatatctcggtagtgggatacgacgataccgaagaca
gctcatgttatatcccgccgttaaccaccatcaaacaggattttcgcctgctggg
gcaaaccagcgtggaccgcttgctgcaactctctcagggccaggcggtgaagggc
aatcagctgttgccgtctcactggtgaaaagaaaaaccaccctggcgcccaata
```

FIG. 23G

```
cgcaaaccgcctctccccgcgcgttggccgattcattaatgcagctggcacgaca
ggtttcccgactggaaagcgggcagagaccgccaaaaaagaagagaaaggtcgac
ggcggtggtgctttgtctcctcagcactctgctgtcactcaaggaagtatcatca
agaacaaggagggcatggatgctaagtcactaactgcctggtcccggacactggt
gaccttcaaggatgtatttgtggacttcaccagggaggagtggaagctgctggac
actgctcagcagatcgtgtacagaaatgtgatgctggagaactataagaacctgg
tttccttgggttatcagcttactaagccagatgtgatcctccggttggagaaggg
agaagagccctggctggtggagagagaaattcaccaagagacccatcctgattca
gagactgcatttgaaatcaaatcatcagtttgag
```

FIG. 23H

SEQ ID NO: 11 cgcgccaagctagcaagttaacaaatcgatccgatccnnnngccctctccctcccccccctaacgttactggccgaagcgcttgaataaggc
cggtgcgtttgtctatatgttatttccaccatattgcgtctttggcaatgtgaggccgccgaaacctggcctgtcttcttgacgagcattcctaggggtc
tttcccctctcgccaaaggaatgcaagtctcgttgaatgtcgtgaaggaagcagttcctctgaagacaaacaacgtctgtagcgaccccttttg
cagcagcggaccccccacctggcgacaagtgcctctgccgacaagcacgtgtataagatacacctgcaaaggcgcacaaccccagtgccac
gttgtgagttggatagttgtggaaagagtcaaatgcctctcctcagcgtattcaacaaggggctgaaggatgccagaaggtaccccattgtatggatct
gatctggggctcggtgtgcacatgctttacatgtttagtcgaggtaaaaaaacgtctaggcccggggttggtgccatcctgttcgagtcgagttgacgtaaacggcc
cgatgataatatggccacaaccatggtgagcaagggcgaggagctgttcaccggggtggtgcccatcctggtcgagctggacggcgacgtaaacggcc
acaagttcagcgtgtccggcgagggcgagggcgatgccacctacggcaagctgaccctgaagttcatctgcaccaccggcaagctgcccgtg
cccacctcgtgaccaccctgacctacggcgtgcagtgcttcagccgctaccccgaccacatgaagcagcacgacttcttcaagtccgccatgcccgaa
ggctacgtcccaggagcgcaccatctcttcaaggacgacggcaactacaagacccgcgccgaggtgaagttcgggcgacaccctggtgaaccgcat
cgagctgaagggcatcgacttcaaggaggacggcaacatcctggggcacaagctgaataacactacaacagccaacaactctatatcatggccgaca
agcagaagaacggcatcaaggtgaacttcaagatccgccacaacatcgaggacggcagcgtgcagctcgccgaccactaccagcagaacacccccat
cggcgacggccccgtgctgctgcccgaccactaccccgacaaccactacctgagcaagcaaccgatcacatggtcctg
ctggagttcgtgaccgccgccgggatcactctcggcatggacgagctgtacaagtaagcggccaatcaacctctgattactacaaattgtgaaagattg
actggtattcttaactattctgctccttttacgctatgtggatacgctgctttatcatgctattactcccgtacgctttcattttcttcctcctgtata

FIG. 24B

```
aatcctggttgctgtctctttatgaggagttgtggcccgttgtcaggcaacgtgg
cgtggtgtgcactgtgtttgctgacgcaaccccactggttggggcattgccacc
acctatcaactcctttccgggactttcgctttccccctccctattgccacggcgg
aactcattgccgcctgccttgcccgctgctggacaggggctcggctgttgggcac
tgacaattccgtggtgttgtcggggaagctgacgtccttccatggctgctcgcc
tgtgttgccaactggattctgcgcgggacgtccttctgctacgtccttcggccc
tcaatccagcggaccttccttcccgcggcctgctgccggttctgcggcctcttcc
gcgtcttcgccttcgccctcagacgagtcggatctccctttgggccgcctcccg
cctgcctgcaggtttgtcgagacctagaaaaacatggagcaatcacaagtagcaa
tacagcagctaccaatgctgattgtgcctggctagaagcacaagaggaggaggag
gtgggttttccagtcacacctcaggtacctttaagaccaatgacttacaaggcag
ctgtagatcttagccacttttaaaagaaaagggggactggaagggctaattca
ctcccaacgaagacaagatctgcttttgcttgtactgggtctctctggttagac
cagatctgagcctgggagctctctggctaactagggaacccactgcttaagcctc
aataaagcttgccttgagtgcttcaagtagtgtgtgcccgtctgttgtgtgactc
tggtaactagagatccctcagacccttttagtcagtgtggaaaatctctagcagg
gcccgtttaaacccgctgatcagcctcgactgtgccttctagttgccagccatct
gttgtttgccctccccgtgccttccttgaccctggaaggtgccactcccactg
tcctttcctaataaaatgaggaaattgcatcgcattgtctgagtaggtgtcattc
tattctgggggtggggtgggcaggacagcaaggggaggattgggaagacaat
agcaggcatgctggggatgcggtgggctctatggcttctgaggcggaaagaacca
gctggggctctagggggtatccccacgcgccctgtagcggcgcattaagcgcggc
gggtgtggtggttacgcgcagcgtgaccgctacacttgccagcgccctagcgccc
gctcctttcgctttcttcccttcctttctcgccacgttcgccggctttccccgtc
aagctctaaatcggggcatcccttagggttccgatttagtgctttacggcacct
cgaccccaaaaaacttgattagggtgatggttcacgtagtgggccatcgccctga
tagacggtttttcgccctttgacgttggagtccacgttctttaatagtggactct
tgttccaaactggaacaacactcaaccctatctcggtctattcttttgatttata
agggattttggggatttcggcctattggttaaaaaatgagctgatttaacaaaaa
tttaacgcgaattaattctgtggaatgtgtgtcagttagggtgtggaaagtcccc
aggctcccaggcaggcagaagtatgcaaagcatgcatctcaattagtcagcaac
caggtgtggaaagtccccaggctcccagcaggcagaagtatgcaaagcatgcat
ctcaattagtcagcaaccatagtcccgcccctaactccgcccatcccgcccctaa
ctccgcccagttccgcccattctccgcccatggctgactaattttttttattta
tgcagaggccgaggccgcctctgcctctgagctattccagaagtagtgaggaggc
ttttttggaggcctaggcttttgcaaaaagctcccgggagcttgtatatccattt
tcggatctgatcagcacgtgttgacaattaatcatcggcatagtatatcggcata
gtataatacgacaaggtgaggaactaaaccatggccaagttgaccagtgccgttc
cggtgctcaccgcgcgcgacgtcgccggagcggtcgagttctggaccgaccggct
cgggttctcccgggacttcgtggaggacgacttcgccggtgtggtccgggacgac
```

FIG. 24C

```
gtgaccctgttcatcagcgcggtccaggaccaggtggtgccggacaacaccctgg
cctgggtgtgggtgcgcggcctggacgagctgtacgccgagtggtcggaggtcgt
gtccacgaacttccgggacgcctccgggccggccatgaccgagatcggcgagcag
ccgtgggggcgggagttcgccctgcgcgacccggccggcaactgcgtgcacttcg
tggccgaggagcaggactgacacgtgctacgagatttcgattccaccgccgcctt
ctatgaaaggtlgggcttcggaatcgttttccgggacgccggctggatgatcctc
cagcgcggggatctcatgctggagttcttcgcccaccccaacttgtttattgcag
cttataatggttacaaataaagcaatagcatcacaaatttcacaaataaagcatt
ttttcactgcattctagttgtggtttgtccaaactcatcaatgtatcttatcat
gtctgtataccgtcgacctctagctagagcttggcgtaatcatggtcatagctgt
ttcctgtgtgaaattgttatccgctcacaattccacacaacatacgagccggaag
cataaagtgtaaagcctggggtgcctaatgagtgagctaactcacattaattgcg
ttgcgctcactgcccgctttccagtcgggaaacctgtcgtgccagctgcattaat
gaatcggccaacgcgcggggagaggcggtttgcgtattgggcgctcttccgcttc
ctcgctcactgactcgctgcgctcggtcgttcggctgcggcgagcggtatcagct
cactcaaaggcggtaatacggttatccacagaatcaggggataacgcaggaaaga
acatgtgagcaaaaggccagcaaaaggccaggaaccgtaaaaaggccgcgttgct
ggcgtttttccataggctccgcccccctgacgagcatcacaaaaatcgacgctca
agtcagaggtggcgaaacccgacaggactataaagataccaggcgtttccccctg
gaagctccctcgtgcgctctcctgttccgaccctgccgcttaccggatacctgtc
cgcctttctcccttcgggaagcgtggcgctttctcaatgctcacgctgtaggtat
ctcagttcggtgtaggtcgttcgctccaagctgggctgtgtgcacgaaccccccg
ttcagcccgaccgctgcgccttatccggtaactatcgtcttgagtccaacccggt
aagacacgacttatcgccactggcagcagccactggtaacaggattagcagagcg
aggtatgtaggcggtgctacagagttcttgaagtggtggcctaactacggctaca
ctagaaggacagtatttggtatctgcgctctgctgaagccagttaccttcggaaa
aagagttggtagctcttgatccggcaaacaaaccaccgctggtagcggtggtttt
tttgtttgcaagcagcagattacgcgcagaaaaaaaggatctcaagaagatcctt
tgatcttttctacggggtctgacgctcagtggaacgaaaactcacgttaagggat
tttggtcatgagattatcaaaaaggatcttcacctagatccttttaaattaaaaa
tgaagttttaaatcaatctaaagtatatatgagtaaacttggtctgacagttacc
aatgcttaatcagtgaggcacctatctcagcgatctgtctatttcgttcatccat
agttgcctgactccccgtcgtgtagataactacgatacgggagggcttaccatct
ggccccagtgctgcaatgataccgcgagacccacgctcaccggctccagatttat
cagcaataaaccagccagccggaagggccgagcgcagaagtggtcctgcaacttt
atccgcctccatccagtctattaattgttgccgggaagctagagtaagtagttcg
ccagttaatagtttgcgcaacgttgttgccattgctacaggcatcgtggtgtcac
gctcgtcgtttggtatggcttcattcagctccggttcccaacgatcaaggcgagt
tacatgatcccccatgttgtgcaaaaaagcggttagctccttcggtcctccgatc
gttgtcagaagtaagttggccgcagtgttatcactcatggttatggcagcactgc
```

FIG. 24D

```
ataattctcttactgtcatgccatccgtaagatgcttttctgtgactggtgagta
ctcaaccaagtcattctgagaatagtgtatgcggcgaccgagttgctcttgcccg
gcgtcaatacgggataataccgcgccacatagcagaactttaaaagtgctcatca
ttggaaaacgttcttcggggcgaaaactctcaaggatcttaccgctgttgagatc
cagttcgatgtaacccactcgtgcacccaactgatcttcagcatcttttactttc
accagcgtttctgggtgagcaaaaacaggaaggcaaaatgccgcaaaaaagggaa
taagggcgacacggaaatgttgaatactcatactcttccttttcaatattattg
aagcatttatcagggttattgtctcatgagcggatacatatttgaatgtatttag
aaaaataaacaatagggGttccgcgcacatttccccgaaaagtgccacctgacg
tcgacggatcgggagatctcccgatcccctatggtgcactctcagtacaatctgc
tctgatgccgcatagttaagccagtatctgctccctgcttgtgtgttggaggtcg
ctgagtagtgcgcgagcaaaatttaagctacaacaaggcaaggcttgaccgacaa
ttgcatgaagaatctgcttagggttaggcgttttgcgctgcttcgcgatgtacgg
gccagatatacgcgttgacattgattattgactagttattaatagtaatcaatta
cggggtcattagttcatagcccatatatggagttccgcgttacataacttacggt
aaatggcccgcctggctgaccgcccaacgacccccgcccattgacgtcaataatg
acgtatgttcccatagtaacgccaatagggactttccattgacgtcaatgggtgg
actatttacggtaaactgcccacttggcagtacatcaagtgtatcatatgccaag
tacgccccctattgacgtcaatgacggtaaatggcccgcctggcattatgcccag
tacatgaccttatgggactttcctacttggcagtacatctacgtattagtcatcg
ctattaccatggtgatgcggttttggcagtacatcaatgggcgtggatagcggtt
tgactcacggggatttccaagtctccaccccattgacgtcaatgggagtttgttt
tggcaccaaaatcaacgggactttccaaaatgtcgtaacaactccgccccattga
cgcaaatgggcggtaggcgtgtacggtgggaggtctatataagcagagctctctg
gctaactagagaacccactgcttactggcttatcgaaattaatacgactcactat
agggagacccaagctggtttaaacttaagcttggtaccgagctcactagtccagt
gtggtggcagatatccagcacagtggcggccgctcgagtctagagggcccgttta
aacnnnnngggtctctctggttagaccagatctgagcctgggagctctctggcta
actagggaacccactgcttaagcctcaataaagcttgccttgagtgcttcaagta
gtgtgtgcccgtctgttgtgtgactctggtaactagagatccctcagaccctttt
agtcagtgtggaaaatctctagcannnnnnnnnnccagcaacttatctgtgtctg
tccgattgtctagtgtctatgtttgatgttatgcgcctgcgtctgtactagttag
ctaactagctctgtatctggcggaccgtggtggaactgacgagttctgaacacc
cggccgcaaccctgggagacgtcccagggactttggggccgttttgtggcccg
acctgaggaagggagtcgatgtggaatccgacccgtcaggatatgtggttctgg
taggagacgagaacctaaaacagttcccgcctccgtctgaattttgctttcggt
ttggaaccgaagccgcgcgtcttgtctgctgcagcgctgcagcatcgttctgtgt
tgtctctgtctgactgtgtttctgtatttgtctgaaaattagggccagactgtta
ccactcccttaagtttgaccttaggtcactggaaagatgtcgagcggatcgctca
caaccagtcggtagatgtcaagaagagacgttgggttaccttctgctctgcagaa
```

FIG. 24E

```
tggccaacctttaacgtcggatggccgcgagacggcacctttaaccgagacctca
tcacccaggttaagatcaaggtcttttcacctggcccgcatggacacccagacca
ggtcccctacatcgtgacctgggaagccttggcttttgaccccctccctgggtc
aagcccttgtacaccctaagcctccgcctcctcttcctccatccgcccgtctc
tcccccttgaacctcctcgttcgaccccgcctcgatcctccctttatccagccct
cactccttctctaggcgccnnnnnggaaaagtttagtaaaacaccatatgtatgt
ttcagggaaagctaggggatggttttatagacatcactatgaaagccctcatcca
agaataagttcagaagtacacatcccactaggggatgctagattggtaataacaa
catattggggtctgcatacaggagaaagagactggcatctgggtcagggagtctc
catagaatggaggaaaaagagatatagcacacaagtagaccctgaactagcagac
caactaattcatctgtattactttgactgttttcagactctgctataagaaagg
ccttattaggacatatagttagccctaggtgtgaatatcaagcaggacataacaa
ggtaggatctctacaatacttggcactagcagcattaataacaccaaaaaagata
aagccacctttgcctagtgttacgaaactgacagaggatagatggaacaagcccc
agaagaccaagggccacagagggagccacacaatgaatggacactagagctttta
gaggagcttaagaatgaagctgttagacattttcctaggatttggctccatggct
tagggcaacatatctatgaaacttatggggatacttgggcaggagtggaagccat
aataatgcaacaactgctgtttatccatttcagaattgggtgtcgacatagcaga
ataggcgttactcaacagaggagagcaagaaatggagccagtagatcctagacta
gagccctggaagcatccaggaagtcagcctaaaactgcttgtaccacttgctatt
gtaaaaagtgttgctttcattgccaagtttgtttcacaacaaaagccttaggcat
ctcctatggcaggaagaagcggagacagcgacgaagacctcctcaaggcagtcag
actcatcaagtttctctatcaaagcagtaagtagtacatgtaatgcaacctatac
aaatagcaatagcagcattagtagtagcaataataatagcaatagttgtgtggtc
catagtaatcatagaatataggaaaatattaagacaaagaaaatagacaggtta
attgatagactaatnnnnnnnnngggcccgaaggaatagaagaagaaggtggagaga
gagacagagacagatccattcgattagtgaacggatcggcactgcgtgcgccaat
tctgcagacaaatggcagtattcatccacaatttaaaagaaaaggggggattgg
ggggtacagtgcaggggaaagaatagtagacataatagcaacagacatacaaact
aaagaattacaaaaacaaattacaaaaattcaaaattttcgggtttattacaggg
acagcagagatccagtttggttaattaatgctgctgagccacgtgaagccttaag
ccgcagggagaccctgaaaatagactgtaagcaaccttggggtggggtaagcctg
ttgcagcgttagtgtatccatgaactcctttaagatacaagctatgtgtcattcc
tcatggagacgccggagagtcttgagcttacatgatggtcctgcggaggccttaa
agtcctgtggggatgctcaggggttgtccctgtgtgtcactgagacctccgaaaga
atttaaatatcacagaaaaaaaacataaagaagaccttaagccttttttaagtt
cccaaggagagccagaagtggtggtatatagctcaacttgggagactgaggcaaa
aagactgactgagtttaagaccagcctagctacaccacaaagctcctttctcaaa
agaaaaagctcccaaggaggttggatcccagtgagaccctcagcaaggccctct
ggcctcactatggtcctgaggacacccctccacactgccctgatcttcttacccc
```

FIG. 24F

```
atcctgcctgagctcttcacctgctctcctcttgcattcaaatatcttctgctac
agtaggtccactggagtctcccaggtacccagagtgtgaatgtctgcagcacttt
ctgggggacaaggagcagagagcaagggacccacaattcgggtctagtgtctgta
aagccttgcggagggtagagttctagttcacacaaggcaccaagtgtttttgctg
gttgcctaggaaacaggacagtgccaaatcaggaacagaaagagtcaaggaaccc
ccaaccactccaagcggaggctgagaaaggttttgtagctggaatagagcatgca
ctaacagatggagacagctggctttgagctctgaagcaagtattacatatggaga
cttgctggccttcaggtgcttatcttgttattggatactgcaggaggatgtacca
cagggcttcagctcagctgaccccaagtgggatatggaaagagagatagaggag
gagggaccattaagtgccttgctgcctgaattctgctttccttctacctctgaga
gagagctggggactcggctgagttaagaacccagctatcaattggaactgtgaaa
cagtccaagggacaaagatactaggtccccaactgcaacttcctggggaatgatg
tggaaaaatgctcagccaaggacaaagaaagcatcaccactctggaacaatgtc
ccctgctgtgaactggttcatcaggccatcagggccccttgttaagactctaatt
accctaggactaagtagaggtgttgacgtccaatgagcgctttctgcagacctag
caccagggaagtgtttggaaactgcagcttcagccctctggccatctgctgacc
tacccacctggagcccttaatgggtcaaacagcaaagtccaggggcagagagg
aggtgctttggtctataaaggtagtggggacccagtaaccaccgg
```

FIG. 24G

SEQ ID NO: 12 tacagtgcaggggaaagaatagtagacataatagcaacagacatacaaactaaagaattacaaaaacaaattcaaaattttcgggttattaca
gggacagcagagatccagtttggttaattaattggctccggtccgtgccgtccgtgcagtggcagagcgcacatcgccacagtcccgagaagttggggggagg
ggtcgcaattgaaccgtgcctagagaaggtggcgcgggtaaactggaaagtgatgtcgtgtactgctcccgcctttttcccgaggtggggaga
accgtatataagtgcagtagtccccttgcgtgcctgaacgttcttttttcgcaacggtttgccgccagaacacagtaagtgccgtgtggttcccgcggcctgcct
ctttacgggttatgcccttgcgtgccttgaattacttccacctggctgctgcagtacgtgattcttgatcccgaccgccgcgaatcttgtcgttgggaggagttcga
ggccttgccttgcttaaggagccccttcgtcgtgcttgagttgaggcctggcgcgcttgcggcgacgctctttttctggcaagatagtcttgtaaatgcggccaagatctgcaca
tctcgctcgtcttcgataagtctctagccattaaaattttgatgacctgtcgctcccagcgcacatgttcggcgaggcggggcctgcgagcgcggccaccgag
ctggtatttcggttttttgggccggccgacgggcccgtgctctggtgcctgcctgctgccgcgcgcgcccgcccgtatcgcccgcaagctgccggt
aatcgacggggtagtctcaagctggaaagatggccgctccagggagctcaggagctcaaaatgaaggagcgcggcgccgagctcggagagcggcgggt
cggcaccagttgcgtgagcggaaaaggccttcccgtccgctccagcgcctcatgtgatgaggtttatgcgatgaggttcattctgactccaggccgcctgactctgattagttct
gagtcaccacacaaaggaaaaaggccttcccgtccgctccagcgcctcatgtgatgaggtttatgcgatgaggttcattctgactccaggccgcctgactctgattagttct
cgagctttggagtacgtcgtcttaggttggggggaggttcgccctttgaattctccttgaatttgccctttgagttcggatcttggttcattctcagactgagtgggagactaggcagcttggc
acttgatgtaattctctcctttgaattgccctttgagttcggatcttggttcattctgactccaggccgcctgactctgattagttctcagtgtcgtgag
gaattcggccattacggccgccaccatgcctagacagagagagccaccatgctagtagtgtagagcagctcacattgtattgtcgatgacgcttgctcgacgcttagcattgagatgt
caacccgtaaactgccagaagctcgggcttaaagtagagcatgtgtaaataacgctattgtattgcatgtaaaaataacgctaaagtgcttgctcgacgcttagcattgagatgt
tagataggcaccatactgccttttgcccttttagaagggaagctggcaagattttttacgtaataacgctaaagtttagatgtgcttactaagtcatcgcga

FIG. 25B tggagcaaaagtacatttaggtacacggcctacagaaaaacagtatgaaactctcg
aaaatcaattagccttttatgccaacaaggttttcactagagaatgcattatat
gcactcagcgctgtggggcattttactttaggttgcgtattggaagatcaagagca
tcaagtcgctaaagaagaaagggaaacacctactactgatagtatgccgccattat
tacgacaagctatcgaattatttgatcaccaaggtgcagagccagccttcttattc
ggccttgaattgatcatatgcggattagaaaaacaacttaaatgtgaaagtgggtc
gccaaaaagaagagaaaggtcgacggcggtggtgctttgtctcctcagcactctg
ctgtcactcaaggaagtatcatcaagaacaaggagggcatggatgctaagtcacta
actgcctggtcccggacactggtgaccttcaaggatgtatttgtggacttcaccag
ggaggagtggaagctgctggacactgctcagcagatcgtgtacagaaatgtgatgc
tggagaactataagaacctggtttccttgggttatcagcttactaagccagatgtg
atcctccggttggagaagggagaagagccctggctggtggagagagaaattcacca
agagacccatcctgattcagagactgcatttgaaatcaaatcatcagtttaaggcc
gcctcggccatcgataaggatccggaatgcccctctcctcccccccccctaacgt
tactggccgaagccgcttggaataaggccggtgtgcgtttgtctatatgttatttt
ccaccatattgccgtcttttggcaatgtgagggcccggaaacctggccctgtcttc
ttgacgagcattcctaggggtctttccctctcgccaaaggaatgcaaggtctgtt
gaatgtcgtgaaggaagcagttcctctggaagcttcttgaagacaaacaacgtctg
tagcgacccttgcaggcagcggaaccccccacctggcgacaggtgcctctgcggc
caaaagccacgtgtataagatacacctgcaaaggcggcacaacccagtgccacgt
tgtgagttggatagttgtggaaagagtcaaatggctctcctcaagcgtattcaaca
aggggctgaaggatgcccagaaggtacccattgtatgggatctgatctggggcct
cggtgcacatgctttacatgtgtttagtcgaggttaaaaaaacgtctaggccccc
gaaccacggggacgtggttttccttttgaaaaacacgatgataatatggccacaacc
atgaccgagtacaagcccacggtgcgcctcgccacccgcgacgacgtccccccgggc
cgtacgcacccttcgccgccgcgttcgccgactacccgccacgcgccacaccgtcg
acccggaccgccacatcgagcgggtcaccgagctgcaagaactcttcctcacgcgc
gtcgggctcgacatcggcaaggtgtgggtcgcggacgacggcgccgcggtggcggt
ctggaccacgccggagagcgtcgaagcggggcggtgttcgccgagatcggcccgc
gcatggccgagttgagcggttcccggctggccgcgcagcaacagatggaaggcctc
ctggcgccgcaccggcccaaggagcccgcgtggttcctggccaccgtcggcgtctc
gcccgaccaccagggcaagggtctgggcagcgccgtcgtgctccccggagtggagg
cggccgagcgcgccggggtgcccgccttcctggagacctccgcgccccgcaacctc
cccttctacgagcggctcggcttcaccgtcaccgccgacgtcgaggtgcccgaagg
accgcgcacctggtgcatgacccgcaagcccggtgcctgagcggccgcaatcaacc
tctggattacaaaatttgtgaaagattgactggtattcttaactatgttgctcctt
ttacgctatgtggatacgctgctttaatgcctttgtatcatgctattacttcccgt
acggctttcattttctcctccttgtataaatcctggttgctgtctctttatgagga
gttgtggcccgttgtcaggcaacgtggcgtggtgtgcactgtgtttgctgacgcaa
ccccactggttggggcattgccaccacctatcaactccttccgggactttcgct
ttcccccctccctattgccacggcggaactcattgccgcctgccttgcccgctgctg
```

FIG.25C

```
gacaggggctcggctgttgggcactgacaattccgtggtgttgtcggggaagctga
cgtcctttccatggctgctcgcctgtgttgccaactggattctgcgcgggacgtcc
ttctgctacgtcccttcggccctcaatccagcggaccttccttcccgcggcctgct
gccggttctgcggcctcttccgcgtcttcgccttcgccctcagacgagtcggatct
cccttttgggccgcctccccgcctgcctgcaggtttgtcgagacctagaaaaacatg
gagcaatcacaagtagcaatacagcagctaccaatgctgattgtgcctggctagaa
gcacaagaggaggaggaggtggggttttccagtcacacctcaggtacctttaagacc
aatgacttacaaggcagctgtagatcttagccacttttttaaaagaaaaggggggac
tggaagggctaattcactcccaacgaagacaagatctgcttttttgcttgtactggg
tctctctggttagaccagatctgagcctgggagctctctggctaactagggaaccc
actgcttaagcctcaataaagcttgccttgagtgcttcaagtagtgtgtgcccgtc
tgttgtgtgactctggtaactagagatccctcagacccttttagtcagtgtggaaa
atctctagcagggcccgtttaaacccgctgatcagcctcgactgtgccttctagtt
gccagccatctgttgtttgcccctcccccgtgccttccttgacctggaaggtgcc
actcccactgtcctttcctaataaaatgaggaaattgcatcgcattgtctgagtag
gtgtcattctattctggggggtggggtggggcaggacagcaaggggggaggattggg
aagacaatagcaggcatgctggggatgcggtgggctctatggcttctgaggcggaa
agaaccagctggggctctaggggggtatccccacgcgccctgtagcggcgcattaag
cgcggcgggtgtggtggttacgcgcagcgtgaccgctacacttgccagcgccctag
cgcccgctcctttcgctttcttccttccttctcgccacgttcgccggctttccc
cgtcaagctctaaatcggggcatcccttttagggttccgatttagtgctttacggca
cctcgaccccaaaaaacttgattagggtgatggttcacgtagtgggccatcgccct
gatagacggtttttcgccctttgacgttggagtccacgttctttaatagtggactc
ttgttccaaactggaacaacactcaacccttatctcggtctattcttttgatttata
agggatttgggggatttcggcctattggttaaaaaatgagctgatttaacaaaaat
ttaacgcgaattaattctgtggaatgtgtgtcagttagggtgtggaaagtccccag
gctccccaggcaggcagaagtatgcaaagcatgcatctcaattagtcagcaaccag
gtgtggaaagtccccaggctccccagcaggcagaagtatgcaaagcatgcatctca
attagtcagcaaccatagtcccgcccctaactccgcccatcccgccccttaactccg
cccagttccgcccattctccgcccatggctgactaattttttttatttatgcaga
ggccgaggccgcctctgcctctgagctattccagaagtagtgaggaggctttttg
gaggcctaggcttttgcaaaaagctcccgggagcttgtatatccattttcggatct
gatcagcacgtgttgacaattaatcatcggcatagtatatcggcatagtataatac
gacaaggtgaggaactaaaccatggccaagttgaccagtgccgttccggtgctcac
cgcgcgcgacgtcgccggagcggtcgagttctggaccgaccggctcgggttctccc
gggacttcgtggaggacgacttcgccggtgtggtccgggacgacgtgaccctgttc
atcagcgcggtccaggaccaggtggtgccggacaacaccctggcctgggtgtgggt
gcgcggcctggacgagctgtacgccgagtggtcggaggtcgtgtccacgaacttcc
gggacgcctccgggccggccatgaccgagatcggcgagcagccgtggggcgggag
ttcgccctgcgcgacccggccggcaactgcgtgcacttcgtggccgaggagcagga
ctgacacgtgctacgagatttcgattccaccgccgccttctatgaaaggttgggct
tcggaatcgttttccgggacgccggctggatgatcctccagcgcggggatctcatg
```

FIG.25D ctggagttcttcgcccaccccaacttgtttattgcagcttataatggttacaaata
aagcaatagcatcacaaatttcacaaataaagcattttttttcactgcattctagtt
gtggtttgtccaaactcatcaatgtatcttatcatgtctgtataccgtcgacctct
agctagagcttggcgtaatcatggtcatagctgtttcctgtgtgaaattgttatcc
gctcacaattccacacaacatacgagccggaagcataaagtgtaaagcctggggtg
cctaatgagtgagctaactcacattaattgcgttgcgctcactgcccgctttccag
tcgggaaacctgtcgtgccagctgcattaatgaatcggccaacgcgcggggagagg
cggtttgcgtattgggcgctcttccgcttcctcgctcactgactcgctgcgctcgg
tcgttcggctgcggcgagcggtatcagctcactcaaaggcggtaatacggttatcc
acagaatcaggggataacgcaggaaagaacatgtgagcaaaaggccagcaaaaggc
caggaaccgtaaaaaggccgcgttgctggcgtttttccataggctccgcccccctg
acgagcatcacaaaaatcgacgctcaagtcagaggtggcgaaacccgacaggacta
taaagataccaggcgtttccccctggaagctccctcgtgcgctctcctgttccgac
cctgccgcttaccggatacctgtccgcctttctcccttcgggaagcgtggcgcttt
ctcaatgctcacgctgtaggtatctcagttcggtgtaggtcgttcgctccaagctg
ggctgtgtgcacgaaccccccgttcagcccgaccgctgcgccttatccggtaacta
tcgtcttgagtccaacccggtaagacacgacttatcgccactggcagcagccactg
gtaacaggattagcagagcgaggtatgtaggcggtgctacagagttcttgaagtgg
tggcctaactacggctacactagaaggacagtatttggtatctgcgctctgctgaa
gccagttaccttcggaaaaagagttggtagctcttgatccggcaaacaaaccaccg
ctggtagcggtggtttttttgtttgcaagcagcagattacgcgcagaaaaaaagga
tctcaagaagatcctttgatcttttctacggggtctgacgctcagtggaacgaaaa
ctcacgttaagggattttggtcatgagattatcaaaaaggatcttcacctagatcc
ttttaaattaaaaatgaagttttaaatcaatctaaagtatatatgagtaaacttgg
tctgacagttaccaatgcttaatcagtgaggcacctatctcagcgatctgtctatt
tcgttcatccatagttgcctgactccccgtcgtgtagataactacgatacgggagg
gcttaccatctggccccagtgctgcaatgataccgcgagacccacgctcaccggct
ccagatttatcagcaataaaccagccagccggaagggccgagcgcagaagtggtcc
tgcaactttatccgcctccatccagtctattaattgttgccgggaagctagagtaa
gtagttcgccagttaatagtttgcgcaacgttgttgccattgctacaggcatcgtg
gtgtcacgctcgtcgtttggtatggcttcattcagctccggttcccaacgatcaag
gcgagttacatgatccccatgttgtgcaaaaaagcggttagctccttcggtcctc
cgatcgttgtcagaagtaagttggccgcagtgttatcactcatggttatggcagca
ctgcataattctcttactgtcatgccatccgtaagatgcttttctgtgactggtga
gtactcaaccaagtcattctgagaatagtgtatgcggcgaccgagttgctcttgcc
cggcgtcaatacgggataataccgcgccacatagcagaactttaaaagtgctcatc
attggaaaacgttcttcggggcgaaaactctcaaggatcttaccgctgttgagatc
cagttcgatgtaacccactcgtgcacccaactgatcttcagcatcttttactttca
ccagcgtttctgggtgagcaaaaacaggaaggcaaaatgccgcaaaaaagggaata
agggcgacacggaaatgttgaatactcatactcttccttttcaatattattgaag
catttatcaggttattgtctcatgagcggatacatatttgaatgtatttagaaaa
ataaacaatagggggttccgcgcacatttccccgaaaagtgccacctgacgtcgac

FIG.25E ggatcgggagatctcccgatcccctatggtgcactctcagtacaatctgctctgat
gccgcatagttaagccagtatctgctccctgcttgtgtgttggaggtcgctgagta
gtgcgcgagcaaaatttaagctacaacaaggcaaggcttgaccgacaattgcatga
agaatctgcttagggttaggcgttttgcgctgcttcgcgatgtacgggccagatat
acgcgttgacattgattattgactagttattaatagtaatcaattacggggtcatt
agttcatagcccatatatggagttccgcgttacataacttacggtaaatggcccgc
ctggctgaccgcccaacgaccccgcccattgacgtcaataatgacgtatgttccc
atagtaacgccaatagggactttccattgacgtcaatgggtggactatttacggta
aactgcccacttggcagtacatcaagtgtatcatatgccaagtacgccccctattg
acgtcaatgacggtaaatggcccgcctggcattatgcccagtacatgaccttatgg
gactttcctacttggcagtacatctacgtattagtcatcgctattaccatggtgat
gcggttttggcagtacatcaatgggcgtggatagcggtttgactcacggggatttc
caagtctccaccccattgacgtcaatgggagtttgttttggcaccaaaatcaacgg
gactttccaaaatgtcgtaacaactccgccccattgacgcaaatgggcggtaggcg
tgtacggtgggaggtctatataagcagagcggtttaaacttaagcttggtaccgag
ctcactagtccagtgtggtggcagatatccagcacagtggcggccgctcgagtcta
gagggcccgttttgcctgtactgggtctctctggttagaccagatctgagcctggg
agctctctggctaactagggaacccactgcttaagcctcaataaagcttgccttga
gtgcttcaagtagtgtgtgcccgtctgttgtgtgactctggtaactagagatccct
cagacccttttagtcagtgtggaaaatctctagcagtggcgcccgaacagggactt
gaaagcgaaagggaaaccagaggagctctctcgacgcaggactcggcttgctgaag
cgcgcacggcaagaggcgaggggcggcgactggtgagtacgccaaaaattttgact
agcggaggctagaaggagagagatgggtgcgagagcgtcagtattaagcgggggag
aattagatcgcgatgggaaaaaattcggttaaggccaggggggaagaaaaaatata
aattaaaacatatagtatgggcaagcagggagctagaacgattcgcagttaatcct
ggcctgttagaaacatcagaaggctgtagacaaatactgggacagctacaaccatc
ccttcagacaggatcagaagaacttagatcattatataatacagtagcaaccctct
attgtgtgcatcaaaggatagagataaaagacaccaaggaagctttagacaagata
gaggaagagcaaaacaaaagtaagaccaccgcacagcaagcggccgctgatcttca
gacctggaggaggagatatgagggacaattggagaagtgaattatataaatataaa
gtagtaaaaattgaaccattaggagtagcacccaccaaggcaaagagaagagtggt
gcagagagaaaaaagagcagtgggaataggagctttgttccttgggttcttgggag
cagcaggaagcactatgggcgcagcgtcaatgacgctgacggtacaggccagacaa
ttattgtctggtatagtgcagcagcagaacaatttgctgagggctattgaggcgca
acagcatctgttgcaactcacagtctggggcatcaagcagctccaggcaagaatcc
tggctgtggaaagatacctaaaggatcaacagctcctggggatttggggttgctct
ggaaaactcatttgcaccactgctgtgccttggaatgctagttggagtaataaatc
tctggaacagatttggaatcacacgacctggatggagtgggacagagaaattaaca
attacacaagcttaatacactccttaattgaagaatcgcaaaaccagcaagaaaag
aatgaacaagaattattggaattagataaatgggcaagtttgtggaattggtttaa
cataacaaattggctgtggtatataaaattattcataatgatagtaggaggcttg
gtaggtttaagaatagttttgctgtactttctatagtgaatagagttaggcaggg

FIG.25F

```
atattcaccattatcgtttcagacccacctcccaaccccgaggggacccgacaggc
ccgaaggaatagaagaagaaggtggagagagagacagagacagatccattcgatta
gtgaacggatcggcactgcgtgcgccaattctgcagacaaatggcagtattcatcc
acaatttttaaaagaaaaggggggattgggggg
```

FIG.25G

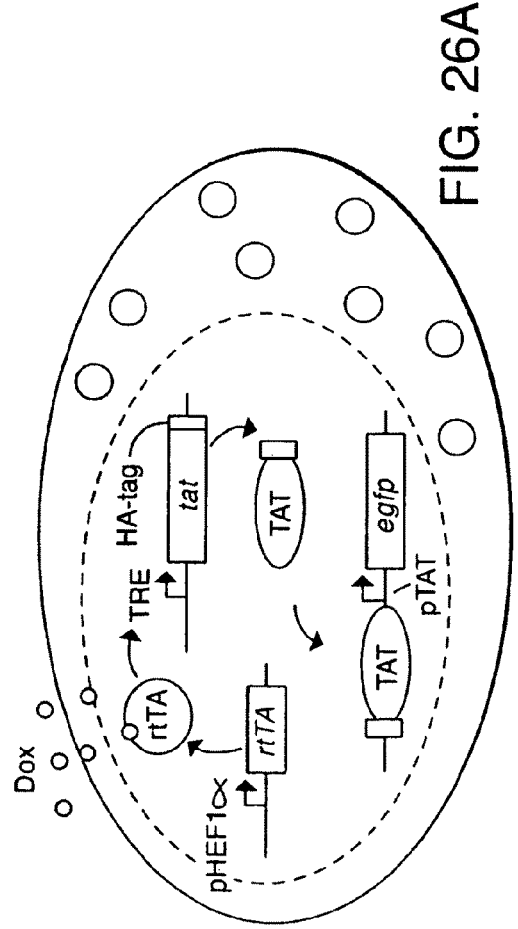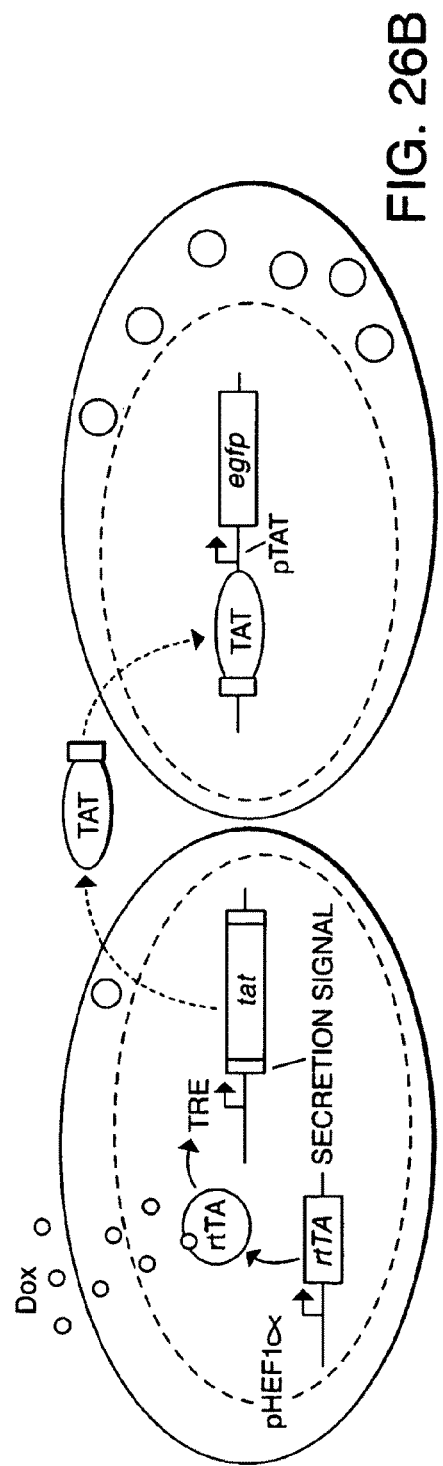

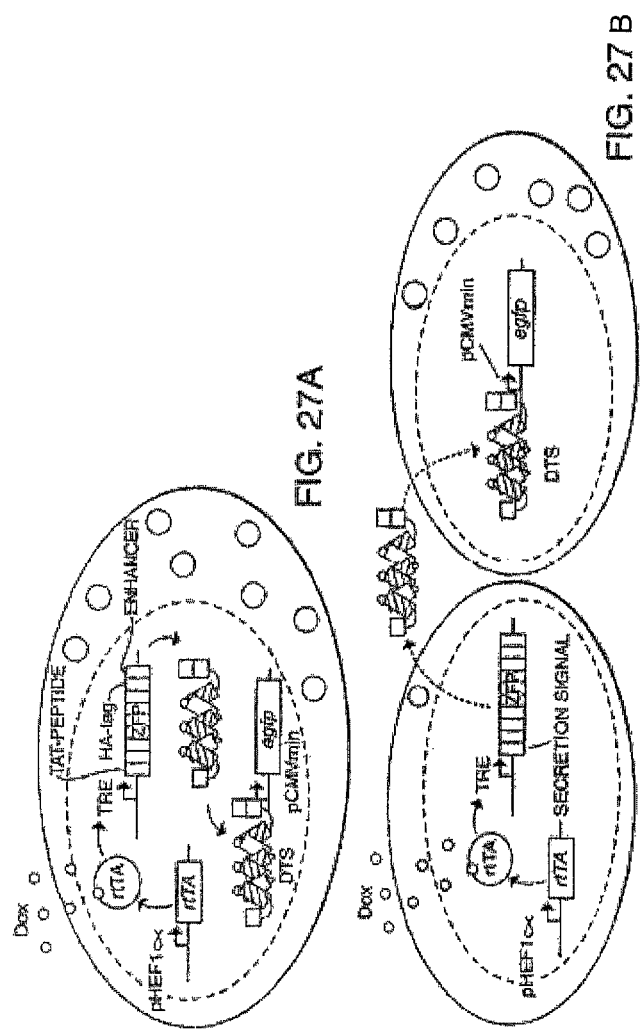

aatgaagctactgtcttctatcgaacaagcatgcgatatttgccgacttaaaaagctcaagtgctccaagaaaaccgaagtgcg
ccaagtgtctgaagaacaactgggagtgtcgctactctcccaaaaccaaaagtctccgctgactaggcacatctgacagaag
tggaatcaaggctagaaagactgaacagctatttctactgattttcctcgagagaccttgacatgattttgaaaatgattcttta
caggatataaaagcattgttaacagattatttgtacaagatagtgcatagaataagtgcgacatcatccgttgatttatgccaggagtaactcgaagagagtagtaacaaagtcaagacagt
actgatatgcctctaacattgagacagcatagaataagtgcgacatcatccgttgattttatgccaggatgctcttcatgatttgatt
tgactgtatcgattgactggcagctcatcatgatgaactccacaatccgttgattttatgccaggatgctcttcatgatttgatt
ggtctgaagaggatgacatgtcgatgtcggatgcttgccttgcccttcctgaaaacggaccccaacaataatggttctttggcgacggttctctc
ttatgtattcttcgatctattgcttaaaccgaaaattacacgaactctaacgttaacaggctccgaccatgattacgatagata
cacgttggcttctagatccacaacatccgtttacttcaaagttatctcaataatttcaccctatgccctatcgtgcactcaccga
cgctaatgatgttgtataataaccagatgaaatcgtcgaaggatcaatgcaaatcctttttaactgcatatgcatatagccatgg
ctggtgtatagaggggaatctactgactgatatagatgttttttactatacaatctcatttgacgagcaaggtcttcgagtcag
gttccataattttggtgacagccctacatcttctgtcgcgataaaaggaccccctcgctttatgtgtcatcatccagcagtccagtgcatttctcagaatacaatctcctt
ctttccataagaatgccatatcattgggcttgaataggaaccccctcgctttatgtgtcatcatccagcagtccagtgcatttctcagaatacaatctcctt
ccgaattggtggtctgtctactctgggagatccaattgtccctgcttttatgtgtcatcatccagcagtccagtgcatttctcagaatacaatctcctt
ccctcttctgtcgacgatgtgcagctgacaactagacaaaacagtaactgcagaaaaaacagtcctatatgtgcaaaaaaatgcttgatgatttgtaatga
ttttcacaaaatctatgaactagacaaaacagtaactgcagaaaaaacagtcctatatgtgcaaaaaaatgcttgatgatttgtaatga
gattgaggagtttcgagacaggcaccaaagtttaacaaatgatcataaatggataatgggaaacagttgtcttcttattaagagattttttcactaatttaccaga
ttgctatcctttacaagattcgaactgaagtggaaacagttgtcttcttattaagagattttttcactaatttaccaga
aaagtcacaactagaacaggatcaaatgatcaaagttatgaagttaaacgatgctcatcatgttaagcgatgcagcaca
aagaactgttatgtctgtaagtagctatatggacaatcatatgtcacccatatttgcctgaattgttcttattacttgttcaatgca

FIG. 28B gtcctagtacccataaagactctactctcaaactcaaaatcgaatgctgagaata
acgagaccgcacaattattacaacaaattaacactgttctgatgctattaaaaaa
actggccacttttaaaatccagacttgtgaaaaatacattcaagtactggaagag
gtatgtgcgccgtttctgttatcacagtgtgcaatcccattaccgcatatcagtt
ataacaatagtaatggtagcgccattaaaaatattgtcggttctgcaactatcgc
ccaatacCctactcttccggaggaaaatgtcaacaatatcagtgttaaatatgtt
tctcctggctcagtagggccttcacctgtgccattgaaatcaggagcaagtttca
gtgatctagtcaagctgttatctaaccgtccaccctctcgtaactctccagtgac
aataccaagaagcacaccttcgcatcgctcagtcacgccttttctagggcaacag
caacagctgcaatcattagtgccactgacccgtctgctttgtttggtggcgcca
attttaatcaaagtgggaatattgctgatagctcattgtccttcactttcactaa
cagtagcaacggtccgaacctcataacaactcaaacaaattctcaagcgctttca
caaccaattgcctcctctaacgttcatgataacttcatgaataatgaaatcacgg
ctagtaaaattgatgatggtaataattcaaaaccactgtcacctggttggacgga
ccaaactgcgtataacgcgtttggaatcactacagggatgtttaataccactaca
atggatgatgtatataactatctattcgatgatgaagataccccaccaaacccaa
aaaagagtaagaattcgatatcaagcttatcgataatcaacctctggattacaa
aatttgtgaaagattgactggtattcttaactatgttgctccttttacgctatgt
ggatacgctgctttaatgcctttgtatcatgctattacttcccgtacggctttca
ttttctcctccttgtataaatcctggttgctgtctctttatgaggagttgtggcc
cgttgtcaggcaacgtggcgtggtgtgcactgtgtttgctgacgcaaccccact
ggttggggcattgccaccacctatcaactcctttccgggactttcgctttcccc
tccctattgccacggcggaactcattgccgcctgccttgcccgctgctggacagg
ggctcggctgtgggcactgacaattccgtggtgttgtcggggaagctgacgtcc
tttccatggctgctcgcctgtgttgccaactggattctgcgcgggacgtccttct
gctacgtcccttcggccctcaatccagcggaccttccttcccgcggcctgctgcc
ggttctgcggcctcttccgcgtcttcgccttcgccctcagacgagtcggatctcc
ctttgggccgcctccccgcctgcctgcaggtttgtcgagacctagaaaaacatgg
agcaatcacaagtagcaatacagcagctaccaatgctgattgtgcctggctagaa
gcacaagaggaggaggaggtgggttttccagtcacacctcaggtacctttaagac
caatgacttacaaggcagctgtagatcttagccacttttaaaagaaaaggggggg
actggaagggctaattcactcccaacgaagacaagatctgcttttgcttgtact
gggtctctctggttagaccagatctgagcctgggagctctctggctaactaggga
acccactgcttaagcctcaataaagcttgccttgagtgcttcaagtagtgtgtgc
ccgtctgttgtgtgactctggtaactagagatccctcagacccttttagtcagtg
tggaaaatctctagcagggcccgtttaaaccgctgatcagcctcgactgtgcct
tctagttgccagccatctgttgtttgcccctcccccgtgccttccttgaccctgg
aaggtgccactcccactgtcctttcctaataaaatgaggaaattgcatcgcattg
tctgagtaggtgtcattctattctggggggtggggtggggcaggacagcaagggg
gaggattgggaagacaatagcaggcatgctggggatgcggtgggctctatggctt

FIG. 28C ctgaggcggaaagaaccagctggggctctaggggggtatccccacgcgccctgtag
cggcgcattaagcgcggcgggtgtggtggttacgcgcagcgtgaccgctacactt
gccagcgccctagcgcccgctcctttcgctttcttcccttcctttctcgccacgt
tcgccggctttccccgtcaagctctaaatcggggcatccctttagggttccgatt
tagtgctttacggcacctcgaccccaaaaaacttgattagggtgatggttcacgt
agtgggccatcgccctgatagacggttttttcgccctttgacgttggagtccacgt
tctttaatagtggactcttgttccaaactggaacaacactcaaccctatctcggt
ctattcttttgatttataagggatttttggggatttcggcctattggttaaaaaat
gagctgatttaacaaaaatttaacgcgaattaattctgtggaatgtgtgtcagtt
agggtgtggaaagtccccaggctccccaggcaggcagaagtatgcaaagcatgca
tctcaattagtcagcaaccaggtgtggaaagtccccaggctccccagcaggcaga
agtatgcaaagcatgcatctcaattagtcagcaaccatagtcccgcccctaactc
cgcccatcccgcccctaactccgcccagttccgcccattctccgccccatggctg
actaatttttttatttatgcagaggccgaggccgcctctgcctctgagctattc
cagaagtagtgaggaggcttttttggaggcctaggcttttgcaaaaagctcccgg
gagcttgtatatccattttcggatctgatcagcacgtgttgacaattaatcatcg
gcatagtatatcggcatagtataatacgacaaggtgaggaactaaaccatggcca
agttgaccagtgccgttccggtgctcaccgcgcgcgacgtcgccggagcggtcga
gttctggaccgaccggctcgggttctcccgggacttcgtggaggacgacttcgcc
ggtgtggtccgggacgacgtgaccctgttcatcagcgcggtccaggaccaggtgg
tgccggacaacaccctggcctgggtgtgggtgcgcggcctggacgagctgtacgc
cgagtggtcggaggtcgtgtccacgaacttccgggacgcctccgggccggccatg
accgagatcggcgagcagccgtgggggcgggagttcgccctgcgcgacccggccg
gcaactgcgtgcacttcgtggccgaggagcaggactgacacgtgctacgagattt
cgattccaccgccgccttctatgaaaggttgggcttcggaatcgttttccgggac
gccggctggatgatcctccagcgcggggatctcatgctggagttcttcgcccacc
ccaacttgtttattgcagcttataatggttacaaataaagcaatagcatcacaaa
tttcacaaataaagcatttttttcactgcattctagttgtggtttgtccaaactc
atcaatgtatcttatcatgtctgtataccgtcgacctctagctagagcttggcgt
aatcatggtcatagctgtttcctgtgtgaaattgttatccgctcacaattccaca
caacatacgagccggaagcataaagtgtaaagcctggggtgcctaatgagtgagc
taactcacattaattgcgttgcgctcactgcccgctttccagtcgggaaacctgt
cgtgccagctgcattaatgaatcggccaacgcgcggggagaggcggtttgcgtat
tgggcgctcttccgcttcctcgctcactgactcgctgcgctcggtcgttcggctg
cggcgagcggtatcagctcactcaaaggcggtaatacggttatccacagaatcag
gggataacgcaggaaagaacatgtgagcaaaaggccagcaaaaggccaggaaccg
taaaaaggccgcgttgctggcgttttccataggctccgcccccctgacgagcat
cacaaaaatcgacgctcaagtcagaggtggcgaaacccgacaggactataaagat
accaggcgtttccccctggaagctccctcgtgcgctctcctgttccgaccctgcc
gcttaccggatacctgtccgcctttctcccttcgggaagcgtggcgctttctcaa

FIG. 28D tgctcacgctgtaggtatctcagttcggtgtaggtcgttcgctccaagctgggct
gtgtgcacgaaccccccgttcagcccgaccgctgcgccttatccggtaactatcg
tcttgagtccaacccggtaagacacgacttatcgccactggcagcagccactggt
aacaggattagcagagcgaggtatgtaggcggtgctacagagttcttgaagtggt
ggcctaactacggctacactagaaggacagtatttggtatctgcgctctgctgaa
gccagttaccttcggaaaaagagttggtagctcttgatccggcaaacaaaccacc
gctggtagcggtggttttttgtttgcaagcagcagattacgcgcagaaaaaaag
gatctcaagaagatcctttgatcttttctacggggtctgacgctcagtggaacga
aaactcacgttaagggattttggtcatgagattatcaaaaaggatcttcacctag
atccttttaaattaaaaatgaagttttaaatcaatctaaagtatatatgagtaaa
cttggtctgacagttaccaatgcttaatcagtgaggcacctatctcagcgatctg
tctatttcgttcatccatagttgcctgactccccgtcgtgtagataactacgata
cgggagggcttaccatctggccccagtgctgcaatgataccgcgagacccacgct
caccggctccagatttatcagcaataaaccagccagccggaagggccgagcgcag
aagtggtcctgcaactttatccgcctccatccagtctattaattgttgccgggaa
gctagagtaagtagttcgccagttaatagtttgcgcaacgttgttgccattgcta
caggcatcgtggtgtcacgctcgtcgtttggtatggcttcattcagctccggttc
ccaacgatcaaggcgagttacatgatccccatgttgtgcaaaaaagcggttagc
tccttcggtcctccgatcgttgtcagaagtaagttggccgcagtgttatcactca
tggttatggcagcactgcataattctcttactgtcatgccatccgtaagatgctt
ttctgtgactggtgagtactcaaccaagtcattctgagaatagtgtatgcggcga
ccgagttgctcttgcccggcgtcaatacgggataataccgcgccacatagcagaa
ctttaaaagtgctcatcattggaaaacgttcttcggggcgaaaactctcaaggat
cttaccgctgttgagatccagttcgatgtaacccactcgtgcacccaactgatct
tcagcatcttttactttcaccagcgtttctgggtgagcaaaaacaggaaggcaaa
atgccgcaaaaagggaataagggcgacacggaaatgttgaatactcatactctt
cctttttcaatattattgaagcatttatcagggttattgtctcatgagcggatac
atatttgaatgtatttagaaaaataaacaatagggggttccgcgcacatttcccc
gaaaagtgccacctgacgtcgacggatcgggagatctcccgatcccctatggtgc
actctcagtacaatctgctctgatgccgcatagttaagccagtatctgctccctg
cttgtgtgttggaggtcgctgagtagtgcgcgagcaaaatttaagctacaacaag
gcaaggcttgaccgacaattgcatgaagaatctgcttagggttaggcgttttgcg
ctgcttcgcgatgtacgggccagatatacgcgttgacattgattattgactagtt
attaatagtaatcaattacggggtcattagttcatagcccatatatggagttccg
cgttacataacttacggtaaatggcccgcctggctgaccgcccaacgacccccgc
ccattgacgtcaataatgacgtatgttcccatagtaacgccaatagggactttcc
attgacgtcaatgggtggactatttacggtaaactgcccacttggcagtacatca
agtgtatcatatgccaagtacgccccctattgacgtcaatgacggtaaatggccc
gcctggcattatgcccagtacatgaccttatgggactttcctacttggcagtaca
tctacgtattagtcatcgctattaccatggtgatgcggttttggcagtacatcaa

```
tgggcgtggatagcggtttgactcacggggatttccaagtctccaccccattgac
gtcaatgggagtttgttttggcaccaaaatcaacgggactttccaaaatgtcgta
acaactccgccccattgacgcaaatgggcggtaggcgtgtacggtgggaggtcta
tataagcagagctctctggctaactagagaacccactgcttactggcttatcgaa
attaatacgactcactatagggagacccaagctggtttaaacttaagcttggtac
cgagctcactagtccagtgtggtggcagatatccagcacagtggcggccgctcga
ggggcccgttttgcctgtactgggtctctctggttagaccagatctgagcctggg
agctctctggctaactagggaacccactgcttaagcctcaataaagcttgccttg
agtgcttcaagtagtgtgtgcccgtctgttgtgtgactctggtaactagagatcc
ctcagacccttttagtcagtgtggaaaatctctagcagtggcgcccgaacaggga
cttgaaagcgaaagggaaaccagaggagctctctcgacgcaggactcggcttgct
gaagcgcgcacggcaagaggcgaggggcggcgactggtgagtacgccaaaaattt
tgactagcggaggctagaaggagagagatgggtgcgagagcgtcagtattaagcg
ggggagaattagatcgcgatgggaaaaaattcggttaaggccaggggga aagaaa
aaatataaattaaaacatatagtatgggcaagcagggagctagaacgattcgcag
ttaatcctggcctgttagaaacatcagaaggctgtagacaaatactgggacagct
acaaccatcccttcagacaggatcagaagaacttagatcattatataatacagta
gcaaccctctattgtgtgcatcaaaggatagagataaaagacaccaaggaagctt
tagacaagatagaggaagagcaaaacaaaagtaagaccaccgcacagcaagcggc
cgctgatcttcagacctggaggaggagatatgagggacaattggagaagtgaatt
atataaatataaagtagtaaaaattgaaccattaggagtagcaccaccaaggca
aagagaagagtggtgcagagagaaaaaagagcagtgggaataggagctttgttcc
ttgggttcttgggagcagcaggaagcactatgggcgcagcgtcaatgacgctgac
ggtacaggccagacaattattgtctggtatagtgcagcagcagaacaatttgctg
agggctattgaggcgcaacagcatctgttgcaactcacagtctggggcatcaagc
agctccaggcaagaatcctggctgtggaaagatacctaaaggatcaacagctcct
ggggatttggggttgctctggaaaactcatttgcaccactgctgtgccttggaat
gctagttggagtaataaatctctggaacagatttggaatcacacgacctggatgg
agtgggacagagaaattaacaattacacaagcttaatacactccttaattgaaga
atcgcaaaaccagcaagaaaagaatgaacaagaattattggaattagataaatgg
gcaagtttgtggaattggtttaacataacaaattggctgtggtatataaaattat
tcataatgatagtaggaggcttggtaggtttaagaatagttttttgctgtactttc
tatagtgaatagagttaggcagggatattcaccattatcgtttcagacccacctc
ccaaccccgaggggacccgacaggcccttaattaatcccctgattctgtggataa
ccgtattaccgcctttgagtgagctgcacctagtacggattagaagccgccgagc
gggtgacagccctccgaaggaagactctcctccgtgcgtcctcgtcttcaccggt
cgcgttcctgaaacgcagatgtgcctcgcgccgcactgctccgaacaatgtcgac
tctagaggtaaactcgacctatataagcagagctcgtttagtgaaccgtcagatc
gcctggagacgccatccacgctgttttgacctccatagaagacaccgggaccgat
```

FIG. 28F ccagcctccgcggccccgaattgaattcgaagcaggagtagacgccggccattac
ggcctgccaccgttaat

FIG. 28G

```
cgcgatcacatgtcctgctggagttcgtgaccgccgccgggatcactctcggcatgacgagctgtacaagtaagcggccgcaatcaa
cctctggattacaaaatttgtgaaagattgactggttcttctcctatgtgctcctttacgctatgtggatacgctgcttaatgcctttgtatcat
gctattacttcccgtacggctttcattttctcctcctgttgctgtctttatgaggagttggcccgttgtcaggcaacgtg
gcgtggtgcactgtgtttgctgacgcaacccccactgttggcgcattgccaccacctcctttccggacttcgcttccccc
tccctattgccaacggcgaactcattgccgcctgcctgctcgcctgttgccaactggattctgcgcgggacgtccttctgcactgacaattccgtggtgtt
gtcggggaagctgacgtccttccatgctgctcgcggctgctgcgcgttctgcccgttctgcgccttctacgtcccttcggcc
tcaatccagcgaccttccttcccgcgacctgcgaggtttgtcgagacctagaaaaacatgagcaatcacaagtagcaatacagcagctaccaatg
ctttgggccgcctcccccgctgctgcagtctttcgagagacacaagaggagggtttttccagtcacacctcaagaccatgactacaagg
cagctgtagatcttagccacttttttaaaagacactgtgaaggctaattcactcccaacgaagacaagatctgctttttgcttgta
ctgggtctctctgttagaccagatctgagcctgtcttgttgtgactctggagctctctggtaactaactaggaaccactgcttaagctcaataaagcttgccttga
gtgcttcaagtagtgtgccgtctgttgttgactctggtaactctagttgccagccatcgttgtttgccctccccgtgccttccttgaccctggaag
cccgtttaaacccgctgatcagcctgacttgccttctagttgccagccatcgcattgtctgagtagtgtcattctattctgggggtgggggc
gtgccactccactgtcctttcctaataaaatgaggaacaatagcaggcatgctgggatgcggtgggctctatgcttctgaggcggaaagaacc
aggacagcaaggggaggattgggaagacaatagcaggccctgtagcgcgcattaagcgcgggtgtggttacggcagcgtgaccgcta
agctgggctcagggctatccccacgcgccgctccttcgttctttctcgtggcgcagcgtgaccgcta
cacttgccagcgcctagcgcctcgctctttaccggcacctgaccccaaaaaacttgattaggtgatgttcacgtagtgggccatcgccctg
catcccttagggttcccgattagtgctttaccggcacctgaccccaaaaaacttgattaggtgatgttcacgtagtgggccatcgccctg
atagacggtttttgcccttgacgttggagttcacgttctgcacgtccttaatagtggactcttgttccaaactggaacaacactcaacctatctcggtct
attcttttgattatatagggatttgggattcggcctattgttaaaaatgagctgattaacaaaattaacgcgaattaattctgtggaa
gtgtgtcagttagggtgtggaaagtcccccaggctccccaggcaggcagaagt
```

FIG. 29B

```
atgcaaagcatgcatctcaattagtcagcaaccaggtgtggaaagtccccaggct
ccccagcaggcagaagtatgcaaagcatgcatctcaattagtcagcaaccatagt
cccgcccctaactccgcccatcccgcccctaactccgcccagttccgcccattct
ccgcccatggctgactaattttttttatttatgcagaggccgaggccgcctctg
cctctgagctattccagaagtagtgaggaggctttttggaggcctaggcttttg
caaaaagctcccgggagcttgtatatccattttcggatctgatcagcacgtgttg
acaattaatcatcggcatagtatatcggcatagtataatacgacaaggtgaggaa
ctaaaccatggccaagttgaccagtgccgttccggtgctcaccgcgcgcgacgtc
gccggagcggtcgagttctggaccgaccggctcgggttctcccgggacttcgtgg
aggacgacttcgccggtgtggtccgggacgacgtgaccctgttcatcagcgcggt
ccaggaccaggtggtgccggacaacaccctggcctgggtgtgggtgcgcggcctg
gacgagctgtacgccgagtggtcggaggtcgtgtccacgaacttccgggacgcct
ccgggccggccatgaccgagatcggcgagcagccgtggggcgggagttcgccct
gcgcgacccggccggcaactgcgtgcacttcgtggccgaggagcaggactgacac
gtgctacgagatttcgattccaccgccgccttctatgaaaggttgggcttcggaa
tcgttttccgggacgccggctggatgatcctccagcgcggggatctcatgctgga
gttcttcgccaccccaacttgtttattgcagcttataatggttacaaataaagc
aatagcatcacaaatttcacaaataaagcattttttcactgcattctagttgtg
gtttgtccaaactcatcaatgtatcttatcatgtctgtataccgtcgacctctag
ctagagcttggcgtaatcatggtcatagctgtttcctgtgtgaaattgttatccg
ctcacaattccacacaacatacgagccggaagcataaagtgtaaagcctggggtg
cctaatgagtgagctaactcacattaattgcgttgcgctcactgcccgctttcca
gtcgggaaacctgtcgtgccagctgcattaatgaatcggccaacgcgcgggga
ggcggtttgcgtattgggcgctcttccgcttcctcgctcactgactcgctgcgct
cggtcgttcggctgcggcgagcggtatcagctcactcaaaggcggtaatacggtt
atccacagaatcaggggataacgcaggaaagaacatgtgagcaaaaggccagcaa
aaggccaggaaccgtaaaaaggccgcgttgctggcgtttttccataggctccgcc
ccctgacgagcatcacaaaaatcgacgctcaagtcagaggtggcgaaacccgac
aggactataaagataccaggcgtttccccctggaagctccctcgtgcgctctcct
gttccgaccctgccgcttaccggatacctgtccgcctttctcccttcgggaagcg
tggcgctttctcaatgctcacgctgtaggtatctcagttcggtgtaggtcgttcg
ctccaagctgggctgtgtgcacgaaccccccgttcagcccgaccgctgcgcctta
tccggtaactatcgtcttgagtccaacccggtaagacacgacttatcgccactgg
cagcagccactggtaacaggattagcagagcgaggtatgtaggcggtgctacaga
gttcttgaagtggtggcctaactacggctacactagaaggacagtatttggtatc
tgcgctctgctgaagccagttaccttcggaaaaagagttggtagctcttgatccg
gcaaacaaaccaccgctggtagcggtggtttttttgtttgcaagcagcagattac
gcgcagaaaaaaggatctcaagaagatcctttgatcttttctacggggtctgac
gctcagtggaacgaaaactcacgttaagggattttggtcatgagattatcaaaaa
ggatcttcacctagatccttttaaattaaaaatgaagttttaaatcaatctaaag
```

FIG. 29C

```
tatatatgagtaaacttggtctgacagttaccaatgcttaatcagtgaggcacct
atctcagcgatctgtctatttcgttcatccatagttgcctgactccccgtcgtgt
agataactacgatacgggagggcttaccatctggccccagtgctgcaatgatacc
gcgagacccacgctcaccggctccagatttatcagcaataaaccagccagccgga
agggccgagcgcagaagtggtcctgcaactttatccgcctccatccagtctatta
attgttgccgggaagctagagtaagtagttcgccagttaatagtttgcgcaacgt
tgttgccattgctacaggcatcgtggtgtcacgctcgtcgtttggtatggcttca
ttcagctccggttcccaacgatcaaggcgagttacatgatcccccatgttgtgca
aaaaagcggttagctccttcggtcctccgatcgttgtcagaagtaagttggccgc
agtgttatcactcatggttatggcagcactgcataattctcttactgtcatgcca
tccgtaagatgcttttctgtgactggtgagtactcaaccaagtcattctgagaat
agtgtatgcggcgaccgagttgctcttgcccggcgtcaatacgggataataccgc
gccacatagcagaactttaaaagtgctcatcattggaaaacgttcttcggggcga
aaactctcaaggatcttaccgctgttgagatccagttcgatgtaacccactcgtg
cacccaactgatcttcagcatcttttactttcaccagcgtttctgggtgagcaaa
aacaggaaggcaaaatgccgcaaaaagggaataagggcgacacggaaatgttga
atactcatactcttcctttttcaatattattgaagcatttatcagggttattgtc
tcatgagcggatacatatttgaatgtatttagaaaaataaacaatagggggttcc
gcgcacatttccccgaaaagtgccacctgacgtcgacggatcgggagatctcccg
atcccctatggtgcactctcagtacaatctgctctgatgccgcatagttaagcca
gtatctgctccctgcttgtgtgttggaggtcgctgagtagtgcgcgagcaaaatt
taagctacaacaaggcaaggcttgaccgacaattgcatgaagaatctgcttaggg
ttaggcgttttgcgctgcttcgcgatgtacgggccagatatacgcgttgacattg
attattgactagttattaatagtaatcaattacggggtcattagttcatagccca
tatatggagttccgcgttacataacttacggtaaatggcccgcctggctgaccgc
ccaacgacccccgcccattgacgtcaataatgacgtatgttcccatagtaacgcc
aatagggactttccattgacgtcaatgggtggactatttacggtaaactgcccac
ttggcagtacatcaagtgtatcatatgccaagtacgccccctattgacgtcaatg
acggtaaatggcccgcctggcattatgcccagtacatgaccttatgggactttcc
tacttggcagtacatctacgtattagtcatcgctattaccatggtgatgcggttt
tggcagtacatcaatgggcgtggatagcggtttgactcacggggatttccaagtc
tccaccccattgacgtcaatgggagtttgttttggcaccaaaatcaacgggactt
tccaaaatgtcgtaacaactccgccccattgacgcaaatgggcggtaggcgtgta
cggtgggaggtctatataagcagagctctctggctaactagagaacccactgctt
actggcttatcgaaattaatacgactcactatagggagacccaagctggtttaaa
cttaagcttggtaccgagctcactagtccagtgtggtggcagatatccagcacag
tggcggccgctcgagtctagagggcccgttttgcctgtactgggtctctctggtt
agaccagatctgagcctgggagctctctggctaactagggaacccactgcttaag
cctcaataaagcttgccttgagtgcttcaagtagtgtgtgcccgtctgttgtgtg
actctggtaactagagatccctcagacccttttagtcagtgtggaaaatctctag
```

FIG. 29D

```
cagtggcgcccgaacagggacttgaaagcgaaagggaaaccagaggagctctctc
gacgcaggactcggcttgctgaagcgcgcacggcaagaggcgaggggcggcgact
ggtgagtacgccaaaaatttt gactagcggaggctagaaggagagagatgggtgc
gagagcgtcagtattaagcgggggagaattagatcgcgatgggaaaaaattcggt
taaggccaggggg aaagaaaaaatataaattaaaacatatagtatgggcaagcag
ggagctagaacgattcgcagttaatcctggcctgttagaaacatcagaaggctgt
agacaaatactgggacagctacaaccatcccttcagacaggatcagaagaactta
gatcattatataatacagtagcaaccctctattgtgtgcatcaaaggatagagat
aaaagacaccaaggaagctttagacaagatagaggaagagcaaaacaaaagtaag
accaccgcacagcaagcggccgctgatcttcagacctggaggaggagatatgagg
gacaattggagaagtgaattatataaatataaagtagtaaaaattgaaccattag
gagtagcacccaccaaggcaaagagaagagtggtgcagagagaaaaaagagcagt
gggaataggagctttgttccttgggttcttgggagcagcaggaagcactatggc
gcagcgtcaatgacgctgacggtacaggccagacaattattgtctggtatagtgc
agcagcagaacaatttgctgagggctattgaggcgcaacagcatctgttgcaact
cacagtctggggcatcaagcagctccaggcaagaatcctggctgtggaaagatac
ctaaaggatcaacagctcctggggatttggggttgctctggaaaactcatttgca
ccactgctgtgccttggaatgctagttggagtaataaatctctggaacagatttg
gaatcacacgacctggatggagtgggacagagaaattaacaattacacaagctta
atacactccttaattgaagaatcgcaaaaccagcaagaaaagaatgaacaagaat
tattggaattagataaatgggcaagtttgtggaattggtttaacataacaaattg
gctgtggtatatagaaattattcataatgatagtaggaggcttggtaggtttaag
aatagttttgctgtactttctatagtgaatagagttaggcagggatattcacca
ttatcgtttcagacccacctcccaaccccgaggggacccgacaggcccgaaggaa
tagaagaagaaggtggagagagagacagagacagatccattcgattagtgaacgg
atcggcactgcgtgcgccaattctgcagacaaatggcagtattcatccacaattt
taaaagaaaagggggg attggggggtacagtgcaggggaaagaatagtagacata
atagcaacagacatacaaactaaagaattacaaaaacaaattacaaaaattcaaa
attttcgggtttattacagggacagcagagatccagtttggggttgctctggaaa
actcatttgcaccactgctgtgccttggaatgctagttggagtaataaatctctg
gaacagatttggaatcacacgacctggatggagtgggacagagaaattaacaatt
acacaagcttaatacactccttaattgaagaatcgcaaaaccagcaagaaaagaa
tgaacaagaattattggaattagataaatgggcaagtttgtggaattggtttaac
ataacaaattggctgtggtatataaaattattcataatgatagtaggaggcttgg
taggtttaagaatagttttgctgtactttctatagtgaatagagttaggcaggg
atattcaccattatcgtttcagacccacctcccaaccccgaggggacccgacagg
cccttaattaattggctccggtgcccgtcagtgggcagagcgcacatcgcccaca
gtccccgagaagttgggggaggggtcggcaattgaaccggtgcctagagaaggt
ggcgcggggtaaactgggaaagtgatgtcgtgtactggctccgcctttttcccga
gggtggggg agaaccgtatataagtgcagtagtcgccgtgaagctagctccctat
```

FIG. 29E

```
cagtgatagagatctccctatcagtgatagagagctagccgttcttttttcgcaac
gggtttgccgccagaacacaggtaagtgccgtgtgtggttcccgcgggcctggcc
tctttacgggttatggcccttgcgtgccttgaattacttccacctggctgcagta
cgtgattcttgatcccgagcttcgggttggaagtgggtgggagagttcgaggcct
tgcgcttaaggagccccttcgcctcgtgcttgagttgaggcctggcctgggcgct
ggggccgccgcgtgcgaatctggtggcaccttcgcgcctgtctcgctgctttcga
taagtctctagccatttaaaattttttgatgacctgctgcgacgcttttttttctgg
caagatagtcttgtaaatgcgggccaagatctgcacactggtatttcggttttttg
gggccgcgggcggcgacggggcccgtgcgtcccagcgcacatgttcggcgaggcg
gggcctgcgagcgcggccaccgagaatcggacggggtagtctcaagctggccgg
cctgctctggtgcctggcctcgcgccgccgtgtatcgccccgccctgggcggcaa
ggctggcccggtcggcaccagttgcgtgagcggaaagatggccgcttcccggccc
tgctgcagggagctcaaaatggaggacgcggcgctcgggagagcgggcgggtgag
tcacccacacaaaggaaaagggcctttccgtcctcagccgtcgcttcatgtgact
ccacggagtaccgggcgccgtccaggcacctcgattagttctcgagcttttggag
tacgtcgtctttaggttgggggagggttttatgcgatggagtttccccacact
gagtgggtggagactgaagttaggccagcttggcacttgatgtaattctccttgg
aatttgccctttttgagtttggatcttggttcattctcaagcctcagacagtggt
tcaaagtttttttcttccatttcaggtgaattcggccattacggcctcccaccat
gaaaccagtaacgttatacgatgtcgcagagtatgccggtgtctcttatcagacc
gtttcccgcgtggtgaaccaggccagccacgtttctgcgaaaacgcgggaaaaag
tggaagcggcgatggcggagctgaattacattcccaaccgcgtggcacaacaact
ggcgggcaaacagtcgttgctgattggcgttgccacctccagtctggccctgcac
gcgccgtcgcaaattgtcgcggcgattaaatctcgcgccgatcaactgggtgcca
gcgtggtggtgtcgatggtagaacgaagcggcgtcgaagcctgtaaagcggcgt
gcacaatcttctcgcgcaacgcgtcagtgggctgatcattaactatccgctggat
gaccaggatgccattgctgtggaagctgcctgcactaatgttccggcgttatttc
ttgatgtctctgaccagacacccatcaacagtattatttctcccatgaagacgg
tacgcgactgggcgtggagcatctggtcgcattgggtcaccagcaaatcgcgctg
ttagcgggcccattaagttctgtctcggcgcgtctgcgtctggctggctggcata
aatatctcactcgcaatcaaattcagccgatagcggaacgggaaggcgactggag
tgccatgtccggttttcaacaaaccatgcaaatgctgaatgagggcatcgttccc
actgcgatgctggttgccaacgatcagatggcgctgggcgcaatgcgcgccatta
ccgagtccgggctgcgcgttggtgcggatatctcggtagtgggatacgacgatac
cgaagacagctcatgttatatcccgccgttaaccaccatcaaacaggattttcgc
ctgctggggcaaaccagcgtggaccgcttgctgcaactctctcagggccaggcgg
tgaagggcaatcagctgttgcccgtctcactggtgaaaagaaaaaccaccctggc
gcccaatacgcaaaccgcctctccccgcgcgttggccgattcattaatgcagctg
gcacgacaggtttcccgactggaaagcgggcagccaaaaagaagagaaaggtcg
acggcggtggtgctttgtctcctcagcactctgctgtcactcaaggaagtatcat
```

FIG. 29F

```
caagaacaaggagggcatggatgctaagtcactaactgcctggtcccggacactg
gtgaccttcaaggatgtatttgtggacttcaccagggaggagtggaagctgctgg
acactgctcagcagatcgtgtacagaaatgtgatgctggagaactataagaacct
ggtttccttgggttatcagcttactaagccagatgtgatcctccggttggagaag
ggagaagagccctggctggtggagagagaaattcaccaagagacccatcctgatt
cagagactgcatttgaaatcaaatcatcagtttaaggccgcct
```

FIG. 29G

```
ttattgccaccatgagccgaaacgccgcaccaggcgaacgcgcgatgaaccgaggcaaactgattgcggcgcgctgggc
gtgctgcgcgaaaaaggctatgcgggctttcgcattgcgatgtgccggcggcgcgtgagcgcggccggccgcgcagagccatcat
tttccgaccaaactgaactgctgctgcgaccttgaatgctgtatgaacagattaccgaacgcagccgcgccgcctgcgaaactg
aaaccgaagatgatgtgattcagcagatgctgatgatgcggcggaatttttctgatgatgatttagcattagcctgatctgattgtgg
cggcggatcgcgatccggccgctgcgcgaaggcattcagcgcaccgtgaacgcaaccgcttttgtggtggaagatatgtggctgggcgt
gctggtgagccgcggcctgagccggcgatgatgcggaagatattctgtgtgctgattttaacagcgtgcgcgcgctgggcgtgcgagcc
tgtggcagaagataaagaaacgctttgaacgcgtgccaacagcaccctggaaattgcgcgaacgctatgcgaaatttaaacgcgc
gtacagccgcgcgctacgaaaacaattacggtctaccatcgagggcctgctgcgatctcccgacgacgacgccccgaagagc
ggggctggcggctccgcgcctgtccttctccccggacacacgcgccatgccgacgactgtcgacgcgctagacgcgatttcgatctgacattggggacgg
ggacgagctccacttagaacggcggagacgtggcgatggcggatccgacactccgcccccacgactccgccctgagtttgagcagatgtttacc
ggatccccgggtccggattacccccacgactggttaataagtgtggaggctaaaggggcgcgttctagagaattcgatatcaagcttatcg
gatgccttgaattgacgagtacggtgggtaataagtgtggaagattgactggtattcttaactatgttgctctcttttacgctatgtggatacgctgcttaatgcct
ataatcaactctgattacttcccgtacgcttcattttctccctcctgtataaatcctggtttgctgtctcttttatgaggagttgtggccgttgtcagg
ttgtatcatgctattactcccgtacgcttcattttctccctcctgtataaatcctggtttgctgtctcttttatgaggagttgtggccgttgtcagg
caacgtgcgtggtgtgcactgtgttttgctgacgcaaccccacccttgggcattgccaccacctgttgggcatggctgttgccgctcggctgttggcactgacaattcc
ttccccctccctattgccaaggcgaactcattgccgcctgtcctttccatgcctgctcgctgcctgcgcgttctgcgtgccaactgattctgcgggacgtcttctgctacgtccct
gtggtgtgtcgggaagctgacgtcctttccatgcctgctcgctgcctgcgcgttctgcgtgccaactgattctgcgggacgtcttctgctacgtccct
tcggccctcaatccagcgacctccttcctccgcgaccctcttccgccttcgcctttcgccttcgccttcgcccttcgcctcagacgagtc
ggatctccttgggccgctccccccgcctgcctgcaggtttgtcgagacctagaaaaacatggagca
```

FIG. 30B

```
atcacaagtagcaatacagcagctaccaatgctgattgtgcctggctagaagcac
aagaggaggaggaggtgggttttccagtcacacctcaggtacctttaagaccaat
gacttacaaggcagctgtagatcttagccactttttaaaagaaaaggggggactg
gaagggctaattcactcccaacgaagacaagatctgcttttttgcttgtactgggt
ctctctggttagaccagatctgagcctgggagctctctggctaactagggaaccc
actgcttaagcctcaataaagcttgccttgagtgcttcaagtagtgtgtgcccgt
ctgttgtgtgactctggtaactagagatccctcagacccttttagtcagtgtgga
aaatctctagcagggcccgtttaaacccgctgatcagcctcgactgtgccttcta
gttgccagccatctgttgtttgcccctccccgtgccttccttgaccctggaagg
tgccactcccactgtcctttcctaataaaatgaggaaattgcatcgcattgtctg
agtaggtgtcattctattctggggggtggggtggggcaggacagcaaggggagg
attgggaagacaatagcaggcatgctggggatgcggtgggctctatggcttctga
ggcggaaagaaccagctggggctctagggggtatccccacgcgccctgtagcggc
gcattaagcgcggcgggtgtggtggttacgcgcagcgtgaccgctacacttgcca
gcgccctagcgcccgctcctttcgctttcttcccttcctttctcgccacgttcgc
cggctttccccgtcaagctctaaatcggggcatcccctttagggttccgatttagt
gctttacggcacctcgaccccaaaaaacttgattagggtgatggttcacgtagtg
ggccatcgccctgatagacggttttcgccctttgacgttggagtccacgttctt
taatagtggactcttgttccaaactggaacaacactcaaccctatctcggtctat
tcttttgatttataagggatttttggggatttcggcctattggttaaaaaatgagc
tgatttaacaaaaatttaacgcgaattaattctgtggaatgtgtgtcagttaggg
tgtggaaagtccccaggctccccaggcaggcagaagtatgcaaagcatgcatctc
aattagtcagcaaccaggtgtggaaagtccccaggctccccagcaggcagaagta
tgcaaagcatgcatctcaattagtcagcaaccatagtcccgcccctaactccgcc
catcccgcccctaactccgcccagttccgcccattctccgccccatggctgacta
atttttttatttatgcagaggccgaggccgcctctgcctctgagctattccaga
agtagtgaggaggcttttttggaggcctaggcttttgcaaaaagctcccgggagc
ttgtatatccatttcggatctgatcagcacgtgttgacaattaatcatcggcat
agtatatcggcatagtataatacgacaaggtgaggaactaaaccatggccaagtt
gaccagtgccgttccggtgctcaccgcgcgcgacgtcgccggagcggtcgagttc
tggaccgaccggctcgggttctcccgggacttcgtggaggacgacttcgccggtg
tggtccgggacgacgtgaccctgttcatcagcgcggtccaggaccaggtggtgcc
ggacaacaccctggcctgggtgtgggtgcgcggcctggacgagctgtacgccgag
tggtcggaggtcgtgtccacgaacttccgggacgcctccgggccggccatgaccg
agatcggcgagcagccgtggggcgggagttcgccctgcgcgacccggccggcaa
ctgcgtgcacttcgtggccgaggagcaggactgacacgtgctacgagatttcgat
tccaccgccgccttctatgaaaggttgggcttcggaatcgttttccgggacgccg
gctggatgatcctccagcgcggggatctcatgctggagttcttcgcccaccccaa
cttgtttattgcagcttataatggttacaaataaagcaatagcatcacaaatttc
acaaataaagcattttttccactgcattctagttgtggtttgtccaaactcatca
```

FIG. 30C atgtatcttatcatgtctgtataccgtcgacctctagctagagcttggcgtaatc
atggtcatagctgtttcctgtgtgaaattgttatccgctcacaattccacacaac
atacgagccggaagcataaagtgtaaagcctggggtgcctaatgagtgagctaac
tcacattaattgcgttgcgctcactgcccgctttccagtcgggaaacctgtcgtg
ccagctgcattaatgaatcggccaacgcgcggggagaggcggtttgcgtattggg
cgctcttccgcttcctcgctcactgactcgctgcgctcggtcgttcggctgcgg
gagcggtatcagctcactcaaaggcggtaatacggttatccacagaatcaggga
taacgcaggaaagaacatgtgagcaaaaggccagcaaaaggccaggaaccgtaaa
aaggccgcgttgctggcgtttttccataggctccgcccccctgacgagcatcaca
aaaatcgacgctcaagtcagaggtggcgaaacccgacaggactataaagatacca
ggcgtttccccctggaagctccctcgtgcgctctcctgttccgaccctgccgctt
accggatacctgtccgcctttctcccttcgggaagcgtggcgctttctcaatgct
cacgctgtaggtatctcagttcggtgtaggtcgttcgctccaagctgggctgtgt
gcacgaaccccccgttcagcccgaccgctgcgccttatccggtaactatcgtctt
gagtccaacccggtaagacacgacttatcgccactggcagcagccactggtaaca
ggattagcagagcgaggtatgtaggcggtgctacagagttcttgaagtggtggcc
taactacggctacactagaaggacagtatttggtatctgcgctctgctgaagcca
gttaccttcggaaaaagagttggtagctcttgatccggcaaacaaaccaccgctg
gtagcggtggtttttttgtttgcaagcagcagattacgcgcagaaaaaaaggatc
tcaagaagatcctttgatcttttctacggggtctgacgctcagtggaacgaaaac
tcacgttaagggattttggtcatgagattatcaaaaaggatcttcacctagatcc
ttttaaattaaaaatgaagttttaaatcaatctaaagtatatatgagtaaacttg
gtctgacagttaccaatgcttaatcagtgaggcacctatctcagcgatctgtcta
tttcgttcatccatagttgcctgactccccgtcgtgtagataactacgatacggg
agggcttaccatctggccccagtgctgcaatgataccgcgagacccacgctcacc
ggctccagatttatcagcaataaaccagccagccggaagggccgagcgcagaagt
ggtcctgcaactttatccgcctccatccagtctattaattgttgccgggaagcta
gagtaagtagttcgccagttaatagtttgcgcaacgttgttgccattgctacagg
catcgtggtgtcacgctcgtcgtttggtatggcttcattcagctccggttcccaa
cgatcaaggcgagttacatgatccccatgttgtgcaaaaaagcggttagctcct
tcggtcctccgatcgttgtcagaagtaagttggccgcagtgttatcactcatggt
tatggcagcactgcataattctcttactgtcatgccatccgtaagatgcttttct
gtgactggtgagtactcaaccaagtcattctgagaatagtgtatgcggcgaccga
gttgctcttgcccggcgtcaatacgggataataccgcgccacatagcagaacttt
aaaagtgctcatcattggaaaacgttcttcggggcgaaaactctcaaggatctta
ccgctgttgagatccagttcgatgtaacccactcgtgcacccaactgatcttcag
catcttttactttcaccagcgtttctgggtgagcaaaaacaggaaggcaaaatgc
cgcaaaaaagggaataagggcgacacggaaatgttgaatactcatactcttcctt
tttcaatattattgaagcatttatcagggttattgtctcatgagcggatacatat
ttgaatgtatttagaaaaataaacaataggggttccgcgcacatttccccgaaa

FIG. 30D

```
agtgccacctgacgtcgacggatcgggagatctcccgatcccctatggtgcactc
tcagtacaatctgctctgatgccgcatagttaagccagtatctgctccctgcttg
tgtgttggaggtcgctgagtagtgcgcgagcaaaatttaagctacaacaaggcaa
ggcttgaccgacaattgcatgaagaatctgcttagggttaggcgttttgcgctgc
ttcgcgatgtacgggccagatatacgcgttgacattgattattgactagttatta
atagtaatcaattacggggtcattagttcatagcccatatatggagttccgcgtt
acataacttacggtaaatggcccgcctggctgaccgcccaacgaccccgcccat
tgacgtcaataatgacgtatgttcccatagtaacgccaatagggactttccattg
acgtcaatgggtggactatttacggtaaactgcccacttggcagtacatcaagtg
tatcatatgccaagtacgccccctattgacgtcaatgacggtaaatggcccgcct
ggcattatgcccagtacatgaccttatgggactttcctacttggcagtacatcta
cgtattagtcatcgctattaccatggtgatgcggttttggcagtacatcaatggg
cgtggatagcggtttgactcacggggatttccaagtctccacccattgacgtca
atgggagtttgttttggcaccaaaatcaacgggactttccaaaatgtcgtaacaa
ctccgccccattgacgcaaatgggcggtaggcgtgtacggtgggaggtctatata
agcagagctctctggctaactagagaacccactgcttactggcttatcgaaatta
atacgactcactatagggagacccaagctggtttaaacttaagcttggtaccgag
ctcactagtccagtgtggtggcagatatccagcacagtggcggccgctcgaggg
cccgttttgcctgtactgggtctctctggttagaccagatctgagcctgggagct
ctctggctaactagggaacccactgcttaagcctcaataaagcttgccttgagtg
cttcaagtagtgtgtgcccgtctgttgtgtgactctggtaactagagatccctca
gacccttttagtcagtgtggaaaatctctagcagtggcgcccgaacagggacttg
aaagcgaaagggaaaccagaggagctctctcgacgcaggactcggcttgctgaag
cgcgcacggcaagaggcgaggggcggcgactggtgagtacgccaaaaatttgac
tagcggaggctagaaggagagagatgggtgcgagagcgtcagtattaagcggggg
agaattagatcgcgatgggaaaaaattcggttaaggccagggggaaagaaaaaat
ataaattaaaacatatagtatgggcaagcagggagctagaacgattcgcagttaa
tcctggcctgttagaaacatcagaaggctgtagacaaatactgggacagctacaa
ccatcccttcagacaggatcagaagaacttagatcattatataatacagtagcaa
ccctctattgtgtgcatcaaaggatagagataaaagacaccaaggaagctttaga
caagatagaggaagagcaaaacaaaagtaagaccaccgcacagcaagcggccgct
gatcttcagacctggaggaggagatatgagggacaattggagaagtgaattatat
aaatataaagtagtaaaaattgaaccattaggagtagcacccaccaaggcaaaga
gaagagtggtgcagagagaaaaaagagcagtgggaataggagctttgttccttgg
gttcttgggagcagcaggaagcactatgggcgcagcgtcaatgacgctgacggta
caggccagacaattattgtctggtatagtgcagcagcagaacaatttgctgaggg
ctattgaggcgcaacagcatctgttgcaactcacagtctggggcatcaagcagct
ccaggcaagaatcctggctgtggaagatacctaaaggatcaacagctcctgggg
atttggggttgctctggaaaactcatttgcaccactgctgtgccttggaatgcta
gttggagtaataaatctctggaacagatttggaatcacacgacctggatggagtg
```

FIG. 30E

```
ggacagagaaattaacaattacacaagcttaatacactccttaattgaagaatcg
caaaaccagcaagaaaagaatgaacaagaattattggaattagataaatgggcaa
gtttgtggaattggtttaacataacaaattggctgtggtatataaaattattcat
aatgatagtaggaggcttggtaggtttaagaatagtttttgctgtactttctata
gtgaatagagttaggcagggatattcaccattatcgtttcagacccacctcccaa
ccccgaggggacccgacaggcccttaattaatcccctgattctgtggataaccgt
attaccgcctttgagtgagctgcacaactgccagatttcacaggaaaagtgaaag
gctacaataggacaactgccagatttcacaggaaaagtgaaaggctacaatagga
caactgccagatttcacaggaaaagtgaaaggctacaataggacaactgccagat
ttcacaggaaaagtgaaaggctacaataggacaactgccagatttcacaggaaaa
gtgaaaggctacaataggacaactgccagatttcacaggaaaagtgaaaggctac
aataggacaaagtgaaaggctacaataggacggtaaactcgacctatataagcag
agctcgtttagtgaaccgtcagatcgcctggagacgccatccacgctgttttgac
ctccatagaagacaccgggaccgatccagcctccgcggccccgaattgaattcga
tgctggtgttaaaaacatatgatgctggtgttaaaaacggccattacggcctgcc
acc
```

FIG. 30F

```
ttatgtgtggagggctaagggcgcgccgttctagagaattcgatatcaagcttatcgataatcaacctctgattacaaaatttgtgaaaga
ttgactggtattcttaactatgttgctccttttacgctatgtggatacgctgctcttaatgcctttgtatcatgctattacttccgtacgctttcatttt
ctcctccttgtataaatcctggttgctgtctctttatgaggagttgtggccgttgtcaggcaacgtgctggtggtgcactgttgctgacg
caaccccactgttggggcattgccaccacctatcaactccttccggactttcgcttccccctcctattgccacggcgaactcattg
ccgctgccttgccgctgctgactgactgaccagggctcggctgttgcccactgcagggctcggtggttgtcgggaagctgacgtccttccatg
gctgctcgcctgtgttgccaactggattctgcgcggacgtcttcgcctgtcgctacgtccttcgctacgtcccttaatccagcgacgtcccttcccgcg
gcctgctgcgcggttctgcgcggtcctcttcgcgtcttgccccttaagacggatctccctttggccgccgctccccccgctgcctgc
aggtttgtcgagacctagaaaacatggagcaatcacaagtagcaatacaagctgattgtgctgctagaagcacaag
aggaggaggtggtttccagtcacactcaggtaccttaagacaagatctgcttttgcttgtactggctctctgttagaccagatctg
gaaaaggggactggaaggctaactagaggaaccactgtcttaagctcaattaaagcttgcctgagtgctcaagtagtgtgccgtctgtt
agcctggagctctctggctaactagaggaaccactgtcttaagctcaataaaagcttgcctgagtgctcaagtagtgtgccgtctgtt
gtgtgactctgtaactagagatccctcagaccctttttagtcagtgtgaaaatctctagcagggccgttaaacccgctgatcagcctcg
actgtgccttctagttgccagccatcgttgtttgccccatcgttgttgccccgaaggtgccactccactgtccttctcctaata
aaatgaggaaattgcatcgcattgtctgagtaggtgtcattctattctggggggtgggcaggacagcaaggggaggattggg
aagacaatagcaggcatgctggggatgcgcgggcggtgtgtggctctatgcgtcttgaggcgcagcgtgaccgtacacttgccagcgccgcct
cgcgccctgagcgcgcattaagcgcgggcattcttccttccttctatgcgttgttacgcgcagcgttacgccttcccctagagcttgcccttttccgccagcgccgct
cctttcgctttcttcccttcttgcgcgttacgcgcagcgttgttacgcgcagcgttcgccttcccctagagcttgcccttaggttccgatttagtgctt
tacggcacctcgaccccaaaaaacttgatttaggtgatggttcacgttggcatgcctgataacgtttctgcccttgacgttg
gagtccacgttcttaatagtggactctgttccaaactgaacaactcaaccctactctcggtctattcttttgatttataaggattttgggg
atttcggcctattgttaaaaatgagctgatttaacaaaaattaacgcgaattaattctgtg
```

FIG. 31B gaatgtgtgtcagttagggtgtggaaagtccccaggctccccaggcaggca
gaagtatgcaaagcatgcatctcaattagtcagcaaccaggtgtggaaagt
ccccaggctccccagcaggcagaagtatgcaaagcatgcatctcaattagt
cagcaaccatagtcccgcccctaactccgcccatcccgcccctaactccgc
ccagttccgcccattctccgccccatggctgactaatttttttatttatg
cagaggccgaggccgcctctgcctctgagctattccagaagtagtgaggag
gcttttttggaggcctaggcttttgcaaaaagctcccgggagcttgtatat
ccattttcggatctgatcagcacgtgttgacaattaatcatcggcatagta
tatcggcatagtataatacgacaaggtgaggaactaaaccatggccaagtt
gaccagtgccgttccggtgctcaccgcgcgcgacgtcgccggagcggtcga
gttctggaccgaccggctcgggttctcccgggacttcgtggaggacgactt
cgccggtgtggtccgggacgacgtgaccctgttcatcagcgcggtccagga
ccaggtggtgccggacaacaccctggcctgggtgtgggtgcgcggcctgga
cgagctgtacgccgagtggtcggaggtcgtgtccacgaacttccgggacgc
ctccgggccggccatgaccgagatcggcgagcagccgtggggcgggagtt
cgccctgcgcgacccggccggcaactgcgtgcacttcgtggccgaggagca
ggactgacacgtgctacgagatttcgattccaccgccgccttctatgaaag
gttgggcttcggaatcgttttccgggacgccggctggatgatcctccagcg
cggggatctcatgctggagttcttcgcccaccccaacttgtttattgcagc
ttataatggttacaaataaagcaatagcatcacaaatttcacaaataaagc
atttttttcactgcattctagttgtggtttgtccaaactcatcaatgtatc
ttatcatgtctgtataccgtcgacctctagctagagcttggcgtaatcatg
gtcatagctgtttcctgtgtgaaattgttatccgctcacaattccacacaa
catacgagccggaagcataaagtgtaaagcctggggtgcctaatgagtgag
ctaactcacattaattgcgttgcgctcactgcccgctttccagtcgggaaa
cctgtcgtgccagctgcattaatgaatcggccaacgcgcggggagaggcgg
tttgcgtattgggcgctcttccgcttcctcgctcactgactcgctgcgctc
ggtcgttcggctgcggcgagcggtatcagctcactcaaaggcggtaatacg
gttatccacagaatcaggggataacgcaggaaagaacatgtgagcaaaagg
ccagcaaaaggccaggaaccgtaaaaaggccgcgttgctggcgtttttcca
taggctccgcccccctgacgagcatcacaaaaatcgacgctcaagtcagag
gtggcgaaacccgacaggactataaagataccaggcgtttccccctggaag
ctccctcgtgcgctctcctgttccgaccctgccgcttaccggatacctgtc
cgcctttctcccttcgggaagcgtggcgctttctcaatgctcacgctgtag
gtatctcagttcggtgtaggtcgttcgctccaagctgggctgtgtgcacga
accccccgttcagcccgaccgctgcgccttatccggtaactatcgtcttga
gtccaacccggtaagacacgacttatcgccactggcagcagccactggtaa
caggattagcagagcgaggtatgtaggcggtgctacagagttcttgaagtg
gtggcctaactacggctacactagaaggacagtatttggtatctgcgctct
gctgaagccagttaccttcggaaaaagagttggtagctcttgatccggcaa

FIG. 31C

```
acaaaccaccgctggtagcggtggttttttgtttgcaagcagcagattac
gcgcagaaaaaaggatctcaagaagatcctttgatcttttctacggggtc
tgacgctcagtggaacgaaaactcacgttaagggattttggtcatgagatt
atcaaaaggatcttcacctagatccttttaaattaaaaatgaagttttaa
atcaatctaaagtatatatgagtaaacttggtctgacagttaccaatgctt
aatcagtgaggcacctatctcagcgatctgtctatttcgttcatccatagt
tgcctgactccccgtcgtgtagataactacgatacgggagggcttaccatc
tggccccagtgctgcaatgataccgcgagacccacgctcaccggctccaga
tttatcagcaataaaccagccagccggaagggccgagcgcagaagtggtcc
tgcaactttatccgcctccatccagtctattaattgttgccgggaagctag
agtaagtagttcgccagttaatagtttgcgcaacgttgttgccattgctac
aggcatcgtggtgtcacgctcgtcgtttggtatggcttcattcagctccgg
ttcccaacgatcaaggcgagttacatgatccccatgttgtgcaaaaaagc
ggttagctccttcggtcctccgatcgttgtcagaagtaagttggccgcagt
gttatcactcatggttatggcagcactgcataattctcttactgtcatgcc
atccgtaagatgcttttctgtgactggtgagtactcaaccaagtcattctg
agaatagtgtatgcggcgaccgagttgctcttgcccggcgtcaatacggga
taataccgcgccacatagcagaactttaaaagtgctcatcattggaaaacg
ttcttcggggcgaaaactctcaaggatcttaccgctgttgagatccagttc
gatgtaacccactcgtgcacccaactgatcttcagcatcttttactttcac
cagcgtttctgggtgagcaaaaacaggaaggcaaaatgccgcaaaaaggg
aataagggcgacacggaaatgttgaatactcatactcttccttttcaata
ttattgaagcatttatcagggttattgtctcatgagcggatacatatttga
atgtatttagaaaaataaacaatagggggttccgcgcacatttccccgaaa
agtgccacctgacgtcgacggatcgggagatctcccgatcccctatggtgc
actctcagtacaatctgctctgatgccgcatagttaagccagtatctgctc
cctgcttgtgtgttggaggtcgctgagtagtgcgcgagcaaaatttaagct
acaacaaggcaaggcttgaccgacaattgcatgaagaatctgcttagggtt
aggcgttttgcgctgcttcgcgatgtacgggccagatatacgcgttgacat
tgattattgactagttattaatagtaatcaattacggggtcattagttcat
agcccatatatggagttccgcgttacataacttacggtaaatggcccgcct
ggctgaccgcccaacgacccccgcccattgacgtcaataatgacgtatgtt
cccatagtaacgccaatagggactttccattgacgtcaatgggtggactat
ttacggtaaactgcccacttggcagtacatcaagtgtatcatatgccaagt
acgccccctattgacgtcaatgacggtaaatggcccgcctggcattatgcc
cagtacatgaccttatggactttcctacttggcagtacatctacgtatta
gtcatcgctattaccatggtgatgcggttttggcagtacatcaatgggcgt
ggatagcggtttgactcacggggatttccaagtctccaccccattgacgtc
aatgggagtttgttttggcaccaaaatcaacgggactttccaaaatgtcgt
aacaactccgccccattgacgcaaatgggcggtaggcgtgtacggtgggag
```

FIG. 31D

```
gtctatataagcagagctctctggctaactagagaacccactgcttactgg
cttatcgaaattaatacgactcactatagggagacccaagctggtttaaac
ttaagcttggtaccgagctcactagtccagtgtggtggcagatatccagca
cagtggcggccgctcgaggggcccgttttgcctgtactgggtctctctggt
tagaccagatctgagcctgggagctctctggctaactagggaacccactgc
ttaagcctcaataaagcttgccttgagtgcttcaagtagtgtgtgcccgtc
tgttgtgtgactctggtaactagagatccctcagacccttttagtcagtgt
ggaaaatctctagcagtggcgcccgaacagggacttgaaagcgaaagggaa
accagaggagctctctcgacgcaggactcggcttgctgaagcgcgcacggc
aagaggcgaggggcggcgactggtgagtacgccaaaaattttgactagcgg
aggctagaaggagagagatgggtgcgagagcgtcagtattaagcgggggag
aattagatcgcgatgggaaaaaattcggttaaggccagggggaaagaaaaa
atataaattaaaacatatagtatgggcaagcagggagctagaacgattcgc
agttaatcctggcctgttagaaacatcagaaggctgtagacaaatactggg
acagctacaaccatcccttcagacaggatcagaagaacttagatcattata
taatacagtagcaaccctctattgtgtgcatcaaaggatagagataaaaga
caccaaggaagctttagacaagatagaggaagagcaaaacaaaagtaagac
caccgcacagcaagcggccgctgatcttcagacctggaggaggagatatga
gggacaattggagaagtgaattatataaatataaagtagtaaaaattgaac
cattaggagtagcacccaccaaggcaaagagaagagtggtgcagagagaaa
aaagagcagtgggaataggagctttgttccttgggttcttgggagcagcag
gaagcactatgggcgcagcgtcaatgacgctgacggtacaggccagacaat
tattgtctggtatagtgcagcagcagaacaatttgctgagggctattgagg
cgcaacagcatctgttgcaactcacagtctggggcatcaagcagctccagg
caagaatcctggctgtggaagatacctaaaggatcaacagctcctgggga
tttggggttgctctggaaaactcatttgcaccactgctgtgccttggaatg
ctagttggagtaataaatctctggaacagatttggaatcacacgacctgga
tggagtgggacagagaaattaacaattacacaagcttaatacactccttaa
ttgaagaatcgcaaaaccagcaagaaaagaatgaacaagaattattggaat
tagataaatgggcaagtttgtggaattggtttaacataacaaattggctgt
ggtatataaaattattcataatgatagtaggaggcttggtaggtttaagaa
tagttttgctgtactttctatagtgaatagagttaggcagggatattcac
cattatcgtttcagacccacctcccaaccccgaggggacccgacaggccct
taattaatcccctgattctgtggataaccgtattaccgcctttgagtgagc
tgcacaactgccagatttcacaggaaagtgaaggctacaataggacaac
tgccagatttcacaggaaagtgaaggctacaataggacaactgccagat
ttcacaggaaagtgaaggctacaataggacaactgccagatttcacagg
aaagtgaaggctacaataggacaactgccagatttcacaggaaagtga
aggctacaataggacaactgccagatttcacaggaaagtgaaggctac
aataggacaaagtgaaggctacaataggacggtaaactcgacctatataa
```

FIG. 31E

```
gcagagctcgtttagtgaaccgtcagatcgcctggagacgccatccacgct
gttttgacctccatagaagacaccgggaccgatccagcctccgcggccccg
aattgaattcgatgctggtgttaaaaacatatgatgctggtgttaaaaacg
gccattacggcctgccacc
```

FIG. 31F

```
ttatgtgtgggaggctaaggcgcgccgttctagagaattcgatatcaagcttatcgataatcaacctctgattacaaaatttgtgaaaga
ttgactggtattcttaactatgttgctccttttacgctatgtggatacgctgcttaatgccttgtatcatgctattacttccgtacgctttcatttt
ctcctccttgtataaatcctggttgctgtctctttatgaggagttgtggccgttgtcaggcaacgtggcgtggtgtgcactgtgtttgctgacg
caaccccactggttggggcattgccaccactatcaactccttcgggacttcgcttcccctcctcctattgccacgcggaactcattg
ccgcctgcctgcccgctgcctgctgacagggctcgcgtgttgggcactgacaattccgtgttgtcggggaagctgacgtccttccatg
gctgctcgcctgtgtgccaactgattctgcgcggacgtcctctgctacgtcccttcggcctcaatccagcggaccttccttcccgcg
gcctgctgccggtttctgcgggcctcttcgcgtcttcgcctcgcctcgagcgagtcggatctcccttgggcgcgcctcccgctgcctgc
aggtttgtcgagaccatagaaaaaacatgaagcaatcacaaagtacccttaagacaatagcagctacatctcgatcttagccactttaaaa
aggaggaggtgggtttccagtcacacctcagtaccttaagacaatgactacaaggcagctgtagatcttagccactttaaaa
gaaaaggggactggaagggctaattcactccaacgaagacaagatctgcttttgcttgtactggtctctcgttagaccagatctg
agcctgggagctctctggctaactagggaaccactgcttaagcctcaataaagcttgcttgagtgctcaagtagtgtgtgcccgtctgtt
gtgactctgtaactagagatccctcagacccttgtttgtgccctccccgtgtcagtggtgtcattctattctgagttgctttaaccgctgatcagcctcg
actgtgccttctagttgccagcatctgtttgctgagtaggtgtcattctattctggggtgggggtgggcaggacagcagctgggctctagggtatccca
aatgaggaaattgcatcgcattgctggggatgcggtgggctctatgtgttcgagggaaaagaaccagctggggctctaggggtatccca
aagacaatagcaggcatgctggggatgcggtgggctctatgtgttcgagggaaaagaaccagctggggctctaggggtatccca
cgcgccctgagcggcgcattaagcgcggggtggtgtggtatacggcagcgtgaccgctacacttgccagcgccctagcgcccgct
cctttcgctttcttcccttcctttctcgccagttcgccggctttccccgtcaagctctaaatcggggcatccctttaggg
```

FIG. 32B

```
ttccgatttagtgctttacggcacctcgaccccaaaaaacttgattagggtgatg
gttcacgtagtgggccatcgccctgatagacggttttcgccctttgacgttgga
gtccacgttctttaatagtggactcttgttccaaactggaacaacactcaaccct
atctcggtctattcttttgatttataagggattttggggatttcggcctattggt
taaaaaatgagctgatttaacaaaaatttaacgcgaattaattctgtggaatgtg
tgtcagttagggtgtggaaagtccccaggctcccaggcaggcagaagtatgcaa
agcatgcatctcaattagtcagcaaccaggtgtggaaagtccccaggctcccag
caggcagaagtatgcaaagcatgcatctcaattagtcagcaaccatagtcccgcc
cctaactccgcccatcccgcccctaactccgcccagttccgccattctccgccc
catggctgactaattttttatttatgcagaggccgaggccgcctctgcctctg
agctattccagaagtagtgaggaggcttttttggaggcctaggcttttgcaaaaa
gctcccgggagcttgtatatccatttcggatctgatcagcacgtgttgacaatt
aatcatcggcatagtatatcggcatagtataatacgacaaggtgaggaactaaac
catggccaagttgaccagtgccgttccggtgctcaccgcgcgcgacgtcgccgga
gcggtcgagttctggaccgaccggctcgggttctcccgggacttcgtggaggacg
acttcgccggtgtggtccgggacgacgtgaccctgttcatcagcgcggtccagga
ccaggtggtgccggacaacaccctggcctgggtgtgggtgcgcggcctggacgag
ctgtacgccgagtggtcggaggtcgtgtccacgaacttccgggacgcctccgggc
cggccatgaccgagatcggcgagcagccgtggggcgggagttcgccctgcgcga
cccggccggcaactgcgtgcacttcgtggccgaggagcaggactgacacgtgcta
cgagatttcgattccaccgccgccttctatgaaaggttgggcttcggaatcgttt
tccgggacgccggctggatgatcctccagcgcggggatctcatgctggagttctt
cgcccacccaacttgtttattgcagcttataatggttacaaataaagcaatagc
atcacaaatttcacaaataaagcattttttcactgcattctagttgtggtttgt
ccaaactcatcaatgtatcttatcatgtctgtataccgtcgacctctagctagag
cttggcgtaatcatggtcatagctgtttcctgtgtgaaattgttatccgctcaca
attccacacaacatacgagccggaagcataaagtgtaaagcctggggtgcctaat
gagtgagctaactcacattaattgcgttgcgctcactgcccgctttccagtcggg
aaacctgtcgtgccagctgcattaatgaatcggccaacgcgcggggagaggcggt
ttgcgtattgggcgctcttccgcttcctcgctcactgactcgctgcgctcggtcg
ttcggctgcggcgagcggtatcagctcactcaaaggcggtaatacggttatccac
agaatcaggggataacgcaggaaagaacatgtgagcaaaaggccagcaaaaggcc
aggaaccgtaaaaaggccgcgttgctggcgtttttccataggctccgcccccctg
acgagcatcacaaaaatcgacgctcaagtcagaggtggcgaaacccgacaggact
ataaagataccaggcgtttccccctggaagctccctcgtgcgctctcctgttccg
accctgccgcttaccggatacctgtccgcctttctcccttcgggaagcgtggcgc
tttctcaatgctcacgctgtaggtatctcagttcggtgtaggtcgttcgctccaa
gctgggctgtgtgcacgaaccccccgttcagcccgaccgctgcgccttatccggt
aactatcgtcttgagtccaacccggtaagacacgacttatcgccactggcagcag
ccactggtaacaggattagcagagcgaggtatgtaggcggtgctacagagttctt
```

FIG. 32C

```
gaagtggtggcctaactacggctacactagaaggacagtatttggtatctgcgct
ctgctgaagccagttaccttcggaaaagagttggtagctcttgatccggcaaac
aaaccaccgctggtagcggtggttttttgtttgcaagcagcagattacgcgcag
aaaaaaaggatctcaagaagatcctttgatcttttctacggggtctgacgctcag
tggaacgaaaactcacgttaagggattttggtcatgagattatcaaaaggatct
tcacctagatccttttaaattaaaaatgaagttttaaatcaatctaaagtatata
tgagtaaacttggtctgacagttaccaatgcttaatcagtgaggcacctatctca
gcgatctgtctatttcgttcatccatagttgcctgactcccgtcgtgtagataa
ctacgatacgggagggcttaccatctggccccagtgctgcaatgataccgcgaga
cccacgctcaccggctccagatttatcagcaataaaccagccagccggaagggcc
gagcgcagaagtggtcctgcaactttatccgcctccatccagtctattaattgtt
gccgggaagctagagtaagtagttcgccagttaatagtttgcgcaacgttgttgc
cattgctacaggcatcgtggtgtcacgctcgtcgtttggtatggcttcattcagc
tccggttcccaacgatcaaggcgagttacatgatccccatgttgtgcaaaaaag
cggttagctccttcggtcctccgatcgttgtcagaagtaagttggccgcagtgtt
atcactcatggttatggcagcactgcataattctcttactgtcatgccatccgta
agatgcttttctgtgactggtgagtactcaaccaagtcattctgagaatagtgta
tgcggcgaccgagttgctcttgcccggcgtcaatacgggataataccgcgccaca
tagcagaactttaaaagtgctcatcattggaaaacgttcttcggggcgaaaactc
tcaaggatcttaccgctgttgagatccagttcgatgtaacccactcgtgcaccca
actgatcttcagcatcttttactttcaccagcgtttctgggtgagcaaaaacagg
aaggcaaaatgccgcaaaaagggaataagggcgacacggaaatgttgaatactc
atactcttccttttcaatattattgaagcatttatcagggttattgtctcatga
gcggatacatatttgaatgtatttagaaaaataaacaataggggttccgcgcac
atttccccgaaaagtgccacctgacgtcgacggatcgggagatctcccgatcccc
tatggtgcactctcagtacaatctgctctgatgccgcatagttaagccagtatct
gctccctgcttgtgtgttggaggtcgctgagtagtgcgcgagcaaaatttaagct
acaacaaggcaaggcttgaccgacaattgcatgaagaatctgcttagggttaggc
gttttgcgctgcttcgcgatgtacgggccagatatacgcgttgacattgattatt
gactagttattaatagtaatcaattacggggtcattagttcatagcccatatatg
gagttccgcgttacataacttacggtaaatggcccgcctggctgaccgcccaacg
acccccgcccattgacgtcaataatgacgtatgttcccatagtaacgccaatagg
gactttccattgacgtcaatgggtggactatttacggtaaactgcccacttggca
gtacatcaagtgtatcatatgccaagtacgccccctattgacgtcaatgacggta
aatggcccgcctggcattatgcccagtacatgaccttatgggactttcctacttg
gcagtacatctacgtattagtcatcgctattaccatggtgatgcggttttggcag
tacatcaatgggcgtggatagcggtttgactcacggggatttccaagtctccacc
ccattgacgtcaatgggagtttgttttggcaccaaaatcaacgggactttccaaa
atgtcgtaacaactccgccccattgacgcaaatgggcggtaggcgtgtacggtgg
gaggtctatataagcagagctctctggctaactagagaacccactgcttactggc
```

FIG. 32D

```
ttatcgaaattaatacgactcactatagggagacccaagctggtttaaacttaag
cttggtaccgagctcactagtccagtgtggtggcagatatccagcacagtggcgg
ccgctcgaggggcccgttttgcctgtactgggtctctctggttagaccagatctg
agcctgggagctctctggctaactagggaacccactgcttaagcctcaataaagc
ttgccttgagtgcttcaagtagtgtgtgcccgtctgttgtgtgactctggtaact
agagatccctcagaccccttttagtcagtgtggaaaatctctagcagtggcgcccg
aacagggacttgaaagcgaaagggaaaccagaggagctctctcgacgcaggactc
ggcttgctgaagcgcgcacggcaagaggcgaggggcggcgactggtgagtacgcc
aaaaattttgactagcggaggctagaaggagagagatgggtgcgagagcgtcagt
attaagcgggggagaattagatcgcgatgggaaaaaattcggttaaggccagggg
gaaagaaaaaatataaattaaaacatatagtatgggcaagcagggagctagaacg
attcgcagttaatcctggcctgttagaaacatcagaaggctgtagacaaatactg
ggacagctacaaccatcccttcagacaggatcagaagaacttagatcattatata
atacagtagcaaccctctattgtgtgcatcaaaggatagagataaaagacaccaa
ggaagctttagacaagatagaggaagagcaaaacaaaagtaagaccaccgcacag
caagcggccgctgatcttcagacctggaggaggagatatgagggacaattggaga
agtgaattatataaatataaagtagtaaaaattgaaccattaggagtagcaccca
ccaaggcaaagagaagagtggtgcagagagaaaaaagagcagtgggaataggagc
tttgttccttgggttcttgggagcagcaggaagcactatgggcgcagcgtcaatg
acgctgacggtacaggccagacaattattgtctggtatagtgcagcagcagaaca
atttgctgagggctattgaggcgcaacagcatctgttgcaactcacagtctgggg
catcaagcagctccaggcaagaatcctggctgtggaaagatacctaaaggatcaa
cagctcctggggatttggggttgctctggaaaactcatttgcaccactgctgtgc
cttggaatgctagttggagtaataaatctctggaacagatttggaatcacacgac
ctggatggagtgggacagagaaattaacaattacacaagcttaatacactcctta
attgaagaatcgcaaaaccagcaagaaaagaatgaacaagaattattggaattag
ataaatgggcaagtttgtggaattggtttaacataacaaattggctgtggtatat
aaaattattcataatgatagtaggaggcttggtaggtttaagaatagttttgct
gtactttctatagtgaatagagttaggcagggatattcaccattatcgtttcaga
cccacctcccaaccccgaggggacccgacaggcccttaattaatcccctgattct
gtggataaccgtattaccgcctttgagtgagctgcacgggagcaattaatctata
gattaaaaagtgaaaggctacaataggacgggagcaattaatctatagattaaaa
agtgaaaggctacaataggacgggagcaattaatctatagattaaaaagtgaaag
gctacaataggacgggagcaattaatctatagattaaaaagtgaaaggctacaat
aggacgggagcaattaatctatagattaaaaagtgaaaggctacaataggacggg
agcaattaatctatagattaaaaagtgaaaggctacaataggacgggagcaatta
atctatagattaaaaagtgaaaggctacaataggacggtaaactcgacctatata
agcagagctcgtttagtgaaccgtcagatcgcctggagacgccatccacgctgtt
ttgacctccatagaagacaccgggaccgatccagcctccgcggccccgaattgaa
ttcggccattacggcctgccaccatgagcacaaaaaagaaaccattaacacaaga
```

FIG. 32E

```
gcagcttgaggacgcacgtcgccttaaagcaatttatgaaaaaaagaaaaatgaa
cttggcttatcccaggaatctgtcgcagacaagatggggatggggcagtcaggcg
ttggtgctttatttaatggcatcaatgcattaaatgcttataacgccgcattgct
tgcaaaaattctcaaagttagcgttgaagaattcagcccttcaatcgccagagag
atctacgagatgtatgaagcggttagtatgcagccgtcacttagaagtgagtatg
agtaccctgttttttctcatgttcaggcagggatgttctcacctgagcttagaac
ctttaccaaaggtgatgcggagagatgggtaagcacaaccaaaaagccagtgat
tctgcattctggcttgaggttgaaggtaattccatgaccgcaccaacaggctcca
agccaagctttcctgacggaatgttaattctcgttgaccctgagcaggctgttga
gcccggggatttctgcatagccagacttgggggtgatgagtttaccttcaagaaa
ctgatcagggatagcggtcaggtgtttttacaaccactaaacccacagtacccaa
tgatcccatgcaatgagagttgttccgttgtggggaaagttatcgctagtcagtg
gcctgaagagacgtttggcccaaaaagaagagaaaggtcgacggcggtggtgct
ttgtctcctcagcactctgctgtcactcaaggaagtatcatcaagaacaaggagg
gcatggatgctaagtcactaactgcctggtcccggacactggtgaccttcaagga
tgtatttgtggacttcaccagggaggagtggaagctgctggacactgctcagcag
atcgtgtacagaaatgtgatgctggagaactataagaacctggtttccttgggtt
atcagcttactaagccagatgtgatcctccggttggagaagggagaagagccctg
gctggtggagagagaaattcaccaagagacccatcctgattcagagactgcattt
gaaatcaaatcatcagtttaatgccacc
```

FIG. 32F

```
ttatgtgtggagggctaaggcgcgccgttctagagaattcgatatcaagcttatcgataatcaacctctgattacaaatttgtgaaaga
ttgactggtattcttaactatgttgctccttttacgctgttggatacgctgcttaatgcctttgtatcatgctattacttccgtacggctttcattt
ctcctccttgtataatcctggttgctgtctcttttatgaggagttggcccgttgtcaggcaacgtggcgtggtgtgcactgtgtttgctgacg
caaccccactgttgggcattgccaccactatcaactcctttcgcttgcttcccctccctattgccacgcgaactcattg
ccgcctgccttgcccgctgctgacaggggctcggtctgttgggcactgacaattccgtgttcccttcgctcctcaatccagcgaccttccttccgcg
gctgctcgcctgttgccaactggattctgcgcggggacgtcctttcgtactgctcctcagcgagtgcctcgtctttccatg
gcctgctgccggttctgcgccctcttccgcgtcttcgccttgccctcagacgagtcagcagctaccaatgctgattgtgcctgaagcacaag
aggtttgtcgagacctagaaaaacatggacaatcacaagtagcaatagacttaagaccaagcttagcccactttttaaaa
aggaggaggtggtttccagtcacacctcagtacctttaagaccaatgactacaaggcagctgtagatcttagccactttttaaaa
gaaaggggggactggaaggctaattcactcccaacgaagacaagatctgcttttgcttgtactgggtctctctggttagaccagatctg
agcctgggagctctctgctaactagggaaccactgcttaagcctcaataaagcttgccttgagtgcttcaagtagtgtgtgcccgtctgtt
gtgtgactctggtaactagagatccctcagacccttttagtcagtgtggaaaatctctagcagggccgtttaaacccgctgatcagcctcg
actgtgccttctagttgccagccatctgttgtttgcccctcccccgtgccttccttgaccctggaaggtgccactcccactgtccttcctaata
aaatgagg
```

FIG. 33B

```
aaattgcatcgcattgtctgagtaggtgtcattctattctggggggtggggtggg
gcaggacagcaaggggggaggattgggaagacaatagcaggcatgctgggga tgcg
gtgggctctatggcttctgaggcggaagaaccagctggggctctagggggtatc
cccacgcgccctgtagcggcgcattaagcgcggcgggtgtggtggttacgcgcag
cgtgaccgctacacttgccagcgccctagcgccgctcctttcgctttcttccct
tcctttctcgccacgttcgccggctttccccgtcaagctctaaatcggggcatcc
ctttagggttccgatttagtgctttacggcacctcgaccccaaaaaacttgatta
gggtgatggttcacgtagtgggccatcgccctgatagacggttttcgccctttg
acgttggagtccacgttctttaatagtggactcttgttccaaactggaacaacac
tcaaccctatctcggtctattcttttgatttataagggatttttggggatttcggc
ctattggttaaaaaatgagctgatttaacaaaaatttaacgcgaattaattctgt
ggaatgtgtgtcagttagggtgtggaaagtccccaggctccccaggcaggcagaa
gtatgcaaagcatgcatctcaattagtcagcaaccaggtgtggaaagtccccagg
ctccccagcaggcagaagtatgcaaagcatgcatctcaattagtcagcaaccata
gtcccgcccctaactccgcccatcccgcccctaactccgcccagttccgccatt
ctccgcccatggctgactaattttttttatttatgcagaggccgaggccgcctc
tgcctctgagctattccagaagtagtgaggaggcttttttggaggcctaggcttt
tgcaaaaagctcccgggagcttgtatatccattttcggatctgatcagcacgtgt
tgacaattaatcatcggcatagtatatcggcatagtataatacgacaaggtgagg
aactaaaccatggccaagttgaccagtgccgttccggtgctcaccgcgcgcgacg
tcgccggagcggtcgagttctggaccgaccggctcgggttctcccgggacttcgt
ggaggacgacttcgccggtgtggtccgggacgacgtgaccctgttcatcagcgcg
gtccaggaccaggtggtgccggacaacaccctggcctgggtgtgggtgcgcggcc
tggacgagctgtacgccgagtggtcggaggtcgtgtccacgaacttccgggacgc
ctccgggccggccatgaccgagatcggcgagcagccgtggggcgggagttcgcc
ctgcgcgacccggccggcaactgcgtgcacttcgtggccgaggagcaggactgac
acgtgctacgagatttcgattccaccgccgccttctatgaaaggttgggcttcgg
aatcgttttccgggacgccggctggatgatcctccagcgcggggatctcatgctg
gagttcttcgcccaccccaacttgtttattgcagcttataatggttacaaataaa
gcaatagcatcacaaatttcacaaataaagcattttttcactgcattctagttg
tggtttgtccaaactcatcaatgtatcttatcatgtctgtataccgtcgacctct
agctagagcttggcgtaatcatggtcatagctgtttcctgtgtgaaattgttatc
cgctcacaattccacacaacatacgagccggaagcataaagtgtaaagcctgggg
tgcctaatgagtgagctaactcacattaattgcgttgcgctcactgcccgctttc
cagtcgggaaacctgtcgtgccagctgcattaatgaatcggccaacgcgcggga
gaggcggtttgcgtattgggcgctcttccgcttcctcgctcactgactcgctgcg
ctcggtcgttcggctgcggcgagcggtatcagctcactcaaaggcggtaatacgg
ttatccacagaatcaggggataacgcaggaaagaacatgtgagcaaaaggccagc
aaaaggccaggaaccgtaaaaaggccgcgttgctggcgtttttccataggctccg
ccccctgacgagcatcacaaaaatcgacgctcaagtcagaggtggcgaaacccg
```

FIG. 33C acaggactataaagataccaggcgtttcccctggaagctccctcgtgcgctctc
ctgttccgaccctgccgcttaccggatacctgtccgcctttctcccttcgggaag
cgtggcgctttctcaatgctcacgctgtaggtatctcagttcggtgtaggtcgtt
cgctccaagctgggctgtgtgcacgaaccccccgttcagcccgaccgctgcgcct
tatccggtaactatcgtcttgagtccaacccggtaagacacgacttatcgcact
ggcagcagccactggtaacaggattagcagagcgaggtatgtaggcggtgctaca
gagttcttgaagtggtggcctaactacggctacactagaaggacagtatttggta
tctgcgctctgctgaagccagttaccttcggaaaaagagttggtagctcttgatc
cggcaaacaaccaccgctggtagcggtggttttttgtttgcaagcagcagatt
acgcgcagaaaaaaggatctcaagaagatcctttgatcttttctacggggtctg
acgctcagtggaacgaaaactcacgttaagggattttggtcatgagattatcaaa
aaggatcttcacctagatccttttaaattaaaaatgaagttttaaatcaatctaa
agtatatgagtaaacttggtctgacagttaccaatgcttaatcagtgaggcac
ctatctcagcgatctgtctatttcgttcatccatagttgcctgactccccgtcgt
gtagataactacgatacgggagggcttaccatctggccccagtgctgcaatgata
ccgcgagacccacgctcaccggctccagatttatcagcaataaaccagccagccg
gaagggccgagcgcagaagtggtcctgcaactttatccgcctccatccagtctat
taattgttgccgggaagctagagtaagtagttcgccagttaatagtttgcgcaac
gttgttgccattgctacaggcatcgtggtgtcacgctcgtcgtttggtatggctt
cattcagctccggttcccaacgatcaaggcgagttacatgatccccatgttgtg
caaaaaagcggttagctccttcggtcctccgatcgttgtcagaagtaagttggcc
gcagtgttatcactcatggttatggcagcactgcataattctcttactgtcatgc
catccgtaagatgcttttctgtgactggtgagtactcaaccaagtcattctgaga
atagtgtatgcggcgaccgagttgctcttgcccggcgtcaatacgggataatacc
gcgccacatagcagaactttaaaagtgctcatcattggaaaacgttcttcggggc
gaaaactctcaaggatcttaccgctgttgagatccagttcgatgtaacccactcg
tgcacccaactgatcttcagcatcttttactttcaccagcgtttctgggtgagca
aaaacaggaaggcaaaatgccgcaaaaagggaataagggcgacacggaaatgtt
gaatactcatactcttcctttttcaatattattgaagcatttatcagggttattg
tctcatgagcggatacatatttgaatgtatttagaaaaataaacaatagggggtt
ccgcgcacatttccccgaaaagtgccacctgacgtcgacggatcgggagatctcc
cgatcccctatggtgcactctcagtacaatctgctctgatgccgcatagttaagc
cagtatctgctccctgcttgtgtgttggaggtcgctgagtagtgcgcgagcaaaa
tttaagctacaacaaggcaaggcttgaccgacaattgcatgaagaatctgcttag
ggttaggcgttttgcgctgcttcgcgatgtacgggccagatatacgcgttgacat
tgattattgactagttattaatagtaatcaattacggggtcattagttcatagcc
catatatggagttccgcgttacataacttacggtaaatggcccgcctggctgacc
gcccaacgacccccgcccattgacgtcaataatgacgtatgttcccatagtaacg
ccaatagggactttccattgacgtcaatgggtggactatttacggtaaactgccc
acttggcagtacatcaagtgtatcatatgccaagtacgccccctattgacgtcaa

FIG. 33D

```
tgacggtaaatggcccgcctggcattatgcccagtacatgaccttatgggactttt
cctacttggcagtacatctacgtattagtcatcgctattaccatggtgatgcggt
tttggcagtacatcaatgggcgtggatagcggtttgactcacggggatttccaag
tctccacccccattgacgtcaatgggagtttgttttggcaccaaaatcaacgggac
tttccaaaatgtcgtaacaactccgccccattgacgcaaatgggcggtaggcgtg
tacggtgggaggtctatataagcagagctctctggctaactagagaacccactgc
ttactggcttatcgaaattaatacgactcactatagggagacccaagctggttta
aacttaagcttggtaccgagctcactagtccagtgtggtggcagatatccagcac
agtggcggccgctcgaggggccgttttgcctgtactgggtctctctggttagac
cagatctgagcctgggagctctctggctaactagggaacccactgcttaagcctc
aataaagcttgccttgagtgcttcaagtagtgtgtgcccgtctgttgtgtgactc
tggtaactagagatccctcagaccccttttagtcagtgtggaaaatctctagcagt
ggcgcccgaacagggacttgaaagcgaaagggaaaccagaggagctctctcgacg
caggactcggcttgctgaagcgcgcacggcaagaggcgaggggcggcgactggtg
agtacgccaaaaattttgactagcggaggctagaaggagagagatgggtgcgaga
gcgtcagtattaagcggggggagaattagatcgcgatgggaaaaaattcggttaag
gccaggggggaaagaaaaaatataaattaaaacatatagtatgggcaagcagggag
ctagaacgattcgcagttaatcctggcctgttagaaacatcagaaggctgtagac
aaatactgggacagctacaaccatcccttcagacaggatcagaagaacttagatc
attatataatacagtagcaaccctctattgtgtgcatcaaaggatagagataaaa
gacaccaaggaagctttagacaagatagaggaagagcaaaacaaaagtaagacca
ccgcacagcaagcggccgctgatcttcagacctggaggaggagatatgagggaca
attggagaagtgaattatataaatataaagtagtaaaaattgaaccattaggagt
agcacccaccaaggcaaagagaagagtggtgcagagagaaaaaagagcagtggga
ataggagctttgttccttgggttcttgggagcagcaggaagcactatgggcgcag
cgtcaatgacgctgacggtacaggccagacaattattgtctggtatagtgcagca
gcagaacaatttgctgagggctattgaggcgcaacagcatctgttgcaactcaca
gtctggggcatcaagcagctccaggcaagaatcctggctgtggaaagatacctaa
aggatcaacagctcctggggatttggggttgctctggaaaactcatttgccacc
tgctgtgccttggaatgctagttggagtaataaatctctggaacagatttggaat
cacacgacctggatggagtgggacagagaaattaacaattacacaagcttaatac
actccttaattgaagaatcgcaaaaccagcaagaaaagaatgaacaagaattatt
ggaattagataaatgggcaagtttgtggaattggtttaacataacaaattggctg
tggtatataaaattattcataatgatagtaggaggcttggtaggtttaagaatag
tttttgctgtactttctatagtgaatagagttaggcagggatattcaccattatc
gtttcagacccacctcccaaccccgaggggacccgacaggcccttaattaatccc
ctgattctgtggataaccgtattaccgcctttgagtgagctgcacgggagcaatt
aatctatagattaaaaagtgaaaggctacaataggacgggagcaattaatctata
gattaaaaagtgaaaggctacaataggacgggagcaattaatctatagattaaaa
agtgaaaggctacaataggacgggagcaattaatctatagattaaaaagtgaaag
```

FIG. 33E

```
gctacaataggacgggagcaattaatctatagattaaaaagtgaaaggctacaat
aggacgggagcaattaatctatagattaaaaagtgaaaggctacaataggacggg
agcaattaatctatagattaaaaagtgaaaggctacaataggacggtaaactcga
cctatataagcagagctcgtttagtgaaccgtcagatcgcctggagacgccatcc
acgctgttttgacctccatagaagacaccgggaccgatccagcctccgcggcccc
gaattgaattctccctatcagtgatagagatctccctatcagtgatagagaggcc
attacggcctgccaccatgttcgttatcatccaggctcacgaataccagaaatac
gctgctgttctggaccagatgttccgtctgcgtaaaaaagttttcgctgacaccc
tgtgctgggacgttccggttatcggtccgtacgaacgtgactcctacgactccct
ggctccggcttacctggtttggtgcaacgactcccgtacccgtctgtacggtggt
atgcgtctgatgccgaccaccggtccgaccctgctgtacgacgttttccgtgaaa
ccttcccggacgctgctgacctgatcgctccgggtatctgggaaggtacccgtat
gtgcatcgacgaagaagctatcgctaaagacttcccggaaatcgacgctggtcgt
gctttctccatgatgctgctggctctgtgcgaatgcgctctggaccacggtatcc
acaccatgatctccaactacgaaccgtacctgaaacgtgtttacaaacgtgctgg
tgctgaagttgaagaactgggtcgtgctgacggttacggtaaatacccggtttgc
tgcggtgctttcgaagtttccgaccgtgttctgcgtaaaatgcgtgctgctctgg
gtctgaccctgccgctgtacgttcgtcacgttccggctcgttccgttgttaccca
gttcctggaaatggctgctgctgctaacgacgaaaactacgctctggttgcttaa
taatgccacc
```

FIG. 33F

```
cggccatcgataaggatccgcggccgcaatcaacctctgattacaaatttgtgaaagattgactggtattcttaactatgttgctcctttta
cgctatgtggatacgctgcttaatgcctttgtatcatgctattacttccgtacggcttcattctctcctgtataaatcctgttgctgtctct
ttatgaggagttgtgccccgttgtcaggcaacgtggctgtggtgcactgtgtttgctgacgcaaccccactgttggggcattgccacc
acctatcaactccttccgggactttgctttcccctccctattgccacggaactcattgccgctgccttgccgctgctgacagg
ggctcggctgttgggcactgacaattccgtgtggtttgtcgggaagctgacgtcctttccatgctcgcctgttgccaactggattct
gcgcgggacgtcctttctgctacgtcccctcggcctcaatccagcggacccttccttcccgcgacctgctgccggttctgcgcctcttccg
cgtcttcgccttcgccctcagacgagtcggatctccctttgggccgccctcccccgcctgcctgcaggtttgtcgagacctagaaaacatgg
agcaatcacaagtagcaatacagcagctaccaatgctgattgtgcct
```

FIG. 34B ggctagaagcacaagaggaggaggaggtgggttttccagtcacacctcaggtacc
tttaagaccaatgacttacaaggcagctgtagatcttagccacttttaaaagaa
aaggggggactggaagggctaattcactcccaacgaagacaagatctgcttttg
cttgtactgggtctctctggttagaccagatctgagcctgggagctctctggcta
actagggaacccactgcttaagcctcaataaagcttgccttgagtgcttcaagta
gtgtgtgcccgtctgttgtgtgactctggtaactagagatccctcagaccctttt
agtcagtgtggaaaatctctagcagggcccgtttaaacccgctgatcagcctcga
ctgtgccttctagttgccagccatctgttgtttgccctccccgtgccttcctt
gaccctggaaggtgccactcccactgtcctttcctaataaaatgaggaaattgca
tcgcattgtctgagtaggtgtcattctattctggggggtggggtggggcaggaca
gcaaggggaggattgggaagacaatagcaggcatgctggggatgcggtgggctc
tatggcttctgaggcggaagaaccagctggggctctagggggtatccccacgcg
ccctgtagcggcgcattaagcgcggcgggtgtggtggttacgcgcagcgtgaccg
ctacacttgccagcgccctagcgcccgctcctttcgctttcttcccttcctttct
cgccacgttcgccggctttccccgtcaagctctaaatcggggcatccctttaggg
ttccgatttagtgctttacggcacctcgacccaaaaaacttgattagggtgatg
gttcacgtagtgggccatcgccctgatagacggttttcgccctttgacgttgga
gtccacgttctttaatagtggactcttgttccaaactggaacaacactcaaccct
atctcggtctattcttttgatttataagggattttggggatttcggcctattggt
taaaaaatgagctgatttaacaaaaatttaacgcgaattaattctgtggaatgtg
tgtcagttagggtgtggaaagtccccaggctccccaggcaggcagaagtatgcaa
agcatgcatctcaattagtcagcaaccaggtgtggaaagtccccaggctccccag
caggcagaagtatgcaaagcatgcatctcaattagtcagcaaccatagtcccgcc
cctaactccgcccatcccgcccctaactccgcccagttccgcccattctccgccc
catggctgactaatttttttatttatgcagaggccgaggccgcctctgcctctg
agctattccagaagtagtgaggaggcttttttggaggcctaggcttttgcaaaaa
gctcccgggagcttgtatatccatttcggatctgatcagcacgtgttgacaatt
aatcatcggcatagtatatcggcatagtataatacgacaaggtgaggaactaaac
catggccaagttgaccagtgccgttccggtgctcaccgcgcgcgacgtcgccgga
gcggtcgagttctggaccgaccggctcgggttctcccgggacttcgtggaggacg
acttcgccggtgtggtccgggacgacgtgaccctgttcatcagcgcggtccagga
ccaggtggtgccggacaacaccctggcctgggtgtgggtgcgcggcctggacgag
ctgtacgccgagtggtcggaggtcgtgtccacgaacttccgggacgcctccggc
cggccatgaccgagatcggcgagcagccgtggggcgggagttcgccctgcgcga
cccggccggcaactgcgtgcacttcgtggccgaggagcaggactgacacgtgcta
cgagatttcgattccaccgccgccttctatgaaaggttgggcttcggaatcgttt
tccgggacgccggctggatgatcctccagcgcggggatctcatgctggagttctt
cgcccaccccaacttgtttattgcagcttataatggttacaaataaagcaatagc
atcacaaatttcacaaataaagcattttttcactgcattctagttgtggtttgt
ccaaactcatcaatgtatcttatcatgtctgtataccgtcgacctctagctagag cttggcgtaatcatggtcatagctgtttcctgtgtgaaattgttatccgctcaca
attccacacaacatacgagccggaagcataaagtgtaaagcctggggtgcctaat
gagtgagctaactcacattaattgcgttgcgctcactgcccgctttccagtcggg
aaacctgtcgtgccagctgcattaatgaatcggccaacgcgcggggagaggcggt
ttgcgtattgggcgctcttccgcttcctcgctcactgactcgctgcgctcggtcg
ttcggctgcggcgagcggtatcagctcactcaaaggcggtaatacggttatccac
agaatcaggggataacgcaggaaagaacatgtgagcaaaaggccagcaaaaggcc
aggaaccgtaaaaaggccgcgttgctggcgtttttccataggctccgcccccctg
acgagcatcacaaaaatcgacgctcaagtcagaggtggcgaaacccgacaggact
ataaagataccaggcgtttccccctggaagctccctcgtgcgctctcctgttccg
accctgccgcttaccggatacctgtccgcctttctcccttcgggaagcgtggcgc
tttctcaatgctcacgctgtaggtatctcagttcggtgtaggtcgttcgctccaa
gctgggctgtgtgcacgaaccccccgttcagcccgaccgctgcgccttatccggt
aactatcgtcttgagtccaacccggtaagacacgacttatcgccactggcagcag
ccactggtaacaggattagcagagcgaggtatgtaggcggtgctacagagttctt
gaagtggtggcctaactacggctacactagaaggacagtatttggtatctgcgct
ctgctgaagccagttaccttcggaaaaagagttggtagctcttgatccggcaaac
aaaccaccgctggtagcggtggtttttttgtttgcaagcagcagattacgcgcag
aaaaaaggatctcaagaagatcctttgatcttttctacggggtctgacgctcag
tggaacgaaaactcacgttaagggattttggtcatgagattatcaaaaggatct
tcacctagatccttttaaattaaaaatgaagttttaaatcaatctaaagtatata
tgagtaaacttggtctgacagttaccaatgcttaatcagtgaggcacctatctca
gcgatctgtctatttcgttcatccatagttgcctgactccccgtcgtgtagataa
ctacgatacgggagggcttaccatctggccccagtgctgcaatgataccgcgaga
cccacgctcaccggctccagatttatcagcaataaaccagccagccggaagggcc
gagcgcagaagtggtcctgcaactttatccgcctccatccagtctattaattgtt
gccgggaagctagagtaagtagttcgccagttaatagtttgcgcaacgttgttgc
cattgctacaggcatcgtggtgtcacgctcgtcgtttggtatggcttcattcagc
tccggttcccaacgatcaaggcgagttacatgatccccatgttgtgcaaaaaag
cggttagctccttcggtcctccgatcgttgtcagaagtaagttggccgcagtgtt
atcactcatggttatggcagcactgcataattctcttactgtcatgccatccgta
agatgcttttctgtgactggtgagtactcaaccaagtcattctgagaatagtgta
tgcggcgaccgagttgctcttgcccggcgtcaatacgggataataccgcgccaca
tagcagaactttaaaagtgctcatcattggaaaacgttcttcggggcgaaaactc
tcaaggatcttaccgctgttgagatccagttcgatgtaacccactcgtgcaccca
actgatcttcagcatcttttactttcaccagcgtttctgggtgagcaaaaacagg
aaggcaaaatgccgcaaaaagggaataaggcgacacggaaatgttgaatactc
atactcttccttttcaatattattgaagcatttatcagggttattgtctcatga
gcggatacatatttgaatgtatttagaaaaataaacaataggggttccgcgcac
atttccccgaaaagtgccacctgacgtcgacggatcgggagatctcccgatcccc

FIG. 34D

```
tatggtgcactctcagtacaatctgctctgatgccgcatagttaagccagtatct
gctccctgcttgtgtgttggaggtcgctgagtagtgcgcgagcaaaatttaagct
acaacaaggcaaggcttgaccgacaattgcatgaagaatctgcttagggttaggc
gttttgcgctgcttcgcgatgtacgggccagatatacgcgttgacattgattatt
gactagttattaatagtaatcaattacggggtcattagttcatagcccatatatg
gagttccgcgttacataacttacggtaaatggcccgcctggctgaccgcccaacg
acccccgcccattgacgtcaataatgacgtatgttcccatagtaacgccaatagg
gactttccattgacgtcaatgggtggactatttacggtaaactgcccacttggca
gtacatcaagtgtatcatatgccaagtacgccccctattgacgtcaatgacggta
aatggcccgcctggcattatgcccagtacatgaccttatgggactttcctacttg
gcagtacatctacgtattagtcatcgctattaccatggtgatgcggttttggcag
tacatcaatgggcgtggatagcggtttgactcacggggatttccaagtctccacc
ccattgacgtcaatgggagtttgttttggcaccaaaatcaacgggactttccaaa
atgtcgtaacaactccgccccattgacgcaaatgggcggtaggcgtgtacggtgg
gaggtctatataagcagagctctctggctaactagagaacccactgcttactggc
ttatcgaaattaatacgactcactatagggagacccaagctggtttaaacttaag
cttggtaccgagctcactagtccagtgtggtggcagatatccagcacagtggcgg
ccgctcgagtctagagggcccgttttgcctgtactgggtctctctggttagacca
gatctgagcctgggagctctctggctaactagggaacccactgcttaagcctcaa
taaagcttgccttgagtgcttcaagtagtgtgtgcccgtctgttgtgtgactctg
gtaactagagatccctcagaccctttagtcagtgtggaaaatctctagcagtgg
cgcccgaacagggacttgaaagcgaaagggaaaccagaggagctctctcgacgca
ggactcggcttgctgaagcgcgcacggcaagaggcgaggggcggcgactggtgag
tacgccaaaaattttgactagcggaggctagaaggagagagatgggtgcgagagc
gtcagtattaagcgggggagaattagatcgcgatgggaaaaaattcggttaaggc
caggggaaagaaaaaatataaattaaaacatatagtatgggcaagcagggagct
agaacgattcgcagttaatcctggcctgttagaaacatcagaaggctgtagacaa
atactgggacagctacaaccatcccttcagacaggatcagaagaacttagatcat
tatataatacagtagcaaccctctattgtgtgcatcaaggatagagataaaga
caccaaggaagctttagacaagatagaggaagagcaaaacaaaagtaagaccacc
gcacagcaagcggccgctgatcttcagacctggaggaggagatatgagggacaat
tggagaagtgaattatataaatataaagtagtaaaaattgaaccattaggagtag
cacccaccaaggcaaagagaagagtggtgcagagagaaaaagagcagtgggaat
aggagctttgttccttgggttcttgggagcagcaggaagcactatgggcgcagcg
tcaatgacgctgacggtacaggccagacaattattgtctggtatagtgcagcag
agaacaatttgctgagggctattgaggcgcaacagcatctgttgcaactcacagt
ctggggcatcaagcagctccaggcaagaatcctggctgtggaaagatacctaaag
gatcaacagctcctggggatttggggttgctctggaaaactcatttgcaccactg
ctgtgccttggaatgctagttggagtaataaatctctggaacagatttggaatca
cacgacctggatggagtgggacagagaaattaacaattacacaagcttaatacac
```

FIG. 34E

```
tccttaattgaagaatcgcaaaaccagcaagaaaagaatgaacaagaattattgg
aattagataaatgggcaagtttgtggaattggtttaacataacaaattggctgtg
gtatataaaattattcataatgatagtaggaggcttggtaggtttaagaatagtt
tttgctgtactttctatagtgaatagagttaggcagggatattcaccattatcgt
ttcagacccacctcccaaccccgaggggacccgacaggcccttaattaattggct
ccggtgccgtcagtgggcagagcgcatcgcccacagtccccgagaagttggg
gggaggggtcggcaattgaaccggtgcctagagaaggtggcgcggggtaaactgg
gaaagtgatgtcgtgtactggctccgccttttcccgagggtgggggagaaccgt
atataagtgcagtagtcgccgtgaagctagcaattgtgagcggataacaattcca
cagtcgacctaggttgtgtcgcgagtgttggatcccagctgacaccaattgtga
gcgctcacaattgctagaagaatacaaccacgactatataagaatacaaccacga
ctccgttctttttcgcaacgggtttgccgccagaacacaggtaagtgccgtgtgt
ggttcccgcgggcctggcctctttacgggttatggcccttgcgtgccttgaatta
cttccacctggctgcagtacgtgattcttgatcccgagcttcgggttggaagtgg
gtgggagagttcgaggccttgcgcttaaggagccccttcgcctcgtgcttgagtt
gaggcctggcctgggcgctggggccgccgcgtgcgaatctggtggccacttcgcg
cctgtctcgctgctttcgataagtctctagccatttaaaattttgatgacctgc
tgcgacgcttttttctggcaagatagtcttgtaaatgcgggccaagatctgcac
actggtatttcggttttggggccgcgggcggcgacggggcccgtgcgtcccagc
gcacatgttcggcgaggcggggcctgcgagcgcggccaccgagaatcggacgggg
gtagtctcaagctggccggcctgctctggtgcctggcctcgcgccgccgtgtatc
gccccgccctgggcggcaaggctggcccggtcggcaccagttgcgtgagcggaaa
gatggccgcttcccggccctgctgcagggagctcaaaatggaggacgcggcgctc
gggagagcgggcgggtgagtcacccacacaaaggaaaagggcctttccgtcctca
gccgtcgcttcatgtgactccacggagtaccgggcgccgtccaggcacctcgatt
agttctcgagcttttggagtacgtcgtctttaggttggggggaggggttttatgc
gatggagtttccccacactgagtgggtggagactgaagttaggccagcttggcac
ttgatgtaattctccttggaatttgccttttttgagtttggatcttggttcattc
tcaagcctcagacagtggttcaaagttttttttcttccatttcaggtgaattcggc
cattacggcccgccaccatggctagattagataaaagtaaagtgattaacagcgc
attagagctgcttaatgaggtcggaatcgaaggtttaacaacccgtaaactcgcc
cagaagctaggtgtagagcagcctacattgtattggcatgtaaaaaataagcggg
ctttgctcgacgccttagccattgagatgttagataggcaccatactcacttttg
cccttagaaggggaaagctggcaagattttttacgtaataacgctaaaagtttt
agatgtgcttactaagtcatcgcgatggagcaaaagtacatttaggtacacggc
ctacagaaaaacagtatgaaactctcgaaaatcaattagccttttatgccaaca
aggttttcactagagaatgcattatatgcactcagcgctgtgggcatttact
ttaggttgcgtattggaagatcaagagcatcaagtcgctaaagaagaaagggaaa
cacctactactgatagtatgccgccattattacgacaagctatcgaattatttga
tcaccaaggtgcagagccagccttcttattcggccttgaattgatcatatgcgga
```

FIG. 34F

```
ttagaaaaacaacttaaatgtgaaagtgggtcgccaaaaaagaagagaaaggtcg
acggcggtggtgctttgtctcctcagcactctgctgtcactcaaggaagtatcat
caagaacaaggagggcatggatgctaagtcactaactgcctggtcccggacactg
gtgaccttcaaggatgtatttgtggacttcaccagggaggagtggaagctgctgg
acactgctcagcagatcgtgtacagaaatgtgatgctggagaactataagaacct
ggtttccttgggttatcagcttactaagccagatgtgatcctccggttggagaag
ggagaagagccctggctggtggagagagaaattcaccaagagacccatcctgatt
cagagactgcatttgaaatcaaatcatcagtttaaggccgcct
```

FIG. 34G agaattcgatatcaagcttatcgataatcaacctctgattacaaatttgtgaaagattgactgtattcttaactatgttgctccttttacgctat
gtggatacgctgcttaatgcctttgtatcatgctattacttcccgtacgcttcattctctccttgtataaatcctgttgctgtctctttatga
ggagttgtgccgttgtcaggcaacgtggcgtggtgtgctgtttgctgacgcaactcattgccgccacactgttgggcattgccaccacctat
caactccttccggacttgctttccccctcccctattgccacggcgaactcattcccatgctgctcgctcgctgctgctgctgacagggctcg
gctgttgggcactgacaattccgtgtgttgtcgggaagctgacgtctcttccatgctgctgtccctgtgttgccaactgattctgcgcg
ggacgtcctcttgctactgtccttcgccgtcgatctcccttttgggccgcctcccgcgtgtctgagacctagaaaaacatggagcaat
gccttcgccctcagacgagtcggatctcccttgggccgcctaccaatgctgattgtgcctgctagaagcacaagaggaggaggtgggtttccagtcacactc
cacaagtagcaatacagcagctaccaatgctgattgtgcctgctagaagcacaagaggaggaggtgggtttccagtcacactc
agtaccttttaagacaagatcgtagatcttagccacttttaaagaccagatctgagcctgagctctctgctctaactagggaacc
ccaacgaagacaagatcgttttgcttgtactggtctctctgttagaccagatctgagcctgttgtgcctgctgactctgtaactagatccctcagacc
cactgcttaagcctcaataaagcttgcctgagtgctcaagtagtgtgcctgctgctcgtcctgctgcctgctcagcctgccatctgttgttg
cttttagtcagtgtggaaaatctctagcaggccctttaaaccctgatcagcctgcttcctcagttgccagcatcgcattgctgagtag
gtgtcattctattctggggggtgggtcaggacagcagttgggcctcaggggggtatcccacgcgccgctccttttgcttcctcttctgccacgtt
gggctctatgcttctgagggcggaagaaccagctgggcctcaggggttagtgcatcccacttgcatctgatttagtgctgcacctgaccccaaaaaacttgatta
cgccggctttcccgctcaagtctcttaaatcgggcatcccttaggttccagtgtttcctcgatttagtgctgcacctgaccccaaaaaacttgatta
gggtgatggttcacgtagtgggccatgccctgatagacgttttcgccctttgacgttgagtccacgttcttaatagtggactcttgttcc
aaactgaacaacactcaaccctatctcgtctattcttttgattttataaggatttgggattcgggtttaaaaatgagctgattt
aacaaaatttaacgcgaattaattagtcagcaaccaggttgttgaatgtgtgtcagttaggtgtgaaagtcccaggctcccaggcaggccagcagccagtcccccagcag
aagcatgcatctcaattagtcagcaaccaggttgtgaaagtcccaggctcccagcag

FIG. 35B gcagaagtatgcaaagcatgcatctcaattagtcagcaaccatagtcccgcccct
aactccgcccatcccgcccctaactccgcccagttccgcccattctccgccccat
ggctgactaattttttttatttatgcagaggccgaggccgcctctgcctctgagc
tattccagaagtagtgaggaggcttttttggaggcctaggcttttgcaaaaagct
cccgggagcttgtatatccattttcggatctgatcagcacgtgttgacaattaat
catcggcatagtatatcggcatagtataatacgacaaggtgaggaactaaaccat
ggccaagttgaccagtgccgttccggtgctaccgcgcgcgacgtcgccggagcg
gtcgagttctggaccgaccggctcgggttctcccgggacttcgtggaggacgact
tcgccggtgtggtccgggacgacgtgaccctgttcatcagcgcggtccaggacca
ggtggtgccggacaacaccctggcctgggtgtgggtgcgcggcctggacgagctg
tacgccgagtggtcggaggtcgtgtccacgaacttccgggacgcctccgggccgg
ccatgaccgagatcggcgagcagccgtggggcgggagttcgccctgcgcgaccc
ggccggcaactgcgtgcacttcgtggccgaggagcaggactgacacgtgctacga
gatttcgattccaccgccgccttctatgaaaggttgggcttcggaatcgttttcc
gggacgccggctggatgatcctccagcgcggggatctcatgctggagttcttcgc
ccaccccaacttgtttattgcagcttataatggttacaaataaagcaatagcatc
acaaatttcacaaataaagcattttttcactgcattctagttgtggtttgtcca
aactcatcaatgtatcttatcatgtctgtataccgtcgacctctagctagagctt
ggcgtaatcatggtcatagctgtttcctgtgtgaaattgttatccgctcacaatt
ccacacaacatacgagccggaagcataaagtgtaaagcctggggtgcctaatgag
tgagctaactcacattaattgcgttgcgctcactgcccgctttccagtcgggaaa
cctgtcgtgccagctgcattaatgaatcggccaacgcgcggggagaggcggtttg
cgtattgggcgctcttccgcttcctcgctcactgactcgctgcgctcggtcgttc
ggctgcggcgagcggtatcagctcactcaaaggcggtaatacggttatccacaga
atcaggggataacgcaggaaagaacatgtgagcaaaaggccagcaaaaggccagg
aaccgtaaaaaggccgcgttgctggcgtttttccataggctccgcccccctgacg
agcatcacaaaaatcgacgctcaagtcagaggtggcgaaacccgacaggactata
aagataccaggcgtttccccctggaagctccctcgtgcgctctcctgttccgacc
ctgccgcttaccggatacctgtccgcctttctcccttcgggaagcgtggcgcttt
ctcaatgctcacgctgtaggtatctcagttcggtgtaggtcgttcgctccaagct
gggctgtgtgcacgaaccccccgttcagcccgaccgctgcgccttatccggtaac
tatcgtcttgagtccaacccggtaagacacgacttatcgccactggcagcagcca
ctggtaacaggattagcagagcgaggtatgtaggcggtgctacagagttcttgaa
gtggtggcctaactacggctacactagaaggacagtatttggtatctgcgctctg
ctgaagccagttaccttcggaaaagagttggtagctcttgatccggcaaacaaa
ccaccgctggtagcggtggtttttttgtttgcaagcagcagattacgcgcagaaa
aaaaggatctcaagaagatcctttgatcttttctacggggtctgacgctcagtgg
aacgaaaactcacgttaagggattttggtcatgagattatcaaaaaggatcttca
cctagatccttttaaattaaaaatgaagttttaaatcaatctaaagtatatatga
gtaaacttggtctgacagttaccaatgcttaatcagtgaggcacctatctcagcg

FIG. 35C

```
atctgtctatttcgttcatccatagttgcctgactccccgtcgtgtagataacta
cgatacgggagggcttaccatctggccccagtgctgcaatgataccgcgagaccc
acgctcaccggctccagatttatcagcaataaaccagccagccggaagggccgag
cgcagaagtggtcctgcaactttatccgcctccatccagtctattaattgttgcc
gggaagctagagtaagtagttcgccagttaatagtttgcgcaacgttgttgccat
tgctacaggcatcgtggtgtcacgctcgtcgtttggtatggcttcattcagctcc
ggttcccaacgatcaaggcgagttacatgatccccatgttgtgcaaaaaagcgg
ttagctccttcggtcctccgatcgttgtcagaagtaagttggccgcagtgttatc
actcatggttatggcagcactgcataattctcttactgtcatgccatccgtaaga
tgcttttctgtgactggtgagtactcaaccaagtcattctgagaatagtgtatgc
ggcgaccgagttgctcttgcccggcgtaatacgggataataccgcgccacatag
cagaactttaaaagtgctcatcattggaaaacgttcttcggggcgaaaactctca
aggatcttaccgctgttgagatccagttcgatgtaacccactcgtgcacccaact
gatcttcagcatcttttactttcaccagcgtttctgggtgagcaaaaacaggaag
gcaaaatgccgcaaaaaagggaataagggcgacacggaaatgttgaatactcata
ctcttccttttcaatattattgaagcatttatcagggttattgtctcatgagcg
gatacatatttgaatgtatttagaaaaataaacaatagggggttccgcgcacatt
tccccgaaaagtgccacctgacgtcgacggatcgggagatctcccgatcccctat
ggtgcactctcagtacaatctgctctgatgccgcatagttaagccagtatctgct
ccctgcttgtgtgttggaggtcgctgagtagtgcgcgagcaaaatttaagctaca
acaaggcaaggcttgaccgacaattgcatgaagaatctgcttagggttaggcgtt
ttgcgctgcttcgcgatgtacgggccagatatacgcgttgacattgattattgac
tagttattaatagtaatcaattacggggtcattagttcatagcccatatatggag
ttccgcgttacataacttacggtaaatggcccgcctggctgaccgcccaacgacc
cccgcccattgacgtcaataatgacgtatgttcccatagtaacgccaatagggac
tttccattgacgtcaatgggtggactatttacggtaaactgcccacttggcagta
catcaagtgtatcatatgccaagtacgccccctattgacgtcaatgacggtaaat
ggcccgcctggcattatgcccagtacatgaccttatgggactttcctacttggca
gtacatctacgtattagtcatcgctattaccatggtgatgcggttttggcagtac
atcaatgggcgtggatagcggtttgactcacggggatttccaagtctccacccca
ttgacgtcaatgggagtttgttttggcaccaaaatcaacgggactttccaaaatg
tcgtaacaactccgccccattgacgcaaatgggcggtaggcgtgtacggtgggag
gtctatataagcagagctctctggctaactagagaacccactgcttactggctta
tcgaaattaatacgactcactatagggagacccaagctggtttaaacttaagctt
ggtaccgagctcactagtccagtgtggtggcagatatccagcacagtggcggccg
ctcgaggggcccgttttgcctgtactgggtctctctggttagaccagatctgagc
ctgggagctctctggctaactagggaacccactgcttaagcctcaataaagcttg
ccttgagtgcttcaagtagtgtgtgcccgtctgttgtgtgactctggtaactaga
gatccctcagacccttttagtcagtgtggaaaatctctagcagtggcgcccgaac
agggacttgaaagcgaaagggaaaccagaggagctctctcgacgcaggactcggc
```

FIG. 35D

```
ttgctgaagcgcgcacggcaagaggcgaggggcggcgactggtgagtacgccaaa
aatttgactagcggaggctagaaggagagagatgggtgcgagagcgtcagtatt
aagcggggagaattagatcgcgatgggaaaaattcggttaaggccaggggg aa
agaaaaatataaattaaaacatatagtatgggcaagcagggagctagaacgatt
cgcagttaatcctggcctgttagaaacatcagaaggctgtagacaaatactggga
cagctacaaccatccttcagacaggatcagaagaacttagatcattatataata
cagtagcaaccctctattgtgtgcatcaaaggatagagataaaagacaccaagga
agctttagacaagatagaggaagagcaaaacaaagtaagaccaccgcacagcaa
gcggccgctgatcttcagacctggaggaggagatatgagggacaattggagaagt
gaattatataaatataaagtagtaaaaattgaaccattaggagtagcacccacca
aggcaaagagaagagtggtgcagagagaaaaagagcagtgggaataggagcttt
gttccttgggttcttgggagcagcaggaagcactatgggcgcagcgtcaatgacg
ctgacggtacaggccagacaattattgtctggtatagtgcagcagcagaacaatt
tgctgagggctattgaggcgcaacagcatctgttgcaactcacagtctggggcat
caagcagctccaggcaagaatcctggctgtggaaagatacctaaaggatcaacag
ctcctggggatttggggttgctctggaaaactcatttgcaccactgctgtgcctt
ggaatgctagttggagtaataaatctctggaacagatttggaatcacacgacctg
gatggagtgggacagagaaattaacaattacacaagcttaatacactccttaatt
gaagaatcgcaaaaccagcaagaaaagaatgaacaagaattattggaattagata
aatgggcaagtttgtggaattggtttaacataacaaattggctgtggtatataaa
attattcataatgatagtaggaggcttggtaggtttaagaatagttttt gctgta
ctttctatagtgaatagagttaggcagggatattcaccattatcgtttcagaccc
acctcccaaccccgaggggacccgacaggcccttaattaatcccctgattctgtg
gataaccgtattaccgcctttgagtgagctgcacctagtacggattagaagccgc
cgagcgggtgacagccctccgaaggaagactctcctccgtgcgtcctcgtcttca
ccggtcgcgttcctgaaacgcagatgtgcctcgcgccgcactgctccgaacaatg
tcgactctagaggtaaactcgacctatataagcagagctcgtttagtgaaccgtc
agatcgcctggagacgccatccacgctgttttgacctccatagaagacaccggga
ccgatccagcctccgcggccccgaattgaattcggccattacggcctgccaccgt
gccaccatgctggagcccggcgagaagccctacaagtgccccgagtgcggcaaga
gcttcagcgactgcagggacctggccaggcaccagaggacccacaccggcgagaa
gccctacaagtgccccgagtgcggcaagagcttcagcgaccccggcaacctggtg
aggcaccagaggacccacaccggcgagaagccctacaagtgccccgagtgcggca
agagcttcagccagagcagcagcctggtgaggcaccagaggacccacaccggcga
gaagccctacaagtgccccgagtgcggcaagagcttcagccagagggcccacctg
gagaggcaccagaggacccacaccggcgagaagccctacaagtgccccgagtgcg
gcaagagcttcagccagagcggcgacctgaggaggcaccagaggacccacaccgg
cgagaagccctacaagtgccccgagtgcggcaagagcttcagccagagcagcaac
ctggtgaggcaccagaggacccacaccggcaagaagaccagcggcccaggcggcc
gatgctaagtcactgactgcctggtcccggacactggtgaccttcaaggatgtgt
```

FIG. 35E

```
ttgtggacttcaccagggaggagtggaagctgctggacactgctcagcagatcct
gtacagaaatgtgatgctggagaactataagaacctggtttccttgggttatcag
cttactaagccagatgtgatcctccggttggagaagggagaagagccctggctgg
tggagagagaaattcaccaagagacccatcctgattcagagactgcatttgaaat
caaatcatcagttgggcgcgccgacgcgctggacgatttcgatctcgacatgctg
ggttctgatgccctcgatgactttgacctggatatgttgggaagcgacgcattgg
atgactttgatctggacatgctcggctccgatgctctggacgatttcgatctcga
tatgttaattaactaattaat
```

FIG. 35F

```
agaattcgatatcaagcttatcgataatcaacctctgattacaaatttgtgaagattgactggtattcttaactatgttgctcctttta
cgctatgtggatacgctgcttaatgccttgtatcatgctattacttccgtacggcttcatttctctcctgtataaatcctggttgc
tgtctcttatgaggagttgtggcccgttgtcaggcaacgtggcgtggtgtcactgtttgctgacgcaaccccccactgttggg
gcattgccaccacctatcaactcctttcgttcgcttccccctccttgccacgcggaactcattgccgcctgcttgc
ccgctgctgacaggggctcggctgttgggcactgacaattccgtgtgttgtcggggaagctgacgtcctttcatgctgctc
gcctgtgttgccaactggattctgcgcggaacgtccttctgccttgccctcaatccagcggaccttccttccgcgg
cctgctgccggttctgcgggcctcttccgcgtcttgccttcgcctcagacgagtcggatctccctttgggcgcctcccccgcctg
cctgcaggtttgtcgagacctagaaaacatggagcaatacacacctcagtaccttaagacaatgacttacaagctgattgtgcctgcta
gaagcacaagagagagagtgggttttccagtcctccaaccaagatctgcttttgcttgtactgg
cttagccactttttaaaagaaaaggggggactgaaggctaattcactccaacgaagacaagatctgcttttgcttgtactgg
gtctctcctgttagaccagatctgagccgtctgttgtgtgacctctgtaactagagatcccctagacctgtttgttgccctcccccgtgccttcct
agtgcttcaagtagtgtgtgccgtctgttgtgtgactgtgactctgtaactagagatccctcagacctgttgttcgccctcccccgtgccttcct
gcagggcccgtttaaacccgctgatcagctccagctgtccttctagttgcctctagttgccagccatctgttgtttgccccctccccgtgccttcct
tgaccctggaagtgccactcccactgtcctttcctaataaaatgaggaattggcatcgcattgtctgagtagtcgttcattctattctg
gggggtggggtggggcaggacagcaaggggggaggattggaagacaatagcaggcatgctggaatgcggtgggctgggctctat
ggcttctgaggcggaaagaaccagctggggctctaggggtatcccccacgcgccctgtagcggcgcattaagcgcggg
tgtggtggttacgcgcagcgtgaccgctacacttgccagcgccctagcgcccgctcctttcgctttcttccctttctccttccgccac
```

FIG. 36B

```
gttcgccggcttttccccgtcaagctctaaatcggggcatcccctttagggttccga
tttagtgctttacggcacctcgaccccaaaaaacttgattagggtgatggttcac
gtagtgggccatcgccctgatagacggttttttcgccctttgacgttggagtccac
gttctttaatagtggactcttgttccaaactggaacaacactcaaccctatctcg
gtctattcttttgatttataagggatttggggggatttcggcctattggttaaaaa
atgagctgatttaacaaaaatttaacgcgaattaattctgtggaatgtgtgtcag
ttagggtgtggaaagtccccaggctccccaggcaggcagaagtatgcaaagcatg
catctcaattagtcagcaaccaggtgtggaaagtccccaggctccccagcaggca
gaagtatgcaaagcatgcatctcaattagtcagcaaccatagtcccgcccctaac
tccgcccatcccgcccctaactccgcccagttccgcccattctccgcccatggc
tgactaatttttttatttatgcagaggccgaggccgcctctgcctctgagctat
tccagaagtagtgaggaggcttttttggaggcctaggcttttgcaaaaagctccc
gggagcttgtatatccattttcggatctgatcagcacgtgttgacaattaatcat
cggcatagtatatcggcatagtataatacgacaaggtgaggaactaaaccatggc
caagttgaccagtgccgttccggtgctcaccgcgcgcgacgtcgccggagcggtc
gagttctggaccgaccggctcgggttctcccgggacttcgtggaggacgacttcg
ccggtgtggtccgggacgacgtgaccctgttcatcagcgcggtccaggaccaggt
ggtgccggacaacaccctggcctgggtgtgggtgcgcggcctggacgagctgtac
gccgagtggtcggaggtcgtgtccacgaacttccgggacgcctccgggccggcca
tgaccgagatcggcgagcagccgtggggcgggagttcgccctgcgcgacccggc
cggcaactgcgtgcacttcgtggccgaggagcaggactgacacgtgctacgagat
ttcgattccaccgccgccttctatgaaaggttgggcttcggaatcgttttccggg
acgccggctggatgatcctccagcgcggggatctcatgctggagttcttcgccca
ccccaacttgtttattgcagcttataatggttacaaataaagcaatagcatcaca
aatttcacaaataaagcattttttttcactgcattctagttgtggtttgtccaaac
tcatcaatgtatcttatcatgtctgtataccgtcgacctctagctagagcttggc
gtaatcatggtcatagctgtttcctgtgtgaaattgttatccgctcacaattcca
cacaacatacgagccggaagcataaagtgtaaagcctggggtgcctaatgagtga
gctaactcacattaattgcgttgcgctcactgcccgctttccagtcgggaaacct
gtcgtgccagctgcattaatgaatcggccaacgcgcggggagaggcggtttgcgt
attgggcgctcttccgcttcctcgctcactgactcgctgcgctcggtcgttcggc
tgcggcgagcggtatcagctcactcaaaggcggtaatacggttatccacagaatc
aggggataacgcaggaaagaacatgtgagcaaaaggccagcaaaaggccaggaac
cgtaaaaaggccgcgttgctggcgtttttccataggctccgcccccctgacgagc
atcacaaaaatcgacgctcaagtcagaggtggcgaaacccgacaggactataaag
ataccaggcgtttccccctggaagctccctcgtgcgctctcctgttccgaccctg
ccgcttaccggatacctgtccgcctttctcccttcgggaagcgtggcgctttctc
aatgctcacgctgtaggtatctcagttcggtgtaggtcgttcgctccaagctggg
ctgtgtgcacgaaccccccgttcagcccgaccgctgcgccttatccggtaactat
cgtcttgagtccaacccggtaagacgacttatcgccactggcagcagccactg
```

FIG. 36C

```
gtaacaggattagcagagcgaggtatgtaggcggtgctacagagttcttgaagtg
gtggcctaactacggctacactagaaggacagtatttggtatctgcgctctgctg
aagccagttaccttcggaaaaagagttggtagctcttgatccggcaaacaaacca
ccgctggtagcggtggttttttgtttgcaagcagcagattacgcgcagaaaaaa
aggatctcaagaagatcctttgatcttttctacggggtctgacgctcagtggaac
gaaaactcacgttaagggattttggtcatgagattatcaaaaggatcttcacct
agatccttttaaattaaaaatgaagttttaaatcaatctaaagtatatatgagta
aacttggtctgacagttaccaatgcttaatcagtgaggcacctatctcagcgatc
tgtctatttcgttcatccatagttgcctgactcccgtcgtgtagataactacga
tacgggagggcttaccatctggccccagtgctgcaatgataccgcgagacccacg
ctcaccggctccagatttatcagcaataaaccagccagccggaagggccgagcgc
agaagtggtcctgcaactttatccgcctccatccagtctattaattgttgccggg
aagctagagtaagtagttcgccagttaatagtttgcgcaacgttgttgccattgc
tacaggcatcgtggtgtcacgctcgtcgtttggtatggcttcattcagctccggt
tcccaacgatcaaggcgagttacatgatccccatgttgtgcaaaaaagcggtta
gctccttcggtcctccgatcgttgtcagaagtaagttggccgcagtgttatcact
catggttatggcagcactgcataattctcttactgtcatgccatccgtaagatgc
ttttctgtgactggtgagtactcaaccaagtcattctgagaatagtgtatgcggc
gaccgagttgctcttgcccggcgtcaatacgggataataccgcgccacatagcag
aactttaaaagtgctcatcattggaaaacgttcttcggggcgaaaactctcaagg
atcttaccgctgttgagatccagttcgatgtaacccactcgtgcacccaactgat
cttcagcatcttttactttcaccagcgtttctgggtgagcaaaaacaggaaggca
aaatgccgcaaaaaagggaataagggcgacacggaaatgttgaatactcatactc
ttcctttttcaatattattgaagcatttatcagggttattgtctcatgagcggat
acatatttgaatgtatttagaaaaataaacaatagggggttccgcgcacatttcc
ccgaaaagtgccacctgacgtcgacggatcgggagatctcccgatcccctatggt
gcactctcagtacaatctgctctgatgccgcatagttaagccagtatctgctccc
tgcttgtgtgttggaggtcgctgagtagtgcgcgagcaaaatttaagctacaaca
aggcaaggcttgaccgacaattgcatgaagaatctgcttagggttaggcgttttg
cgctgcttcgcgatgtacgggccagatatacgcgttgacattgattattgactag
ttattaatagtaatcaattacggggtcattagttcatagcccatatatggagttc
cgcgttacataacttacggtaaatggcccgcctggctgaccgcccaacgacccc
gcccattgacgtcaataatgacgtatgttcccatagtaacgccaatagggacttt
ccattgacgtcaatgggtggactatttacggtaaactgcccacttggcagtacat
caagtgtatcatatgccaagtacgccccctattgacgtcaatgacggtaaatggc
ccgcctggcattatgcccagtacatgaccttatgggactttcctacttggcagta
catctacgtattagtcatcgctattaccatggtgatgcggttttggcagtacatc
aatgggcgtggatagcggtttgactcacggggatttccaagtctccaccccattg
acgtcaatgggagtttgttttggcaccaaaatcaacgggactttccaaaatgtcg
taacaactccgccccattgacgcaaatgggcggtaggcgtgtacggtgggaggtc
```

FIG. 36D

```
tatataagcagagctctctggctaactagagaacccactgcttactggcttatcg
aaattaatacgactcactatagggagacccaagctggtttaaacttaagcttggt
accgagctcactagtccagtgtggtggcagatatccagcacagtggcggccgctc
gaggggcccgttttgcctgtactgggtctctctggttagaccagatctgagcctg
ggagctctctggctaactagggaacccactgcttaagcctcaataaagcttgcct
tgagtgcttcaagtagtgtgtgcccgtctgttgtgtgactctggtaactagagat
ccctcagacccttttagtcagtgtggaaaatctctagcagtggcgcccgaacagg
gacttgaaagcgaaagggaaaccagaggagctctctcgacgcaggactcggcttg
ctgaagcgcgcacggcaagaggcgaggggcggcgactggtgagtacgccaaaaat
tttgactagcggaggctagaaggagagagatgggtgcgagagcgtcagtattaag
cgggggagaattagatcgcgatgggaaaaaattcggttaaggccagggggaaaga
aaaaatataaattaaaacatatagtatgggcaagcagggagctagaacgattcgc
agttaatcctggcctgttagaaacatcagaaggctgtagacaaatactgggacag
ctacaaccatcccttcagacaggatcagaagaacttagatcattatataatacag
tagcaaccctctattgtgtgcatcaaaggatagagataaaagacaccaaggaagc
tttagacaagatagaggaagagcaaaacaaaagtaagaccaccgcacagcaagcg
gccgctgatcttcagacctggaggaggagatatgagggacaattggagaagtgaa
ttatataaatataaagtagtaaaaattgaaccattaggagtagcacccaccaagg
caaagagaagagtggtgcagagagaaaaaagagcagtgggaataggagctttgtt
ccttgggttcttgggagcagcaggaagcactatgggcgcagcgtcaatgacgctg
acggtacaggccagacaattattgtctggtatagtgcagcagcagaacaatttgc
tgagggctattgaggcgcaacagcatctgttgcaactcacagtctggggcatcaa
gcagctccaggcaagaatcctggctgtggaagataccta aaggatcaacagctc
ctggggatttggggttgctctggaaaactcatttgcaccactgctgtgccttgga
atgctagttggagtaataaatctctggaacagatttggaatcacacgacctggat
ggagtgggacagagaaattaacaattacacaagcttaatacactccttaattgaa
gaatcgcaaaaccagcaagaaaagaatgaacaagaattattggaattagataaat
gggcaagtttgtggaattggtttaacataacaaattggctgtggtatataaaatt
attcataatgatagtaggaggcttggtaggtttaagaatagttttgctgtactt
tctatagtgaatagagttaggcagggatattcaccattatcgtttcagacccacc
tcccaaccccgaggggacccgacaggcccttaattaatcccctgattctgtggat
aaccgtattaccgcctttgagtgagctgcacctagtacggattagaagccgcga
gcgggtgacagccctccgaaggaagactctcctccgtgcgtcctcgtcttaccg
gtcgcgttcctgaaacgcagatgtgcctcgcgccgcactgctccgacaatgtcg
actctagaggtaaactcgacctatataagcagagctcgtttagtgaaccgtcaga
tcgcctggagacgccatccacgctgttttgacctccatagaagacaccgggaccg
atccagcctccgcggccccgaattgaattcggccattacggcctgccaccgtgcc
accatgctggagcccggcgagaagccctacaagtgccccgagtgcggcaagagct
tcagcaggagcgacgagctggtgaggcaccagaggacccacaccggcgagaagcc
ctacaagtgccccgagtgcggcaagagcttcagcaggagcgacaagctggtgagg
```

FIG. 36E

```
caccagaggacccacaccggcgagaagccctacaagtgccccgagtgcggcaaga
gcttcagcaggagcgacgacctggtgaggcaccagaggacccacaccggcgagaa
gccctacaagtgccccgagtgcggcaagagcttcagcaggagcgacaacctggtg
aggcaccagaggacccacaccggcgagaagccctacaagtgccccgagtgcggca
agagcttcagcgaccccggcgccctggtgaggcaccagaggacccacaccggcga
gaagccctacaagtgccccgagtgcggcaagagcttcagcgaccccggccacctg
gtgaggcaccagaggacccacaccggcaagaagaccagcggcccaggcggccgat
gctaagtcactgactgcctggtcccggacactggtgaccttcaaggatgtgtttg
tggacttcaccagggaggagtggaagctgctggacactgctcagcagatcctgta
cagaaatgtgatgctggagaactataagaacctggtttccttgggttatcagctt
actaagccagatgtgatcctccggttggagaagggagaagagccctggctggtgg
agagagaaattcaccaagagacccatcctgattcagagactgcatttgaaatcaa
atcatcagttgggcgcgccgacgcgctggacgatttcgatctcgacatgctgggt
tctgatgccctcgatgactttgacctggatatgttgggaagcgacgcattggatg
actttgatctggacatgctcggctccgatgctctggacgatttcgatctcgatat
gttaattaactaattaat
```

FIG. 36F

```
cgtgccaccatgctggagcccggcgagaagcgctacaagtgcccgagtgcggcaagagcttcagcgacagcggcaacctgagggt
gcaccagaggaccccacaccggcgagaagcgcgagaagcgctacaagtgcccgagtgcggcaagagcttcagccagagggccaacctgaggcc
caccagaggaccccacaccggcgagaagcgcgagaagcgctacaagtgcccgagtgcggcaagagcttcagcaccagcggcagcctggtgaggc
accagaggaccccacaccggcgagaagcgcgagaagcgctacaagtgcccgagtgcggcaagagcttcagcaccagcggccacctggtgaggca
ccagaggaccccacaccggcgagaagcgcgagaagcgctacaagtgcccgagtgcggcaagagcttcagcaccagcagcgcgagctggtgaggcac
cagaggaccccacaccggcgagaagcgcgagaagcgctacaagtgcccgagtgcggcaagagcttcagcaccagcagcgcgcaacctggtgaggcacc
agaggaccccacaccggcgagaagcgcgagaagcgctacaagtgcccgagtgcggccaggcggccagcgctaagtcactgactgcctgtcccgacactggtgaccttc
aaggatgtgtttgtggacttcaccaggagggagtgtgaagctgctgacactgctcagcagatcctgtacagaaatgtgatgctggagaac
tataagaacctggttcccttggttatcagcttactagaccagatgtgatcctccgttggagaagggagaagagccctggctggtggaga
gagaaattcaccaagagaccatcctgattcagagactgcattgaaatcaaatcatcagttgggcgcgcgacgcgctgacgatttcg
atctcgacatgctgggttctgatgcctcgatgactttgacctggatatgttgggaagcgacgcattgatgacttgatctgacatgctcg
gctccgatgctctgctgacgattcga
```

FIG. 37B

```
tctcgatatgttaattaacgatcacatggtcctgctggagttcgtgaccgc
cgccgggatcactctcggcatggacgagctgtacaagtaagcggccgcaatcaac
ctctggattacaaaatttgtgaaagattgactggtattcttaactatgttgctcc
ttttacgctatgtggatacgctgctttaatgcctttgtatcatgctattacttcc
cgtacggctttcatttctcctccttgtataaatcctggttgctgtctctttatg
aggagttgtggcccgttgtcaggcaacgtggcgtggtgtgcactgtgtttgctga
cgcaaccccactggttggggcattgccaccacctatcaactcctttccgggact
ttcgctttccccctccctattgccacggcggaactcattgccgcctgccttgccc
gctgctggacaggggctcggctgtgggcactgacaattccgtggtgttgtcggg
gaagctgacgtccttccatggctgctcgcctgtgttgccaactggattctgcgc
gggacgtccttctgctacgtcccttcggccctcaatccagcggaccttccttccc
gcggcctgctgccggttctgcggcctcttccgcgtcttcgccttcgccctcagac
gagtcggatctcccctttgggccgcctccccgcctgcctgcaggtttgtcgagacc
tagaaaaacatggagcaatcacaagtagcaatacagcagctaccaatgctgattg
tgcctggctagaagcacaagaggaggaggaggtgggttttccagtcacacctcag
gtacctttaagaccaatgacttacaaggcagctgtagatcttagccacttttaa
aagaaaaggggggactggaagggctaattcactcccaacgaagacaagatctgct
ttttgcttgtactgggtctctctggttagaccagatctgagcctgggagctctct
ggctaactagggaacccactgcttaagcctcaataaagcttgccttgagtgcttc
aagtagtgtgtgcccgtctgttgtgtgactctggtaactagagatccctcagacc
cttttagtcagtgtggaaaatctctagcagggcccgtttaaacccgctgatcagc
ctcgactgtgccttctagttgccagccatctgttgtttgcccctcccccgtgcct
tccttgaccctggaaggtgccactcccactgtcctttcctaataaaatgaggaaa
ttgcatcgcattgtctgagtaggtgtcattctattctgggggtggggtggggca
ggacagcaaggggaggattgggaagacaatagcaggcatgctggggatgcggtg
ggctctatggcttctgaggcggaaagaaccagctggggctctaggggtatcccc
acgcgccctgtagcggcgcattaagcgcggcgggtgtggtggttacgcgcagcgt
gaccgctacacttgccagcgccctagcgcccgctcctttcgctttcttcccttcc
tttctcgccacgttcgccggctttccccgtcaagctctaaatcggggcatccctt
tagggttccgatttagtgctttacggcacctcgaccccaaaaaacttgattaggg
tgatggttcacgtagtgggccatcgccctgatagacggtttttcgccctttgacg
ttggagtccacgttctttaatagtggactcttgttccaaactggaacaacactca
accctatctcggtctattcttttgatttataagggattttggggatttcggccta
ttggttaaaaaatgagctgatttaacaaaaatttaacgcgaattaattctgtgga
atgtgtgtcagttagggtgtggaaagtccccaggctcccaggcaggcagaagta
tgcaaagcatgcatctcaattagtcagcaaccaggtgtggaaagtccccaggctc
cccagcaggcagaagtatgcaaagcatgcatctcaattagtcagcaaccatagtc
ccgcccctaactccgcccatcccgccctaactccgcccagttccgcccattctc
cgccccatggctgactaattttttttatttatgcagaggccgaggccgcctctgc
ctctgagctattccagaagtagtgaggaggcttttttggaggcctaggcttttgc
```

FIG. 37C

```
aaaaagctcccgggagcttgtatatccattttcggatctgatcagcacgtgttga
caattaatcatcggcatagtatatcggcatagtataatacgacaaggtgaggaac
taaaccatggccaagttgaccagtgccgttccggtgctcaccgcgcgacgtcg
ccggagcggtcgagttctggaccgaccggctcgggttctcccgggacttcgtgga
ggacgacttcgccggtgtggtccgggacgacgtgaccctgttcatcagcgcggtc
caggaccaggtggtgccggacaacaccctggcctgggtgtgggtgcgcggcctgg
acgagctgtacgccgagtggtcggaggtcgtgtccacgaacttccgggacgcctc
cgggccggccatgaccgagatcggcgagcagccgtgggggcgggagttcgccctg
cgcgacccggccggcaactgcgtgcacttcgtggccgaggagcaggactgacacg
tgctacgagatttcgattccaccgccgccttctatgaaaggttgggcttcggaat
cgttttccgggacgccggctggatgatcctccagcgcggggatctcatgctggag
ttcttcgcccaccccaacttgtttattgcagcttataatggttacaaataaagca
atagcatcacaaatttcacaaataaagcattttttcactgcattctagttgtgg
tttgtccaaactcatcaatgtatcttatcatgtctgtataccgtcgacctctagc
tagagcttggcgtaatcatggtcatagctgtttcctgtgtgaaattgttatccgc
tcacaattccacacaacatacgagccggaagcataaagtgtaaagcctggggtgc
ctaatgagtgagctaactcacattaattgcgttgcgctcactgcccgctttccag
tcgggaaacctgtcgtgccagctgcattaatgaatcggccaacgcgcgggagag
gcggtttgcgtattgggcgctcttccgcttcctcgctcactgactcgctgcgctc
ggtcgttcggctgcggcgagcggtatcagctcactcaaaggcggtaatacggtta
tccacagaatcaggggataacgcaggaaagaacatgtgagcaaaaggccagcaaa
aggccaggaaccgtaaaaaggccgcgttgctggcgtttttccataggctccgccc
ccctgacgagcatcacaaaaatcgacgctcaagtcagaggtggcgaaacccgaca
ggactataaagataccaggcgtttccccctggaagctccctcgtgcgctctcctg
ttccgaccctgccgcttaccggatacctgtccgcctttctcccttcgggaagcgt
ggcgctttctcaatgctcacgctgtaggtatctcagttcggtgtaggtcgttcgc
tccaagctgggctgtgtgcacgaaccccccgttcagcccgaccgctgcgccttat
ccggtaactatcgtcttgagtccaacccggtaagacacgacttatcgccactggc
agcagccactggtaacaggattagcagagcgaggtatgtaggcggtgctacagag
ttcttgaagtggtggcctaactacggctacactagaaggacagtatttggtatct
gcgctctgctgaagccagttaccttcggaaaaagagttggtagctcttgatccgg
caaacaaaccaccgctggtagcggtggtttttttgtttgcaagcagcagattacg
cgcagaaaaaaggatctcaagaagatcctttgatcttttctacggggtctgacg
ctcagtggaacgaaaactcacgttaagggattttggtcatgagattatcaaaaag
gatcttcacctagatccttttaaattaaaaatgaagttttaaatcaatctaaagt
atatatgagtaaacttggtctgacagttaccaatgcttaatcagtgaggcaccta
tctcagcgatctgtctatttcgttcatccatagttgcctgactccccgtcgtgta
gataactacgatacgggagggcttaccatctggccccagtgctgcaatgataccg
cgagacccacgctcaccggctccagatttatcagcaataaaccagccagccggaa
gggccgagcgcagaagtggtcctgcaactttatccgcctccatccagtctattaa
```

FIG. 37D ttgttgccgggaagctagagtaagtagttcgccagttaatagtttgcgcaacgtt
gttgccattgctacaggcatcgtggtgtcacgctcgtcgtttggtatggcttcat
tcagctccggttcccaacgatcaaggcgagttacatgatcccccatgttgtgcaa
aaaagcggttagctccttcggtcctccgatcgttgtcagaagtaagttggccgca
gtgttatcactcatggttatggcagcactgcataattctcttactgtcatgccat
ccgtaagatgcttttctgtgactggtgagtactcaaccaagtcattctgagaata
gtgtatgcggcgaccgagttgctcttgcccggcgtcaatacgggataataccgcg
ccacatagcagaactttaaaagtgctcatcattggaaaacgttcttcggggcgaa
aactctcaaggatcttaccgctgttgagatccagttcgatgtaacccactcgtgc
acccaactgatcttcagcatcttttactttcaccagcgtttctgggtgagcaaaa
acaggaaggcaaaatgccgcaaaaagggaataagggcgacacggaaatgttgaa
tactcatactcttcctttttcaatattattgaagcatttatcaggttattgtct
catgagcggatacatatttgaatgtatttagaaaaataaacaataggggttccg
cgcacatttccccgaaaagtgccacctgacgtcgacggatcgggagatctcccga
tcccctatggtgcactctcagtacaatctgctctgatgccgcatagttaagccag
tatctgctccctgcttgtgtgttggaggtcgctgagtagtgcgcgagcaaaattt
aagctacaacaaggcaaggcttgaccgacaattgcatgaagaatctgcttagggt
taggcgttttgcgctgcttcgcgatgtacgggccagatatacgcgttgacattga
ttattgactagttattaatagtaatcaattacggggtcattagttcatagcccat
atatggagttccgcgttacataacttacggtaaatggcccgcctggctgaccgcc
caacgacccccgcccattgacgtcaataatgacgtatgttcccatagtaacgcca
atagggactttccattgacgtcaatgggtggactatttacggtaaactgcccact
tggcagtacatcaagtgtatcatatgccaagtacgccccctattgacgtcaatga
cggtaaatggcccgcctggcattatgcccagtacatgaccttatgggactttcct
acttggcagtacatctacgtattagtcatcgctattaccatggtgatgcggtttt
ggcagtacatcaatgggcgtggatagcggtttgactcacggggatttccaagtct
ccaccccattgacgtcaatgggagtttgttttggcaccaaaatcaacgggacttt
ccaaaatgtcgtaacaactccgccccattgacgcaaatgggcggtaggcgtgtac
ggtgggaggtctatataagcagagctctctggctaactagagaacccactgctta
ctggcttatcgaaattaatacgactcactatagggagacccaagctggtttaaac
ttaagcttggtaccgagctcactagtccagtgtggtggcagatatccagcacagt
ggcggccgctcgagtctagagggcccgttttgcctgtactgggtctctctggtta
gaccagatctgagcctgggagctctctggctaactagggaacccactgcttaagc
ctcaataaagcttgccttgagtgcttcaagtagtgtgtgcccgtctgttgtgtga
ctctggtaactagagatccctcagaccctttagtcagtgtggaaaatctctagc
agtggcgcccgaacagggacttgaaagcgaaagggaaaccagaggagctctctcg
acgcaggactcggcttgctgaagcgcgcacggcaagaggcgaggggcggcgactg
gtgagtacgccaaaaattttgactagcggaggctagaaggagagatgggtgcg
agagcgtcagtattaagcggggagaattagatcgcgatgggaaaaaattcggtt
aaggccagggggaagaaaaaatataaattaaaacatatagtatgggcaagcagg

FIG. 37E

```
gagctagaacgattcgcagttaatcctggcctgttagaaacatcagaaggctgta
gacaaatactgggacagctacaaccatcccttcagacaggatcagaagaacttag
atcattatataatacagtagcaaccctctattgtgtgcatcaaaggatagagata
aaagacaccaaggaagctttagacaagatagaggaagagcaaaacaaaagtaaga
ccaccgcacagcaagcggccgctgatcttcagacctggaggaggagatatgaggg
acaattggagaagtgaattatataaatataaagtagtaaaaattgaaccattagg
agtagcacccaccaaggcaaagagaagagtggtgcagagagaaaaagagcagtg
ggaataggagctttgttccttgggttcttgggagcagcaggaagcactatgggcg
cagcgtcaatgacgctgacggtacaggccagacaattattgtctggtatagtgca
gcagcagaacaatttgctgagggctattgaggcgcaacagcatctgttgcaactc
acagtctggggcatcaagcagctccaggcaagaatcctggctgtggaaagatacc
taaaggatcaacagctcctggggatttggggttgctctggaaaactcatttgcac
cactgctgtgccttggaatgctagttggagtaataaatctctggaacagatttgg
aatcacacgacctggatggagtgggacagagaaattaacaattacacaagcttaa
tacactccttaattgaagaatcgcaaaaccagcaagaaaagaatgaacaagaatt
attggaattagataaatgggcaagtttgtggaattggtttaacataacaaattgg
ctgtggtatatagaaattattcataatgatagtaggaggcttggtaggtttaaga
atagttttgctgtactttctatagtgaatagagttaggcagggatattccat
tatcgtttcagacccacctcccaaccccgaggggacccgacaggcccgaaggaat
agaagaagaaggtggagagagagacagagacagatccattcgattagtgaacgga
tcggcactgcgtgcgccaattctgcagacaaatggcagtattcatccacaatttt
aaaagaaaggggggattggggggtacagtgcaggggaaagaatagtagacataa
tagcaacagacatacaaactaaagaattacaaaaacaaattacaaaaattcaaaa
ttttcgggtttattacagggacagcagagatccagtttggggttgctctggaaaa
ctcatttgcaccactgctgtgccttggaatgctagttggagtaataaatctctgg
aacagatttggaatcacacgacctggatggagtgggacagagaaattaacaatta
cacaagcttaatacactccttaattgaagaatcgcaaaaccagcaagaaaagaat
gaacaagaattattggaattagataaatgggcaagtttgtggaattggtttaaca
taacaaattggctgtggtatataaaattattcataatgatagtaggaggcttggt
aggtttaagaatagttttgctgtactttctatagtgaatagagttaggcaggga
tattccattatcgtttcagacccacctcccaaccccgaggggacccgacaggc
ccttaattaattggctccggtgccgtcagtgggcagagcgcacatcgcccacag
tccccgagaagttggggggaggggtcggcaattgaaccggtgcctagagaaggtg
gcgcggggtaaactgggaaagtgatgtcgtgtactggctccgcctttttcccgag
ggtggggagaaccgtatataagtgcagtagtcgccgtgaagctagcggcgtcga
ggcggggtgatatggcgtcgaggcggggtggctagccgttcttttcgcaacg
ggtttgccgccagaacacaggtaagtgccgtgtgtggttcccgcgggcctggcct
ctttacgggttatggcccttgcgtgccttgaattacttccacctggctgcagtac
gtgattcttgatcccgagcttcggggttggaagtgggtgggagagttcgaggcctt
gcgcttaaggagccccttcgcctcgtgcttgagttgaggcctggcctgggcgctg
```

FIG. 37F gggccgccgcgtgcgaatctggtggcaccttcgcgcctgtctcgctgctttcgat
aagtctctagccatttaaaattttttgatgacctgctgcgacgcttttttttctggc
aagatagtcttgtaaatgcgggccaagatctgcacactggtatttcggttttttgg
ggccgcgggcggcgacggggcccgtgcgtcccagcgcacatgttcggcgaggcgg
ggcctgcgagcgcggccaccgagaatcggacggggtagtctcaagctggccggc
ctgctctggtgcctggcctcgcgccgccgtgtatcgcccgccctgggcggcaag
gctggcccggtcggcaccagttgcgtgagcggaaagatggccgcttcccggccct
gctgcagggagctcaaaatggaggacgcggcgctcgggagagcgggcgggtgagt
cacccacacaaaggaaaagggcctttccgtcctcagccgtcgcttcatgtgactc
cacggagtaccgggcgccgtccaggcacctcgattagttctcgagcttttggagt
acgtcgtctttaggttggggggagggttttatgcgatggagtttccccacactg
agtgggtggagactgaagttaggccagcttggcacttgatgtaattctccttgga
atttgccttttttgagtttggatcttggttcattctcaagcctcagacagtggtt
caaagttttttttcttccatttcaggtgaattcggccattacggcctcccaccggc
cgcct ttgccaccatgctggagccggcgagaagccctacaagtgcccgagtgcggcaagagcttcagcaccacctggacctgatcaggc
accagagaccacaccggcgagaagccctacaagtgcccgagtgcggcaagagcttcagcaggaccgacaccctgagggacca
ccagaggaccacaccggcgagaagccctacaagtgcccgagtgcggcaagagcttcagcgacaagaaggacctgaccaggcac
cagaggaccacaccggcgagaagccctacaagtgcccgagtgcggcaagagcttcagcgacagccccgacctgaccaggcacc
agaggaccacaccggcgagaagccctacaagtgcccgagtgcggcaagagcttcagcaccacccggcaacctgaccgtgcaccag
aggacccacaccggcgagaagccctacaagtgcccgagtgcggcaagagcttc

FIG. 38B

```
agcaggaaggacaacctgaagaaccaccagaggacccacaccggcaagaagacca
gcggcccaggcggccgatgctaagtcactgactgcctggtcccggacactggtga
ccttcaaggatgtgtttgtggacttcaccagggaggagtggaagctgctggacac
tgctcagcagatcctgtacagaaatgtgatgctggagaactataagaacctggtt
tccttgggttatcagcttactaagccagatgtgatcctccggttggagaagggag
aagagccctggctggtggagagagaaattcaccaagagacccatcctgattcaga
gactgcatttgaaatcaaatcatcagttgggcgcgccgacgcgctggacgatttc
gatctcgacatgctgggttctgatgccctcgatgactttgacctggatatgttgg
gaagcgacgcattggatgactttgatctggacatgctcggctccgatgctctgga
cgatttcgatctcgatatgttaattaactaatatgtgtgggagggctaagggcgc
gccgttctagagaattcgatatcaagcttatcgataatcaacctctggattacaa
aatttgtgaaagattgactggtattcttaactatgttgctccttttacgctatgt
ggatacgctgctttaatgcctttgtatcatgctattacttcccgtacggctttca
ttttctcctccttgtataaatcctggttgctgtctctttatgaggagttgtggcc
cgttgtcaggcaacgtggcgtggtgtgcactgtgtttgctgacgcaaccccact
ggttggggcattgccaccacctatcaactcctttccgggactttcgctttccccc
tccctattgccacggcggaactcattgccgcctgccttgcccgctgctggacagg
ggctcggctgttgggcactgacaattccgtggtgttgtcggggaagctgacgtcc
tttccatggctgctcgcctgtgttgccaactggattctgcgcgggacgtccttct
gctacgtccttcggccctcaatccagcggaccttccttcccgcggcctgctgcc
ggttctgcggcctcttccgcgtcttcgccttcgccctcagacgagtcggatctcc
ctttgggccgcctccccgcctgcctgcaggtttgtcgagacctagaaaaacatgg
agcaatcacaagtagcaatacagcagctaccaatgctgattgtgcctggctagaa
gcacaagaggaggaggaggtgggttttccagtcacacctcaggtacctttaagac
caatgacttacaaggcagctgtagatcttagccactttttaaaagaaaaggggg
actggaagggctaattcactcccaacgaagacaagatctgcttttgcttgtact
gggtctctctggttagaccagatctgagcctgggagctctctggctaactaggga
acccactgcttaagcctcaataaagcttgccttgagtgcttcaagtagtgtgtgc
ccgtctgttgtgtgactctggtaactagagatccctcagacccttttagtcagtg
tggaaaatctctagcagggcccgtttaaacccgctgatcagcctcgactgtgcct
tctagttgccagccatctgttgtttgcccctcccccgtgccttccttgaccctgg
aaggtgccactcccactgtccttttcctaataaaatgaggaaattgcatcgcattg
tctgagtaggtgtcattctattctggggggtggggtggggcaggacagcaagggg
gaggattgggaagacaatagcaggcatgctggggatgcggtgggctctatgctt
ctgaggcggaaagaaccagctggggctctagggggtatccccacgcgccctgtag
cggcgcattaagcgcggcgggtgtggtggttacgcgcagcgtgaccgctacactt
gccagcgccctagcgcccgctcctttcgctttcttcccttcctttctcgccacgt
tcgccggctttccccgtcaagctctaaatcgggcatcccttagggttccgatt
tagtgctttacggcacctcgaccccaaaaaacttgattagggtgatggttcacgt
agtgggccatcgccctgatagacggtttttcgccctttgacgttggagtccacgt
```

FIG. 38C

```
tctttaatagtggactcttgttccaaactggaacaacactcaaccctatctcggt
ctattcttttgatttataagggatttTggggatttcggcctattggttaaaaat
gagctgatttaacaaaaatttaacgcgaattaattctgtggaatgtgtgtcagtt
agggtgtggaaagtccccaggctcccaggcaggcagaagtatgcaaagcatgca
tctcaattagtcagcaaccaggtgtggaaagtccccaggctccccagcaggcaga
agtatgcaaagcatgcatctcaattagtcagcaaccatagtcccgcccctaactc
cgcccatcccgccctaactccgcccagttccgcccattctccgcccatggctg
actaattttttttatttatgcagaggccgaggccgcctctgcctctgagctattc
cagaagtagtgaggaggctttttTggaggcctaggcttttgcaaaaagctcccgg
gagcttgtatatccatTTTcggatctgatcagcacgtgttgacaattaatcatcg
gcatagtatatcggcatagtataatacgacaaggtgaggaactaaaccatggcca
agttgaccagtgccgttccggtgctcaccgcgcgcgacgtcgccggagcggtcga
gttctggaccgaccggctcgggttctcccgggacttcgtggaggacgacttcgcc
ggtgtggtccgggacgacgtgaccctgttcatcagcgcggtccaggaccaggtgg
tgccggacaacaccctggcctgggtgtgggtgcgcggcctggacgagctgtacgc
cgagtggtcggaggtcgtgtccacgaacttccgggacgcctccgggccggccatg
accgagatcggcgagcagccgtggggcgggagttcgccctgcgcgacccggccg
gcaactgcgtgcacttcgtggccgaggagcaggactgacacgtgctacgagattt
cgattccaccgccgccttctatgaaaggttgggcttcggaatcgttttccgggac
gccggctggatgatcctccagcgcggggatctcatgctggagttcttcgcccacc
ccaacttgtttattgcagcttataatggttacaaataaagcaatagcatcacaaa
tttcacaaataaagcatttttttcactgcattctagttgtggtttgtccaaactc
atcaatgtatcttatcatgtctgtataccgtcgacctctagctagagcttggcgt
aatcatggtcatagctgtttcctgtgtgaattgttatccgctcacaattccaca
caacatacgagccggaagcataaagtgtaaagcctggggtgcctaatgagtgagc
taactcacattaattgcgttgcgctcactgcccgctttccagtcgggaaacctgt
cgtgccagctgcattaatgaatcggccaacgcgcggggagaggcggtttgcgtat
tgggcgctcttccgcttcctcgctcactgactcgctgcgctcggtcgttcggctg
cggcgagcggtatcagctcactcaaaggcggtaatacggttatccacagaatcag
gggataacgcaggaaagaacatgtgagcaaaaggccagcaaaaggccaggaaccg
taaaaaggccgcgttgctggcgttttccataggctccgcccccctgacgagcat
cacaaaaatcgacgctcaagtcagaggtggcgaaacccgacaggactataaagat
accaggcgtttccccctggaagctccctcgtgcgctctcctgttccgaccctgcc
gcttaccggatacctgtccgcctttctcccttcgggaagcgtggcgctttctcaa
tgctcacgctgtaggtatctcagttcggtgtaggtcgttcgctccaagctgggct
gtgtgcacgaaccccccgttcagcccgaccgctgcgccttatccggtaactatcg
tcttgagtccaacccggtaagacacgacttatcgccactggcagcagccactggt
aacaggattagcagagcgaggtatgtaggcggtgctacagagttcttgaagtggt
ggcctaactacggctacactagaaggacagtatttggtatctgcgctctgctgaa
gccagttaccttcggaaaaagagttggtagctcttgatccggcaaacaaaccacc
```

FIG. 38D

```
gctggtagcggtggttttttttgtttgcaagcagcagattacgcgcagaaaaaaag
gatctcaagaagatcctttgatcttttctacggggtctgacgctcagtggaacga
aaactcacgttaagggattttggtcatgagattatcaaaaaggatcttcacctag
atccttttaaattaaaaatgaagttttaaatcaatctaaagtatatatgagtaaa
cttggtctgacagttaccaatgcttaatcagtgaggcacctatctcagcgatctg
tctatttcgttcatccatagttgcctgactcccgtcgtgtagataactacgata
cgggagggcttaccatctggccccagtgctgcaatgataccgcgagacccacgct
caccggctccagatttatcagcaataaaccagccagccggaagggccgagcgcag
aagtggtcctgcaactttatccgcctccatccagtctattaattgttgccgggaa
gctagagtaagtagttcgccagttaatagtttgcgcaacgttgttgccattgcta
caggcatcgtggtgtcacgctcgtcgtttggtatggcttcattcagctccggttc
ccaacgatcaaggcgagttacatgatccccatgttgtgcaaaaaagcggttagc
tccttcggtcctccgatcgttgtcagaagtaagttggccgcagtgttatcactca
tggttatggcagcactgcataattctcttactgtcatgccatccgtaagatgctt
ttctgtgactggtgagtactcaaccaagtcattctgagaatagtgtatgcggcga
ccgagttgctcttgcccggcgtcaatacgggataataccgcgccacatagcagaa
ctttaaaagtgctcatcattggaaaacgttcttcggggcgaaaactctcaaggat
cttaccgctgttgagatccagttcgatgtaacccactcgtgcacccaactgatct
tcagcatcttttactttcaccagcgtttctgggtgagcaaaaacaggaaggcaaa
atgccgcaaaaagggaataagggcgacacggaaatgttgaatactcatactctt
cctttttcaatattattgaagcatttatcagggttattgtctcatgagcggatac
atatttgaatgtatttagaaaaataaacaatagggggttccgcgcacatttcccc
gaaaagtgccacctgacgtcgacggatcgggagatctcccgatcccctatggtgc
actctcagtacaatctgctctgatgccgcatagttaagccagtatctgctccctg
cttgtgtgttggaggtcgctgagtagtgcgcgagcaaaatttaagctacaacaag
gcaaggcttgaccgacaattgcatgaagaatctgcttagggttaggcgttttgcg
ctgcttcgcgatgtacgggccagatatacgcgttgacattgattattgactagtt
attaatagtaatcaattacggggtcattagttcatagcccatatatggagttccg
cgttacataacttacggtaaatggcccgcctggctgaccgcccaacgacccccgc
ccattgacgtcaataatgacgtatgttcccatagtaacgccaatagggactttcc
attgacgtcaatgggtggactatttacggtaaactgcccacttggcagtacatca
agtgtatcatatgccaagtacgccccctattgacgtcaatgacggtaaatggccc
gcctggcattatgcccagtacatgaccttatgggactttcctacttggcagtaca
tctacgtattagtcatcgctattaccatggtgatgcggttttggcagtacatcaa
tgggcgtggatagcggtttgactcacggggatttccaagtctccaccccattgac
gtcaatgggagtttgttttggcaccaaaatcaacgggactttccaaaatgtcgta
acaactccgccccattgacgcaaatgggcggtaggcgtgtacggtgggaggtcta
tataagcagagctctctggctaactagagaaccactgcttactggcttatcgaa
attaatacgactcactatagggagacccaagctggtttaaacttaagcttggtac
cgagctcactagtccagtgtggtggcagatatccagcacagtggcggccgctcga
```

FIG. 38E ggggcccgttttgcctgtactgggtctctctggttagaccagatctgagcctggg
agctctctggctaactagggaacccactgcttaagcctcaataaagcttgccttg
agtgcttcaagtagtgtgtgcccgtctgttgtgtgactctggtaactagagatcc
ctcagaccctttagtcagtgtggaaaatctctagcagtggcgcccgaacaggga
cttgaaagcgaaagggaaaccagaggagctctctcgacgcaggactcggcttgct
gaagcgcgcacggcaagaggcgaggggcggcgactggtgagtacgccaaaaattt
tgactagcggaggctagaaggagagagatgggtgcgagagcgtcagtattaagcg
ggggagaattagatcgcgatgggaaaaaattcggttaaggccaggggaaagaaa
aaatataaattaaaacatatagtatgggcaagcagggagctagaacgattcgcag
ttaatcctggcctgttagaaacatcagaaggctgtagacaaatactgggacagct
acaaccatcccttcagacaggatcagaagaacttagatcattatataatacagta
gcaaccctctattgtgtgcatcaaaggatagagataaaagacaccaaggaagctt
tagacaagatagaggaagagcaaaacaaaagtaagaccaccgcacagcaagcggc
cgctgatcttcagacctggaggaggagatatgagggacaattggagaagtgaatt
atataaatataaagtagtaaaaattgaaccattaggagtagcacccaccaaggca
aagagaagagtggtgcagagagaaaaaagagcagtgggaataggagctttgttcc
ttgggttcttgggagcagcaggaagcactatgggcgcagcgtcaatgacgctgac
ggtacaggccagacaattattgtctggtatagtgcagcagcagaacaatttgctg
agggctattgaggcgcaacagcatctgttgcaactcacagtctggggcatcaagc
agctccaggcaagaatcctggctgtggaaagatacctaaaggatcaacagctcct
ggggatttggggttgctctggaaaactcatttgcaccactgctgtgccttggaat
gctagttggagtaataaatctctggaacagatttggaatcacacgacctggatgg
agtgggacagagaaattaacaattacacaagcttaatacactccttaattgaaga
atcgcaaaaccagcaagaaaagaatgaacaagaattattggaattagataaatgg
gcaagtttgtggaattggtttaacataacaaattggctgtggtatataaaattat
tcataatgatagtaggaggcttggtaggtttaagaatagttttgctgtactttc
tatagtgaatagagttaggcagggatattccattatcgtttcagacccacctc
ccaaccccgaggggacccgacaggcccttaattaatcccctgattctgtggataa
ccgtattaccgcctttgagtgagctgcacaaagaaacaaaccaacctgtctgtat
tatcaaagtgaaaggctacaataggacaaagaaacaaaccaacctgtctgtatta
tcaaagtgaaaggctacaataggacaaagaaacaaaccaacctgtctgtattatc
aaagtgaaaggctacaataggacaaagaaacaaaccaacctgtctgtattatcaa
agtgaaaggctacaataggacaaagaaacaaaccaacctgtctgtattatcaaag
tgaaaggctacaataggacaaagaaacaaaccaacctgtctgtattatcaaagtg
aaaggctacaataggacaaagaaacaaaccaacctgtctgtattatcaaagtgaa
aggctacaataggacggtaaactcgacctatataagcagagctcgtttagtgaac
cgtcagatcgcctggagacgccatccacgctgttttgacctccatagaagacacc
gggaccgatccagcctccgcggccccgaattgaattctaacaccgtgcgtgttga
ctattttacctctggcggtgataggccattacggcctgccacc

FIG. 38F

… # ENGINEERED CELLULAR PATHWAYS FOR PROGRAMMED AUTOREGULATION OF DIFFERENTIATION

This application is the U.S. National stage filing of PCT Application No. PCT/US2007/023227, filed on Nov. 1, 2007, which claims priority to U.S. provisional Patent Application Ser. No. 60/856,531 filed on Nov. 3, 2006, and to U.S. provisional Patent Application Ser. No. 60/905,483 filed on Mar. 7, 2007, each of which is herein incorporated by reference in its entirety for all purposes.

FIELD OF THE INVENTION

The present invention provides compositions and methods for programming mammalian cells to perform desired functions. In particular, the present invention provides compositions and methods for programming stem cells to differentiate into a desired cell type.

BACKGROUND OF THE INVENTION

Diabetes Mellitus is a heterogeneous mix of genetic abnormalities in the insulin-producing machinery ranging from the body's inability to produce enough insulin to the body's inability to recognize and/or use insulin. Type I diabetes is an autoimmune disease which systematically destroys insulin-producing β cells in the pancreas. Type II diabetes is caused by various genetic abnormalities in the pancreas and onset is directly correlated to obesity. The current standard treatment for diabetes is to maintain insulin levels by monitoring blood glucose and diet, to provide exogenous doses of insulin when necessary and to treat the consequences of diabetes such as loss of circulation to the extremities, glaucoma, and sepsis, as the disease progresses [Couper et al., Medical Journal of Australia, 179(8):441-447, 2003]. More radical treatments include full organ transplants, islet cell transplants or β cell transplants. Pancreatic transplantation candidates are put on a long waiting list for a suitable organ. Even when patients are lucky enough to be chosen for an allogeneic pancreatic organ transplant, they must take immunosuppressants in order to battle graft vs. host disease. A recent attempt to use islet cell transplant therapy provided short-lived relief in most patients but the transplanted β cells subsequently died or ceased to produce insulin in a majority of the initial successful transplants [Shapiro et al., New England Journal of Medicine, 355(13):1318-1330, 2006]. Clearly another approach is necessary to alleviate the problems caused by diabetes and address the root cause of the disease.

Recent developments in genome technologies, tissue engineering and synthetic biology offer possibilities to establish, highly accurate and robust approaches for predictable and controllable cell fate regulation both temporally and spatially. Stem cell research promises to revolutionize the way many inherited and acquired diseases are treated and will also provide unprecedented insights into fetal development and the etiology of numerous disorders [Hochedlinger et al., N Engl J Med, 349(3):275-286, July 2003; Weissman, Science, 287 (5457):1442-1446, February 2000; Lagasse et al., Immunity, 14(4):425-436, April 2001; Reya et al., Nature, 414(6859): 105-111, November 2001]. Mouse embryonic stem (mES) cells are an attractive platform for this research because they are amenable to extensive genetic manipulation. When introduced into the appropriate in vitro or in vivo contexts, mES cells contribute to all tissue types of adult mice, including the germ line [Nagy et al., Development, 110(3):815-821, November 1990].

Consequently, there has been much excitement about the potential of these cells as an unlimited source of differentiated cell populations for transplantation or other therapies. Although potentially exciting and ground-breaking, ES cell-based therapies depend on the ability to reliably and controllably produce the necessary mature cell populations. In addition, directed differentiation must be absolute, given the tumorigenic potential of ES cells. With few exceptions, such directed production of desired cell populations has not been possible yet.

Current approaches towards tissue engineering and transplantation rely on carefully creating environments that induce cells to differentiate into desired tissues or organs. While these approaches have proven partially effective for certain applications, they are inherently limited since they rely on innate cellular response to existing host conditions or exogenous cues. Often, naturally occurring host conditions are insufficient to trigger the correct differentiation pathways. In those instances, researchers have attempted to provide appropriate environmental cues using scaffolds and exogenous signals. However, it is often difficult, if not impossible, to create and maintain the precise conditions that are required for tissue regeneration using such means.

What is needed in the art are systems and methods that can be used to cause stem cells to reliably differentiate into a desired cell type based on expression of genes introduced into the stem cells.

SUMMARY OF THE INVENTION

The present invention provides compositions and methods for programming mammalian cells to perform desired functions. In particular, the present invention provides compositions and methods for programming stem cells to differentiate into a desired cell type. Accordingly, in some embodiments, the present invention provides systems for directing differentiation of an undifferentiated cell type comprising: a) a first mammalian vector comprising a first gene encoding a protein that synthesizes an autoinducer; b) a second mammalian vector comprising a second gene encoding a regulatory protein that interacts with the autoinducer; c) a third mammalian vector comprising a promoter that binds to the regulatory protein in the presence of the autoinducer, the promoter operably linked to a third gene of interest encoding a first cell fate regulator. In some embodiments, the systems of the present invention further comprise a fourth mammalian vector comprising a promoter comprising a response element that binds to a regulatory protein produced in response to expression of the first cell fate regulator. The present invention is not limited to the use of any particular type of mammalian vector. Indeed, the use of a variety of mammalian vectors is contemplated, including, but not limited to lentiviral vectors, retroviral vectors, pseudotyped retroviral or lentiviral vectors, adenoviral vectors, AAV vectors, plasmids, artificial chromosomes, transposon vectors and the like.

In some embodiments, the first mammalian vector further comprises a promoter operably linked to the first gene. The present invention is not limited to the use of any particular promoter. Indeed, the use of a variety of promoters is contemplated. In some embodiments, the promoter is a repressible promoter. In some embodiments the promoter comprises a lac repressor. In some embodiments, the promoter is an inducible promoter. In some embodiments, the inducible promoter is a Tet promoter. The present invention is not limited to vectors encoding genes that synthesize any particular autoinducer. Indeed, the use of a variety of autoinducers is contemplated, including, but not limited to 3OC6HSL, C4HSL, and 3OC14HSL. The present invention is not limited to the use of genes encoding any particular autoinducer. Indeed, the use of several genes that encode proteins that catalyze the synthesis of autoinducers is contemplated, included but not limited to the LuxI, RhlI, and CinI proteins. The present inventions is not limited to the use of the any particular genes encoding LuxI, RhlI, or CinI. In some embodiments, the genes comprise codons that are optimized for expression in mammalian cells. In other embodiments, the genes utilized are at least 70%, 80%, 90% or 95% identical to the wild type LuxI, RhlI or CinI wild-type genes.

In some preferred embodiments, the second mammalian vector comprises a gene encoding a regulatory protein that interacts with the autoinducer synthesized by the protein encoded by the gene of interest in the first vector. The present invention is not limited to the use of any particular regulatory protein. Indeed, the use of a variety of regulatory proteins is contemplated, including, but not limited to LuxR, RhlR, and CinR. The present inventions is not limited to the use of the any particular genes encoding LuxR, RhlR, or CinR. In some embodiments, the genes comprise codons that are optimized for expression in mammalian cells. In other embodiments, the genes utilized are at least 70%, 80%, 90% or 95% identical to the wild type LuxR, RhlR or CinR wild-type genes.

The present invention is not limited to the use of any particular promoter in the third vector of the system of the present invention. In some embodiments, the third mammalian vector comprises a promoter selected from the group consisting of lux and LasR promoters. In some preferred embodiments, the lux promoter comprises multiple repeats of the lux binding sequence, which binds LuxR/autoinducer complex. Likewise, the vectors for use in the systems of the present invention may comprise promoters comprising multiple repeats of the binding sequences recognized by the RhlI and CinI autoinducer complexes. The present invention is not limited to the use of vectors encoding any particular cell fate regulator. In some embodiments, the first cell fate regulator is selected from the group consisting of Sox17, Gata4, and Gata6 and combinations thereof. In further embodiments, the vectors used in the systems of the present invention encode two or more of the cell fate regulators selected from the group consisting of Sox17, Gata4, Gata6, Pdx1, Ngn3, Nkx6.1, Nkx2.2, Fgf4, BRA, Wnt9, NCAD, CER, FoxA2, CxcR4, Hnf1B, Hnf4A, Hnf6, HlxB9, Pax4, Cgc, GHRL, SST, PPY, Activin, Fgf10, Cyc, RA, Ex4, DAPT, HGF and Igf1.

In some embodiments of the systems of the present invention, the fourth mammalian vector further comprises a gene encoding a second cell fate regulator. The present invention is not limited to the use of any particular second cell fate messenger. In some embodiments, the second cell fate regulator is selected from the group consisting of Pdx1, Ngn3, Nkx6.1, Nkx2.2, Fgf4, BRA, Wnt9, NCAD, CER, FoxA2, CxcR4, Hnf1B, Hnf4A, Hnf6, HlxB9, Pax4, Cgc, GHRL, SST, PPY, Activin, Fgf10, Cyc, RA, Ex4, DAPT, HGF and Igf1. In some embodiments, the systems of the present invention comprise multiple vectors encoding one or more of the foregoing cell fate regulators. The fourth vectors of the systems of the present invention are not limited to the use of any particular promoter. Indeed, a variety of stage specific promoters may be utilized. In some embodiments, the promoter comprising a response element that binds to a regulatory protein produced in response to expression of the first cell fate regulator comprises an α-fetoprotein promoter.

In some embodiments, the systems of the present invention comprise vectors encoding additional proteins involved in a quorum sensing pathway. Accordingly, in some embodiments, the systems of the present invention comprise a fifth mammalian vector comprising a gene encoding an acyl carrier protein (ACP). In further embodiments, the systems of the present invention comprise a sixth mammalian vector comprising a gene encoding acyl-acyl carrier protein synthase (AAS). The present invention is not limited to vectors comprising any particular ACP or AAS genes. In some embodiments, the genes comprise codons optimized for expression in a mammalian cells. In further embodiments, the genes are at least 70%, 80%, 90% or 95% identical to the wild type ACP or ASS genes.

In some embodiments, the systems of the present invention further comprise a separate vector encoding comprising a gene encoding RhlR. In some embodiments, the systems of the present invention further comprise a separate mammalian vector comprising a gene encoding Growth Arrest Factor. In some embodiments, the systems of the present invention further comprise a mammalian vector comprising a gene encoding TetR. In some embodiments, the systems of the present invention further comprise a separate mammalian vector comprising a gene of interest encoding a protein selected from the group consisting of TetR, LacI and CinI operably linked to a Mouse Insulin promoter.

In some embodiments, the present invention provides a culture of mammalian cells comprising one or more of the foregoing vectors of the system of the present invention. In some embodiments, the present invention provides a mammalian cell comprising one or more of the foregoing vectors of the system of the present invention. The present invention is not limited to the use of any particular type of mammalian cells. In some embodiments, the cell is totipotent cell. In some embodiments, the cell is a multipotent cell. In some embodiments, the cell is a differentiated cell. In some embodiments, the cell or cell culture comprises cells selected from the group consisting of embryonic stem cells, adult stem cells or cord blood stem cells. The present invention is not limited to mammalian cells of any particular species. In some embodiments, the cells are human, primate, mouse, cow, hamster, rat, pig, sheep or goat cells. In some embodiments, the differentiated cells are β-cells. In some embodiments, the cells produce insulin.

In some embodiments, the present invention provides methods of treating a patient comprising: providing a patient in need of treatment and the mammalian cells described in the foregoing paragraphs, and introducing the cells into the patient. In some embodiments, the patient is diabetic. In some embodiments, the mammalian cells produce insulin after introduction into the patient.

In some embodiments, the present invention provides methods of programming mammalian cells comprising: introducing a quorum sensing system into a mammalian cell, wherein the system causes production of an autoinducer molecule and a regulatory partner of the autoinducer; introducing an expression system for at least one cell fate regulator into the mammalian cell; culturing the cell under conditions such that the cell produces the autoinducer, wherein the autoinducer interacts with the regulatory partner to induce expression of the at least one cell fate regulator.

In some embodiments, the present invention provides methods of programming mammalian cells comprising 1) providing i) a mammalian cell, ii) a first vector encoding a protein that synthesizes an autoinducer molecule; iii) a second vector encoding a regulatory partner of the autoinducer; iv) a third vector encoding a gene of interest operably linked to a promoter activated by the interaction of the autoinducer and the regulatory partner; 2)

introducing the vectors into the mammalian cell; 3) culturing the mammalian cell under conditions such that the regulatory partner and the autoinducer are synthesized and activate expression of the gene of interest.

In some embodiments, the present invention provides a mammalian cell comprising an exogenous gene selected from the group consisting of genes encoding LuxI, LuxR, RhlI, RhlR, CinI, and CinR. In some embodiments, the present invention provides a mammalian cell comprising an exogenous gene selected from the group consisting of Sox17, Gata4, and Gata6, wherein the exogenous gene is operably linked to a lux promoter. In some embodiments, the present invention provides a mammalian cell comprising an exogenous gene selected from the group consisting of Pdx1, Ngn3, Nkx6.1, Nkx2.2, Fgf4, BRA, Wnt9, NCAD, CER, FoxA2, CxcR4, Hnf1B, Hnf4A, Hnf6, HlxB9, Pax4, Cgc, GHRL, SST, PPY, Activin, Fgf10, Cyc, RA, Ex4, DAPT, HGF and Igf1, wherein the exogenous gene is operably linked to a endoderm specific promoter. In some embodiments, the endoderm specific promoter is the α-fetoprotein promoter.

In some embodiments, the present invention provides a mammalian cell comprising a quorum sensing pathway. In some embodiments, the quorum sensing pathway comprises one or more exogenous genes encoding LuxI, LuxR, acyl carrier protein and acyl-acyl carrier protein synthase.

In some embodiments, the present invention provides a system for use in establishing tissue homeostasis in a differentiating cell system comprising mammalian vectors encoding at least one cell-cell communication system, wherein said at least a first cell-cell communication system controls proliferation or differentiation of cells in said differentiating cell system. In some embodiments, the systems further comprise at least a second cell-cell communication system, wherein said first and second cell-cell communication systems interact to establish homeostasis in said differentiating cell system. In some embodiments, the differentiating cells system comprises differentiable cells and differentiated cells produced from said differentiable cells. In some embodiments, the homeostasis is characterized by the controlled proliferation of said differentiable cells comprising said at least two cell-cell communication systems and the controlled production of said differentiated cells. In further embodiments, the at least two cell-cell communication systems interact to establish tissue homeostasis in a differentiating cell system comprising differentiable cells and differentiated cells by sensing the number of differentiating cells via the first cell-cell communication system and the number of differentiated cells via the second cell-cell communication system so that when the number of differentiable cells is low proliferation of the differentiable cells is induced, when the number of differentiable cells is high the proliferation of the differentiable is cells in inhibited, when the number of differentiated cells is low the differentiation of the differentiable cells is induced and the proliferation of the differentiable cells is induced, and when the number of differentiated cells is high the differentiation of the differentiable cells is inhibited. The present invention is not limited to the use of any particular cell-cell communication systems. Indeed, the use of a variety of cell-cell communication systems is contemplated. In some embodiments, the at least one cell-cell communication system is a bacterial cell-cell communication systems. In other embodiments, the at least one cell-cell communication system is selected from the group consisting of the LuxI, RhlI, and CinI cell-cell communication systems. The present invention is not limited to the use of any particular type of vector. Indeed, the use of a variety of vectors is contemplated. In some embodiments, the mammalian vectors are retroviral vectors. In further embodiments, the systems of the present invention further comprise a cell differentiation control system.

In some embodiments, the present invention provides a differentiable cell comprising the foregoing systems, wherein said differentiable cell is cultured in vitro. In further embodiments, the present invention provides a differentiable mammalian cell comprising at least a first cell-cell communication pathway, wherein said first cell-cell communication pathway is encoded by exogenous genes. In some embodiments, the cells further comprise at least a second cell communication pathway. In some embodiments, the cell differentiates into a target differentiated cell. The present invention is not limited to any particular type of cell. Indeed, the use of a variety of cell types is contemplated. In some embodiments, the cell is a pluripotent, multipotent or totipotent cell. The present invention is not limited to the use of any particular cell-cell communication systems. Indeed, the use of a variety of cell-cell communication systems is contemplated. In some embodiments, the at least one cell-cell communication system is a bacterial cell-cell communication systems. In other embodiments, the at least one cell-cell communication system is selected from the group consisting of the LuxI, RhlI, and CinI cell-cell communication systems. In some embodiments, the cell further comprises an exogenous cell differentiation pathway. In some embodiments, the first cell-cell communication pathway is a CinI/CinR cell-cell communication pathway. In some embodiments, the CinI/CinR cell-cell communication pathway comprises at least a first gene encoding CinI, a second gene encoding CinR, and a third gene of interest operably linked to a CinR/30C14HSL inducible promoter. In some embodiments, the second cell-cell communication pathway is a RhlI/RhlR cell-cell communication pathway. In some embodiments, the RhlI/RhlR cell-cell communication pathway comprises at least a first gene encoding RhlI, a second gene encoding RhlR, and a third gene of interest operably linked to a RhlR/C4HSL inducible promoter. In some embodiments, the cell comprises a cell differentiation pathway. In some embodiments, the cell differentiation pathway comprises at least one exogenous gene encoding a cell fate regulator. The present invention is not limited to the use of any particular cell fate regulator. Indeed, the use of a variety of cell fate regulators is contemplated, including, but not limited to, Sox17, Gata4, Gata6, Pdx1, Ngn3, Nkx6.1, Nkx2.2, Fgf4, BRA, Wnt9, NCAD, CER, FoxA2, CxcR4, Hnf1B, Hnf4A, Hnf6, HlxB9, Pax4, Cgc, GHRL, SST, PPY, Activin, Fgf10, Cyc, RA, Ex4, DAPT, HGF and Igf1. In some embodiments, the third gene of interest operably linked to a RhlR/C4HSL inducible promoter is a protein that inhibits growth in a cell. In further embodiments, the protein that inhibits growth in a cell is Growth Arrest Factor. In some embodiments, the third gene of interest operably linked to a CinR/30C14HSL inducible promoter is a repressor. In some embodiments, the repressor is lambda repressor. In some embodiments, the first and second cell-cell communication pathways interact to control proliferation and differentiation of said mammalian cell. In some embodiments, the cell differentiation pathway comprises at least one gene encoding a protein that causes said cell to differentiate into a target differentiated cell. In some embodiments, the target differentiated cell is a beta cell. In some embodiments, the second cell-cell communication pathway is activated in said target differentiated cell and comprises at least one gene encoding a protein that inhibits the proliferation of undifferentiated cells comprising said first and second cell-cell communication pathways. In some embodiments, the cell differentiation pathway is activated in said target differentiated cell and comprises at least one gene encoding a protein that regulates expression of said at least one gene encoding a protein that causes undifferentiated cells comprising said first and second cell-cell communication pathways to differentiate into a target differentiated cell. In some embodiments, the gene encoding a protein that regulates expression of said at least one gene encoding a protein that causes undifferentiated cells comprising said first and second cell-cell communication pathways to differentiate into a target differentiated cell is a repressor. In some embodiments, the repressor is a lambda repressor. In some embodiments, the cell is maintained in vitro.

The present invention further provides methods of controlling proliferation and differentiation of a differentiable cell comprising: a) providing: i) a differentiable cell; and ii) at least one cell-cell communication pathway; and b) introducing said at least one cell-cell communication pathway into said differentiable cell so that when said at least one cell-cell communication pathway is expressed in said differentiable cell, the proliferation and differentiation of said differentiable cell is controlled. In some embodiments, the two cell-cell communication pathways are introduced into said differentiable cells and wherein said two cell communication pathways interact to control proliferation and differentiation of said differentiable cell and proliferation of target differentiated cells that differentiate from said differentiable cells. In some embodiments, the at least one of said two cell-cell communication pathways provides regulatory feedback on differentiation of said differentiable cells. The present invention is not limited to the use of any particular cell-cell communication pathway. Indeed, the use of a variety of cell-cell communication pathways is contemplated. In some embodiments, the at least one cell-cell communication pathway is a bacterial cell-cell communication systems. In other embodiments, the at least one cell-cell communication pathway is selected from the group consisting of the LuxI, RhlI, and CinI cell-cell communication systems.

In some embodiments, the present invention provides methods of treating a subject comprising: a) providing a plurality of mammalian cells as described above; and b) introducing said cells into a subject under conditions such that the proliferation and differentiation of said cells is controlled to provide a source of differentiated target cells in said subject. In some embodiments, the subject is human.

In some embodiments, the present invention provides a symmetry breaking system for mammalian cells comprising a first vector comprising an activator operably linked to a promoter responsive to the activator and a repressor and a second vector encoding a repressor operably linked to promoter responsive to said activator. In some embodiments, the present invention provides a population of cells comprising the symmetry breaking system, wherein expression of the activator causes activation of the activator and the repressor and expression of the repressor causes repression of the activator, so that at any given time only a portion of the cells within the population have high levels of expression of the activator as compared to the repressor.

In some embodiments, the present invention provides a cascade system for mammalian cells comprising a first vector encoding a first repressor operably linked to a promoter responsive to a first activator, a second vector encoding a second repressor operably linked to promoter repressed by said first repressor, and a third vector encoding a second activator operably linked to a promoter repressed by said second repressor, and a fourth vector encoding a repressor operably linked to a promoter that is activated by said second activator and repressed by a third repressor. In some embodiments, the present invention provides a population of cells comprising the cascade system.

In some embodiments, the present invention provides a toggle switch system for mammalian cells comprising a first vector encoding first repressor operably linked to a promoter repressed by a second repressor and a second vector encoding said second repressor operably linked to a promoter repressed by said first repressor. In some embodiments, the first repressor is TetR and said second repressor is LacI. In some embodiments, the present invention provides cells comprising the toggle switch system.

In some embodiments, the present invention provides a population of uncommitted and committed cells comprising: a) a cell population control module comprising a first cell-cell communication pathway; b) a cell commitment module comprising a symmetry breaking system and a second cell-cell communication system; and c) a cell differentiation module; wherein said cell population control module senses the concentration of uncommitted cells in the population via said first cell-cell communication system, the cell commitment module senses the concentration of committed cells in the population via said second cell-cell communication system and controls which cells within the population are allowed to commit via said symmetry breaking system, so that when the concentration of uncommitted cells in the population is high, the concentration of committed cells in the population is low, and there are cells that allowed to commit, said cell differentiation module is activated. In some embodiments, the cell communication module further comprises a cascade system and a toggle switch system that interact with said symmetry breaking system and said second cell-cell communication system to control the commitment of cells within the population to differentiate. In some embodiments, the cells further comprise an apoptosis module. In some embodiments, the apoptosis module comprises a vectors encoding a repressor operably linked to a tissue-specific promoter and a vector encoding an apoptosis gene operably linked to a promoter regulated by said repressor, so that said apoptosis gene is not expressed in a tissue wherein said tissue-specific promoter is active.

In some embodiments, the present invention provides a fusion protein comprising a secretion signal, cell penetrating polypeptide, and trans acting domain in operable combination, wherein at least one of said secretion signal, cell penetrating polypeptide and trans acting domain are from different proteins. The present invention is not limited to the use of any particular secretion signal. Indeed, the use of a variety of secretion signals is contemplated, including, but not limited to IgG, tPA, serum albumin, lactoferrin, and growth hormone secretion signals. The present invention is not limited to the use of any particular cell penetrating polypeptide. Indeed, the use of a variety of cell penetrating polypeptides is contemplated, including, but not limited to, TAT cell penetrating polypeptide and penetratin. The present invention is not limited to the use of any particular trans-acting domain. Indeed, the use of variety of trans-acting domains is contemplated, including, but not limited to, zinc finger binding domains. In further embodiments, the present invention provides nucleic acids encoding the fusion proteins. In further embodiments, the present invention provides a vector comprising the nucleic acid encoding the fusion protein. In still further embodiments, the present invention provides a cell comprising the nucleic acid.

In some embodiments, the present invention provides a cell-cell communication system comprising: a) a first vector comprising a nucleic acid encoding a fusion protein comprising a secretion signal, cell penetrating polypeptide, and trans-acting domain in operable combination and b) a second vector comprising a nucleic acid encoding a promoter comprising an element that binds said trans-acting domain operably linked to a protein of interest. In further embodiments, the present invention provides a population of cells comprising the system.

DESCRIPTION OF THE FIGURES

FIG. 5 provides the sequence (SEQ ID NO:01) for the LuxI vector—pLV-Hef1a-LuxIm-IRES2-DsRed2.

FIG. 7 provides a description and sequence (SEQ ID NO:02) for the LuxR vector—pLV-Hef1a-p65H4LuxRFm-IRES2-DsRed2.

FIG. 9 provides a description and sequence (SEQ ID NO:03) for the lux promoter vector for expression of Gata4/Sox17—pLV-minCMVLuxO7-IRES2-EGFP.

FIG. 11 provides a description and sequence (SEQ ID NO:04) for the ACP vector—pLV-Hef1a-ACPm-IRES2-DsRed2

FIG. 13 provides a description and sequence (SEQ ID NO:05) for the AAS vector—pLV-Hef1a-AAS-IRES2-EGFP.

FIG. 15 provides a description and sequence (SEQ ID NO:06) for the AFP promoter vector PDX1—pLV-AFP-Pdx1-IRES2-DsRed2.

FIG. 17 provides a description and sequence (SEQ ID NO:07) for the AFP promoter vector Ngn3—pLV-AFP-Ngn3-IRES2-DsRed2.

FIG. 19 provides a description and sequence (SEQ ID NO:08) for the AFP promoter vector for TetRKRAB—pLV-AFP-TetRKRAB-IRES2-DsRed2.

FIG. 21 provides a description and sequence (SEQ ID NO:09) for the RhlI vector—pLV-Hef1a-RhlI-IRES2-DsRed2.

FIG. 26 provides a diagram of a synthetic signaling circuit utilizing cell penetrating polypeptide elements. Panel (A) depicts internal signaling. TAT is expressed upon the addition of Dox, binds to is promoter pTAT, and induces expression of EGFP. Panel (B) depicts cell-cell signaling. Sender and receiver circuits are infected into separate cells. Sender cells express TAT upon addition of Dox; TAT is secreted, and enters receiver cells, where is localizes to the nucleus and induces the expression of EGFP.

FIG. 27 provides a diagram of a synthetic signaling circuit utilizing cell penetrating polypeptide elements. Panel (A) depicts internal signaling. TAT is expressed upon the addition of Dox, binds to is promoter pTAT, and induces expression of EGFP. Panel (B) depicts cell-cell signaling. Sender and receiver circuits are infected into separate cells. Sender cells express TAT upon addition of Dox; TAT is secreted, and enters receiver cells, where is localizes to the nucleus and induces the expression of EGFP.

DEFINITIONS

Figure 1A:
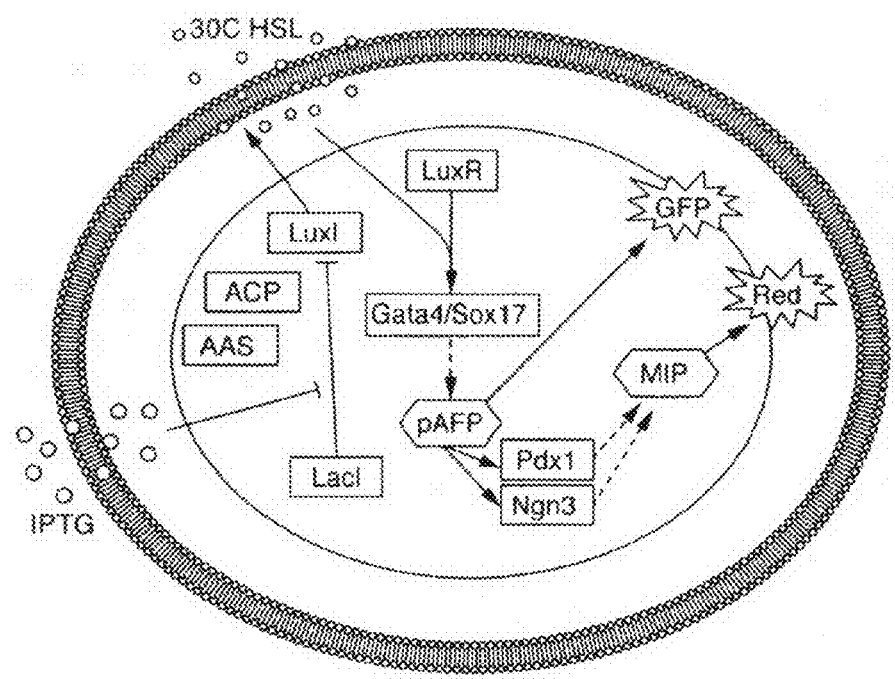
FIG. 1: Autoregulated quorum sensing based two-step differentiation from mES to endoderm to β cells. (a) Circuit diagram of the system. Details are in the text. Gata4/Sox17 activates the α-fetoprotein promoter (pAFP) indirectly by stimulating expression of AFP (dashed line). Likewise, Pdx1 and Ngn3 activate the Mouse Insulin Promoter (MIP) indirectly by stimulating insulin production (dashed lines). AFP production results in green fluorescence and insulin production results in red fluorescence. (b) Progress of system from a single cell to a collection of β cells. Due to quorum sensing, a population of mES cells is necessary in order to differentiate into endoderm.
Figure 1B:
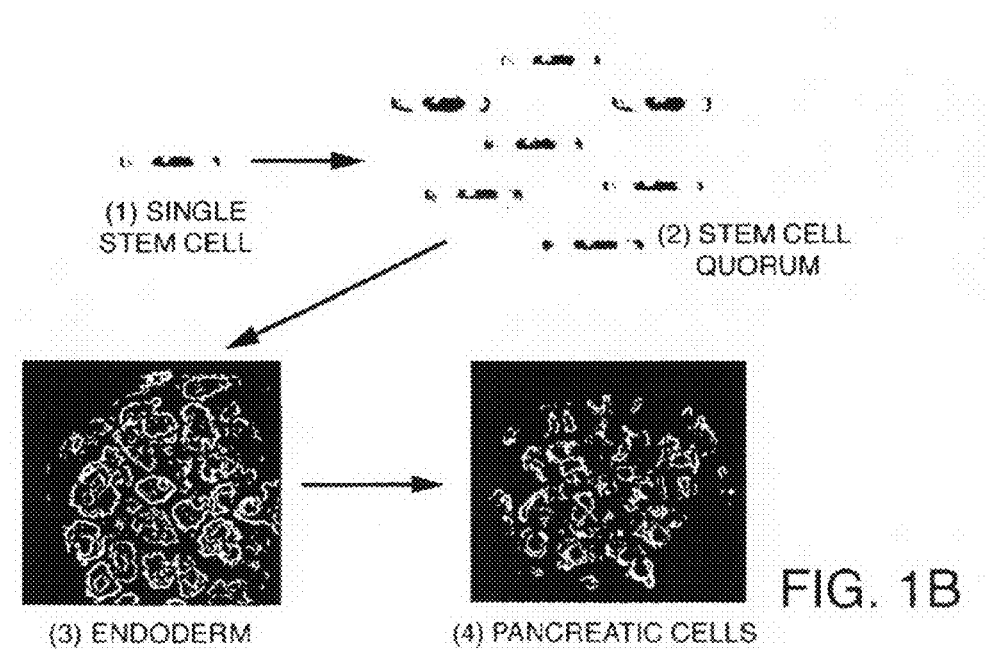

As used herein, the term "quorum sensing" refers to the detection of the density of a cell type by means of cell-cell communications. In some embodiments, "quorum sensing" is associated with an action upon achievement of a certain cell density.

As used herein, the term "quorum sensing system" refers to a system of genes that provides components for quorum sensing.

As used herein, the term "totipotent" means the ability of a cell to differentiate into any type of cell in a differentiated organism.

As used herein, the term "pluripotent" refers to a cell line capable of differentiating into several differentiated cell types.

As used herein, the term "multipotent" refers to a cell line capable of differentiating into at least two differentiated cell types.

As used herein, the term "host cell" refers to any eukaryotic cell (e.g., mammalian cells, avian cells, amphibian cells, plant cells, fish cells, and insect cells), whether located in vitro or in vivo.

As use herein, the term "stem cells" means cells that are totipotent or pluripotent and are capable of differentiating into one or more different cell types.

As use herein, the term "embryonic stem cells" means stem cells derived from an embryo.

As used herein, the term "adult stem cells" means stem cells derived from an organism after birth.

As used herein, the term "mesodermal cell line" means a cell line displaying characteristics associated with mesodermal cells.

As used herein, the term "endodermal cell line" means a cell line displaying characteristics normally associated with endodermal cells.

As used herein, the term "neural cell line" means a cell line displaying characteristics normally associated with neural cell lines. Examples of such characteristics include, but are not limited to, expression of GFAP, neuron-specific enolase, Neu-N, neurofilament-N, or tau.

As used herein the term "differentiable cell" refers to a cell that can differentiate into another cell type and includes multipotent, pluripotent and totipotent cells.

As used herein, the term "target differentiated cell" refers to a predetermined cell type that differentiates from a differentiable cell.

As used herein, the term "differentiating cell system" refers to a population of differentiable cells and target differentiated cells.

As used herein, the term "tissue homeostasis" refers to a steady state achieved between a population of differentiable cells and target differentiated cells in a differentiating cell system wherein cell-cell communication between the differentiable cells and the target differentiated cells controls the number of differentiable cells and target differentiated cells in the system.

As used herein, the term "proliferation" as used with respect to cells in a differentiating cell system refers to the production of cells of like type from a given cell population, such as the production of additional differentiable cells from a population of differentiable cells.

As used herein, the term "differentiation" as used with respect to cells in a differentiating cell system refers to the process by which cells differentiate from one cell type (e.g., a multipotent, totipotent or pluripotent differentiable cell) to another cell type such as a target differentiated cell (e.g., a beta cell).

The term "cell-cell communication pathway" refers to a network of two or more genes encoding proteins (e.g., LuxR, CinR, RhlR) and proteins that synthesize products (e.g., $3OC_6HSL$, $C_{14}HSL$, $C_4HSL$) that are involved in cell-cell communication. Exemplary cell-cell communication pathways include, but are not limited to the LuxI/LuxR, CinI/CinR, RhlI/RhlR. As a further example, the LuxI/LuxR cell-cell communication pathway can include the LuxI and LuxR genes. Additionally the LuxI/LuxR cell-cell communication pathway can include a gene of interest operably linked to promoter induced by LuxR/$3OC_6HSL$. The CinI/CinR cell-cell communication pathway can include the CinI and CinR genes. Additionally the CinI/CinR cell-cell communication pathway can include a gene of interest operably linked to promoter induced by CinR/$C_{14}HSL$. The RhlI/RhlR cell-cell communication pathway can include the RhlI and RhlR genes. Additionally the RhlI/RhlR cell-cell communication pathway can include a gene of interest operably linked to promoter induced by RhlR/$C_4HSL$.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "multiplicity of infection" or "MOI" refers to the ratio of integrating vectors:host cells used during transfection or transduction of host cells. For example, if 100,000 vectors are used to transduce 100,000 host cells, the multiplicity of infection is 1. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chomosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well, that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk cell lines, the CAD gene, which is used in conjunction with CAD-deficient cells, and the mammalian hypoxanthine-guanine phosphoribosyl transferase (hprt) gene, which is used in conjunction with hprt cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element that is capable of directing selective expression of a nucleotide sequence of interest in a specific type of cell in the relative absence of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immuno-histochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.), which is different from the level of transcription of the operably linked nucleic acid sequence in the absence of the stimulus.

As used herein, the term "nucleic acid binding protein" refers to proteins that bind to nucleic acid, and in particular to proteins that cause increased (i.e., activators or transcription factors) or decreased (i.e., inhibitors, repressors) transcription from a gene.

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which are incorporated herein by reference) and woodchuck mRNA processing enhancer (WPRE; WO99/14310 and U.S. Pat. No. 6,136,597, each of which is incorporated herein by reference).

As used herein, the term "polycistronic" refers to an mRNA encoding more than polypeptide chain (See, e.g., WO 93/03143, WO 88/05486, and European Pat. No. 117058, all of which are incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (gDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMOLV), Moloney murine sarcoma virus (MoMSV), and Mouse mammary tumor virus (MMTV), Spumavirinae, amd Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells that are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola) that are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus that is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus Vesiculovirus that includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the Vesiculovirus genera are virally-encoded integral membrane proteins that form externally projecting homotrimeric spike glycoproteins complexes that are required for receptor binding and membrane fusion. The G proteins of viruses in the Vesiculovirus genera have a covalently bound palmititic acid ($C_{16}$) moiety. The amino acid sequences of the G proteins from the Vesiculoviruses are fairly well conserved. For example, the Piry virus G protein share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins, and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins which show about 31% identity and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the Rhabdoviridae family such as VSV, Piry, Chandipura and Mokola).

As used herein, the term "transposon" refers to transposable elements (e.g., Tn5, Tn7, and Tn10) that can move or transpose from one position to another in a genome. In general, the transposition is controlled by a transposase. The term "transposon vector," as used herein, refers to a vector encoding a nucleic acid of interest flanked by the terminal ends of transposon. Examples of transposon vectors include, but are not limited to, those described in U.S. Pat. Nos. 6,027,722; 5,958,775; 5,968,785; 5,965,443; and 5,719,055, all of which are incorporated herein by reference.

As used herein, the term "adeno-associated virus (AAV) vector" refers to a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. A "recombinant AAV vector plasmid" refers to one type of recombinant AAV vector wherein the vector comprises a plasmid. As with AAV vectors in general, 5' and 3' ITRs flank the selected heterologous nucleotide sequence.

AAV vectors can also include transcription sequences such as polyadenylation sites, as well as selectable markers or reporter genes, enhancer sequences, and other control elements that allow for the induction of transcription. Such control elements are described above.

As used herein, the term "AAV virion" refers to a complete virus particle. An AAV virion may be a wild type AAV virus particle (comprising a linear, single-stranded AAV nucleic acid genome associated with an AAV capsid, i.e., a protein coat), or a recombinant AAV virus particle (described below). In this regard, single-stranded AAV nucleic acid molecules (either the sense/coding strand or the antisense/anticoding strand as those terms are generally defined) can be packaged into an AAV virion; both the sense and the antisense strands are equally infectious.

As used herein, the term "recombinant AAV virion" or "rAAV" is defined as an infectious, replication-defective virus composed of an AAV protein shell encapsidating (i.e., surrounding with a protein coat) a heterologous nucleotide sequence, which in turn is flanked 5' and 3' by AAV ITRs. A number of techniques for constructing recombinant AAV virions are known in the art (See, e.g., U.S. Pat. No. 5,173,414; WO 92/01070; WO 93/03769; Lebkowski et al., Molec. Cell. Biol. 8:3988-3996 [1988]; Vincent et al., Vaccines 90 [1990] (Cold Spring Harbor Laboratory Press); Carter, Current Opinion in Biotechnology 3:533-539 [1992]; Muzyczka, Current Topics in Microbiol. and Immunol. 158:97-129 [1992]; Kotin, Human Gene Therapy 5:793-801 [1994]; Shelling and Smith, Gene Therapy 1:165-169 [1994]; and Zhou et al., J. Exp. Med. 179:1867-1875 [1994], all of which are incorporated herein by reference).

Suitable nucleotide sequences for use in AAV vectors (and, indeed, any of the vectors described herein) include any functionally relevant nucleotide sequence. Thus, the AAV vectors of the present invention can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. (See, e.g., Han et al., Proc. Natl. Acad. Sci. USA 88:4313-4317 [1991]; Uhlmann et al., Chem. Rev. 90:543-584 [1990]; Helene et al., Biochim. Biophys. Acta. 1049:99-125 [1990]; Agarwal et al., Proc. Natl. Acad. Sci. USA 85:7079-7083 [1989]; and Heikkila et al., Nature 328:445-449 [1987]). For a discussion of suitable ribozymes, see, e.g., Cech et al. (1992) J. Biol. Chem. 267:17479-17482 and U.S. Pat. No. 5,225,347, incorporated herein by reference.

By "adeno-associated virus inverted terminal repeats" or "AAV ITRs" is meant the art-recognized palindromic regions found at each end of the AAV genome which function together in cis as origins of DNA replication and as packaging signals for the virus. For use with the present invention, flanking AAV ITRs are positioned 5' and 3' of one or more selected heterologous nucleotide sequences and, together with the rep coding region or the Rep expression product, provide for the integration of the selected sequences into the genome of a target cell.

The nucleotide sequences of AAV ITR regions are known (See, e.g., Kotin, Human Gene Therapy 5:793-801 [1994]; Berns, K. I. "Parvoviridae and their Replication" in Fundamental Virology, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. The 5' and 3' ITRs which flank a selected heterologous nucleotide sequence need not necessarily be identical or derived from the same AAV serotype or isolate, so long as they function as intended, i.e., to allow for the integration of the associated heterologous sequence into the target cell genome when the rep gene is present (either on the same or on a different vector), or when the Rep expression product is present in the target cell.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "passage" refers to the process of diluting a culture of cells that has grown to a particular density or confluency (e.g., 70% or 80% confluent), and then allowing the diluted cells to regrow to the particular density or confluency desired (e.g., by replating the cells or establishing a new roller bottle culture with the cells.

As used herein, the term "stable," when used in reference to genome, refers to the stable maintenance of the information content of the genome from one generation to the next, or, in the particular case of a cell line, from one passage to the next. Accordingly, a genome is considered to be stable if no gross changes occur in the genome (e.g., a gene is deleted or a chromosomal translocation occurs). The term "stable" does not exclude subtle changes that may occur to the genome such as point mutations.

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

GENERAL DESCRIPTION OF THE INVENTION

The present invention uses the novel paradigm of utilizing exogenous cell-cell communication pathways to autoregulate cell proliferation and differentiation. In some embodiments, the present invention provides a variety of cell-cell communication pathways and regulatory motifs that can be incorporated into any desired cell type.

In some preferred embodiments, the systems, compositions and methods of the present invention allow for tissue homeostasis to be achieved between a source of differentiable cells such as stem cells and target differentiated cells produced from the differentiable cells so that) both cell populations are maintained. In some embodiments, the systems, compositions and methods control the proliferation and differentiation of the differentiable cell population so that a population of differentiable cells is maintained over time that can differentiate into the desired target differentiated cells. In preferred embodiments, the differentiable cells are subject to a regulatory feedback mechanism that controls a) the proliferation or inhibition of proliferation of differentiable cells into additional differentiable cells so that a source of differentiable cells is stably maintained and b) the differentiation of differentiable cells into target differentiated cells so that a stable population of target differentiated cells is maintained.

In some embodiments, the present invention utilizes a series of modules to control proliferation and differentiation of differentiable cells. In some embodiments, the modules each comprise one more genes. In further embodiments, the genes are provided on vectors that can be introduced into a desired cell line. In some embodiments, the first module comprises one or more nucleic acid constructs that interact to provide population control for a population of proliferating cells. In some embodiments, the proliferating cells are differentiable cells. In some embodiments, the second module comprises one or more nucleic acid constructs that interact to control commitment of the differentiable cells to differentiate. In some preferred embodiments, if the differentiable cell population is above a certain threshold and the target differentiated cells are below a certain threshold, some of the differentiable cells commit to differentiate into the target differentiated cells. In some embodiments, the third module comprises one or more nucleic acid constructs that interact to cause differentiation of differentiable cells into target differentiated cells. In some embodiments, the fourth module comprises one or more nucleic acid constructs that trigger apoptosis if the differentiable cell migrates out of a desired location.

Precise in vivo control of stem cell differentiation into desired cell types, such as insulin-producing β cells, the cell type that is adversely affected in Diabetes Mellitus, is achievable through use of the compositions and methods described herein. In some preferred embodiments, the approaches described herein ensure a constant and steady supply of precursor cells and β cells which autoregulate insulin production. This approach also has the potential to bypass graft vs. host disease by using naive embryonic stem cells [Burt et al., Journal of Experimental Medicine, 199(7):895-904, 2004] or the patient's own adult stem cells. Finally, the approach is modular, controllable and flexible, allowing us to genetically engineer pathways that best address a patient's disease state.

This approach represents a paradigm shift in tissue engineering and diabetes treatment. Artificial cell-cell communication coordinates cell population behavior and the formation of insulin-producing β cells by precisely controlling gene expression in a two-step differentiation process. In the systems of the present invention, cells are not simply induced exogenously to differentiate, but rather are programmed to sense and respond to changes in their environment and coordinate their collective behavior based on the needs of the organism. It is important to initially build a large, undifferentiated reservoir of cells. Quorum sensing allows for controlled growth of mES cells until they reach the required density before they are directed to differentiate. Once mES cells have terminally differentiated into beta cells, they either stop dividing or divide at a very slow rate. Importantly, once these beta cells lose function or die due for example to an attack by the immune system, the ES cell reservoir detects this condition and produces new beta cells.

DETAILED DESCRIPTION OF THE INVENTION

Figure 3:
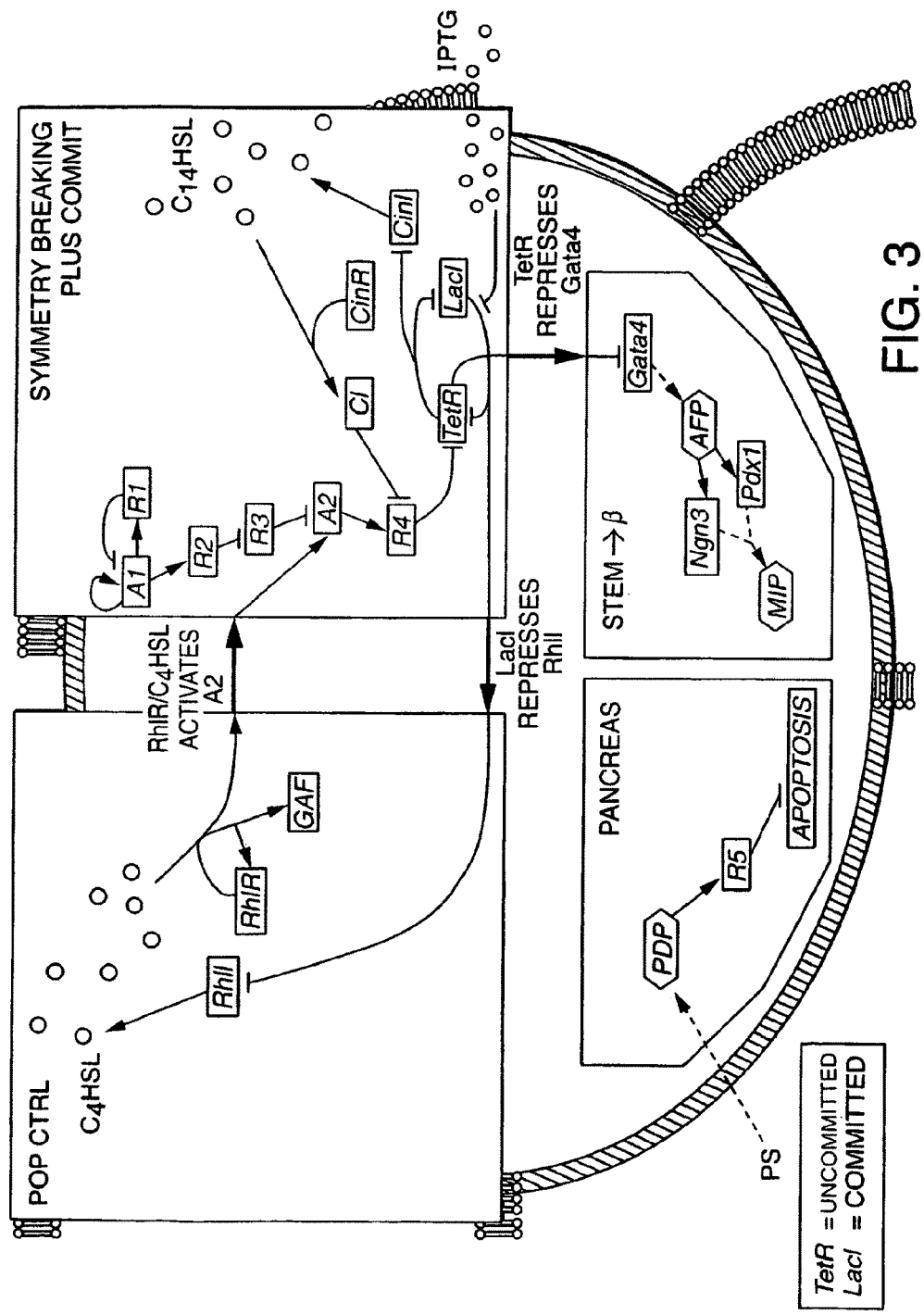
FIG. 3: Diagram of a four module system for cell proliferation and differentiation control.

The present invention utilizes artificial cell-cell communication pathways to control proliferation and differentiation of a population of differentiable cells. In some embodiments, multiple exogenous cell-cell communication pathways are introduced into a population of differentiable cells to provide a regulatory feedback control system. A schematic representation of an exemplary system is provided in FIG. 3. FIG. 3 depicts a modular system for control of proliferation and differentiation of cells. In preferred embodiments, the cells of the present invention comprise one or more of the depicted modules or components of the depicted modules. The depicted modules comprise stem cell population control modules, commitment to differentiation modules, cell differentiation modules, and apoptosis modules. In some preferred embodiments, the cells of the present invention comprise at least one population control module and commitment module that interface with a differentiation module and an apoptosis module. In some preferred embodiments, the cell population control module and commitment module interface to control the number of uncommitted cells in the population (i.e., cells that retain the ability to differentiate) and the number of committed cells in the) population (i.e., cells that have committed to differentiate, but have not necessarily differentiated into the desired target cell type).

In preferred embodiments, the modules of the present invention comprise separate motifs or circuit designs that interact to produce a desired outcome. In particularly preferred embodiments, cell-cell communication, oscillator, cascade, and/or toggle switch motifs are incorporated into one or more of the modules of the present invention. In preferred embodiments, these motifs interact to provide a symmetry breaking condition so that a population of stem cells is maintained and not exhausted. These individual components and their interaction with one another is described in detail below.

In some embodiments, the present invention provides artificial cell-cell communication systems for use in mammalian cells. In some embodiments, cell-cell communication systems are derived from bacterial cell-cell communication systems from organisms such as *Pseudomonas aeruginosa*, *Rhizobium leguminosarum*, and *Vibrio fischeri*. These systems comprise genes that catalyze the synthesis of chemical signals of the acyl-homoserine lactone (AHL) family. In other embodiments, the cell-cell communication systems utilize secretion signals and viral internalization signals.

A. Population Control Module

As shown in FIG. 3, in some embodiments, the present invention provides a population control module comprising a pathway of exogenous genes that are preferably introduced into a population of stem cells. The population control module interacts with the commitment module to control the proliferation and differentiation of the cells within the system. The population control module is utilized to detect the number of stem cells in the system. If the stem cell population is low, then stem cell proliferation is allowed. If the stem cell population is high, then proliferation is inhibited. The commitment module (explained in more detail below) is used to detect the number of differentiated cells in the system (in this example, beta cells). If the beta cell population is high, proliferation of stem cells in inhibited. If the beta cell population is low, differentiation of stem cells is induced along with stem cell proliferation. A third module, described in more detail below, interacts with the two cell-cell communication modules to cause differentiation of stem cells into the desired target differentiated cell, in this example beta cells.

Referring to FIG. 3, in some embodiments, the population control module preferably comprises genes encoding a cell-cell communication pathway, preferably a RhlI/RhlR cell-cell communication pathway. The invention is not limited to the use of any particular cell-cell communication pathway in the first module. In other embodiments, LuxI/LuxR, CinI/CinR, or viral-based cell-cell communication systems are utilized. In preferred embodiments, bacterial cell-cell signaling pathways are utilized. As shown in FIG. 3, the population control module senses the density of the stem cell population. In some embodiments, the population control module comprises an exogenous RhlI gene operably linked to a repressor element, preferably a LacI repressor element. In the absence of the repressor, the exogenous RhlI gene catalyzes the synthesis of $C_4HSL$. The population control module further comprises an exogenous RhrR gene and an exogenous gene comprising a Growth Arrest Factor (GAF) operably linked to a promoter responsive to the $C_4HSL$/RhrR complex. Under conditions of a high density of stem cells, the corresponding high amount of $C_4HSL$ interacts with the gene product of RhrR to form a complex, which activates expression of GAF, thus inhibiting proliferation of the stem cells.

Exemplary vectors for the components shown in FIG. 3 are provided in FIGS. 28-37, where A1=Gal4, R1=ZF1, R2=ZF2, R3=ZF3, R4=ZF4, A2=CymVP16, and P is either Hef1a or minCMV.

B. Commitment Module

Referring to FIG. 3, in some embodiments, the present invention provides a commitment module comprising multiple motifs or circuit elements that allow for symmetry breaking and control the commitment of cell to differentiate. In some embodiments, the module comprises one or more of the following motifs: an oscillator, a cascade, a toggle switch, and a cell-cell communication pathway. In some preferred embodiments, these motifs interact, as described in detail below, to allow commitment to differentiate when three conditions are met within the population of cells containing the modules: a) there is a high level of uncommitted cells; b) there are cells that allowed to commit; and c) there is a low level of committed cells.

Referring to FIG. 3, an embodiment of an oscillator is depicted by A1 and R1. In preferred embodiments, A1 is an activator and R1 is a repressor that are connected in way so that they oscillate. In some embodiments, as depicted, the activator A1 activates itself and the repressor R1 and the repressor R1 represses the activator A1. This oscillation provides symmetry breaking for the population of cells containing the motif. Due to the oscillation of activator A1 and repressor R1, the population of cells containing activator A1 and repressor R1 is asynchronous. At any given time, only a portion of the cells in the population will have a high level of activator A1. In some embodiments, as depicted, only cells with high activator A1 are allowed to commit to differentiate, thus the remaining portion of the cells with low levels of activator A1 is reserved in an uncommitted state. This ensures that a population of uncommitted stem cells will be maintained. Otherwise, all uncommitted stem cells could commit to differentiate, allowing the exhaustion of the stem cells from the population.

Referring to FIG. 3, an embodiment of a cascade is depicted by repressor R2, repressor R3, activator A2, and repressor R4. In some embodiments, activator A2 is operably linked to a promoter responsive to $C_4HSL$/RhrR and thus interfaces with the population control module. In some embodiments, as depicted, activator A1 from the oscillator activates repressor R2, which in turn represses repressor R3, which is a repressor of activator A2. Activator A2 interfaces with the population control module and is activated by the $C_4HSL$/RhrR complex. Thus, if the level of activator A1 is high, repressor R2 is activated which represses repressor R3, allowing the level of activator A2 to be high if there is a concomitant high concentration of uncommitted stem cells that are producing $C_4HSL$/RhrR. As a result, the level of activator A2 can only be high when two conditions are met: 1) there is a high level of A1 within the cell; and 2) there is a high concentration of uncommitted stem cells. When these two conditions are met, activator A2 in turn activates repressor R4, which interfaces with the cell-cell communication and toggle switch motifs.

Still referring to FIG. 3, in order for cells within the population to commit as described above, a third condition must be met: a low concentration of committed cells. In some embodiments, the level of committed cells is detected via a cell-cell communication pathway, preferably a CinI/CinR cell-cell communication pathway. The invention is not limited to the use of any particular cell-cell communication pathway in the second module, although the particular cell-cell communication pathway utilized should preferably be different than the cell-cell communication pathway selected for the cell population module. In other embodiments, LuxI/LuxR, RhlI/RhlR, or viral-based cell-cell communication systems are utilized.

In some embodiments, as depicted in FIG. 3, the cell-cell communication pathway comprises an exogenous CinI gene, and exogenous CinR gene, and an exogenous gene encoding the repressor CI operably linked to a promoter responsive to the $C_{14}HSL$/CinR complex. High levels of $C_{14}HSL$ are indicative of a high concentration of committed cells. Under these conditions, repressor CI is activated and in turn represses repressor R4. In some embodiments, repressor R4 interacts with the toggle switch motif as detailed below. When the level of repressor R4 is low, there is no commitment. As can be seen, the level of R4 can only be high when the level of activator A2 is high and the level of CI is low. Low levels of $C_{14}HSL$ are indicative of a low concentration of committed cells and under these conditions, the level of repressor CI is low, allowing the level repressor R4 to be high.

Still referring to FIG. 3, in some embodiments, the commitment module further comprises a toggle switch motif that switches cells between an uncommitted state and a committed state. In some embodiments, as depicted in FIG. 3, the toggle switch motif comprises two repressors, in preferred embodiments, TetR and LacI. In some embodiments, TetR and LacI cross repress each other. High levels of TetR within a cell are indicative of an uncommitted state. As shown in FIG. 3, IPTG can be added to the cells to repress LacI, thus causing the cells to enter into an uncommitted state. Alternatively, as described above, repressor R4 is high in cells where activator A1 is high and where there is a high concentration of uncommitted stem cells. When these two conditions are met, along with the condition of low number of committed cells, repressor R4 represses TetR, allowing a high level of LacI. High levels of LacI in a cell trigger the transition from an uncommitted cell to a committed cell by repressing TetR. As depicted in FIG. 3, when LacI is high, repression of CinI is released, causing the synthesis of $C_{14}HSL$, the activation of CI and the repression of R4. These events are indicative of a committed cell. As also depicted in FIG. 3, high LacI within a cell represses RhlI of the cell population module, inhibiting synthesis of $C_4HSL$.

Exemplary vectors for the components shown in FIG. 3 are provided in FIGS. 28-37, where A1=Gal4, R1=ZF1, R2=ZF2, R3=ZF3, R4=ZF4, A2=CymVP16, and P is either Hef1a or minCMV.

C. Cell Differentiation Module

As shown in FIG. 3, in some embodiments, the present invention provides a cell differentiation module that is responsive to the commitment module. In some embodiments, the cell-differentiation module comprises at least an exogenous gene encoding a first cell fate regulator that is operably linked to a repressor, such as the TetR repressor. In some embodiments, as depicted in FIG. 3, the TetR/LacI toggle switch controls the expression of the cell fate regulator. When the three conditions of a) high level of uncommitted cells, b) cell that that is allowed to commit, and c) low level of committed cells are met, TetR is repressed, releasing the repression of the a cell fate regulator such as Gata4 or Sox 17 (not shown). Gata4 expression is the initial step in the programmed two-step differentiation of ES cells into β cells using established cell fate regulators. In some preferred embodiments, two-step differentiation of ES cells first to visceral or definitive endoderm and then to pancreatic β cells is facilitated by using controlled expression of established cell fate regulators triggered by cell-cell communication. A preferred system for the integration of the relevant cell fate regulators with the cell population and commitment modules is shown in FIG. 3. When the three conditions are met, either Gata4 is expressed. These two cell fate regulators were chosen because they are both expressed in mammalian visceral endoderm [Ritz-Laser et al., Molecular Endocrinology, 19(3):759-770, 2005; Ku et al., Stem Cells, 22:1205-1217, 2004]. Both Gata4 and Sox17 are required transcription factors in pancreatic organogenesis. Gata4 is present in very early visceral endoderm that differentiates into both insulin-producing and glucagon-producing cells [42]. Sox17 is expressed exclusively in insulin-producing cells and appears slightly later than Gata4 [43]. In preferred embodiments, endoderm differentiation is verified by visualizing the presence of endodermal markers such as Hnf3β or lamininB1 using immunohistochemistry and Western blots. Cells that remain in the stem cell state are identified by staining with alkaline phosphatase in a standard ES cell assay.

In some preferred embodiments, the cell-cell communication systems of the present invention comprise vectors that express cell fate regulators that regulate the differentiation of endoderm to β cells. Differentiation into endoderm triggers the expression of endoderm specific factors. In preferred embodiments, the genes encoding cell fate regulators are operably linked, to a promoter that is regulated (preferably induced) by one or more endoderm specific factors. It is contemplated that cells that differentiate into endoderm naturally express the endodermal marker α-fetoprotein (AFP) which binds the AFP promoter. In the third module) of the present invention, AFP regulates expression of Ngn3, Pdx1 and/or other cell fate regulators such as EGFP via the AFP promoter, hence the differentiation from ES to endoderm is visualized with the appearance of green fluorescence. In vivo, Ngn3 and Pdx1 are both expressed at various points during cellular differentiation from endoderm to β cells [Soria, Differentiation, 68:205-219, 2001] and both have been found to be necessary for terminal differentiation into β cells. Naturally occurring in vivo specialization of endodermal cells into β cells depends on the existence of a complex set of environmental cues which may not be present in the disease state. In the engineered system of the present invention, however, differentiation of mES cells into endoderm internally forces the cell to subsequently specialize into β cells. Upon terminal β cell differentiation, insulin production activates DsRed expression from the Mouse Insulin Promoter (MIP). Cells expressing the fluorescent red protein are assayed for terminal differentiation by immunohistochemical assays and Western blotting of β cell markers such as C-peptide, insulin and Nkx6.1. Cells not expressing fluorescent red protein are histochemically assayed for the presence of AFP, Pdx1, Ngn3 and also for stem cell character using the standard ES cell assay. Cells not initially induced with IPTG should not fluoresce red and should remain in the ES cell state.

In other preferred embodiments, other cell fate regulators are expressed via the differentiation module. Examples of the cell fate regulators include, but are not limited to, Nkx6.1, Nkx2.2, Is1-1, NeuroD, Pax6, Fgf4, BRA, Wnt9, NCAD, CER, FoxA2, CxcR4, Hnf1B, Hnf4A, Hnf6, H1xB9, Pax4, Cgc, GHRL, SST, PPY, Activin, Fgf10, Cyc, RA, Ex4, DAPT, HGF and Igf1. In preferred embodiments, these cell fate regulators are inserted into lentiviral vectors and introduced into the cell line of interest. In some preferred embodiments, the cell fate regulators are operably linked to a stage specific promoter. Stage specific promoters are promoters that are expressed at a particular stage of differentiation, such as differentiation into endoderm, ectoderm or mesoderm. In some preferred embodiments, the cell fate regulators are operably linked to an AFP promoter.

Exemplary vectors for the components shown in FIG. 3 are provided in FIGS. 28-37, where A1=Gal4, R1=ZF1, R2=ZF2, R3=ZF3, R4=ZF4, A2=CymVP16, and P is either Hef1a or minCMV.

D. Apoptosis Module

As shown in Figure, in some embodiments, the cells of the present invention further comprise an apoptosis module. In some embodiments, the apopstosis module comprises a series of vectors comprising genes that trigger apoptosis is the cell migrate to an undesired location. In preferred embodiments, the stem cells of the present invention would undergo apoptosis if the cells leave the pancreas. As shown in FIG. 3, genes encoding an apoptosis pathway are operably linked to a repressor element responsive to a repressor that is synthesized in the presence of a signal for the pancreas (PS). In the absence of PS, the repressor is not synthesized and apoptosis is triggered.

E. Cell Penetration Element Based Cell-Cell Communication Systems

In some embodiments, the present invention provides cell-cell communication systems that utilize cell penetrating polypeptide elements. In some embodiments, the present invention provides a fusion protein comprising a secretion signal, cell penetrating polypeptide, and trans acting domain in operable combination, wherein at least one of said secretion signal, cell penetrating polypeptide and trans acting domain are from at least two different proteins. In further embodiments, the present invention provides a nucleic acid encoding the fusion protein. In further preferred embodiments, the present invention provides vectors comprising a nucleic acid encoding the fusion protein. In still other embodiments, the present invention provides cells that express the fusion protein. In some embodiments, the present invention further provides a nucleic acid comprising a promoter comprising an element that binds or is responsive to the trans-acting domain, wherein the promoter is operably linked to a protein of interest.

The present invention is not limited to the use of any particular secretion signals, cell penetrating polypeptides or trans-acting domains. Indeed, the present invention contemplates a modular and highly expandable library of artificial cell-cell communication signals by using translational fusions of cell permeable peptides with in silico designed zinc finger proteins and an enhancer or repressor. Such fusion proteins are exported by sender cells, translocate to the nucleus of receiver cells, where they control expression of genes in synthetic as well as endogenous signaling pathways by binding their cognate DNA binding sites.

CPPs are peptide sequences with the ability to translocate across the plasma membrane and to reach cytoplasmic and/or nuclear compartments in live cells after internalization. CPPs have been first described in the HIV TAT-1 and the Antennapedia proteins, where the translocation seems to reflect in vivo biological process. In the last decade, fusion proteins containing such CPPs have been widely used to deliver effector proteins into the cytoplasm or nucleus of target cells, predominantly by adding the purified fusion protein to the cell culture supernatant or injecting it intraperitoneally in vivo. The binding of TAT to the cell surface thought to involve heparan sulfate proteoglycans, and in vitro evidences suggest that the uptake is mediated by an energy-depending endocytic process involving lipid rafts. The release from these endocytic vesicles into the cytoplasm is less well understood, and has been shown to be a rate-limiting step in the transduction process. For TAT, the subsequent localization to the nucleus is achieved through an effective nuclear localization sequence (NLS), endogenously present in this protein.

The present invention is not limited to the use any particular CPP peptide. The following CPP peptides find use in the present invention:

```
TAT:         SGYGRKKRRQRRRC
             (SEQ ID NO: 24)

Antp:        SGRQIKIWFQNRRMKWKKC
             (SEQ ID NO: 25)

TAT:         GRKKRRQRRRPPQG
             (SEQ ID NO: 26)

TAT:         (47-60), N-Cys-Tyr⁴⁷-Gly-Arg-Lys-Lys-
             Arg-Arg-Gln-Arg-Arg-Arg-Pro-Pro-Gln⁶⁰-
             COOH;
             (SEQ ID NO: 27)

ANTP:        N-Cys-Arg⁴³-Gln-Ile-Lys-Ile-Trp-Phe-
             Gln-Asn-Arg-Arg-Met-Lys-Trp-Lys-Lys⁵⁸-
             COOH
             (SEQ ID NO: 28)

Vectocell ®  DPV3 sense, 5' GATCCCGTAAAAAGCGTCGTC
             GAGAAAGCCGTAAGAAACGTCGACGTGAAAGCA-3';
             (SEQ ID NO: 29)
             DPV3 antisense, 5'-AGCTTGCTTTCACGTCG
             ACGTTTCTTACGGCTTTCTCGACGACGCTTTTTACG
             G-3';
             (SEQ ID NO: 30)
             DPV15b sense, 5'-GATCCGGTGCGTATGATCT
             GCGTCGTCGAGAACGTCAGAGCCGTCTGCGTCGACG
             TGAAAGACAGAGCAGAA-3';
             (SEQ ID NO: 31)
             DPV3 antisense, 5'-AGCTTTCTGCTCTGTCT
             TTCACGTCGACGCAGACGGCTCTGACGTTCTCGACG
             ACGCAGATCATACGCACCG-3';
             (SEQ ID NO: 32)
             DPV1047 sense, 5'-GATCCGTTAAACGTGGAC
             TGAAACTTCGTCATGTTCGTCCGCGTGTGACCCGTG
             ATGTGA-3';
             (SEQ ID NO: 33)
             DPV1047 antisense, 5'-AGCTTCACATCACG
             GGTCACACGCGGACGAACATGACGAAGTTTCAGTCC
             ACGTTTAACG-3'.
             (SEQ ID NO: 34)
```

ZFs of the Cys2His2 type contain about 30 amino acids that code for two b-strands and an a-helix that mediates interaction with a nucleotide triplet. The human genome contains at least 4000 such domains in over 700 proteins, which represents about 2% of human genes. ZFs recognizing many of the 64 triplets possible have been isolated and described. Such a ZF domain can be treated as modular, which means that multiple concatenated ZF domains (polydactyl ZFs) do bind to DTS with a multiple of three triplets length. Recently, databases and tools became available to easily engineer ZFP-DTS pairs in silico to further streamline this process (16-18). The optimal linker sequences to connect such single ZF domains to a ZFP have also been described, as well as the optimal positioning of transcriptional activators or inhibitors.

A translational fusion of a CPP with a ZFP, when exported by a sender cell, translocates into the nucleus of receiver cells. The transcellular delivery of such ZFPs would massively expand the possibilities we have at our disposition to manipulate synthetic as well as endogenous signaling pathways in stem cells. This would facilitate the programmed differentiation of stem cells into tissue patterns by design. By engineering cells that can be manipulated to decide between cell fates based on the given signal and working within a 3D matrix system in vitro, we will study the potential of this system in promoting organogenesis and tissue repair. The long-term goal would be to have safe self-regulating and self-regenerating tissue/organs for clinical applications. Another purpose is to elucidate the architecture and dynamics of endogenous cell fate regulatory networks as they function to promote lineage choices.

An additional application for such an artificial cell-cell communication system would be the delivery of cell-permeable therapeutic proteins influencing cell signaling at the level of protein-protein interactions in a controlled fashion in vivo. As an example, the secretion of cell-permeable peptides of the wild-type tumor suppressor p53 from artificially engineered cells or tissue, would restore cell growth control of tumor cells with mutated forms of p53, which are present in almost all human cancers.

The present invention is likewise not limited to the use of any particular secretion signal. A secretion signal is any DNA sequence which when operably linked to a recombinant DNA sequence encodes a signal peptide which is capable of causing the secretion of the recombinant polypeptide. In general, the signal peptides comprise a series of about 15 to 30 hydrophobic amino acid residues (See, e.g., Zwizinski et al., J. Biol. Chem. 255(16): 7973-77 [1980], Gray et al., Gene 39(2): 247-54 [1985], and Martial et al., Science 205: 602-607 [1979]). Such secretion signal sequences are preferably derived from genes encoding polypeptides secreted from the cell type targeted for tissue specific expression. Secretory DNA sequences, however, are not limited to such sequences. Secretory DNA sequences from proteins secreted from many cell types and organisms may also be used (e.g., the secretion signals for t PA, serum albumin, lactoferrin, and growth hormone, and secretion signals from microbial genes encoding secreted polypeptides such as from yeast, filamentous fungi, and bacteria).

FIGS. 26 and 27 provide examples of a synthetic cell-cell communication circuit that utilizes CPP elements. Panel (A) depicts internal signaling. TAT is expressed upon the addition of Dox, binds to is promoter pTAT, and induces expression of EGFP. Panel (B) depicts cell-cell signaling. Sender and receiver circuits are infected into separate cells. Sender cells express TAT upon addition of Dox; TAT is secreted, and enters receiver cells, where is localizes to the nucleus and induces the expression of EGFP.

F. Vector Systems

In some embodiments, the various exogenous genes described above are provided on vectors that are introduced into the desired cell line, such as a stem cell line. In some preferred embodiments, the vectors are lentiviral vectors. In some embodiments, additional genes required for the synthesis of precursors of $C_4HSL$, $C_{14}HSL$, or $30C_6HSL$ are also introduced into the desired cell line. In some preferred embodiments, vectors encoding one or more genes from the Type II bacterial fatty acid synthesis (FAS) system are also introduced into mammalian cells. In some embodiments, the vectors encode Acyl Carrier Protein and Acyl-Acyl Carrier (ACP) Protein Synthase (AAS) including ACP and AAS.

In preferred embodiments, the components of the cell-cell communication system are included in separate vectors. The individual vectors are then introduced into the desired cell line. In preferred embodiments, where lentiviral vectors are utilized, the target cell line is transduced with the lentiviral vectors. The cell line may be co-infected with the vectors or the vectors may be introduced serially.

In some preferred embodiments, the genes for the components of the cell-cell communication system of the present invention (e.g., LuxI, ACP, and AAS) are optimized for expression in mammalian cells. In other embodiments, genes comprising the entire bacterial Type II Fatty Acid Synthase system are included on vectors and introduced in the cell line.

In preferred embodiments, as described in more detail below, the components of the cell-cell communication systems are introduced into a mammalian cell line. The present invention is not limited to the use of any particular cell lines. In some embodiments, the cell lines are pluripotent, multipotent or totipotent cell lines. In some preferred embodiments, the cells lines are stem cell lines. In preferred embodiments, the components are incorporated into expression vectors that are introduced into mammalian cells. In some preferred embodiments, the genes encoding the components of the cell-cell communication system are operably linked to exogenous promoters.

The modules and motifs of the present invention generally comprise multiple exogenous genes operably linked to promoters. In preferred embodiments, the exogenous genes operably linked to promoters are included in a vector. In preferred embodiments, the vectors are introduced into a cell. The present invention is not limited to the use of any particular vector system. Indeed, the use of a variety of vector systems is contemplated. In some preferred embodiments, the vectors are lentiviral vectors. In other embodiments, the vectors are retroviral vectors, pseudotyped retroviral vectors, pseudotyped lentiviral vectors, adenovirus vectors, plasmids, transposons, or artificial chromosomes.

The present invention also contemplates the use of lentiviral vectors to generate high copy number cell lines. The lentiviruses (e.g., equine infectious anemia virus, caprine arthritis-encephalitis virus, human immunodeficiency virus) are a subfamily of retroviruses that are able: to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described above for retroviral vectors.

In general, retroviruses (family Retroviridae) are divided into three groups: the spurnaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses which infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying a gene of interest is typically achieved in two stages.

First, the gene of interest is inserted into a retroviral vector which contains the sequences necessary for the efficient expression of the gene of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (−PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); therefore, the resulting virus is said to be replication defective.

Second, following the construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles, which contain the membrane-associated protein expressed by the transfected packaging cell line; these viral particles, which contain viral genomic RNA derived from one virus encapsidated by the envelope proteins of another virus are said to be pseudotyped virus particles.

The retroviral vectors of the present invention can be further modified to include additional regulatory sequences. As described above, the retroviral vectors of the present invention include the following elements in operable association: a) a 5' LTR; b) a packaging signal; c) a 3' LTR and d) a nucleic acid encoding a protein of interest located between the 5' and 3' LTRs. In some embodiments, the nucleic acid of interest is operably linked to a promoter of interest. As described above, in preferred embodiments, the nucleic acid of interest is a gene encoding a protein from a quorum sensing system, or a gene encoding a cell fate regulator. In some preferred embodiments, the promoter is a promoter responsive to an autoinducer/regulatory partner complex synthesized by the quorum sensing pathway, an inducible promoter, a repressible promoter, or a stage specific promoter such as the AFP promoter. In some embodiments of the present invention, the nucleic acid of interest may be arranged in opposite orientation to the 5' LTR when transcription from an internal promoter is desired.

In other embodiments of the present invention, the vectors are modified by incorporating an RNA export element (See, e.g., U.S. Pat. Nos. 5,914,267; 6,136,597; and 5,686,120; and WO99/14310, all of which are incorporated herein by reference) either 3' or 5' to the nucleic acid sequence encoding the protein of interest. It is contemplated that the use of RNA export elements allows high levels of expression of the protein of interest without incorporating splice signals or introns in the nucleic acid sequence encoding the protein of interest.

In still other embodiments, the vector further comprises at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different proteins of interest or subunits of a multisubunit protein such as an antibody) to form a polycistronic sequence so that the two transcriptional units are transcribed from the same promoter.

The retroviral vectors of the present invention may also further comprise a selectable marker allowing selection of transformed cells. A number of selectable markers find use in the present invention, including, but not limited to the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. In some embodiments, the selectable marker gene is provided as part of polycistronic sequence that also encodes the protein of interest.

Viral vectors, including recombinant lentiviral vectors, provide a more efficient means of transferring genes into cells as compared to other techniques such as calcium phosphate-DNA co-precipitation or DEAE-dextran-mediated transfection, electroporation or microinjection of nucleic acids. It is, believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MoMLV) (See e.g., Miller and Baltimore Mol. Cell. Biol. 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

In some preferred embodiments, the retroviral vector is pseudotyped. (See, e.g., U.S. Pat. No. 5,512,421, which is incorporated herein by reference). In some preferred embodiments, the pseudotyped retrovirus contains the G protein of VSV as the membrane associated protein. Unlike retroviral envelope proteins that bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90:8033 [1993]).

The present invention also contemplates the use of adeno associated virus (AAV) vectors. AAV is a human DNA parvovirus, which belongs to the genus Dependovirus. The AAV genome is composed of a linear, single-stranded DNA molecule that contains approximately 4680 bases. The genome includes inverted terminal repeats (ITRs) at each end that function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. A family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3 (for a detailed description of the AAV genome, see e.g., Muzyczka, Current Topics Microbiol. Immunol. 158:97-129 [1992]; Kotin, Human Gene Therapy 5:793-801 [1994]).

AAV requires coinfection with an unrelated helper virus, such as adenovirus, a herpesvirus or vaccinia, in order for a productive infection to occur. In the absence of such coinfection, AAV establishes a latent state by insertion of its genome into a host cell chromosome. Subsequent infection by a helper virus rescues the integrated copy, which can then replicate to produce infectious viral progeny. Unlike the non-pseudotyped retroviruses, AAV has a wide host range and is able to replicate in cells from any species so long as there is coinfection with a helper virus that will also multiply in that species. Thus, for example, human AAV will replicate in canine cells coinfected with a canine adenovirus. Furthermore, unlike the retroviruses, AAV is not associated with any human or animal disease, does not appear to alter the biological properties of the host cell upon integration and is able to integrate into nondividing cells. It has also recently been found that AAV is capable of site-specific integration into a host cell genome.

In light of the above-described properties, a number of recombinant AAV vectors have been developed for gene delivery (See, e.g., U.S. Pat. Nos. 5,173,414; 5,139,941; WO 92/01070 and WO 93/03769, both of which are incorporated herein by reference; Lebkowski et al., Molec. Cell. Biol. 8:3988-3996 [1988]; Carter, Current Opinion in Biotechnology 3:533-539 [1992]; Muzyczka, Current Topics in Microbiol. and Immunol. 158:97-129 [1992]; Kotin, (1994) Human Gene Therapy 5:793-801; Shelling and Smith, Gene Therapy 1:165-169 [1994]; and Zhou et al., J. Exp. Med. 179:1867-1875 [1994]).

Recombinant AAV virions can be produced in a suitable host cell that has been transfected with both an AAV helper plasmid and an AAV vector. An AAV helper plasmid generally includes AAV rep and cap coding regions, but lacks AAV ITRs. Accordingly, the helper plasmid can neither replicate nor package itself. An AAV vector generally includes a selected gene of interest bounded by AAV ITRs that provide for viral replication and packaging functions. Both the helper plasmid and the AAV vector bearing the selected gene are introduced into a suitable host cell by transient transfection. The transfected cell is then infected with a helper virus, such as an adenovirus, which transactivates the AAV promoters present on the helper plasmid that direct the transcription and translation of AAV rep and cap regions. Recombinant AAV virions harboring the selected gene are formed and can be purified from the preparation. Once the AAV vectors are produced, they may be used to transfect (See, e.g., U.S. Pat. No. 5,843,742, herein incorporated by reference) host cells at the desired multiplicity of infection to produce high copy number host cells. As will be understood by those skilled in the art, the AAV vectors may also be modified as described above to contain various regulatory sequences (e.g., signal peptide sequences, RNA export elements, and IRES's).

The present invention also contemplates the use of transposon vectors. Transposons are mobile genetic elements that can move or transpose from one location another in the genome. Transposition within the genome is controlled by a transposase enzyme that is encoded by the transposon. Many examples of transposons are known in the art, including, but not limited to, Tn5 (See e.g., de la Cruz et al., J. Bact. 175: 6932-38 [1993], Tn7 (See e.g., Craig, Curr. Topics Microbiol. Immunol. 204: 27-48 [1996]), and Tn10 (See e.g., Morisato and Kleckner, Cell 51:101-111 [1987]). The ability of transposons to integrate into genomes has been utilized to create transposon vectors (See, e.g., U.S. Pat. Nos. 5,719,055; 5,968,785; 5,958,775; and 6,027,722; all of which are incorporated herein by reference.) Because transposons are not infectious, transposon vectors are introduced into host cells via methods known in the art (e.g., electroporation, lipofection, or microinjection). Therefore, the ratio of transposon vectors to host cells may be adjusted to provide the desired multiplicity of infection to produce the high copy number host cells of the present invention.

Transposon vectors suitable for use in the present invention generally comprise a nucleic acid encoding a protein of interest interposed between two transposon insertion sequences. Some vectors also comprise a nucleic acid sequence encoding a transposase enzyme. In these vectors, the one of the insertion sequences is positioned between the transposase enzyme and the nucleic acid encoding the protein of interest so that it is not incorporated into the genome of the host cell during recombination. Alternatively, the transposase enzyme may be provided by a suitable method (e.g., lipofection or microinjection). As will be understood by those skilled in the art, the transposon vectors may also be modified as described above to contain various regulatory sequences (e.g., signal peptide sequences, RNA export elements, and IRES's).

Figure 6:
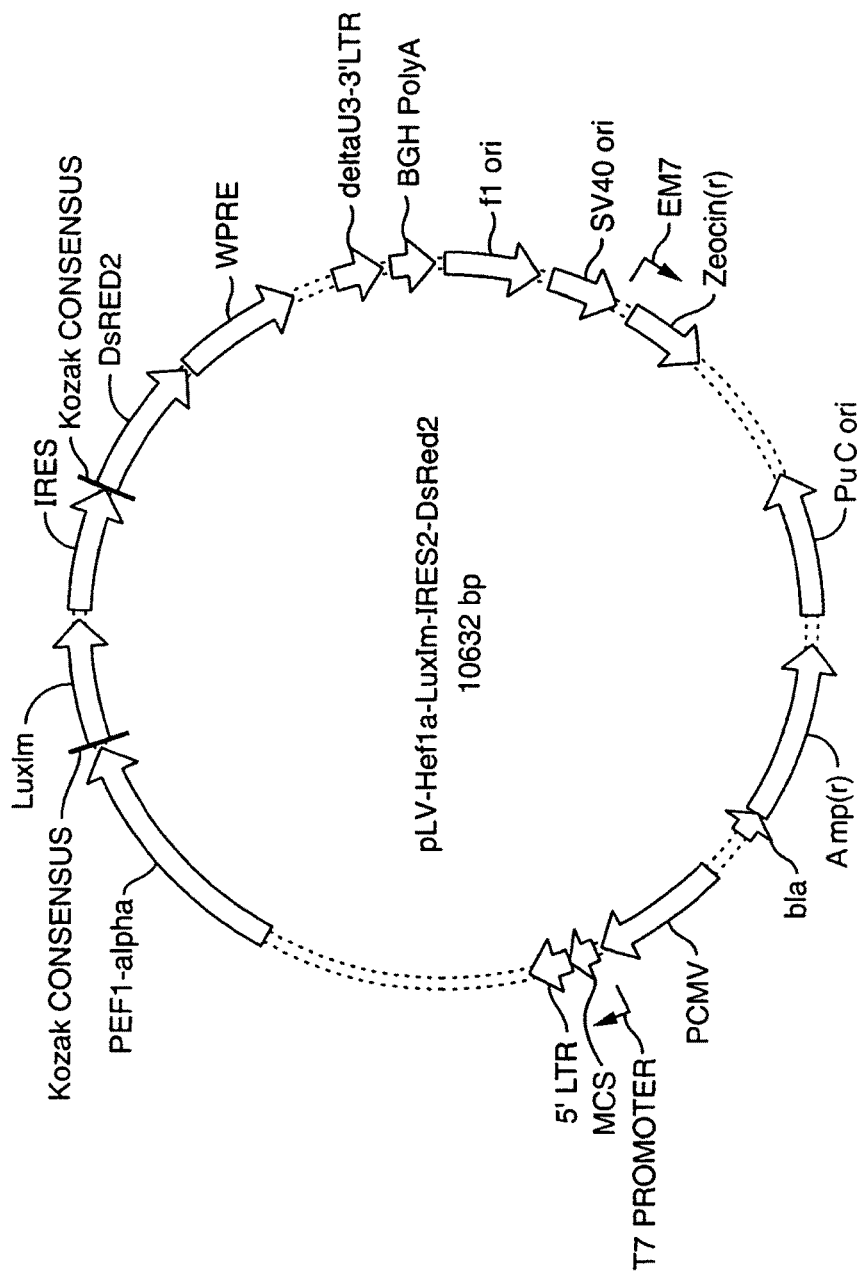
FIG. 6 provides a diagram of the vector of FIG. 5.
Figure 8:
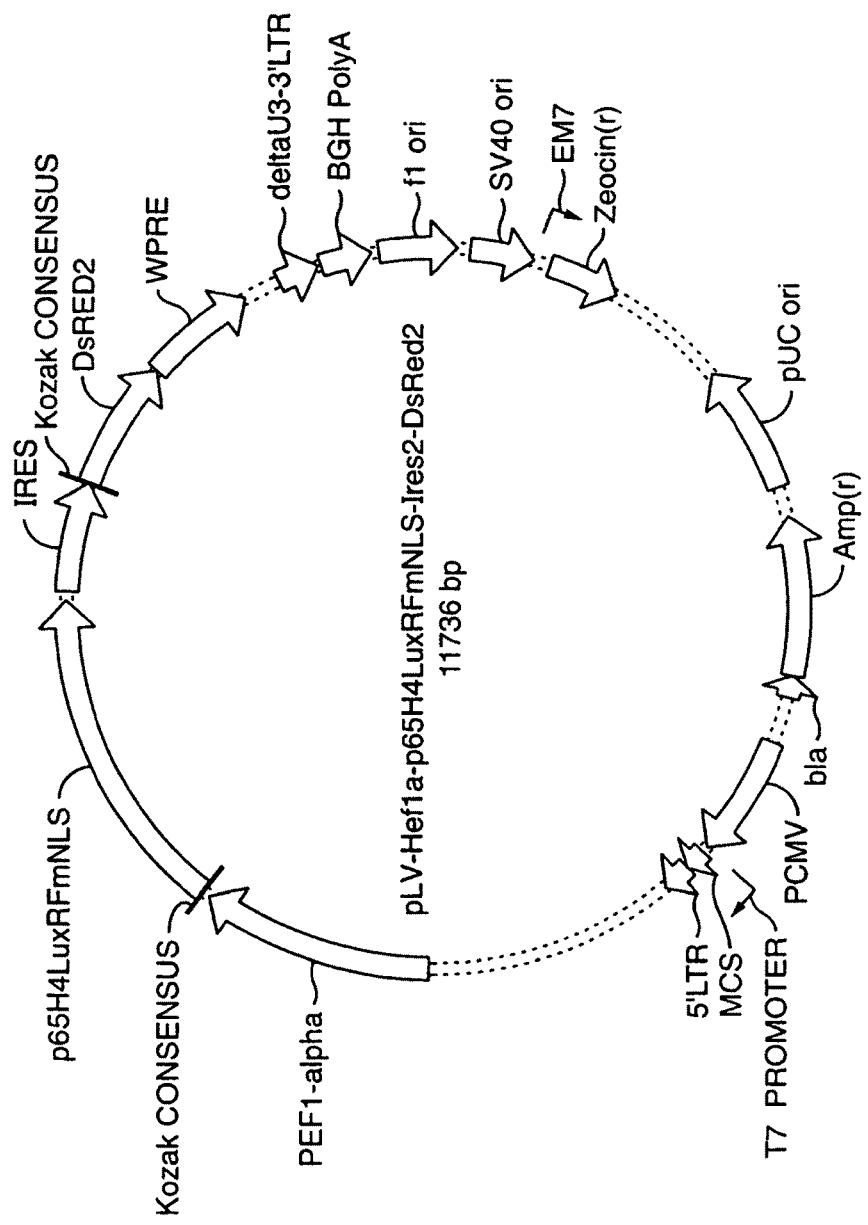
FIG. 8 provides a diagram of the vector of FIG. 7.
Figure 10:
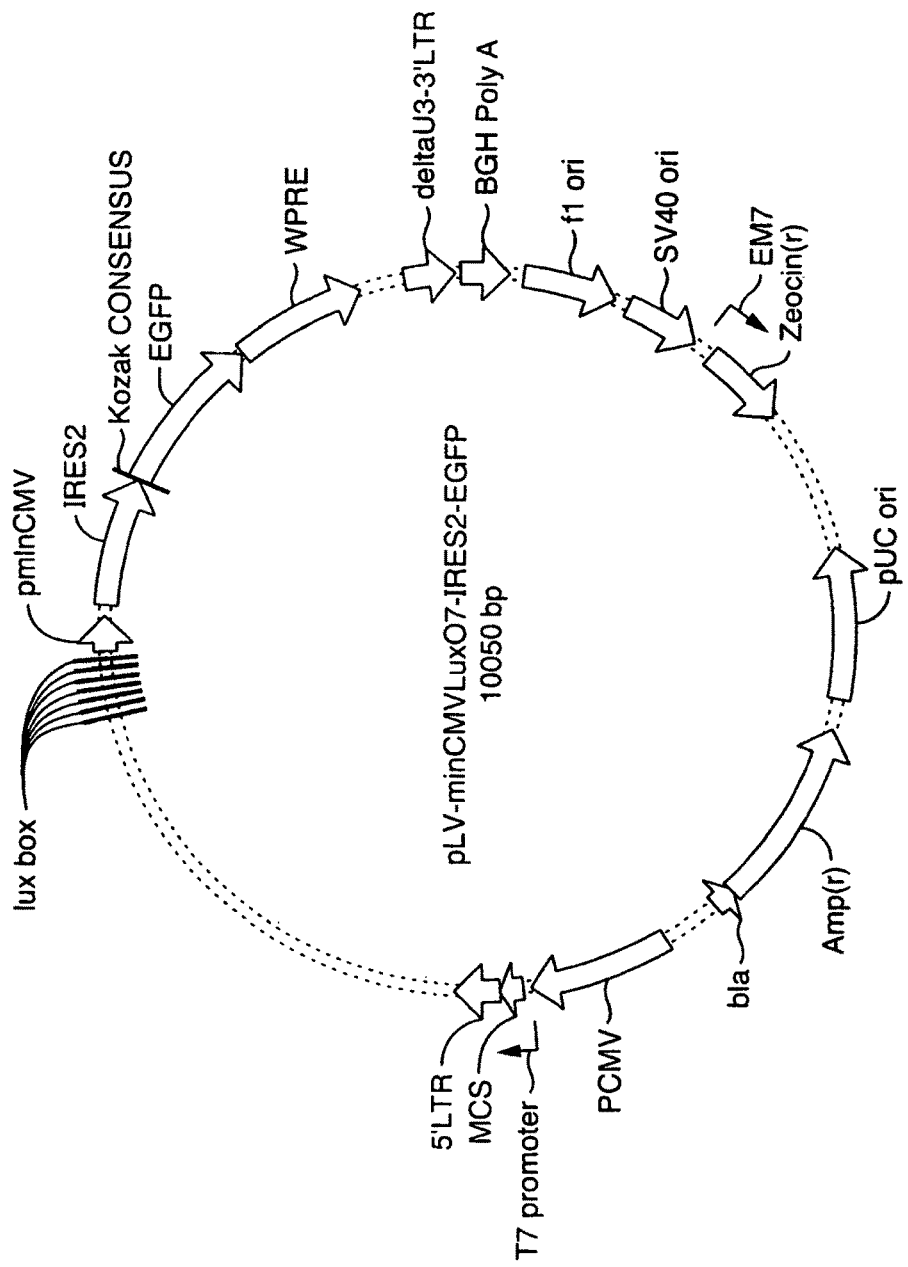
FIG. 10 provides a diagram of the vector of FIG. 9.
Figure 12:
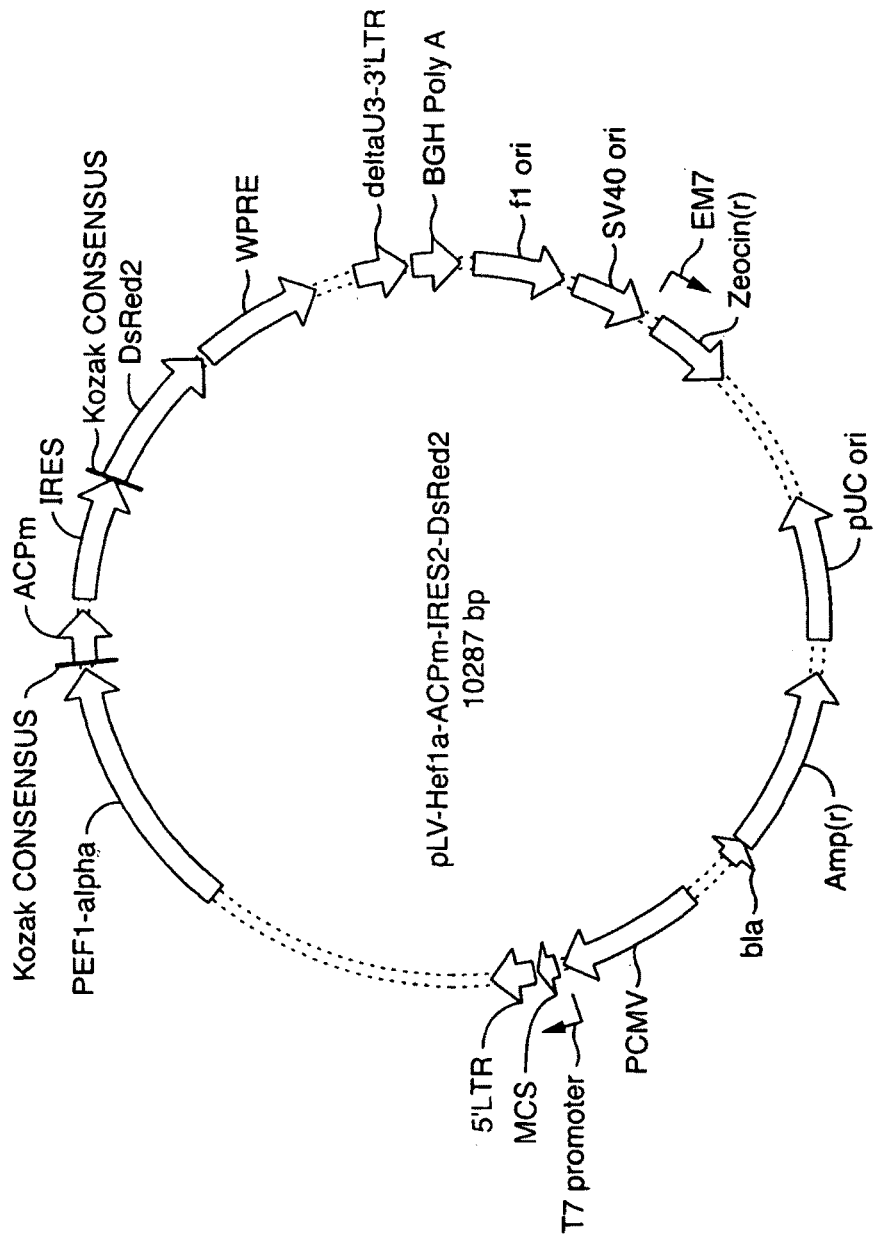
FIG. 12 provides a diagram of the vector of FIG. 11.
Figure 14:
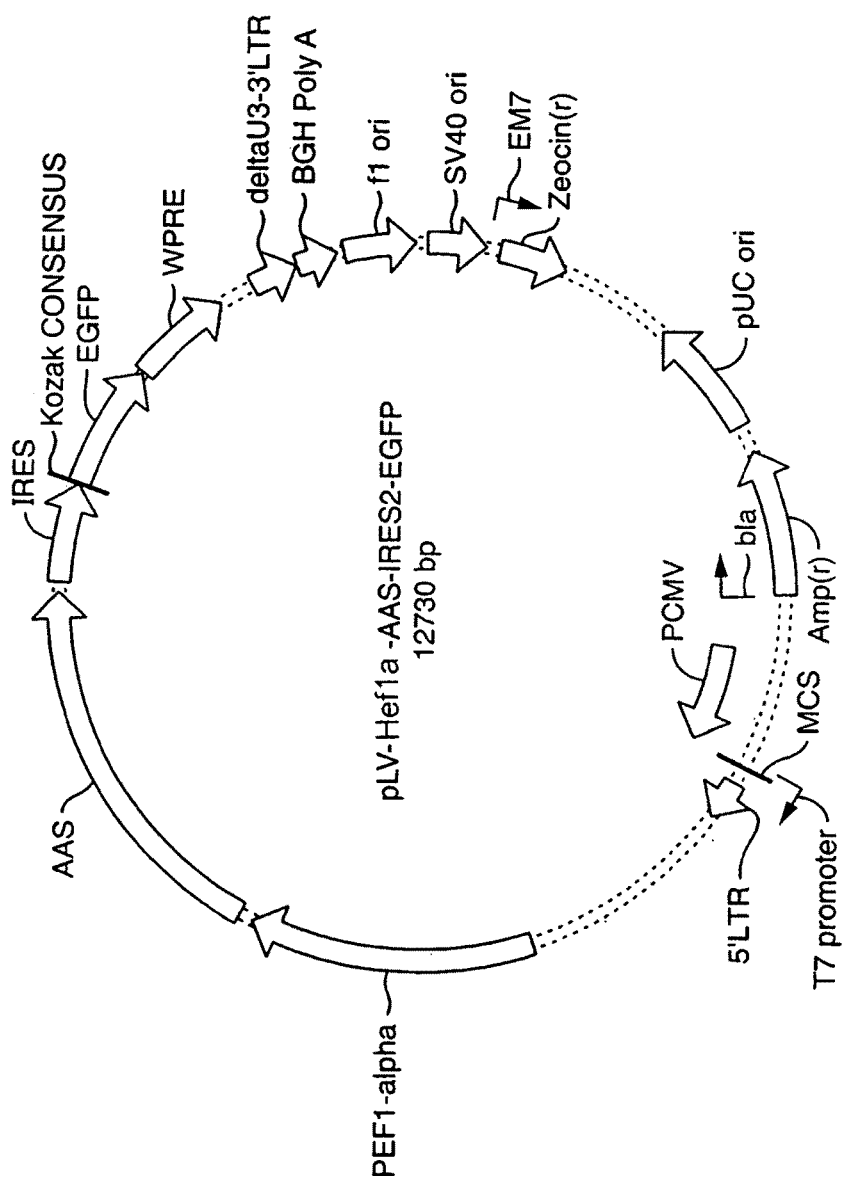
FIG. 14 provides a diagram of the vector of FIG. 13.
Figure 16:
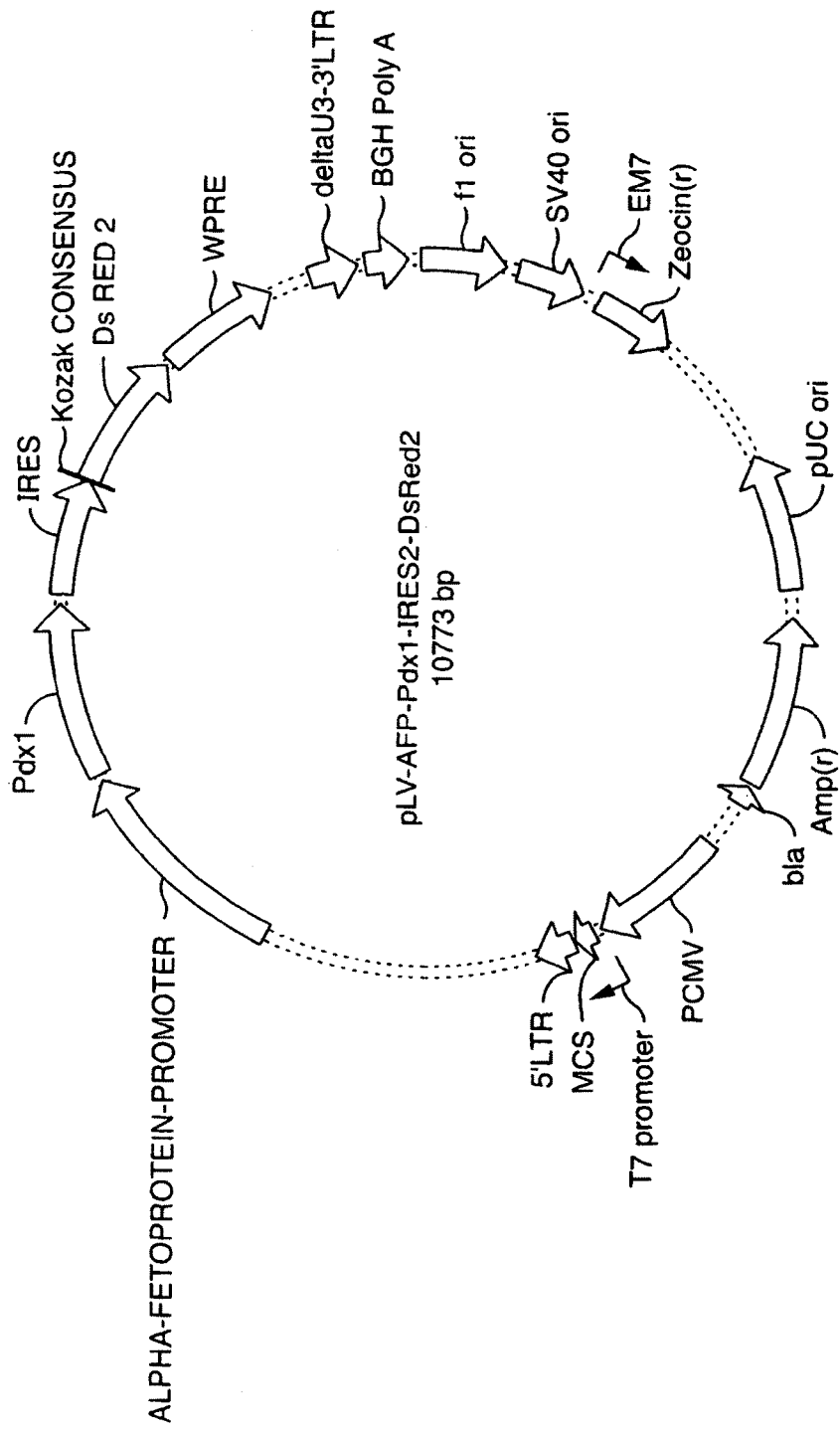
FIG. 16 provides a diagram of the vector of FIG. 15.
Figure 18:
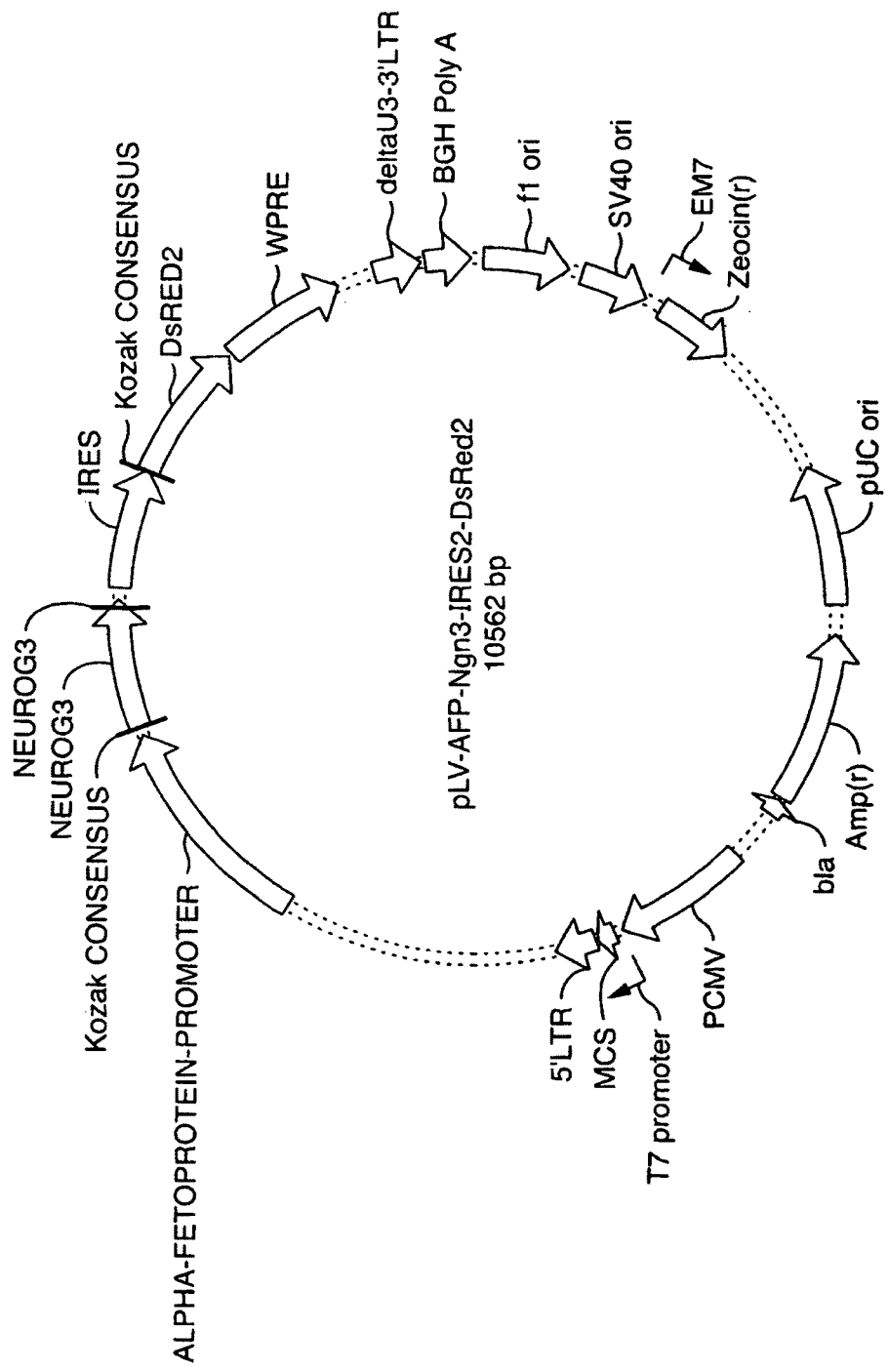
FIG. 18 provides a diagram of the vector of FIG. 17.
Figure 20:
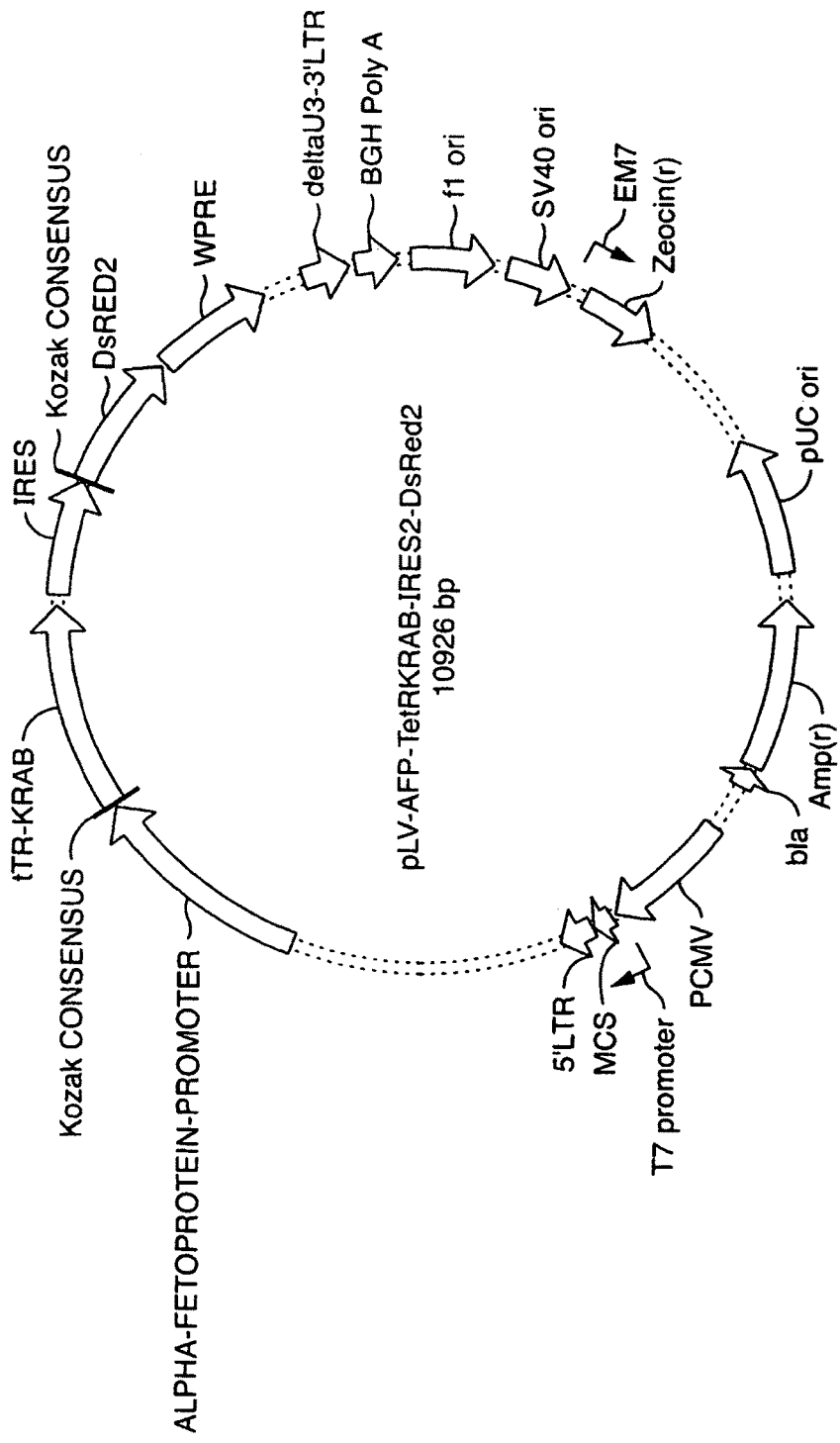
FIG. 20 provides a diagram of the vector of FIG. 19.
Figure 22:
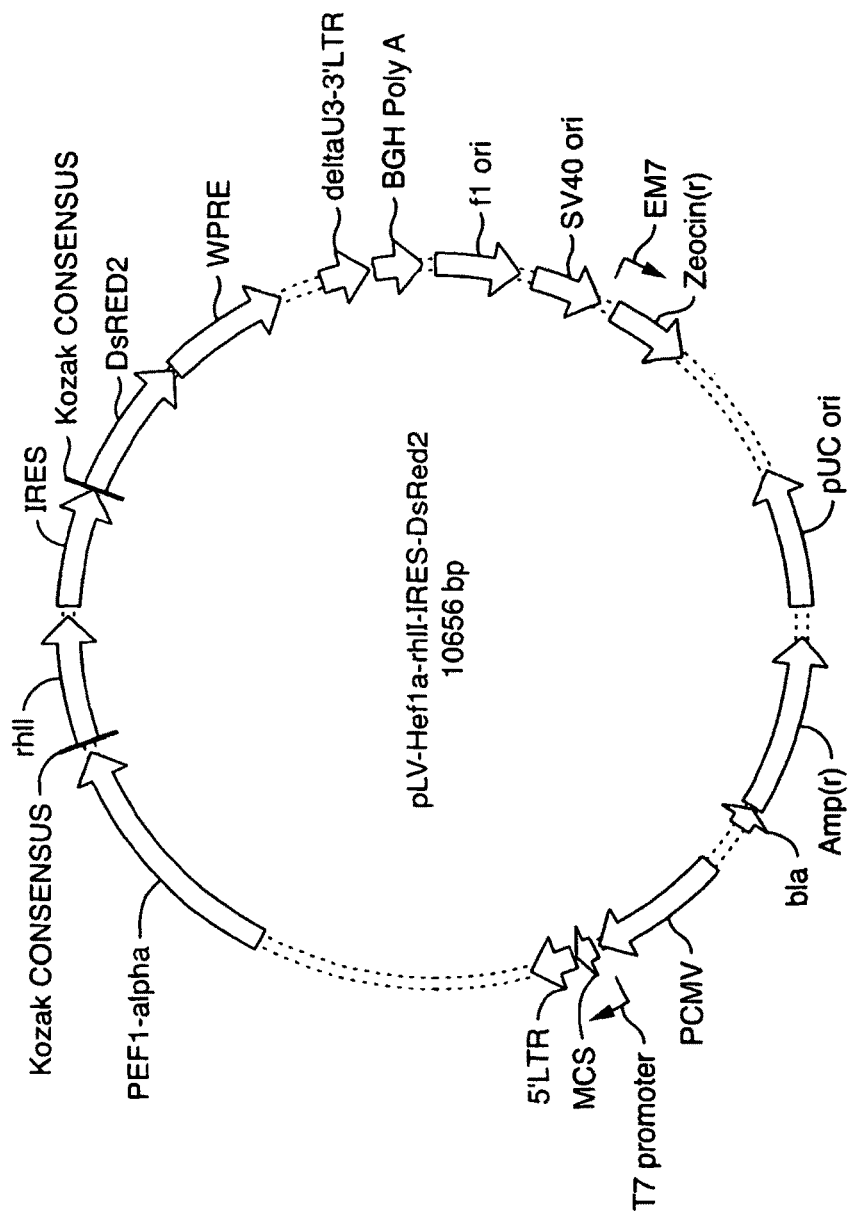
FIG. 22 provides a diagram of the vector of FIG. 21.
Figure 23A:
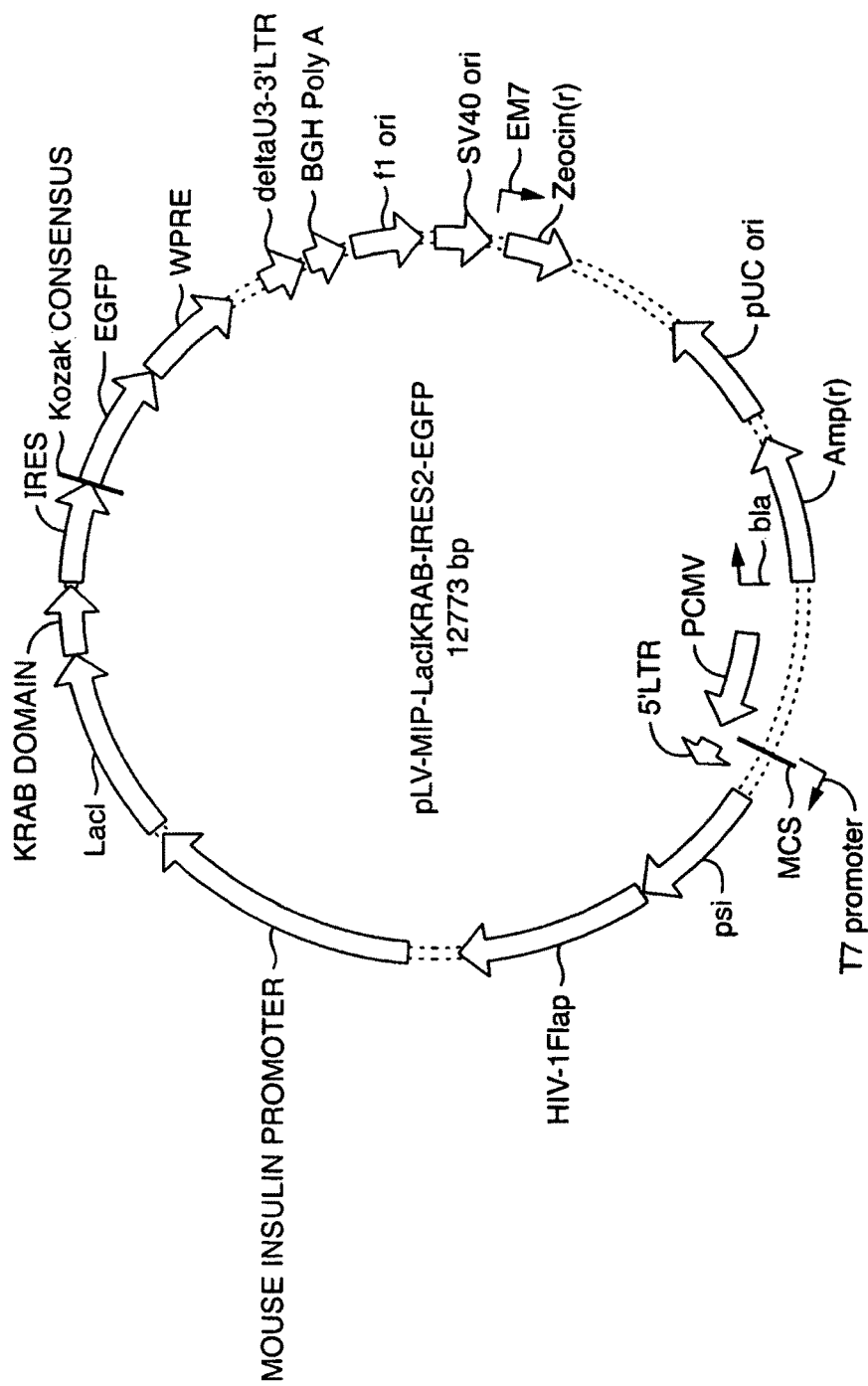
FIG. 23 provides a diagram and sequence (SEQ ID NO:10) for the vector pLV-MIP-LacIKRAB-IRES2-EGFP.
Figure 24A:
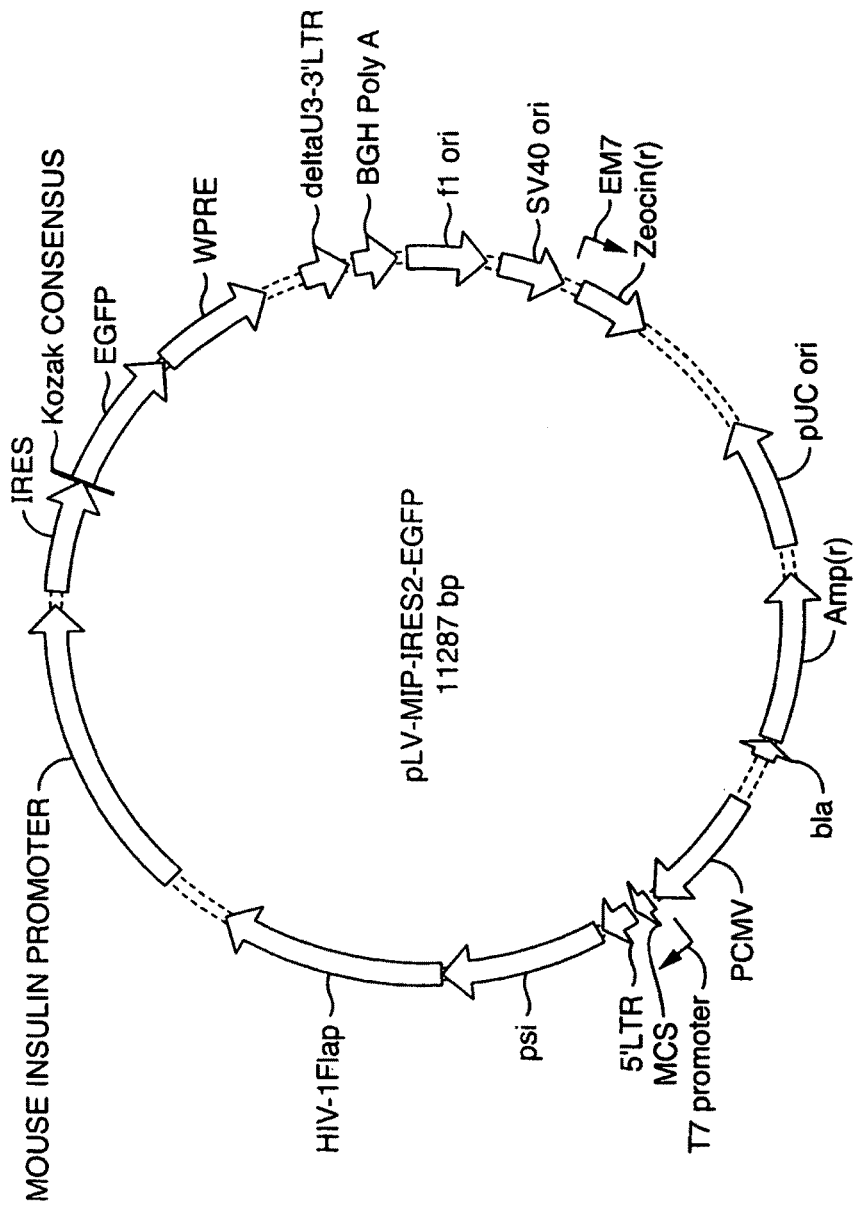
FIG. 24 provides a diagram and sequence (SEQ ID NO:11) for the vector pLV-MIP-IRES2-EGFP.
Figure 25A:
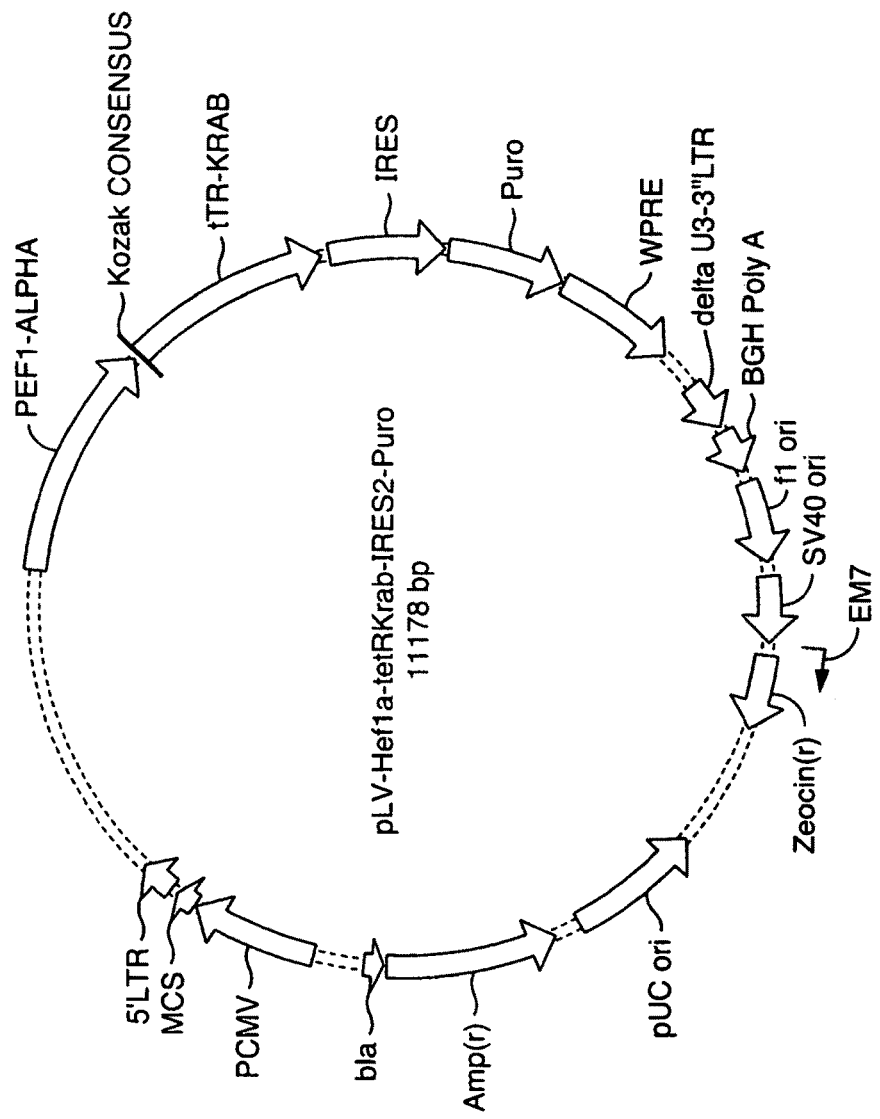
FIG. 25 provides a diagram and sequence for SEQ ID NO:12) for the vector pLV-TetRKRAB-IRES2-Puro.
Figure 28A:
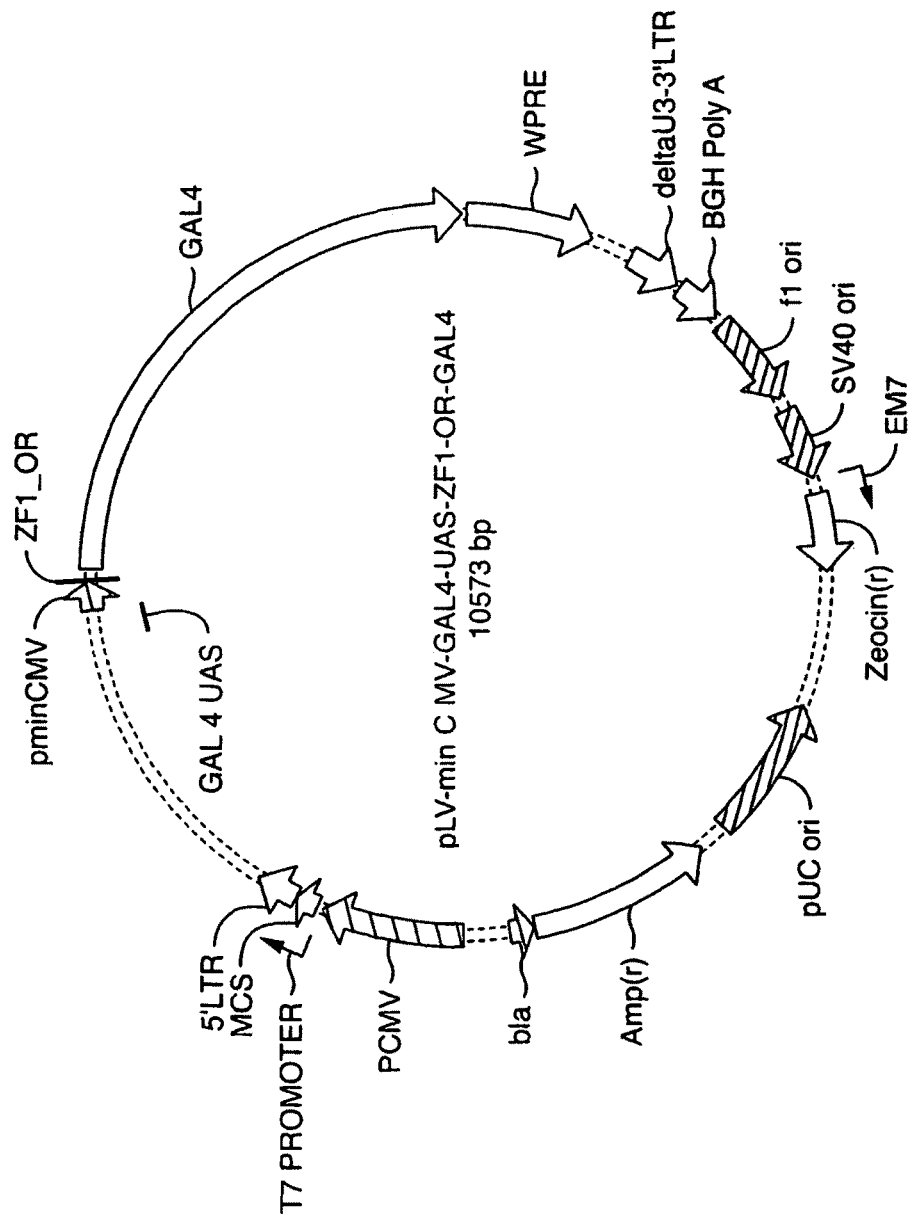
FIG. 28 provides a plasmid and sequence for P_A1_R1/A1 (SEQ ID NO: 13).
Figure 29A:
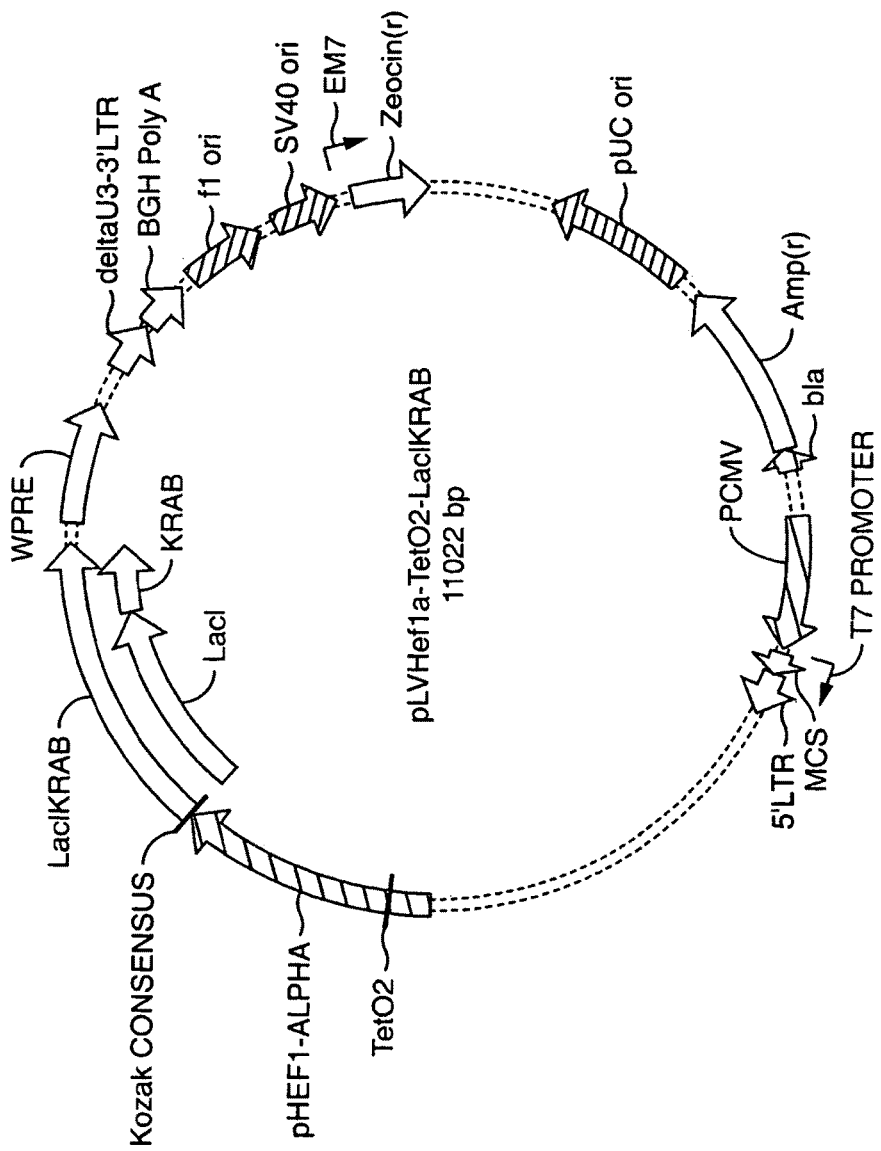
FIG. 29 provides a plasmid and sequence for p_tetO/LacI (SEQ ID NO: 14).
Figure 30A:
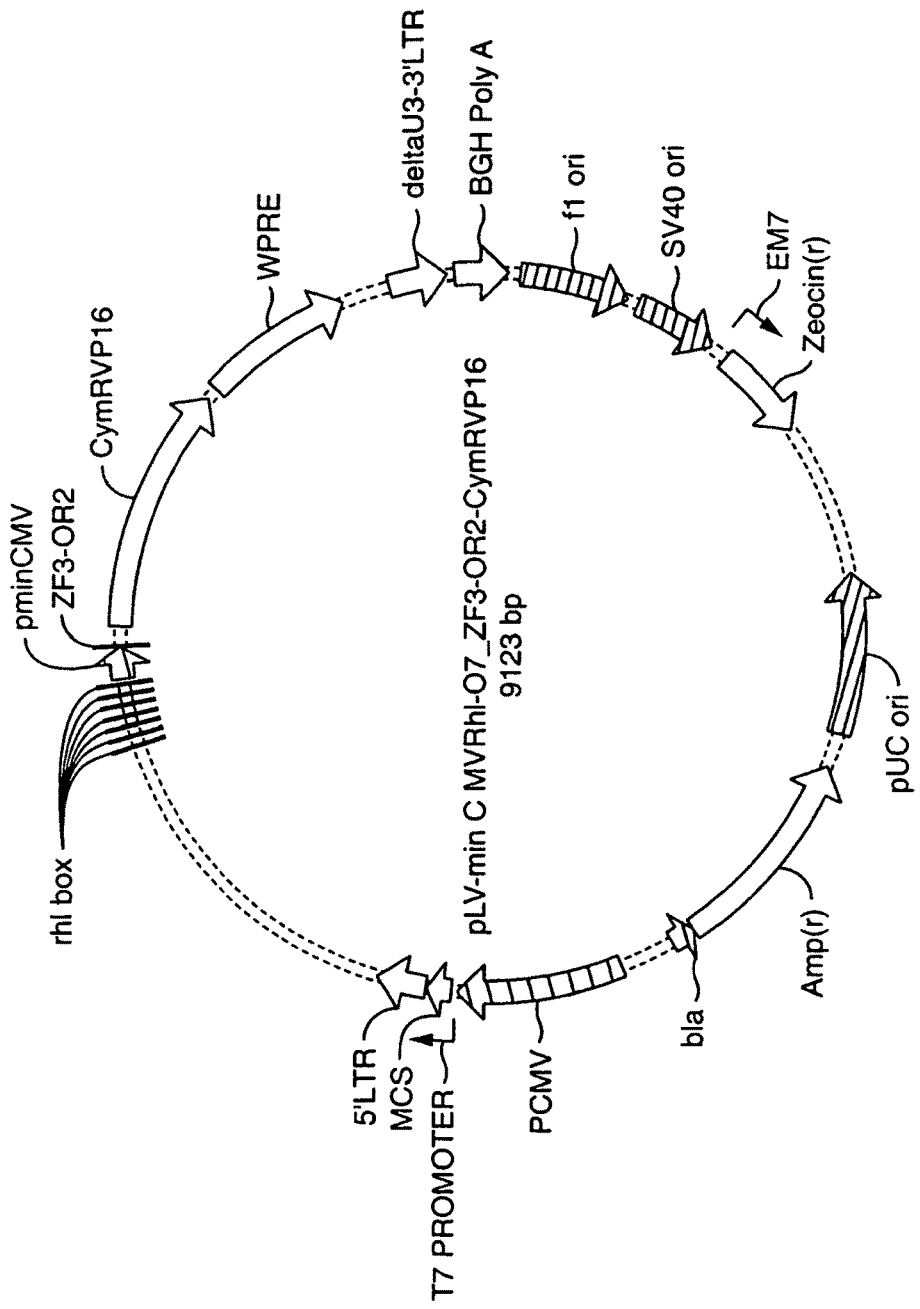
FIG. 30 provides a plasmid and sequence for p_RhlI_R3/A2 (SEQ ID NO: 15).
Figure 31A:
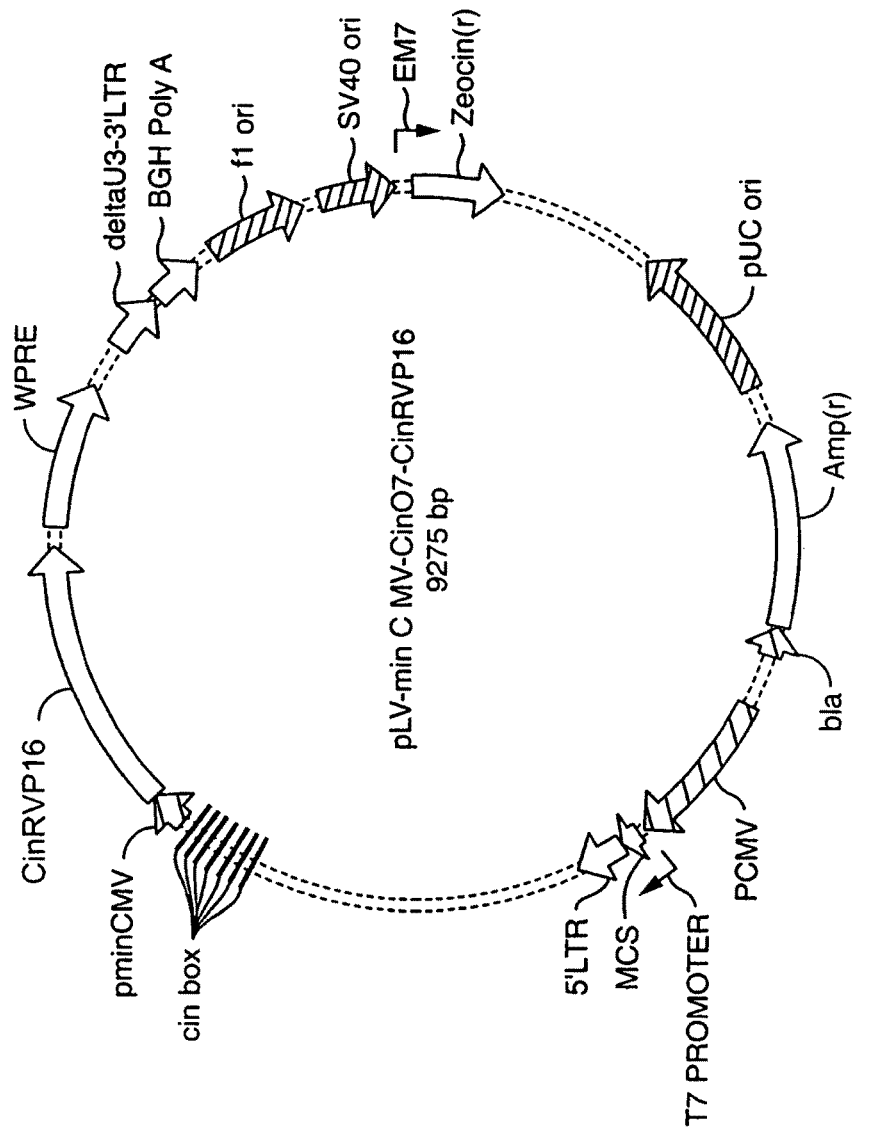
FIG. 31 provides a plasmid and sequence for P_Cin/CinR (SEQ ID NO: 16).
Figure 32A:
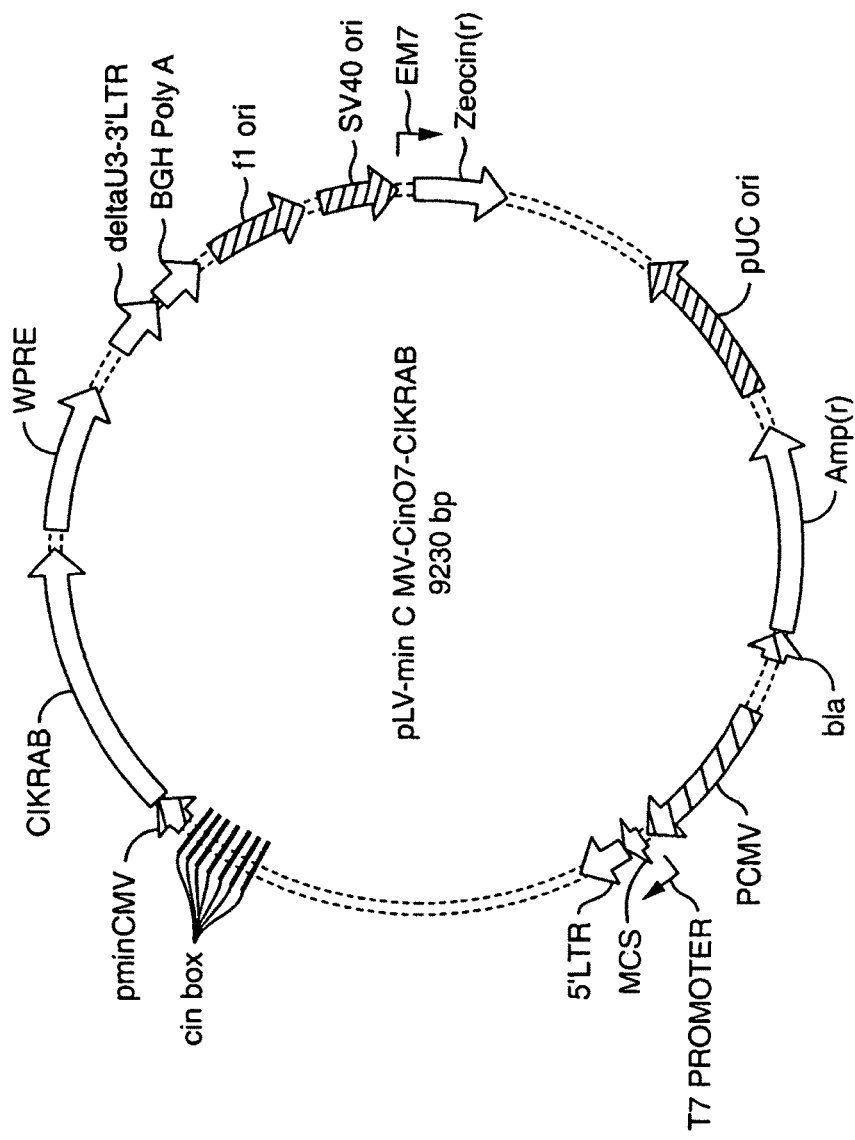
FIG. 32 provides a plasmid and sequence for P_Cin/CI (SEQ ID NO: 17).
Figure 33A:
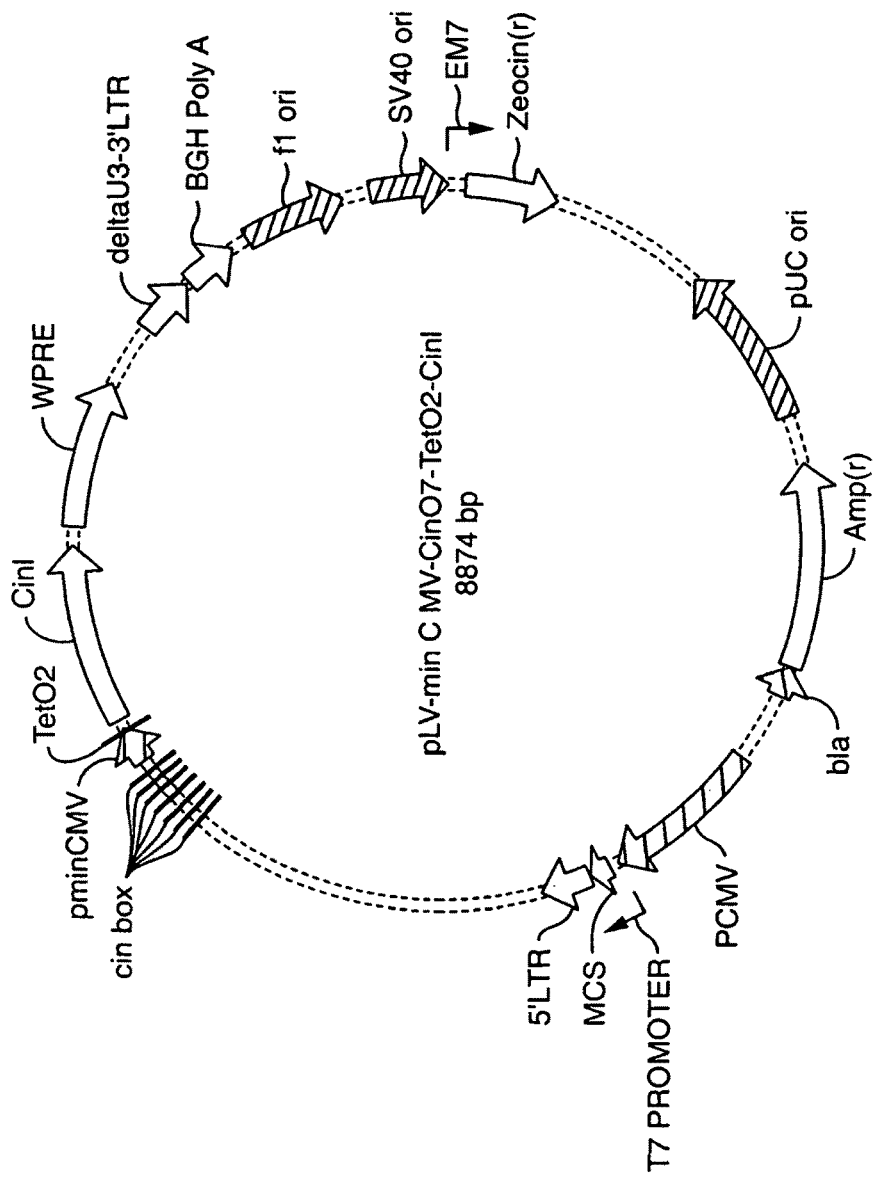
FIG. 33 provides a plasmid and sequence for P_Cin_tetO/CinI (SEQ ID NO: 18).
Figure 34A:
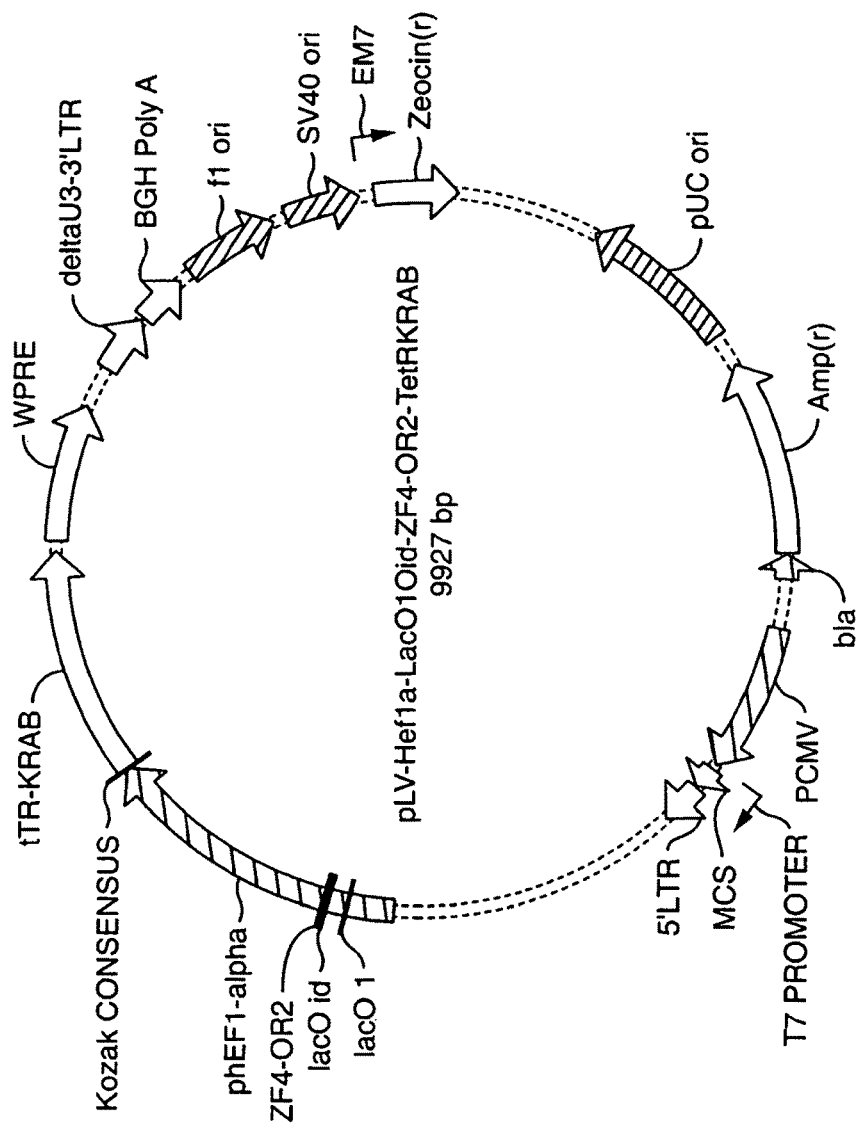
FIG. 34 provides a plasmid and sequence for P_lacO_R4/TetR (SEQ ID NO: 19).
Figure 35A:
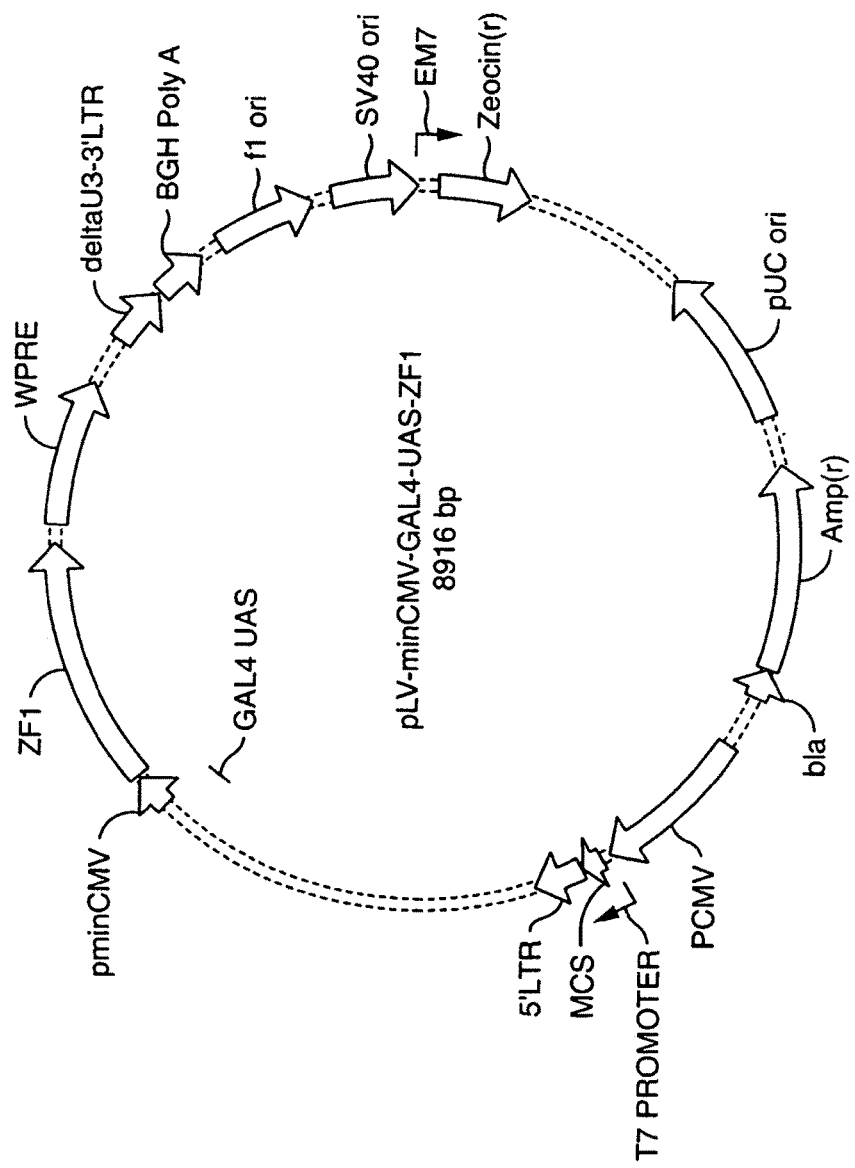
FIG. 35 provides a plasmid and sequence for P_A1/R1 (SEQ ID NO: 20).
Figure 36A:
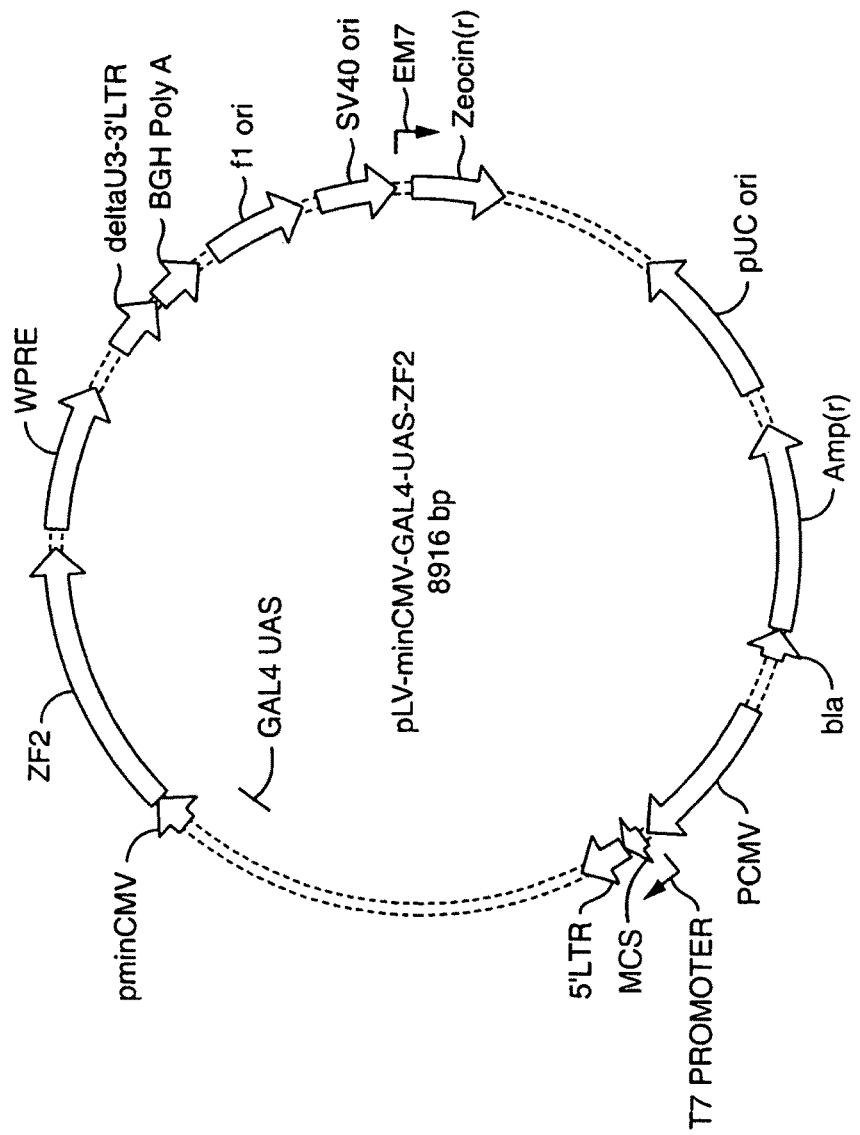
FIG. 36 provides a plasmid and sequence for P_A1/R2 (SEQ ID NO: 21).
Figure 37A:
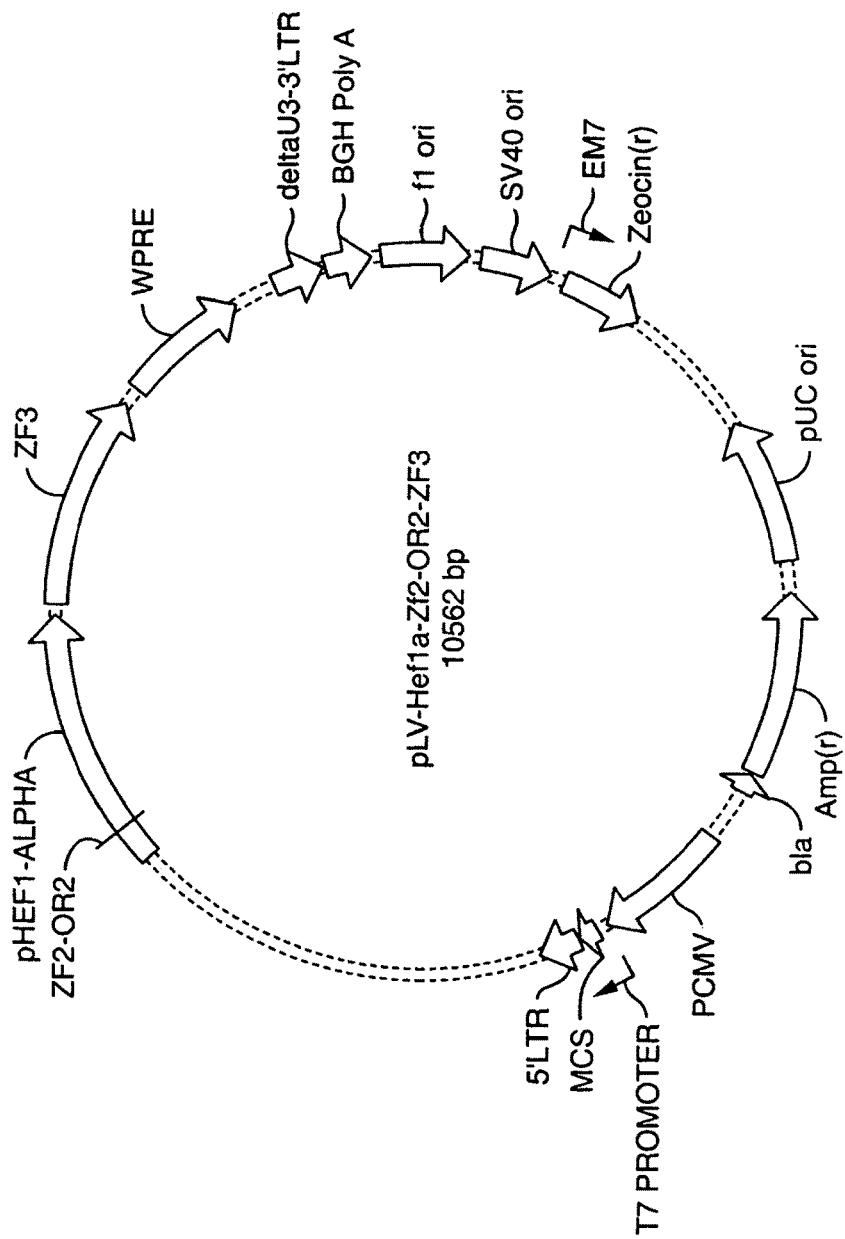
FIG. 37 provides a plasmid and sequence for P_R2/R3 (SEQ ID NO: 22).
Figure 38A:
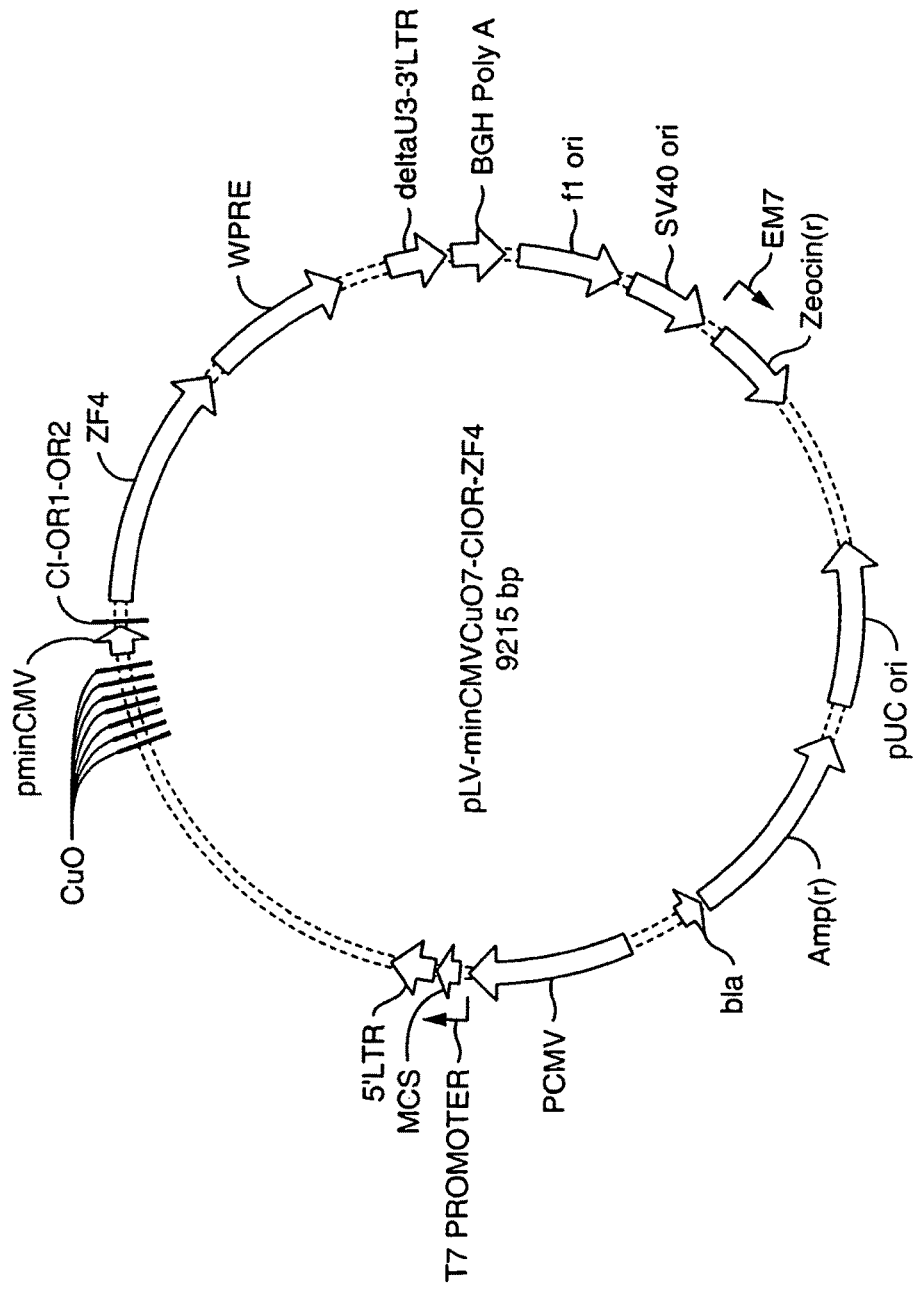
FIG. 38 provides a plasmid and sequence for P_A2/CIOR/R4 (SEQ ID NO: 23).

In some preferred embodiments, the quorum sensing system of the present invention comprises one or more of the vectors described in FIGS. 5-25, and SEQ ID Nos:01-12. FIGS. 5 and 6 provide a map and sequence (SEQ ID NO:01) for the LuxI vector—pLV-Hef1a-LuxIm-IRES2-DsRed2; FIGS. 7 and 8 provide a map and sequence (SEQ ID NO:02) for the LuxR vector—pLV-Hef1a-p65H4LuxRFm-IRES2-DsRed2; FIGS. 9 and 10 provide a map and sequence (SEQ ID NO:03) for the lux promoter vector for expression of Gata4/Sox17—pLV-minCMVLuxO7-IRES2-EGFP; FIGS. 11 and 12 provide a map and sequence (SEQ ID NO:04) for the ACP vector—pLV-Hef1a-ACPm-IRES2-DsRed2; FIGS. 13 and 14 provide a map and sequence (SEQ ID NO:05) for the AAS vector—pLV-Hef1a-AAS-IRES2-EGFP; FIGS. 15 and 16 provide a map and sequence (SEQ ID NO:06) for the AFP promoter vector PDX1—pLV-AFP-Pdx1-IRES2-DsRed2; FIGS. 17 and 18 provide a map and sequence (SEQ ID NO:07) for the AFP promoter vector Ngn3—pLV-AFP-Ngn3-IRES2-DsRed2; FIGS. 19 and 20 provide a map and sequence (SEQ ID NO:08) for the AFP promoter vector for TetRKRAB—pLV-AFP-TetRKRAB-IRES2-DsRed2; FIGS. 21 and 22 provide a map and sequence (SEQ ID NO:09) for the RhlI vector—pLV-Hef1a-RhlI-IRES2-DsRed2.

It will be recognized that forgoing vectors are plasmid vectors utilized for the production of lentiviral vectors that are used to transducer target cells such as embryonic stems cells or adult stem cells. The quorum sensing pathway components are derived from bacterial genes. In preferred embodiments, the bacterial genes are codon optimized for expression in mammalian cells. It will also be recognized that the sequences of the components of the vectors may be varied. Accordingly, the present invention encompasses the use of vector components, including the genes of interest such as LuxI, CinI, RhlI, LuxR, CinR, RhlR, and any of the cell fate regulators that are at least 50%, 70%, 80%, 90%, or 95% identical to the wild type gene of interest and maintain the function of the gene of interest. Likewise, the present invention encompasses the use of promoters that that are at least 50%, 70%, 80%, 90%, or 95% identical to the promoter sequences described herein such as the lux promoter, AFP promoter, etc. In some preferred embodiments, the genes encoding LuxR, CinR, or RhlR are modified to include a mammalian activation domain. In preferred embodiments, the mammalian activation domain is the P65 mammalian activation domain. In preferred embodiments, the LuxR-, CinR-, or RhlI-regulator proteins are therefore a fusion with a mammalian activation domain. Accordingly, in some embodiments, the present invention provides vectors and systems comprising vectors that comprise a gene encoding a regulator protein-mammalian activation domain fusion protein.

In further embodiments, the present invention provides promoters that are inducible by a regulatory protein-autoinducer complex. In some embodiments, the promoter comprises at least one, and preferably 2, 3, 4, 5, 6, 7, 8, 9, or 10 sequences that bind the regulatory protein-autoinducer complex. In some embodiments, the promoter further comprises a minimal element from a mammalian promoter. In some embodiments, the minimal element is derived from the cytomegalovirus promoter, an example of such a promoter is provided in FIGS. 9 and 10, SEQ ID NO:3.

Accordingly, in some preferred embodiments, the present invention provides vectors with the following components in operable association:

5'LTR-Promoter-Mammalian codon optimized LuxI-3'LTR

5'LTR-Promoter-Mammalian codon optimized LuxI-IRES—Reporter-3'LTR

5'LTR-Repressible promoter-Mammalian codon optimized LuxI-3'LTR

5'LTR-LacI promoter-Mammalian codon optimized LuxI-3'LTR

5'LTR-Promoter-Mammalian codon optimized RhlI-3'LTR

5'LTR-Promoter-Mammalian codon optimized RhlI-IRES—Reporter-3'LTR

5'LTR-Repressible promoter-Mammalian codon optimized RhlI-3'LTR

5'LTR-LacI promoter-Mammalian codon optimized RhlI-3'LTR

5'LTR-Promoter-Mammalian codon optimized CinI-3'LTR

5'LTR-Promoter-Mammalian codon optimized CinI-IRES—Reporter-3'LTR

5'LTR-Repressible promoter-Mammalian codon optimized CinI-3'LTR

5'LTR-LacI promoter-Mammalian codon optimized CinI-3'LTR

5'LTR-Promoter-Mammalian codon optimized LuxR-3'LTR

5'LTR-Promoter-Mammalian codon optimized LuxR-IRES—Reporter-3'LTR

5'LTR-Repressible promoter-Mammalian codon optimized LuxR-3'LTR

5'LTR-LacI promoter-Mammalian codon optimized LuxR-3'LTR

5'LTR-Promoter-Mammalian codon optimized RhlR-3'LTR

5'LTR-Promoter-Mammalian codon optimized RhlR-IRES—Reporter-3'LTR

5'LTR-Repressible promoter-Mammalian codon optimized RhlR-3'LTR

5'LTR-LacI promoter-Mammalian codon optimized RhlR-3'LTR

5'LTR-Promoter-Mammalian codon optimized CinR-3'LTR

5'LTR-Promoter-Mammalian codon optimized CinR-IRES—Reporter-3'LTR

5'LTR-Repressible promoter-Mammalian codon optimized CinR-3'LTR

5'LTR-LacI promoter-Mammalian codon optimized CinR-3'LTR

5'LTR-Promoter-Mammalian codon optimized LuxR P65 fusion-3'LTR

5'LTR-Promoter-Mammalian codon optimized LuxR P65 fusion-IRES—Reporter-3'LTR

5'LTR-Repressible promoter-Mammalian codon optimized LuxR P65 fusion-3'LTR

5'LTR-LacI promoter-Mammalian codon optimized LuxR P65 fusion-3'LTR

5'LTR-Promoter-Mammalian codon optimized RhlR P65 fusion-3'LTR

5'LTR-Promoter-Mammalian codon optimized RhlR P65 fusion-IRES—Reporter-3'LTR

5'LTR-Repressible promoter-Mammalian codon optimized RhlR P65 fusion-3'LTR

5'LTR-LacI promoter-Mammalian codon optimized RhlR P65 fusion-3'LTR

5'LTR-Promoter-Mammalian codon optimized CinR P65 fusion-3'LTR

5'LTR-Promoter-Mammalian codon optimized CinR P65 fusion-IRES—Reporter-3'LTR

5'LTR-Repressible promoter-Mammalian codon optimized CinR P65 fusion 3'LTR

5'LTR-LacI promoter-Mammalian codon optimized CinR P65 fusion-3'LTR

5'LTR-regulatory protein/autoinducer responsive promoter—cell fate regulator gene—3'LTR 5'LTR-regulatory protein/autoinducer responsive promoter—cell fate regulator gene—IRES—reporter gene—3'LTR 5'LTR-regulatory protein/autoinducer responsive promoter—cell fate regulator gene—IRES—selectable marker—3'LTR 5'LTR-lux promoter—cell fate regulator gene—3'LTR 5'LTR-regulatory protein/autoinducer responsive promoter—Gata4 gene—3'LTR 5'LTR-regulatory protein/autoinducer responsive promoter—Sox 17—3'LTR 5'LTR-promoter-mammalian codon optimized ACP-3'LTR 5'LTR-promoter-mammalian codon optimized AAS-3'LTR 5'LTR-stage specific promoter-cell fate regulator-3'LTR 5'LTR-AFP promoter-cell fate regulator-3'LTR 5'LTR-stage specific promoter-cell fate regulator-IRES-reporter-3'LTR 5'LTR-AFP promoter-cell fate regulator-IRES-reporter-3'LTR 5'LTR-stage specific promoter-cell fate regulator-IRES-selectable marker-3'LTR 5'LTR-AFP promoter-cell fate regulator-IRES-selectable marker-3'LTR 5'LTR-stage specific promoter-Pdx1 gene-3'LTR 5'LTR-AFP promoter-Pdx1 gene-3'LTR 5'LTR-stage specific promoter-Pdx1 gene-IRES-reporter-3'LTR 5'LTR-AFP promoter-Pdx1 gene-IRES-reporter-3'LTR 5'LTR-stage specific promoter-Pdx1 gene-IRES-selectable marker-3'LTR 5'LTR-AFP promoter-Pdx1 gene-IRES-selectable marker-3'LTR 5'LTR-stage specific promoter-Ngn3 gene-3'LTR 5'LTR-AFP promoter-Ngn3 gene-3'LTR 5'LTR-stage specific promoter-Ngn3 gene-IRES-reporter-3'LTR 5'LTR-AFP promoter-Ngn3 gene-IRES-reporter-3'LTR 5'LTR-stage specific promoter-Ngn3 gene-IRES-selectable marker-3'LTR 5'LTR-AFP promoter-Ngn3 gene-IRES-selectable marker-3'LTR 5'LTR-stage specific promoter-TetR-3'LTR 5'LTR-AFP promoter-TetRr-3'LTR 5'LTR-stage specific promoter-TetR-IRES-reporter-3'LTR 5'LTR-AFP promoter-TetR-IRES-reporter-3'LTR 5'LTR-stage specific promoter-TetR-IRES-selectable marker-3'LTR 5'LTR-AFP promoter-TetR-IRES-selectable marker-3'LTR 5'LTR-terminal differentiation promoter-repressor-3'LTR 5'LTR-MIP promoter-repressor-3'LTR 5'LTR-stage specific promoter-repressor-IRES-reporter-3'LTR 5'LTR-MIP promoter-repressor-IRES-reporter-3'LTR 5'LTR-stage specific promoter-repressor-RES-selectable marker-3'LTR 5'LTR-MIP promoter-repressor-IRES-selectable marker-3'LTR 5'LTR-terminal differentiation promoter-LacI-3'LTR 5'LTR-MIP promoter-LacI-3'LTR 5'LTR-stage specific promoter-LacI-IRES-reporter-3'LTR 5'LTR-MIP promoter-LacI-IRES-reporter-3'LTR 5'LTR-stage specific promoter-LacI-IRES-selectable marker-3'LTR 5'LTR-MIP promoter-LacI-IRES-selectable marker-3'LTR In the vectors described above, the 5' and 3' LTRs are preferably retroviral LTRs and most preferably lentiviral LTRs. The vectors can preferably comprise additional elements in additional to the listed elements.

G. Cells

The quorum sensing system of the present invention may be introduced into a variety of mammalian cell types. In preferred embodiments, the quorum sensing system is introduced into embryonic or adult stem cells. However, the quorum sensing systems may be introduced into any mammalian cell lines, including, but not limited to, 293 cells, to Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); and a human hepatoma line (Hep G2).

The present invention is not limited to the use of any particular type of embryonic stem cells. Indeed, the use of embryonic stem cells from a number of animal species is contemplated. Methods for obtaining totipotent or pluripotent cells from humans, monkeys, mice, rats, pigs, cattle and sheep have been previously described. See, e.g., U.S. Pat. Nos. 5,453,357; 5,523,226; 5,589,376; 5,340,740; and 5,166,065 (all of which are specifically incorporated herein by reference); as well as, Evans, et al., Theriogenology 33(1): 125-128, 1990; Evans, et al., Theriogenology 33(1):125-128, 1990; Notarianni, et al., J. Reprod. Fertil. 41(Suppl.):51-56, 1990; Giles, et al., Mol. Reprod. Dev. 36:130-138, 1993; Graves, et al., Mol. Reprod. Dev. 36:424-433, 1993; Sukoyan, et al., Mol. Reprod. Dev. 33:418-431, 1992; Sukoyan, et al., Mol. Reprod. Dev. 36:148-158, 1993; Iannaccone, et al., Dev. Biol. 163:288-292, 1994; Evans & Kaufman, Nature 292: 154-156, 1981; Martin, Proc Natl Acad Sci USA 78:7634-7638, 1981; Doetschman et al. Dev Biol 127:224-227, 1988); Giles et al. Mol Reprod Dev 36:130-138, 1993; Graves & Moreadith, Mol Reprod Dev 36:424-433, 1993 and Bradley, et al., Nature 309:255-256, 1984.

Primate embryonic stem cells may be preferably obtained by the methods disclosed in U.S. Pat. Nos. 5,843,780 and 6,200,806, each of which is incorporated herein by reference. Primate (including human) stem cells may also be obtained from commercial sources such as WiCell, Madison, Wis. A preferable medium for isolation of embryonic stem cells is "ES medium." ES medium consists of 80% Dulbecco's modified Eagle's medium (DMEM; no pyruvate, high glucose formulation, Gibco BRL), with 20% fetal bovine serum (FBS; Hyclone), 0.1 mM β-mercaptoethanol (Sigma), 1% non-essential amino acid stock (Gibco BRL). Preferably, fetal bovine serum batches are compared by testing clonal plating efficiency of a low passage mouse ES cell line ($ES_{jt3}$), a cell line developed just for the purpose of this test. FBS batches must be compared because it has been found that batches vary dramatically in their ability to support embryonic cell growth, but any other method of assaying the competence of FBS batches for support of embryonic cells will work as an alternative.

Primate ES cells are isolated on a confluent layer of murine embryonic fibroblast in the presence of ES cell medium. Embryonic fibroblasts are preferably obtained from 12 day old fetuses from outbred CF1 mice (SASCO), but other strains may be used as an alternative. Tissue culture dishes are preferably treated with 0.1% gelatin (type I; Sigma). Recovery of rhesus monkey embryos has been demonstrated, with recovery of an average 0.4 to 0.6 viable embryos per rhesus monkey per month, Seshagiri et al. Am J Primatol 29:81-91, 1993. Embryo collection from marmoset monkey is also well documented (Thomson et al. "Non-surgical uterine stage pre-implantation embryo collection from the common marmoset," J Med Primatol, 23:333-336 (1994)). Here, the zona pellucida is removed from blastocysts by brief exposure to pronase (Sigma). For immunosurgery, blastocysts are exposed to a 1:50 dilution of rabbit anti-marmoset spleen cell antiserum (for marmoset blastocysts) or a 1:50 dilution of rabbit anti-rhesus monkey (for rhesus monkey blastocysts) in DMEM for 30 minutes, then washed for 5 minutes three times in DMEM, then exposed to a 1:5 dilution of Guinea pig complement (Gibco) for 3 minutes.

After two further washes in DMEM, lysed trophectoderm cells are removed from the intact inner cell mass (ICM) by gentle pipetting, and the ICM plated on mouse inactivated (3000 rads gamma irradiation) embryonic fibroblasts. After 7-21 days, ICM-derived masses are removed from endoderm outgrowths with a micropipette with direct observation under a stereo microscope, exposed to 0.05% Trypsin-EDTA (Gibco) supplemented with 1% chicken serum for 3-5 minutes and gently dissociated by gentle pipetting through a flame polished micropipette.

Dissociated cells are replated on embryonic feeder layers in fresh ES medium, and observed for colony formation. Colonies demonstrating ES-like morphology are individually selected, and split again as described above. The ES-like morphology is defined as compact colonies having a high nucleus to cytoplasm ratio and prominent nucleoli. Resulting ES cells are then routinely split by brief trypsinization or exposure to Dulbecco's Phosphate Buffered Saline (without calcium or magnesium and with 2 mM EDTA) every 1-2 weeks as the cultures become dense. Early passage cells are also frozen and stored in liquid nitrogen.

The present invention is not limited to the use of any particular adult stem cell. The adult stem cell is an undifferentiated (unspecialized) cell that is found in a differentiated (specialized) tissue; it can renew itself and become specialized to yield specialized cell types of the tissue from which it originated. These precursor cells exist within the differentiated tissues of the adult of all multicellular organisms. Precursor cells derived from adults can be divided into three categories based on their potential for differentiation. These three categories of precursor cells are epiblast-like stem cells, germ layer lineage stem cells, and progenitor cells. Precursor cells have been isolated from a wide variety of tissues, including, but not limited to, skeletal muscle, dermis, fat, cardiac muscle, granulation tissue, periosteum, perichondrium, brain, meninges, nerve sheaths, ligaments, tendons, blood vessels, bone marrow, trachea, lungs, esophagus, stomach, liver, intestines, spleen, pancreas, kidney, urinary bladder, and testis. Precursor cells can be released from the connective tissue compartments throughout the body by mechanical disruption and/or enzymatic digestion and have been isolated from, but not limited to, newborns, adolescent, and geriatric mice, rats and humans, and adult rabbits, dogs, goats, sheep, and pigs.

The first category of precursor cells, epiblast-like stem cells (ELSCs), consists of a stem cell that will form cells from all three embryonic germ layer lineages. Stem cells from adult rats and stem cells from adult humans can be released from the connective tissue compartments throughout the body by mechanical disruption and/or enzymatic digestion. The stem cells from either adult rats or adult humans can be preferentially slow frozen and stored at −80° C. ±5° C. using 7.5% ultra-pure dimethyl sulfoxide. Fast thawing of stem cells from both species from the frozen state to ambient temperature yields recovery rates exceeding 98%. These cells in the undifferentiated state express the Oct-3/4 gene that is characteristic of embryonic stem cells. ELSCs do not spontaneously differentiate in a serum free environment lacking progression agents, proliferation agents, lineage-induction agents, and/or inhibitory factors, such as recombinant human leukemia inhibitory factor (LIF), recombinant murine leukemia inhibitory factor (ESGRO), or recombinant human anti-differentiation factor (ADF). Embryonic stem cells spontaneously differentiate under these conditions. In contrast, ELSCs derived from both species remain quiescent unless acted upon by specific proliferative and/or inductive agents and/or environment.

ELSCs proliferate to form multiple confluent layers of cells in vitro in the presence of proliferation agents such as platelet-derived growth factors and respond to lineage-induction agents. ELSCs respond to hepatocyte growth factor by forming cells belonging to the endodermal lineage. Cell lines have expressed phenotypic markers for many discrete cell types of ectodermal, mesodermal, and endodermal origin when exposed to general and specific induction agents.

The second category of precursor cells consists of three separate stem cells. Each of the cells forms cells of a specific embryonic germ layer lineage (ectodermal stem cells, mesodermal stem cells and endodermal stem cells). When exposed to general and specific inductive agents, germ layer lineage ectodermal stem cells can differentiated into, for example, neuronal progenitor cells, neurons, ganglia, oligodendrocytes, astrocytes, synaptic vesicles, radial glial cells, and keratinocytes.

The third category of precursor cells present in adult tissues is composed of a multitude of multipotent, tripotent, bipotent, and unipotent progenitor cells. In solid tissues these cells are located near their respective differentiated cell types. Progenitor cells do not typically display phenotypic expression markers for pluripotent ELSCs, such as stage specific embryonic antigen-4, stage-specific embryonic antigen-1 or stage-specific embryonic antigen-3, or carcinoembryonic antigen cell adhesion molecule-1. Similarly, progenitor cells do not typically display phenotypic expression markers for germ layer lineage stem cells, such as nestin for cells of the ectodermal lineage or fetoprotein for cells of the endodermal lineage.

A progenitor cell may be multipotent, having the ability to form multiple cell types. A precursor cell of ectodermal origin residing in the adenohypophysis and designated the adenohypophyseal progenitor cell is an example of a multipotent progenitor cell. This cell will form gonadotrophs, somatotrophs, thyrotrophs, corticotrophs, and mammotrophs. Progenitor cells for particular cell lineages have unique profiles of cell surface cluster of differentiation (CD) markers and unique profiles of phenotypic differentiation expression markers. Progenitor cells do not typically spontaneously differentiate in serum-free defined medium in the absence of a differentiation agent, such as LIF or ADF. Thus, unlike embryonic stem cells which spontaneously differentiate under these conditions, progenitor cells remain quiescent unless acted upon by proliferative agents (such as platelet-derived growth factor) and/or progressive agents (such as insulin, insulin-like growth factor-I or insulin-like growth factor-II).

Progenitor cells can regulate their behavior according to changing demands such that after transplantation they activate from quiescence to proliferate and generate both new satellite cells and substantial amounts of new differentiated cells. For example, the contractile units of muscle are myofibers, elongated syncytial cells each containing many hundreds of postmitotic myonuclei. Satellite cells are resident beneath the basal lamina of myofibers and function as myogenic precursors during muscle regeneration. In response to muscle injury, satellite cells are activated, proliferate, and differentiate, during which they fuse together to repair or replace damaged myofibers. When satellite cells are removed from their myofibers by a non-enzymatic physical titration method, they retain their ability to generate substantial quantities of new muscle after grafting that they are not able to attain by enzymatic digestion. Conventional enzymatic disaggregation techniques impair myogenic potential. Collins and Partridge "Self-Renewal of the Adult Skeletal Muscle Satellite Cell" Cell Cycle 4:10, 1338-1341 (2005).

Accordingly, the present invention also contemplates the use of non-embryonic stem cells, such as those described above. In some embodiments, mesenchymal stem cells (MSCs) can be derived from marrow, periosteum, dermis and other tissues of mesodermal origin (See, e.g., U.S. Pat. Nos. 5,591,625 and 5,486,359, each of which is incorporated herein by reference). MSCs are the formative pluripotential blast cells that differentiate into the specific types of connective tissues (i.e. the tissues of the body that support the specialized elements; particularly adipose, areolar, osseous, cartilaginous, elastic, marrow stroma, muscle, and fibrous connective tissues) depending upon various in vivo or in vitro environmental influences. Although these cells are normally present at very low frequencies in bone marrow, various methods have been described for isolating, purifying, and greatly replicating the marrow-derived mesenchymal stems cells in culture, i.e. in vitro (See also U.S. Pat. Nos. 5,197,985 and 5,226,914 and PCT Publication No. WO 92/22584, each of which are incorporated herein by reference).

Various methods have also been described for the isolation of hematopoietic stem cells (See, e.g., U.S. Pat. Nos. 5,061,620; 5,750,397; 5,716,827 all of which are incorporated herein by reference). It is contemplated that the methods of the present invention can be used to produce lymphoid, myeloid and erythroid cells from hematopoietic stem cells. The lymphoid lineage, comprising B-cells and T-cells, provides for the production of antibodies, regulation of the cellular immune system, detection of foreign agents in the blood, detection of cells foreign to the host, and the like. The myeloid lineage, which includes monocytes, granulocytes, megakaryocytes as well as other cells, monitors for the presence of foreign bodies in the blood stream, provides protection against neoplastic cells, scavenges foreign materials in the blood stream, produces platelets, and the like. The erythroid lineage provides the red blood cells, which act as oxygen carriers.

Accordingly, the present invention also contemplates the use of neural stem cells, which are generally isolated from developing fetuses. The isolation, culture, and use of neural stem cells are described in U.S. Pat. Nos. 5,654,183; 5,672,499; 5,750,376; 5,849,553; and 5,968,829, all of which are incorporated herein by reference. It is contemplated that the methods of the present invention can use neural stem cells to produce neurons, glia, melanocytes, cartilage and connective tissue of the head and neck, stroma of various secretory glands and cells in the outflow tract of the heart.

In some embodiments, the quorum sensing systems are incorporated into cord blood cells. Transplantation of umbilical-cord blood has been successfully performed to treat individuals with blood-diseases; donors, used have been newborn siblings being perfect HLA matches for the affects sibling. The advantages of cord blood as a source of hematopoietic stem cells for transplantation are clear. First, the proliferative capacity of hematopoietic stem cells in cord blood is superior to that of cells in marrow or blood from adults. Because they proliferate rapidly, the stem cells in a single unit of cord blood can reconstitute the entire hematopoietic system. Second, the use of cord blood reduces the risk of graft-versus-host disease, the main obstacle to the success of allogeneic transplantation of hematopoietic stem cells. Graft-versus-host disease is caused by a reaction of T cells in the graft to HLA antigens in the recipient; the immaturity of lymphocytes in cord blood dampens that reaction. A joint European study showed that recipients of cord blood from HLA-identical siblings had a lower risk of acute or chronic graft-versus-host disease than recipients of marrow from HLA-identical siblings. Children with acute leukemia who received HLA-mismatched cord blood from an unrelated donor also had a lower risk of graft-versus-host disease than recipients of HLA-mismatched marrow from an unrelated donor (Hematopoietic stem-cell transplants using umbilical-cord blood, *New England Journal of Medicine,* 2001, 344(24):1860-1861, editorial). Cord blood cells from siblings or children with matching HLA could be used to produce cell lines for use as contemplated by this invention.

H. Treatment Methods

In preferred embodiments, cells incorporating the vectors or systems of vectors described are introduced into a subject in need of treatment. In some embodiments, where the subject is diabetic, synthetic β cells comprising the quorum sensing system described above are introduced into the diabetic subject. In preferred embodiments, the synthetic β cells produce insulin. It will be recognized that the systems described above can be adapted to cause the differentiation of embryonic stem cells, adult stem cells and cord blood stem cells into a variety of cell types that can be utilized for therapeutic purposes, including neurons, chondrocytes, myocytes, and keratinocytes of various types.

In some embodiments, banks of cells comprising the quorum sensing systems described above are provided. In preferred embodiments, the banks of cells include cell lines that are programmed to attain a particular differentiated states, such as β cells. In some embodiments, the banks of cells comprise multiple cell lines expressing different combinations of HLA antigens. It is contemplated that such banks will result in an increased likelihood of obtaining a 6-6, 10-10 or greater match for a particular subject.

I. Identification of Additional Genes Involved in Beta Cell Differentiation

In some embodiments, the systems of the present invention are used to identify genes involved in pancreatic p cell differentiation using RNAi knockdown assays. In preferred embodiments, the assays utilize a large library of shRNAs comprising >100,000 hairpins which target ~21,000 human and ~17,000 mouse genes, 30,000 of which are cloned into a tet-inducible microRNA-embedded shRNA lentiviral vector.

Figure 4A:
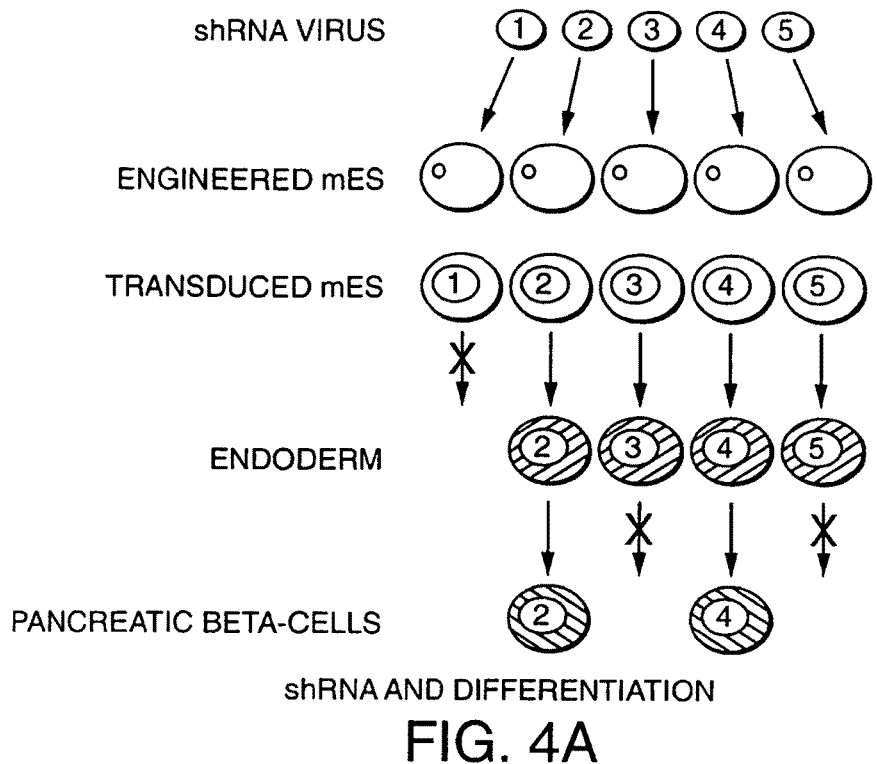
FIG. 4: (a) shRNA is transduced into engineered mES cells and cells are allowed to differentiate into pancreatic β cells. (b) Before differentiation, shRNAs will be uniformly present in mES cells. After differentiation there will be different pools of cell types (undifferentiated mES cells, endodermal cells or pancreatic β cells, e.g.) depending on the effect of the transduced shRNAs. The resulting shRNA ratios compared with the shRNA ratios before differentiation will allow identification of genes necessary for differentiation.
Figure 4B:
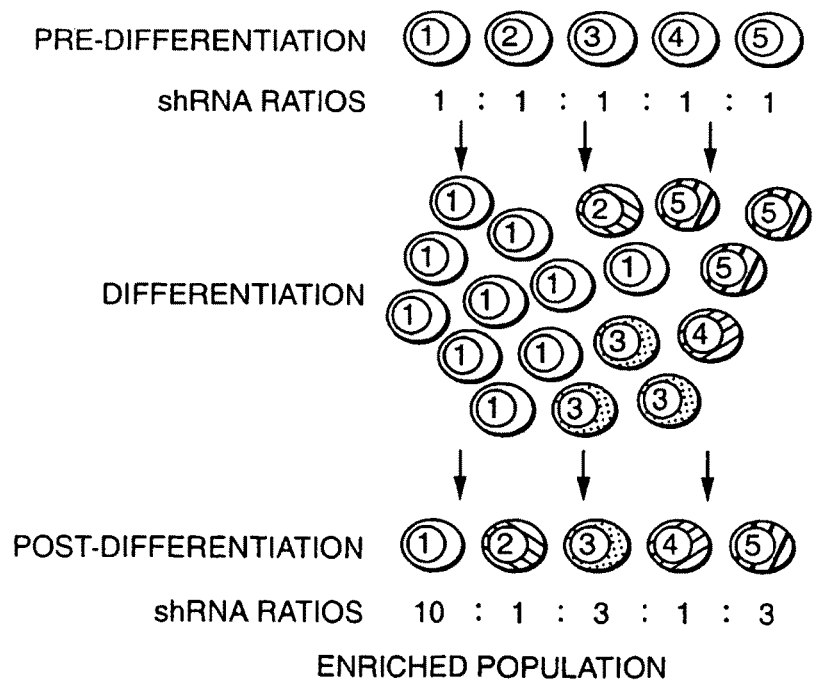

The RNAi knockdown assay is illustrated in FIG. 4. First, engineered ES cells are transduced with a lentiviral shRNA library at an MOI of 1, so that each post-transduction cell will have one shRNA. After quorum sensing and two-step differentiation occurs in the transduced cells, three unique pools of cells emerge in the population. The first consists of cells in which shRNA interferes with the differentiation of mES cells to endoderm, causing cells to retain stem cell character and proliferate rapidly. The second pool consists of cells in which shRNA interferes with the differentiation of endodermal cells to β cells, causing cells to retain endoderm character and proliferate more slowly than the stem cells. The last pool consists of cells in which shRNA does not interfere with the two-step differentiation process from mES cells, resulting in slowly- or non-dividing β cells. Two populations of cells, a sample of the initial population after transduction and a sample of the population directed to differentiate, will be subjected to microarray analysis. Comparisons of the relative ratios of individual shRNA will allow identification of genes that are involved at each step of the differentiation process.

EXAMPLES

Example 1

Figure 2A:
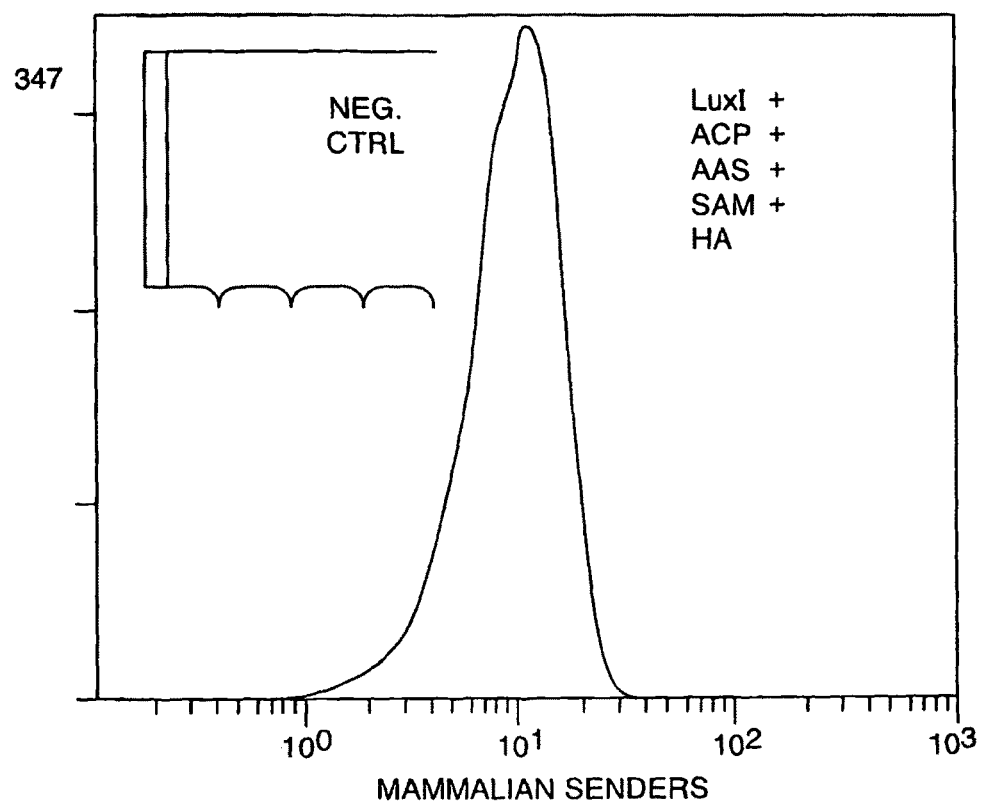
FIG. 2: (a) 30C6HSL synthesis by mammalian 293FT cells. Supernatant from the cells' growth media was collected and filter sterilized. Histograms show the fluorescence intensities of bacterial cells sensitive to 30C6HSL grown in the filtered supernatant, expressing green fluorescent protein due to 30C6HSL from the mammalian cells. (b) 30C6HSL detection by mammalian receiver cells. 293FT Cells express DsRed constitutively, but express EGFP only upon induction with exogenous 30C6HSL. (c) Controlled stem cell differentiation with genetically inducible systems. Three different lentiviral genetic constructs were built, enabling exogenous chemical induction into myoblasts, adipocytes, or maintenance of stem cell properties. Dox-induced mES cells expressing MyoD causes visible changes to a myoblast morphology. In addition, the marker protein for myoblasts, dystrophin, was expressed from these cells (data not shown). PPARγ expression resulted in an adipocyte morphology. In a separate experiment, induced expression of Nanog supplanted the need for a growth factor usually required to maintain the overall character of mES cells.
Figure 2B:
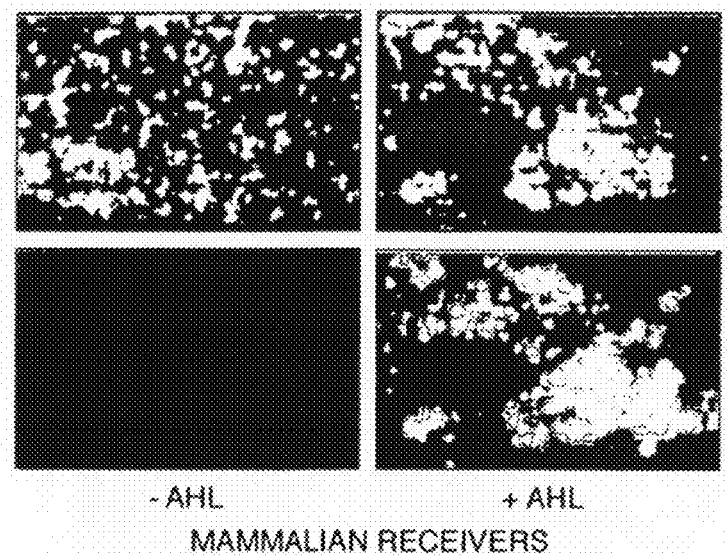
Figure 2C:
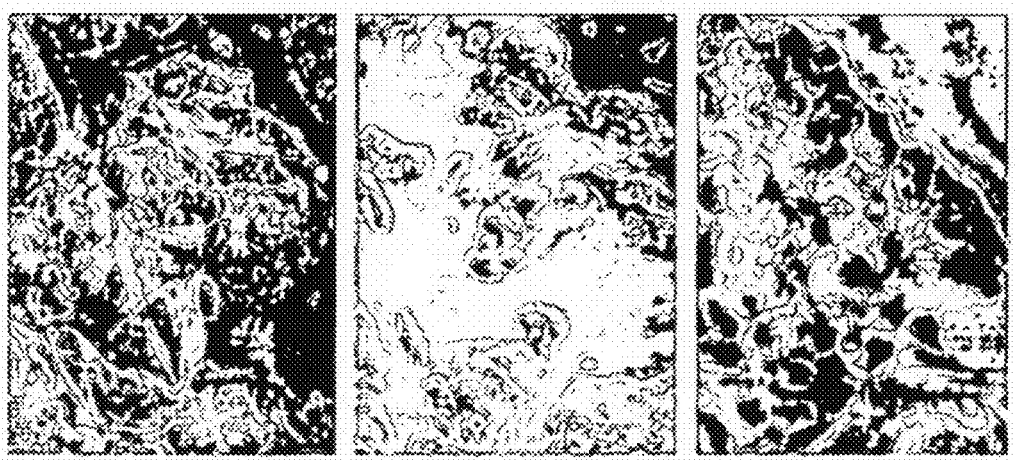

293FT cells that were genetically engineered to synthesize 3OC6HSL were grown in liquid media, and this media was found to contain 3OC6HSL (FIG. 2a). The 3OC6HSL detection pathway consists of a signal transducer that binds 3OC6HSL and activates transcription of genes controlled by a synthetic lux promoter. The 3OC6HSL signal transducer is a chimeric LuxR-activator protein created by the fusion of a P65 mammalian activation domain to a codon optimized mammalian version of a bacterial LuxR. Initial testing of the mammalian version of LuxR in 293FT cells shows a strong response to the addition of 3OC6HSL (FIG. 2b).

Example 2

Synthetic Gene Networks in Mammalian Cells—the rtTA Switch

A reverse Tetracycline-controlled transactivator (rtTA) switch, where gene expression is upregulated by the addition of Doxycycline (Dox), has been implemented. rtTA is constitutively expressed in the Ainv15 mES cell line and activates transcription of a give cell fate regulator (CFR) and a EGFP as control from the TRE promoter in the presence of Dox. A dosage response curve (not shown) demonstrates that the expression level (as measured by flourescence depending of the Dox concentration.

Controlled Induction of Cell Fate Regulators in mES.

Ngn1, MyoD and Nanog Ainv15 mES stem cells constitutively expressing the Dox-inducible circuit can be infected with a virus encoding Ngn1/EGFP or MyoD/EGFP under the control of a TRE promoter. The cell maintains self-renewal in the absence of Dox, while the presence of Dox results in the differentiation into either cells with a neuronal morphology (Ngn1), muscle cell morphology (MyoD).

Matrigel-Embedded mES—MyoD Expression.

To verify the conditions required for mES cell growth and differentiation in semi-solid media, embedded mES cells were infected with the Dox inducible circuit encoding MyoD/EGFP in Matrigel and subsequently induced with 1 mg/ml Dox over several days. Cells not induced with Dox grow, do not express EGFP and maintained stem cell morphology in a Matrigel matrix. The addition of Dox results in EGFP expression and formation of multinucleated syncitia 60 hours post induction, which is one key development step in formation of muscle fibers.

Example 3

293FT and CHO cells were infected with virus encoding pLV-pTat-IRES2-EGFP, and then exposed three different types of TAT communication molecules with various secretion tags. The 293FT cells are able to internalize the TAT protein, while CHO cells cannot. In the experiment, sender cells were grown for 2 days, and then receiver 293FT cells were grown in the supernatant. As expected, the supernatant from 293FT cells that can internalize the TAT molecule did not yield much communication, while supernatant from the CHO cells was able to active GFP expression significantly in the receiver cells.

Example 4

This example describes the assessment of the transactivatory properties of TAT and the functionality of the signaling modules by having sender and receiver modules in the same cell. Sender cells expressing TAT containing a secretion signal and receiver cells containing the detection module separated by a permeable barrier (e.g. transwell inserts), are used to validate and optimize the cell-cell transducing capabilities of TAT. A hemagglutinin tag (HA-tag) is added as a translational fusion to the C-terminus of TAT, to confirm its expression by means of immunofluorescence (IF) and western blotting (WB).

Engineering TAT Internal Signaling:

By having receiver and mock TAT sender (no secretion signal for export) in the same cell, the transactivatory properties of TAT as well as the detector functionality is validated. As described above, the rtTA switch, where gene expression is upregulated by the addition of Dox, is operational. Full-length HIV-1 TAT with a C-terminal HA-tag is placed under the control of the TRE promoter, enabling induction of TAT expression by adding Dox to the cell culture media. The receiver contains the wild-type HIV-1 pTAT promoter with the TAR element driving expression of EGFP upon TAT binding. To test, the TAT transactivation capabilities, Dox is added to cells, whereupon TAT expression is induced. TAT binds to pTAT and induces the expression of EGFP, which is detected by FACS and/or fluorescence microscopy (FIG. 26).

Engineering TAT Senders:

By co-infecting the rtTA switch and the TAT gene with an N-terminal secretion tag and an C-terminal HA-tag under control of the pTRE promoter into cells, Dox-inducible secretion of TAT is achieved (FIG. 26b). To get a high level of secretion to the extracellular milieu, the N-terminal export signal sequence present in IL-2 to the N-terminus of TAT is added. To verify protein expression and export, cell lysates and cell supernatants is checked by a WB against the HA tag. Low levels of TAT in the supernatant can be concentrated by precipitation of the protein fraction with triacetic acid.

Engineering TAT Receivers:

By infecting the module containing the pTAT promoter controlling the expression of EGFP, TAT-inducible expression is of EGFP achieved (FIG. 26b). Using the TAT senders secreting the protein into the supernatant described in the previous paragraph, EGFP expression in receivers is detectable by fluorescence microscopy or FACS. The uptake of TAT by receiver cells will also be confirmed by IF staining against the HA-tag. Using transwell inserts as a permeable barrier to keep sender and receiver cells separate, cell-cell communication of the secreted TAT can be assessed by measuring the EGFP protein expression levels in the receiver cells (FACS/fluorescence microscopy).

The presence of TAT in the sender cell, in the supernatant, in the cytoplasm or nucleus of the receiver cell will be confirmed by IF and WB against the HA-tag in TAT. Recently, reports have suggested the release from macropinosomes is the limiting factor in the transduction of cells by using a HIS-tag purified TAT-peptide/Cre fusion protein. The addition of an N-terminal 20 amino acids of the influenza virus hemagglutinin protein HA2—which is a fusogenic peptide that destabilizes lipid membranes at low pH in mature endosomes—to the C-terminus of the TAT-peptide, markedly increased its release from the macropinosomes, and subsequently the effectiveness of transduction. As a consequence, the addition of this fusogenic peptide might also increase the effectiveness of cell-cell transduction.

If TAT receiver sensitivity is too low, a TAT-Cre fusion protein with a secretion signal in the sender cells will be made and used to transduce a reporter module into receiver cells where the expression of EGFP from a constitutive promoter is blocked by a terminator with two loxP sites. In principle, the translocation of one TAT-Cre molecule into the nucleus of a receiver cell should be sufficient to trigger the Cre mediated recombination/removal of the terminator, hence full expression of EGFP. Such a TAT-Cre fusion expressing module could also be very useful in tracing the dispersion of TAT in vivo, by using a reporter mouse cell line expressing EGFP upon recombination of a terminator located in its promoter.

Example 5

This example describes the assessment of the effectiveness of in silico designed ZFP-DTS pairs and the functionality of the signaling modules by having sender and receiver modules in the same cell. In a second step, sender cells expressing TAT-ZFP fusions and receiver cells containing the detection module separated by a barrier (e.g. transwell inserts) are used to check and optimize the cell-cell transducing capabilities of TAT-ZFP fusion proteins with their cognate DTS.

Published in silico designed ZFP-DTS pairs, as for example Jazz, EPOZFP-862c and ZFP-809 binding to the DTSs "GCTGCTGCG", "GCGGTGGCT", "G(G/c)GGG(T/a)G(A/g)C" (5-fold, 15-fold and 46-130 fold induction of reporter genes respectively) (37-39) will be used first to demonstrate the functionality of my reporter system. Subsequently, novel in silico ZFP-DTS pairs are designed.

Engineering ZFP-DTS Pairs (in Silico):

Described ZF—nucleotide triplet interactions will be used to assemble novel ZFP-DTS pairs in silico by using existing knowledge on how to engineer translational fusions of such single zinc finger to a ZFP, which is also integrated into the online ZFP design toolset "ZF Tools" developed by the Barbas group (Mandell, J. G. & Barbas, C. F., 3rd (2006) Nucleic acids research 34, W516-523; Mandell, J. G. (2006) (on the world wide web at scripps.edu/mb/barbas/zfdesign/zfdesignhome.php), p. Zinc Finger Tools Version 3.0). Care will be taken to design ZFP-DTS pairs for which the DTS has no significant homologies in the human or mouse genome (nucleotide blast against the genome sequence), to reduce the probability of ZFP binding to endogenous sequences.

Engineering the Internal ZFP-DTS Signaling:

By having receiver and mock sender (no secretion signal for export) in the same cell, the transactivatory properties of the ZFP-DTS pairs as well as the detector functionality will be validated. As described above, the reverse Tetracycline-controlled transactivator (rtTA) switch, where gene expression is upregulated by the addition of Dox is operational. For the mock secretion module, a TAT-ZFP-VP64 fusion (VP64 as a strong enhancer) will be placed under the control of the TRE promoter, enabling induction of TAT-ZFP-VP64 expression by adding Dox to the cell culture media. The receiver module contains a minimal CMV promoter with the cognate DTS for the ZFP driving the expression of EGFP upon TAT-ZFP-VP64 binding. To test the transactivation capabilities, Dox is added to cells containing the artificial network, whereupon TAT-ZFP-VP64 is expressed, exported to the extracellular milieu by the virtue of its N-terminal IL-2 signal peptide, re-enter the cell with the help of the transducing TAT domain and localize to the nucleus where binds to its cognate DTS. The binding of fusion protein to the minimal CMV promoter will induce expression of EGFP (detectable by FACS and/or fluorescence microscopy) (FIG. 27a).

Engineering ZFP Senders:

By co-infecting the rtTA switch and the

TAT-ZFP-VP64 fusion gene with a secretion signal under control of the TRE promoter into cells, Dox-inducible secretion of TAT-ZFP-VP64 is achieved (FIG. 27b). This fusion protein is exported by the virtue of its N-terminal secretion system to the extracellular milieu, where it can be detected by using receiver cells, or, at an earlier stage, by WB. The expression of the fusion protein in the sender cells can be verified by WB of cell lysates or IF staining against the HA-tag.

Engineering ZFP Receivers:

By infecting the module containing the minimal CMV promoter with the DTS for the cognate ZFP controlling the expression of EGFP, TAT-ZFP-VP64-inducible expression of EGFP is achieved (FIG. 27b). Specifically, the secretion signal-containing TAT-ZFP-VP64 fusion protein is exported by sender cells separated by a transwell membrane into in the cell supernatant will transduce into receiver cells, localize to the nucleus and bind its cognate DTS in the minimal CMV promoter, thereby expressing EGFP (detectable by FACS and/or fluorescence microscopy). The uptake of the fusion protein will also be tracked by IF staining against the HA-tag.

If the engineering of cognate ZFP-DBP pairs and/or the export of ZFPs is problematic, the ZFP will be replaced by Gal4 and use the well-described Gal4 DTS in the receiver cells. This library could then be expanded by replacing Gal4 with known DNA-binding proteins/transcription factors (e.g. LacI, cI, TetR, rtTA) and their cognate DTS on the receiver side. Also, different endocytic domains and different secretion tags (from IL-11, GM-CSF . . . ) can be used.

Full length TAT might bind to endogenous regulatory elements, where it would have undesirable effects on the expression of endogenous genes. By using only a minimal TAT-peptide of 10 amino acids needed for cellular uptake and nuclear localization, it should be possible to reduce these undesirable interactions. Alternatively, other transducing/NLS-containing peptide sequences could be used in the delivery, as for example the 34 amino acid sequence of the Beta2/NeuroD transcription factor or the third a-helix of the Antennapedia, homeoprotein.

Example 6

This example demonstrates that the artificial cell-cell communication signals described in Example 5 can be used to induce differentiation of mouse embryonic stem cells in vitro. Two types of sender cells will express TAT-ZFP1-VP64 or TAT-ZFP2-VP64. ZFP1 activates MyoD expression, while ZFP2 activates Ngn1 expression. By placing patches of sender cells on a Matrigel matrix with embedded receiver cells, the gradient of the two synthetic morphogens should induce differentiation of the receiver cells into a myoblast- or neuron-like morphology, depending on their location.

Engineering Senders:

By infecting the rtTA switch, the TAT-ZFP-VP64 fusion expressing module from above and additionally a module with a distinct ZFP (TAT-ZFP2-VP64), two sender cell types are created expressing TAT-ZFP-VP64 or TAT-ZFP2-VP64 upon addition of Dox.

Engineering Receivers:

By co-infecting the two modules containing a DTS1 or DTS2, a minimal CMV promoter, the myoD or ngn1 genes, an internal ribosome entry site (TIRES) and a egfp or dsred2 gene into receiver cells, they will express MyoD and EGFP in response to ZFP1, Ngn1 and DsRed2 in response to ZFP2. These signaling circuits will be first tested with mES in liquid cell culture. If the communication and differentiation in the liquid media with transwell insert works, the receiver mES cells will be embedded in a Matrigel matrix and the sender cells filled into holes of various diameter at the surface of this matrix. This to induce three-dimensional differentiation patterns in the receiver cells. The differentiation success in both liquid as well matrix approach can be assessed by morphological changes, IF stainings, or RT-PCR for relevant markers (e.g. Desmin, Mef2, Cx2 for myocyte assays; Lim 1/2, Map2 and NSE for neural assays)

Other substrates than Matrigel might provide better growth and differentiation capabilities for mES, as for example a collagen-agarose matrix. The diffusion properties of the TAT-ZFP fusions proteins will be critical, as well as the positioning and the number the sender cells on the matrix. Suboptimal expression of MyoD/Ngn1 could be overcome by incorporating signal amplifying circuits into the receiver cells. Crosstalk between the ZFP-DTS pairs should have been ruled out earlier in the ZFP-DTS optimization procedure, nevertheless the ZFP and/or DTS coding sequences could be exchanged for other variants.

SEQUENCE LISTING

```
<160> NUMBER OF SEQ ID NOS: 34

<210> SEQ ID NO 1
<211> LENGTH: 10632
<212> TYPE: DNA
<213> ORGANISM: Artificial Sequence
<220> FEATURE:
<223> OTHER INFORMATION: Synthetic

<400> SEQUENCE: 1
cggccatcga taaggatccg ccctctccc tccccccccc ctaacgttac tggccgaagc      60
cgcttggaat aaggccggtg tgcgtttgtc tatatgttat tttccaccat attgccgtct    120
tttggcaatg tgagggcccg gaaacctggc cctgtcttct tgacgagcat tcctaggggt    180
ctttcccctc tcgccaaagg aatgcaaggt ctgttgaatg tcgtgaagga agcagttcct    240
ctggaagctt cttgaagaca aacaacgtct gtagcgaccc tttgcaggca gcggaaccc     300 ccacctggcg acaggtgcct ctgcggccaa aagccacgtg tataagatac acctgcaaag    360
gcggcacaac cccagtgcca cgttgtgagt tggatagttg tggaaagagt caaatggctc    420
tcctcaagcg tattcaacaa ggggctgaag gatgcccaga aggtacccca ttgtatggga    480
tctgatctgg ggcctcggtg cacatgcttt acatgtgttt agtcgaggtt aaaaaaacgt    540
ctaggccccc cgaaccacgg ggacgtggtt ttcctttgaa aaacacgatg ataatatggc    600
cacaaccatg gcctcctccg aggacgtcat caaggagttc atgcgcttca aggtgcgcat    660
ggagggctcc gtgaacggcc acgagttcga gatcgagggc gagggcgagg gccgccccta    720
cgagggcacc cagaccgcca agctgaaggt gaccaagggc ggcccctgc ccttcgcctg     780 ggacatcctg tcccccagt tccagtacgg ctccaaggtg tacgtgaagc accccgccga    840
catccccgac tacaagaagc tgtccttccc cgagggcttc aagtgggagc gcgtgatgaa    900
cttcgaggac ggcggcgtgg tgaccgtgac ccaggactcc tccctgcagg acggctcctt    960
catctacaag gtgaagttca tcggcgtgaa cttcccctcc gacggccccg taatgcagaa   1020
gaagactatg ggctgggagg cctccaccga gcgcctgtac cccgcgacg gcgtgctgaa   1080
```

```
gggcgagatc cacaaggccc tgaagctgaa ggacggcggc cactacctgg tggagttcaa    1140
gtccatctac atggccaaga agcccgtgca gctgcccggc tactactacg tggactccaa    1200
gctggacatc acctcccaca acgaggacta caccatcgtg gagcagtacg agcgcgccga    1260
gggccgccac cacctgttcc tgtaggcggc cgcaatcaac ctctggatta caaaatttgt    1320
gaaagattga ctggtattct taactatgtt gctccttta cgctatgtgg atacgctgct    1380
ttaatgcctt tgtatcatgc tattacttcc cgtacggctt tcattttctc ctccttgtat    1440
aaatcctggt tgctgtctct ttatgaggag ttgtggcccg ttgtcaggca acgtggcgtg    1500
gtgtgcactg tgtttgctga cgcaaccccc actggttggg gcattgccac cacctatcaa    1560
ctcctttccg ggactttcgc tttccccctc cctattgcca cggcggaact cattgccgcc    1620
tgccttgccc gctgctggac aggggctcgg ctgttgggca ctgacaattc cgtggtgttg    1680
tcggggaagc tgacgtcctt tccatggctg ctcgcctgtg ttgccaactg gattctgcgc    1740
gggacgtcct tctgctacgt cccttcggcc ctcaatccag cggaccttcc ttcccgcggc    1800
ctgctgccgg ttctgcggcc tcttccgcgt cttcgccttc gccctcagac gagtcggatc    1860
tccctttggg ccgcctcccc gcctgcctgc aggtttgtcg agacctagaa aaacatggag    1920
caatcacaag tagcaataca gcagctacca atgctgattg tgcctggcta gaagcacaag    1980
aggaggagga ggtgggtttt ccagtcacac ctcaggtacc tttaagacca atgacttaca    2040
aggcagctgt agatcttagc cacttttta aagaaaaggg gggactggaa gggctaattc    2100
actcccaacg aagacaagat ctgcttttg cttgtactgg gtctctctgg ttagaccaga    2160
tctgagcctg ggagctctct ggctaactag ggaacccact gcttaagcct caataaagct    2220
tgccttgagt gcttcaagta gtgtgtgccc gtctgttgtg tgactctggt aactagagat    2280
ccctcagacc cttttagtca gtgtggaaaa tctctagcag ggcccgttta aacccgctga    2340
tcagcctcga ctgtgccttc tagttgccag ccatctgttg tttgccctc ccccgtgcct    2400
tccttgaccc tggaaggtgc cactcccact gtcctttcct aataaaatga ggaaattgca    2460
tcgcattgtc tgagtaggtg tcattctatt ctgggggtg gggtggggca ggacagcaag    2520
ggggaggatt gggaagacaa tagcaggcat gctgggatg cggtgggctc tatggcttct    2580
gaggcggaaa gaaccagctg gggctctagg gggtatcccc acgcgccctg tagcggcgca    2640
ttaagcgcgg cgggtgtggt ggttacgcgc agcgtgaccg ctacacttgc cagcgcccta    2700
gcgcccgctc ctttcgcttt cttcccttcc tttctcgcca cgttcgccgg ctttccccgt    2760
caagctctaa atcggggcat ccctttaggg ttccgattta gtgctttacg gcacctcgac    2820
cccaaaaaac ttgattaggg tgatggttca cgtagtgggc catcgccctg atagacggtt    2880
tttcgccctt tgacgttgga gtccacgttc tttaatagtg actcttgtt ccaaactgga    2940
acaacactca accctatctc ggtctattct tttgatttat aagggatttt ggggatttcg    3000
gcctattggt taaaaaatga gctgatttaa caaaaattta cgcgaatta attctgtgga    3060
atgtgtgtca gttagggtgt ggaaagtccc caggctcccc aggcaggcag aagtatgcaa    3120
agcatgcatc tcaattagtc agcaaccagg tgtggaaagt ccccaggctc cccagcaggc    3180
agaagtatgc aaagcatgca tctcaattag tcagcaacca tagtcccgcc cctaactccg    3240
cccatcccgc ccctaactcc gcccagttcc gcccattctc cgccccatgg ctgactaatt    3300
tttttattt atgcagaggc cgaggccgcc tctgcctctg agctattcca gaagtagtga    3360
ggaggctttt ttggaggcct aggcttttgc aaaaagctcc cgggagcttg tatatccatt    3420
ttcggatctg atcagcacgt gttgacaatt aatcatcggc atagtatatc ggcatagtat    3480
```

-continued

| | |
|---|---|
| aatacgacaa ggtgaggaac taaaccatgg ccaagttgac cagtgccgtt ccggtgctca | 3540 |
| ccgcgcgcga cgtcgccgga gcggtcgagt tctggaccga ccggctcggg ttctcccggg | 3600 |
| acttcgtgga ggacgacttc gccggtgtgg tccgggacga cgtgaccctg ttcatcagcg | 3660 |
| cggtccagga ccaggtggtg ccggacaaca ccctggcctg ggtgtgggtg cgcggcctgg | 3720 |
| acgagctgta cgccgagtgg tcggaggtcg tgtccacgaa cttccgggac gcctccgggc | 3780 |
| cggccatgac cgagatcggc gagcagccgt ggggcgggga gttcgccctg cgcgacccgg | 3840 |
| ccggcaactg cgtgcacttc gtggccgagg agcaggactg acacgtgcta cgagatttcg | 3900 |
| attccaccgc cgccttctat gaaaggttgg gcttcggaat cgttttccgg gacgccggct | 3960 |
| ggatgatcct ccagcgcggg gatctcatgc tggagttctt cgcccacccc aacttgttta | 4020 |
| ttgcagctta taatggttac aaataaagca atagcatcac aaatttcaca aataaagcat | 4080 |
| ttttttcact gcattctagt tgtggttttgt ccaaactcat caatgtatct tatcatgtct | 4140 |
| gtataccgtc gacctctagc tagagcttgg cgtaatcatg gtcatagctg tttcctgtgt | 4200 |
| gaaattgtta tccgctcaca attccacaca acatacgagc cggaagcata agtgtaaag | 4260 |
| cctggggtgc ctaatgagtg agctaactca cattaattgc gttgcgctca ctgcccgctt | 4320 |
| tccagtcggg aaacctgtcg tgccagctgc attaatgaat cggccaacgc gcggggagag | 4380 |
| gcggtttgcg tattgggcgc tcttccgctt cctcgctcac tgactcgctg cgctcggtcg | 4440 |
| ttcggctgcg gcgagcggta tcagctcact caaaggcggt aatacggtta ccacagaat | 4500 |
| caggggataa cgcaggaaag aacatgtgag caaaaggcca gcaaaaggcc aggaaccgta | 4560 |
| aaaaggccgc gttgctggcg ttttttccata ggctccgccc ccctgacgag catcacaaaa | 4620 |
| atcgacgctc aagtcagagg tggcgaaacc cgacaggact ataaagatac caggcgtttc | 4680 |
| cccctggaag ctccctcgtg cgctctcctg ttccgaccct gccgcttacc ggatacctgt | 4740 |
| ccgcctttct cccttcggga agcgtggcgc tttctcaatg ctcacgctgt aggtatctca | 4800 |
| gttcggtgta ggtcgttcgc tccaagctgg gctgtgtgca cgaaccccc gttcagcccg | 4860 |
| accgctgcgc cttatccggt aactatcgtc ttgagtccaa cccggtaaga cacgacttat | 4920 |
| cgccactggc agcagccact ggtaacagga ttagcagagc gaggtatgta ggcggtgcta | 4980 |
| cagagttctt gaagtggtgg cctaactacg gctacactag aaggacagta tttggtatct | 5040 |
| gcgctctgct gaagccagtt accttcggaa aaagagttgg tagctcttga tccggcaaac | 5100 |
| aaaccaccgc tggtagcggt ggtttttttg tttgcaagca gcagattacg cgcagaaaaa | 5160 |
| aaggatctca agaagatcct ttgatctttt ctacggggtc tgacgctcag tggaacgaaa | 5220 |
| actcacgtta agggattttg gtcatgagat tatcaaaaag gatcttcacc tagatccttt | 5280 |
| taaattaaaa atgaagtttt aaatcaatct aaagtatata tgagtaaact tggtctgaca | 5340 |
| gttaccaatg cttaatcagt gaggcaccta tctcagcgat ctgtctattt cgttcatcca | 5400 |
| tagttgcctg actccccgtc gtgtagataa ctacgatacg ggagggctta ccatctggcc | 5460 |
| ccagtgctgc aatgataccg cgagacccac gctcaccggc tccagattta tcagcaataa | 5520 |
| accagccagc cggaagggcc gagcgcagaa gtggtcctgc aactttatcc gcctccatcc | 5580 |
| agtctattaa ttgttgccgg gaagctagag taagtagttc gccagttaat agtttgcgca | 5640 |
| acgttgttgc cattgctaca ggcatcgtgg tgtcacgctc gtcgtttggt atggcttcat | 5700 |
| tcagctccgg ttcccaacga tcaaggcgag ttacatgatc ccccatgttg tgcaaaaaag | 5760 |
| cggttagctc cttcggtcct ccgatcgttg tcagaagtaa gttggccgca gtgttatcac | 5820 |
| tcatggttat ggcagcactg cataattctc ttactgtcat gccatccgta agatgctttt | 5880 |

```
ctgtgactgg tgagtactca accaagtcat tctgagaata gtgtatgcgg cgaccgagtt   5940
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacgaaaatg ttgaatactc atactcttcc tttttcaata ttattgaagc atttatcagg   6240
gttattgtct catgagcgga tacatatttg aatgtattta gaaaaataaa caaataggggg  6300
ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagaccctt ttagtcagtg   7500
tggaaaatct ctagcagtgg cgcccgaaca gggacttgaa agcgaaaggg aaaccagagg   7560
agctctctcg acgcaggact cggcttgctg aagcgcgcac ggcaagaggc gaggggcggc   7620
gactggtgag tacgccaaaa attttgacta gcggaggcta aaggagaga gatgggtgcg   7680
agagcgtcag tattaagcgg gggagaatta gatcgcgatg ggaaaaaatt cggttaaggc   7740
caggggggaaa gaaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga agagcaaaac aaaagtaaga ccaccgcaca gcaagcggcc gctgatcttc   8040
agacctggag gaggagatat gagggacaat tggagaagtg aattatataa atataaagta   8100
gtaaaaattg aaccattagg agtagcaccc accaaggcaa agagaagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
```

-continued

```
gtgcagcagc agaacaattt gctgagggct attgaggcgc aacagcatct gttgcaactc    8340
acagtctggg gcatcaagca gctccaggca agaatcctgg ctgtggaaag atacctaaag    8400
gatcaacagc tcctggggat ttggggttgc tctggaaaac tcatttgcac cactgctgtg    8460
ccttggaatg ctagttggag taataaatct ctggaacaga tttggaatca cacgacctgg    8520
atggagtggg acagagaaat taacaattac acaagcttaa tacactcctt aattgaagaa    8580
tcgcaaaacc agcaagaaaa gaatgaacaa gaattattgg aattagataa atgggcaagt    8640
ttgtggaatt ggtttaacat aacaaattgg ctgtggtata taaaattatt cataatgata    8700
gtaggaggct tggtaggttt aagaatagtt tttgctgtac tttctatagt gaatagagtt    8760
aggcagggat attcaccatt atcgtttcag acccacctcc caaccccgag gggacccgac    8820
aggcccttaa ttaattggct ccggtgcccg tcagtgggca gagcgcacat cgcccacagt    8880
ccccgagaag ttgggggggag ggtcggcaa ttgaaccggt gcctagagaa ggtggcgcgg    8940
ggtaaactgg gaaagtgatg tcgtgtactg gctccgcctt tttcccgagg gtgggggaga    9000
accgtatata agtgcagtag tcgccgtgaa cgttctttttt cgcaacgggt ttgccgccag    9060
aacacaggta agtgccgtgt gtggttcccg cgggcctggc ctctttacgg gttatggccc    9120
ttgcgtgcct tgaattactt ccacctggct gcagtacgtg attcttgatc ccgagcttcg    9180
ggttggaagt gggtgggaga gttcgaggcc ttgcgcttaa ggagcccctt cgcctcgtgc    9240
ttgagttgag gcctggcctg ggcgctgggg ccgccgcgtg cgaatctggt ggcaccttcg    9300
cgcctgtctc gctgctttcg ataagtctct agccatttaa aattttttgat gacctgctgc    9360 gacgcttttt ttctggcaag atagtcttgt aaatgcgggc caagatctgc acactggtat    9420
ttcggttttt ggggccgcgg gcggcgacgg ggcccgtgcg tcccagcgca catgttcggc    9480 gaggcgggc ctgcgagcgc ggccaccgag aatcggacgg gggtagtctc aagctggccg    9540
gcctgctctg gtgcctggcc tcgcgccgcc gtgtatcgcc ccgccctggg cggcaaggct    9600
ggcccggtcg gcaccagttg cgtgagcgga aagatggccg cttcccggcc ctgctgcagg    9660
gagctcaaaa tggaggacgc ggcgctcggg agagcgggcg ggtgagtcac ccacacaaag    9720
gaaaagggcc tttccgtcct cagccgtcgc ttcatgtgac tccacggagt accgggcgcc    9780
gtccaggcac ctcgattagt tctcgagctt ttggagtacg tcgtctttag gttgggggga    9840
ggggttttat gcgatggagt ttccccacac tgagtgggtg gagactgaag ttaggccagc    9900
ttggcacttg atgtaattct ccttggaatt tgcccttttt gagtttggat cttggttcat    9960
tctcaagcct cagacagtgg ttcaaagttt ttttcttcca tttcaggtgt cgtgaggaat   10020
tcggccatta cggcccgcca ccatgaccat catgatcaag aagagcgact tcctggccat   10080
ccccagcgag gagtacaagg gcatcctgag cctgagatac caggtgttca gcagaggct   10140 ggagtgggac ctggtggtgg agaacaacct ggagagcgac gagtacgaca acagcaacgc   10200
cgagtacatc tacgcctgcg acgacaccga aacgtgagc ggctgctggc gcctgctgcc   10260
caccaccggc gactacatgc tgaagagcgt gttccccgag ctgctgggcc agcagagcgc   10320
ccccaaggac cccaacatcg tggagctgtc caggttcgcc gtgggcaaga acagcagcaa   10380
gatcaacaac agcgccagcg agatcaccat gaagctgttc gaggccatct acaagcacgc   10440
cgtgagccag gcatcaccg agtacgtgac cgtgaccagc accgccatcg agagatttct   10500
gaagaggatc aaggtgccct gccacaggat cggcgacaag gagatccacg tcctgggcga   10560
caccaagagc gtggtgctgt ccatgcccat caacgagcag ttcaaaaagg ccgtgctgaa   10620
ctgaggccgc ct                                                      10632
```

<210> SEQ ID NO 2
<211> LENGTH: 11736
<212> TYPE: DNA
<213> ORGANISM: Artificial Sequence
<220> FEATURE:
<223> OTHER INFORMATION: Synthetic

<400> SEQUENCE: 2

| | | | | | |
|---|---|---|---|---|---|
| cggccatcga | taaggatccg | ccctctccc | tccccccccc | ctaacgttac | tggccgaagc | 60 |
| cgcttggaat | aaggccggtg | tgcgtttgtc | tatatgttat | tttccaccat | attgccgtct | 120 |
| tttggcaatg | tgagggcccg | gaaacctggc | cctgtcttct | tgacgagcat | cctaggggt | 180 |
| ctttcccctc | tcgccaaagg | aatgcaaggt | ctgttgaatg | tcgtgaagga | agcagttcct | 240 |
| ctggaagctt | cttgaagaca | acaacgtct | gtagcgaccc | tttgcaggca | gcggaacccc | 300 |
| ccacctggcg | acaggtgcct | ctgcggccaa | aagccacgtg | tataagatac | acctgcaaag | 360 |
| gcggcacaac | cccagtgcca | cgttgtgagt | tggatagttg | tggaaagagt | caaatggctc | 420 |
| tcctcaagcg | tattcaacaa | ggggctgaag | gatgcccaga | aggtacccca | ttgtatggga | 480 |
| tctgatctgg | ggcctcggtg | cacatgcttt | acatgtgttt | agtcgaggtt | aaaaaaacgt | 540 |
| ctaggccccc | cgaaccacgg | ggacgtggtt | ttccttttgaa | aaacacgatg | ataatatggc | 600 |
| cacaaccatg | gcctcctccg | aggacgtcat | caaggagttc | atgcgcttca | aggtgcgcat | 660 |
| ggagggctcc | gtgaacggcc | acgagttcga | gatcgagggc | gagggcgagg | ccgcccccta | 720 |
| cgagggcacc | cagaccgcca | agctgaaggt | gaccaagggc | ggccccctgc | ccttcgcctg | 780 |
| ggacatcctg | tccccccagt | tccagtacgg | ctccaaggtg | tacgtgaagc | accccgccga | 840 |
| catccccgac | tacaagaagc | tgtccttccc | cgagggcttc | aagtgggagc | gcgtgatgaa | 900 |
| cttcgaggac | ggcggcgtgg | tgaccgtgac | ccaggactcc | tccctgcagg | acggctcctt | 960 |
| catctacaag | gtgaagttca | tcggcgtgaa | cttcccctcc | gacggccccg | taatgcagaa | 1020 |
| gaagactatg | ggctgggagg | cctccaccga | gcgcctgtac | ccccgcgacg | gcgtgctgaa | 1080 |
| gggcgagatc | cacaaggccc | tgaagctgaa | ggacggcggc | cactacctgg | tggagttcaa | 1140 |
| gtccatctac | atggccaaga | agcccgtgca | gctgcccggc | tactactacg | tggactccaa | 1200 |
| gctggacatc | acctcccaca | acgaggacta | caccatcgtg | gagcagtacg | agcgcgccga | 1260 |
| gggccgccac | cacctgttcc | tgtaggcggc | cgcaatcaac | ctctggatta | caaaatttgt | 1320 |
| gaaagattga | ctggtattct | taactatgtt | gctccttta | cgctatgtgg | atacgctgct | 1380 |
| ttaatgcctt | tgtatcatgc | tattacttcc | cgtacggctt | tcattttctc | ctccttgtat | 1440 |
| aaatcctggt | tgctgtctct | ttatgaggag | ttgtggcccg | ttgtcaggca | acgtggcgtg | 1500 |
| gtgtgcactg | tgtttgctga | cgcaaccccc | actggttggg | gcattgccac | cacctatcaa | 1560 |
| ctcctttccg | ggactttcgc | tttccccctc | cctattgcca | cggcggaact | cattgccgcc | 1620 |
| tgccttgccc | gctgctggac | aggggctcgg | ctgttgggca | ctgacaattc | cgtggtgttg | 1680 |
| tcggggaagc | tgacgtcctt | tccatggctg | ctcgcctgtg | ttgccaactg | gattctgcgc | 1740 |
| gggacgtcct | tctgctacgt | cccttcggcc | ctcaatccag | cggaccttcc | ttcccgcggc | 1800 |
| ctgctgccgg | ttctgcggcc | tcttccgcgt | cttcgccttc | gccctcagac | gagtcggatc | 1860 |
| tccctttggg | ccgcctcccc | gcctgcctgc | aggtttgtcg | agacctagaa | aaacatggag | 1920 |
| caatcacaag | tagcaataca | gcagctacca | atgctgattg | tgcctggcta | gaagcacaag | 1980 |
| aggaggagga | ggtgggtttt | ccagtcacac | ctcaggtacc | tttaagacca | atgacttaca | 2040 |
| aggcagctgt | agatcttagc | cactttttaa | aagaaaaggg | gggactggaa | gggctaattc | 2100 |

```
actcccaacg aagacaagat ctgctttttg cttgtactgg gtctctctgg ttagaccaga    2160
tctgagcctg ggagctctct ggctaactag ggaacccact gcttaagcct caataaagct    2220
tgccttgagt gcttcaagta gtgtgtgccc gtctgttgtg tgactctggt aactagagat    2280
ccctcagacc cttttagtca gtgtggaaaa tctctagcag ggcccgttta aacccgctga    2340
tcagcctcga ctgtgccttc tagttgccag ccatctgttg tttgcccctc cccgtgcct     2400 tccttgaccc tggaaggtgc cactcccact gtcctttcct aataaaatga ggaaattgca    2460
tcgcattgtc tgagtaggtg tcattctatt ctgggggtg gggtggggca ggacagcaag    2520
ggggaggatt gggaagacaa tagcaggcat gctgggatg cggtgggctc tatggcttct    2580
gaggcggaaa gaaccagctg ggctctagg gggtatcccc acgcgccctg tagcggcgca    2640
ttaagcgcgg cggtgtggt ggttacgcgc agcgtgaccg ctacacttgc cagcgcccta    2700
gcgcccgctc ctttcgcttt cttcccttcc tttctcgcca cgttcgccgg ctttccccgt    2760
caagctctaa atcggggcat ccctttaggg ttccgattta gtgctttacg gcacctcgac    2820
cccaaaaaac ttgattaggg tgatggttca cgtagtgggc catcgccctg atagacggtt    2880
tttcgccctt tgacgttgga gtccacgttc tttaatagtg gactcttgtt ccaaactgga    2940
acaacactca accctatctc ggtctattct tttgatttat aagggatttt ggggatttcg    3000
gcctattggt taaaaatga gctgatttaa caaaaattta acgcgaatta attctgtgga    3060
atgtgtgtca gttagggtgt ggaaagtccc caggctcccc aggcaggcag aagtatgcaa    3120
agcatgcatc tcaattagtc agcaaccagg tgtggaaagt ccccaggctc ccagcaggc     3180 agaagtatgc aaagcatgca tctcaattag tcagcaacca tagtcccgcc cctaactccg    3240
cccatcccgc ccctaactcc gcccagttcc gcccattctc cgccccatgg ctgactaatt    3300 tttttattt atgcagaggc cgaggccgcc tctgcctctg agctattcca gaagtagtga    3360
ggaggctttt ttggaggcct aggcttttgc aaaaagctcc cgggagcttg tatatccatt    3420
ttcggatctg atcagcacgt gttgacaatt aatcatcggc atagtatatc ggcatagtat    3480
aatacgacaa ggtgaggaac taaaccatgg ccaagttgac cagtgccgtt ccggtgctca    3540
ccgcgcgcga cgtcgccgga gcggtcgagt tctggaccga ccggctcggg ttctcccggg    3600
acttcgtgga ggacgacttc gccggtgtgg tccgggacga cgtgaccctg ttcatcagcg    3660
cggtccagga ccaggtggtg ccggacaaca ccctggcctg ggtgtgggtg cgcggcctgg    3720
acgagctgta cgccgagtgg tcggaggtcg tgtccacgaa cttccgggac gcctccgggc    3780
cggccatgac cgagatcggc gagcagccgt ggggggcggga gttcgccctg cgcgacccgg    3840
ccggcaactg cgtgcacttc gtggccgagg agcaggactg acacgtgcta cgagatttcg    3900
attccaccgc cgccttctat gaaaggttgg gcttcggaat cgttttccgg gacgccggct    3960
ggatgatcct ccagcgcggg gatctcatgc tggagttctt cgcccacccc aacttgttta    4020
ttgcagctta taatggttac aaataaagca atagcatcac aaatttcaca aataaagcat    4080
ttttttcact gcattctagt tgtggtttgt ccaaactcat caatgtatct tatcatgtct    4140
gtataccgtc gacctctagc tagagcttgg cgtaatcatg gtcatagctg tttcctgtgt    4200
gaaattgtta tccgctcaca attccacaca acatacgagc cggaagcata aagtgtaaag    4260
cctggggtgc ctaatgagtg agctaactca cattaattgc gttgcgctca ctgcccgctt    4320
tccagtcggg aaacctgtcg tgccagctgc attaatgaat cggccaacgc gcggggagag    4380
gcggtttgcg tattgggcgc tcttccgctt cctcgctcac tgactcgctg cgctcggtcg    4440
ttcggctgcg gcgagcggta tcagctcact caaaggcggt aatacggtta tccacagaat    4500
```

```
cagggggataa cgcaggaaag aacatgtgag caaaaggcca gcaaaaggcc aggaaccgta    4560
aaaaggccgc gttgctggcg ttttccata ggctccgccc ccctgacgag catcacaaaa     4620
atcgacgctc aagtcagagg tggcgaaacc cgacaggact ataaagatac caggcgtttc    4680
cccctggaag ctccctcgtg cgctctcctg ttccgaccct gccgcttacc ggatacctgt    4740
ccgcctttct cccttcggga agcgtggcgc tttctcaatg ctcacgctgt aggtatctca    4800
gttcggtgta ggtcgttcgc tccaagctgg gctgtgtgca cgaaccccc gttcagcccg     4860 accgctgcgc cttatccggt aactatcgtc ttgagtccaa cccggtaaga cacgacttat    4920
cgccactggc agcagccact ggtaacagga ttagcagagc gaggtatgta ggcggtgcta    4980
cagagttctt gaagtggtgg cctaactacg gctacactag aaggacagta tttggtatct    5040
gcgctctgct gaagccagtt accttcggaa aaagagttgg tagctcttga tccggcaaac    5100
aaaccaccgc tggtagcggt ggtttttttg tttgcaagca gcagattacg cgcagaaaaa    5160
aaggatctca agaagatcct ttgatctttt ctacggggtc tgacgctcag tggaacgaaa    5220
actcacgtta agggattttg gtcatgagat tatcaaaaag gatcttcacc tagatccttt    5280
taaattaaaa atgaagtttt aaatcaatct aaagtatata tgagtaaact tggtctgaca    5340
gttaccaatg cttaatcagt gaggcaccta tctcagcgat ctgtctattt cgttcatcca    5400
tagttgcctg actccccgtc gtgtagataa ctacgatacg ggagggctta ccatctggcc    5460
ccagtgctgc aatgataccg cgagacccac gctcaccggc tccagattta tcagcaataa    5520
accagccagc cggaagggcc gagcgcagaa gtggtcctgc aactttatcc gcctccatcc    5580
agtctattaa ttgttgccgg gaagctagag taagtagttc gccagttaat agtttgcgca    5640
acgttgttgc cattgctaca ggcatcgtgg tgtcacgctc gtcgtttggt atggcttcat    5700
tcagctccgg ttcccaacga tcaaggcgag ttacatgatc ccccatgttg tgcaaaaaag    5760
cggttagctc cttcggtcct ccgatcgttg tcagaagtaa gttggccgca gtgttatcac    5820
tcatggttat ggcagcactg cataattctc ttactgtcat gccatccgta agatgctttt    5880
ctgtgactgg tgagtactca accaagtcat tctgagaata gtgtatgcgg cgaccgagtt    5940
gctcttgccc ggcgtcaata cgggataata ccgcgccaca tagcagaact ttaaaagtgc    6000
tcatcattgg aaaacgttct tcggggcgaa aactctcaag gatcttaccg ctgttgagat    6060
ccagttcgat gtaacccact cgtgcaccca actgatcttc agcatctttt actttcacca    6120
gcgtttctgg gtgagcaaaa acaggaaggc aaaatgccgc aaaaaaggga taagggcga    6180 cacggaaatg ttgaatactc atactcttcc ttttcaata ttattgaagc atttatcagg    6240
gttattgtct catgagcgga tacatatttg aatgtattta gaaaaataaa caaatagggg    6300
ttccgcgcac atttccccga aaagtgccac ctgacgtcga cggatcggga gatctcccga    6360
tcccctatgg tgcactctca gtacaatctg ctctgatgcc gcatagttaa gccagtatct    6420
gctccctgct tgtgtgttgg aggtcgctga gtagtgcgcg agcaaaattt aagctacaac    6480
aaggcaaggc ttgaccgaca attgcatgaa gaatctgctt agggttaggc gttttgcgct    6540
gcttcgcgat gtacgggcca gatatacgcg ttgacattga ttattgacta gttattaata    6600
gtaatcaatt acggggtcat tagttcatag cccatatatg gagttccgcg ttacataact    6660
tacggtaaat ggcccgcctg gctgaccgcc caacgacccc cgcccattga cgtcaataat    6720
gacgtatgtt cccatagtaa cgccaatagg gactttccat tgacgtcaat gggtggacta    6780
tttacggtaa actgcccact tggcagtaca tcaagtgtat catatgccaa gtacgccccc    6840
tattgacgtc aatgacggta aatggcccgc ctggcattat gcccagtaca tgaccttatg    6900
```

```
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa atcaacggga ctttccaaa    7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagacccct ttagtcagtg   7500
tggaaaatct ctagcagtgg cgcccgaaca gggacttgaa agcgaagggg aaaccagagg   7560
agctctctcg acgcaggact cggcttgctg aagcgcgcac ggcaagaggc gaggggcggc   7620
gactggtgag tacgccaaaa attttgacta gcggaggcta aaggagagag atgggtgcg    7680
agagcgtcag tattaagcgg gggagaatta gatcgcgatg ggaaaaaatt cggttaaggc   7740
caggggggaaa gaaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga agagcaaaac aaaagtaaga ccaccgcaca gcaagcggcc gctgatcttc   8040
agacctggag gaggagatat gagggacaat tggagaagtg aattatataa atataaagta   8100
gtaaaaattg aaccattagg agtagcaccc accaaggcaa agaagagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
gtgcagcagc agaacaattt gctgagggct attgaggcgc aacagcatct gttgcaactc   8340
acagtctggg gcatcaagca gctccaggca agaatcctgg ctgtggaaag atacctaaag   8400
gatcaacagc tcctggggat ttggggttgc tctggaaaac tcatttgcac cactgctgtg   8460
ccttggaatg ctagttggag taataaatct ctggaacaga tttggaatca cacgacctgg   8520
atggagtggg acagagaaat taacaattac acaagcttaa tacactcctt aattgaagaa   8580
tcgcaaaacc agcaagaaaa gaatgaacaa gaattattgg aattagataa atgggcaagt   8640
ttgtggaatt ggtttaacat aacaaattgg ctgtggtata taaaattatt cataatgata   8700
gtaggaggct tggtaggttt aagaatagtt tttgctgtac tttctatagt gaatagagtt   8760
aggcagggat attcaccatt atcgtttcag acccacctcc caaccccgag gggacccgac   8820
aggcccttaa ttaattggct ccggtgcccg tcagtgggca gagcgcacat cgcccacagt   8880
ccccgagaag ttgggggggag gggtcggcaa ttgaaccggt gcctagagaa ggtggcgcgg   8940
ggtaaactgg gaaagtgatg tcgtgtactg gctccgcctt tttcccgagg gtgggggaga   9000
accgtatata agtgcagtag tcgccgtgaa cgttcttttt cgcaacgggt ttgccgccag   9060
aacacaggta agtgccgtgt gtggttcccg cgggcctggc ctctttacgg gttatggccc   9120
ttgcgtgcct tgaattactt ccacctggct gcagtacgtg attcttgatc ccgagcttcg   9180
ggttggaagt gggtgggaga gttcgaggcc ttgcgcttaa ggagccccctt cgcctcgtgc   9240
ttgagttgag gcctggcctg ggcgctgggg ccgccgcgtg cgaatctggt ggcaccttcg   9300
```

```
cgcctgtctc gctgctttcg ataagtctct agccatttaa aattttttgat gacctgctgc   9360 gacgctttt  ttctggcaag atagtcttgt aaatgcgggc caagatctgc acactggtat   9420
ttcggttttt ggggccgcgg gcggcgacgg ggcccgtgcg tcccagcgca catgttcggc   9480
gaggcggggc ctgcgagcgc ggccaccgag aatcggacgg gggtagtctc aagctggccg   9540
gcctgctctg gtgcctggcc tcgcgccgcc gtgtatcgcc ccgccctggg cggcaaggct   9600
ggcccggtcg gcaccagttg cgtgagcgga aagatggccg cttcccggcc ctgctgcagg   9660
gagctcaaaa tggaggacgc ggcgctcggg agagcgggcg ggtgagtcac ccacacaaag   9720
gaaaagggcc tttccgtcct cagccgtcgc ttcatgtgac tccacggagt accgggcgcc   9780
gtccaggcac ctcgattagt tctcgagctt ttggagtacg tcgtctttag gttgggggga   9840
ggggttttat gcgatggagt ttccccacac tgagtgggtg gagactgaag ttaggccagc   9900
ttggcacttg atgtaattct ccttggaatt tgccttttt  gagtttggat cttggttcat   9960
tctcaagcct cagacagtgg ttcaaagttt ttttcttcca tttcaggtgt cgtgaggaat  10020
tcggccatta cggcctgcca ccatggacca gtacctgccc gacaccgacg acaggcacag  10080
gatcgaggag aagaggaaga ggacctacga gaccttcaag agcatcatga agaagagccc  10140
cttcaacggc cccaccgagc ccagaccccc caccaggcgg atcgccgtgc ccacaaggaa  10200
cagcaccagc gtgcccaagc ctgcccccca gccctacacc ttccccgcca gcctgagcac  10260
catcaacttc gacgagttca gccccatgct gctgcccagc ggccagatca gcaaccaggc  10320
cctggccctg gctcctagca gcgccccctg tgctggccca ccatggtgc  ccagcagcgc  10380 catggtgcct ctggcccagc ctcctgcccc tgccccgtg  ctgaccccctg gccccctca   10440 gagcctgagc gccccagtgc ccaagagcac ccaggccggc gagggcacac tgagcgaggc  10500
cctgctgcac ctgcagttcg acgccgacga ggacctgggc gccctgctgg caacagcac   10560 cgacccggc  gtgttcaccg acctggccag cgtggacaac agcgagttcc agcagctgct  10620
gaaccagggc gtgagcatga ccacagcac  cgccgagccc atgctgatgg agtaccccga  10680
ggccatcacc aggctggtga ccggcagcca gagacccccc gaccctgccc ctacccctct  10740
gggcaccagc ggcctgccca acggcctgag cggcgacgag gacttcagca gcatcgccga  10800
catggacttc tccgccctgc tgtcccagat cagctccctg gagctggccg aggccgctgc  10860
caaggaggct gccgctaagg aggccgctgc taaggaggct gctgccaagg ccgctgccat  10920
gaagaacatc aacgccgacg acacctacag gatcatcaac aagatcaagg cctgcagaag  10980
caacaacgac atcaaccagt gcctgagcga catggccaag atggtgcact gcagtactac  11040
cctgctggcc ttcatctacc cccacagcat ggtgaagagc gacatcagca tcctggacaa  11100
ctaccccaag aagtggaggc agtactacga cgacgccaac ctgatcaagt acgacccat   11160 cgtggactac agcaacagca accacagccc catcaactgg aacatcttcg agaacaacgc  11220
cgtgaacaaa aagtccccca acgtgatcaa ggaggccaag acagccggcc tgatcaccgg  11280
cttcagcttc cccatccaca ccgccaacaa cggcttcggc atgctgtcct tcgcccacag  11340
cgagaaggac aactacatcg acagcctgtt tctgcacgcc tgcatgaaca tcccccctgat  11400 cgtgcccagc ctggtggata actaccggaa gatcaacatc gccaacaaca gtccaacaa   11460 cgacctgacc aagcgggaga aggagtgcct ggcctgggcc tgcagggca  agagcagctg  11520 ggacatcagc aagatcctgg gctgcagcga gaggaccgtg accttccacc tgaccaacgc  11580
ccagatgaag ctgaacacca ccaacaggtg ccagagcatc agcaaggcca tcctgaccgg  11640
cgccatcgac tgcccctact tcaagaacag cagcctgagg ccccccaaaa agaaaagaaa  11700
```

| | |
|---|---|
| ggtgcaccac caccaccacc actgatgagg ccgcct | 11736 |

<210> SEQ ID NO 3
<211> LENGTH: 10050
<212> TYPE: DNA
<213> ORGANISM: Artificial Sequence
<220> FEATURE:
<223> OTHER INFORMATION: Synthetic

<400> SEQUENCE: 3

| | |
|---|---|
| aattcggcca ttacggccgc tagcgttaac gtcgacggcc gcctcggcca tcgataagga | 60 |
| tccggaatgc ccctctccct cccccccccc taacgttact ggccgaagcc gcttggaata | 120 |
| aggccggtgt gcgtttgtct atatgttatt ttccaccata ttgccgtctt ttggcaatgt | 180 |
| gagggcccgg aaacctggcc ctgtcttctt gacgagcatt cctagggtc tttcccctct | 240 |
| cgccaaagga atgcaaggtc tgttgaatgt cgtgaaggaa gcagttcctc tggaagcttc | 300 |
| ttgaagacaa caacgtctg tagcgaccct ttgcaggcag cggaacccc cacctggcga | 360 |
| caggtgcctc tgcggccaaa agccacgtgt ataagataca cctgcaaagg cggcacaacc | 420 |
| ccagtgccac gttgtgagtt ggatagttgt ggaaagagtc aaatggctct cctcaagcgt | 480 |
| attcaacaag gggctgaagg atgcccagaa ggtaccccat tgtatgggat ctgatctggg | 540 |
| gcctcggtgc acatgcttta catgtgttta gtcgaggtta aaaaaacgtc taggcccccc | 600 |
| gaaccacggg gacgtggttt tcctttgaaa aacacgatga taatatggcc acaaccatgg | 660 |
| tgagcaaggg cgaggagctg ttcaccgggg tggtgcccat cctggtcgag ctggacggcg | 720 |
| acgtaaacgg ccacaagttc agcgtgtccg gcgagggcga gggcgatgcc acctacggca | 780 |
| agctgaccct gaagttcatc tgcaccaccg gcaagctgcc cgtgccctgg cccaccctcg | 840 |
| tgaccaccct gacctacggc gtgcagtgct tcagccgcta ccccgaccac atgaagcagc | 900 |
| acgacttctt caagtccgcc atgcccgaag gctacgtcca ggagcgcacc atcttcttca | 960 |
| aggacgacgg caactacaag acccgcgccg aggtgaagtt cgagggcgac accctggtga | 1020 |
| accgcatcga gctgaagggc atcgacttca aggaggacgg caacatcctg gggcacaagc | 1080 |
| tggagtacaa ctacaacagc cacaacgtct atatcatggc cgacaagcag aagaacggca | 1140 |
| tcaaggtgaa cttcaagatc cgccacaaca tcgaggacgg cagcgtgcag ctcgccgacc | 1200 |
| actaccagca gaacaccccc atcggcgacg gccccgtgct gctgcccgac aaccactacc | 1260 |
| tgagcaccca gtccgccctg agcaaagacc ccaacgagaa gcgcgatcac atggtcctgc | 1320 |
| tggagttcgt gaccgccgcc gggatcactc tcggcatgga cgagctgtac aagtaagcgg | 1380 |
| ccgcaatcaa cctctggatt acaaaatttg tgaaagattg actggtattc ttaactatgt | 1440 |
| tgctcctttt acgctatgtg gatacgctgc tttaatgcct ttgtatcatg ctattacttc | 1500 |
| ccgtacggct ttcattttct cctccttgta taaatcctgg ttgctgtctc tttatgagga | 1560 |
| gttgtggccc gttgtcaggc aacgtggcgt ggtgtgcact gtgtttgctg acgcaaccc | 1620 |
| cactggttgg ggcattgcca ccacctatca actcctttcc gggactttcg ctttccccct | 1680 |
| ccctattgcc acgcggaac tcattgccgc ctgccttgcc cgctgctgga caggggctcg | 1740 |
| gctgttgggc actgacaatt ccgtggtgtt gtcggggaag ctgacgtcct ttccatggct | 1800 |
| gctcgcctgt gttgccaact ggattctgcg cgggacgtcc ttctgctacg tcccttcggc | 1860 |
| cctcaatcca gcggaccttc cttcccgcgg cctgctgccg gttctgcggc tcttccgcg | 1920 |
| tcttcgcctt cgccctcaga cgagtcggat ctcccttttgg gccgcctccc cgcctgcctg | 1980 |
| caggtttgtc gagacctaga aaaacatgga gcaatcacaa gtagcaatac agcagctacc | 2040 |

```
aatgctgatt gtgcctggct agaagcacaa gaggaggagg aggtgggttt tccagtcaca    2100
cctcaggtac ctttaagacc aatgacttac aaggcagctg tagatcttag ccactttta     2160
aaagaaaagg ggggactgga agggctaatt cactcccaac gaagacaaga tctgcttttt    2220
gcttgtactg ggtctctctg gttagaccag atctgagcct gggagctctc tggctaacta    2280
gggaacccac tgcttaagcc tcaataaagc ttgccttgag tgcttcaagt agtgtgtgcc    2340
cgtctgttgt gtgactctgg taactagaga tccctcagac ccttttagtc agtgtggaaa    2400
atctctagca gggcccgttt aaacccgctg atcagcctcg actgtgcctt ctagttgcca    2460
gccatctgtt gtttgcccct cccccgtgcc ttccttgacc ctggaaggtg ccactcccac    2520
tgtcctttcc taataaaatg aggaaattgc atcgcattgt ctgagtaggt gtcattctat    2580
tctgggggt ggggtgggc aggacagcaa ggggaggat tgggaagaca atagcaggca       2640
tgctggggat gcggtgggct ctatggcttc tgaggcggaa agaaccagct ggggctctag    2700
ggggtatccc cacgcgccct gtagcggcgc attaagcgcg gcgggtgtgg tggttacgcg    2760
cagcgtgacc gctacacttg ccagcgccct agcgcccgct cctttcgctt tcttcccttc    2820
cttctcgcc acgttcgccg ctttccccg tcaagctcta atcggggca tccctttagg       2880
gttccgattt agtgctttac ggcacctcga ccccaaaaaa cttgattagg gtgatggttc    2940
acgtagtggg ccatcgccct gatagacggt ttttcgccct ttgacgttgg agtccacgtt    3000
ctttaatagt ggactcttgt tccaaactgg aacaacactc aaccctatct cggtctattc    3060
ttttgattta aagggatttt ggggattttc ggcctattgg ttaaaaaatg agctgattta    3120
acaaaaattt aacgcgaatt aattctgtgg aatgtgtgtc agttagggtg tggaaagtcc    3180
ccaggctccc caggcaggca gaagtatgca aagcatgcat ctcaattagt cagcaaccag    3240
gtgtggaaag tccccaggct ccccagcagg cagaagtatg caaagcatgc atctcaatta    3300
gtcagcaacc atagtcccgc ccctaactcc gcccatcccg ccctaactc cgcccagttc     3360
cgcccattct ccgccccatg gctgactaat ttttttatt tatgcagagg ccgaggccgc     3420
ctctgcctct gagctattcc agaagtagtg aggaggcttt tttggaggcc taggcttttg    3480
caaaaagctc ccgggagctt gtatatccat tttcggatct gatcagcacg tgttgacaat    3540
taatcatcgg catagtatat cggcatagta taatacgaca aggtgaggaa ctaaaccatg    3600
gccaagttga ccagtgccgt tccggtgctc accgcgcgcg acgtcgccgg agcggtcgag    3660
ttctggaccg accggctcgg gttctcccgg gacttcgtgg aggacgactt cgccggtgtg    3720
gtccgggacg acgtgaccct gttcatcagc gcggtccagg accaggtggt gccggacaac    3780
accctggcct gggtgtgggt gcgcggcctg gacgagctgt acgccgagtg gtcggaggtc    3840
gtgtccacga acttccggga cgcctccggg ccggccatga ccgagatcgg cgagcagccg    3900
tggggcggg agttcgccct gcgcgacccg gccggcaact gcgtgcactt cgtggccgag    3960
gagcaggact gacacgtgct acgagatttc gattccaccg ccgccttcta tgaaaggttg    4020
ggcttcggaa tcgttttccg gacgccggc tggatgatcc tccagcgcgg ggatctcatg     4080
ctggagttct tcgcccaccc caacttgttt attgcagctt ataatggtta caaataaagc    4140
aatagcatca caaatttcac aaataaagca tttttttcac tgcattctag ttgtggtttg    4200
tccaaactca tcaatgtatc ttatcatgtc tgtataccgt cgacctctag ctagagcttg    4260
gcgtaatcat ggtcatagct gtttcctgtg tgaaattgtt atccgctcac aattccacac    4320
aacatacgag ccggaagcat aaagtgtaaa gcctggggtg cctaatgagt gagctaactc    4380
acattaattg cgttgcgctc actgcccgct ttccagtcgg gaaacctgtc gtgccagctg    4440
```

| | |
|---|---|
| cattaatgaa tcggccaacg cgcggggaga ggcggtttgc gtattgggcg ctcttccgct | 4500 |
| tcctcgctca ctgactcgct gcgctcggtc gttcggctgc ggcgagcggt atcagctcac | 4560 |
| tcaaaggcgg taatacggtt atccacagaa tcaggggata acgcaggaaa gaacatgtga | 4620 |
| gcaaaaggcc agcaaaaggc caggaaccgt aaaaaggccg cgttgctggc gtttttccat | 4680 |
| aggctccgcc cccctgacga gcatcacaaa aatcgacgct caagtcagag gtggcgaaac | 4740 |
| ccgacaggac tataaagata ccaggcgttt ccccctggaa gctccctcgt gcgctctcct | 4800 |
| gttccgaccc tgccgcttac cggatacctg tccgcctttc tcccttcggg aagcgtggcg | 4860 |
| ctttctcaat gctcacgctg taggtatctc agttcggtgt aggtcgttcg ctccaagctg | 4920 |
| ggctgtgtgc acgaacccccc cgttcagccc gaccgctgcg ccttatccgg taactatcgt | 4980 |
| cttgagtcca acccggtaag acacgactta tcgccactgg cagcagccac tggtaacagg | 5040 |
| attagcagag cgaggtatgt aggcggtgct acagagttct tgaagtggtg cctaactac | 5100 |
| ggctacacta aaggacagt atttggtatc tgcgctctgc tgaagccagt taccttcgga | 5160 |
| aaaagagttg gtagctcttg atccggcaaa caaaccaccg ctggtagcgg tggtttttttt | 5220 |
| gtttgcaagc agcagattac gcgcagaaaa aaaggatctc aagaagatcc tttgatcttt | 5280 |
| tctacggggt ctgacgctca gtggaacgaa aactcacgtt aagggatttt ggtcatgaga | 5340 |
| ttatcaaaaa ggatcttcac ctagatcctt ttaaattaaa aatgaagttt taaatcaatc | 5400 |
| taaagtatat atgagtaaac ttggtctgac agttaccaat gcttaatcag tgaggcacct | 5460 |
| atctcagcga tctgtctatt tcgttcatcc atagttgcct gactccccgt cgtgtagata | 5520 |
| actacgatac gggagggctt accatctggc cccagtgctg caatgatacc gcgagaccca | 5580 |
| cgctcaccgg ctccagattt atcagcaata aaccagccag ccggaagggc cgagcgcaga | 5640 |
| agtggtcctg caactttatc cgcctccatc cagtctatta attgttgccg ggaagctaga | 5700 |
| gtaagtagtt cgccagttaa tagtttgcgc aacgttgttg ccattgctac aggcatcgtg | 5760 |
| gtgtcacgct cgtcgtttgg tatggcttca ttcagctccg gttcccaacg atcaaggcga | 5820 |
| gttacatgat cccccatgtt gtgcaaaaaa gcggttagct ccttcggtcc tccgatcgtt | 5880 |
| gtcagaagta agttggccgc agtgttatca ctcatggtta tggcagcact gcataattct | 5940 |
| cttactgtca tgccatccgt aagatgcttt tctgtgactg gtgagtactc aaccaagtca | 6000 |
| ttctgagaat agtgtatgcg gcgaccgagt tgctcttgcc cggcgtcaat acgggataat | 6060 |
| accgcgccac atagcagaac tttaaaagtg ctcatcattg gaaaacgttc ttcggggcga | 6120 |
| aaactctcaa ggatcttacc gctgttgaga tccagttcga tgtaacccac tcgtgcaccc | 6180 |
| aactgatctt cagcatcttt tactttcacc agcgtttctg ggtgagcaaa aacaggaagg | 6240 |
| caaaatgccg caaaaaaggg aataagggcg acacggaaat gttgaatact catactcttc | 6300 |
| cttttttcaat attattgaag catttatcag ggttattgtc tcatgagcgg atacatattt | 6360 |
| gaatgtattt agaaaaataa acaaataggg gttccgcgca catttccccg aaaagtgcca | 6420 |
| cctgacgtcg acggatcggg agatctcccg atcccctatg gtgcactctc agtacaatct | 6480 |
| gctctgatgc cgcatagtta agccagtatc tgctccctgc ttgtgtgttg gaggtcgctg | 6540 |
| agtagtgcgc gagcaaaatt taagctacaa caaggcaagg cttgaccgac aattgcatga | 6600 |
| agaatctgct tagggttagg cgttttgcgc tgcttcgcga tgtacgggcc agatatacgc | 6660 |
| gttgacattg attattgact agttattaat agtaatcaat tacgggtca ttagttcata | 6720 |
| gcccatatat ggagttccgc gttacataac ttacggtaaa tggcccgcct ggctgaccgc | 6780 |
| ccaacgaccc ccgcccattg acgtcaataa tgacgtatgt tcccatagta acgccaatag | 6840 |

```
ggactttcca ttgacgtcaa tgggtggact atttacggta aactgcccac ttggcagtac    6900
atcaagtgta tcatatgcca agtacgcccc ctattgacgt caatgacggt aaatggcccg    6960
cctggcatta tgcccagtac atgaccttat gggactttcc tacttggcag tacatctacg    7020
tattagtcat cgctattacc atggtgatgc ggttttggca gtacatcaat gggcgtggat    7080
agcggtttga ctcacgggga tttccaagtc tccaccccat tgacgtcaat gggagtttgt    7140
tttggcacca aaatcaacgg gactttccaa aatgtcgtaa caactccgcc ccattgacgc    7200
aaatgggcgg taggcgtgta cggtgggagg tctatataag cagagctctc tggctaacta    7260
gagaacccac tgcttactgg cttatcgaaa ttaatacgac tcactatagg gagacccaag    7320
ctggtttaaa cttaagcttg gtaccgagct cactagtcca gtgtggtggc agatatccag    7380
cacagtggcg gccgctcgag tctagagggc ccgttttgcc tgtactgggt ctctctggtt    7440
agaccagatc tgagcctggg agctctctgg ctaactaggg aacccactgc ttaagcctca    7500
ataaagcttg ccttgagtgc ttcaagtagt gtgtgcccgt ctgttgtgtg actctggtaa    7560
ctagagatcc ctcagaccct tttagtcagt gtggaaaatc tctagcagtg gcgcccgaac    7620
agggacttga aagcgaaagg gaaaccagag gagctctctc gacgcaggac tcggcttgct    7680
gaagcgcgca cggcaagagg cgaggggcgg cgactggtga gtacgccaaa aattttgact    7740
agcggaggct agaaggagag agatgggtgc gagagcgtca gtattaagcg ggggagaatt    7800
agatcgcgat gggaaaaaat tcggttaagg ccagggggaa agaaaaaata taaattaaaa    7860
catatagtat gggcaagcag ggagctagaa cgattcgcag ttaatcctgg cctgttagaa    7920
acatcagaag gctgtagaca aatactggga cagctacaac catcccttca gacaggatca    7980
gaagaactta gatcattata taatacagta gcaaccctct attgtgtgca tcaaaggata    8040
gagataaaag acaccaagga agctttagac aagatagagg aagagcaaaa caaaagtaag    8100
accaccgcac agcaagcggc cgctgatctt cagacctgga ggaggagata tgagggacaa    8160
ttggagaagt gaattatata aatataaagt agtaaaaatt gaaccattag gagtagcacc    8220
caccaaggca aagagaagag tggtgcagag agaaaaaaga gcagtgggaa taggagcttt    8280
gttccttggg ttcttgggag cagcaggaag cactatgggc gcagcgtcaa tgacgctgac    8340
ggtacaggcc agacaattat tgtctggtat agtgcagcag cagaacaatt tgctgagggc    8400
tattgaggcg caacagcatc tgttgcaact cacagtctgg ggcatcaagc agctccaggc    8460
aagaatcctg gctgtggaaa gatacctaaa ggatcaacag ctcctgggga tttggggttg    8520
ctctggaaaa ctcatttgca ccactgctgt gccttggaat gctagttgga gtaataaatc    8580
tctggaacag atttggaatc acacgacctg gatggagtgg gacagagaaa ttaacaatta    8640
cacaagctta atacactcct taattgaaga atcgcaaaac cagcaagaaa agaatgaaca    8700
agaattattg gaattagata atgggcaag tttgtggaat tggtttaaca taacaaattg    8760
gctgtggtat ataaaatta ttcataatga tagtaggagg cttggtaggt ttaagaatag    8820
tttttgctgt actttctata gtgaatagag ttaggcaggg atattcacca ttatcgtttc    8880
agacccacct cccaacccc agggaccccg acaggcccga aggaatagaa gaagaaggtg    8940
gagagagaga cagagacaga tccattcgat tagtgaacgg atcggcactg cgtgcgccaa    9000
ttctgcagac aaatggcagt attcatccac aattttaaaa gaaaggggg gattgggggg    9060 tacagtgcag gggaaagaat agtagacata atagcaacag acatacaaac taaagaatta    9120
caaaaacaaa ttacaaaaat tcaaaatttt cgggtttatt acaggacag cagagatcca    9180 gtttggggtt gctctggaaa actcatttgc accactgctg tgccttggaa tgctagttgg    9240
```

-continued

| | |
|---|---|
| agtaataaat ctctggaaca gatttggaat cacacgacct ggatggagtg ggacagagaa | 9300 |
| attaacaatt acacaagctt aatacactcc ttaattgaag aatcgcaaaa ccagcaagaa | 9360 |
| aagaatgaac aagaattatt ggaattagat aaatgggcaa gtttgtggaa ttggtttaac | 9420 |
| ataacaaatt ggctgtggta tataaaatta ttcataatga tagtaggagg cttggtaggt | 9480 |
| ttaagaatag ttttttgctgt actttctata gtgaatagag ttaggcaggg atattcacca | 9540 |
| ttatcgtttc agacccacct cccaaccccg aggggacccg acaggccctt aattaatccc | 9600 |
| ctgattctgt ggataaccgt attaccgcct ttgagtgagc tgcacacctg taggatcgta | 9660 |
| caggtaaagt gaaaggctac aataggacac ctgtaggatc gtacaggtgg taaactcgag | 9720 |
| agcgcccaat aacctgtagg atcgtacagg tagcgcacta gagagcgccc aataacctgt | 9780 |
| aggatcgtac aggtaaagtg aaaggctaca ataggacacc tgtaggatcg tacaggtggt | 9840 |
| aaactcgaga gcgcccaata acctgtagga tcgtacaggt aaagtgaaag gctacaatag | 9900 |
| gacacctgta ggatcgtaca ggtggtaaac tcgacctata taagcagagc tcgtttagtg | 9960 |
| aaccgtcaga tcgcctggag acgccatcca cgctgttttg acctccatag aagacaccgg | 10020 |
| gaccgatcca gcctccgcgg ccccgaattg | 10050 |

<210> SEQ ID NO 4
<211> LENGTH: 10287
<212> TYPE: DNA
<213> ORGANISM: Artificial Sequence
<220> FEATURE:
<223> OTHER INFORMATION: Synthetic

<400> SEQUENCE: 4

| | |
|---|---|
| cggccatcga taaggatccg cccctctccc tccccccccc ctaacgttac tggccgaagc | 60 |
| cgcttggaat aaggccggtg tgcgtttgtc tatatgttat tttccaccat attgccgtct | 120 |
| tttggcaatg tgagggcccg gaaacctggc cctgtcttct tgacgagcat tcctaggggt | 180 |
| cttttcccctc tcgccaaagg aatgcaaggt ctgttgaatg tcgtgaagga agcagttcct | 240 |
| ctggaagctt cttgaagaca acaacgtct gtagcgaccc tttgcaggca gcggaacccc | 300 |
| ccacctggcg acaggtgcct ctgcggccaa aagccacgtg tataagatac acctgcaaag | 360 |
| gcggcacaac cccagtgcca cgttgtgagt tggatagttg tggaaagagt caaatggctc | 420 |
| tcctcaagcg tattcaacaa ggggctgaag gatgcccaga aggtacccca ttgtatggga | 480 |
| tctgatctgg ggcctcggtg cacatgcttt acatgtgttt agtcgaggtt aaaaaaacgt | 540 |
| ctaggccccc cgaaccacgg ggacgtggtt ttcctttgaa aaacacgatg ataatatggc | 600 |
| cacaaccatg gcctcctccg aggacgtcat caaggagttc atgcgcttca aggtgcgcat | 660 |
| ggagggctcc gtgaacggcc acgagttcga gatcgagggc gagggcgagg ccgcccccta | 720 |
| cgagggcacc cagaccgcca agctgaaggt gaccaagggc ggccccctgc cttcgcctg | 780 |
| ggacatcctg tcccccccagt tccagtacgg ctccaaggtg tacgtgaagc accccgccga | 840 |
| catccccgac tacaagaagc tgtccttccc cgagggcttc aagtgggagc gcgtgatgaa | 900 |
| cttcgaggac ggcggcgtgg tgaccgtgac ccaggactcc tccctgcagg acggctcctt | 960 |
| catctacaag gtgaagttca tcggcgtgaa cttcccctcc gacggccccg taatgcagaa | 1020 |
| gaagactatg ggctgggagg cctccaccga gcgcctgtac ccccgcgacg gcgtgctgaa | 1080 |
| gggcgagatc cacaaggccc tgaagctgaa ggacggcggc cactacctgg tggagttcaa | 1140 |
| gtccatctac atggccaaga gcccgtgca gctgccccgg ctactacacg tggactccaa | 1200 |
| gctggacatc acctcccaca acgaggacta caccatcgtg gagcagtacg agcgcgccga | 1260 |

```
gggccgccac cacctgttcc tgtaggcggc cgcaatcaac ctctggatta caaaatttgt    1320
gaaagattga ctggtattct taactatgtt gctccttta cgctatgtgg atacgctgct     1380
ttaatgcctt tgtatcatgc tattacttcc cgtacggctt tcattttctc ctccttgtat    1440
aaatcctggt tgctgtctct ttatgaggag ttgtggcccg ttgtcaggca acgtggcgtg    1500
gtgtgcactg tgtttgctga cgcaaccccc actggttggg gcattgccac cacctatcaa    1560
ctcctttccg ggactttcgc tttcccctc cctattgcca cggcggaact cattgccgcc      1620
tgccttgccc gctgctggac aggggctcgg ctgttgggca ctgacaattc cgtggtgttg    1680
tcggggaagc tgacgtcctt tccatggctg ctcgcctgtg ttgccaactg gattctgcgc    1740
gggacgtcct tctgctacgt cccttcggcc ctcaatccag cggaccttcc ttcccgcggc    1800
ctgctgccga ttctgcggcc tcttccgcgt cttcgccttc gccctcagac gagtcggatc    1860 tcccttggg ccgcctcccc gcctgcctgc aggtttgtcg agacctagaa aaacatggag     1920
caatcacaag tagcaataca gcagctacca atgctgattg tgcctggcta aagcacaag     1980 aggaggagga ggtgggtttt ccagtcacac ctcaggtacc tttaagacca atgacttaca    2040
aggcagctgt agatcttagc cactttttaa aagaaaaggg gggactggaa gggctaattc    2100
actcccaacg aagacaagat ctgcttttg cttgtactgg gtctctctgg ttagaccaga      2160
tctgagcctg ggagctctct ggctaactag ggaacccact gcttaagcct caataaagct    2220
tgccttgagt gcttcaagta gtgtgtgccc gtctgttgtg tgactctggt aactagagat    2280
ccctcagacc cttttagtca gtgtggaaaa tctctagcag ggcccgttta aacccgctga    2340
tcagcctcga ctgtgccttc tagttgccag ccatctgttg tttgcccctc cccgtgcct      2400 tccttgaccc tggaaggtgc cactcccact gtcctttcct aataaaatga ggaaattgca    2460
tcgcattgtc tgagtaggtg tcattctatt ctggggggtg gggtggggca ggacagcaag    2520
ggggaggatt gggaagacaa tagcaggcat gctgggatg cggtgggctc tatggcttct      2580
gaggcggaaa gaaccagctg gggctctagg gggtatcccc acgcgccctg tagcggcgca    2640
ttaagcgcgg cgggtgtggt ggttacgcgc agcgtgaccg ctacacttgc cagcgcccta    2700
gcgcccgctc ctttcgcttt cttcccttcc tttctcgcca cgttcgccgg ctttccccgt    2760
caagctctaa atcggggcat ccctttaggg ttccgattta gtgctttacg gcacctcgac    2820
cccaaaaaac ttgattaggg tgatggttca cgtagtgggc catcgccctg atagacggtt    2880
tttcgccctt tgacgttgga gtccacgttc tttaatagtg gactcttgtt ccaaactgga    2940
acaacactca accctatctc ggtctattct tttgatttat aagggatttt ggggatttcg    3000
gcctattggt taaaaatga gctgatttaa caaaaattta acgcgaatta attctgtgga    3060
atgtgtgtca gttagggtgt ggaaagtccc caggctcccc aggcaggcag aagtatgcaa    3120
agcatgcatc tcaattagtc agcaaccagg tgtggaaagt ccccaggctc cccagcaggc    3180
agaagtatgc aaaagcatgca tctcaattag tcagcaacca tagtcccgcc ctaactccg    3240 cccatcccgc ccctaactcc gcccagttcc gcccattctc cgccccatgg ctgactaatt    3300
ttttttattt atgcagaggc cgaggccgcc tctgcctctg agctattcca gaagtagtga    3360
ggaggctttt ttggaggcct aggcttttgc aaaaagctcc cgggagcttg tatatccatt    3420
ttcggatctg atcagcacgt gttgacaatt aatcatcggc atagtatatc ggcatagtat    3480
aatacgacaa ggtgaggaac taaaccatgg ccaagttgac cagtgccgtt ccggtgctca    3540
ccgcgcgcga cgtcgccgga gcggtcgagt tctggaccga ccggctcggg ttctcccggg    3600
acttcgtgga ggacgacttc gccggtgtgg tccgggacga cgtgaccctg ttcatcagcg    3660
```

-continued

```
cggtccagga ccaggtggtg ccggacaaca ccctggcctg ggtgtgggtg cgcggcctgg    3720
acgagctgta cgccgagtgg tcggaggtcg tgtccacgaa cttccgggac gcctccgggc    3780
cggccatgac cgagatcggc gagcagccgt gggggcggga gttcgccctg cgcgacccgg    3840
ccggcaactg cgtgcacttc gtggccgagg agcaggactg acacgtgcta cgagatttcg    3900
attccaccgc cgccttctat gaaaggttgg gcttcggaat cgttttccgg gacgccggct    3960
ggatgatcct ccagcgcggg gatctcatgc tggagttctt cgcccacccc aacttgttta    4020
ttgcagctta taatggttac aaataaagca atagcatcac aaatttcaca aataaagcat    4080 tttttttcact gcattctagt tgtggttttgt ccaaactcat caatgtatct tatcatgtct    4140
gtataccgtc gacctctagc tagagcttgg cgtaatcatg gtcatagctg tttcctgtgt    4200
gaaattgtta tccgctcaca attccacaca acatacgagc cggaagcata aagtgtaaag    4260
cctggggtgc ctaatgagtg agctaactca cattaattgc gttgcgctca ctgcccgctt    4320
tccagtcggg aaacctgtcg tgccagctgc attaatgaat cggccaacgc gcggggagag    4380
gcggtttgcg tattgggcgc tcttccgctt cctcgctcac tgactcgctg cgctcggtcg    4440
ttcggctgcg gcgagcggta tcagctcact caaaggcggt aatacggtta tccacagaat    4500
caggggataa cgcaggaaag aacatgtgag caaaaggcca gcaaaaggcc aggaaccgta    4560
aaaaggccgc gttgctggcg ttttccata ggctccgccc ccctgacgag catcacaaaa    4620
atcgacgctc aagtcagagg tggcgaaacc cgacaggact ataaagatac caggcgtttc    4680
cccctggaag ctccctcgtg cgctctcctg ttccgaccct gccgcttacc ggatacctgt    4740
ccgcctttct cccttcggga agcgtggcgc tttctcaatg ctcacgctgt aggtatctca    4800
gttcggtgta ggtcgttcgc tccaagctgg gctgtgtgca cgaaccccc gttcagcccg    4860 accgctgcgc cttatccggt aactatcgtc ttgagtccaa cccggtaaga cacgacttat    4920
cgccactggc agcagccact ggtaacagga ttagcagagc gaggtatgta ggcggtgcta    4980
cagagttctt gaagtggtgg cctaactacg gctacactag aaggacagta tttggtatct    5040
gcgctctgct gaagccagtt accttcggaa aaagagttgg tagctcttga tccggcaaac    5100
aaaccaccgc tggtagcggt ggtttttttg tttgcaagca gcagattacg cgcagaaaaa    5160
aaggatctca agaagatcct ttgatctttt ctacggggtc tgacgctcag tggaacgaaa    5220
actcacgtta agggattttg gtcatgagat tatcaaaaag gatcttcacc tagatccttt    5280
taaattaaaa atgaagtttt aaatcaatct aaagtatata tgagtaaact tggtctgaca    5340
gttaccaatg cttaatcagt gaggcaccta tctcagcgat ctgtctattt cgttcatcca    5400
tagttgcctg actccccgtc gtgtagataa ctacgatacg ggagggctta ccatctggcc    5460
ccagtgctgc aatgataccg cgagacccac gctcaccggc tccagattta tcagcaataa    5520
accagccagc cggaagggcc gagcgcagaa gtggtcctgc aactttatcc gcctccatcc    5580
agtctattaa ttgttgccgg gaagctagag taagtagttc gccagttaat agtttgcgca    5640
acgttgttgc cattgctaca ggcatcgtgg tgtcacgctc gtcgtttggt atggcttcat    5700
tcagctccgg ttcccaacga tcaaggcgag ttacatgatc ccccatgttg tgcaaaaaag    5760
cggttagctc cttcggtcct ccgatcgttg tcagaagtaa gttggccgca gtgttatcac    5820
tcatggttat ggcagcactg cataattctc ttactgtcat gccatccgta agatgctttt    5880
ctgtgactgg tgagtactca accaagtcat tctgagaata gtgtatgcgg cgaccgagtt    5940
gctcttgccc ggcgtcaata cgggataata ccgcgccaca tagcagaact ttaaaagtgc    6000
tcatcattgg aaaacgttct cgggggcgaa aactctcaag gatcttaccg ctgttgagat    6060
```

```
ccagttcgat gtaacccact cgtgcaccca actgatcttc agcatctttt actttcacca    6120
gcgtttctgg gtgagcaaaa acaggaaggc aaaatgccgc aaaaaaggga ataagggcga    6180
cacggaaatg ttgaatactc atactcttcc tttttcaata ttattgaagc atttatcagg    6240
gttattgtct catgagcgga tacatatttg aatgtattta gaaaaataaa caaatagggg    6300
ttccgcgcac atttccccga aaagtgccac ctgacgtcga cggatcggga gatctcccga    6360
tcccctatgg tgcactctca gtacaatctg ctctgatgcc gcatagttaa gccagtatct    6420
gctccctgct tgtgtgttgg aggtcgctga gtagtgcgcg agcaaaattt aagctacaac    6480
aaggcaaggc ttgaccgaca attgcatgaa gaatctgctt agggttaggc gttttgcgct    6540
gcttcgcgat gtacgggcca gatatacgcg ttgacattga ttattgacta gttattaata    6600
gtaatcaatt acggggtcat tagttcatag cccatatatg gagttccgcg ttacataact    6660
tacggtaaat ggcccgcctg gctgaccgcc caacgacccc cgcccattga cgtcaataat    6720
gacgtatgtt cccatagtaa cgccaatagg gactttccat tgacgtcaat gggtggacta    6780
tttacggtaa actgcccact tggcagtaca tcaagtgtat catatgccaa gtacgccccc    6840
tattgacgtc aatgacggta aatggcccgc ctggcattat gcccagtaca tgaccttatg    6900
ggactttcct acttggcagt acatctacgt attagtcatc gctattacca tggtgatgcg    6960
gttttggcag tacatcaatg ggcgtggata gcggtttgac tcacggggat ttccaagtct    7020
ccaccccatt gacgtcaatg ggagtttgtt ttggcaccaa aatcaacggg actttccaaa    7080
atgtcgtaac aactccgccc cattgacgca aatgggcggt aggcgtgtac ggtgggaggt    7140
ctatataagc agagctctct ggctaactag agaacccact gcttactggc ttatcgaaat    7200
taatacgact cactataggg agacccaagc tggtttaaac ttaagcttgg taccgagctc    7260
actagtccag tgtggtggca gatatccagc acagtggcgg ccgctcgagt ctagagggcc    7320
cgttttgcct gtactgggtc tctctggtta gaccagatct gagcctggga gctctctggc    7380
taactaggga acccactgct taagcctcaa taaagcttgc cttgagtgct tcaagtagtg    7440
tgtgcccgtc tgttgtgtga ctctggtaac tagagatccc tcagaccctt ttagtcagtg    7500
tggaaaatct ctagcagtgg cgcccgaaca gggacttgaa agcgaaaggg aaaccagagg    7560
agctctctcg acgcaggact cggcttgctg aagcgcgcac ggcaagaggc gaggggcggc    7620
gactggtgag tacgccaaaa attttgacta gcggaggcta aaggagaga  gatgggtgcg    7680
agagcgtcag tattaagcgg gggagaatta gatcgcgatg gaaaaaatt  cggttaaggc    7740
caggggggaaa gaaaaaatat aaattaaaac atatagtatg ggcaagcagg gagctagaac    7800
gattcgcagt taatcctggc ctgttagaaa catcagaagg ctgtagacaa atactgggac    7860
agctacaacc atcccttcag acaggatcag aagaacttag atcattatat aatacagtag    7920
caaccctcta ttgtgtgcat caaaggatag agataaaaga caccaaggaa gctttagaca    7980
agatagagga gagcaaaac aaaagtaaga ccaccgcaca gcaagcggcc gctgatcttc    8040
agacctggag gaggagatat gagggacaat tggagaagtg aattatataa atataaagta    8100
gtaaaaattg aaccattagg agtagcaccc accaaggcaa agagaagagt ggtgcagaga    8160
gaaaaaagag cagtgggaat aggagctttg ttccttgggt tcttgggagc agcaggaagc    8220
actatgggcg cagcgtcaat gacgctgacg gtacaggcca gacaattatt gtctggtata    8280
gtgcagcagc agaacaattt gctgagggct attgaggcgc aacagcatct gttgcaactc    8340
acagtctggg gcatcaagca gctccaggca agaatcctgg ctgtggaaag atacctaaag    8400
gatcaacagc tcctggggat ttggggttgc tctggaaaac tcatttgcac cactgctgtg    8460
```

```
ccttggaatg ctagttggag taataaatct ctggaacaga tttggaatca cacgacctgg    8520
atggagtggg acagagaaat taacaattac acaagcttaa tacactcctt aattgaagaa    8580
tcgcaaaacc agcaagaaaa gaatgaacaa gaattattgg aattagataa atgggcaagt    8640
ttgtggaatt ggtttaacat aacaaattgg ctgtggtata taaaattatt cataatgata    8700
gtaggaggct tggtaggttt aagaatagtt tttgctgtac tttctatagt gaatagagtt    8760
aggcagggat attcaccatt atcgtttcag acccacctcc caaccccgag ggacccgac    8820 aggcccttaa ttaattggct ccggtgcccg tcagtgggca gagcgcacat cgcccacagt    8880
ccccgagaag ttgggggag gggtcggcaa ttgaaccggt gcctagagaa ggtgcgcgg    8940 ggtaaactgg gaaagtgatg tcgtgtactg gctccgcctt tttcccgagg gtgggggaga    9000
accgtatata agtgcagtag tcgccgtgaa cgttctttt cgcaacgggt ttgccgccag    9060
aacacaggta agtgccgtgt gtggttcccg cgggcctggc ctctttacgg gttatggccc    9120
ttgcgtgcct tgaattactt ccacctggct gcagtacgtg attcttgatc ccgagcttcg    9180
ggttggaagt gggtgggaga gttcgaggcc ttgcgcttaa ggagccccct cgcctcgtgc    9240
ttgagttgag gcctggcctg ggcgctgggg ccgccgcgtg cgaatctggt ggcaccttcg    9300
cgcctgtctc gctgctttcg ataagtctct agccattaa aattttgat gacctgctgc    9360 gacgctttt ttctggcaag atagtcttgt aaatgcgggc caagatctgc acactggtat    9420
ttcggttttt ggggccgcgg gcggcgacgg ggcccgtgcg tcccagcgca catgttcggc    9480 gaggcgggc ctgcgagcgc ggccaccgag aatcggacgg gggtagtctc aagctggccg    9540
gcctgctctg gtgcctggcc tcgcgccgcc gtgtatcgcc ccgccctggg cggcaaggct    9600
ggcccggtcg gcaccagttg cgtgagcgga aagatggccg cttcccggcc ctgctgcagg    9660
gagctcaaaa tggaggacgc ggcgctcggg agagcgggcg ggtgagtcac ccacacaaag    9720
gaaaagggcc tttccgtcct cagccgtcgc ttcatgtgac tccacggagt accgggcgcc    9780
gtccaggcac ctcgattagt tctcgagctt ttggagtacg tcgtctttag gttgggggga    9840
ggggttttat gcgatggagt ttccccacac tgagtgggtg gagactgaag ttaggccagc    9900
ttggcacttg atgtaattct ccttggaatt tgccctttt gagtttggat cttggttcat    9960
tctcaagcct cagacagtgg ttcaaagttt ttttcttcca tttcaggtgt cgtgaggaat   10020
tcggccatta cggcccgcca ccatgagcac catcgaggag agggtgaaga agatcatcgg   10080
cgagcagctg ggcgtgaagc aggaggaggt caccaacaac gccagcttcg tggaggacct   10140
gggcgccgac agcctggaca ccgtggagct ggtgatggcc ctggaggagg agttcgacac   10200
cgagatcccc gacgaggagg ccgagaagat caccaccgtg caggccgcca tcgactacat   10260
caacggccac caggcctgag gccgcct                                       10287

<210> SEQ ID NO 5
<211> LENGTH: 12730
<212> TYPE: DNA
<213> ORGANISM: Artificial Sequence
<220> FEATURE:
<223> OTHER INFORMATION: Synthetic

<400> SEQUENCE: 5
cgcgccaagc tagcaagtta acaaatcgat ccggatccgc ccctctccct cccccccccc     60
taacgttact ggccgaagcc gcttggaata aggccggtgt gcgtttgtct atatgttatt    120
ttccaccata ttgccgtctt ttggcaatgt gagggcccgg aaacctggcc ctgtcttctt    180
gacgagcatt cctaggggtc tttcccctct cgccaaagga atgcaaggtc tgttgaatgt    240
```

```
cgtgaaggaa gcagttcctc tggaagcttc ttgaagacaa acaacgtctg tagcgaccct    300
ttgcaggcag cggaaccccc cacctggcga caggtgcctc tgcggccaaa agccacgtgt    360
ataagataca cctgcaaagg cggcacaacc ccagtgccac gttgtgagtt ggatagttgt    420
ggaaagagtc aaatggctct cctcaagcgt attcaacaag gggctgaagg atgcccagaa    480
ggtacsccat tgtatgggat ctgatctggg gcctcggtgc acatgcttta catgtgttta    540
gtcgaggtta aaaaaacgtc taggcccccc gaaccacggg gacgtggttt tcctttgaaa    600
aacacgatga taatatggcc acaaccatgg tgagcaaggg cgaggagctg ttcaccgggg    660
tggtgcccat cctggtcgag ctggacgcg acgtaaacgg ccacaagttc agcgtgtccg    720
gcgagggcga gggcgatgcc acctacggca agctgaccct gaagttcatc tgcaccaccg    780
gcaagctgcc cgtgccctgg cccaccctcg tgaccaccct gacctacggc gtgcagtgct    840
tcagccgcta ccccgaccac atgaagcagc acgacttctt caagtccgcc atgcccgaag    900
gctacgtcca ggagcgcacc atcttcttca aggacgacgg caactacaag acccgcgccg    960
aggtgaagtt cgagggcgac accctggtga accgcatcga gctgaagggc atcgacttca   1020
aggaggacgg caacatcctg ggcacaagc tggagtacaa ctacaacagc cacaacgtct   1080
atatcatggc cgacaagcag aagaacggca tcaaggtgaa cttcaagatc cgccacaaca   1140
tcgaggacgg cagcgtgcag ctcgccgacc actaccagca gaacacccc atcggcgacg   1200 gccccgtgct gctgcccgac aaccactacc tgagcaccca gtccgccctg agcaaagacc   1260
ccaacgagaa gcgcgatcac atggtcctgc tggagttcgt gaccgccgcc gggatcactc   1320
tcggcatgga cgagctgtac aagtaagcgg ccgcaatcaa cctctggatt acaaaatttg   1380
tgaaagattg actggtattc ttaactatgt tgctcctttt acgctatgtg gatacgctgc   1440
tttaatgcct ttgtatcatg ctattacttc ccgtacggct tcatttttct cctccttgta   1500
taaatcctgg ttgctgtctc tttatgagga gttgtggccc gttgtcaggc aacgtggcgt   1560
ggtgtgcact gtgtttgctg acgcaacccc cactggttgg gcattgcca ccacctatca   1620 actccttttcc gggactttcg ctttccccct ccctattgcc acggcggaac tcattgccgc   1680
ctgccttgcc cgctgctgga caggggctcg gctgttgggc actgacaatt ccgtggtgtt   1740
gtcggggaag ctgacgtcct ttccatggct gctcgcctgt gttgccaact ggattctgcg   1800
cgggacgtcc ttctgctacg tcccttcggc cctcaatcca gcggaccttc cttcccgcgg   1860
cctgctgccg gttctgcggc ctcttccgcg tcttcgcctt cgccctcaga cgagtcggat   1920
ctccctttgg gccgcctccc cgcctgctgc aggtttgtc gagacctaga aaaacatgga   1980
gcaatcacaa gtagcaatac agcagctacc aatgctgatt gtgcctggct agaagcacaa   2040
gaggaggagg aggtgggttt tccagtcaca cctcaggtac cttaagacc aatgacttac   2100 aaggcagctg tagatcttag ccactttta aaagaaaagg ggggactgga agggctaatt   2160
cactcccaac gaagacaaga tctgcttttt gcttgtactg ggtctctctg ttagaccag    2220 atctgagcct gggagctctc tggctaacta gggaacccac tgcttaagcc tcaataaagc   2280
ttgccttgag tgcttcaagt agtgtgtgcc cgtctgttgt gtgactctgg taactagaga   2340
tccctcagac ccttttagtc agtgtggaaa atctctagca gggcccgttt aaacccgctg   2400
atcagcctcg actgtgcctt ctagttgcca gccatctgtt gtttgcccct cccccgtgcc   2460
ttccttgacc ctggaaggtg ccactcccac tgtccttttcc taataaaatg aggaaattgc   2520
atcgcattgt ctgagtaggt gtcattctat tctgggggt ggggtggggc aggacagcaa   2580
gggggaggat tgggaagaca atagcaggca tgctgggat gcggtgggct ctatggcttc   2640
```

```
tgaggcggaa agaaccagct ggggctctag ggggtatccc cacgcgccct gtagcggcgc    2700
attaagcgcg gcgggtgtgg tggttacgcg cagcgtgacc gctacacttg ccagcgccct    2760
agcgcccgct cctttcgctt tcttcccttc ctttctcgcc acgttcgccg gctttccccg    2820
tcaagctcta aatcggggca tccctttagg gttccgattt agtgctttac ggcacctcga    2880
ccccaaaaaa cttgattagg gtgatggttc acgtagtggg ccatcgccct gatagacggt    2940
ttttcgccct tgacgttgg agtccacgtt ctttaatagt ggactcttgt tccaaactgg     3000
aacaacactc aaccctatct cggtctattc ttttgattta taagggattt tggggatttc    3060
ggcctattgg ttaaaaaatg agctgattta acaaaaattt aacgcgaatt aattctgtgg    3120
aatgtgtgtc agttagggtg tggaaagtcc ccaggctccc caggcaggca gaagtatgca    3180
aagcatgcat ctcaattagt cagcaaccag gtgtggaaag tccccaggct ccccagcagg    3240
cagaagtatg caaagcatgc atctcaatta gtcagcaacc atagtcccgc ccctaactcc    3300
gcccatcccg cccctaactc cgcccagttc cgcccattct ccgccccatg gctgactaat    3360 ttttttatt tatgcagagg ccgaggccgc ctctgcctct gagctattcc agaagtagtg     3420
aggaggcttt tttggaggcc taggcttttg caaaaagctc ccgggagctt gtatatccat    3480
tttcggatct gatcagcacg tgttgacaat taatcatcgg catagtatat cggcatagta    3540
taatacgaca aggtgaggaa ctaaaccatg gccaagttga ccagtgccgt tccggtgctc    3600
accgcgcgcg acgtcgccgg agcggtcgag ttctggaccg accggctcgg gttctcccgg    3660
gacttcgtgg aggacgactt cgccggtgtg gtccgggacg acgtgaccct gttcatcagc    3720
gcggtccagg accaggtggt gccggacaac accctggcct gggtgtgggt gcgcggcctg    3780
gacgagctgt acgccgagtg gtcggaggtc gtgtccacga acttccggga cgcctccggg    3840
ccggccatga ccgagatcgg cgagcagccg tggggcgggg agttcgccct gcgcgacccc    3900
gccggcaact gcgtgcactt cgtggccgag gagcaggact gacacgtgct acgagatttc    3960
gattccaccg ccgccttcta tgaaaggttg gcttcggaa tcgttttccg ggacgccggc     4020
tggatgatcc tccagcgcgg ggatctcatg ctggagttct cgccccaccc caacttgttt    4080
attgcagctt ataatggtta caaataaagc aatagcatca caaatttcac aaataaagca    4140
tttttttcac tgcattctag ttgtggtttg tccaaactca tcaatgtatc ttatcatgtc    4200
tgtataccgt cgacctctag ctagagcttg gcgtaatcat ggtcatagct gtttcctgtg    4260
tgaaattgtt atccgctcac aattccacac aacatacgag ccggaagcat aaagtgtaaa    4320
gcctggggtg cctaatgagt gagctaactc acattaattg cgttgcgctc actgcccgct    4380
ttccagtcgg gaaacctgtc gtgccagctg cattaatgaa tcggccaacg cgcggggaga    4440
ggcggtttgc gtattgggcg ctcttccgct tcctcgctca ctgactcgct gcgctcggtc    4500
gttcggctgc ggcgagcggt atcagctcac tcaaaggcgg taatacggtt atccacagaa    4560 tcagggata acgcaggaaa gaacatgtga gcaaaaggcc agcaaaggc caggaaccgt       4620 aaaaaggccg cgttgctggc gttttccat aggctccgcc cccctgacga gcatcacaaa     4680
aatcgacgct caagtcagag gtggcgaaac ccgacaggac tataaagata ccaggcgttt    4740
ccccctggaa gctccctcgt gcgctctcct gttccgaccc tgccgcttac cggatacctg    4800
tccgcctttc tcccttcggg aagcgtggcg ctttctcaat gctcacgctg taggtatctc    4860
agttcggtgt aggtcgttcg ctccaagctg ggctgtgtgc acgaaccccc cgttcagccc    4920
gaccgctgcg ccttatccgg taactatcgt cttgagtcca acccggtaag acacgactta    4980
tcgccactgg cagcagccac tggtaacagg attagcagag cgaggtatgt aggcggtgct    5040
```

```
acagagttct tgaagtggtg gcctaactac ggctacacta gaaggacagt atttggtatc   5100
tgcgctctgc tgaagccagt taccttcgga aaaagagttg gtagctcttg atccggcaaa   5160
caaaccaccg ctggtagcgg tggttttttt gtttgcaagc agcagattac gcgcagaaaa   5220
aaaggatctc aagaagatcc tttgatcttt tctacgggt ctgacgctca gtggaacgaa    5280
aactcacgtt aagggatttt ggtcatgaga ttatcaaaaa ggatcttcac ctagatcctt   5340
ttaaattaaa aatgaagttt taaatcaatc taaagtatat atgagtaaac ttggtctgac   5400
agttaccaat gcttaatcag tgaggcacct atctcagcga tctgtctatt tcgttcatcc   5460
atagttgcct gactccccgt cgtgtagata actacgatac gggagggctt accatctggc   5520
cccagtgctg caatgatacc gcgagaccca cgctcaccgg ctccagattt atcagcaata   5580
aaccagccag ccggaagggc cgagcgcaga agtggtcctg caactttatc cgcctccatc   5640
cagtctatta attgttgccg ggaagctaga gtaagtagtt cgccagttaa tagtttgcgc   5700
aacgttgttg ccattgctac aggcatcgtg gtgtcacgct cgtcgtttgg tatggcttca   5760
ttcagctccg gttcccaacg atcaaggcga gttacatgat cccccatgtt gtgcaaaaaa   5820
gcggttagct ccttcggtcc tccgatcgtt gtcagaagta agttggccgc agtgttatca   5880
ctcatggtta tggcagcact gcataattct cttactgtca tgccatccgt aagatgcttt   5940
tctgtgactg gtgagtactc aaccaagtca ttctgagaat agtgtatgcg gcgaccgagt   6000
tgctcttgcc cggcgtcaat acgggataat accgcgccac atagcagaac tttaaaagtg   6060
ctcatcattg gaaaacgttc ttcggggcga aaactctcaa ggatcttacc gctgttgaga   6120
tccagttcga tgtaacccac tcgtgcaccc aactgatctt cagcatcttt tactttcacc   6180
agcgtttctg ggtgagcaaa aacaggaagg caaaatgccg caaaaaaggg aataagggcg   6240
acacggaaat gttgaatact catactcttc cttttcaat attattgaag catttatcag    6300
ggttattgtc tcatgagcgg atacatattt gaatgtattt agaaaaataa acaaataggg   6360
gttccgcgca catttccccg aaaagtgcca cctgacgtcg acggatcggg agatctcccg   6420 atccccatg gtgcactctc agtacaatct gctctgatgc cgcatagtta agccagtatc    6480
tgctccctgc ttgtgtgttg gaggtcgctg agtagtgcgc gagcaaaatt taagctacaa   6540
caaggcaagg cttgaccgac aattgcatga agaatctgct tagggttagg cgttttgcgc   6600
tgcttcgcga tgtacgggcc agatatacgc gttgacattg attattgact agttattaat   6660
agtaatcaat tacggggtca ttagttcata gcccatatat ggagttccgc gttacataac   6720
ttacggtaaa tggcccgcct ggctgaccgc ccaacgaccc cgcccattg acgtcaataa     6780 tgacgtatgt tcccatagta acgccaatag ggactttcca ttgacgtcaa tgggtggact   6840
atttacggta aactgcccac ttggcagtac atcaagtgta tcatatgcca agtacgcccc   6900
ctattgacgt caatgacggt aaatggcccg cctggcatta tgcccagtac atgaccttat   6960
gggactttcc tacttggcag tacatctacg tattagtcat cgctattacc atggtgatgc   7020
ggttttggca gtacatcaat gggcgtggat agcggtttga ctcacgggga tttccaagtc   7080
tccaccccat tgacgtcaat gggagtttgt tttggcacca aaatcaacgg gactttccaa   7140
aatgtcgtaa caactccgcc ccattgacgc aaatgggcgg taggcgtgta cggtgggagg   7200
tctatataag cagagctctc tggctaacta gagaacccac tgcttactgg cttatcgaaa   7260
ttaatacgac tcactatagg gagacccaag ctggtttaaa cttaagcttg gtaccgagct   7320
cactagtcca gtgtggtggc agatatccag cacagtggcg gccgctcgag tctagagggc   7380
ccgttttgcc tgtactgggt ctctctggtt agaccagatc tgagcctggg agctctctgg   7440
```

```
ctaactaggg aacccactgc ttaagcctca ataaagcttg ccttgagtgc ttcaagtagt   7500
gtgtgcccgt ctgttgtgtg actctggtaa ctagagatcc ctcagaccct tttagtcagt   7560
gtggaaaatc tctagcagtg gcgcccgaac agggacttga aagcgaaagg gaaaccagag   7620
gagctctctc gacgcaggac tcggcttgct gaagcgcgca cggcaagagg cgaggggcgg   7680
cgactggtga gtacgccaaa aattttgact agcggaggct agaaggagag agatgggtgc   7740
gagagcgtca gtattaagcg ggggagaatt agatcgcgat gggaaaaaat tcggttaagg   7800
ccagggggaa agaaaaaata taaattaaaa catatagtat gggcaagcag ggagctagaa   7860
cgattcgcag ttaatcctgg cctgttagaa acatcagaag gctgtagaca atactggga   7920 cagctacaac catcccttca gacaggatca gaagaactta gatcattata taatacagta   7980
gcaaccctct attgtgtgca tcaaggata gagataaaag acaccaagga agctttagac   8040
aagatagagg aagagcaaaa caaaagtaag accaccgcac agcaagcggc cgctgatctt   8100
cagacctgga ggaggagata tgagggacaa ttggagaagt gaattatata aatataaagt   8160
agtaaaaatt gaaccattag gagtagcacc caccaaggca aagagaagag tggtgcagag   8220
agaaaaaaga gcagtgggaa taggagcttt gttccttggg ttcttgggag cagcaggaag   8280
cactatgggc gcagcgtcaa tgacgctgac ggtacaggcc agacaattat tgtctggtat   8340
agtgcagcag cagaacaatt tgctgagggc tattgaggcg caacagcatc tgttgcaact   8400
cacagtctgg ggcatcaagc agctccaggc aagaatcctg gctgtggaaa gatacctaaa   8460
ggatcaacag ctcctgggga tttggggttg ctctggaaaa ctcatttgca ccactgctgt   8520
gccttggaat gctagttgga gtaataaatc tctggaacag atttggaatc acacgacctg   8580
gatggagtgg gacagagaaa ttaacaatta cacaagctta atacactcct taattgaaga   8640
atcgcaaaac cagcaagaaa agaatgaaca agaattattg gaattagata atgggcaag   8700 tttgtggaat tggtttaaca taacaaattg gctgtggtat ataaaattat tcataatgat   8760
agtaggaggc ttggtaggtt taagaatagt ttttgctgta ctttctatag tgaatagagt   8820
taggcaggga tattcaccat tatcgtttca gacccacctc ccaaccccga ggggacccga   8880
caggccctta attaagctac atcatcaata atatacctta ttttggattg aagccaatat   8940
gataatgagg gggtggagtt tgtgacgtgg cgcggggcgt gggaacgggg cgggtgacgt   9000
agtagtgtgt cggaagtgtg atgttgcaag tgtggcggaa cacatgtaag cgacggatgt   9060
ggcaaaagtg acgttttttgg tgtgcgccgg tgtacacagg aagtgacaat tttcgcgcgg   9120 tttttaggcgg atgttgtagt aaatttgggc gtaaccgagt aagatttggc catttttcgcg   9180 ggaaaactga ataagaggaa gtgaaatctg aataattttg tgttactcat agcgcgtaat   9240
atttgtctag ggagatccga gctttgcaaa gatggataaa gttttaaaca gagaggaatc   9300
tttgcagcta atggaccttc taggtcttga aaggagtggg aattggctcc ggtgcccgtc   9360
agtgggcaga gcgcacatcg cccacagtcc ccgagaagtt gggggagggg tcggcaattc   9420
gaaccggtgc ctagagaagg tggcgcgggg taaactggga aagtgatgtc gtgtactggc   9480
tccgcctttt tcccgagggt gggggagaac cgtatataag tgcagtagtc gccgtgaacg   9540
ttctttttcg caacgggttt gccgccagaa cacaggtaag tgccgtgtgt ggttcccgcg   9600
ggcctggcct ctttacgggt tatggccctt gcgtgccttg aattacttcc acctggctgc   9660
agtacgtgat tcttgatccc gagcttcggg ttggaagtgg gtgggagagt tcgaggcctt   9720
gcgcttaagg agccccttcg cctcgtgctt gagttgaggc ctggcctggg cgctgggggcc   9780 gccgcgtgcg aatctggtgg caccttcgcg cctgtctcgc tgctttcgat aagtctctag   9840
```

```
ccatttaaaa tttttgatga cctgctgcga cgcttttttt ctggcaagat agtcttgtaa      9900
atgcgggcca agatctgcac actggtattt cggttttgg ggccgcgggc ggcgacgggg       9960
cccgtgcgtc ccagcgcaca tgttcggcga ggcggggcct gcgagcgcgg ccaccgagaa     10020
tcggacgggg gtagtctcaa gctggccggc ctgctctggt gcctggcctc cgccgccgt      10080 gtatcgcccc gccctgggcg gcaaggctgg cccggtcggc accagttgcg tgagcggaaa    10140 gatgccgct tcccgccct gctgcaggga gctcaaaatg gaggacgcgg cgctcggag        10200 agcgggcggg tgagtcaccc acacaaagga aaagggcctt tccgtcctca gccgtcgctt    10260
catgtgactc cacggagtac cgggcgccgt ccaggcacct cgattagttc tcgagctttt    10320
ggagtacgtc gtctttaggt tgggggagg ggttttatgc gatggagttt ccccacactg     10380
agtgggtgga gactgaagtt aggccagctt ggcacttgat gtaattctcc ttggaatttg    10440 cccttttga gtttggatct tggttcattc tcaagcctca gacagtggtt caaagttttt    10500
ttcttccatt tcaggtgtcg tgaggaattc gctactagct cgagaagaat tcaaggcgcg    10560
ccgccaccat gctttttagc tttttcgaa atttgtgccg tgttttgtat cgcgttcgcg    10620
ttacgggtga cacccaggca ctgaagggcg agcgcgttct aattacgcct aatcacgtct    10680
cttttattga tggcatttg cttggactgt ttttacctgt gcgtccagtg tttgccgttt     10740
acacctcaat aagccaacag tggtatatgc gttggctgaa atcatttatc gactttgttc    10800
ctctcgaccc gacgcaacct atggctatta acatctggt acgtctggtg gaacagggcc     10860
gaccagtggt gattttccct gaaggacgca tcaccacgac aggctcgctg atgaaaatct    10920
acgatggcgc gggttttgtc gcggcgaagt ctggtgcaac ggttattcct gtgcgtattg    10980
aaggggcgga acttacgcac ttcagccgcc tgaaaggtct ggttaaacgt cgcttgttcc    11040
cgcaaattac tctgcatatt ttgccaccaa cgcaggtggc gatgccggat gcgccgcgtg    11100
cccgtgaccg tcgcaaaatc gctggcgaaa tgctgcatca ataatgatg gaagcgcgaa     11160 tggcggtgcg cccgcgtgaa acgctgtacg aatctttact gagtgcaatg taccgcttcg    11220
gagccgggaa gaaatgtgtc gaagacgtca actttacccc agactcctat cgcaaattgc    11280
ttacgaaaac gctgtttgtt ggacgcatcc ttgaaaaata cagtgttgaa ggcgaacgca    11340
tcggcttaat gctgcccaat gcaggcatca gtgcggcagt gatttttggg gccatcgccc    11400
gtcgccgcat gcccgcaatg atgaactaca ctgccggggt aaaagggctg accagtgcta    11460
ttacggcggc tgaaatcaaa accatcttca cttcccgcca gtttctcgat aaaggcaaac    11520
tctggcatct gccggagcaa cttactcagg tgcgctgggt ctatctggaa gatttaaaag    11580
cagatgtcac cactgccgac aaagtatgga tcttcgctca tttgctgatg ccgcgtctgg    11640
cacaggttaa acagcagccg gaagaagagg cgctgatcct ttttacctcc ggttctgaag    11700
gccatccgaa aggcgtcgtc catagccata aaagcattct ggcgaatgtc gagcagatta    11760
aaacgattgc cgacttcacc accaacgatc gctttatgtc ggcgttaccg ctgtttcact    11820
cctttgggct gacggtaggc ctgtttacgc cactgcttac aggtgcagaa gtgttccttt    11880
atccaagccc gctgcattac cgcattgtgc cggagttggt gtatgaccgc agttgcaccg    11940
tgttgttcgg cacctcgact ttcctcggtc actacgcgcg tttcgccaac ccgtatgact    12000
tctatcgtct acgctatgtg gtggcaggcg cagaaaaatt acaagaaagt accaaacagc    12060
tttggcagga taaatttggc ctgcgcatcc ttgaaggcta cggcgtgacc gaatgcgcgc    12120
ctgtcgtttc tatcaacgta ccgatggcgg cgaaacccgg tacggtaggg cgtattctac    12180
caggaatgga tgcgcgcctg ttgtcggtcc ctggtatcga agagggcgga cgcctgcaac    12240
```

| | |
|---|---|
| tgaaagggcc gaacataatg aacggctatc tgcgggtgga aagccaggt gtactggaag | 12300 |
| tgcccaccgc cgagaatgtt cgcggcgaaa tggagcgcgg ctggtatgac actggcgata | 12360 |
| ttgtgcgttt tgacgagcag ggctttgtgc agattcaggg ccgcgcaaaa cgctttgcca | 12420 |
| aaattgcagg cgaaatggtg tcgctggaaa tggtggaaca actggcactt ggtgtttcgc | 12480 |
| cagataaagt ccatgccact gcgattaaga gcgatgccag caaaggcgag gcactggtgc | 12540 |
| ttttcaccac agataacgaa ctgacgcgcg ataagttgca acagtatgcc cgcgagcacg | 12600 |
| gcgtgccgga gcttgctgta ccgcgcgata ttcgctatct gaaacagatg ccattacttg | 12660 |
| gcagcggcaa acctgacttt gtcacgttga aaagctgggt agacgaagcg gaacaacacg | 12720 |
| atgagtgagg | 12730 |

<210> SEQ ID NO 6
<211> LENGTH: 10773
<212> TYPE: DNA
<213> ORGANISM: Artificial Sequence
<220> FEATURE:
<223> OTHER INFORMATION: Synthetic

<400> SEQUENCE: 6

| | |
|---|---|
| cggccatcga taaggatccg ccctctccc tcccccccc ctaacgttac tggccgaagc | 60 |
| cgcttggaat aaggccggtg tgcgtttgtc tatatgttat tttccaccat attgccgtct | 120 |
| tttggcaatg tgagggcccg gaaacctggc cctgtcttct tgacgagcat tcctagggg | 180 |
| ctttcccctc tcgccaaagg aatgcaaggt ctgttgaatg tcgtgaagga agcagttcct | 240 |
| ctggaagctt cttgaagaca acaacgtctg tagcgaccc tttgcaggca gcggaaccc | 300 |
| ccacctggcg acaggtgcct ctgcggccaa aagccacgtg tataagatac acctgcaaag | 360 |
| gcggcacaac cccagtgcca cgttgtgagt tggatagttg tggaaagagt caaatggctc | 420 |
| tcctcaagcg tattcaacaa ggggctgaag gatgcccaga aggtaccca ttgtatggga | 480 |
| tctgatctgg ggcctcggtg cacatgcttt acatgtgttt agtcgaggtt aaaaaaacgt | 540 |
| ctaggccccc cgaaccacgg ggacgtggtt ttcctttgaa aaacacgatg ataatatggc | 600 |
| cacaaccatg gcctcctccg aggacgtcat caaggagttc atgcgcttca aggtgcgcat | 660 |
| ggagggctcc gtgaacggcc acgagttcga gatcgagggc gagggcgagg ccgcccccta | 720 |
| cgagggcacc cagaccgcca agctgaaggt gaccaagggc ggccccctgc ccttcgcctg | 780 |
| ggacatcctg tccccccagt tccagtacgg ctccaaggtg tacgtgaagc accccgccga | 840 |
| catccccgac tacaagaagc tgtccttccc cgagggcttc aagtgggagc gcgtgatgaa | 900 |
| cttcgaggac ggcggcgtgg tgaccgtgac ccaggactcc tccctgcagg acggctcctt | 960 |
| catctacaag gtgaagttca tcggcgtgaa cttccccctcc gacggccccg taatgcagaa | 1020 |
| gaagactatg ggctgggagg cctccaccga gcgcctgtac cccgcgacg gcgtgctgaa | 1080 |
| gggcgagatc cacaaggccc tgaagctgaa ggacggcggc cactacctgg tggagttcaa | 1140 |
| gtccatctac atggccaaga gcccgtgca gctgcccggc tactactacg tggactccaa | 1200 |
| gctggacatc acctcccaca acgaggacta caccatcgtg gagcagtacg agcgcgccga | 1260 |
| gggccgccac cacctgttcc tgtaggcggc cgcaatcaac ctctggatta caaaatttgt | 1320 |
| gaaagattga ctggtattct taactatgtt gctccttta cgctatgtgg atacgctgct | 1380 |
| ttaatgcctt tgtatcatgc tattacttcc cgtacggctt tcattttctc ctccttgtat | 1440 |
| aaatcctggt tgctgtctct ttatgaggag ttgtggcccg ttgtcaggca acgtggcgtg | 1500 |
| gtgtgcactg tgtttgctga cgcaaccccc actggttggg gcattgccac cacctatcaa | 1560 |

```
ctcctttccg ggactttcgc tttcccccctc cctattgcca cggcggaact cattgccgcc    1620
tgccttgccc gctgctggac aggggctcgg ctgttgggca ctgacaattc cgtggtgttg    1680
tcggggaagc tgacgtcctt tccatggctg ctcgcctgtg ttgccaactg gattctgcgc    1740
gggacgtcct tctgctacgt cccttcggcc ctcaatccag cggaccttcc ttcccgcggc    1800
ctgctgccgg ttctgcggcc tcttccgcgt cttcgccttc gccctcagac gagtcggatc    1860 tcccttttggg ccgcctcccc gcctgcctgc aggtttgtcg agacctagaa aaacatggag   1920
caatcacaag tagcaataca gcagctacca atgctgattg tgcctggcta aagcacaag    1980 aggaggagga ggtgggtttt ccagtcacac ctcaggtacc tttaagacca atgacttaca    2040
aggcagctgt agatcttagc cacttttttaa aagaaaaggg gggactggaa gggctaattc    2100
actcccaacg aagacaagat ctgcttttttg cttgtactgg gtctctctgg ttagaccaga   2160
tctgagcctg ggagctctct ggctaactag ggaacccact gcttaagcct caataaagct   2220
tgccttgagt gcttcaagta gtgtgtgccc gtctgttgtg tgactctggt aactagagat   2280
ccctcagacc cttttagtca gtgtggaaaa tctctagcag ggcccgttta aacccgctga    2340
tcagcctcga ctgtgccttc tagttgccag ccatctgttg tttgccctc ccccgtgcct     2400 tccttgaccc tggaaggtgc cactcccact gtcctttcct aataaaatga ggaaattgca    2460
tcgcattgtc tgagtaggtg tcattctatt ctgggggtg gggtggggca ggacagcaag    2520
ggggaggatt gggaagacaa tagcaggcat gctggggatg cggtgggctc tatggcttct    2580
gaggcggaaa gaaccagctg gggctctagg gggtatcccc acgcgccctg tagcggcgca    2640
ttaagcgcgg cgggtgtggt ggttacgcgc agcgtgaccg ctacacttgc cagcgcccta    2700
gcgcccgctc ctttcgcttt cttcccttcc tttctcgcca cgttcgccgg ctttccccgt    2760
caagctctaa atcggggcat ccctttaggg ttccgattta gtgctttacg gcacctcgac    2820
cccaaaaaac ttgattaggg tgatggttca cgtagtgggc catcgccctg atagacggtt    2880
tttcgccctt tgacgttgga gtccacgttc tttaatagtg gactcttgtt ccaaactgga    2940
acaacactca accctatctc ggtctattct tttgatttat aagggatttt ggggatttcg    3000
gcctattggt taaaaaatga gctgatttaa caaaaattta acgcgaatta attctgtgga    3060
atgtgtgtca gttagggtgt ggaaagtccc caggctcccc aggcaggcag aagtatgcaa    3120
agcatgcatc tcaattagtc agcaaccagg tgtggaaagt ccccaggctc cccagcaggc    3180
agaagtatgc aaagcatgca tctcaattag tcagcaacca tagtcccgcc cctaactccg    3240
cccatcccgc cctaactccg cccagttccc gcccattctc cgccccatgg ctgactaatt    3300
ttttttattt atgcagaggc cgaggccgcc tctgcctctg agctattcca gaagtagtga    3360
ggaggctttt ttggaggcct aggcttttgc aaaaagctcc cgggagcttg tatatccatt    3420
ttcggatctg atcagcacgt gttgacaatt aatcatcggc atagtatatc ggcatagtat    3480
aatacgacaa ggtgaggaac taaaccatgc caagttgac cagtgccgtt ccggtgctca    3540
ccgcgcgcga cgtcgccgga gcggtcgagt tctggaccga ccggctcggg ttctcccggg    3600
acttcgtgga ggacgacttc gccggtgtgg tccgggacga cgtgaccctg ttcatcagcg    3660
cggtccagga ccaggtggtg ccggacaaca ccctggcctg ggtgtgggtg cgcggcctgg    3720 acagctgta cgccgagtgg tcggaggtcg tgtccacgaa cttccgggac gcctccgggc    3780
cggccatgac cgagatcgc gagcagccgt gggggcggga gttcgccctg cgcgacccgg    3840
ccggcaactg cgtgcacttc gtggccgagg agcaggactg acacgtgcta cgagatttcg    3900
attccaccgc cgccttctat gaaaggttgg gcttcggaat cgttttccgg gacgccggct    3960
```

```
ggatgatcct ccagcgcggg gatctcatgc tggagttctt cgcccacccc aacttgttta    4020
ttgcagctta taatggttac aaataaagca atagcatcac aaatttcaca aataaagcat    4080
ttttttcact gcattctagt tgtggtttgt ccaaactcat caatgtatct tatcatgtct    4140
gtataccgtc gacctctagc tagagcttgg cgtaatcatg gtcatagctg tttcctgtgt    4200
gaaattgtta tccgctcaca attccacaca acatacgagc cggaagcata aagtgtaaag    4260
cctggggtgc ctaatgagtg agctaactca cattaattgc gttgcgctca ctgcccgctt    4320
tccagtcggg aaacctgtcg tgccagctgc attaatgaat cggccaacgc gcgggagag    4380 gcggtttgcg tattgggcgc tcttccgctt cctcgctcac tgactcgctg cgctcggtcg    4440
ttcggctgcg gcgagcggta tcagctcact caaaggcggt aatacggtta ccacagaat    4500 caggggataa cgcaggaaag aacatgtgag caaaaggcca gcaaaaggcc aggaaccgta    4560
aaaaggccgc gttgctggcg tttttccata ggctccgccc ccctgacgag catcacaaaa    4620
atcgacgctc aagtcagagg tggcgaaacc cgacaggact ataaagatac caggcgtttc    4680
cccctggaag ctccctcgtg cgctctcctg ttccgaccct gccgcttacc ggatacctgt    4740
ccgcctttct cccttcggga agcgtggcgc tttctcaatg ctcacgctgt aggtatctca    4800
gttcggtgta ggtcgttcgc tccaagctgg gctgtgtgca cgaaccccc gttcagcccg    4860 accgctgcgc cttatccggt aactatcgtc ttgagtccaa cccggtaaga cacgacttat    4920
cgccactggc agcagccact ggtaacagga ttagcagagc gaggtatgta ggcggtgcta    4980
cagagttctt gaagtggtgg cctaactacg gctacactag aaggacagta tttggtatct    5040
gcgctctgct gaagccagtt accttcggaa aaagagttgg tagctcttga tccggcaaac    5100
aaaccaccgc tggtagcggt ggtttttttg tttgcaagca gcagattacg cgcagaaaaa    5160
aaggatctca agaagatcct ttgatctttt ctacggggtc tgacgctcag tggaacgaaa    5220
actcacgtta agggattttg gtcatgagat tatcaaaaag gatcttcacc tagatccttt    5280
taaattaaaa atgaagtttt aaatcaatct aaagtatata tgagtaaact tggtctgaca    5340
gttaccaatg cttaatcagt gaggcaccta tctcagcgat ctgtctattt cgttcatcca    5400
tagttgcctg actccccgtc gtgtagataa ctacgatacg ggagggctta ccatctggcc    5460
ccagtgctgc aatgataccg cgagacccac gctcaccggc tccagattta tcagcaataa    5520
accagccagc cggaagggcc gagcgcagaa gtggtcctgc aactttatcc gcctccatcc    5580
agtctattaa ttgttgccgg gaagctagag taagtagttc gccagttaat agtttgcgca    5640
acgttgttgc cattgctaca ggcatcgtgg tgtcacgctc gtcgtttggt atggcttcat    5700
tcagctccgg ttcccaacga tcaaggcgag ttacatgatc ccccatgttg tgcaaaaaag    5760
cggttagctc cttcggtcct ccgatcgttg tcagaagtaa gttggccgca gtgttatcac    5820
tcatggttat ggcagcactg cataattctc ttactgtcat gccatccgta agatgctttt    5880
ctgtgactgg tgagtactca accaagtcat tctgagaata gtgtatgcgg cgaccgagtt    5940
gctcttgccc ggcgtcaata cgggataata ccgcgccaca tagcagaact ttaaaagtgc    6000
tcatcattgg aaaacgttct tcggggcgaa aactctcaag gatcttaccg ctgttgagat    6060
ccagttcgat gtaacccact cgtgcaccca actgatcttc agcatctttt actttcacca    6120
gcgtttctgg gtgagcaaaa acaggaaggc aaaatgccgc aaaaaaggga ataagggcga    6180
cacggaaatg ttgaatactc atactcttcc ttttcaata ttattgaagc atttatcagg    6240
gttattgtct catgagcgga tacatatttg aatgtattta gaaaaataaa caaatagggg    6300
ttccgcgcac atttccccga aaagtgccac ctgacgtcga cggatcggga gatctcccga    6360
```

```
tccccuatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acggggtcat tagttcatag cccatatatg gagttccgcg ttacataact   6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
ccacccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagaccctt ttagtcagtg   7500
tggaaaatct ctagcagtgg cgcccgaaca gggacttgaa agcgaaaggg aaaccagagg   7560
agctctctcg acgcaggact cggcttgctg aagcgcgcac ggcaagaggc gaggggcggc   7620
gactggtgag tacgccaaaa attttgacta gcggaggcta aaggagaga datgggtgcg   7680
agagcgtcag tattaagcgg gggagaatta gatcgcgatg ggaaaaaatt cggttaaggc   7740
caggggaaa gaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga gagcaaaac aaaagtaaga ccaccgcaca gcaagcggcc gctgatcttc   8040
agacctggag gaggagatat gagggacaat tggagaagtg aattatataa atataaagta   8100
gtaaaaattg aaccattagg agtagcaccc accaaggcaa agagaagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
gtgcagcagc agaacaattt gctgagggct attgaggcgc aacagcatct gttgcaactc   8340
acagtctggg gcatcaagca gctccaggca agaatcctgg ctgtggaaag atacctaaag   8400
gatcaacagc tcctggggat ttggggttgc tctggaaaac tcatttgcac cactgctgtg   8460
ccttggaatg ctagttggag taataaatct ctggaacaga tttggaatca cacgacctgg   8520
atggagtggg acagagaaat taacaattac acaagcttaa tacactcctt aattgaagaa   8580
tcgcaaaacc agcaagaaaa gaatgaacaa gaattattgg aattagataa atgggcaagt   8640
ttgtggaatt ggtttaacat aacaaattgg ctgtggtata taaaattatt cataatgata   8700
gtaggaggct tggtaggttt aagaatagtt tttgctgtac tttctatagt gaatagagtt   8760
```

| | |
|---|---|
| aggcagggat attcaccatt atcgtttcag acccacctcc caaccccgag gggacccgac | 8820 |
| aggcccttaa ttaagccacc tatcctcttc agacctcttc aggaaacagc tatgcacata | 8880 |
| gcacacaggc atatgttcaa ccaaaacact gaaacacata aagaaatgt ttaaagaatg | 8940 |
| aatttaaaaa aataaaaaat aaactcaact acatatgaag ccttagcaaa catgtctgga | 9000 |
| cctctagaca cacagactct gacacgccaa cgtctgagtt ctagtttcga tacgcactgg | 9060 |
| gaagttttaa aagttttcca tcaactctaa tgtgtagaga aatggaaact atcatagact | 9120 |
| ctacggcatt gagggtgaag gtatgagtga agcactctta gggtcagaag tatgtcagtg | 9180 |
| cccatttgtt gctgttagca tcatcatctt agggcttgag aggatgttgc agctgaccca | 9240 |
| tgcacctgtg acatacatat ggaattattc tttggcacat aaaattagaa tgggagctgg | 9300 |
| ctcatcaggt tttgtgctgt aagttttcta tgttaaacca gatgcgatac actaaataaa | 9360 |
| ataaaatata cttgaccgat ggttttgagc gaaataataa ctggataatc aagaaatata | 9420 |
| tccactaatg aatagcctga actactgaaa caatttgttc agtgcctagc atatggtgtg | 9480 |
| cattttatta tttctttcaa aaagaatgta tttggagtta catagtaagt ctgctacctt | 9540 |
| ttctttatgg ctatatctat gtcttatgtt gagatgaatg aattattctt caggggaaat | 9600 |
| aatctatttg aacagtttag atggtgaaga acatttgcag catttgcaag attttttttcc | 9660 |
| actctgaagt ggtctttgtc cttgaacata ggatacaagt gaccctgct ctgttaatta | 9720 |
| ttggcaaatt gcctaacttc aacgtaagga aatagagtca tatgtttgct cactgaaggt | 9780 |
| tactagttaa caggcatccc ttaaacagga tataaaagga cttcagcagg actgctcgaa | 9840 |
| acatcccact tccagcactg cctgcggtga aggaaccagc agccgaattc ggccattacg | 9900 |
| gcctgccacc atgaacagtg aggagcagta ctacgcggcc acacagctct acaaggaccc | 9960 |
| gtgcgcattc cagaggggcc cggtgccaga gttcagcgct aaccccctg cgtgcctgta | 10020 |
| catgggccgc cagccccac ctccgccgcc accccagttt acaagctcgc tgggatcact | 10080 |
| ggagcaggga agtcctccgg acatctcccc atacgaagtg cccccgctcg cctccgacga | 10140 |
| cccggctggc gctcacctcc accaccacct tccagctcag ctcgggctcg cccatccacc | 10200 |
| tcccggacct ttcccgaatg gaaccgagcc tgggggcctg gaagagccca accgcgtcca | 10260 |
| gctcccttc ccgtggatga aatccaccaa agctcacgcg tggaaaggcc agtgggcagg | 10320 |
| aggtgcttac acagcggaac ccgaggaaaa caagaggacc cgtactgcct acacccgggc | 10380 |
| gcagctgctg gagctggaga aggaattctt atttaacaaa tacatctccc ggccccgccg | 10440 |
| ggtggagctg gcagtgatgt tgaacttgac cgagagacac atcaaaatct ggttccaaaa | 10500 |
| ccgtcgcatg aagtggaaaa agaggaaga taagaaacgt agtagcggga ccccgagtgg | 10560 |
| gggcggtggg ggcgaagagc cggagcaaga ttgtgcggtg acctcgggcg aggagctgct | 10620 |
| ggcagtgcca ccgctgccac ctccggagg tgccgtgccc ccaggcgtcc cagctgcagt | 10680 |
| ccgggagggc ctactgcctt cgggccttag cgtgtcgcca cagccctcca gcatcgcgcc | 10740 |
| actgcgaccg caggaaccc ggtgaggccg cct | 10773 |

<210> SEQ ID NO 7
<211> LENGTH: 10562
<212> TYPE: DNA
<213> ORGANISM: Artificial Sequence
<220> FEATURE:
<223> OTHER INFORMATION: Synthetic

<400> SEQUENCE: 7

| | |
|---|---|
| cggccatcga taaggatccg cccctctccc tccccccccc ctaacgttac tggccgaagc | 60 |

-continued

```
cgcttggaat aaggccggtg tgcgtttgtc tatatgttat tttccaccat attgccgtct    120
tttggcaatg tgagggcccg gaaacctggc cctgtcttct tgacgagcat tcctaggggt    180
ctttcccctc tcgccaaagg aatgcaaggt ctgttgaatg tcgtgaagga agcagttcct    240
ctggaagctt cttgaagaca acaacgtct gtagcgaccc tttgcaggca gcggaacccc    300
ccacctggcg acaggtgcct ctgcggccaa aagccacgtg tataagatac acctgcaaag    360
gcggcacaac cccagtgcca cgttgtgagt tggatagttg tggaaagagt caaatggctc    420
tcctcaagcg tattcaacaa ggggctgaag gatgcccaga aggtacccca ttgtatggga    480
tctgatctgg ggcctcggtg cacatgcttt acatgtgttt agtcgaggtt aaaaaaacgt    540
ctaggccccc cgaaccacgg ggacgtggtt ttcctttgaa aaacacgatg ataatatggc    600
cacaaccatg gcctcctccg aggacgtcat caaggagttc atgcgcttca aggtgcgcat    660
ggagggctcc gtgaacggcc acgagttcga gatcgagggc gagggcgagg gccgccccta    720
cgagggcacc cagaccgcca agctgaaggt gaccaagggc ggccccctgc ccttcgcctg    780
ggacatcctg tcccccagt tccagtacgg ctccaaggtg tacgtgaagc accccgccga    840
catccccgac tacaagaagc tgtccttccc cgagggcttc aagtgggagc gcgtgatgaa    900
cttcgaggac ggcggcgtgg tgaccgtgac ccaggactcc tccctgcagg acggctcctt    960
catctacaag gtgaagttca tcggcgtgaa cttcccctcc gacggcccccg taatgcagaa   1020 gaagactatg ggctgggagg cctccaccga gcgcctgtac cccgcgacg gcgtgctgaa   1080 gggcgagatc cacaaggccc tgaagctgaa ggacggcggc cactacctgg tggagttcaa   1140
gtccatctac atggccaaga gccccgtgca gctgcccggc tactactacg tggactccaa   1200
gctggacatc acctcccaca acgaggacta caccatcgtg gagcagtacg agcgcgccga   1260
gggccgccac cacctgttcc tgtaggcggc cgcaatcaac ctctggatta caaaatttgt   1320
gaaagattga ctggtattct taactatgtt gctccttta cgctatgtgg atacgctgct   1380
ttaatgcctt tgtatcatgc tattacttcc cgtacggctt tcattttctc ctccttgtat   1440
aaatcctggt tgctgtctct ttatgaggag ttgtggcccg ttgtcaggca acgtggcgtg   1500
gtgtgcactg tgtttgctga cgcaaccccc actggttggg gcattgccac cacctatcaa   1560
ctcctttccg ggactttcgc tttcccccctc cctattgcca cggcggaact cattgccgcc   1620
tgccttgccc gctgctggac aggggctcgg ctgttgggca ctgacaattc cgtggtgttg   1680
tcggggaagc tgacgtcctt tccatggctg ctcgcctgtg ttgccaactg gattctgcgc   1740
gggacgtcct tctgctacgt ccccttcggcc ctcaatccag cggaccttcc ttcccgcggc   1800
ctgctgccgg ttctgcggcc tcttccgcgt cttcgccttc gccctcagac gagtcggatc   1860
tccctttggg ccgcctcccc gcctgcctgc aggtttgtcg agacctagaa aaacatggag   1920
caatcacaag tagcaataca gcagctacca atgctgattg tgcctggcta aagcacaag    1980 aggaggagga ggtgggtttt ccagtcacac ctcaggtacc tttaagacca atgacttaca   2040
aggcagctgt agatcttagc cacttttta aagaaaaggg gggactggaa gggctaattc   2100
actcccaacg aagacaagat ctgcttttgg cttgtactgg gtctctctgg ttagaccaga   2160
tctgagcctg ggagctctct ggctaactag gaacccact gcttaagcct caataaagct   2220
tgccttgagt gcttcaagta gtgtgtgccc gtctgttgtg tgactctggt aactagagat   2280
ccctcagacc ctttagtca gtgtggaaaa tctctagcag ggcccgtta aacccgctga   2340 tcagcctcga ctgtgccttc tagttgccag ccatctgttg tttgccctc cccgtgcct    2400 tccttgaccc tggaaggtgc cactcccact gtcctttcct aataaaatga ggaaattgca   2460
```

```
tcgcattgtc tgagtaggtg tcattctatt ctgggggtg gggtggggca ggacagcaag    2520
ggggaggatt gggaagacaa tagcaggcat gctggggatg cggtgggctc tatggcttct    2580
gaggcggaaa gaaccagctg gggctctagg gggtatcccc acgcgccctg tagcggcgca    2640
ttaagcgcgg cggtgtggt ggttacgcgc agcgtgaccg ctacacttgc cagcgcccta    2700
gcgcccgctc ctttcgcttt cttcccttcc tttctcgcca cgttcgccgg ctttccccgt    2760
caagctctaa atcggggcat ccctttaggg ttccgattta gtgctttacg gcacctcgac    2820
cccaaaaaac ttgattaggg tgatggttca cgtagtgggc catcgccctg atagacggtt    2880
tttcgccctt tgacgttgga gtccacgttc tttaatagtg gactcttgtt ccaaactgga    2940
acaacactca accctatctc ggtctattct tttgatttat aagggatttt ggggatttcg    3000
gcctattggt taaaaatga gctgatttaa caaaaattta acgcgaatta attctgtgga    3060
atgtgtgtca gttagggtgt ggaaagtccc caggctcccc aggcaggcag aagtatgcaa    3120
agcatgcatc tcaattagtc agcaaccagg tgtggaaagt ccccaggctc ccagcaggc    3180 agaagtatgc aaagcatgca tctcaattag tcagcaacca tagtcccgcc cctaactccg    3240
cccatcccgc ccctaactcc gcccagtcc gcccattctc cgccccatgg ctgactaatt    3300 tttttattt atgcagaggc cgaggccgcc tctgcctctg agctattcca gaagtagtga    3360
ggaggctttt ttggaggcct aggcttttgc aaaaagctcc cgggagcttg tatatccatt    3420
ttcggatctg atcagcacgt gttgacaatt aatcatcggc atagtatatc ggcatagtat    3480
aatacgacaa ggtgaggaac taaaccatgg ccaagttgac cagtgccgtt ccggtgctca    3540
ccgcgcgcga cgtcgccgga gcggtcgagt tctggaccga ccggctcggg ttctcccggg    3600
acttcgtgga ggacgacttc gccggtgtgg tccgggacga cgtgaccctg ttcatcagcg    3660
cggtccagga ccaggtggtg ccggacaaca ccctggcctg ggtgtgggtg cgcggcctgg    3720
acgagctgta cgccgagtgg tcggaggtcg tgtccacgaa cttccgggac gcctccgggc    3780
cggccatgac cgagatcggc gagcagccgt ggggcggga gttcgccctg cgcgacccgg    3840
ccggcaactg cgtgcacttc gtggccgagg agcaggactg acacgtgcta cgagatttcg    3900
attccaccgc cgccttctat gaaaggttgg gcttcggaat cgttttccgg gacgccggct    3960
ggatgatcct ccagcgcggg gatctcatgc tggagttctt cgcccacccc aacttgttta    4020
ttgcagctta taatggttac aaataaagca atagcatcac aaatttcaca aataaagcat    4080
ttttttcact gcattctagt tgtggtttgt ccaaactcat caatgtatct tatcatgtct    4140
gtataccgtc gacctctagc tagagcttgg cgtaatcatg gtcatagctg tttcctgtgt    4200
gaaattgtta tccgctcaca attccacaca acatacgagc cggaagcata agtgtaaag    4260 cctggggtgc ctaatgagtg agctaactca cattaattgc gttgcgctca ctgcccgctt    4320
tccagtcggg aaacctgtcg tgccagctgc attaatgaat cggccaacgc gcgggagag    4380 gcggtttgcg tattgggcgc tcttccgctt cctcgctcac tgactcgctg cgctcggtcg    4440
ttcggctgcg gcgagcggta tcagctcact caaaggcggt aatacggtta tccacagaat    4500
caggggataa cgcaggaaag aacatgtgag caaaaggcca gcaaaggcc aggaaccgta    4560 aaaaggccgc gttgctggcg ttttccata ggctccgccc cctgacgag catcacaaaa    4620 atcgacgctc aagtcagagg tggcgaaacc cgacaggact ataaagatac caggcgtttc    4680
cccctggaag ctccctcgtg cgctctcctg ttccgaccct gccgcttacc ggatacctgt    4740
ccgcctttct cccttcggga agcgtggcgc tttctcaatg ctcacgctgt aggtatctca    4800
gttcggtgta ggtcgttcgc tccaagctgg gctgtgtgca cgaacccccc gttcagcccg    4860
```

```
accgctgcgc cttatccggt aactatcgtc ttgagtccaa cccggtaaga cacgacttat    4920
cgccactggc agcagccact ggtaacagga ttagcagagc gaggtatgta ggcggtgcta    4980
cagagttctt gaagtggtgg cctaactacg gctacactag aaggacagta tttggtatct    5040
gcgctctgct gaagccagtt accttcggaa aaagagttgg tagctcttga tccggcaaac    5100
aaaccaccgc tggtagcggt ggtttttttg tttgcaagca gcagattacg cgcagaaaaa    5160
aaggatctca agaagatcct ttgatctttt ctacggggtc tgacgctcag tggaacgaaa    5220
actcacgtta agggattttg gtcatgagat tatcaaaaag gatcttcacc tagatccttt    5280
taaattaaaa atgaagtttt aaatcaatct aaagtatata tgagtaaact tggtctgaca    5340
gttaccaatg cttaatcagt gaggcaccta tctcagcgat ctgtctattt cgttcatcca    5400
tagttgcctg actccccgtc gtgtagataa ctacgatacg ggagggctta ccatctggcc    5460
ccagtgctgc aatgataccg cgagacccac gctcaccggc tccagattta tcagcaataa    5520
accagccagc cggaagggcc gagcgcagaa gtggtcctgc aactttatcc gcctccatcc    5580
agtctattaa ttgttgccgg gaagctagag taagtagttc gccagttaat agtttgcgca    5640
acgttgttgc cattgctaca ggcatcgtgg tgtcacgctc gtcgtttggt atggcttcat    5700
tcagctccgg ttcccaacga tcaaggcgag ttacatgatc ccccatgttg tgcaaaaaag    5760
cggttagctc cttcggtcct ccgatcgttg tcagaagtaa gttggccgca gtgttatcac    5820
tcatggttat ggcagcactg cataattctc ttactgtcat gccatccgta agatgctttt    5880
ctgtgactgg tgagtactca accaagtcat tctgagaata gtgtatgcgg cgaccgagtt    5940
gctcttgccc ggcgtcaata cgggataata ccgcgccaca tagcagaact ttaaaagtgc    6000
tcatcattgg aaaacgttct tcggggcgaa aactctcaag gatcttaccg ctgttgagat    6060
ccagttcgat gtaacccact cgtgcaccca actgatcttc agcatctttt actttcacca    6120
gcgtttctgg gtgagcaaaa acaggaaggc aaaatgccgc aaaaaaggga ataagggcga    6180
cacggaaatg ttgaatactc atactcttcc tttttcaata ttattgaagc atttatcagg    6240
gttattgtct catgagcgga tacatatttg aatgtattta gaaaaataaa caaataggggg    6300 ttccgcgcac atttccccga aaagtgccac ctgacgtcga cggatcggga gatctcccga    6360
tcccctatgg tgcactctca gtacaatctg ctctgatgcc gcatagttaa gccagtatct    6420
gctccctgct tgtgtgttgg aggtcgctga gtagtgcgcg agcaaaattt aagctacaac    6480
aaggcaaggc ttgaccgaca attgcatgaa gaatctgctt agggttaggc gttttgcgct    6540
gcttcgcgat gtacgggcca gatatacgcg ttgacattga ttattgacta gttattaata    6600
gtaatcaatt acggggtcat tagttcatag cccatatatg gagttccgcg ttacataact    6660
tacggtaaat ggcccgcctg gctgaccgcc caacgacccc cgcccattga cgtcaataat    6720
gacgtatgtt cccatagtaa cgccaatagg gactttccat tgacgtcaat gggtggacta    6780
tttacggtaa actgcccact tggcagtaca tcaagtgtat catatgccaa gtacgccccc    6840
tattgacgtc aatgacggta aatggcccgc ctggcattat gcccagtaca tgaccttatg    6900
ggactttcct acttggcagt acatctacgt attagtcatc gctattacca tggtgatgcg    6960
gttttggcag tacatcaatg ggcgtggata gcggtttgac tcacggggat ttccaagtct    7020
ccaccccatt gacgtcaatg ggagtttgtt ttggcaccaa aatcaacggg actttccaaa    7080
atgtcgtaac aactccgccc cattgacgca aatgggcggt aggcgtgtac ggtgggaggt    7140
ctatataagc agagctctct ggctaactag agaacccact gcttactggc ttatcgaaat    7200
taatacgact cactataggg agacccaagc tggtttaaac ttaagcttgg taccgagctc    7260
```

```
actagtccag tgtggtggca gatatccagc acagtggcgg ccgctcgagt ctagagggcc    7320
cgttttgcct gtactgggtc tctctggtta gaccagatct gagcctggga gctctctggc    7380
taactaggga acccactgct taagcctcaa taaagcttgc cttgagtgct tcaagtagtg    7440
tgtgcccgtc tgttgtgtga ctctggtaac tagagatccc tcagacccct ttagtcagtg    7500
tggaaaatct ctagcagtgg cgcccgaaca gggacttgaa agcgaaaggg aaaccagagg    7560
agctctctcg acgcaggact cggcttgctg aagcgcgcac ggcaagaggc gaggggcggc    7620
gactggtgag tacgccaaaa attttgacta gcggaggcta aaggagaga tgggtgcg     7680 agagcgtcag tattaagcgg gggagaatta gatcgcgatg ggaaaaaatt cggttaaggc    7740 caggggaaa gaaaaaatat aaattaaaac atatagtatg ggcaagcagg gagctagaac    7800
gattcgcagt taatcctggc ctgttagaaa catcagaagg ctgtagacaa atactgggac    7860
agctacaacc atcccttcag acaggatcag aagaacttag atcattatat aatacagtag    7920
caaccctcta ttgtgtgcat caaaggatag agataaaaga caccaaggaa gctttagaca    7980
agatagagga agagcaaaac aaaagtaaga ccaccgcaca gcaagcggcc gctgatcttc    8040
agacctggag gaggagatat gagggacaat tggagaagtg aattatataa atataaagta    8100
gtaaaaattg aaccattagg agtagcaccc accaaggcaa agagaagagt ggtgcagaga    8160
gaaaaaagag cagtgggaat aggagctttg ttccttgggt tcttgggagc agcaggaagc    8220
actatgggcg cagcgtcaat gacgctgacg gtacaggcca gacaattatt gtctggtata    8280
gtgcagcagc agaacaattt gctgagggct attgaggcgc aacagcatct gttgcaactc    8340
acagtctggg gcatcaagca gctccaggca agaatcctgg ctgtggaaag atacctaaag    8400
gatcaacagc tcctggggat ttggggttgc tctggaaaac tcatttgcac cactgctgtg    8460
ccttggaatg ctagttggag taataaatct ctggaacaga tttggaatca cacgacctgg    8520
atggagtggg acagagaaat taacaattac acaagcttaa tacactcctt aattgaagaa    8580
tcgcaaaacc agcaagaaaa gaatgaacaa gaattattgg aattagataa atgggcaagt    8640
ttgtggaatt ggtttaacat aacaaattgg ctgtggtata taaaattatt cataatgata    8700
gtaggaggct tggtaggttt aagaatagtt tttgctgtac tttctatagt gaatagagtt    8760
aggcagggat attcaccatt atcgtttcag acccacctcc caaccccgag gggacccgac    8820
aggcccttaa ttaagccacc tatcctcttc agacctcttc aggaaacagc tatgcacata    8880
gcacacaggc atatgttcaa ccaaaacact gaaacacata aagaaatgt ttaaagaatg    8940 aatttaaaaa ataaaaaat aaactcaact acatatgaag ccttagcaaa catgtctgga    9000
cctctagaca cacagactct gacacgccaa cgtctgagtt ctagtttcga tacgcactgg    9060
gaagttttaa aagttttcca tcaactctaa tgtgtagaga aatggaaact atcatagact    9120
ctacggcatt gagggtgaag gtatgagtga agcactctta gggtcagaag tatgtcagtg    9180
cccatttgtt gctgttagca tcatcatctt agggcttgag aggatgttgc agctgaccca    9240
tgcacctgtg acatacatat ggaattattc tttggcacat aaaattagaa tgggagctgg    9300
ctcatcaggt tttgtgctgt aagttttcta tgttaaacca gatgcgatac actaaataaa    9360
ataaaatata cttgaccgat ggttttgagc gaaataataa ctggataatc aagaaatata    9420
tccactaatg aatagcctga actactgaaa caatttgttc agtgcctagc atatggtgtg    9480
cattttatta tttctttcaa aaagaatgta tttggagtta catagtaagt ctgctacctt    9540
ttctttatgg ctatatctat gtcttatgtt gagatgaatg aattattctt caggggaaat    9600
aatctatttg aacagtttag atggtgaaga acatttgcag catttgcaag atttttttcc    9660
```

| | |
|---|---|
| actctgaagt ggtctttgtc cttgaacata ggatacaagt gaccoctgct ctgttaatta | 9720 |
| ttggcaaatt gcctaacttc aacgtaagga aatagagtca tatgtttgct cactgaaggt | 9780 |
| tactagttaa caggcatccc ttaaacagga tataaaagga cttcagcagg actgctcgaa | 9840 |
| acatcccact tccagcactg cctgcggtga aggaaccagc agccgaattc ggccattacg | 9900 |
| gccaccacca tgacgcctca accctcgggt gcgcccactg tccaagtgac ccgtgagacg | 9960 |
| gagcggtcct tccccagagc ctcggaagac gaagtgacct gccccacgtc cgccccgccc | 10020 |
| agccccactc gcacacgggg gaactgcgca gaggcggaag agggaggctg ccgaggggcc | 10080 |
| ccgaggaagc tccgggcacg gcgcggggga cgcagccggc ctaagagcga gttggcactg | 10140 |
| agcaagcagc gacggagtcg gcgaaagaag gccaacgacc gcgagcgcaa tcgaatgcac | 10200 |
| aacctcaact cggcactgga cgccctgcgc ggtgtcctgc ccaccttccc agacgacgcg | 10260 |
| aagctcacca agatcgagac gctgcgcttc gcccacaact acatctgggc gctgactcaa | 10320 |
| acgctgcgca tagcggacca cagcttgtac gcgctggagc cgccggcgcc gcactgcggg | 10380 |
| gagctgggca gccaggcgg ttcccccggg gactgggggt ccctctactc cccagtctcc | 10440 |
| caggctggca gcctgagtcc cgccgcgtcg ctggaggagc gacccgggct gctggggcc | 10500 |
| acctcttccg cctgcttgag cccaggcagt ctggctttct cagattttct gtgaggccgc | 10560 |
| ct | 10562 |

<210> SEQ ID NO 8
<211> LENGTH: 10926
<212> TYPE: DNA
<213> ORGANISM: Artificial Sequence
<220> FEATURE:
<223> OTHER INFORMATION: Synthetic

<400> SEQUENCE: 8

| | |
|---|---|
| cggccatcga taaggatccg cccctctccc tcccccccc ctaacgttac tggccgaagc | 60 |
| cgcttggaat aaggccggtg tgcgtttgtc tatatgttat tttccaccat attgccgtct | 120 |
| tttggcaatg tgagggcccg gaaacctggc cctgtcttct tgacgagcat tcctaggggt | 180 |
| ctttcccctc tcgccaaagg aatgcaaggt ctgttgaatg tcgtgaagga agcagttcct | 240 |
| ctggaagctt cttgaagaca acaacgtct gtagcgaccc tttgcaggca gcggaacccc | 300 |
| ccacctggcg acaggtgcct ctgcggccaa aagccacgtg tataagatac acctgcaaag | 360 |
| gcggcacaac cccagtgcca cgttgtgagt tggatagttg tggaaagagt caaatggctc | 420 |
| tcctcaagcg tattcaacaa ggggctgaag gatgcccaga aggtacccca ttgtatggga | 480 |
| tctgatctgg ggcctcggtg cacatgcttt acatgtgttt agtcgaggtt aaaaaaacgt | 540 |
| ctaggccccc cgaaccacgg ggacgtggtt ttcctttgaa aaacacgatg ataatatggc | 600 |
| cacaaccatg gcctcctccg aggacgtcat caaggagttc atgcgcttca aggtgcgcat | 660 |
| ggagggctcc gtgaacggcc acgagttcga gatcgagggc gagggcgagg ccgcccta | 720 |
| cgagggcacc cagaccgcca agctgaaggt gaccaagggc ggccccctgc ccttcgcctg | 780 |
| ggacatcctg tcccccagt tccagtacgg ctccaaggtg tacgtgaagc accccgccga | 840 |
| catccccgac tacaagaagc tgtccttccc cgagggcttc aagtgggagc gcgtgatgaa | 900 |
| cttcgaggac ggcggcgtgg tgaccgtgac ccaggactcc tccctgcagg acggctcctt | 960 |
| catctacaag gtgaagttca tcggcgtgaa cttcccctcc gacggccccg taatgcagaa | 1020 |
| gaagactatg ggctgggagg cctccaccga gcgcctgtac cccgcgacg gcgtgctgaa | 1080 |
| gggcgagatc cacaaggccc tgaagctgaa ggacggcggc cactacctgg tggagttcaa | 1140 |

```
gtccatctac atggccaaga agcccgtgca gctgcccggc tactactacg tggactccaa    1200
gctggacatc acctcccaca acgaggacta caccatcgtg gagcagtacg agcgcgccga    1260
gggccgccac cacctgttcc tgtaggcggc cgcaatcaac ctctggatta caaaatttgt    1320
gaaagattga ctggtattct taactatgtt gctccttta cgctatgtgg atacgctgct    1380
ttaatgcctt tgtatcatgc tattacttcc cgtacggctt tcattttctc ctccttgtat    1440
aaatcctggt tgctgtctct ttatgaggag ttgtggcccg ttgtcaggca acgtggcgtg    1500
gtgtgcactg tgtttgctga cgcaacccc actggttggg gcattgccac cacctatcaa    1560
ctcctttccg ggactttcgc tttccccctc cctattgcca cggcggaact cattgccgcc    1620
tgccttgccc gctgctggac aggggctcgg ctgttgggca ctgacaattc cgtggtgttg    1680
tcggggaagc tgacgtcctt ccatggctg ctcgcctgtg ttgccaactg gattctgcgc    1740
gggacgtcct tctgctacgt cccttcggcc ctcaatccag cggaccttcc ttcccgcggc    1800
ctgctgccgt ttctgcggcc tcttccgcgt cttcgccttc gccctcagac gagtcggatc    1860
tccctttggg ccgcctcccc gcctgcctgc aggtttgtcg agacctagaa aaacatggag    1920
caatcacaag tagcaataca gcagctacca atgctgattg tgcctggcta gaagcacaag    1980
aggaggagga ggtgggtttt ccagtcacac ctcaggtacc tttaagacca atgacttaca    2040
aggcagctgt agatcttagc cactttttaa aagaaaaggg gggactggaa gggctaattc    2100
actcccaacg aagacaagat ctgctttttg cttgtactgg gtctctctgg ttagaccaga    2160
tctgagcctg ggagctctct ggctaactag ggaacccact gcttaagcct caataaagct    2220
tgccttgagt gcttcaagta gtgtgtgccc gtctgttgtg tgactctggt aactagagat    2280
ccctcagacc cttttagtca gtgtggaaaa tctctagcag ggcccgttta acccgctga    2340 tcagcctcga ctgtgccttc tagttgccag ccatctgttg tttgccctc cccgtgcct    2400 tccttgaccc tggaaggtgc cactcccact gtcctttcct aataaatga ggaaattgca    2460 tcgcattgtc tgagtaggtg tcattctatt ctggggggtg ggtgggca ggacagcaag    2520 ggggaggatt gggaagacaa tagcaggcat gctgggatg cggtgggctc tatgcttct    2580 gaggcggaaa gaaccagctg gggctctagg gggtatcccc acgcgcctg tagcggcgca    2640 ttaagcgcgg cgggtgtggt ggttacgcgc agcgtgaccg ctacacttgc cagcgcccta    2700
gcgcccgctc ctttcgcttt cttcccttcc tttctcgcca cgttcgccgg ctttccccgt    2760
caagctctaa atcggggcat ccctttaggg ttccgattta gtgctttacg gcacctcgac    2820
cccaaaaaac ttgattaggg tgatggttca cgtagtgggc catcgccctg atagacggtt    2880
tttcgccctt tgacgttgga gtccacgttc tttaatagtg gactcttgtt ccaaactgga    2940
acaacactca accctatctc ggtctattct tttgatttat aagggatttt ggggatttcg    3000
gcctattggt taaaaatga gctgatttaa caaaaattta acgcgaatta attctgtgga    3060
atgtgtgtca gttagggtgt ggaaagtccc caggctcccc aggcaggcag aagtatgcaa    3120
agcatgcatc tcaattagtc agcaaccagg tgtggaaagt ccccaggctc cccagcaggc    3180
agaagtatgc aaagcatgca tctcaattag tcagcaacca tagtcccgcc cctaactccg    3240
cccatcccgc ccctaactcc gcccagttcc gcccattctc cgccccatgg ctgactaatt    3300
ttttttattt atgcagaggc cgaggccgcc tctgcctctg agctattcca gaagtagtga    3360
ggaggctttt ttggaggcct aggcttttgc aaaaagctcc cgggagcttg tatatccatt    3420
ttcggatctg atcagcacgt gttgacaatt aatcatcggc atagtatatc ggcatagtat    3480
aatacgacaa ggtgaggaac taaaccatgg ccaagttgac cagtgccgtt ccggtgctca    3540
```

```
ccgcgcgcga cgtcgccgga gcggtcgagt tctggaccga ccggctcggg ttctcccggg   3600
acttcgtgga ggacgacttc gccggtgtgg tccgggacga cgtgaccctg ttcatcagcg   3660
cggtccagga ccaggtggtg ccggacaaca ccctggcctg ggtgtgggtg cgcggcctgg   3720
acgagctgta cgccgagtgg tcggaggtcg tgtccacgaa cttccgggac gcctccgggc   3780
cggccatgac cgagatcggc gagcagccgt gggggcggga gttcgccctg cgcgacccgg   3840
ccggcaactg cgtgcacttc gtggccgagg agcaggactg acacgtgcta cgagatttcg   3900
attccaccgc cgccttctat gaaaggttgg gcttcggaat cgttttccgg gacgccggct   3960
ggatgatcct ccagcgcggg gatctcatgc tggagttctt cgcccacccc aacttgttta   4020
ttgcagctta taatggttac aaataaagca atagcatcac aaatttcaca aataaagcat   4080
tttttttcact gcattctagt tgtggttttgt ccaaactcat caatgtatct tatcatgtct   4140
gtataccgtc gacctctagc tagagcttgg cgtaatcatg gtcatagctg tttcctgtgt   4200
gaaattgtta tccgctcaca attccacaca catacgagc cggaagcata agtgtaaag    4260
cctggggtgc ctaatgagtg agctaactca cattaattgc gttgcgctca ctgcccgctt   4320
tccagtcggg aaacctgtcg tgccagctgc attaatgaat cggccaacgc gcggggagag   4380
gcggtttgcg tattgggcgc tcttccgctt cctcgctcac tgactcgctg cgctcggtcg   4440
ttcggctgcg gcgagcggta tcagctcact caaaggcggt aatacggtta tccacagaat   4500
caggggataa cgcaggaaag aacatgtgag caaaaggcca gcaaaaggcc aggaaccgta   4560
aaaaggccgc gttgctggcg ttttttccata ggctccgccc ccctgacgag catcacaaaa   4620
atcgacgctc aagtcagagg tggcgaaacc cgacaggact ataaagatac caggcgtttc   4680
cccctggaag ctccctcgtg cgctctcctg ttccgaccct gccgcttacc ggatacctgt   4740
ccgcctttct cccttcggga agcgtggcgc tttctcaatg ctcacgctgt aggtatctca   4800
gttcggtgta ggtcgttcgc tccaagctgg gctgtgtgca cgaaccccc gttcagcccg    4860
accgctgcgc cttatccggt aactatcgtc ttgagtccaa cccggtaaga cacgacttat   4920
cgccactggc agcagccact ggtaacagga ttagcagagc gaggtatgta ggcggtgcta   4980
cagagttctt gaagtggtgg cctaactacg gctacactag aaggacagta tttggtatct   5040
gcgctctgct gaagccagtt accttcggaa aaagagttgg tagctcttga tccggcaaac   5100
aaaccaccgc tggtagcggt ggttttttg tttgcaagca gcagattacg cgcagaaaaa    5160
aaggatctca agaagatcct ttgatctttt ctacggggtc tgacgctcag tggaacgaaa   5220
actcacgtta agggattttg gtcatgagat tatcaaaaag gatcttcacc tagatccttt   5280
taaattaaaa atgaagtttt aaatcaatct aaagtatata tgagtaaact tggtctgaca   5340
gttaccaatg cttaatcagt gaggcaccta tctcagcgat ctgtctattt cgttcatcca   5400
tagttgcctg actccccgtc gtgtagataa ctacgatacg ggagggctta ccatctggcc   5460
ccagtgctgc aatgataccg cgagacccac gctcaccggc tccagattta tcagcaataa   5520
accagccagc cggaagggcc gagcgcagaa gtggtcctgc aactttatcc gcctccatcc   5580
agtctattaa ttgttgccgg gaagctagag taagtagttc gccagttaat agtttgcgca   5640
acgttgttgc cattgctaca ggcatcgtgg tgtcacgctc gtcgtttggt atggcttcat   5700
tcagctccgg ttcccaacga tcaaggcgag ttacatgatc ccccatgttg tgcaaaaaag   5760
cggttagctc cttcggtcct ccgatcgttg tcagaagtaa gttggccgca gtgttatcac   5820
tcatggttat ggcagcactg cataattctc ttactgtcat gccatccgta agatgctttt   5880
ctgtgactgg tgagtactca accaagtcat tctgagaata gtgtatgcgg cgaccgagtt   5940
```

```
gctcttgccc ggcgtcaata cgggataata ccgcgccaca tagcagaact ttaaaagtgc   6000
tcatcattgg aaaacgttct tcggggcgaa aactctcaag gatcttaccg ctgttgagat   6060
ccagttcgat gtaacccact cgtgcaccca actgatcttc agcatctttt actttcacca   6120
gcgtttctgg gtgagcaaaa acaggaaggc aaaatgccgc aaaaaaggga ataagggcga   6180
cacggaaatg ttgaatactc atactcttcc tttttcaata ttattgaagc atttatcagg   6240
gttattgtct catgagcgga tacatatttg aatgtattta gaaaaataaa caatagggg    6300 ttccgcgcac atttccccga aaagtgccac ctgacgtcga cggatcggga gatctcccga   6360
tcccctatgg tgcactctca gtacaatctg ctctgatgcc gcatagttaa gccagtatct   6420
gctccctgct tgtgtgttgg aggtcgctga gtagtgcgcg agcaaaattt aagctacaac   6480
aaggcaaggc ttgaccgaca attgcatgaa gaatctgctt agggttaggc gttttgcgct   6540
gcttcgcgat gtacgggcca gatatacgcg ttgacattga ttattgacta gttattaata   6600
gtaatcaatt acgggtcat tagttcatag cccatatatg gagttccgcg ttacataact    6660
tacggtaaat ggcccgcctg gctgaccgcc caacgacccc cgcccattga cgtcaataat   6720
gacgtatgtt cccatagtaa cgccaatagg gactttccat tgacgtcaat gggtggacta   6780
tttacggtaa actgcccact tggcagtaca tcaagtgtat catatgccaa gtacgccccc   6840
tattgacgtc aatgacggta aatggcccgc ctggcattat gcccagtaca tgaccttatg   6900
ggactttcct acttggcagt acatctacgt attagtcatc gctattacca tggtgatgcg   6960
gttttggcag tacatcaatg ggcgtggata gcggtttgac tcacggggat ttccaagtct   7020
ccaccccatt gacgtcaatg ggagtttgtt ttggcaccaa aatcaacggg actttccaaa   7080
atgtcgtaac aactccgccc cattgacgca aatgggcggt aggcgtgtac ggtgggaggt   7140
ctatataagc agagctctct ggctaactag agaacccact gcttactggc ttatcgaaat   7200
taatacgact cactataggg agacccaagc tggtttaaac ttaagcttgg taccgagctc   7260
actagtccag tgtggtggca gatatccagc acagtggcgg ccgctcgagt ctagagggcc   7320
cgttttgcct gtactgggtc tctctggtta gaccagatct gagcctggga gctctctggc   7380
taactaggga acccactgct taagcctcaa taaagcttgc cttgagtgct tcaagtagtg   7440
tgtgcccgtc tgttgtgtga ctctggtaac tagagatccc tcagacccct ttagtcagtg   7500
tggaaaatct ctagcagtgg cgcccgaaca gggacttgaa agcgaaaggg aaaccagagg   7560
agctctctcg acgcaggact cggcttgctg aagcgcgcac ggcaagaggc gaggggcggc   7620
gactggtgag tacgccaaaa attttgacta gcggaggcta aaggagaga gatgggtgcg    7680 agagcgtcag tattaagcgg gggagaatta gatcgcgatg gaaaaaatt cggttaaggc    7740 caggggggaaa gaaaaatat aaattaaaac atatagtatg ggcaagcagg gagctagaac   7800
gattcgcagt taatcctggc ctgttagaaa catcagaagg ctgtagacaa atactgggac   7860
agctacaacc atcccttcag acaggatcag aagaacttag atcattatat aatacagtag   7920
caaccctcta ttgtgtgcat caaaggatag agataaaaga caccaaggaa gctttagaca   7980
agatagagga gagcaaaac aaaagtaaga ccaccgcaca gcaagcggcc gctgatcttc     8040
agacctggag gaggagatat gagggacaat tggagaagtg aattatataa atataaagta   8100
gtaaaaattg aaccattagg agtagcaccc accaaggcaa agagaagagt ggtgcagaga   8160
gaaaaaagag cagtgggaat aggagctttg ttccttgggt tcttgggagc agcaggaagc   8220
actatgggcg cagcgtcaat gacgctgacg gtacaggcca gacaattatt gtctggtata   8280
gtgcagcagc agaacaattt gctgagggct attgaggcgc aacagcatct gttgcaactc   8340
```

```
acagtctggg gcatcaagca gctccaggca agaatcctgg ctgtggaaag atacctaaag   8400
gatcaacagc tcctggggat ttggggttgc tctggaaaac tcatttgcac cactgctgtg   8460
ccttggaatg ctagttggag taataaatct ctggaacaga tttggaatca cacgacctgg   8520
atggagtggg acagagaaat taacaattac acaagcttaa tacactcctt aattgaagaa   8580
tcgcaaaacc agcaagaaaa gaatgaacaa gaattattgg aattagataa atgggcaagt   8640
ttgtggaatt ggtttaacat aacaaattgg ctgtggtata taaaattatt cataatgata   8700
gtaggaggct tggtaggttt aagaatagtt tttgctgtac tttctatagt gaatagagtt   8760
aggcagggat attcaccatt atcgtttcag acccacctcc caaccccgag ggacccgac    8820 aggcccttaa ttaagccacc tatcctcttc agacctcttc aggaaacagc tatgcacata   8880
gcacacaggc atatgttcaa ccaaaacact gaaacacata aaagaaatgt ttaaagaatg   8940
aatttaaaaa aataaaaaat aaactcaact acatatgaag ccttagcaaa catgtctgga   9000
cctctagaca cacagactct gacacgccaa cgtctgagtt ctagtttcga tacgcactgg   9060
gaagttttaa aagttttcca tcaactctaa tgtgtagaga aatggaaact atcatagact   9120
ctacggcatt gagggtgaag gtatgagtga agcactctta gggtcagaag tatgtcagtg   9180
cccatttgtt gctgttagca tcatcatctt agggcttgag aggatgttgc agctgaccca   9240
tgcacctgtg acatacatat ggaattattc tttggcacat aaaattagaa tgggagctgg   9300
ctcatcaggt tttgtgctgt aagttttcta tgttaaacca gatgcgatac actaaataaa   9360
ataaaatata cttgaccgat ggttttgagc gaaataataa ctggataatc aagaaatata   9420
tccactaatg aatagcctga actactgaaa caatttgttc agtgcctagc atatggtgtg   9480
cattttatta tttctttcaa aaagaatgta tttggagtta catagtaagt ctgctacctt   9540
ttctttatgg ctatatctat gtcttatgtt gagatgaatg aattattctt cagggaaat   9600 aatctatttg aacagtttag atggtgaaga acatttgcag catttgcaag atttttttcc   9660
actctgaagt ggtctttgtc cttgaacata ggatacaagt gaccctgct ctgttaatta    9720 ttggcaaatt gcctaacttc aacgtaagga aatagagtca tatgtttgct cactgaaggt   9780
tactagttaa caggcatccc ttaaacagga tataaaagga cttcagcagg actgctcgaa   9840
acatcccact tccagcactg cctgcggtga aggaaccagc agccgaattc ggccattacg   9900
gcccgccacc atggctagat tagataaaag taaagtgatt aacagcgcat tagagctgct   9960
taatgaggtc ggaatcgaag gtttaacaac ccgtaaactc gcccagaagc taggtgtaga  10020
gcagcctaca ttgtattggc atgtaaaaaa taagcgggct ttgctcgacg ccttagccat  10080
tgagatgtta gataggcacc atactcactt ttgcccttta gaaggggaaa gctggcaaga  10140
ttttttacgt aataacgcta aaagttttag atgtgcttta ctaagtcatc gcgatggagc  10200
aaaagtacat ttaggtacac ggcctacaga aaaacagtat gaaactctcg aaaatcaatt  10260 agcctttttta tgccaacaag gttttttcact agagaatgca ttatatgcac tcagcgctgt  10320
ggggcatttt actttaggtt gcgtattgga agatcaagag catcaagtcg ctaaagaaga  10380
aagggaaaca cctactactg atagtatgcc gccattatta cgacaagcta tcgaattatt  10440
tgatcaccaa ggtgcagagc cagccttctt attcggcctt gaattgatca tatgcggatt  10500
agaaaaacaa cttaaatgtg aaagtgggtc gccaaaaaag aagagaaagg tcgacggcgg  10560
tggtgctttg tctcctcagc actctgctgt cactcaagga agtatcatca agaacaagga  10620
gggcatggat gctaagtcac taactgcctg gtcccggaca ctggtgacct tcaaggatgt  10680
atttgtggac ttcaccaggg aggagtggaa gctgctggac actgctcagc agatcgtgta  10740
```

-continued

| | |
|---|---|
| cagaaatgtg atgctggaga actataagaa cctggtttcc ttgggttatc agcttactaa | 10800 |
| gccagatgtg atcctccggt tggagaaggg agaagagccc tggctggtgg agagagaaat | 10860 |
| tcaccaagag acccatcctg attcagagac tgcatttgaa atcaaatcat cagtttaagg | 10920 |
| ccgcct | 10926 |

<210> SEQ ID NO 9
<211> LENGTH: 10656
<212> TYPE: DNA
<213> ORGANISM: Artificial Sequence
<220> FEATURE:
<223> OTHER INFORMATION: Synthetic

<400> SEQUENCE: 9

| | |
|---|---|
| cggccatcga taaggatccg cccctctccc tccccccccc ctaacgttac tggccgaagc | 60 |
| cgcttggaat aaggccggtg tgcgtttgtc tatatgttat tttccaccat attgccgtct | 120 |
| tttggcaatg tgagggcccg gaaacctggc cctgtcttct tgacgagcat tcctaggggt | 180 |
| cttccccctc tcgccaaagg aatgcaaggt ctgttgaatg tcgtgaagga agcagttcct | 240 |
| ctggaagctt cttgaagaca acaacgtct gtagcgaccc tttgcaggca gcggaaccc | 300 |
| ccacctggcg acaggtgcct ctgcggccaa aagccacgtg tataagatac acctgcaaag | 360 |
| gcggcacaac cccagtgcca cgttgtgagt tggatagttg tggaaagagt caaatggctc | 420 |
| tcctcaagcg tattcaacaa ggggctgaag gatgcccaga aggtacccca ttgtatggga | 480 |
| tctgatctgg ggcctcggtg cacatgcttt acatgtgttt agtcgaggtt aaaaaaacgt | 540 |
| ctaggccccc cgaaccacgg ggacgtggtt ttcctttgaa aaacacgatg ataatatggc | 600 |
| cacaaccatg gcctcctccg aggacgtcat caaggagttc atgcgcttca aggtgcgcat | 660 |
| ggagggctcc gtgaacggcc acgagttcga gatcgagggc gagggcgagg gccgccccta | 720 |
| cgagggcacc cagaccgcca agctgaaggt gaccaagggc ggccccctgc ccttcgcctg | 780 |
| ggacatcctg tcccccagt tccagtacgg ctccaaggtg tacgtgaagc accccgccga | 840 |
| catccccgac tacaagaagc tgtccttccc cgagggcttc aagtgggagc gcgtgatgaa | 900 |
| cttcgaggac ggcggcgtgg tgaccgtgac ccaggactcc tccctgcagg acggctcctt | 960 |
| catctacaag gtgaagttca tcggcgtgaa cttcccctcc gacggccccg taatgcagaa | 1020 |
| gaagactatg ggctgggagg cctccaccga gcgcctgtac cccgcgacg gcgtgctgaa | 1080 |
| gggcgagatc cacaaggccc tgaagctgaa ggacggcggc cactacctgg tggagttcaa | 1140 |
| gtccatctac atggccaaga agcccgtgca gctgcccggc tactactacg tggactccaa | 1200 |
| gctggacatc acctcccaca acgaggacta caccatcgtg gagcagtacg agcgcgccga | 1260 |
| gggccgccac cacctgttcc tgtaggcggc gcaatcaac ctctggatta caaaatttgt | 1320 |
| gaaagattga ctggtattct aactatgtt gctccttta cgctatgtgg atacgctgct | 1380 |
| ttaatgcctt tgtatcatgc tattacttcc cgtacggctt tcattttctc ctccttgtat | 1440 |
| aaatcctggt tgctgtctct ttatgaggag ttgtggcccg ttgtcaggca acgtggcgtg | 1500 |
| gtgtgcactg tgtttgctga cgcaaccccc actggttggg gcattgccac cacctatcaa | 1560 |
| ctcctttccg ggactttcgc tttccccctc cctattgcca cggcggaact cattgccgcc | 1620 |
| tgccttgccc gctgctggac aggggctcgg ctgttgggca ctgacaattc cgtggtgttg | 1680 |
| tcggggaagc tgacgtcctt tccatggctg ctcgcctgtg ttgccaactg gattctgcgc | 1740 |
| gggacgtcct tctgctacgt cccttcggcc ctcaatccag cggaccttcc ttcccgcggc | 1800 |
| ctgctgccgg ttctgcggcc tcttccgcgt cttcgccttc gccctcagac gagtcggatc | 1860 |

```
tcccttttggg ccgcctcccc gcctgcctgc aggtttgtcg agacctagaa aaacatggag    1920
caatcacaag tagcaataca gcagctacca atgctgattg tgcctggcta aagcacaag     1980 aggaggagga ggtgggtttt ccagtcacac ctcaggtacc tttaagacca atgacttaca    2040
aggcagctgt agatcttagc cactttttaa aagaaaaggg gggactggaa gggctaattc    2100
actcccaacg aagacaagat ctgcttttg cttgtactgg gtctctctgg ttagaccaga     2160
tctgagcctg ggagctctct ggctaactag ggaacccact gcttaagcct caataaagct    2220
tgccttgagt gcttcaagta gtgtgtgccc gtctgttgtg tgactctggt aactagagat    2280
ccctcagacc cttttagtca gtgtggaaaa tctctagcag ggcccgttta acccgctga    2340 tcagcctcga ctgtgccttc tagttgccag ccatctgttg tttgccctc ccgtgcct      2400 tccttgaccc tggaaggtgc cactcccact gtcctttcct aataaaatga ggaaattgca    2460
tcgcattgtc tgagtaggtg tcattctatt ctggggggtg gggtggggca ggacagcaag    2520
ggggaggatt gggaagacaa tagcaggcat gctgggggatg cggtgggctc tatggcttct   2580
gaggcggaaa gaaccagctg ggctctagg gggtatccccc acgcgcctg tagcggcgca     2640 ttaagcgcgg cgggtgtggt ggttacgcgc agcgtgaccg ctacacttgc cagcgcccta    2700
gcgcccgctc ctttcgcttt cttccctcc tttctcgcca cgttcgccgg ctttccccgt     2760
caagctctaa atcggggcat ccctttaggg ttccgattta gtgctttacg gcacctcgac    2820
cccaaaaaac ttgattaggg tgatggttca cgtagtgggc catcgccctg atagacggtt    2880
tttcgccctt tgacgttgga gtccacgttc tttaatagtg gactcttgtt ccaaactgga    2940
acaacactca accctatctc ggtctattct tttgatttat aagggatttt ggggatttcg    3000
gcctattggt taaaaaatga gctgatttaa caaaaattta acgcgaatta attctgtgga    3060
atgtgtgtca gttagggtgt ggaaagtccc caggctcccc aggcaggcag aagtatgcaa    3120
agcatgcatc tcaattagtc agcaaccagg tgtggaaagt ccccaggctc cccagcaggc    3180
agaagtatgc aaagcatgca tctcaattag tcagcaacca tagtcccgcc cctaactccg    3240
cccatcccgc ccctaactcc gcccagttcc gcccattctc cgccccatgg ctgactaatt    3300
ttttttattt atgcagaggc cgaggccgcc tctgcctctg agctattcca gaagtagtga    3360
ggaggctttt ttggaggcct aggcttttgc aaaaagctcc cgggagcttg tatatccatt    3420
ttcggatctg atcagcacgt gttgacaatt aatcatcggc atagtatatc ggcatagtat    3480
aatacgacaa ggtgaggaac taaaccatgg ccaagttgac cagtgccgtt ccggtgctca    3540
ccgcgcgcga cgtcgccgga gcggtcgagt tctggaccga ccggctcggg ttctcccggg    3600
acttcgtgga ggacgacttc gccggtgtgg tccgggacga cgtgaccctg ttcatcagcg    3660
cggtccagga ccaggtggtg ccggacaaca ccctggcctg ggtgtgggtg cgcggcctgg    3720
acgagctgta cgccgagtgg tcggaggtcg tgtccacgaa cttccgggac gcctccgggc    3780
cggccatgac cgagatcggc gagcagccgt ggggcggga gttcgccctg cgcgacccgg    3840
ccggcaactg cgtgcacttc gtggccgagg agcaggactg acacgtgcta cgagatttcg    3900
attccaccgc cgccttctat gaaaggttgg gcttcggaat cgttttccgg gacgccggct    3960
ggatgatcct ccagcgcggg gatctcatgc tggagttctt cgcccacccc aacttgttta    4020
ttgcagctta taatggttac aaataaagca atagcatcac aaatttcaca aataaagcat    4080
ttttttcact gcattctagt tgtggtttgt ccaaactcat caatgtatct tatcatgtct    4140
gtataccgtc gacctctagc tagagcttgg cgtaatcatg gtcatagctg tttcctgtgt    4200
gaaattgtta tccgctcaca attccacaca acatacgagc cggaagcata aagtgtaaag    4260
```

```
                                   -continued
cctgggtgc ctaatgagtg agctaactca cattaattgc gttgcgctca ctgcccgctt    4320
tccagtcggg aaacctgtcg tgccagctgc attaatgaat cggccaacgc gcggggagag    4380
gcggtttgcg tattgggcgc tcttccgctt cctcgctcac tgactcgctg cgctcggtcg    4440
ttcggctgcg gcgagcggta tcagctcact caaaggcggt aatacggtta ccacagaat    4500 caggggataa cgcaggaaag aacatgtgag caaaaggcca gcaaaaggcc aggaaccgta    4560
aaaaggccgc gttgctggcg ttttccata ggctccgccc ccctgacgag catcacaaaa    4620
atcgacgctc aagtcagagg tggcgaaacc cgacaggact ataaagatac caggcgtttc    4680
cccctggaag ctccctcgtg cgctctcctg ttccgaccct gccgcttacc ggatacctgt    4740
ccgcctttct cccttcggga agcgtggcgc tttctcaatg ctcacgctgt aggtatctca    4800
gttcggtgta ggtcgttcgc tccaagctgg gctgtgtgca cgaaccccc gttcagcccg    4860 accgctgcgc cttatccggt aactatcgtc ttgagtccaa cccggtaaga cacgacttat    4920
cgccactggc agcagccact ggtaacagga ttagcagagc gaggtatgta ggcggtgcta    4980
cagagttctt gaagtggtgg cctaactacg gctacactag aaggacagta tttggtatct    5040
gcgctctgct gaagccagtt accttcggaa aaagagttgg tagctcttga tccggcaaac    5100
aaaccaccgc tggtagcggt ggttttttg tttgcaagca gcagattacg cgcagaaaaa    5160
aaggatctca agaagatcct ttgatctttt ctacggggtc tgacgctcag tggaacgaaa    5220
actcacgtta agggattttg gtcatgagat tatcaaaaag gatcttcacc tagatccttt    5280
taaattaaaa atgaagtttt aaatcaatct aaagtatata tgagtaaact tggtctgaca    5340
gttaccaatg cttaatcagt gaggcaccta tctcagcgat ctgtctattt cgttcatcca    5400
tagttgcctg actccccgtc gtgtagataa ctacgatacg ggagggctta ccatctggcc    5460
ccagtgctgc aatgataccg cgagacccac gctcaccggc tccagattta tcagcaataa    5520
accagccagc cggaagggcc gagcgcagaa gtggtcctgc aactttatcc gcctccatcc    5580
agtctattaa ttgttgccgg gaagctagag taagtagttc gccagttaat agtttgcgca    5640
acgttgttgc cattgctaca ggcatcgtgg tgtcacgctc gtcgtttggt atggcttcat    5700
tcagctccgg ttcccaacga tcaaggcgag ttacatgatc ccccatgttg tgcaaaaaag    5760
cggttagctc cttcggtcct ccgatcgttg tcagaagtaa gttggccgca gtgttatcac    5820
tcatggttat ggcagcactg cataattctc ttactgtcat gccatccgta agatgctttt    5880
ctgtgactgg tgagtactca accaagtcat tctgagaata gtgtatgcgg cgaccgagtt    5940
gctcttgccc ggcgtcaata cgggataata ccgcgccaca tagcagaact ttaaaagtgc    6000
tcatcattgg aaaacgttct tcggggcgaa aactctcaag gatcttaccg ctgttgagat    6060
ccagttcgat gtaacccact cgtgcaccca actgatcttc agcatctttt actttcacca    6120
gcgtttctgg gtgagcaaaa acaggaaggc aaaatgccgc aaaaaaggga taagggcga    6180 cacgaaaatg ttgaatactc atactcttcc ttttcaata ttattgaagc atttatcagg    6240
gttattgtct catgagcgga tacatatttg aatgtattta gaaaaataaa caaatagggg    6300
ttccgcgcac atttccccga aaagtgccac ctgacgtcga cggatcggga gatctcccga    6360
tcccctatgg tgcactctca gtacaatctg ctctgatgcc gcatagttaa gccagtatct    6420
gctccctgct tgtgtgttgg aggtcgctga gtagtgcgcg agcaaaattt aagctacaac    6480
aaggcaaggc ttgaccgaca attgcatgaa gaatctgctt agggttaggc gttttgcgct    6540
gcttcgcgat gtacgggcca gatatacgcg ttgacattga ttattgacta gttattaata    6600
gtaatcaatt acgggtcat tagttcatag cccatatatg gagttccgcg ttacataact    6660
```

```
tacggtaaat ggcccgcctg gctgaccgcc caacgacccc cgcccattga cgtcaataat    6720
gacgtatgtt cccatagtaa cgccaatagg gactttccat tgacgtcaat gggtggacta    6780
tttacggtaa actgcccact tggcagtaca tcaagtgtat catatgccaa gtacgccccc    6840
tattgacgtc aatgacggta aatggcccgc ctggcattat gcccagtaca tgaccttatg    6900
ggactttcct acttggcagt acatctacgt attagtcatc gctattacca tggtgatgcg    6960
gttttggcag tacatcaatg ggcgtggata gcggtttgac tcacggggat ttccaagtct    7020
ccaccccatt gacgtcaatg ggagtttgtt ttggcaccaa aatcaacggg actttccaaa    7080
atgtcgtaac aactccgccc cattgacgca aatgggcggt aggcgtgtac ggtgggaggt    7140
ctatataagc agagctctct ggctaactag agaacccact gcttactggc ttatcgaaat    7200
taatacgact cactataggg agacccaagc tggtttaaac ttaagcttgg taccgagctc    7260
actagtccag tgtggtggca gatatccagc acagtggcgg ccgctcgagt ctagagggcc    7320
cgttttgcct gtactgggtc tctctggtta ccagatct gagcctggga gctctctggc    7380
taactaggga acccactgct taagcctcaa taaagcttgc cttgagtgct tcaagtagtg    7440
tgtgcccgtc tgttgtgtga ctctggtaac tagagatccc tcagaccctt ttagtcagtg    7500
tggaaaatct ctagcagtgg cgcccgaaca gggacttgaa agcgaaaggg aaaccagagg    7560
agctctctcg acgcaggact cggcttgctg aagcgcgcac ggcaagaggc gaggggcggc    7620
gactggtgag tacgccaaaa attttgacta gcggaggcta aaggagaga gatgggtgcg    7680
agagcgtcag tattaagcgg gggagaatta gatcgcgatg ggaaaaaatt cggttaaggc    7740
caggggggaaa gaaaaaatat aaattaaaac atatagtatg ggcaagcagg gagctagaac    7800
gattcgcagt taatcctggc ctgttagaaa catcagaagg ctgtagacaa atactgggac    7860
agctacaacc atcccttcag acaggatcag aagaacttag atcattatat aatacagtag    7920
caaccctcta ttgtgtgcat caaaggatag agataaaaga caccaaggaa gctttagaca    7980
agatagagga agagcaaaac aaaagtaaga ccaccgcaca gcaagcggcc gctgatcttc    8040
agacctggag gaggagatat gagggacaat tggagaagtg aattatataa atataaagta    8100
gtaaaaattg aaccattagg agtagcaccc accaaggcaa agagaagagt ggtgcagaga    8160
gaaaaaagag cagtgggaat aggagctttg ttccttgggt tcttgggagc agcaggaagc    8220
actatgggcg cagcgtcaat gacgctgacg gtacaggcca gacaattatt gtctggtata    8280
gtgcagcagc agaacaattt gctgagggct attgaggcgc aacagcatct gttgcaactc    8340
acagtctggg gcatcaagca gctccaggca agaatcctgg ctgtggaaag atacctaaag    8400
gatcaacagc tcctggggat ttggggttgc tctggaaaac tcatttgcac cactgctgtg    8460
ccttggaatg ctagttggag taataaatct ctggaacaga tttggaatca cacgacctgg    8520
atggagtggg acagagaaat taacaattac acaagcttaa tacactcctt aattgaagaa    8580
tcgcaaaacc agcaagaaaa gaatgaacaa gaattattgg aattagataa atgggcaagt    8640
ttgtggaatt ggtttaacat aacaaattgg ctgtggtata taaaattatt cataatgata    8700
gtaggaggct tggtaggttt aagaatagtt tttgctgtac tttctatagt gaatagagtt    8760
aggcagggat attcaccatt atcgtttcag acccacctcc caaccccgag gggacccgac    8820
aggcccttaa ttaattggct ccggtgcccg tcagtgggca gagcgcacat cgcccacagt    8880
ccccgagaag ttgggggggag gggtcggcaa ttgaaccggt gcctagagaa ggtggcgcgg    8940
ggtaaactgg gaaagtgatg tcgtgtactg gctccgcctt tttcccgagg gtgggggaga    9000
accgtatata agtgcagtag tcgccgtgaa cgttcttttt cgcaacgggt ttgccgccag    9060
```

| | | | | |
|---|---|---|---|---|
| aacacaggta | agtgccgtgt | gtggttcccg | cgggcctggc | ctctttacgg gttatggccc | 9120 |
| ttgcgtgcct | tgaattactt | ccacctggct | gcagtacgtg | attcttgatc ccgagcttcg | 9180 |
| ggttggaagt | gggtgggaga | gttcgaggcc | ttgcgcttaa | ggagcccctt cgcctcgtgc | 9240 |
| ttgagttgag | gcctggcctg | ggcgctgggg | ccgccgcgtg | cgaatctggt ggcaccttcg | 9300 |
| cgcctgtctc | gctgctttcg | ataagtctct | agccatttaa | aattttgat gacctgctgc | 9360 |
| gacgcttttt | ttctggcaag | atagtcttgt | aaatgcgggc | caagatctgc acactggtat | 9420 |
| ttcggttttt | ggggccgcgg | gcggcgacgg | ggcccgtgcg | tcccagcgca catgttcggc | 9480 |
| gaggcggggc | ctgcgagcgc | ggccaccgag | aatcggacgg | gggtagtctc aagctggccg | 9540 |
| gcctgctctg | gtgcctggcc | tcgcgccgcc | gtgtatcgcc | ccgccctggg cggcaaggct | 9600 |
| ggcccggtcg | gcaccagttg | cgtgagcgga | aagatggccg | cttcccggcc ctgctgcagg | 9660 |
| gagctcaaaa | tggaggacgc | ggcgctcggg | agagcgggcg | ggtgagtcac ccacacaaag | 9720 |
| gaaaagggcc | tttccgtcct | cagccgtcgc | ttcatgtgac | tccacggagt accgggcgcc | 9780 |
| gtccaggcac | ctcgattagt | tctcgagctt | ttggagtacg | tcgtctttag gttgggggga | 9840 |
| ggggttttat | gcgatggagt | ttccccacac | tgagtgggtg | gagactgaag ttaggccagc | 9900 |
| ttggcacttg | atgtaattct | ccttggaatt | tgccctttt | gagtttggat cttggttcat | 9960 |
| tctcaagcct | cagacagtgg | ttcaaagttt | ttttcttcca | tttcaggtgt cgtgaggaat | 10020 |
| tcggccatta | cggcccgcca | ccatgatcga | attgctctct | gaatcgctgg aagggcttc | 10080 |
| cgccgccatg | atcgccgagc | tgggacgcta | ccggcatcag | gtcttcatcg agaagctggg | 10140 |
| ctgggacgtg | gtctccacct | ccagggtccg | cgaccaggaa | ttcgaccagt tcgaccatcc | 10200 |
| gcaaacccgc | tacatcgtcg | ccatgagccg | ccagggcatc | tgcggttgcg cccgcctgct | 10260 |
| gccgacgacc | gacgcctacc | tgctcaagga | cgtcttcgcc | tacctgtgca gcgaaacccc | 10320 |
| gccgagcgat | ccgtcggtct | gggagctttc | gcgctacgcc | gccagcgcgg cggacgatcc | 10380 |
| gcagctggcg | atgaagatat | tctggtccag | cctgcaatgc | gcctggtacc tgggcgccag | 10440 |
| ttcggtggtg | gcggtgacca | ccacggccat | ggagcgctat | ttcgttcgca acggcgtgat | 10500 |
| cctccagcgc | ctcggcccgc | cgcagaaggt | caagggcgag | acgctggtcg cgatcagctt | 10560 |
| cccggcctac | caggagcgcg | gcctggagat | gctgctgcgc | taccacccgg aatggctgca | 10620 |
| gggcgtaccg | ctgtcgatgg | cggtgtgagg | ccgcct | | 10656 |

<210> SEQ ID NO 10
<211> LENGTH: 12768
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7358)..(7362)
<223> OTHER INFORMATION: n is a, c, g, or t
<220> FEATURE:
<221> NAME/KEY: misc_feature
<222> LOCATION: (7544)..(7553)
<223> OTHER INFORMATION: n is a, c, g, or t
<220> FEATURE:
<221> NAME/KEY: misc_feature
<222> LOCATION: (8364)..(8368)
<223> OTHER INFORMATION: n is a, c, g, or t
<220> FEATURE:
<221> NAME/KEY: misc_feature
<222> LOCATION: (9459)..(9466)
<223> OTHER INFORMATION: n is a, c, g, or t

<400> SEQUENCE: 10

```
gatccgcccc tctccctccc cccccccctaa cgttactggc cgaagccgct tggaataagg    60
ccggtgtgcg tttgtctata tgttattttc caccatattg ccgtcttttg gcaatgtgag   120
ggcccggaaa cctggccctg tcttcttgac gagcattcct aggggtcttt ccctctcgc    180 caaaggaatg caaggtctgt tgaatgtcgt gaaggaagca gttcctctgg aagcttcttg   240
aagacaaaca acgtctgtag cgaccctttg caggcagcgg aaccccccac ctggcgacag   300
gtgcctctgc ggccaaaagc cacgtgtata agatacacct gcaaaggcgg cacaacccca   360
gtgccacgtt gtgagttgga tagttgtgga aagagtcaaa tggctctcct caagcgtatt   420
caacaagggg ctgaaggatg cccagaaggt accccattgt atgggatctg atctggggcc   480
tcggtgcaca tgctttacat gtgtttagtc gaggttaaaa aaacgtctag gccccccgaa   540
ccacggggac gtggttttcc tttgaaaaac acgatgataa tatggccaca accatggtga   600
gcaagggcga ggagctgttc accggggtgg tgcccatcct ggtcgagctg gacggcgacg   660
taaacggcca caagttcagc gtgtccggcg agggcgaggg cgatgccacc tacggcaagc   720
tgaccctgaa gttcatctgc accaccggca agctgcccgt gccctggccc accctcgtga   780
ccaccctgac ctacggcgtg cagtgcttca gccgctaccc cgaccacatg aagcagcacg   840
acttcttcaa gtccgccatg cccgaaggct acgtccagga gcgcaccatc ttcttcaagg   900
acgacggcaa ctacaagacc cgcgccgagg tgaagttcga gggcgacacc ctggtgaacc   960
gcatcgagct gaagggcatc gacttcaagg aggacggcaa catcctgggg cacaagctgg  1020
agtacaacta caacagccac aacgtctata tcatggccga caagcagaag aacggcatca  1080
aggtgaactt caagatccgc cacaacatcg aggacggcag cgtgcagctc gccgaccact  1140
accagcagaa cacccccatc ggcgacggcc ccgtgctgct gcccgacaac cactacctga  1200
gcacccagtc cgccctgagc aaagacccca acgagaagcg cgatcacatg gtcctgctgg  1260
agttcgtgac cgccgccggg atcactctcg gcatggacga gctgtacaag taagcggccg  1320
caatcaacct ctggattaca aaatttgtga aagattgact ggtattctta actatgttgc  1380
tccttttacg ctatgtggat acgctgcttt aatgcctttg tatcatgcta ttacttcccg  1440
tacggctttc attttctcct ccttgtataa atcctggttg ctgtctcttt atgaggagtt  1500
gtggcccgtt gtcaggcaac gtggcgtggt gtgcactgtg tttgctgacg caaccccac   1560 tggttggggc attgccacca cctatcaact cctttccggg actttcgctt tccccctccc  1620
tattgccacg gcggaactca ttgccgcctg ccttgcccgc tgctggacag gggctcggct  1680
gttgggcact gacaattccg tggtgttgtc ggggaagctg acgtcctttc catggctgct  1740
cgcctgtgtt gccaactgga ttctgcgcgg gacgtccttc tgctacgtcc cttcggccct  1800
caatccagcg gaccttcctt cccgcggcct gctgccggtt ctgcggcctc ttccgcgtct  1860
tcgccttcgc cctcagacga gtcggatctc cctttgggcc gcctccccgc ctgcctgcag  1920
gtttgtcgag acctagaaaa acatggagca atcacaagta gcaatacagc agctaccaat  1980
gctgattgtg cctggctaga agcacaagag gaggaggagg tgggttttcc agtcacacct  2040
caggtacctt aagaccaat gacttacaag gcagctgtag atcttagcca cttttttaaaa    2100 gaaaagggggg gactggaagg gctaattcac tcccaacgaa gacaagatct gcttttgct   2160 tgtactgggt ctctctggtt agaccagatc tgagcctggg agctctctgg ctaactaggg   2220
aacccactgc ttaagcctca ataaagcttg ccttgagtgc ttcaagtagt gtgtgcccgt   2280
ctgttgtgtg actctggtaa ctagagatcc ctcagaccct tttagtcagt gtggaaaatc   2340
tctagcaggg cccgtttaaa cccgctgatc agcctcgact gtgccttcta gttgccagcc   2400
```

-continued

```
atctgttgtt tgcccctccc ccgtgccttc cttgaccctg gaaggtgcca ctcccactgt    2460
cctttcctaa taaaatgagg aaattgcatc gcattgtctg agtaggtgtc attctattct    2520 gggggggtggg gtggggcagg acagcaaggg ggaggattgg gaagacaata gcaggcatgc   2580
tggggatgcg gtgggctcta tggcttctga ggcggaaaga accagctggg gctctagggg    2640
gtatccccac gcgccctgta gcggcgcatt aagcgcggcg ggtgtggtgg ttacgcgcag    2700
cgtgaccgct acacttgcca gcgccctagc gcccgctcct ttcgctttct tcccttcctt    2760
tctcgccacg ttcgccggct ttccccgtca agctctaaat cggggcatcc ctttagggtt    2820
ccgatttagt gctttacggc acctcgaccc caaaaaactt gattagggtg atggttcacg    2880
tagtgggcca tcgccctgat agacggtttt tcgccctttg acgttggagt ccacgttctt    2940
taatagtgga ctcttgttcc aaactggaac aacactcaac cctatctcgg tctattcttt    3000
tgatttataa gggattttgg ggatttcggc ctattggtta aaaatgagc tgatttaaca     3060 aaaatttaac gcgaattaat tctgtggaat gtgtgtcagt tagggtgtgg aaagtcccca    3120
ggctccccag gcaggcagaa gtatgcaaag catgcatctc aattagtcag caaccaggtg    3180
tggaaagtcc ccaggctccc cagcaggcag aagtatgcaa agcatgcatc tcaattagtc    3240
agcaaccata gtcccgcccc taactccgcc catcccgccc ctaactccgc ccagttccgc    3300
ccattctccg ccccatggct gactaatttt ttttatttat gcagaggccg aggccgcctc    3360
tgcctctgag ctattccaga agtagtgagg aggcttttt ggaggcctag gcttttgcaa     3420
aaagctcccg ggagcttgta tatccatttt cggatctgat cagcacgtgt tgacaattaa    3480
tcatcggcat agtatatcgg catagtataa tacgacaagg tgaggaacta aaccatggcc    3540
aagttgacca gtgccgttcc ggtgctcacc gcgcgcgacg tcgccggagc ggtcgagttc    3600
tggaccgacc ggctcgggtt ctcccgggac ttcgtggagg acgacttcgc cggtgtggtc    3660
cgggacgacg tgaccctgtt catcagcgcg gtccaggacc aggtggtgcc ggacaacacc    3720
ctggcctggg tgtgggtgcg cggcctggac gagctgtacg ccgagtggtc ggaggtcgtg    3780
tccacgaact tccgggacgc ctccgggccg gccatgaccg agatcggcga gcagccgtgg    3840
gggcgggagt tcgccctgcg cgacccggcc ggcaactgcg tgcacttcgt ggccgaggag    3900
caggactgac acgtgctacg agatttcgat tccaccgccg ccttctatga aggttgggc    3960 ttcggaatcg ttttccggga cgccggctgg atgatcctcc agcgcgggga tctcatgctg    4020
gagttcttcg cccaccccaa cttgtttatt gcagcttata atggttacaa ataaagcaat    4080
agcatcacaa atttcacaaa taaagcattt ttttcactgc attctagttg tggtttgtcc    4140
aaactcatca atgtatctta tcatgtctgt ataccgtcga cctctagcta gagcttggcg    4200
taatcatggt catagctgtt tcctgtgtga aattgttatc cgctcacaat tccacacaac    4260
atacgagccg gaagcataaa gtgtaaagcc tggggtgcct aatgagtgag ctaactcaca    4320
ttaattgcgt tgcgctcact gcccgctttc cagtcgggaa acctgtcgtg ccagctgcat    4380
taatgaatcg gccaacgcgc ggggagaggc ggtttgcgta ttgggcgctc ttccgcttcc    4440
tcgctcactg actcgctgcg ctcggtcgtt cggctgcggc gagcggtatc agctcactca    4500
aaggcggtaa tacggttatc cacagaatca ggggataacg caggaaagaa catgtgagca    4560
aaaggccagc aaaaggccag gaaccgtaaa aaggccgcgt tgctggcgtt tttccatagg    4620
ctccgccccc ctgacgagca tcacaaaaat cgacgctcaa gtcagaggtg gcgaaacccg    4680
acaggactat aaagatacca ggcgtttccc cctggaagct ccctcgtgcg ctctcctgtt    4740
ccgaccctgc cgcttaccgg atacctgtcc gcctttctcc cttcgggaag cgtggcgctt    4800
```

```
tctcaatgct cacgctgtag gtatctcagt tcggtgtagg tcgttcgctc caagctgggc    4860
tgtgtgcacg aaccccccgt tcagcccgac cgctgcgcct tatccggtaa ctatcgtctt    4920
gagtccaacc cggtaagaca cgacttatcg ccactggcag cagccactgg taacaggatt    4980
agcagagcga ggtatgtagg cggtgctaca gagttcttga agtggtggcc taactacggc    5040
tacactagaa ggacagtatt tggtatctgc gctctgctga agccagttac cttcggaaaa    5100
agagttggta gctcttgatc cggcaaacaa accaccgctg gtagcggtgg ttttttttgtt   5160
tgcaagcagc agattacgcg cagaaaaaaa ggatctcaag aagatccttt gatcttttct    5220
acggggtctg acgctcagtg gaacgaaaac tcacgttaag gattttggt catgagatta     5280
tcaaaaagga tcttcaccta gatccttttta aattaaaaat gaagttttaa atcaatctaa   5340
agtatatatg agtaaacttg gtctgacagt taccaatgct taatcagtga ggcacctatc    5400
tcagcgatct gtctatttcg ttcatccata gttgcctgac tccccgtcgt gtagataact    5460
acgatacggg agggcttacc atctggcccc agtgctgcaa tgataccgcg agacccacgc    5520
tcaccggctc cagatttatc agcaataaac cagccagccg aagggccga gcgcagaagt     5580
ggtcctgcaa ctttatccgc ctccatccag tctattaatt gttgccggga agctagagta    5640
agtagttcgc cagttaatag tttgcgcaac gttgttgcca ttgctacagg catcgtggtg    5700
tcacgctcgt cgtttggtat ggcttcattc agctccggtt cccaacgatc aaggcgagtt    5760
acatgatccc ccatgttgtg caaaaaagcg gttagctcct tcggtcctcc gatcgttgtc    5820
agaagtaagt tggccgcagt gttatcactc atggttatgg cagcactgca taattctctt    5880
actgtcatgc catccgtaag atgcttttct gtgactggtg agtactcaac caagtcattc    5940
tgagaatagt gtatgcggcg accgagttgc tcttgcccgg cgtcaatacg ggataatacc    6000
gcgccacata gcagaacttt aaaagtgctc atcattggaa aacgttcttc ggggcgaaaa    6060
ctctcaagga tcttaccgct gttgagatcc agttcgatgt aacccactcg tgcacccaac    6120
tgatcttcag catcttttac tttcaccagc gtttctgggt gagcaaaaac aggaaggcaa    6180
aatgccgcaa aaaagggaat aagggcgaca cggaaatgtt gaatactcat actcttcctt    6240
tttcaatatt attgaagcat ttatcagggt tattgtctca tgagcggata catatttgaa    6300
tgtatttaga aaaataaaca ataggggtt ccgcgcacat ttccccgaaa agtgccacct     6360
gacgtcgacg gatcgggaga tctcccgatc ccctatggtg cactctcagt acaatctgct    6420
ctgatgccgc atagttaagc cagtatctgc tccctgcttg tgtgttggag gtcgctgagt    6480
agtgcgcgag caaaatttaa gctacaacaa ggcaaggctt gaccgacaat tgcatgaaga    6540
atctgcttag ggttaggcgt tttgcgctgc ttcgcgatgt acgggccaga tatacgcgtt    6600
gacattgatt attgactagt tattaatagt aatcaattac ggggtcatta gttcatagcc    6660
catatatgga gttccgcgtt acataactta cggtaaatgg cccgcctggc tgaccgccca    6720
acgaccccg cccattgacg tcaataatga cgtatgttcc catagtaacg ccaatagga     6780
ctttccattg acgtcaatgg gtggactatt tacggtaaac tgcccacttg gcagtacatc    6840
aagtgtatca tatgccaagt acgccccta ttgacgtcaa tgacggtaaa tggcccgcct     6900
ggcattatgc ccagtacatg accttatggg actttcctac ttggcagtac atctacgtat    6960
tagtcatcgc tattaccatg gtgatgcggt tttggcagta catcaatggg cgtggatagc    7020
ggtttgactc acggggattt ccaagtctcc accccattga cgtcaatggg agtttgtttt    7080
ggcaccaaaa tcaacgggac tttccaaaat gtcgtaacaa ctccgcccca ttgacgcaaa    7140
tgggcggtag gcgtgtacgg tgggaggtct atataagcag agctctctgg ctaactagag    7200
```

```
aacccactgc ttactggctt atcgaaatta atacgactca ctatagggag acccaagctg   7260
gtttaaactt aagcttggta ccgagctcac tagtccagtg tggtggcaga tatccagcac   7320
agtggcggcc gctcgagtct agagggcccg tttaaacnnn nngggtctct ctggttagac   7380
cagatctgag cctgggagct ctctggctaa ctagggaacc cactgcttaa gcctcaataa   7440
agcttgcctt gagtgcttca agtagtgtgt gcccgtctgt tgtgtgactc tggtaactag   7500
agatccctca gacccttta gtcagtgtgg aaaatctcta gcannnnnnn nnccagcaa   7560
cttatctgtg tctgtccgat tgtctagtgt ctatgtttga tgttatgcgc ctgcgtctgt   7620
actagttagc taactagctc tgtatctggc ggacccgtgg tggaactgac gagttctgaa   7680
cacccggccg caaccctggg agacgtccca gggactttgg gggccgtttt tgtggcccga   7740
cctgaggaag ggagtcgatg tggaatccga ccccgtcagg atatgtggtt ctggtaggag   7800
acgagaacct aaaacagttc ccgcctccgt ctgaattttt gctttcggtt tggaaccgaa   7860
gccgcgcgtc ttgtctgctg cagcgctgca gcatcgttct gtgttgtctc tgtctgactg   7920
tgtttctgta tttgtctgaa aattagggcc agactgttac cactccctta agtttgacct   7980
taggtcactg gaaagatgtc gagcggatcg ctcacaacca gtcggtagat gtcaagaaga   8040
gacgttgggt taccttctgc tctgcagaat ggccaacctt taacgtcgga tggccgcgag   8100
acggcacctt taaccgagac ctcatcaccc aggttaagat caaggtcttt tcacctggcc   8160
cgcatggaca cccagaccag gtcccctaca tcgtgacctg ggaagccttg gcttttgacc   8220
cccctccctg ggtcaagccc tttgtacacc ctaagcctcc gcctcctctt cctccatccg   8280
ccccgtctct ccccttgaa cctcctcgtt cgaccccgcc tcgatcctcc ctttatccag   8340
ccctcactcc ttctctaggc gccnnnnggg aaaagtttag taaaacacca tatgtatgtt   8400
tcagggaaag ctaggggatg gttttataga catcactatg aaagccctca tccaagaata   8460
agttcagaag tacacatccc actagggat gctagattgg taataacaac atattggggt   8520
ctgcatacag gagaaagaga ctggcatctg ggtcagggag tctccataga atggaggaaa   8580
aagagatata gcacacaagt agaccctgaa ctagcagacc aactaattca tctgtattac   8640
tttgactgtt tttcagactc tgctataaga aaggccttat taggacatat agttagccct   8700
aggtgtgaat atcaagcagg acataacaag gtaggatctc tacaatactt ggcactagca   8760
gcattaataa caccaaaaaa gataaagcca ccttttgccta gtgttacgaa actgacagag   8820
gatagatgga acaagcccca gaagaccaag ggccacagag ggagccacac aatgaatgga   8880
cactagagct tttagaggag cttaagaatg aagctgttag acattttcct aggatttggc   8940
tccatggctt agggcaacat atctatgaaa cttatgggga tacttgggca ggagtggaag   9000
ccataataat gcaacaactg ctgtttatcc atttcagaat tgggtgtcga catagcagaa   9060
taggcgttac tcaacagagg agagcaagaa atggagccag tagatcctag actagagccc   9120
tggaagcatc caggaagtca gcctaaaact gcttgtacca cttgctattg taaaaagtgt   9180
tgctttcatt gccaagtttg tttcacaaca aaagccttag gcatctccta tggcaggaag   9240
aagcggagac agcgacgaag acctcctcaa ggcagtcaga ctcatcaagt ttctctatca   9300
aagcagtaag tagtacatgt aatgcaacct atacaaatag caatagcagc attagtagta   9360
gcaataataa tagcaatagt tgtgtggtcc atagtaatca tagaatatag gaaaatatta   9420
agacaaagaa aaatagacag gttaattgat agactaatnn nnnnnnggcc cgaaggaata   9480
gaagaagaag gtggagagag agacagagac agatccattc gattagtgaa cggatcggca   9540
ctgcgtgcgc caattctgca gacaaatggc agtattcatc cacaatttta aagaaaagg   9600
```

```
ggggattggg gggtacagtg caggggaaag aatagtagac ataatagcaa cagacataca    9660
aactaaagaa ttacaaaaac aaattacaaa aattcaaaat tttcgggttt attacaggga    9720
cagcagagat ccagtttggt taattaatgc tgctgagcca cgtgaagcct taagccgcag    9780
ggagaccctg aaaatagact gtaagcaacc ttggggtggg gtaagcctgt tgcagcgtta    9840
gtgtatccat gaactccttt aagatacaag ctatgtgtca ttcctcatgg agacgccgga    9900
gagtcttgag cttacatgat ggtcctgcgg aggccttaaa gtcctgtggg gatgctcagg    9960
gttgtccctg tgtgtcactg agacctccga aagaatttaa atatcacaga aaaaaaaaac   10020
ataaagaaga ccttaagcct ttttaagttc ccaaggagag ccagaagtgg tggtatatag   10080
ctcaacttgg gagactgagg caaaaagact gactgagttt aagaccagcc tagctacacc   10140
acaaagctcc tttctcaaaa gaaaagctcc caaggaggt tggatcccca gtgagaccct   10200
cagcaaggcc ctctggcctc actatggtcc tgaggacacc cctccacact gccctgatct   10260
tcttacccca tcctgcctga gctcttacc tgctctcctc ttgcattcaa atatcttctg   10320
ctacagtagg tccactggag tctcccaggt acccagagtg tgaatgtctg cagcactttc   10380 tggggacaa ggagcagaga gcaagggacc cacaattcgg gtctagtgtc tgtaaagcct   10440
tgcggagggt agagttctag ttcacacaag gcaccaagtg ttttttgctgg ttgcctagga   10500 aacaggacag tgccaaatca ggaacagaaa gagtcaagga accccaacc actccaagcg   10560 gaggctgaga aaggttttgt agctggaata gagcatgcac taacagatgg agacagctgg   10620 cttttgagctc tgaagcaagt attacatatg gagacttgct ggccttcagg tgcttatctt   10680
gttattggat actgcaggag gatgtaccac agggcttcag ctcagctgac ccccaagtgg   10740
gatatggaaa gagagataga ggaggaggga ccattaagtg ccttgctgcc tgaattctgc   10800
tttccttcta cctctgagag agagctgggg actcggctga gttaagaacc cagctatcaa   10860
ttggaactgt gaaacagtcc aagggacaaa gatactaggt ccccaactgc aacttcctgg   10920
ggaatgatgt ggaaaaatgc tcagccaagg acaaagaaag catcacccac tctggaacaa   10980
tgtcccctgc tgtgaactgg ttcatcaggc catcagggcc ccttgttaag actctaatta   11040
ccctaggact aagtagaggt gttgacgtcc aatgagcgct ttctgcagac ctagcaccag   11100
ggaagtgttt ggaaactgca gcttcagccc ctctggccat ctgctgacct accccacctg   11160
gagcccttaa tgggtcaaac agcaaagtcc aggggcaga gaggaggtgc tttggtctat   11220
aaaggtagtg gggacccagt aaccaccggc gcgccaagct agcaagttaa caaatcgatc   11280
cggatcctcc caccatgaaa ccagtaacgt tatacgatgt cgcagagtat gccggtgtct   11340
cttatcagac cgtttcccgc gtggtgaacc aggccagcca cgtttctgcg aaaacgcggg   11400
aaaaagtgga agcggcgatg gcggagctga attacattcc caaccgcgtg gcacaacaac   11460
tggcgggcaa acagtcgttg ctgattggcg ttgccacctc cagtctggcc ctgcacgcgc   11520
cgtcgcaaat tgtcgcggcg attaaatctc gcgccgatca actgggtgcc agcgtggtgg   11580
tgtcgatggt agaacgaagc ggcgtcgaag cctgtaaagc ggcggtgcac aatcttctcg   11640
cgcaacgcgt cagtgggctg atcattaact atccgctgga tgaccaggat gccattgctg   11700
tggaagctgc ctgcactaat gttccggcgt tatttcttga tgtctctgac cagacaccca   11760
tcaacagtat tattttctcc catgaagacg gtacgcgact gggcgtggag catctggtcg   11820
cattgggtca ccagcaaatc gcgctgttag cgggcccatt aagttctgtc tcggcgcgtc   11880
tgcgtctggc tggctggcat aaatatctca ctcgcaatca aattcagccg atagcggaac   11940
gggaaggcga ctggagtgcc atgtccggtt ttcaacaaac catgcaaatg ctgaatgagg   12000
```

-continued

```
gcatcgttcc cactgcgatg ctggttgcca acgatcagat ggcgctgggc gcaatgcgcg    12060
ccattaccga gtccgggctg cgcgttggtg cggatatctc ggtagtggga tacgacgata    12120
ccgaagacag ctcatgttat atcccgccgt taaccaccat caaacaggat tttcgcctgc    12180
tggggcaaac cagcgtggac cgcttgctgc aactctctca gggccaggcg gtgaagggca    12240
atcagctgtt gcccgtctca ctggtgaaaa gaaaaaccac cctggcgccc aatacgcaaa    12300
ccgcctctcc ccgcgcgttg gccgattcat taatgcagct ggcacgacag gtttcccgac    12360
tggaaagcgg gcagagaccg ccaaaaaaga agagaaaggt cgacggcggt ggtgctttgt    12420
ctcctcagca ctctgctgtc actcaaggaa gtatcatcaa gaacaaggag ggcatggatg    12480
ctaagtcact aactgcctgg tcccggacac tggtgacctt caaggatgta tttgtggact    12540
tcaccaggga ggagtggaag ctgctggaca ctgctcagca gatcgtgtac agaaatgtga    12600
tgctggagaa ctataagaac ctggtttcct tgggttatca gcttactaag ccagatgtga    12660
tcctccggtt ggagaaggga gaagagccct ggctggtgga gagagaaatt caccaagaga    12720
cccatcctga ttcagagact gcatttgaaa tcaaatcatc agtttgag                 12768
```

<210> SEQ ID NO 11
<211> LENGTH: 11287
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (39)..(43)
<223> OTHER INFORMATION: n is a, c, g, or t
<220> FEATURE:
<221> NAME/KEY: misc_feature
<222> LOCATION: (7396)..(7400)
<223> OTHER INFORMATION: n is a, c, g, or t
<220> FEATURE:
<221> NAME/KEY: misc_feature
<222> LOCATION: (7582)..(7591)
<223> OTHER INFORMATION: n is a, c, g, or t
<220> FEATURE:
<221> NAME/KEY: misc_feature
<222> LOCATION: (8402)..(8406)
<223> OTHER INFORMATION: n is a, c, g, or t
<220> FEATURE:
<221> NAME/KEY: misc_feature
<222> LOCATION: (9497)..(9504)
<223> OTHER INFORMATION: n is a, c, g, or t

<400> SEQUENCE: 11

```
cgcgccaagc tagcaagtta acaaatcgat ccggatccnn nnngcccctc tccctccccc      60 cccctaacg ttactggccg aagccgcttg gaataaggcc ggtgtgcgtt tgtctatatg     120
ttattttcca ccatattgcc gtcttttggc aatgtgaggg cccggaaacc tggccctgtc    180
ttcttgacga gcattcctag gggtcttttcc cctctcgcca aaggaatgca aggtctgttg    240
aatgtcgtga aggaagcagt tcctctggaa gcttcttgaa gacaaacaac gtctgtagcg    300 acccttgca ggcagcggaa ccccccacct ggcgacaggt gcctctgcgg ccaaaagcca    360
cgtgtataag atacacctgc aaaggcggca caaccccagt gccacgttgt gagttggata    420
gttgtggaaa gagtcaaatg gctctcctca gcgtattca acaaggggct gaaggatgcc    480
cagaaggtac cccattgtat gggatctgat ctggggcctc ggtgcacatg ctttacatgt    540
gtttagtcga ggttaaaaaa acgtctaggc cccccgaacc acggggacgt ggttttcctt    600
tgaaaaacac gatgataata tggccacaac catggtgagc aagggcgagg agctgttcac    660
cggggtggtg cccatcctgg tcgagctgga cggcgacgta aacggccaca gttcagcgt    720
```

```
gtccggcgag ggcgagggcg atgccaccta cggcaagctg accctgaagt tcatctgcac    780
caccggcaag ctgcccgtgc cctggcccac cctcgtgacc accctgacct acggcgtgca    840
gtgcttcagc cgctaccccg accacatgaa gcagcacgac ttcttcaagt ccgccatgcc    900
cgaaggctac gtccaggagc gcaccatctt cttcaaggac gacggcaact acaagacccg    960
cgccgaggtg aagttcgagg gcgacaccct ggtgaaccgc atcgagctga agggcatcga   1020
cttcaaggag gacggcaaca tcctggggca caagctggag tacaactaca cagccacaa   1080 cgtctatatc atggccgaca gcagaagaa cggcatcaag gtgaacttca agatccgcca   1140
caacatcgag gacggcagcg tgcagctcgc cgaccactac cagcagaaca ccccatcgg   1200 cgacggcccc gtgctgctgc ccgacaacca ctacctgagc acccagtccg ccctgagcaa   1260
agacccaaac gagaagcgcg atcacatggt cctgctggag ttcgtgaccg ccgccgggat   1320
cactctcggc atggacgagc tgtacaagta agcggccgca atcaacctct ggattacaaa   1380
atttgtgaaa gattgactgg tattcttaac tatgttgctc cttttacgct atgtggatac   1440
gctgctttaa tgcctttgta tcatgctatt acttcccgta cggctttcat tttctcctcc   1500
ttgtataaat cctggttgct gtctctttat gaggagttgt ggcccgttgt caggcaacgt   1560
ggcgtggtgt gcactgtgtt tgctgacgca acccccactg gttggggcat tgccaccacc   1620
tatcaactcc tttccgggac tttcgctttc cccctcccta ttgccacggc ggaactcatt   1680
gccgcctgcc ttgcccgctg ctggacaggg gctcggctgt tgggcactga caattccgtg   1740
gtgttgtcgg ggaagctgac gtcctttcca tggctgctcg cctgtgttgc caactggatt   1800
ctgcgcggga cgtccttctg ctacgtccct tcggccctca atccagcgga ccttccttcc   1860
cgcggcctgc tgccggttct gcggcctctt ccgcgtcttc gccttcgccc tcagacgagt   1920
cggatctccc tttgggccgc ctccccgcct gcctgcaggt ttgtcgagac ctagaaaaac   1980
atggagcaat cacaagtagc aatacagcag ctaccaatgc tgattgtgcc tggctagaag   2040
cacaagagga ggaggaggtg ggttttccag tcacacctca ggtaccttta agaccaatga   2100
cttacaaggc agctgtagat cttagccact ttttaaaaga aaaggggggga ctggaagggc   2160 taattcactc ccaacgaaga caagatctgc tttttgcttg tactgggtct ctctggttag   2220
accagatctg agcctgggag ctctctggct aactagggaa cccactgctt aagcctcaat   2280
aaagcttgcc ttgagtgctt caagtagtgt gtgcccgtct gttgtgtgac tctggtaact   2340
agagatccct cagacccttt tagtcagtgt ggaaaatctc tagcagggcc cgtttaaacc   2400
cgctgatcag cctcgactgt gccttctagt tgccagccat ctgttgtttg ccctcccccc   2460
gtgccttcct tgaccctgga aggtgccact cccactgtcc tttcctaata aaatgaggaa   2520
attgcatcgc attgtctgag taggtgtcat tctattctgg ggggtggggt ggggcaggac   2580
agcaaggggg aggattggga agacaatagc aggcatgctg gggatgcggt gggctctatg   2640
gcttctgagg cggaaagaac cagctggggc tctagggggt atccccacgc gccctgtagc   2700
ggcgcattaa gcgcggcggg tgtggtggtt acgcgcagcg tgaccgctac acttgccagc   2760
gccctagcgc ccgctccttt cgctttcttc ccttcctttc tcgccacgtt cgccggcttt   2820
ccccgtcaag ctctaaatcg gggcatccct ttagggttcc gatttagtgc tttacggcac   2880
ctcgacccca aaaaacttga ttagggtgat ggttcacgta gtgggccatc gccctgatag   2940 acggttttc gccctttgac gttggagtcc acgttcttta atagtggact cttgttccaa   3000
actggaacaa cactcaaccc tatctcggtc tattcttttg atttataagg gattttgggg   3060
atttcggcct attggttaaa aaatgagctg atttaacaaa aatttaacgc gaattaattc   3120
```

```
tgtggaatgt gtgtcagtta gggtgtggaa agtccccagg ctccccaggc aggcagaagt   3180
atgcaaagca tgcatctcaa ttagtcagca accaggtgtg gaaagtcccc aggctcccca   3240
gcaggcagaa gtatgcaaag catgcatctc aattagtcag caaccatagt cccgcccta    3300
actccgccca tcccgcccct aactccgccc agttccgccc attctccgcc ccatggctga   3360
ctaattttt ttatttatgc agaggccgag gccgcctctg cctctgagct attccagaag    3420
tagtgaggag gcttttttgg aggcctaggc ttttgcaaaa agctcccggg agcttgtata   3480
tccattttcg gatctgatca gcacgtgttg acaattaatc atcggcatag tatatcggca   3540
tagtataata cgacaaggtg aggaactaaa ccatggccaa gttgaccagt gccgttccgg   3600
tgctcaccgc gcgcgacgtc gccggagcgg tcgagttctg gaccgaccgg ctcgggttct   3660
cccgggactt cgtggaggac gacttcgccg gtgtggtccg ggacgacgtg accctgttca   3720
tcagcgcggt ccaggaccag gtggtgccgg acaacaccct ggcctgggtg tgggtgcgcg   3780
gcctggacga gctgtacgcc gagtggtcgg aggtcgtgtc cacgaacttc cgggacgcct   3840
ccgggccggc catgaccgag atcggcgagc agccgtgggg gcgggagttc gccctgcgcg   3900
acccggccgg caactgcgtg cacttcgtgg ccgaggagca ggactgacac gtgctacgag   3960
atttcgattc caccgccgcc ttctatgaaa ggttgggctt cggaatcgtt ttccgggacg   4020
ccggctggat gatcctccag cgcggggatc tcatgctgga gttcttcgcc cacccccaact  4080
tgtttattgc agcttataat ggttacaaat aaagcaatag catcacaaat ttcacaaata   4140
aagcattttt ttcactgcat tctagttgtg gtttgtccaa actcatcaat gtatcttatc   4200
atgtctgtat accgtcgacc tctagctaga gcttggcgta atcatggtca tagctgtttc   4260
ctgtgtgaaa ttgttatccg ctcacaattc cacacaacat acgagccgga agcataaagt   4320
gtaaagcctg gggtgcctaa tgagtgagct aactcacatt aattgcgttg cgctcactgc   4380
ccgctttcca gtcgggaaac ctgtcgtgcc agctgcatta tgaatcggc caacgcgcgg   4440
ggagaggcgg tttgcgtatt gggcgctctt ccgcttcctc gctcactgac tcgctgcgct   4500
cggtcgttcg gctgcggcga gcggtatcag ctcactcaaa ggcggtaata cggttatcca   4560
cagaatcagg ggataacgca ggaaagaaca tgtgagcaaa aggccagcaa aaggccagga   4620
accgtaaaaa ggccgcgttg ctggcgtttt tccataggct ccgcccccct gacgagcatc   4680
acaaaaatcg acgctcaagt cagaggtggc gaaacccgac aggactataa agataccagg   4740
cgtttccccc tggaagctcc ctcgtgcgct ctcctgttcc gaccctgccg cttaccggat   4800
acctgtccgc ctttctccct tcgggaagcg tggcgctttc tcaatgctca cgctgtaggt   4860
atctcagttc ggtgtaggtc gttcgctcca agctgggctg tgtgcacgaa ccccccgttc   4920
agcccgaccg ctgcgcctta tccggtaact atcgtcttga gtccaacccg gtaagacacg   4980
acttatcgcc actggcagca gccactggta acaggattag cagagcgagg tatgtaggcg   5040
gtgctacaga gttcttgaag tggtggccta actacggcta cactagaagg acagtatttg   5100
gtatctgcgc tctgctgaag ccagttacct tcggaaaaag agttggtagc tcttgatccg   5160
gcaaacaaac caccgctggt agcggtggtt ttttgtttg caagcagcag attacgcgca   5220
gaaaaaaagg atctcaagaa gatcctttga tcttttctac ggggtctgac gctcagtgga   5280
acgaaaactc acgttaaggg attttggtca tgagattatc aaaaaggatc ttcacctaga   5340
tccttttaaa ttaaaaatga agttttaaat caatctaaag tatatatgag taaacttggt   5400
ctgacagtta ccaatgctta atcagtgagg cacctatctc agcgatctgt ctatttcgtt   5460
catccatagt tgcctgactc cccgtcgtgt agataactac gatacgggag gcttaccat    5520
```

```
ctggccccag tgctgcaatg ataccgcgag acccacgctc accggctcca gatttatcag    5580
caataaacca gccagccgga agggccgagc gcagaagtgg tcctgcaact ttatccgcct    5640
ccatccagtc tattaattgt tgccgggaag ctagagtaag tagttcgcca gttaatagtt    5700
tgcgcaacgt tgttgccatt gctacaggca tcgtggtgtc acgctcgtcg tttggtatgg    5760
cttcattcag ctccggttcc caacgatcaa ggcgagttac atgatccccc atgttgtgca    5820
aaaaagcggt tagctccttc ggtcctccga tcgttgtcag aagtaagttg gccgcagtgt    5880
tatcactcat ggttatggca gcactgcata attctcttac tgtcatgcca tccgtaagat    5940
gcttttctgt gactggtgag tactcaacca agtcattctg agaatagtgt atgcggcgac    6000
cgagttgctc ttgcccggcg tcaatacggg ataataccgc gccacatagc agaactttaa    6060
aagtgctcat cattggaaaa cgttcttcgg ggcgaaaact ctcaaggatc ttaccgctgt    6120
tgagatccag ttcgatgtaa cccactcgtg cacccaactg atcttcagca tcttttactt    6180
tcaccagcgt ttctgggtga gcaaaaacag gaaggcaaaa tgccgcaaaa aagggaataa    6240
gggcgacacg gaaatgttga atactcatac tcttcctttt tcaatattat tgaagcattt    6300
atcaggggtta ttgtctcatg agcggataca tatttgaatg tatttagaaa aataaacaaa    6360
taggggttcc gcgcacattt ccccgaaaag tgccacctga cgtcgacgga tcgggagatc    6420
tcccgatccc ctatggtgca ctctcagtac aatctgctct gatgccgcat agttaagcca    6480
gtatctgctc cctgcttgtg tgttggaggt cgctgagtag tgcgcgagca aaatttaagc    6540
tacaacaagg caaggcttga ccgacaattg catgaagaat ctgcttaggg ttaggcgttt    6600
tgcgctgctt cgcgatgtac gggccagata tacgcgttga cattgattat tgactagtta    6660
ttaatagtaa tcaattacgg ggtcattagt tcatagccca tatatggagt tccgcgttac    6720
ataacttacg gtaaatggcc cgcctggctg accgcccaac gacccccgcc cattgacgtc    6780
aataatgacg tatgttccca tagtaacgcc aatagggact ttccattgac gtcaatgggt    6840
ggactattta cggtaaactg cccacttggc agtacatcaa gtgtatcata tgccaagtac    6900
gccccctatt gacgtcaatg acggtaaatg gcccgcctgg cattatgccc agtacatgac    6960
cttatgggac tttcctactt ggcagtacat ctacgtatta gtcatcgcta ttaccatggt    7020
gatgcggttt tggcagtaca tcaatgggcg tggatagcgg tttgactcac ggggatttcc    7080
aagtctccac cccattgacg tcaatgggag tttgttttgg caccaaaatc aacgggactt    7140
tccaaaatgt cgtaacaact ccgccccatt gacgcaaatg ggcggtaggc gtgtacggtg    7200
ggaggtctat ataagcagag ctctctggct aactagagaa cccactgctt actggcttat    7260
cgaaattaat acgactcact atagggagac ccaagctggt ttaaacttaa gcttggtacc    7320
gagctcacta gtccagtgtg gtggcagata tccagcacag tggcggccgc tcgagtctag    7380
agggcccgtt taaacnnnnn gggtctctct ggttagacca gatctgagcc tgggagctct    7440
ctggctaact agggaaccca ctgcttaagc ctcaataaag cttgccttga gtgcttcaag    7500
tagtgtgtgc ccgtctgttg tgtgactctg gtaactagag atccctcaga ccctttagt    7560
cagtgtggaa aatctctagc annnnnnnnn nccagcaact tatctgtgtc tgtccgattg    7620
tctagtgtct atgtttgatg ttatgcgcct gcgtctgtac tagttagcta actagctctg    7680
tatctggcgg acccgtggtg gaactgacga gttctgaaca cccggccgca accctgggag    7740
acgtcccagg gactttgggg gccgtttttg tggcccgacc tgaggaaggg agtcgatgtg    7800
gaatccgacc ccgtcaggat atgtggttct ggtaggagac gagaacctaa aacagttccc    7860
gcctccgtct gaattttttgc tttcggttttg gaaccgaagc cgcgcgtctt gtctgctgca    7920
```

```
gcgctgcagc atcgttctgt gttgtctctg tctgactgtg tttctgtatt tgtctgaaaa   7980
ttagggccag actgttacca ctcccttaag tttgaccttg ggtcactgga aagatgtcga   8040
gcggatcgct cacaaccagt cggtagatgt caagaagaga cgttgggtta ccttctgctc   8100
tgcagaatgg ccaaccttta acgtcggatg gccgcgagac ggcacctttg accgagacct   8160
catcacccag gttaagatca aggtcttttc acctggcccg catggacacc cagaccaggt   8220
cccctacatc gtgacctggg aagccttggc ttttgacccc cctccctggg tcaagccctt   8280
tgtacaccct aagcctccgc ctcctcttcc tccatccgcc ccgtctctcc cccttgaacc   8340
tcctcgttcg accccgcctc gatcctccct ttatccagcc ctcactcctt ctctaggcgc   8400
cnnnnnggaa aagtttagta aaacaccata tgtatgtttc agggaaagct aggggatggt   8460
tttatagaca tcactatgaa agccctcatc caagaataag ttcagaagta cacatcccac   8520
taggggatgc tagattggta ataacaacat attggggtct gcatacagga gaaagagact   8580
ggcatctggg tcagggagtc tccatagaat ggaggaaaaa gagatatagc acacaagtag   8640
accctgaact agcagaccaa ctaattcatc tgtattactt tgactgtttt tcagactctg   8700
ctataagaaa ggccttatta ggacatatag ttagccctag gtgtgaatat caagcaggac   8760
ataacaaggt aggatctcta caatacttgg cactagcagc attaataaca ccaaaaaaga   8820
taaagccacc tttgcctagt gttacgaaac tgacagagga tagatggaac aagcccagag   8880
agaccaaggg ccacagaggg agccacacaa tgaatggaca ctagagcttt tagaggagct   8940
taagaatgaa gctgttagac attttcctag gatttggctc catggcttag gcaacatat    9000 ctatgaaact tatggggata cttgggcagg agtggaagcc ataataatgc aacaactgct   9060
gtttatccat ttcagaattg ggtgtcgaca tagcagaata ggcgttactc aacagaggag   9120
agcaagaaat ggagccagta gatcctagac tagagccctg gaagcatcca ggaagtcagc   9180
ctaaaactgc ttgtaccact tgctattgta aaaagtgttg cttccattgc caagtttgtt   9240
tcacaacaaa agccttaggc atctcctatg gcaggaagaa gcggagacag cgacgaagac   9300
ctcctcaagg cagtcagact catcaagttt ctctatcaaa gcagtaagta gtacatgtaa   9360
tgcaacctat acaaatagca atagcagcat tagtagtagc aataataata gcaatagttg   9420
tgtggtccat agtaatcata gaatatagga aaatattaag acaaagaaaa atagacaggt   9480
taattgatag actaatnnnn nnnnggcccg aaggaataga agaagaaggt ggagagagag   9540
acagagacag atccattcga ttagtgaacg gatcggcact gcgtgcgcca attctgcaga   9600
caaatggcag tattcatcca caattttaaa agaaaggggg gattggggg gtacagtgca   9660 ggggaaagaa tagtagacat aatagcaaca gacatacaaa ctaaagaatt acaaaaacaa   9720
attacaaaaa ttcaaaattt tcgggtttat tacagggaca gcagagatcc agtttggtta   9780
attaatgctg ctgagccacg tgaagcctta agccgcaggg agaccctgaa aatagactgt   9840
aagcaacctt ggggtggggt aagcctgttg cagcgttagt gtatccatga actccttta    9900 gatacaagct atgtgtcatt cctcatggag acgccggaga gtcttgagct tacatgatgg   9960
tcctgcggag gccttaaagt cctgtgggga tgctcagggt tgtccctgtg tgtcactgag  10020
acctccgaaa gaatttaaat atcacagaaa aaaaaaacat aaagaagacc ttaagccttt  10080
ttaagttccc aaggagagcc agaagtggtg gtatatagct caacttggga gactgaggca  10140
aaaagactga ctgagtttaa gaccagccta gctacaccac aaagctcctt tctcaaaaga  10200
aaaagctccc aaggaggttg gatccccagt gagaccctca gcaggccct ctggcctcac   10260 tatggtcctg aggacacccc tccacactgc cctgatcttc ttaccccatc ctgcctgagc  10320
```

| | |
|---|---|
| tcttcacctg ctctcctctt gcattcaaat atcttctgct acagtaggtc cactggagtc | 10380 |
| tcccaggtac ccagagtgtg aatgtctgca gcactttctg ggggacaagg agcagagagc | 10440 |
| aagggaccca caattcgggt ctagtgtctg taaagccttg cggagggtag agttctagtt | 10500 |
| cacacaaggc accaagtgtt tttgctggtt gcctaggaaa caggacagtg ccaaatcagg | 10560 |
| aacagaaaga gtcaaggaac ccccaaccac tccaagcgga ggctgagaaa ggttttgtag | 10620 |
| ctggaataga gcatgcacta acagatggag acagctggct ttgagctctg aagcaagtat | 10680 |
| tacatatgga gacttgctgg ccttcaggtg cttatcttgt tattggatac tgcaggagga | 10740 |
| tgtaccacag ggcttcagct cagctgaccc ccaagtggga tatggaaaga gagatagagg | 10800 |
| aggagggacc attaagtgcc ttgctgcctg aattctgctt tccttctacc tctgagagag | 10860 |
| agctggggac tcggctgagt taagaaccca gctatcaatt ggaactgtga acagtccaa | 10920 |
| gggacaaaga tactaggtcc ccaactgcaa cttcctgggg aatgatgtgg aaaaatgctc | 10980 |
| agccaaggac aaagaaagca tcacccactc tggaacaatg tcccctgctg tgaactggtt | 11040 |
| catcaggcca tcagggcccc ttgttaagac tctaattacc ctaggactaa gtagaggtgt | 11100 |
| tgacgtccaa tgagcgcttt ctgcagacct agcaccaggg aagtgtttgg aaactgcagc | 11160 |
| ttcagcccct ctggccatct gctgacctac cccacctgga gcccttaatg ggtcaaacag | 11220 |
| caaagtccag ggggcagaga ggaggtgctt tggtctataa aggtagtggg gacccagtaa | 11280 |
| ccaccgg | 11287 |

<210> SEQ ID NO 12
<211> LENGTH: 11178
<212> TYPE: DNA
<213> ORGANISM: Artificial Sequence
<220> FEATURE:
<223> OTHER INFORMATION: Synthetic

<400> SEQUENCE: 12

| | |
|---|---|
| tacagtgcag gggaaagaat agtagacata atagcaacag acatacaaac taaagaatta | 60 |
| caaaaacaaa ttacaaaaat tcaaaatttt cgggtttatt acagggacag cagagatcca | 120 |
| gtttggttaa ttaattggct ccggtgcccg tcagtgggca gagcgcacat cgcccacagt | 180 |
| ccccgagaag ttgggggag gggtcggcaa ttgaaccggt gcctagagaa ggtggcgcgg | 240 |
| ggtaaactgg gaaagtgatg tcgtgtactg gctccgcctt tttcccgagg gtggggaga | 300 |
| accgtatata agtgcagtag tcgccgtgaa cgttcttttt cgcaacgggt ttgccgccag | 360 |
| aacacaggta agtgccgtgt gtggttcccg cgggcctggc ctctttacgg gttatggccc | 420 |
| ttgcgtgcct tgaattactt ccacctggct gcagtacgtg attcttgatc ccgagcttcg | 480 |
| ggttggaagt gggtgggaga gttcgaggcc ttgcgcttaa ggagcccctt cgcctcgtgc | 540 |
| ttgagttgag gcctggcctg ggcgctgggg ccgccgcgtg cgaatctggt ggcaccttcg | 600 |
| cgcctgtctc gctgctttcg ataagtctct agccatttaa aatttttgat gacctgctgc | 660 |
| gacgcttttt ttctggcaag atagtcttgt aaatgcgggc caagatctgc acactggtat | 720 |
| ttcggttttt ggggccgcgg gcggcgacgg ggcccgtgcg tcccagcgca catgttcggc | 780 |
| gaggcggggc ctgcgagcgc ggccaccgag aatcggacgg gggtagtctc aagctggccg | 840 |
| gcctgctctg tgcctggcc tcgcgccgcc gtgtatcgcc ccgccctggg cggcaaggct | 900 |
| ggcccggtcg gcaccagttg cgtgagcgga aagatggccg cttcccggcc ctgctgcagg | 960 |
| gagctcaaaa tggaggacgc ggcgctcggg agagcgggcg ggtgagtcac ccacacaaag | 1020 |
| gaaagggcc tttccgtcct cagccgtcgc ttcatgtgac tccacggagt accgggcgcc | 1080 |

-continued

```
gtccaggcac ctcgattagt tctcgagctt ttggagtacg tcgtctttag gttgggggga   1140
ggggttttat gcgatggagt ttccccacac tgagtgggtg gagactgaag ttaggccagc   1200
ttggcacttg atgtaattct ccttggaatt tgccctttt  gagtttggat cttggttcat   1260
tctcaagcct cagacagtgg ttcaaagttt ttttcttcca tttcaggtgt cgtgaggaat   1320
tcggccatta cggcccgcca ccatggctag attagataaa agtaaagtga ttaacagcgc   1380
attagagctg cttaatgagg tcggaatcga aggtttaaca acccgtaaac tcgcccagaa   1440
gctaggtgta gagcagccta cattgtattg gcatgtaaaa aataagcggg ctttgctcga   1500
cgccttagcc attgagatgt tagataggca ccatactcac ttttgccctt tagaagggga   1560
aagctggcaa gatttttttac gtaataacgc taaaagtttt agatgtgctt tactaagtca   1620
tcgcgatgga gcaaaagtac atttaggtac acggcctaca gaaaaacagt atgaaactct   1680
cgaaaatcaa ttagcctttt tatgccaaca aggttttca  ctagagaatg cattatatgc   1740
actcagcgct gtgggcatt  ttactttagg ttgcgtattg gaagatcaag agcatcaagt   1800
cgctaaagaa gaaagggaaa cacctactac tgatagtatg ccgccattat tacgacaagc   1860
tatcgaatta tttgatcacc aaggtgcaga gccagccttc ttattcggcc ttgaattgat   1920
catatgcgga ttagaaaaac aacttaaatg tgaaagtggg tcgccaaaaa agaagagaaa   1980
ggtcgacggc ggtggtgctt tgtctcctca gcactctgct gtcactcaag gaagtatcat   2040
caagaacaag gagggcatgg atgctaagtc actaactgcc tggtcccgga cactggtgac   2100
cttcaaggat gtatttgtgg acttcaccag ggaggagtgg aagctgctgg acactgctca   2160
gcagatcgtg tacagaaatg tgatgctgga gaactataag aacctggttt ccttgggtta   2220
tcagcttact aagccagatg tgatcctccg gttggagaag ggagaagagc cctggctggt   2280
ggagagagaa attcaccaag agacccatcc tgattcagag actgcatttg aaatcaaatc   2340
atcagtttaa ggccgcctcg gccatcgata aggatccgga atgcccctct ccctcccccc   2400
cccctaacgt tactggccga agccgcttgg aataaggccg gtgtgcgttt gtctatatgt   2460
tattttccac catattgccg tcttttggca atgtgagggc ccggaaacct ggccctgtct   2520
tcttgacgag cattcctagg ggtctttccc ctctcgccaa aggaatgcaa ggtctgttga   2580
atgtcgtgaa ggaagcagtt cctctggaag cttcttgaag acaaacaacg tctgtagcga   2640
ccctttgcag cagcggaac  cccccacctg gcgacaggtg cctctgcggc caaaagccac   2700
gtgtataaga tacacctgca aaggcggcac aaccccagtg ccacgttgtg agttggatag   2760
ttgtggaaag agtcaaatgg ctctcctcaa gcgtattcaa caaggggctg aaggatgccc   2820
agaaggtacc ccattgtatg ggatctgatc tggggcctcg gtgcacatgc tttacatgtg   2880
tttagtcgag gttaaaaaaa cgtctaggcc ccccgaacca cggggacgtg gttttccttt   2940
gaaaaacacg atgataatat ggccacaacc atgaccgagt acaagcccac ggtgcgcctc   3000
gccacccgcg acgacgtccc ccgggccgta cgcaccctcg ccgccgcgtt cgccgactac   3060
cccgccacgc gccacaccgt cgacccggac cgccacatcg agcgggtcac cgagctgcaa   3120
gaactcttcc tcacgcgcgt cgggctcgac atcggcaagg tgtgggtcgc ggacgacggc   3180
gccgcggtgg cggtctggac cacgccggag agcgtcgaag cgggggcggt gttcgccgag   3240
atcgcccgc  gcatggccga gttgagcggt tccggctgg  ccgcgcagca acagatggaa   3300
ggcctcctgg cgccgcaccg gcccaaggag cccgcgtggt tcctggccac cgtcggcgtc   3360
tcgcccgacc accagggcaa gggtctgggc agcgccgtcg tgctccccgg agtggaggcg   3420
gccgagcgcg ccggggtgcc cgccttcctg gagacctccg cgccccgcaa cctccccttc   3480
```

-continued

| | |
|---|---|
| tacgagcggc tcggcttcac cgtcaccgcc gacgtcgagg tgcccgaagg accgcgcacc | 3540 |
| tggtgcatga cccgcaagcc cggtgcctga gcggccgcaa tcaacctctg gattacaaaa | 3600 |
| tttgtgaaag attgactggt attcttaact atgttgctcc ttttacgcta tgtggatacg | 3660 |
| ctgctttaat gcctttgtat catgctatta cttcccgtac ggctttcatt ttctcctcct | 3720 |
| tgtataaatc ctggttgctg tctctttatg aggagttgtg gcccgttgtc aggcaacgtg | 3780 |
| gcgtggtgtg cactgtgttt gctgacgcaa cccccactgg ttggggcatt gccaccacct | 3840 |
| atcaactcct ttccgggact ttcgctttcc cctccctat tgccacggcg gaactcattg | 3900 |
| ccgcctgcct tgcccgctgc tggacagggg ctcggctgtt gggcactgac aattccgtgg | 3960 |
| tgttgtcggg gaagctgacg tcctttccat ggctgctcgc ctgtgttgcc aactggattc | 4020 |
| tgcgcgggac gtccttctgc tacgtcccct cggccctcaa tccagcggac cttccttccc | 4080 |
| gcggcctgct gccggttctg cggcctcttc cgcgtcttcg ccttcgccct cagacgagtc | 4140 |
| ggatctccct ttgggccgcc tccccgcctg cctgcaggtt tgtcgagacc tagaaaaaca | 4200 |
| tggagcaatc acaagtagca atacagcagc taccaatgct gattgtgcct ggctagaagc | 4260 |
| acaagaggag gaggaggtgg gttttccagt cacacctcag gtacctttaa gaccaatgac | 4320 |
| ttacaaggca gctgtagatc ttagccactt tttaaaagaa aaggggggac tggaagggct | 4380 |
| aattcactcc caacgaagac aagatctgct ttttgcttgt actgggtctc tctggttaga | 4440 |
| ccagatctga gcctgggagc tctctggcta actagggaac ccactgctta agcctcaata | 4500 |
| aagcttgcct tgagtgcttc aagtagtgtg tgcccgtctg ttgtgtgact ctggtaacta | 4560 |
| gagatccctc agaccctttt agtcagtgtg gaaaatctct agcagggccc gtttaaaccc | 4620 |
| gctgatcagc ctcgactgtg ccttctagtt gccagccatc tgttgtttgc cctcccccg | 4680 |
| tgccttcctt gaccctggaa ggtgccactc ccactgtcct ttcctaataa aatgaggaaa | 4740 |
| ttgcatcgca ttgtctgagt aggtgtcatt ctattctggg gggtggggtg ggcaggaca | 4800 |
| gcaaggggga ggattgggaa gacaatagca ggcatgctgg ggatgcggtg gctctatgg | 4860 |
| cttctgaggc ggaaagaacc agctggggct ctaggggta tccccacgcg ccctgtagcg | 4920 |
| gcgcattaag cgcggcgggt gtggtggtta cgcgcagcgt gaccgctaca cttgccagcg | 4980 |
| ccctagcgcc cgctcctttc gctttcttcc cttcctttct cgccacgttc gccggctttc | 5040 |
| cccgtcaagc tctaaatcgg ggcatccctt tagggttccg atttagtgct ttacggcacc | 5100 |
| tcgaccccaa aaaacttgat tagggtgatg gttcacgtag tgggccatcg ccctgataga | 5160 |
| cggtttttcg ccctttgacg ttggagtcca cgttctttaa tagtggactc ttgttccaaa | 5220 |
| ctggaacaac actcaaccct atctcggtct attcttttga tttataaggg attttgggga | 5280 |
| tttcggccta ttggttaaaa atgagctga tttaacaaaa atttaacgcg aattaattct | 5340 |
| gtggaatgtg tgtcagttag ggtgtggaaa gtccccaggc tccccaggca ggcagaagta | 5400 |
| tgcaaagcat gcatctcaat tagtcagcaa ccaggtgtgg aaagtcccca ggctccccag | 5460 |
| caggcagaag tatgcaaagc atgcatctca attagtcagc aaccatagtc cgcccctaa | 5520 |
| ctccgcccat cccgcccta actccgccca gttccgccca ttctccgccc catggctgac | 5580 |
| taattttttt tatttatgca gaggccgagg ccgcctctgc ctctgagcta ttccagaagt | 5640 |
| agtgaggagg cttttttgga ggcctaggct tttgcaaaaa gctcccggga gcttgtatat | 5700 |
| ccattttcgg atctgatcag cacgtgttga caattaatca tcggcatagt atatcggcat | 5760 |
| agtataatac gacaaggtga ggaactaaac catggccaag ttgaccagtg ccgttccggt | 5820 |
| gctcaccgcg cgcgacgtcg ccggagcggt cgagttctgg accgaccggc tcgggttctc | 5880 |

```
ccgggacttc gtggaggacg acttcgccgg tgtggtccgg gacgacgtga ccctgttcat   5940
cagcgcggtc caggaccagg tggtgccgga caacaccctg gcctgggtgt gggtgcgcgg   6000
cctggacgag ctgtacgccg agtggtcgga ggtcgtgtcc acgaacttcc gggacgcctc   6060
cgggccggcc atgaccgaga tcggcgagca gccgtggggg cggagttcg ccctgcgcga    6120
cccggccggc aactgcgtgc acttcgtggc cgaggagcag gactgacacg tgctacgaga   6180
tttcgattcc accgccgcct tctatgaaag gttgggcttc ggaatcgttt ccgggacgc    6240
cggctggatg atcctccagc gcgggatct catgctggag ttcttcgccc accccaactt    6300
gtttattgca gcttataatg gttacaaata aagcaatagc atcacaaatt tcacaaataa   6360
agcatttttt tcactgcatt ctagttgtgg tttgtccaaa ctcatcaatg tatcttatca   6420
tgtctgtata ccgtcgacct ctagctagag cttggcgtaa tcatggtcat agctgtttcc   6480
tgtgtgaaat tgttatccgc tcacaattcc acacaacata cgagccggaa gcataaagtg   6540
taaagcctgg ggtgcctaat gagtgagcta actcacatta attgcgttgc gctcactgcc   6600
cgctttccag tcgggaaacc tgtcgtgcca gctgcattaa tgaatcggcc aacgcgcggg   6660
gagaggcggt ttgcgtattg ggcgctcttc cgcttcctcg ctcactgact cgctgcgctc   6720
ggtcgttcgg ctgcggcgag cggtatcagc tcactcaaag gcggtaatac ggttatccac   6780
agaatcaggg gataacgcag gaaagaacat gtgagcaaaa ggccagcaaa aggccaggaa   6840
ccgtaaaaag gccgcgttgc tggcgttttt ccataggctc cgcccccctg acgagcatca   6900
caaaatcga cgctcaagtc agaggtggcg aaacccgaca ggactataaa gataccaggc    6960
gtttccccct ggaagctccc tcgtgcgctc tcctgttccg accctgccgc ttaccggata   7020
cctgtccgcc tttctccctt cgggaagcgt ggcgctttct caatgctcac gctgtaggta   7080
tctcagttcg gtgtaggtcg ttcgctccaa gctgggctgt gtgcacgaac cccccgttca   7140
gcccgaccgc tgcgccttat ccggtaacta tcgtcttgag tccaacccgg taagacacga   7200
cttatcgcca ctggcagcag ccactggtaa caggattagc agagcgaggt atgtaggcgg   7260
tgctacagag ttcttgaagt ggtggcctaa ctacggctac actagaagga cagtatttgg   7320
tatctgcgct ctgctgaagc cagttacctt cggaaaaaga gttggtagct cttgatccgg   7380
caaacaaacc accgctggta gcggtggttt ttttgtttgc aagcagcaga ttacgcgcag   7440
aaaaaaagga tctcaagaag atcctttgat cttttctacg gggtctgacg ctcagtggaa   7500
cgaaaactca cgttaaggga ttttggtcat gagattatca aaaaggatct tcacctagat   7560
ccttttaaat taaaaatgaa gttttaaatc aatctaaagt atatatgagt aaacttggtc   7620
tgacagttac caatgcttaa tcagtgaggc acctatctca gcgatctgtc tatttcgttc   7680
atccatagtt gcctgactcc ccgtcgtgta gataactacg atacgggagg gcttaccatc   7740
tggccccagt gctgcaatga taccgcgaga cccacgctca ccggctccag atttatcagc   7800
aataaaccag ccagccggaa gggccgagcg cagaagtggt cctgcaactt tatccgcctc   7860
catccagtct attaattgtt gccgggaagc tagagtaagt agttcgccag ttaatagttt   7920
gcgcaacgtt gttgccattg ctacaggcat cgtggtgtca cgctcgtcgt ttggtatggc   7980
ttcattcagc tccggttccc aacgatcaag gcgagttaca tgatccccca tgttgtgcaa   8040
aaaagcggtt agctccttcg gtcctccgat cgttgtcaga agtaagttgg ccgcagtgtt   8100
atcactcatg gttatggcag cactgcataa ttctcttact gtcatgccat ccgtaagatg   8160
cttttctgtg actggtgagt actcaaccaa gtcattctga gaatagtgta tgcggcgacc   8220
gagttgctct tgcccggcgt caatacggga taataccgcg ccacatagca gaactttaaa   8280
```

```
agtgctcatc attggaaaac gttcttcggg gcgaaaactc tcaaggatct taccgctgtt   8340
gagatccagt tcgatgtaac ccactcgtgc acccaactga tcttcagcat cttttacttt   8400
caccagcgtt tctgggtgag caaaaacagg aaggcaaaat gccgcaaaaa agggaataag   8460
ggcgacacgg aaatgttgaa tactcatact cttccttttt caatattatt gaagcattta   8520
tcagggttat tgtctcatga gcggatacat atttgaatgt atttagaaaa ataaacaaat   8580
aggggttccg cgcacatttc cccgaaaagt gccacctgac gtcgacggat cgggagatct   8640
cccgatcccc tatggtgcac tctcagtaca atctgctctg atgccgcata gttaagccag   8700
tatctgctcc ctgcttgtgt gttggaggtc gctgagtagt gcgcgagcaa aatttaagct   8760
acaacaaggc aaggcttgac cgacaattgc atgaagaatc tgcttagggt taggcgtttt   8820
gcgctgcttc gcgatgtacg ggccagatat acgcgttgac attgattatt gactagttat   8880
taatagtaat caattacggg gtcattagtt catagcccat atatggagtt ccgcgttaca   8940
taacttacgg taaatggccc gcctggctga ccgcccaacg acccccgccc attgacgtca   9000
ataatgacgt atgttcccat agtaacgcca atagggactt tccattgacg tcaatgggtg   9060
gactatttac ggtaaactgc ccacttggca gtacatcaag tgtatcatat gccaagtacg   9120
cccccctattg acgtcaatga cggtaaatgg cccgcctggc attatgccca gtacatgacc   9180
ttatgggact ttcctacttg gcagtacatc tacgtattag tcatcgctat taccatggtg   9240
atgcggtttt ggcagtacat caatgggcgt ggatagcggt ttgactcacg gggatttcca   9300
agtctccacc ccattgacgt caatgggagt ttgttttggc accaaaatca acgggacttt   9360
ccaaaatgtc gtaacaactc cgccccattg acgcaaatgg gcggtaggcg tgtacggtgg   9420
gaggtctata taagcagagc ggtttaaact taagcttggt accgagctca ctagtccagt   9480
gtggtggcag atatccagca cagtggcggc cgctcgagtc tagagggccc gttttgcctg   9540
tactgggtct ctctggttag accagatctg agcctgggag ctctctggct aactagggaa   9600
cccactgctt aagcctcaat aaagcttgcc ttgagtgctt caagtagtgt gtgcccgtct   9660
gttgtgtgac tctggtaact agagatccct cagaccctttt tagtcagtgt ggaaaatctc   9720
tagcagtggc gcccgaacag ggacttgaaa gcgaaaggga accagagga gctctctcga   9780
cgcaggactc ggcttgctga agcgcgcacg gcaagaggcg aggggcggcg actggtgagt   9840
acgccaaaaa ttttgactag cggaggctag aaggagagag atgggtgcga gagcgtcagt   9900
attaagcggg ggagaattag atcgcgatgg gaaaaaattc ggttaaggcc agggggaaag   9960
aaaaaatata aattaaaaca tatagtatgg gcaagcaggg agctagaacg attcgcagtt  10020
aatcctggcc tgttagaaac atcagaaggc tgtagacaaa tactgggaca gctacaacca  10080
tcccttcaga caggatcaga agaacttaga tcattatata atacagtagc aaccctctat  10140
tgtgtgcatc aaaggataga gataaaagac accaaggaag ctttagacaa gatagaggaa  10200
gagcaaaaca aaagtaagac caccgcacag caagcggccg ctgatcttca gacctggagg  10260
aggagatatg agggacaatt ggagaagtga attatataaa tataaagtag taaaaattga  10320
accattagga gtagcaccca ccaaggcaaa gagaagagtg gtgcagagag aaaaaagagc  10380
agtgggaata ggagctttgt tccttgggtt cttgggagca gcaggaagca ctatgggcgc  10440
agcgtcaatg acgctgacgg tacaggccag acaattattg tctggtatag tgcagcagca  10500
gaacaatttg ctgagggcta ttgaggcgca acagcatctg ttgcaactca cagtctgggg  10560
catcaagcag ctccaggcaa gaatcctggc tgtggaaaga tacctaaagg atcaacagct  10620
cctggggatt tggggttgct ctggaaaact catttgcacc actgctgtgc cttggaatgc  10680
```

| | |
|---|---|
| tagttggagt aataaatctc tggaacagat ttggaatcac acgacctgga tggagtggga | 10740 |
| cagagaaatt aacaattaca caagcttaat acactcctta attgaagaat cgcaaaacca | 10800 |
| gcaagaaaag aatgaacaag aattattgga attagataaa tgggcaagtt tgtggaattg | 10860 |
| gtttaacata acaaattggc tgtggtatat agaaattatt caatgata gtaggaggct | 10920 |
| tggtaggttt aagaatagtt tttgctgtac tttctatagt gaatagagtt aggcagggat | 10980 |
| attcaccatt atcgtttcag acccacctcc caaccccgag gggacccgac aggcccgaag | 11040 |
| gaatagaaga agaaggtgga gagagagaca gagacagatc cattcgatta gtgaacggat | 11100 |
| cggcactgcg tgcgccaatt ctgcagacaa atggcagtat tcatccacaa ttttaaaaga | 11160 |
| aaagggggga ttgggggg | 11178 |

<210> SEQ ID NO 13
<211> LENGTH: 10573
<212> TYPE: DNA
<213> ORGANISM: Artificial Sequence
<220> FEATURE:
<223> OTHER INFORMATION: Synthetic

<400> SEQUENCE: 13

| | |
|---|---|
| aatgaagcta ctgtcttcta tcgaacaagc atgcgatatt tgccgactta aaaagctcaa | 60 |
| gtgctccaaa gaaaaaccga agtgcgccaa gtgtctgaag aacaactggg agtgtcgcta | 120 |
| ctctcccaaa accaaaaggt ctccgctgac tagggcacat ctgacagaag tggaatcaag | 180 |
| gctagaaaga ctggaacagc tatttctact gattttcct cgagaagacc ttgacatgat | 240 |
| tttgaaaatg gattctttac aggatataaa agcattgtta acaggattat ttgtacaaga | 300 |
| taatgtgaat aaagatgccg tcacagatag attggcttca gtggagactg atatgcctct | 360 |
| aacattgaga cagcatagaa taagtgcgac atcatcatcg aagagagta gtaacaaagg | 420 |
| tcaaagacag ttgactgtat cgattgactc ggcagctcat catgataact ccacaattcc | 480 |
| gttggatttt atgcccaggg atgctcttca tggatttgat tggtctgaag aggatgacat | 540 |
| gtcggatggc ttgccccttcc tgaaaacgga ccccaacaat aatgggttct ttggcgacgg | 600 |
| ttctctctta tgtattcttc gatctattgg ctttaaaccg gaaaattaca cgaactctaa | 660 |
| cgttaacagg ctcccgacca tgattacgga tagatacacg ttggcttcta gatccacaac | 720 |
| atcccgttta cttcaaagtt atctcaataa ttttcacccc tactgcccta tcgtgcactc | 780 |
| accgacgcta atgatgttgt ataataacca gattgaaatc gcgtcgaagg atcaatggca | 840 |
| aatccttttt aactgcatat tagccattgg agcctggtgt atagagggg aatctactga | 900 |
| tatagatgtt ttttactatc aaaatgctaa atctcatttg acgagcaagg tcttcgagtc | 960 |
| aggttccata atttggtga cagccctaca tcttctgtcg cgatatacac agtggaggca | 1020 |
| gaaaacaaat actagctata atttcacag cttttccata agaatggcca tatcattggg | 1080 |
| cttgaatagg gacctcccct cgtccttcag tgatagcagc attctggaac aaagacgccg | 1140 |
| aatttggtgg tctgtctact cttgggagat ccaattgtcc ctgctttatg gtcgatccat | 1200 |
| ccagcttttct cagaatacaa tctccttccc ttcttctgtc gacgatgtgc agcgtaccac | 1260 |
| aacaggtccc accatatatc atggcatcat tgaaacagca aggctcttac aagttttcac | 1320 |
| aaaaatctat gaactagaca aaacagtaac tgcagaaaaa agtccatatat gtgcaaaaaa | 1380 |
| atgcttgatg atttgtaatg agattgagga ggtttcgaga caggcaccaa gttttttaca | 1440 |
| aatggatatt tccaccaccg ctctaaccaa tttgttgaag gaacacccctt ggctatcctt | 1500 |
| tacaagattc gaactgaagt ggaaacagtt gtctcttatc atttatgtat taagagattt | 1560 |

-continued

```
tttcactaat tttacccaga aaaagtcaca actagaacag gatcaaaatg atcatcaaag      1620
ttatgaagtt aaacgatgct ccatcatgtt aagcgatgca gcacaaagaa ctgttatgtc      1680
tgtaagtagc tatatggaca atcataatgt cacccccatat tttgcctgga attgttctta    1740
ttacttgttc aatgcagtcc tagtacccat aaagactcta ctctcaaact caaaatcgaa      1800
tgctgagaat aacgagaccg cacaattatt acaacaaatt aacactgttc tgatgctatt     1860
aaaaaaactg gccacttta aaatccgac ttgtgaaaaa tacattcaag tactggaaga       1920
ggtatgtgcg ccgtttctgt tatcacagtg tgcaatccca ttaccgcata tcagttataa    1980
caatagtaat ggtagcgcca ttaaaaatat tgtcggttct gcaactatcg cccaataccc    2040
tactcttccg gaggaaaatg tcaacaatat cagtgttaaa tatgtttctc ctggctcagt     2100
agggccttca cctgtgccat tgaaatcagg agcaagtttc agtgatctag tcaagctgtt    2160
atctaaccgt ccaccctctc gtaactctcc agtgacaata ccaagaagca ccttcgca      2220 tcgctcagtc acgccttttc tagggcaaca gcaacagctg caatcattag tgccactgac     2280
cccgtctgct ttgtttggtg gcgccaattt taatcaaagt gggaatattg ctgatagctc    2340
attgtccttc actttcacta acagtagcaa cggtccgaac ctcataacaa ctcaaacaaa    2400
ttctcaagcg ctttcacaac caattgcctc ctctaacgtt catgataact tcatgaataa     2460
tgaaatcacg gctagtaaaa ttgatgatgg taataattca aaaccactgt cacctggttg    2520
gacggaccaa actgcgtata acgcgtttgg aatcactaca gggatgttta ataccactac    2580
aatggatgat gtataataact atctattcga tgatgaagat accccaccaa acccaaaaaa    2640
agagtaagaa ttcgatatca agcttatcga taatcaacct ctggattaca aaatttgtga    2700
aagattgact ggtattctta actatgttgc tccttttacg ctatgtggat acgctgcttt    2760
aatgcctttg tatcatgcta ttacttcccg tacggctttc attttctcct ccttgtataa    2820
atcctggttg ctgtctcttt atgaggagtt gtggcccgtt gtcaggcaac gtggcgtggt     2880
gtgcactgtg tttgctgacg caaccccac tggttgggc attgccacca cctatcaact    2940
cctttccggg actttcgctt tccccctccc tattgccacg gcggaactca ttgccgcctg    3000
ccttgcccgc tgctggacag gggctcggct gttgggcact gacaattccg tggtgttgtc    3060
ggggaagctg acgtcctttc catggctgct cgcctgtgtt gccaactgga ttctgcgcgg    3120
gacgtccttc tgctacgtcc cttcggccct caatccagcg gaccttcctt cccgcggcct    3180
gctgccggtt ctgcggcctc ttccgcgtct tcgccttcgc cctcagacga gtcggatctc    3240
cctttgggcc gcctccccgc ctgcctgcag gtttgtcgag acctagaaaa acatggagca    3300
atcacaagta gcaatacagc agctaccaat gctgattgtg cctggctaga agcacaagag    3360
gaggaggagg tgggttttcc agtcacacct caggtacctt taagaccaat gacttacaag    3420
gcagctgtag atcttagcca cttttttaaa gaaaaggggg gactggaagg gctaattcac    3480
tcccaacgaa gacaagatct gcttttttgct tgtactgggt ctctctggtt agaccagatc    3540
tgagcctggg agctctctgg ctaactaggg aacccactgc ttaagcctca ataaagcttg    3600
ccttgagtgc ttcaagtagt gtgtgcccgt ctgttgtgtg actctggtaa ctagagatcc    3660
ctcagaccct tttagtcagt gtggaaaatc tctagcaggg cccgtttaaa cccgctgatc    3720
agcctcgact gtgccttcta gttgccagcc atctgttgtt tgcccctccc ccgtgccttc    3780
cttgaccctg gaaggtgcca ctcccactgt cctttcctaa taaaatgagg aaattgcatc    3840
gcattgtctg agtaggtgtc attctattct ggggggtggg gtgggcagg acagcaaggg    3900 ggaggattgg gaagacaata gcaggcatgc tggggatgcg gtgggctcta tggcttctga    3960
```

```
ggcggaaaga accagctggg gctctagggg gtatccccac gcgcctgta gcggcgcatt    4020 aagcgcggcg ggtgtggtgg ttacgcgcag cgtgaccgct acacttgcca gcgccctagc    4080
gcccgctcct ttcgctttct tcccttcctt tctcgccacg ttcgccggct ttccccgtca    4140
agctctaaat cggggcatcc ctttaggggtt ccgatttagt gctttacggc acctcgaccc    4200
caaaaaactt gattagggtg atggttcacg tagtgggcca tcgccctgat agacggtttt    4260
tcgccctttg acgttggagt ccacgttctt taatagtgga ctcttgttcc aaactggaac    4320
aacactcaac cctatctcgg tctattcttt tgatttataa gggattttgg ggatttcggc    4380
ctattggtta aaaaatgagc tgatttaaca aaaatttaac gcgaattaat tctgtggaat    4440
gtgtgtcagt tagggtgtgg aaagtcccca ggctccccag gcaggcagaa gtatgcaaag    4500
catgcatctc aattagtcag caaccaggtg tggaaagtcc ccaggctccc cagcaggcag    4560
aagtatgcaa agcatgcatc tcaattagtc agcaaccata gtcccgcccc taactccgcc    4620
catcccgccc ctaactccgc ccagttccgc ccattctccg ccccatggct gactaatttt    4680
ttttatttat gcagaggccg aggccgcctc tgcctctgag ctattccaga agtagtgagg    4740 aggcttttt ggaggcctag gcttttgcaa aaagctcccg ggagcttgta tatccatttt    4800
cggatctgat cagcacgtgt tgacaattaa tcatcggcat agtatatcgg catagtataa    4860
tacgacaagg tgaggaacta aaccatggcc aagttgacca gtgccgttcc ggtgctcacc    4920
gcgcgcgacg tcgccggagc ggtcgagttc tggaccgacc ggctcgggtt ctcccgggac    4980
ttcgtggagg acgacttcgc cggtgtggtc cgggacgacg tgaccctgtt catcagcgcg    5040
gtccaggacc aggtggtgcc ggacaacacc ctggcctggg tgtgggtgcg cggcctggac    5100
gagctgtacg ccgagtggtc ggaggtcgtg tccacgaact tccgggacgc ctccgggccg    5160
gccatgaccg agatcggcga gcagccgtgg gggcgggagt tcgccctgcg cgacccggcc    5220
ggcaactgcg tgcacttcgt ggccgaggag caggactgac acgtgctacg agatttcgat    5280
tccaccgccg ccttctatga aaggttgggc ttcggaatcg ttttccggga cgccggctgg    5340
atgatcctcc agcgcgggga tctcatgctg gagttcttcg cccacccaa cttgtttatt    5400 gcagcttata atggttacaa ataaagcaat agcatcacaa atttcacaaa taaagcattt    5460
ttttcactgc attctagttg tggtttgtcc aaactcatca atgtatctta tcatgtctgt    5520
ataccgtcga cctctagcta gagcttggcg taatcatggt catagctgtt tcctgtgtga    5580
aattgttatc cgctcacaat tccacacaac atacgagccg gaagcataaa gtgtaaagcc    5640
tggggtgcct aatgagtgag ctaactcaca ttaattgcgt tgcgctcact gcccgctttc    5700
cagtcgggaa acctgtcgtg ccagctgcat taatgaatcg gccaacgcgc ggggagaggc    5760
ggtttgcgta ttgggcgctc ttccgcttcc tcgctcactg actcgctgcg ctcggtcgtt    5820
cggctgcggc gagcggtatc agctcactca aaggcggtaa tacggttatc cacagaatca    5880
ggggataacg caggaaagaa catgtgagca aaaggccagc aaaaggccag gaaccgtaaa    5940
aaggccgcgt tgctggcgtt tttccatagg ctccgccccc ctgacgagca tcacaaaaat    6000
cgacgctcaa gtcagaggtg gcgaaacccg acaggactat aaagatacca ggcgtttccc    6060
cctggaagct ccctcgtgcg ctctcctgtt ccgaccctgc cgcttaccgg atacctgtcc    6120
gcctttctcc cttcgggaag cgtggcgctt tctcaatgct cacgctgtag gtatctcagt    6180
tcggtgtagg tcgttcgctc caagctgggc tgtgtgcacg aaccccccgt tcagcccgac    6240
cgctgcgcct tatccggtaa ctatcgtctt gagtccaacc cggtaagaca cgacttatcg    6300
ccactggcag cagccactgg taacaggatt agcagagcga ggtatgtagg cggtgctaca    6360
```

```
gagttcttga agtggtggcc taactacggc tacactagaa ggacagtatt tggtatctgc    6420
gctctgctga agccagttac cttcggaaaa agagttggta gctcttgatc cggcaaacaa    6480
accaccgctg gtagcggtgg ttttttttgtt tgcaagcagc agattacgcg cagaaaaaaa    6540
ggatctcaag aagatccttt gatcttttct acggggtctg acgctcagtg gaacgaaaac    6600
tcacgttaag ggattttggt catgagatta tcaaaaagga tcttcaccta gatccttta    6660 aattaaaaat gaagttttaa atcaatctaa agtatatatg agtaaacttg gtctgacagt    6720
taccaatgct taatcagtga ggcacctatc tcagcgatct gtctatttcg ttcatccata    6780
gttgcctgac tccccgtcgt gtagataact acgatacggg agggcttacc atctggcccc    6840
agtgctgcaa tgataccgcg agacccacgc tcaccggctc cagatttatc agcaataaac    6900
cagccagccg aagggccga gcgcagaagt ggtcctgcaa ctttatccgc ctccatccag    6960
tctattaatt gttgccggga agctagagta agtagttcgc cagttaatag tttgcgcaac    7020
gttgttgcca ttgctacagg catcgtggtg tcacgctcgt cgtttggtat ggcttcattc    7080
agctccggtt cccaacgatc aaggcgagtt acatgatccc ccatgttgtg caaaaaagcg    7140
gttagctcct tcggtcctcc gatcgttgtc agaagtaagt tggccgcagt gttatcactc    7200
atggttatgg cagcactgca taattctctt actgtcatgc catccgtaag atgcttttct    7260
gtgactggtg agtactcaac caagtcattc tgagaatagt gtatgcggcg accgagttgc    7320
tcttgcccgg cgtcaatacg ggataatacc gcgccacata gcagaacttt aaaagtgctc    7380
atcattggaa aacgttcttc ggggcgaaaa ctctcaagga tcttaccgct gttgagatcc    7440
agttcgatgt aacccactcg tgcacccaac tgatcttcag catcttttac tttcaccagc    7500
gtttctgggt gagcaaaaac aggaaggcaa aatgccgcaa aaaagggaat aagggcgaca    7560
cggaaatgtt gaatactcat actcttcctt tttcaatatt attgaagcat ttatcagggt    7620
tattgtctca tgagcggata catatttgaa tgtatttaga aaaataaaca aatagggggtt    7680 ccgcgcacat ttccccgaaa agtgccacct gacgtcgacg gatcgggaga tctcccgatc    7740
ccctatggtg cactctcagt acaatctgct ctgatgccgc atagttaagc cagtatctgc    7800
tccctgcttg tgtgttggag gtcgctgagt agtgcgcgag caaaatttaa gctacaacaa    7860
ggcaaggctt gaccgacaat tgcatgaaga atctgcttag ggttaggcgt tttgcgctgc    7920
ttcgcgatgt acgggccaga tatacgcgtt gacattgatt attgactagt tattaatagt    7980
aatcaattac ggggtcatta gttcatagcc catatatgga gttccgcgtt acataactta    8040
cggtaaatgg cccgcctggc tgaccgccca acgacccccg cccattgacg tcaataatga    8100
cgtatgttcc catagtaacg ccaatagggga ctttccattg acgtcaatgg gtggactatt    8160
tacggtaaac tgcccacttg gcagtacatc aagtgtatca tatgccaagt acgccccta    8220 ttgacgtcaa tgacggtaaa tggcccgcct ggcattatgc ccagtacatg accttatggg    8280
actttcctac ttggcagtac atctacgtat tagtcatcgc tattaccatg gtgatgcggt    8340
tttggcagta catcaatggg cgtggatagc ggtttgactc acggggattt ccaagtctcc    8400
accccattga cgtcaatggg agtttgtttt ggcaccaaaa tcaacgggac tttccaaaat    8460
gtcgtaacaa ctccgcccca ttgacgcaaa tgggcggtag cgtgtacgg tgggaggtct    8520 atataagcag agctctctgg ctaactagag aacccactgc ttactggctt atcgaaatta    8580
atacgactca ctatagggag acccaagctg gtttaaactt aagcttggta ccgagctcac    8640
tagtccagtg tggtggcaga tatccagcac agtggcggcc gctcgagggg cccgttttgc    8700
ctgtactggg tctctctggt tagaccagat ctgagcctgg gagctctctg gctaactagg    8760
```

-continued

| | |
|---|---|
| gaacccactg cttaagcctc aataaagctt gccttgagtg cttcaagtag tgtgtgcccg | 8820 |
| tctgttgtgt gactctggta actagagatc cctcagaccc ttttagtcag tgtggaaaat | 8880 |
| ctctagcagt ggcgcccgaa cagggacttg aaagcgaaag ggaaaccaga ggagctctct | 8940 |
| cgacgcagga ctcggcttgc tgaagcgcgc acggcaagag gcgaggggcg cgactggtg | 9000 |
| agtacgccaa aaattttgac tagcggaggc tagaaggaga gagatgggtg cgagagcgtc | 9060 |
| agtattaagc gggggagaat tagatcgcga tgggaaaaaa ttcggttaag gccaggggga | 9120 |
| aagaaaaaat ataaattaaa acatatagta tgggcaagca gggagctaga acgattcgca | 9180 |
| gttaatcctg gcctgttaga aacatcagaa ggctgtagac aaatactggg acagctacaa | 9240 |
| ccatcccttc agacaggatc agaagaactt agatcattat ataatacagt agcaaccctc | 9300 |
| tattgtgtgc atcaaaggat agagataaaa gacaccaagg aagctttaga caagatagag | 9360 |
| gaagagcaaa acaaaagtaa gaccaccgca cagcaagcgg ccgctgatct tcagacctgg | 9420 |
| aggaggagat atgagggaca attggagaag tgaattatat aaatataaag tagtaaaaat | 9480 |
| tgaaccatta ggagtagcac ccaccaaggc aaagagaaga gtggtgcaga gagaaaaaag | 9540 |
| agcagtggga ataggagctt tgttccttgg gttcttggga gcagcaggaa gcactatggg | 9600 |
| cgcagcgtca atgacgctga cggtacaggc cagacaatta ttgtctggta tagtgcagca | 9660 |
| gcagaacaat ttgctgaggg ctattgaggc gcaacagcat ctgttgcaac tcacagtctg | 9720 |
| gggcatcaag cagctccagg caagaatcct ggctgtggaa agatacctaa aggatcaaca | 9780 |
| gctcctgggg atttggggtt gctctggaaa actcatttgc accactgctg tgccttggaa | 9840 |
| tgctagttgg agtaataaat ctctggaaca gatttggaat cacacgacct ggatggagtg | 9900 |
| ggacagagaa attaacaatt acacaagctt aatacactcc ttaattgaag aatcgcaaaa | 9960 |
| ccagcaagaa aagaatgaac aagaattatt ggaattagat aaatgggcaa gtttgtggaa | 10020 |
| ttggtttaac ataacaaatt ggctgtggta tataaaatta ttcataatga tagtaggagg | 10080 |
| cttggtaggt ttaagaatag tttttgctgt actttctata gtgaatagag ttaggcaggg | 10140 |
| atattcacca ttatcgtttc agacccacct cccaaccccg aggggacccg acaggccctt | 10200 |
| aattaatccc ctgattctgt ggataaccgt attaccgcct tgagtgagc tgcacctagt | 10260 |
| acggattaga agccgccgag cgggtgacag ccctccgaag gaagactctc ctccgtgcgt | 10320 |
| cctcgtcttc accggtcgcg ttcctgaaac gcagatgtgc ctcgcgccgc actgctccga | 10380 |
| acaatgtcga ctctagaggt aaactcgacc tatataagca gagctcgttt agtgaaccgt | 10440 |
| cagatcgcct ggagacgcca tccacgctgt tttgacctcc atagaagaca ccgggaccga | 10500 |
| tccagcctcc gcggccccga attgaattcg aagcaggagt agacgccggc cattacggcc | 10560 |
| tgccaccgtt aat | 10573 |

<210> SEQ ID NO 14
<211> LENGTH: 11022
<212> TYPE: DNA
<213> ORGANISM: Artificial Sequence
<220> FEATURE:
<223> OTHER INFORMATION: Synthetic

<400> SEQUENCE: 14

| | |
|---|---|
| cgcgatcaca tggtcctgct ggagttcgtg accgccgccg ggatcactct cggcatggac | 60 |
| gagctgtaca agtaagcggc cgcaatcaac ctctggatta caaaatttgt gaaagattga | 120 |
| ctggtattct taactatgtt gctccttta cgctatgtgg atacgctgct ttaatgcctt | 180 |
| tgtatcatgc tattacttcc cgtacggctt tcatttctc ctccttgtat aaatcctggt | 240 |

```
tgctgtctct ttatgaggag ttgtggcccg ttgtcaggca acgtggcgtg gtgtgcactg    300
tgtttgctga cgcaaccccc actggttggg gcattgccac cacctatcaa ctccttttccg   360 ggactttcgc tttccccctc cctattgcca cggcggaact cattgccgcc tgccttgccc    420
gctgctggac aggggctcgg ctgttgggca ctgacaattc cgtggtgttg tcggggaagc    480
tgacgtcctt tccatggctg ctcgcctgtg ttgccaactg gattctgcgc gggacgtcct    540
tctgctacgt cccttcggcc ctcaatccag cggaccttcc ttcccgcggc ctgctgccgg    600
ttctgcggcc tcttccgcgt cttcgccttc gccctcagac gagtcggatc tccctttggg    660
ccgcctcccc gcctgcctgc aggtttgtcg agacctagaa aaacatggag caatcacaag    720
tagcaataca gcagctacca atgctgattg tgcctggcta aagcacaag aggaggagga    780 ggtgggtttt ccagtcacac ctcaggtacc tttaagacca atgacttaca aggcagctgt    840
agatcttagc cacttttttaa aagaaaaggg gggactggaa gggctaattc actcccaacg    900
aagacaagat ctgctttttg cttgtactgg gtctctctgg ttagaccaga tctgagcctg    960
ggagctctct ggctaactag ggaacccact gcttaagcct caataaagct tgccttgagt   1020
gcttcaagta gtgtgtgccc gtctgttgtg tgactctggt aactagagat ccctcagacc   1080
cttttagtca gtgtggaaaa tctctagcag ggcccgttta aacccgctga tcagcctcga   1140
ctgtgccttc tagttgccag ccatctgttg tttgcccctc cccgtgcct tccttgaccc    1200 tggaaggtgc cactcccact gtcctttcct aataaaatga ggaaattgca tcgcattgtc   1260
tgagtaggtg tcattctatt ctggggggtg ggtggggca ggacagcaag ggggaggatt    1320
gggaagacaa tagcaggcat gctggggatg cggtgggctc tatggcttct gaggcggaaa   1380
gaaccagctg gggctctagg gggtatcccc acgcgccctg tagcggcgca ttaagcgcgg   1440
cgggtgtggt ggttacgcgc agcgtgaccg ctacacttgc cagcgcccta gcgcccgctc   1500 cttttcgcttt cttcccttcc tttctcgcca cgttcgccgg ctttccccgt caagctctaa   1560
atcggggcat ccctttaggg ttccgattta gtgctttacg gcacctcgac cccaaaaaac   1620
ttgattaggg tgatggttca cgtagtgggc catcgccctg atagacggtt tttcgccctt   1680
tgacgttgga gtccacgttc tttaatagtg gactcttgtt ccaaactgga acaacactca   1740
accctatctc ggtctattct tttgatttat aagggatttt ggggatttcg gcctattggt   1800
taaaaaatga gctgatttaa caaaaattta acgcgaatta attctgtgga atgtgtgtca   1860
gttagggtgt ggaaagtccc caggctcccc aggcaggcag aagtatgcaa agcatgcatc   1920
tcaattagtc agcaaccagg tgtggaaagt ccccaggctc cccagcaggc agaagtatgc   1980
aaagcatgca tctcaattag tcagcaacca tagtcccgcc cctaactccg cccatcccgc   2040
ccctaactcc gcccagttcc gcccattctc cgccccatgg ctgactaatt ttttttattt   2100
atgcagaggc cgaggccgcc tctgcctctg agctattcca gaagtagtga ggaggctttt   2160
ttggaggcct aggcttttgc aaaaagctcc cgggagcttg tatatccatt ttcggatctg   2220
atcagcacgt gttgacaatt aatcatcggc atagtatatc ggcatagtat aatacgacaa   2280
ggtgaggaac taaaccatgg ccaagttgac cagtgccgtt ccggtgctca ccgcgcgcga   2340
cgtcgccgga gcggtcgagt tctggaccga ccggctcggg ttctcccggg acttcgtgga   2400
ggacgacttc gccggtgtgg tccgggacga cgtgaccctg ttcatcagcg cggtccagga   2460
ccaggtggtg ccggacaaca ccctggcctg ggtgtgggtg cgcggcctgg acgagctgta   2520
cgccgagtgg tcggaggtcg tgtccacgaa cttccgggac gcctccggcc ggccatgac   2580 cgagatcggc gagcagccgt gggggcggga gttcgccctg cgcgaccgg ccggcaactg   2640
```

```
cgtgcacttc gtggccgagg agcaggactg acacgtgcta cgagatttcg attccaccgc   2700
cgccttctat gaaaggttgg gcttcggaat cgttttccgg gacgccggct ggatgatcct   2760
ccagcgcggg gatctcatgc tggagttctt cgcccacccc aacttgttta ttgcagctta   2820
taatggttac aaataaagca atagcatcac aaatttcaca aataaagcat tttttttcact  2880
gcattctagt tgtggtttgt ccaaactcat caatgtatct tatcatgtct gtataccgtc   2940
gacctctagc tagagcttgg cgtaatcatg gtcatagctg tttcctgtgt gaaattgtta   3000
tccgctcaca attccacaca catacgagc cggaagcata agtgtaaag cctggggtgc      3060
ctaatgagtg agctaactca cattaattgc gttgcgctca ctgcccgctt ccagtcggg    3120
aaacctgtcg tgccagctgc attaatgaat cggccaacgc gcggggagag gcggtttgcg   3180
tattgggcgc tcttccgctt cctcgctcac tgactcgctg cgctcggtcg ttcggctgcg   3240
gcgagcggta tcagctcact caaaggcggt aatacggtta ccacagaat caggggataa    3300
cgcaggaaag aacatgtgag caaaaggcca gcaaaaggcc aggaaccgta aaaaggccgc   3360
gttgctggcg ttttttccata ggctccgccc ccctgacgag catcacaaaa atcgacgctc  3420
aagtcagagg tggcgaaacc cgacaggact ataaagatac caggcgtttc ccctggaag    3480
ctccctcgtg cgctctcctg ttccgaccct gccgcttacc ggatacctgt ccgcctttct   3540
cccttcggga agcgtggcgc tttctcaatg ctcacgctgt aggtatctca gttcggtgta   3600
ggtcgttcgc tccaagctgg gctgtgtgca cgaaccccc gttcagcccg accgctgcgc    3660
cttatccggt aactatcgtc ttgagtccaa cccggtaaga cacgacttat cgccactggc   3720
agcagccact ggtaacagga ttagcagagc gaggtatgta ggcggtgcta cagagttctt   3780
gaagtggtgg cctaactacg gctacactag aaggacagta tttggtatct gcgctctgct   3840
gaagccagtt accttcggaa aaagagttgg tagctcttga tccggcaaac aaaccaccgc   3900
tggtagcggt ggttttttg tttgcaagca gcagattacg cgcagaaaaa aaggatctca    3960
agaagatcct ttgatcttt ctacggggtc tgacgctcag tggaacgaaa actcacgtta    4020
agggattttg gtcatgagat tatcaaaaag gatcttcacc tagatccttt taaattaaaa  4080
atgaagtttt aaatcaatct aaagtatata tgagtaaact tggtctgaca gttaccaatg   4140
cttaatcagt gaggcaccta tctcagcgat ctgtctattt cgttcatcca tagttgcctg   4200
actccccgtc gtgtagataa ctacgatacg ggagggctta ccatctggcc ccagtgctgc   4260
aatgataccg cgagacccac gctcaccggc tccagattta tcagcaataa accagccagc   4320
cggaagggcc gagcgcagaa gtggtcctgc aactttatcc gcctccatcc agtctattaa   4380
ttgttgccgg gaagctagag taagtagttc gccagttaat agtttgcgca acgttgttgc   4440
cattgctaca ggcatcgtgg tgtcacgctc gtcgtttggt atggcttcat tcagctccgg   4500
ttcccaacga tcaaggcgag ttacatgatc ccccatgttg tgcaaaaaag cggttagctc   4560
cttcggtcct ccgatcgttg tcagaagtaa gttggccgca gtgttatcac tcatggttat   4620
ggcagcactg cataattctc ttactgtcat gccatccgta agatgctttt ctgtgactgg   4680
tgagtactca accaagtcat tctgagaata gtgtatgcgg cgaccgagtt gctcttgccc   4740
ggcgtcaata cgggataata ccgcgccaca tagcagaact ttaaaagtgc tcatcattgg   4800
aaaacgttct cggggcgaa aactctcaag gatcttaccg ctgttgagat ccagttcgat    4860
gtaacccact cgtgcaccca actgatcttc agcatctttt actttcacca gcgtttctgg   4920
gtgagcaaaa acaggaaggc aaaatgccgc aaaaaaggga ataagggcga cacggaaatg   4980
ttgaatactc atactcttcc ttttcaata ttattgaagc atttatcagg gttattgtct    5040
```

```
catgagcgga tacatatttg aatgtattta gaaaaataaa caaatagggg ttccgcgcac    5100
atttccccga aaagtgccac ctgacgtcga cggatcggga gatctcccga tcccctatgg    5160
tgcactctca gtacaatctg ctctgatgcc gcatagttaa gccagtatct gctccctgct    5220
tgtgtgttgg aggtcgctga gtagtgcgcg agcaaaattt aagctacaac aaggcaaggc    5280
ttgaccgaca attgcatgaa gaatctgctt agggttaggc gttttgcgct gcttcgcgat    5340
gtacgggcca gatatacgcg ttgacattga ttattgacta gttattaata gtaatcaatt    5400
acggggtcat tagttcatag cccatatatg gagttccgcg ttacataact tacggtaaat    5460
ggcccgcctg gctgaccgcc caacgacccc cgcccattga cgtcaataat gacgtatgtt    5520
cccatagtaa cgccaatagg gactttccat tgacgtcaat gggtggacta tttacggtaa    5580
actgcccact tggcagtaca tcaagtgtat catatgccaa gtacgccccc tattgacgtc    5640
aatgacggta aatggcccgc ctggcattat gcccagtaca tgaccttatg ggactttcct    5700
acttggcagt acatctacgt attagtcatc gctattacca tggtgatgcg gttttggcag    5760
tacatcaatg ggcgtggata gcggtttgac tcacggggat ttccaagtct ccaccccatt    5820
gacgtcaatg ggagtttgtt ttggcaccaa aatcaacggg actttccaaa atgtcgtaac    5880
aactccgccc cattgacgca aatgggcggt aggcgtgtac ggtgggaggt ctatataagc    5940
agagctctct ggctaactag agaacccact gcttactggc ttatcgaaat taatacgact    6000
cactataggg agacccaagc tggtttaaac ttaagcttgg taccgagctc actagtccag    6060
tgtggtggca gatatccagc acagtggcgg ccgctcgagt ctagagggcc cgttttgcct    6120
gtactgggtc tctctggtta gaccagatct gagcctggga gctctctggc taactaggga    6180
acccactgct taagcctcaa taaagcttgc cttgagtgct tcaagtagtg tgtgcccgtc    6240
tgttgtgtga ctctggtaac tagagatccc tcagaccctt ttagtcagtg tggaaaatct    6300
ctagcagtgg cgcccgaaca gggacttgaa agcgaaaggg aaaccagagg agctctctcg    6360
acgcaggact cggcttgctg aagcgcgcac ggcaagaggc gaggggcggc gactggtgag    6420
tacgccaaaa attttgacta gcggaggcta agaggagaga gatgggtgcg agagcgtcag    6480
tattaagcgg gggagaatta gatcgcgatg ggaaaaaatt cggttaaggc caggggggaaa    6540
gaaaaaatat aaattaaaac atatagtatg ggcaagcagg gagctagaac gattcgcagt    6600
taatcctggc ctgttagaaa catcagaagg ctgtagacaa atactgggac agctacaacc    6660
atcccttcag acaggatcag aagaacttag atcattatat aatacagtag caaccctcta    6720
ttgtgtgcat caaaggatag agataaaaga caccaaggaa gctttagaca agatagagga    6780
agagcaaaac aaaagtaaga ccaccgcaca gcaagcggcc gctgatcttc agacctggag    6840
gaggagatat gagggacaat tggagaagtg aattatataa atataaagta gtaaaaattg    6900
aaccattagg agtagcaccc accaaggcaa agagaagagt ggtgcagaga gaaaaaagag    6960
cagtgggaat aggagctttg ttccttgggt tcttgggagc agcaggaagc actatgggcg    7020
cagcgtcaat gacgctgacg gtacaggcca gacaattatt gtctggtata gtgcagcagc    7080
agaacaattt gctgagggct attgaggcgc aacagcatct gttgcaactc acagtctggg    7140
gcatcaagca gctccaggca agaatcctgg ctgtggaaag atacctaaag gatcaacagc    7200
tcctgggat ttggggttgc tctggaaaac tcatttgcac cactgctgtg ccttggaatg    7260
ctagttggag taataaatct ctggaacaga tttggaatca cacgacctgg atggagtggg    7320
acagagaaat taacaattac acaagcttaa tacactcctt aattgaagaa tcgcaaaacc    7380
agcaagaaaa gaatgaacaa gaattattgg aattagataa atgggcaagt ttgtggaatt    7440
```

```
ggtttaacat aacaaattgg ctgtggtata tagaaattat tcataatgat agtaggaggc    7500
ttggtaggtt taagaatagt ttttgctgta ctttctatag tgaatagagt taggcaggga    7560
tattcaccat tatcgtttca gacccacctc ccaaccccga ggggacccga caggcccgaa    7620
ggaatagaag aagaaggtgg agagagagac agagacagat ccattcgatt agtgaacgga    7680
tcggcactgc gtgcgccaat tctgcagaca aatggcagta ttcatccaca attttaaaag    7740 aaaaggggg attgggggt acagtgcagg ggaaagaata gtagacataa tagcaacaga    7800
catacaaact aaagaattac aaaaacaaat tacaaaaatt caaaattttc gggtttatta    7860
cagggacagc agagatccag tttggggttg ctctggaaaa ctcatttgca ccactgctgt    7920
gccttggaat gctagttgga gtaataaatc tctggaacag atttggaatc acacgacctg    7980
gatggagtgg gacagagaaa ttaacaatta cacaagctta atacactcct taattgaaga    8040
atcgcaaaac cagcaagaaa agaatgaaca agaattattg gaattagata aatgggcaag    8100
tttgtggaat tggtttaaca taacaaattg gctgtggtat ataaaattat tcataatgat    8160
agtaggaggc ttggtaggtt taagaatagt ttttgctgta ctttctatag tgaatagagt    8220
taggcaggga tattcaccat tatcgtttca gacccacctc ccaaccccga ggggacccga    8280
caggccctta attaattggc tccggtgccc gtcagtgggc agagcgcaca tcgcccacag    8340
tccccgagaa gttgggggga ggggtcggca attgaaccgg tgcctagaga aggtggcgcg    8400
gggtaaactg ggaaagtgat gtcgtgtact ggctccgcct ttttcccgag ggtgggggag    8460
aaccgtatat aagtgcagta gtcgccgtga agctagctcc ctatcagtga tagagatctc    8520
cctatcagtg atagagagct agccgttctt tttcgcaacg ggtttgccgc cagaacacag    8580
gtaagtgccg tgtgtggttc ccgcgggcct ggcctcttta cgggttatgg cccttgcgtg    8640
ccttgaatta cttccacctg gctgcagtac gtgattcttg atcccgagct tcgggttgga    8700
agtgggtggg agagttcgag gccttgcgct taaggagccc cttcgcctcg tgcttgagtt    8760
gaggcctggc ctgggcgctg gggccgccgc gtgcgaatct ggtggcacct tcgcgcctgt    8820
ctcgctgctt tcgataagtc tctagccatt taaaattttt gatgacctgc tgcgacgctt    8880
tttttctggc aagatagtct tgtaaatgcg ggccaagatc tgcacactgg tatttcggtt    8940 tttgggccg cgggcggcga cggggcccgt gcgtcccagc gcacatgttc ggcgaggcgg    9000
ggcctgcgag cgcggccacc gagaatcgga cgggggtagt ctcaagctgg ccggcctgct    9060
ctggtgcctg gcctcgcgcc gccgtgtatc gccccgccct gggcggcaag gctggcccgg    9120
tcggcaccag ttgcgtgagc ggaaagatgg ccgcttcccg gccctgctgc agggagctca    9180
aaatggagga cgcggcgctc gggagagcgg gcgggtgagt cacccacaca aaggaaaagg    9240
gcctttccgt cctcagccgt cgcttcatgt gactccacgg agtaccgggc gccgtccagg    9300
cacctcgatt agttctcgag cttttggagt acgtcgtctt taggttgggg ggaggggttt    9360
tatgcgatgg agtttcccca cactgagtgg gtggagactg aagttaggcc agcttggcac    9420
ttgatgtaat tctccttgga atttgccctt tttgagtttg gatcttggtt cattctcaag    9480
cctcagacag tggttcaaag ttttttttctt ccatttcagg tgaattcggc cattacggcc    9540
tcccaccatg aaaccagtaa cgttatacga tgtcgcagag tatgccggtg tctcttatca    9600 gaccgttttcc cgcgtggtga accaggccag ccacgtttct gcgaaaacgc gggaaaaagt    9660
ggaagcggcg atggcggagc tgaattacat tcccaaccgc gtggcacaac aactggcggg    9720
caaacagtcg ttgctgattg gcgttgccac ctccagtctg gccctgcacg cgccgtcgca    9780
aattgtcgcg gcgattaaat ctcgcgccga tcaactgggt gccagcgtgg tggtgtcgat    9840
```

| | | | | |
|---|---|---|---|---|
| ggtagaacga | agcggcgtcg | aagcctgtaa | agcggcggtg | cacaatcttc tcgcgcaacg | 9900
| cgtcagtggg | ctgatcatta | actatccgct | ggatgaccag | gatgccattg ctgtggaagc | 9960
| tgcctgcact | aatgttccgg | cgttatttct | tgatgtctct | gaccagacac ccatcaacag | 10020
| tattattttc | tcccatgaag | acggtacgcg | actgggcgtg | gagcatctgg tcgcattggg | 10080
| tcaccagcaa | atcgcgctgt | tagcgggccc | attaagttct | gtctcggcgc gtctgcgtct | 10140
| ggctggctgg | cataaatatc | tcactcgcaa | tcaaattcag | ccgatagcgg aacgggaagg | 10200
| cgactggagt | gccatgtccg | gttttcaaca | aaccatgcaa | atgctgaatg agggcatcgt | 10260
| tcccactgcg | atgctggttg | ccaacgatca | gatggcgctg | ggcgcaatgc gcgccattac | 10320
| cgagtccggg | ctgcgcgttg | gtgcggatat | ctcggtagtg | ggatacgacg ataccgaaga | 10380
| cagctcatgt | tatatcccgc | cgttaaccac | catcaaacag | gattttcgcc tgctgggca | 10440
| aaccagcgtg | gaccgcttgc | tgcaactctc | tcagggccag | gcggtgaagg gcaatcagct | 10500
| gttgcccgtc | tcactggtga | aaagaaaaac | caccctggcg | cccaatacgc aaaccgcctc | 10560
| tccccgcgcg | ttggccgatt | cattaatgca | gctggcacga | caggtttccc gactggaaag | 10620
| cgggcagcca | aaaagaaga | gaaggtcga | cggcggtggt | gctttgtctc ctcagcactc | 10680
| tgctgtcact | caaggaagta | tcatcaagaa | caaggagggc | atggatgcta agtcactaac | 10740
| tgcctggtcc | cggacactgg | tgaccttcaa | ggatgtattt | gtggacttca ccagggagga | 10800
| gtggaagctg | ctggacactg | ctcagcagat | cgtgtacaga | aatgtgatgc tggagaacta | 10860
| taagaacctg | gtttccttgg | gttatcagct | tactaagcca | gatgtgatcc tccggttgga | 10920
| gaagggagaa | gagccctggc | tggtggagag | agaaattcac | caagagaccc atcctgattc | 10980
| agagactgca | tttgaaatca | aatcatcagt | ttaaggccgc | ct | 11022

<210> SEQ ID NO 15
<211> LENGTH: 9123
<212> TYPE: DNA
<213> ORGANISM: Artificial Sequence
<220> FEATURE:
<223> OTHER INFORMATION: Synthetic

<400> SEQUENCE: 15

| | | | | |
|---|---|---|---|---|
| ttattgccac | catgagcccg | aaacgccgca | cccaggcgga | acgcgcgatg gaaacccagg | 60
| gcaaactgat | tgcggcggcg | ctgggcgtgc | tgcgcgaaaa | aggctatgcg ggctttcgca | 120
| ttgcggatgt | gccgggcgcg | gcgggcgtga | gccgcggcgc | gcagagccat cattttccga | 180
| ccaaactgga | actgctgctg | gcgacctttg | aatggctgta | tgaacagatt accgaacgca | 240
| gccgcgcgcg | cctggcgaaa | ctgaaaccgg | aagatgatgt | gattcagcag atgctggatg | 300
| atgcggcgga | atttttctg | gatgatgatt | ttagcattag | cctggatctg attgtggcgg | 360
| cggatcgcga | tccggcgctg | cgcgaaggca | ttcagcgcac | cgtggaacgc aaccgctttg | 420
| tggtggaaga | tatgtggctg | ggcgtgctgg | tgagccgcgg | cctgagccgc gatgatgcgg | 480
| aagatattct | gtggctgatt | tttaacagcg | tgcgcggcct | ggcggtgcgc agcctgtggc | 540
| agaaagataa | agaacgcttt | gaacgcgtgc | gcaacagcac | cctggaaatt gcgcgcgaac | 600
| gctatgcgaa | atttaaacgc | gcgtacagcc | gcgcgcgtac | gaaaaacaat tacgggtcta | 660
| ccatcgaggg | cctgctcgat | ctcccggacg | acgacgcccc | cgaagaggcg gggctggcgg | 720
| ctccgcgcct | gtcctttctc | cccgcgggac | acacgcgcag | actgtcgacg gccccccga | 780
| ccgatgtcag | cctgggggac | gagctccact | tagacgcgga | ggacgtggcg atggcgcatg | 840
| ccgacgcgct | agacgatttc | gatctggaca | tgttggggga | cggggattcc ccgggtccgg | 900

```
gatttacccc ccacgactcc gcccctacg gcgctctgga tatggccgac ttcgagtttg    960
agcagatgtt taccgatgcc cttggaattg acgagtacgg tgggtaataa gtgtgggagg   1020
gctaagggcg cgccgttcta gagaattcga tatcaagctt atcgataatc aacctctgga   1080
ttacaaaatt tgtgaaagat tgactggtat tcttaactat gttgctcctt ttacgctatg   1140
tggatacgct gctttaatgc ctttgtatca tgctattact ccccgtacgg cttcatttt    1200
ctcctccttg tataaatcct ggttgctgtc tctttatgag gagttgtggc ccgttgtcag   1260
gcaacgtggc gtggtgtgca ctgtgtttgc tgacgcaacc cccactggtt ggggcattgc   1320
caccacctat caactccttt ccgggacttt cgctttcccc ctccctattg ccacggcgga   1380
actcattgcc gcctgccttg cccgctgctg acagggggct cggctgttgg cactgacaa    1440
ttccgtggtg ttgtcgggga agctgacgtc ctttccatgg ctgctcgcct gtgttgccaa   1500
ctggattctg cgcgggacgt ccttctgcta cgtcccttcg gccctcaatc cagcggacct   1560
tccttcccgc ggcctgctgc cggttctgcg gcctcttccg cgtcttcgcc ttcgccctca   1620
gacgagtcgg atctcccttt gggccgcctc cccgcctgcc tgcaggtttg tcgagaccta   1680
gaaaaacatg gagcaatcac aagtagcaat acagcagcta ccaatgctga ttgtgcctgg   1740
ctagaagcac aagaggagga ggaggtgggt tttccagtca cacctcaggt acctttaaga   1800
ccaatgactt acaaggcagc tgtagatctt agccactttt taaaagaaaa ggggggactg   1860
gaagggctaa ttcactccca acgaagacaa gatctgcttt ttgcttgtac tgggtctctc   1920
tggttagacc agatctgagc ctgggagctc tctggctaac tagggaaccc actgcttaag   1980
cctcaataaa gcttgccttg agtgcttcaa gtagtgtgtg cccgtctgtt gtgtgactct   2040
ggtaactaga gatccctcag acccttttag tcagtgtgga aaatctctag cagggcccgt   2100
ttaaacccgc tgatcagcct cgactgtgcc ttctagttgc cagccatctg ttgtttgccc   2160
ctcccccgtg ccttccttga ccctggaagg tgccactccc actgtccttt cctaataaaa   2220
tgaggaaatt gcatcgcatt gtctgagtag gtgtcattct attctggggg gtggggtggg   2280
gcaggacagc aagggggagg attgggaaga caatagcagg catgctgggg atgcggtggg   2340
ctctatggct tctgaggcgg aaagaaccag ctggggctct agggggtatc cccacgcgcc   2400
ctgtagcggc gcattaagcg cggcgggtgt ggtggttacg cgcagcgtga ccgctacact   2460
tgccagcgcc ctagcgcccg ctcctttcgc tttcttccct tcctttctcg ccacgttcgc   2520
cggctttccc cgtcaagctc taaatcgggg catccctta gggttccgat ttagtgcttt   2580
acggcacctc gaccccaaaa aacttgatta gggtgatggt tcacgtagtg gccatcgcc    2640
ctgatagacg gtttttcgcc ctttgacgtt ggagtccacg ttctttaata gtggactctt   2700
gttccaaact ggaacaacac tcaaccctat ctcggtctat tcttttgatt tataagggat   2760
tttggggatt tcggcctatt ggttaaaaaa tgagctgatt taacaaaaat ttaacgcgaa   2820
ttaattctgt ggaatgtgtg tcagttaggg tgtggaaagt ccccaggctc cccaggcagg   2880
cagaagtatg caaagcatgc atctcaatta gtcagcaacc aggtgtggaa agtccccagg   2940
ctcccccagca ggcagaagta tgcaaagcat gcatctcaat tagtcagcaa ccatagtccc   3000
gcccctaact ccgcccatcc cgcccctaac tccgcccagt tccgcccatt ctccgcccca   3060
tggctgacta ttttttttta tttatgcaga ggccgaggcc gcctctgcct ctgagctatt   3120
ccagaagtag tgaggaggct ttttggagg cctaggcttt tgcaaaaagc tcccgggagc    3180
ttgtatatcc attttcggat ctgatcagca cgtgttgaca attaatcatc ggcatagtat   3240
atcggcatag tataatacga caaggtgagg aactaaacca tggccaagtt gaccagtgcc   3300
```

```
gttccggtgc tcaccgcgcg cgacgtcgcc ggagcggtcg agttctggac cgaccggctc    3360
gggttctccc gggacttcgt ggaggacgac ttcgccggtg tggtccggga cgacgtgacc    3420
ctgttcatca gcgcggtcca ggaccaggtg gtgccggaca acaccctggc ctgggtgtgg    3480
gtgcgcggcc tggacgagct gtacgccgag tggtcggagg tcgtgtccac gaacttccgg    3540
gacgcctccg ggccggccat gaccgagatc ggcgagcagc cgtggggggcg ggagttcgcc    3600
ctgcgcgacc cggccggcaa ctgcgtgcac ttcgtggccg aggagcagga ctgacacgtg    3660
ctacgagatt tcgattccac cgccgccttc tatgaaaggt tgggcttcgg aatcgttttc    3720
cgggacgccg gctggatgat cctccagcgc ggggatctca tgctggagtt cttcgcccac    3780
cccaacttgt ttattgcagc ttataatggt tacaaataaa gcaatagcat cacaaatttc    3840
acaaataaag cattttttc actgcattct agttgtggtt tgtccaaact catcaatgta    3900
tcttatcatg tctgtatacc gtcgacctct agctagagct tggcgtaatc atggtcatag    3960
ctgtttcctg tgtgaaattg ttatccgctc acaattccac acaacatacg agccggaagc    4020
ataaagtgta aagcctgggg tgcctaatga gtgagctaac tcacattaat tgcgttgcgc    4080
tcactgcccg ctttccagtc gggaaacctg tcgtgccagc tgcattaatg aatcggccaa    4140
cgcgcgggga gaggcggttt gcgtattggg cgctcttccg cttcctcgct cactgactcg    4200
ctgcgctcgg tcgttcggct gcggcgagcg gtatcagctc actcaaaggc ggtaatacgg    4260
ttatccacag aatcagggga taacgcagga aagaacatgt gagcaaaagg ccagcaaaag    4320
gccaggaacc gtaaaaaggc cgcgttgctg gcgtttttcc ataggctccg ccccctgac    4380
gagcatcaca aaaatcgacg ctcaagtcag aggtggcgaa acccgacagg actataaaga    4440
taccaggcgt ttccccctgg aagctccctc gtgcgctctc ctgttccgac cctgccgctt    4500
accggatacc tgtccgcctt tctcccttcg ggaagcgtgg cgctttctca atgctcacgc    4560
tgtaggtatc tcagttcggt gtaggtcgtt cgctccaagc tgggctgtgt gcacgaaccc    4620
cccgttcagc ccgaccgctg cgccttatcc ggtaactatc gtcttgagtc aacccggta    4680
agacacgact tatcgccact ggcagcagcc actggtaaca ggattagcag agcgaggtat    4740
gtaggcggtg ctacagagtt cttgaagtgg tggcctaact acggctacac tagaaggaca    4800
gtatttggta tctgcgctct gctgaagcca gttaccttcg aaaaagagt tggtagctct    4860
tgatccggca aacaaaccac cgctggtagc ggtggttttt ttgtttgcaa gcagcagatt    4920
acgcgcagaa aaaaggatc tcaagaagat cctttgatct tttctacggg gtctgacgct    4980
cagtggaacg aaaactcacg ttaagggatt ttggtcatga gattatcaaa aaggatcttc    5040
acctagatcc ttttaaatta aaaatgaagt tttaaatcaa tctaaagtat atatgagtaa    5100
acttggtctg acagttacca atgcttaatc agtgaggcac ctatctcagc gatctgtcta    5160
tttcgttcat ccatagttgc ctgactcccc gtcgtgtaga taactacgat acgggagggc    5220
ttaccatctg gccccagtgc tgcaatgata ccgcgagacc cacgctcacc ggctccagat    5280
ttatcagcaa taaaccagcc agccggaagg gccgagcgca gaagtggtcc tgcaacttta    5340
tccgcctcca tccagtctat taattgttgc cgggaagcta gagtaagtag ttcgccagtt    5400
aatagtttgc gcaacgttgt tgccattgct acaggcatcg tggtgtcacg ctcgtcgttt    5460
ggtatggctt cattcagctc cggttcccaa cgatcaaggc gagttacatg atccccatg    5520
ttgtgcaaaa aagcggttag ctccttcggt cctccgatcg ttgtcagaag taagttggcc    5580
gcagtgttat cactcatggt tatggcagca ctgcataatt ctcttactgt catgccatcc    5640
gtaagatgct tttctgtgac tggtgagtac tcaaccaagt cattctgaga atagtgtatg    5700
```

```
cggcgaccga gttgctcttg cccggcgtca atacgggata ataccgcgcc acatagcaga   5760
actttaaaag tgctcatcat tggaaaacgt tcttcgggc  gaaaactctc aaggatctta   5820
ccgctgttga gatccagttc gatgtaaccc actcgtgcac ccaactgatc ttcagcatct   5880
tttactttca ccagcgtttc tgggtgagca aaaacaggaa ggcaaaatgc cgcaaaaaag   5940
ggaataaggg cgacacggaa atgttgaata ctcatactct tccttttca  atattattga   6000 agcatttatc agggttattg tctcatgagc ggatacatat ttgaatgtat ttagaaaaat   6060
aaacaaatag gggttccgcg cacatttccc cgaaaagtgc cacctgacgt cgacggatcg   6120
ggagatctcc cgatcccta  tggtgcactc tcagtacaat ctgctctgat gccgcatagt   6180
taagccagta tctgctccct gcttgtgtgt tggaggtcgc tgagtagtgc gcgagcaaaa   6240
tttaagctac aacaaggcaa ggcttgaccg acaattgcat gaagaatctg cttagggtta   6300
ggcgttttgc gctgcttcgc gatgtacggg ccagatatac gcgttgacat tgattattga   6360
ctagttatta atagtaatca attacggggt cattagttca tagcccatat atggagttcc   6420
gcgttacata acttacggta aatggcccgc ctggctgacc gcccaacgac ccccgcccat   6480
tgacgtcaat aatgacgtat gttcccatag taacgccaat agggactttc cattgacgtc   6540
aatgggtgga ctatttacgg taaactgccc acttggcagt acatcaagtg tatcatatgc   6600
caagtacgcc ccctattgac gtcaatgacg gtaaatggcc cgcctggcat tatgcccagt   6660
acatgacctt atgggacttt cctacttggc agtacatcta cgtattagtc atcgctatta   6720
ccatggtgat gcggttttgg cagtacatca atgggcgtgg atagcggttt gactcacggg   6780
gatttccaag tctccacccc attgacgtca atgggagttt gttttggcac caaaatcaac   6840
gggactttcc aaaatgtcgt aacaactccg ccccattgac gcaaatgggc ggtaggcgtg   6900
tacggtggga ggtctatata agcagagctc tctggctaac tagagaaccc actgcttact   6960
ggcttatcga aattaatacg actcactata gggagaccca gctggttta  aacttaagct   7020 tggtaccgag ctcactagtc cagtgtggtg gcagatatcc agcacagtgg cggccgctcg   7080
aggggcccgt tttgcctgta ctgggtctct ctggttagac cagatctgag cctgggagct   7140
ctctggctaa ctagggaacc cactgcttaa gcctcaataa agcttgcctt gagtgcttca   7200
agtagtgtgt gcccgtctgt tgtgtgactc tggtaactag agatccctca gacccttta   7260 gtcagtgtgg aaaatctcta gcagtggcgc ccgaacaggg acttgaaagc gaagggaaa   7320 ccagaggagc tctctcgacg caggactcgg cttgctgaag cgcgcacggc aagaggcgag   7380
gggcggcgac tggtgagtac gccaaaaatt ttgactagcg gaggctagaa ggagagagat   7440
gggtgcgaga gcgtcagtat taagcggggg agaattagat cgcgatggga aaaaattcgg   7500
ttaaggccag ggggaagaa  aaaatataaa ttaaaacata tagtatgggc aagcagggag   7560
ctagaacgat tcgcagttaa tcctggcctg ttagaaacat cagaaggctg tagacaaata   7620
ctgggacagc tacaaccatc ccttcagaca ggatcagaag aacttagatc attatataat   7680
acagtagcaa ccctctattg tgtgcatcaa aggatagaga taaagacac  caaggaagct   7740 ttagacaaga tagaggaaga gcaaaacaaa agtaagacca ccgcacagca agcggccgct   7800
gatcttcaga cctggaggag gagatatgag ggacaattgg agaagtgaat tatataaata   7860
taaagtagta aaaattgaac cattaggagt agcacccacc aaggcaaaga gaagagtggt   7920
gcagagagaa aaaagagcag tgggaatagg agctttgttc cttgggttct tgggagcagc   7980
aggaagcact atgggcgcag cgtcaatgac gctgacggta caggccagac aattattgtc   8040
tggtatagtg cagcagcaga acaatttgct gagggctatt gaggcgcaac agcatctgtt   8100
```

-continued

| | |
|---|---|
| gcaactcaca gtctggggca tcaagcagct ccaggcaaga atcctggctg tggaaagata | 8160 |
| cctaaaggat caacagctcc tggggatttg gggttgctct ggaaaactca tttgcaccac | 8220 |
| tgctgtgcct tggaatgcta gttggagtaa taaatctctg aacagatttt ggaatcacac | 8280 |
| gacctggatg gagtgggaca gagaaattaa caattcacac agcttaatac actccttaat | 8340 |
| tgaagaatcg caaaccagc aagaaaagaa tgaacaagaa ttattggaat tagataaatg | 8400 |
| ggcaagtttg tggaattggt ttaacataac aaattggctg tggtatataa aattattcat | 8460 |
| aatgatagta ggaggcttgg taggtttaag aatagttttt gctgtacttt ctatagtgaa | 8520 |
| tagagttagg cagggatatt caccattatc gtttcagacc cacctcccaa ccccgagggg | 8580 |
| acccgacagg cccttaatta atcccctgat tctgtggata accgtattac cgcctttgag | 8640 |
| tgagctgcac aactgccaga tttcacagga aaagtgaaag gctacaatag gacaactgcc | 8700 |
| agatttcaca ggaaaagtga aggctacaa taggacaact gccagatttc acaggaaaag | 8760 |
| tgaaaggcta caataggaca actgccagat ttcacaggaa aagtgaaagg ctacaatagg | 8820 |
| acaactgcca gatttcacag gaaaagtgaa aggctacaat aggacaactg ccagatttca | 8880 |
| caggaaaagt gaaaggctac aataggacaa agtgaaaggc tacaatagga cggtaaactc | 8940 |
| gacctatata agcagagctc gtttagtgaa ccgtcagatc gcctggagac gccatccacg | 9000 |
| ctgttttgac ctccatagaa gacaccggga ccgatccagc ctccgcggcc ccgaattgaa | 9060 |
| ttcgatgctg gtgttaaaaa catatgatgc tggtgttaaa acggccatt acggcctgcc | 9120 |
| acc | 9123 |

<210> SEQ ID NO 16
<211> LENGTH: 9275
<212> TYPE: DNA
<213> ORGANISM: Artificial Sequence
<220> FEATURE:
<223> OTHER INFORMATION: Synthetic

<400> SEQUENCE: 16

| | |
|---|---|
| ttatgtgtgg gagggctaag ggcgcgccgt tctagagaat tcgatatcaa gcttatcgat | 60 |
| aatcaacctc tggattacaa aatttgtgaa agattgactg gtattcttaa ctatgttgct | 120 |
| ccttttacgc tatgtggata cgctgcttta atgcctttgt atcatgctat tacttcccgt | 180 |
| acggctttca ttttctcctc cttgtataaa tcctggttgc tgtctcttta tgaggagttg | 240 |
| tggcccgttg tcaggcaacg tggcgtggtg tgcactgtgt ttgctgacgc aacccccact | 300 |
| ggttggggca ttgccaccac ctatcaactc ctttccggga cttttcgctt tccccctccct | 360 |
| attgccacgg cggaactcat tgccgcctgc cttgcccgct gctggacagg ggctcggctg | 420 |
| ttgggcactg acaattccgt ggtgttgtcg gggaagctga cgtcctttcc atggctgctc | 480 |
| gcctgtgttg ccaactggat tctgcgcggg acgtccttct gctacgtccc ttcggccctc | 540 |
| aatccagcgg accttccttc ccgcggcctg ctgccggttc tgcggcctct tccgcgtctt | 600 |
| cgccttcgcc ctcagacgag tcggatctcc ctttgggccg cctccccgcc tgcctgcagg | 660 |
| tttgtcgaga cctagaaaaa catggagcaa tcacaagtag caatacagca gctaccaatg | 720 |
| ctgattgtgc ctggctagaa gcacaagagg aggaggaggt gggttttcca gtcacacctc | 780 |
| aggtaccttt aagaccaatg acttacaagg cagctgtaga tcttagccac ttttttaaaag | 840 |
| aaaaggggggg actggaaggg ctaattcact cccaacgaag acaagatctg cttttttgctt | 900 |
| gtactgggtc tctctggtta gaccagatct gagcctggga gctctctggc taactaggga | 960 |
| acccactgct taagcctcaa taaagcttgc cttgagtgct tcaagtagtg tgtgcccgtc | 1020 |

```
tgttgtgtga ctctggtaac tagagatccc tcagacccTT ttagtcagtg tggaaaatct    1080
ctagcagggc ccgtttaaac ccgctgatca gcctcgactg tgccttctag ttgccagcca    1140
tctgttgttt gcccctcccc cgtgccttcc ttgaccctgg aaggtgccac tcccactgtc    1200
ctttcctaat aaaatgagga aattgcatcg cattgtctga gtaggtgtca ttctattctg    1260
gggggtgggg tggggcagga cagcaagggg gaggattggg aagacaatag caggcatgct    1320
ggggatgcgg tgggctctat ggcttctgag gcggaaagaa ccagctgggg ctctagggg     1380 tatccccacg cgccctgtag cggcgcatta agcgcggcgg gtgtggtggt tacgcgcagc    1440
gtgaccgcta cacttgccag cgccctagcg cccgctcctt tcgctttctt cccttccttt    1500
ctcgccacgt tcgccggctt tccccgtcaa gctctaaatc ggggcatccc tttagggttc    1560
cgatttagtg ctttacggca cctcgacccc aaaaaacttg attagggtga tggttcacgt    1620
agtgggccat cgccctgata cacggttttt cgcccttTga cgttggagtc cacgttcttt    1680
aatagtggac tcttgttcca aactggaaca acactcaacc ctatctcggt ctattctttt    1740
gatttataag ggattttggg gatttcggcc tattggttaa aaatgagct gatttaacaa    1800 aaatttaacg cgaattaatt ctgtggaatg tgtgtcagtt agggtgtgga aagtccccag    1860
gctccccagg caggcagaag tatgcaaagc atgcatctca attagtcagc aaccaggtgt    1920
ggaaagtccc caggctcccc agcaggcaga agtatgcaaa gcatgcatct caattagtca    1980
gcaaccatag tcccgcccct aactccgccc atcccgcccc taactccgcc cagttccgcc    2040
cattctccgc cccatggctg actaattttt tttatttatg cagaggccga ggccgcctct    2100
gcctctgagc tattccagaa gtagtgagga ggcttttttg gaggcctagg cttttgcaaa    2160
aagctcccgg gagcttgtat atccattttc ggatctgatc agcacgtgtt gacaattaat    2220
catcggcata gtatatcggc atagtataat acgacaaggt gaggaactaa accatggcca    2280
agttgaccag tgccgttccg gtgctcaccg cgcgcgacgt cgccgagcg tcgagttct     2340 ggaccgaccg gctcgggttc tcccgggact tcgtggagga cgacttcgcc ggtgtggtcc    2400
gggacgacgt gaccctgttc atcagcgcgg tccaggacca ggtggtgccg gacaacaccc    2460
tggcctgggt gtgggtgcgc ggcctggacg agctgtacgc cgagtggtcg gaggtcgtgt    2520
ccacgaactt ccgggacgcc tccgggccgg ccatgaccga gatcggcgag cagccgtggg    2580
ggcgggagtt cgccctgcgc gacccggccg gcaactgcgt gcacttcgtg gccgaggagc    2640
aggactgaca cgtgctacga gatttcgatt ccaccgccgc cttctatgaa aggttgggct    2700
tcggaatcgt tttccgggac gccggctgga tgatcctcca gcgcgggat ctcatgctgg    2760 agttcttcgc ccaccccaac ttgtttattg cagcttataa tggttacaaa taaagcaata    2820
gcatcacaaa tttcacaaat aaagcatttt tttcactgca ttctagttgt ggtttgtcca    2880
aactcatcaa tgtatcttat catgtctgta taccgtcgac ctctagctag agcttggcgt    2940
aatcatggtc atagctgttt cctgtgtgaa attgttatcc gctcacaatt ccacacaaca    3000
tacgagccgg aagcataaag tgtaaagcct ggggtgccta atgagtgagc taactcacat    3060
taattgcgtt gcgctcactg cccgctttcc agtcggaaa cctgtcgtgc cagctgcatt    3120
aatgaatcgg ccaacgcgcg gggagaggcg gtttgcgtat tgggcgctct tccgcttcct    3180
cgctcactga ctcgctgcgc tcggtcgttc ggctgcggcg agcggtatca gctcactcaa    3240
aggcggtaat acggttatcc acagaatcag gggataacgc aggaaagaac atgtgagcaa    3300
aaggccagca aaaggccagg aaccgtaaaa aggccgcgtt gctggcgttt ttccataggc    3360
tccgcccccc tgacgagcat cacaaaaatc gacgctcaag tcagaggtgg cgaaacccga    3420
```

```
caggactata aagataccag gcgtttcccc ctggaagctc cctcgtgcgc tctcctgttc   3480
cgaccctgcc gcttaccgga tacctgtccg cctttctccc ttcgggaagc gtggcgcttt   3540
ctcaatgctc acgctgtagg tatctcagtt cggtgtaggt cgttcgctcc aagctgggct   3600
gtgtgcacga accccccgtt cagcccgacc gctgcgcctt atccggtaac tatcgtcttg   3660
agtccaaccc ggtaagacac gacttatcgc cactggcagc agccactggt aacaggatta   3720
gcagagcgag gtatgtaggc ggtgctacag agttcttgaa gtggtggcct aactacggct   3780
acactagaag gacagtattt ggtatctgcg ctctgctgaa gccagttacc ttcggaaaaa   3840
gagttggtag ctcttgatcc ggcaaacaaa ccaccgctgg tagcggtggt ttttttgttt   3900
gcaagcagca gattacgcgc agaaaaaaag gatctcaaga agatcctttg atcttttcta   3960
cggggtctga cgctcagtgg aacgaaaact cacgttaagg gattttggtc atgagattat   4020 caaaaggat cttcacctag atccttttaa attaaaaatg aagttttaaa tcaatctaaa   4080
gtatatatga gtaaacttgg tctgacagtt accaatgctt aatcagtgag gcacctatct   4140
cagcgatctg tctatttcgt tcatccatag ttgcctgact ccccgtcgtg tagataacta   4200
cgatacggga gggcttacca tctggcccca gtgctgcaat gataccgcga gacccacgct   4260
caccggctcc agatttatca gcaataaacc agccagccgg aagggccgag cgcagaagtg   4320
gtcctgcaac tttatccgcc tccatccagt ctattaattg ttgccgggaa gctagagtaa   4380
gtagttcgcc agttaatagt ttgcgcaacg ttgttgccat tgctacaggc atcgtggtgt   4440
cacgctcgtc gtttggtatg gcttcattca gctccggttc ccaacgatca aggcgagtta   4500
catgatcccc catgttgtgc aaaaaagcgg ttagctcctt cggtcctccg atcgttgtca   4560
gaagtaagtt ggccgcagtg ttatcactca tggttatggc agcactgcat aattctctta   4620
ctgtcatgcc atccgtaaga tgcttttctg tgactggtga gtactcaacc aagtcattct   4680
gagaatagtg tatgcggcga ccgagttgct cttgcccggc gtcaatacgg gataataccg   4740
cgccacatag cagaacttta aaagtgctca tcattggaaa acgttcttcg ggcgaaaac   4800 tctcaaggat cttaccgctg ttgagatcca gttcgatgta acccactcgt gcacccaact   4860
gatcttcagc atcttttact ttcaccagcg tttctgggtg agcaaaaaca ggaaggcaaa   4920
atgccgcaaa aaagggaata agggcgacac ggaaatgttg aatactcata ctcttccttt   4980
ttcaatatta ttgaagcatt tatcagggtt attgtctcat gagcggatac atatttgaat   5040
gtatttagaa aaataaacaa ataggggttc cgcgcacatt tccccgaaaa gtgccacctg   5100
acgtcgacgg atcgggagat ctcccgatcc cctatggtgc actctcagta caatctgctc   5160
tgatgccgca tagttaagcc agtatctgct ccctgcttgt gtgttggagg tcgctgagta   5220
gtgcgcgagc aaaatttaag ctacaacaag gcaaggcttg accgacaatt gcatgaagaa   5280
tctgcttagg gttaggcgtt ttgcgctgct tcgcgatgta cgggccagat atacgcgttg   5340
acattgatta ttgactagtt attaatagta atcaattacg gggtcattag ttcatagccc   5400
atatatggag ttccgcgtta cataacttac ggtaaatggc ccgcctggct gaccgcccaa   5460
cgacccccgc ccattgacgt caataatgac gtatgttccc atagtaacgc caatagggac   5520
tttccattga cgtcaatggg tggactattt acggtaaact gcccacttgg cagtacatca   5580
agtgtatcat atgccaagta cgccccctat tgacgtcaat gacggtaaat ggcccgcctg   5640
gcattatgcc cagtacatga ccttatggga ctttcctact tggcagtaca tctacgtatt   5700
agtcatcgct attaccatgg tgatgcggtt ttggcagtac atcaatgggc gtggatagcg   5760
gtttgactca cggggatttc caagtctcca ccccattgac gtcaatggga gtttgttttg   5820
```

```
gcaccaaaat caacgggact ttccaaaatg tcgtaacaac tccgccccat tgacgcaaat    5880
gggcggtagg cgtgtacggt gggaggtcta tataagcaga gctctctggc taactagaga    5940
acccactgct tactggctta tcgaaattaa tacgactcac tatagggaga cccaagctgg    6000
tttaaactta agcttggtac cgagctcact agtccagtgt ggtggcagat atccagcaca    6060
gtggcggccg ctcgagggc ccgttttgcc tgtactgggt ctctctggtt agaccagatc    6120
tgagcctggg agctctctgg ctaactaggg aacccactgc ttaagcctca ataaagcttg    6180
ccttgagtgc ttcaagtagt gtgtgcccgt ctgttgtgtg actctggtaa ctagagatcc    6240
ctcagaccct tttagtcagt gtggaaaatc tctagcagtg gcgcccgaac agggacttga    6300
aagcgaaagg gaaaccagag gagctctctc gacgcaggac tcggcttgct gaagcgcgca    6360
cggcaagagg cgaggggcgg cgactggtga gtacgccaaa aattttgact agcggaggct    6420
agaaggagag agatgggtgc gagagcgtca gtattaagcg ggggagaatt agatcgcgat    6480
gggaaaaaat tcggttaagg ccaggggaa agaaaaaata taaattaaaa catatagtat    6540
gggcaagcag ggagctagaa cgattcgcag ttaatcctgg cctgttagaa acatcagaag    6600
gctgtagaca aatactggga cagctacaac catcccttca gacaggatca gaagaactta    6660
gatcattata taatacagta gcaaccctct attgtgtgca tcaaaggata gagataaaag    6720
acaccaagga agctttagac aagatagagg aagagcaaaa caaaagtaag accaccgcac    6780
agcaagcggc cgctgatctt cagacctgga ggaggagata tgagggacaa ttggagaagt    6840
gaattatata aatataaagt agtaaaaatt gaaccattag gagtagcacc caccaaggca    6900
aagagaagag tggtgcagag agaaaaaaga gcagtgggaa taggagcttt gttccttggg    6960
ttcttgggag cagcaggaag cactatgggc gcagcgtcaa tgacgctgac ggtacaggcc    7020
agacaattat tgtctggtat agtgcagcag cagaacaatt tgctgagggc tattgaggcg    7080
caacagcatc tgttgcaact cacagtctgg ggcatcaagc agctccaggc aagaatcctg    7140
gctgtggaaa gatacctaaa ggatcaacag ctcctgggga tttggggttg ctctggaaaa    7200
ctcatttgca ccactgctgt gccttggaat gctagttgga gtaataaatc tctggaacag    7260
atttggaatc acacgacctg gatggagtgg gacagagaaa ttaacaatta cacaagctta    7320
atacactcct taattgaaga atcgcaaaac cagcaagaaa agaatgaaca agaattattg    7380
gaattagata aatgggcaag tttgtggaat tggtttaaca taacaaattg gctgtggtat    7440
ataaaattat tcataatgat agtaggaggc ttggtaggtt taagaatagt ttttgctgta    7500
ctttctatag tgaatagagt taggcaggga tattcaccat tatcgtttca gacccacctc    7560
ccaaccccga ggggacccga caggcccttc attaatcccc tgattctgtg gataaccgta    7620
ttaccgcctt tgagtgagct gcacgggagc aattaatcta tagattaaaa agtgaaaggc    7680
tacaatagga cgggagcaat taatctatag attaaaaagt gaaaggctac aataggacgg    7740
gagcaattaa tctatagatt aaaaagtgaa aggctacaat aggacgggag caattaatct    7800
atagattaaa aagtgaaagg ctacaatagg acgggagcaa ttaatctata gattaaaaag    7860
tgaaaggcta caataggacg ggagcaatta atctatagat taaaaagtga aaggctacaa    7920
taggacggga gcaattaatc tatagattaa aaagtgaaag gctacaatag gacggtaaac    7980
tcgacctata taagcagagc tcgtttagtg aaccgtcaga tcgcctggag acgccatcca    8040
cgctgttttg acctccatag aagacaccgg gaccgatcca gcctccgcgg ccccgaattg    8100
aattcggcca ttacggcctg ccaccatgat tgagaatacc tatagcgaaa agttcgagtc    8160
cgcgttcgaa cagatcaagg cggcggccaa cgtggatgcc gccatccgta ttctccaggc    8220
```

| | | | | |
|---|---|---|---|---|
| ggaatataac | ctcgatttcg | tcacctacca | tctcgcccag | acgatcgcga gcaagatcga | 8280 |
| ttcgcccttc | gtgcgcacca | cctatccgga | tgcctgggtt | tcccgctacc tcctcaacag | 8340 |
| ctatgtgaag | gtcgatccga | tcgtcaagca | gggcttcgaa | cgccagctgc ccttcgactg | 8400 |
| gagcgaggtc | gaaccgacgc | cggaggccta | tgccatgctg | gtcgacgccc agaaacacgg | 8460 |
| catcggtggc | aatggctact | ccatccccgt | cgccgacaag | gcgcagcgcc gcgccctgct | 8520 |
| gtcgctgaat | gcccgtatac | cggccgacga | atggaccgag | ctcgtgcgcc gctgccgcaa | 8580 |
| cgagtggatc | gagatcgccc | atctgatcca | ccgcaaggcc | gtctatgagc tgcatggcga | 8640 |
| aaacgatccg | gtgccggcat | tgtcgccgcg | cgagatcgag | tgtctgcact ggaccgccct | 8700 |
| cggcaaggat | tacaaggata | tttcggtcat | cctgggcata | tcagagcata ccacacgcga | 8760 |
| ttacctgaag | accgcccgct | tcaagctcgg | ctgcgccacg | atctcggccg ccgcgtcgcg | 8820 |
| ggctgttcaa | ttgcgcatca | tcaatcccgc | tgcaaacgac | gaaaactacg ctttagtagc | 8880 |
| tgcgtacagc | cgcgcgcgta | cgaaaaacaa | ttacgggtct | accatcgagg gcctgctcga | 8940 |
| tctcccggac | gacgacgccc | ccgaagaggc | ggggctggcg | gctccgcgcc tgtcctttct | 9000 |
| ccccgcggga | cacacgcgca | gactgtcgac | ggccccccg | accgatgtca gcctggggga | 9060 |
| cgagctccac | ttagacggcg | aggacgtggc | gatggcgcat | gccgacgcgc tagacgattt | 9120 |
| cgatctggac | atgttggggg | acggggattc | cccgggtccg | ggatttaccc cccacgactc | 9180 |
| cgcccctac | ggcgctctgg | atatggccga | cttcgagttt | gagcagatgt ttaccgatgc | 9240 |
| ccttggaatt | gacgagtacg | gtgggtaatg | ccacc | | 9275 |

<210> SEQ ID NO 17
<211> LENGTH: 9230
<212> TYPE: DNA
<213> ORGANISM: Artificial Sequence
<220> FEATURE:
<223> OTHER INFORMATION: Synthetic

<400> SEQUENCE: 17

| | | | | |
|---|---|---|---|---|
| ttatgtgtgg | gagggctaag | ggcgcgccgt | tctagagaat | tcgatatcaa gcttatcgat | 60 |
| aatcaacctc | tggattacaa | aatttgtgaa | agattgactg | gtattcttaa ctatgttgct | 120 |
| ccttttacgc | tatgtggata | cgctgcttta | atgcctttgt | atcatgctat tacttcccgt | 180 |
| acggctttca | ttttctcctc | cttgtataaa | tcctggttgc | tgtctcttta tgaggagttg | 240 |
| tggcccgttg | tcaggcaacg | tggcgtggtg | tgcactgtgt | ttgctgacgc aaccccact | 300 |
| ggttggggca | ttgccaccac | ctatcaactc | ctttccggga | cttcgctttc cccctccct | 360 |
| attgccacgg | cggaactcat | tgccgcctgc | cttgcccgct | gctggacagg gctcggctg | 420 |
| ttgggcactg | acaattccgt | ggtgttgtcg | gggaagctga | cgtcctttcc atggctgctc | 480 |
| gcctgtgttg | ccaactggat | tctgcgcggg | acgtccttct | gctacgtccc ttcggccctc | 540 |
| aatccagcgg | accttccttc | ccgcggcctg | ctgccggttc | tgcggcctct tccgcgtctt | 600 |
| cgccttcgcc | ctcagacgag | tcggatctcc | ctttgggccg | cctccccgcc tgcctgcagg | 660 |
| tttgtcgaga | cctagaaaaa | catggagcaa | tcacaagtag | caatacagca gctaccaatg | 720 |
| ctgattgtgc | ctggctagaa | gcacaagagg | aggaggaggt | gggttttcca gtcacacctc | 780 |
| aggtaccttt | aagaccaatg | acttacaagg | cagctgtaga | tcttagccac tttttaaaag | 840 |
| aaaaggggg | actggaaggg | ctaattcact | cccaacgaag | acaagatctg cttttgctt | 900 |
| gtactgggtc | tctctggtta | gaccagatct | gagcctggga | gctctctggc taactaggga | 960 |
| acccactgct | taagcctcaa | taaagcttgc | cttgagtgct | tcaagtagtg tgtgcccgtc | 1020 |

```
tgttgtgtga ctctggtaac tagagatccc tcagacccct ttagtcagtg tggaaaatct    1080
ctagcagggc ccgtttaaac ccgctgatca gcctcgactg tgccttctag ttgccagcca    1140
tctgttgttt gccccctccc cgtgccttcc ttgaccctgg aaggtgccac tcccactgtc    1200
ctttcctaat aaaatgagga aattgcatcg cattgtctga gtaggtgtca ttctattctg    1260
gggggtgggg tggggcagga cagcaagggg gaggattggg aagacaatag caggcatgct    1320
ggggatgcgg tgggctctat ggcttctgag gcggaaagaa ccagctgggg ctctaggggg    1380
tatccccacg cgccctgtag cggcgcatta agcgcggcgg gtgtggtggt tacgcgcagc    1440
gtgaccgcta cacttgccag cgccctagcg cccgctcctt tcgctttctt cccttccttt    1500
ctcgccacgt tcgccggctt tccccgtcaa gctctaaatc ggggcatccc tttagggttc    1560
cgatttagtg ctttacggca cctcgacccc aaaaaacttg attagggtga tggttcacgt    1620
agtgggccat cgccctgata cggttttttc gccctttga cgttggagtc cacgttcttt    1680
aatagtggac tcttgttcca aactggaaca acactcaacc ctatctcggt ctattctttt    1740
gatttataag ggattttggg gatttcggcc tattggttaa aaaatgagct gatttaacaa    1800
aaatttaacg cgaattaatt ctgtggaatg tgtgtcagtt agggtgtgga agtccccag     1860 gctccccagg caggcagaag tatgcaaagc atgcatctca attagtcagc aaccaggtgt    1920
ggaaagtccc caggctcccc agcaggcaga agtatgcaaa gcatgcatct caattagtca    1980
gcaaccatag tcccgcccct aactccgccc atcccgcccc taactccgcc cagttccgcc    2040
cattctccgc cccatggctg actaattttt tttatttatg cagaggccga ggccgcctct    2100
gcctctgagc tattccagaa gtagtgagga ggctttttg gaggcctagg cttttgcaaa     2160
aagctcccgg gagcttgtat atccattttc ggatctgatc agcacgtgtt gacaattaat    2220
catcggcata gtatatcggc atagtataat acgacaaggt gaggaactaa accatggcca    2280
agttgaccag tgccgttccg gtgctcaccg cgcgcgacgt cgccgagcg gtcgagttct     2340 ggaccgaccg gctcgggttc tcccgggact tcgtggagga cgacttcgcc ggtgtggtcc    2400
gggacgacgt gaccctgttc atcagcgcgg tccaggacca ggtggtgccg gacaacaccc    2460
tggcctgggt gtgggtgcgc ggcctggacg agctgtacgc cgagtggtcg gaggtcgtgt    2520
ccacgaactt ccgggacgcc tccgggccgg ccatgaccga gatcggcgag cagccgtggg    2580
ggcgggagtt cgccctgcgc gacccggccg gcaactgcgt gcacttcgtg gccgaggagc    2640
aggactgaca cgtgctacga gatttcgatt ccaccgccgc cttctatgaa aggttgggct    2700
tcggaatcgt tttccgggac gccggctgga tgatcctcca gcgcgggat ctcatgctgg     2760 agttcttcgc ccacccccaac ttgtttattg cagcttataa tggttacaaa taaagcaata    2820
gcatcacaaa tttcacaaat aaagcatttt tttcactgca ttctagttgt ggtttgtcca    2880
aactcatcaa tgtatcttat catgtctgta taccgtcgac ctctagctag agcttggcgt    2940
aatcatggtc atagctgttt cctgtgtgaa attgttatcc gctcacaatt ccacacaaca    3000
tacgagccgg aagcataaag tgtaaagcct ggggtgccta atgagtgagc taactcacat    3060
taattgcgtt gcgctcactg cccgctttcc agtcggggaa cctgtcgtgc cagctgcatt    3120
aatgaatcgg ccaacgcgcg gggagaggcg gtttgcgtat tgggcgctct tccgcttcct    3180
cgctcactga ctcgctgcgc tcggtcgttc ggctgcggcg agcggtatca gctcactcaa    3240
aggcggtaat acggttatcc acagaatcag gggataacgc aggaaagaac atgtgagcaa    3300
aaggccagca aaaggccagg aaccgtaaaa aggccgcgtt gctggcgttt ttccataggc    3360
tccgcccccc tgacgagcat cacaaaaatc gacgctcaag tcagaggtgg cgaaacccga    3420
```

```
caggactata aagataccag gcgtttcccc ctggaagctc cctcgtgcgc tctcctgttc    3480
cgaccctgcc gcttaccgga tacctgtccg cctttctccc ttcgggaagc gtggcgcttt    3540
ctcaatgctc acgctgtagg tatctcagtt cggtgtaggt cgttcgctcc aagctgggct    3600
gtgtgcacga accccccgtt cagcccgacc gctgcgcctt atccggtaac tatcgtcttg    3660
agtccaaccc ggtaagacac gacttatcgc cactggcagc agccactggt aacaggatta    3720
gcagagcgag gtatgtaggc ggtgctacag agttcttgaa gtggtggcct aactacggct    3780
acactagaag gacagtattt ggtatctgcg ctctgctgaa gccagttacc ttcggaaaaa    3840
gagttggtag ctcttgatcc ggcaaacaaa ccaccgctgg tagcggtggt ttttttgttt    3900
gcaagcagca gattacgcgc agaaaaaaag gatctcaaga agatcctttg atcttttcta    3960
cggggtctga cgctcagtgg aacgaaaact cacgttaagg gattttggtc atgagattat    4020
caaaaaggat cttcacctag atccttttaa attaaaaatg aagttttaaa tcaatctaaa    4080
gtatatatga gtaaacttgg tctgacagtt accaatgctt aatcagtgag gcacctatct    4140
cagcgatctg tctatttcgt tcatccatag ttgcctgact ccccgtcgtg tagataacta    4200
cgatacggga gggcttacca tctggcccca gtgctgcaat gataccgcga acccacgct    4260
caccggctcc agatttatca gcaataaacc agccagccgg aagggccgag cgcagaagtg    4320
gtcctgcaac tttatccgcc tccatccagt ctattaattg ttgccgggaa gctagagtaa    4380
gtagttcgcc agttaatagt ttgcgcaacg ttgttgccat tgctacaggc atcgtggtgt    4440
cacgctcgtc gtttggtatg gcttcattca gctccggttc ccaacgatca aggcgagtta    4500
catgatcccc catgttgtgc aaaaaagcgg ttagctcctt cggtcctccg atcgttgtca    4560
gaagtaagtt ggccgcagtg ttatcactca tggttatggc agcactgcat aattctctta    4620
ctgtcatgcc atccgtaaga tgcttttctg tgactggtga gtactcaacc aagtcattct    4680
gagaatagtg tatgcggcga ccgagttgct cttgcccggc gtcaatacgg gataataccg    4740
cgccacatag cagaacttta aaagtgctca tcattggaaa acgttcttcg ggcgaaaac    4800
tctcaaggat cttaccgctg ttgagatcca gttcgatgta acccactcgt gcacccaact    4860
gatcttcagc atcttttact ttcaccagcg tttctgggtg agcaaaaaca ggaaggcaaa    4920
atgccgcaaa aaagggaata agggcgacac ggaaatgttg aatactcata ctcttccttt    4980
ttcaatatta ttgaagcatt tatcagggtt attgtctcat gagcggatac atatttgaat    5040
gtatttagaa aaataaacaa ataggggttc cgcgcacatt tccccgaaaa gtgccacctg    5100
acgtcgacgg atcgggagat ctcccgatcc cctatggtgc actctcagta caatctgctc    5160
tgatgccgca tagttaagcc agtatctgct ccctgcttgt gtgttggagg tcgctgagta    5220
gtgcgcgagc aaaatttaag ctacaacaag gcaaggcttg accgacaatt gcatgaagaa    5280
tctgcttagg gttaggcgtt ttgcgctgct tcgcgatgta cgggccagat atacgcgttg    5340
acattgatta ttgactagtt attaatagta atcaattacg ggtcattag ttcatagccc    5400
atatatggag ttccgcgtta cataacttac ggtaaatggc ccgcctggct gaccgcccaa    5460
cgaccccgc ccattgacgt caataatgac gtatgttccc atagtaacgc caatagggac    5520
tttccattga cgtcaatggg tggactattt acggtaaact gcccacttgg cagtacatca    5580
agtgtatcat atgccaagta cgccccctat tgacgtcaat gacggtaaat ggcccgcctg    5640
gcattatgcc cagtacatga ccttatggga ctttcctact tggcagtaca tctacgtatt    5700
agtcatcgct attaccatgg tgatgcggtt ttggcagtac atcaatgggc gtggatagcg    5760
gtttgactca cggggatttc caagtctcca ccccattgac gtcaatggga gtttgttttg    5820
```

```
gcaccaaaat caacgggact ttccaaaatg tcgtaacaac tccgcccat  tgacgcaaat    5880 gggcggtagg cgtgtacggt gggaggtcta tataagcaga gctctctggc taactagaga    5940
acccactgct tactggctta tcgaaattaa tacgactcac tatagggaga cccaagctgg    6000
tttaaactta agcttggtac cgagctcact agtccagtgt ggtggcagat atccagcaca    6060
gtggcggccg ctcgagggc  ccgttttgcc tgtactgggt ctctctggtt agaccagatc    6120
tgagcctggg agctctctgg ctaactaggg aacccactgc ttaagcctca ataaagcttg    6180
ccttgagtgc ttcaagtagt gtgtgcccgt ctgttgtgtg actctggtaa ctagagatcc    6240
ctcagaccct tttagtcagt gtggaaaatc tctagcagtg gcgcccgaac agggacttga    6300
aagcgaaagg gaaaccagag gagctctctc gacgcaggac tcggcttgct gaagcgcgca    6360
cggcaagagg cgagggggg  cgactggtga gtacgccaaa aattttgact agcggaggct    6420
agaaggagag agatgggtgc gagagcgtca gtattaagcg ggggagaatt agatcgcgat    6480
gggaaaaaat tcggttaagg ccaggggga  agaaaaaata taaattaaaa catatagtat    6540
gggcaagcag ggagctagaa cgattcgcag ttaatcctgg cctgttagaa acatcagaag    6600
gctgtagaca aatactggga cagctacaac catcccttca gacaggatca gaagaactta    6660
gatcattata taatacagta gcaaccctct attgtgtgca tcaaaggata gagataaaag    6720
acaccaagga agctttagac aagatagagg aagagcaaaa caaaagtaag accaccgcac    6780
agcaagcggc cgctgatctt cagacctgga ggaggagata tgagggacaa ttggagaagt    6840
gaattatata aatataaagt agtaaaaatt gaaccattag gagtagcacc caccaaggca    6900
aagagaagag tggtgcagag agaaaaaaga gcagtgggaa taggagcttt gttccttggg    6960
ttcttgggag cagcaggaag cactatgggc gcagcgtcaa tgacgctgac ggtacaggcc    7020
agacaattat tgtctggtat agtgcagcag cagaacaatt tgctgagggc tattgaggcg    7080
caacagcatc tgttgcaact cacagtctgg ggcatcaagc agctccaggc aagaatcctg    7140
gctgtggaaa gatacctaaa ggatcaacag ctcctgggga tttggggttg ctctggaaaa    7200
ctcatttgca ccactgctgt gccttggaat gctagttgga gtaataaatc tctggaacag    7260
atttggaatc acacgacctg gatggagtgg gacagagaaa ttaacaatta cacaagctta    7320
atacactcct taattgaaga atcgcaaaac cagcaagaaa agaatgaaca agaattattg    7380
gaattagata aatgggcaag tttgtggaat tggtttaaca taacaaattg gctgtggtat    7440
ataaaattat tcataatgat agtaggaggc ttggtaggtt taagaatagt ttttgctgta    7500
ctttctatag tgaatagagt taggcaggga tattcaccat tatcgtttca gacccacctc    7560
ccaaccccga ggggacccga caggccctta  ttaatccccc tgattctgtg gataaccgta    7620
ttaccgcctt tgagtgagct gcacgggagc aattaatcta tagattaaaa agtgaaaggc    7680
tacaatagga cgggagcaat taatctatag attaaaagt  gaaaggctac aataggacgg    7740
gagcaattaa tctatagatt aaaaagtgaa aggctacaat aggacgggag caattaatct    7800
atagattaaa aagtgaaagg ctacaatagg acgggagcaa ttaatctata gattaaaaag    7860
tgaaaggcta caataggacg ggagcaatta atctatagat taaaaagtga aaggctacaa    7920
taggacggga gcaattaatc tatagattaa aaagtgaaag gctacaatag gacggtaaac    7980
tcgacctata taagcagagc tcgtttagtg aaccgtcaga tcgcctggag acgccatcca    8040
cgctgttttg acctccatag aagacaccgg gaccgatcca gcctccgcgg ccccgaattg    8100
aattcggcca ttcgccctg  ccaccatgag cacaaaaaag aaaccattaa cacaagagca    8160
gcttgaggac gcacgtcgcc ttaaagcaat ttatgaaaaa agaaaaatg  aacttggctt    8220
```

| | | | | |
|---|---|---|---|---|
| atcccaggaa | tctgtcgcag | acaagatggg | gatggggcag | tcaggcgttg gtgctttatt | 8280 |
| taatggcatc | aatgcattaa | atgcttataa | cgccgcattg | cttgcaaaaa ttctcaaagt | 8340 |
| tagcgttgaa | gaattcagcc | cttcaatcgc | cagagagatc | tacgagatgt atgaagcggt | 8400 |
| tagtatgcag | ccgtcactta | gaagtgagta | tgagtaccct | gttttttctc atgttcaggc | 8460 |
| agggatgttc | tcacctgagc | ttagaacctt | taccaaaggt | gatgcggaga gatgggtaag | 8520 |
| cacaaccaaa | aaagccagtg | attctgcatt | ctggcttgag | gttgaaggta attccatgac | 8580 |
| cgcaccaaca | ggctccaagc | caagcttttcc | tgacggaatg | ttaattctcg ttgaccctga | 8640 |
| gcaggctgtt | gagcccgggg | atttctgcat | agccagactt | gggggtgatg agtttacctt | 8700 |
| caagaaactg | atcagggata | gcggtcaggt | gttttacaa | ccactaaacc cacagtaccc | 8760 |
| aatgatccca | tgcaatgaga | gttgttccgt | tgtggggaaa | gttatcgcta gtcagtggcc | 8820 |
| tgaagagacg | tttggcccaa | aaaagaagag | aaaggtcgac | ggcggtggtg cttttgtctcc | 8880 |
| tcagcactct | gctgtcactc | aaggaagtat | catcaagaac | aaggagggca tggatgctaa | 8940 |
| gtcactaact | gcctggtccc | ggacactggt | gaccttcaag | gatgtatttg tggacttcac | 9000 |
| cagggaggag | tggaagctgc | tggacactgc | tcagcagatc | gtgtacagaa atgtgatgct | 9060 |
| ggagaactat | aagaacctgg | tttccttggg | ttatcagctt | actaagccag atgtgatcct | 9120 |
| ccggttggag | aagggagaag | agccctggct | ggtggagaga | gaaattcacc aagagaccca | 9180 |
| tcctgattca | gagactgcat | ttgaaatcaa | atcatcagtt | taatgccacc | 9230 |

<210> SEQ ID NO 18
<211> LENGTH: 8874
<212> TYPE: DNA
<213> ORGANISM: Artificial Sequence
<220> FEATURE:
<223> OTHER INFORMATION: Synthetic

<400> SEQUENCE: 18

| | | | | |
|---|---|---|---|---|
| ttatgtgtgg | gagggctaag | ggcgcgccgt | tctagagaat | tcgatatcaa gcttatcgat | 60 |
| aatcaacctc | tggattacaa | aatttgtgaa | agattgactg | gtattcttaa ctatgttgct | 120 |
| ccttttacgc | tatgtggata | cgctgcttta | atgcctttgt | atcatgctat tacttcccgt | 180 |
| acggctttca | ttttctcctc | cttgtataaa | tcctggttgc | tgtctcttta tgaggagttg | 240 |
| tggcccgttg | tcaggcaacg | tggcgtggtg | tgcactgtgt | ttgctgacgc aaccccact | 300 |
| ggttggggca | ttgccaccac | ctatcaactc | cttccgggga | cttttgcttt cccctccct | 360 |
| attgccacgg | cggaactcat | tgccgcctgc | cttgcccgct | gctggacagg gctcggctg | 420 |
| ttgggcactg | acaattccgt | ggtgttgtcg | gggaagctga | cgtcctttcc atggctgctc | 480 |
| gcctgtgttg | ccaactggat | tctgcgcggg | acgtccttct | gctacgtccc ttcggccctc | 540 |
| aatccagcgg | accttccttc | ccgcggcctg | ctgccggttc | tgcggcctct tccgcgtctt | 600 |
| cgccttcgcc | ctcagacgag | tcggatctcc | ctttgggccg | cctccccgcc tgcctgcagg | 660 |
| tttgtcgaga | cctagaaaaa | catggagcaa | tcacaagtag | caatacagca gctaccaatg | 720 |
| ctgattgtgc | ctggctagaa | gcacaagagg | aggaggaggt | gggttttcca gtcacacctc | 780 |
| aggtaccttt | aagaccaatg | acttacaagg | cagctgtaga | tcttagccac ttttttaaaag | 840 |
| aaaagggggg | actggaaggg | ctaattcact | cccaacgaag | acaagatctg cttttttgctt | 900 |
| gtactgggtc | tctctggtta | gaccagatct | gagcctggga | gctctctggc taactaggga | 960 |
| acccactgct | taagcctcaa | taaagcttgc | cttgagtgct | tcaagtagtg tgtgcccgtc | 1020 |
| tgttgtgtga | ctctggtaac | tagagatccc | tcagaccctt | ttagtcagtg tggaaaatct | 1080 |

```
ctagcagggc cgtttaaaac ccgctgatca gcctcgactg tgccttctag ttgccagcca   1140
tctgttgttt gccccctccc cgtgccttcc ttgaccctgg aaggtgccac tcccactgtc   1200
ctttcctaat aaaatgagga aattgcatcg cattgtctga gtaggtgtca ttctattctg   1260
gggggtgggg tggggcagga cagcaagggg gaggattggg aagacaatag caggcatgct   1320
ggggatgcgg tgggctctat ggcttctgag gcggaaagaa ccagctgggg ctctaggggg   1380
tatccccacg cgccctgtag cggcgcatta agcgcggcgg gtgtggtggt tacgcgcagc   1440
gtgaccgcta cacttgccag cgccctagcg cccgctcctt tcgctttctt cccttccttt   1500
ctcgccacgt tcgccggctt tccccgtcaa gctctaaatc gggcatccc tttagggttc     1560 cgatttagtg ctttacggca cctcgacccc aaaaaacttg attagggtga tggttcacgt   1620
agtgggccat cgccctgata gacggttttt cgccctttga cgttggagtc cacgttcttt   1680
aatagtggac tcttgttcca aactggaaca acactcaacc ctatctcggt ctattctttt   1740
gatttataag ggattttggg gatttcggcc tattggttaa aaaatgagct gatttaacaa   1800
aaatttaacg cgaattaatt ctgtggaatg tgtgtcagtt agggtgtgga aagtccccag   1860 gctcccagg caggcagaag tatgcaaagc atgcatctca attagtcagc aaccaggtgt    1920
ggaaagtccc caggctcccc agcaggcaga agtatgcaaa gcatgcatct caattagtca   1980
gcaaccatag tccgcccct aactccgccc atcccgcccc taactccgcc cagttccgcc     2040
cattctccgc cccatggctg actaattttt tttatttatg cagaggccga ggccgcctct   2100
gcctctgagc tattccagaa gtagtgagga ggcttttttg gaggcctagg cttttgcaaa   2160
aagctcccgg gagcttgtat atccattttc ggatctgatc agcacgtgtt gacaattaat   2220
catcggcata gtatatcggc atagtataat acgacaaggt gaggaactaa accatggcca   2280
agttgaccag tgccgttccg gtgctcaccg cgcgcgacg cgccggagcg gtcgagttct     2340
ggaccgaccg gctcgggttc tcccgggact tcgtggagga cgacttcgcc ggtgtggtcc   2400
gggacgacgt gaccctgttc atcagcgcgg tccaggacca ggtggtgccg gacaacaccc   2460
tggcctgggt gtgggtgcgc ggcctggacg agctgtacgc cgagtggtcg gaggtcgtgt   2520
ccacgaactt ccgggacgcc tccgggccgg ccatgaccga gatcggcgag cagccgtggg   2580
ggcgggagtt cgccctgcgc gacccggccg gcaactgcgt gcacttcgtg gccgaggagc   2640
aggactgaca cgtgctacga gatttcgatt ccaccgccgc cttctatgaa aggttgggct   2700
tcggaatcgt tttccgggac gccggctgga tgatcctcca gcgcgggat ctcatgctgg    2760 agttcttcgc ccaccccaac ttgttttattg cagcttataa tggttacaaa taaagcaata   2820
gcatcacaaa tttcacaaat aaagcatttt tttcactgca ttctagttgt ggtttgtcca   2880
aactcatcaa tgtatcttat catgtctgta taccgtcgac ctctagctag agcttggcgt   2940
aatcatggtc atagctgttt cctgtgtgaa attgttatcc gctcacaatt ccacacaaca   3000
tacgagccgg aagcataaag tgtaaagcct ggggtgccta atgagtgagc taactcacat   3060
taattgcgtt gcgctcactg cccgctttcc agtcgggaaa cctgtcgtgc cagctgcatt   3120
aatgaatcgg ccaacgcgcg gggagaggcg gtttgcgtat tgggcgctct tccgcttcct   3180
cgctcactga ctcgctgcgc tcggtcgttc ggctgcggcg agcggtatca gctcactcaa   3240
aggcggtaat acggttatcc acagaatcag gggataacgc aggaaagaac atgtgagcaa   3300
aaggccagca aaaggccagg aaccgtaaaa aggccgcgtt gctggcgttt ttccataggc   3360
tccgcccccc tgacgagcat cacaaaaatc gacgctcaag tcagaggtgg cgaaacccga   3420
caggactata aagataccag gcgtttcccc ctggaagctc cctcgtgcgc tctcctgttc   3480
```

```
cgaccctgcc gcttaccgga tacctgtccg cctttctccc ttcgggaagc gtggcgcttt    3540
ctcaatgctc acgctgtagg tatctcagtt cggtgtaggt cgttcgctcc aagctgggct    3600
gtgtgcacga accccccgtt cagcccgacc gctgcgcctt atccggtaac tatcgtcttg    3660
agtccaaccc ggtaagacac gacttatcgc cactggcagc agccactggt aacaggatta    3720
gcagagcgag gtatgtaggc ggtgctacag agttcttgaa gtggtggcct aactacggct    3780
acactagaag gacagtattt ggtatctgcg ctctgctgaa gccagttacc ttcggaaaaa    3840
gagttggtag ctcttgatcc ggcaaacaaa ccaccgctgg tagcggtggt ttttttgttt    3900
gcaagcagca gattacgcgc agaaaaaaag gatctcaaga agatcctttg atcttttcta    3960
cggggtctga cgctcagtgg aacgaaaact cacgttaagg gattttggtc atgagattat    4020
caaaaaggat cttcacctag atccttttaa attaaaaatg aagttttaaa tcaatctaaa    4080
gtatatatga gtaaacttgg tctgacagtt accaatgctt aatcagtgag gcacctatct    4140
cagcgatctg tctatttcgt tcatccatag ttgcctgact ccccgtcgtg tagataacta    4200
cgatacggga gggcttacca tctggcccca gtgctgcaat gataccgcga gacccacgct    4260
caccggctcc agatttatca gcaataaacc agccagccgg aagggccgag cgcagaagtg    4320
gtcctgcaac tttatccgcc tccatccagt ctattaattg ttgccgggaa gctagagtaa    4380
gtagttcgcc agttaatagt ttgcgcaacg ttgttgccat tgctacaggc atcgtggtgt    4440
cacgctcgtc gtttggtatg gcttcattca gctccggttc ccaacgatca aggcgagtta    4500
catgatcccc catgttgtgc aaaaaagcgg ttagctcctt cggtcctccg atcgttgtca    4560
gaagtaagtt ggccgcagtg ttatcactca tggttatggc agcactgcat aattctctta    4620
ctgtcatgcc atccgtaaga tgcttttctg tgactggtga gtactcaacc aagtcattct    4680
gagaatagtg tatgcggcga ccgagttgct cttgcccggc gtcaatacgg gataataccg    4740
cgccacatag cagaacttta aaagtgctca tcattggaaa acgttcttcg gggcgaaaac    4800
tctcaaggat cttaccgctg ttgagatcca gttcgatgta acccactcgt gcacccaact    4860
gatcttcagc atcttttact ttcaccagcg tttctgggtg agcaaaaaca ggaaggcaaa    4920
atgccgcaaa aaagggaata agggcgacac ggaaatgttg aatactcata ctcttccttt    4980
ttcaatatta ttgaagcatt tatcagggtt attgtctcat gagcggatac atatttgaat    5040
gtatttagaa aaataaacaa ataggggttc cgcgcacatt tccccgaaaa gtgccacctg    5100
acgtcgacgg atcgggagat ctcccgatcc cctatggtgc actctcagta caatctgctc    5160
tgatgccgca tagttaagcc agtatctgct ccctgcttgt gtgttggagg tcgctgagta    5220
gtgcgcgagc aaaatttaag ctacaacaag gcaaggcttg accgacaatt gcatgaagaa    5280
tctgcttagg gttaggcgtt ttgcgctgct tcgcgatgta cgggccagat atacgcgttg    5340
acattgatta ttgactagtt attaatagta atcaattacg gggtcattag ttcatagccc    5400
atatatggag ttccgcgtta cataacttac ggtaaatggc ccgcctggct gaccgcccaa    5460
cgacccccgc ccattgacgt caataatgac gtatgttccc atagtaacgc caatagggac    5520
tttccattga cgtcaatggg tggactattt acggtaaact gcccacttgg cagtacatca    5580
agtgtatcat atgccaagta cgccccctat tgacgtcaat gacggtaaat ggcccgcctg    5640
gcattatgcc cagtacatga ccttatggga ctttcctact tggcagtaca tctacgtatt    5700
agtcatcgct attaccatgg tgatgcggtt ttggcagtac atcaatgggc gtggatagcg    5760
gtttgactca cggggatttc caagtctcca ccccattgac gtcaatggga gtttgttttg    5820
gcaccaaaat caacgggact ttccaaaatg tcgtaacaac tccgccccat tgacgcaaat    5880
```

```
gggcggtagg cgtgtacggt gggaggtcta tataagcaga gctctctggc taactagaga    5940
acccactgct tactggctta tcgaaattaa tacgactcac tatagggaga cccaagctgg    6000
tttaaactta agcttggtac cgagctcact agtccagtgt ggtggcagat atccagcaca    6060
gtggcggccg ctcgagggc ccgttttgcc tgtactgggt ctctctggtt agaccagatc    6120
tgagcctggg agctctctgg ctaactaggg aacccactgc ttaagcctca ataaagcttg    6180
ccttgagtgc ttcaagtagt gtgtgcccgt ctgttgtgtg actctggtaa ctagagatcc    6240
ctcagaccct tttagtcagt gtggaaaatc tctagcagtg gcgcccgaac agggacttga    6300
aagcgaaagg gaaaccagag gagctctctc gacgcaggac tcggcttgct gaagcgcgca    6360
cggcaagagg cgaggggcgg cgactggtga gtacgccaaa aattttgact agcggaggct    6420
agaaggagag agatgggtgc gagagcgtca gtattaagcg gggagaatt agatcgcgat    6480 gggaaaaaat tcggttaagg ccaggggaa agaaaaaata taaattaaaa catatagtat    6540
gggcaagcag ggagctagaa cgattcgcag ttaatcctgg cctgttagaa acatcagaag    6600
gctgtagaca aatactggga cagctacaac catcccttca gacaggatca gaagaactta    6660
gatcattata taatacagta gcaaccctct attgtgtgca tcaaaggata gagataaaag    6720
acaccaagga agctttagac aagatagagg aagagcaaaa caaaagtaag accaccgcac    6780
agcaagcggc cgctgatctt cagacctgga ggaggagata tgagggacaa ttggagaagt    6840
gaattatata aatataaagt agtaaaaatt gaaccattag gagtagcacc caccaaggca    6900
aagagaagag tggtgcagag agaaaaaaga gcagtgggaa taggagcttt gttccttggg    6960
ttcttgggag cagcaggaag cactatgggc gcagcgtcaa tgacgctgac ggtacaggcc    7020
agacaattat tgtctggtat agtgcagcag cagaacaatt tgctgagggc tattgaggcg    7080
caacagcatc tgttgcaact cacagtctgg ggcatcaagc agctccaggc aagaatcctg    7140
gctgtggaaa gatacctaaa ggatcaacag ctcctgggga tttggggttg ctctggaaaa    7200
ctcatttgca ccactgctgt gccttggaat gctagttgga gtaataaatc tctggaacag    7260
atttggaatc acacgacctg gatggagtgg gacagagaaa ttaacaatta cacaagctta    7320
atacactcct taattgaaga atcgcaaaac cagcaagaaa agaatgaaca agaattattg    7380
gaattagata atgggcaag tttgtggaat tggtttaaca taacaaattg gctgtggtat    7440
ataaaattat tcataatgat agtaggaggc ttggtaggtt taagaatagt ttttgctgta    7500
ctttctatag tgaatagagt taggcaggga tattcaccat tatcgtttca gacccacctc    7560
ccaaccccga gggacccga caggcccta ttaatcccc tgattctgtg gataaccgta    7620
ttaccgcctt tgagtgagct gcacgggagc aattaatcta tagattaaaa agtgaaaggc    7680
tacaatagga cgggagcaat taatctatag attaaaagt gaaaggctac aataggacgg    7740
gagcaattaa tctatagatt aaaagtgaa aggctacaat aggacgggag caattaatct    7800
atagattaaa aagtgaaagg ctacaatagg acggagcaa ttaatctata gattaaaaag    7860
tgaaaggcta caataggacg ggagcaatta atctatagat taaaaagtga aaggctacaa    7920
taggacggga gcaattaatc tatagattaa aagtgaaag ctacaatag acggtaaac    7980 tcgacctata taagcagagc tcgtttagtg aaccgtcaga tcgcctggag acgccatcca    8040
cgctgttttg acctccatag aagacaccgg gaccgatcca gcctccgcgg ccccgaattg    8100
aattctccct atcagtgata gagatctccc tatcagtgat agagaggcca ttacggcctg    8160
ccaccatgtt cgttatcatc caggctcacg aataccagaa atacgctgct gttctggacc    8220
agatgttccg tctgcgtaaa aaagttttcg ctgacaccct gtgctgggac gttccggtta    8280
```

-continued

| | |
|---|---|
| tcggtccgta cgaacgtgac tcctacgact ccctggctcc ggcttacctg gtttggtgca | 8340 |
| acgactcccg tacccgtctg tacggtggta tgcgtctgat gccgaccacc ggtccgaccc | 8400 |
| tgctgtacga cgttttccgt gaaaccttcc cggacgctgc tgacctgatc gctccgggta | 8460 |
| tctgggaagg tacccgtatg tgcatcgacg aagaagctat cgctaaagac ttcccggaaa | 8520 |
| tcgacgctgg tcgtgctttc tccatgatgc tgctggctct gtgcgaatgc gctctggacc | 8580 |
| acggtatcca caccatgatc tccaactacg aaccgtacct gaaacgtgtt acaaacgtg | 8640 |
| ctggtgctga agttgaagaa ctgggtcgtg ctgacggtta cggtaaatac ccggtttgct | 8700 |
| gcggtgcttt cgaagtttcc gaccgtgttc tgcgtaaaat gcgtgctgct ctgggtctga | 8760 |
| ccctgccgct gtacgttcgt cacgttccgg ctcgttccgt tgttacccag ttcctggaaa | 8820 |
| tggctgctgc tgctaacgac gaaaactacg ctctggttgc ttaataatgc cacc | 8874 |

```
<210> SEQ ID NO 19
<211> LENGTH: 9927
<212> TYPE: DNA
<213> ORGANISM: Artificial Sequence
<220> FEATURE:
<223> OTHER INFORMATION: Synthetic

<400> SEQUENCE: 19
```

| | |
|---|---|
| cggccatcga taaggatccg cggccgcaat caacctctgg attacaaaat ttgtgaaaga | 60 |
| ttgactggta ttcttaacta tgttgctcct tttacgctat gtggatacgc tgctttaatg | 120 |
| cctttgtatc atgctattac ttcccgtacg gctttcattt tctcctcctt gtataaatcc | 180 |
| tggttgctgt ctctttatga ggagttgtgg cccgttgtca ggcaacgtgg cgtggtgtgc | 240 |
| actgtgtttg ctgacgcaac ccccactggt tggggcattg ccaccaccta tcaactcctt | 300 |
| tccgggactt tcgctttccc cctccctatt gccacggcgg aactcattgc cgcctgcctt | 360 |
| gcccgctgct ggacaggggc tcggctgttg ggcactgaca attccgtggt gttgtcgggg | 420 |
| aagctgacgt cctttccatg gctgctcgcc tgtgttgcca ctggattct gcgcgggacg | 480 |
| tccttctgct acgtcccttc ggccctcaat ccagcggacc ttccttcccg cggcctgctg | 540 |
| ccggttctgc ggcctcttcc gcgtcttcgc cttcgccctc agacgagtcg gatctccctt | 600 |
| tgggccgcct ccccgcctgc ctgcaggttt gtcgagacct agaaaaacat ggagcaatca | 660 |
| caagtagcaa tacagcagct accaatgctg attgtgcctg gctagaagca caagaggagg | 720 |
| aggaggtggg ttttccagtc acacctcagg tacctttaag accaatgact tacaaggcag | 780 |
| ctgtagatct tagccacttt ttaaaagaaa aggggggact ggaagggcta attcactccc | 840 |
| aacgaagaca agatctgctt tttgcttgta ctgggtctct ctggttagac cagatctgag | 900 |
| cctgggagct ctctggctaa ctaggaacc cactgcttaa gcctcaataa agcttgcctt | 960 |
| gagtgcttca agtagtgtgt gcccgtctgt tgtgtgactc tggtaactag agatccctca | 1020 |
| gaccctttta gtcagtgtgg aaaatctcta gcagggcccg tttaaacccg ctgatcagcc | 1080 |
| tcgactgtgc cttctagttg ccagccatct gttgtttgcc cctcccccgt gccttccttg | 1140 |
| accctggaag gtgccactcc cactgtcctt tcctaataaa atgaggaaat tgcatcgcat | 1200 |
| tgtctgagta ggtgtcattc tattctgggg gtgggtgg ggcaggacag caaggggag | 1260 |
| gattgggaag acaatagcag gcatgctggg gatgcggtgg gctctatggc ttctgaggcg | 1320 |
| gaaagaacca gctggggctc tagggggtat ccccacgcgc cctgtagcgg cgcattaagc | 1380 |
| gcggcgggtg tggtggttac gcgcagcgtg accgctacac ttgccagcgc cctagcgccc | 1440 |
| gctcctttcg ctttcttccc ttcctttctc gccacgttcg ccggctttcc ccgtcaagct | 1500 |

-continued

```
ctaaatcggg gcatcccttt agggttccga tttagtgctt tacggcacct cgaccccaaa    1560
aaacttgatt agggtgatgg ttcacgtagt gggccatcgc cctgatagac ggttttttcgc   1620 cctttgacgt tggagtccac gttctttaat agtggactct tgttccaaac tggaacaaca    1680
ctcaacccta tctcggtcta ttcttttgat ttataaggga ttttggggat ttcggcctat    1740
tggttaaaaa atgagctgat ttaacaaaaa tttaacgcga attaattctg tggaatgtgt    1800
gtcagttagg gtgtggaaag tccccaggct ccccaggcag gcagaagtat gcaaagcatg    1860
catctcaatt agtcagcaac caggtgtgga aagtccccag gctccccagc aggcagaagt    1920
atgcaaagca tgcatctcaa ttagtcagca accatagtcc cgcccctaac tccgcccatc    1980
ccgcccctaa ctccgcccag ttccgcccat tctccgcccc atggctgact aattttttttt   2040 atttatgcag aggccgaggc cgcctctgcc tctgagctat tccagaagta gtgaggaggc    2100
ttttttggag gcctaggctt ttgcaaaaag ctcccgggag cttgtatatc cattttcgga    2160
tctgatcagc acgtgttgac aattaatcat cggcatagta tatcggcata gtataatacg    2220
acaaggtgag gaactaaacc atggccaagt tgaccagtgc cgttccggtg ctcaccgcgc    2280
gcgacgtcgc cggagcggtc gagttctgga ccgaccggct cgggttctcc cgggacttcg    2340
tggaggacga cttcgccggt gtggtccggg acgacgtgac cctgttcatc agcgcggtcc    2400
aggaccaggt ggtgccggac aacaccctgg cctgggtgtg ggtgcgcggc ctggacgagc    2460
tgtacgccga gtggtcggag gtcgtgtcca cgaacttccg ggacgcctcc gggccggcca    2520
tgaccgagat cggcgagcag ccgtgggggc gggagttcgc cctgcgcgac ccggccggca    2580
actgcgtgca cttcgtggcc gaggagcagg actgacacgt gctacgagat ttcgattcca    2640
ccgccgcctt ctatgaaagg ttgggcttcg aatcgttttc cgggacgcc ggctggatga    2700 tcctccagcg cggggatctc atgctggagt tcttcgccca ccccaacttg tttattgcag    2760
cttataatgg ttacaaataa agcaatagca tcacaaattt cacaaataaa gcatttttttt  2820 cactgcattc tagttgtggt ttgtccaaac tcatcaatgt atcttatcat gtctgtatac    2880
cgtcgacctc tagctagagc ttggcgtaat catggtcata gctgtttcct gtgtgaaatt    2940
gttatccgct cacaattcca cacaacatac gagccggaag cataaagtgt aaagcctggg    3000
gtgcctaatg agtgagctaa ctcacattaa ttgcgttgcg ctcactgccc gctttccagt    3060
cgggaaacct gtcgtgccag ctgcattaat gaatcggcca acgcgcgggg agaggcggtt    3120
tgcgtattgg gcgctcttcc gcttcctcgc tcactgactc gctgcgctcg tcgttcggc    3180 tgcggcgagc ggtatcagct cactcaaagg cggtaatacg ttatccaca gaatcagggg    3240 ataacgcagg aaagaacatg tgagcaaaag gccagcaaaa ggccaggaac cgtaaaaagg    3300
ccgcgttgct ggcgtttttc cataggctcc gcccccctga cgagcatcac aaaaatcgac    3360
gctcaagtca gaggtggcga aacccgacag gactataaag ataccaggcg tttccccctg    3420
gaagctccct cgtgcgctct cctgttccga ccctgccgct taccggatac ctgtccgcct    3480
ttctcccttc gggaagcgtg gcgctttctc aatgctcacg ctgtaggtat ctcagttcgg    3540
tgtaggtcgt tcgctccaag ctgggctgtg tgcacgaacc ccccgttcag cccgaccgct    3600
gcgccttatc cggtaactat cgtcttgagt ccaacccggt aagacacgac ttatcgccac    3660
tggcagcagc cactggtaac aggattagca gagcgaggta tgtaggcggt gctacagagt    3720
tcttgaagtg gtggcctaac tacggctaca ctagaaggac agtatttggt atctgcgctc    3780
tgctgaagcc agttaccttc ggaaaaagag ttggtagctc ttgatccggc aaacaaacca    3840
ccgctggtag cggtggtttt tttgtttgca agcagcagat tacgcgcaga aaaaaaggat    3900
```

```
ctcaagaaga tcctttgatc ttttctacgg ggtctgacgc tcagtggaac gaaaactcac    3960
gttaagggat tttggtcatg agattatcaa aaaggatctt cacctagatc cttttaaatt    4020
aaaaatgaag ttttaaatca atctaaagta tatatgagta aacttggtct gacagttacc    4080
aatgcttaat cagtgaggca cctatctcag cgatctgtct atttcgttca tccatagttg    4140
cctgactccc cgtcgtgtag ataactacga tacgggaggg cttaccatct ggccccagtg    4200
ctgcaatgat accgcgagac ccacgctcac cggctccaga tttatcagca ataaaccagc    4260
cagccggaag ggccgagcgc agaagtggtc ctgcaacttt atccgcctcc atccagtcta    4320
ttaattgttg ccgggaagct agagtaagta gttcgccagt taatagtttg cgcaacgttg    4380
ttgccattgc tacaggcatc gtggtgtcac gctcgtcgtt tggtatggct tcattcagct    4440
ccggttccca acgatcaagg cgagttacat gatcccccat gttgtgcaaa aaagcggtta    4500
gctccttcgg tcctccgatc gttgtcagaa gtaagttggc cgcagtgtta tcactcatgg    4560
ttatggcagc actgcataat tctcttactg tcatgccatc cgtaagatgc ttttctgtga    4620
ctggtgagta ctcaaccaag tcattctgag aatagtgtat gcggcgaccg agttgctctt    4680
gcccggcgtc aatacgggat aataccgcgc cacatagcag aactttaaaa gtgctcatca    4740
ttggaaaacg ttcttcgggg cgaaaactct caaggatctt accgctgttg agatccagtt    4800
cgatgtaacc cactcgtgca cccaactgat cttcagcatc ttttactttc accagcgttt    4860
ctgggtgagc aaaaacagga aggcaaaatg ccgcaaaaaa gggaataagg gcgacacgga    4920
aatgttgaat actcatactc ttcctttttc aatattattg aagcatttat cagggttatt    4980
gtctcatgag cggatacata tttgaatgta tttagaaaaa taaacaaata ggggttccgc    5040
gcacatttcc ccgaaaagtg ccacctgacg tcgacggatc gggagatctc ccgatcccct    5100
atggtgcact ctcagtacaa tctgctctga tgccgcatag ttaagccagt atctgctccc    5160
tgcttgtgtg ttggaggtcg ctgagtagtg cgcgagcaaa atttaagcta caacaaggca    5220
aggcttgacc gacaattgca tgaagaatct gcttagggtt aggcgttttg cgctgcttcg    5280
cgatgtacgg gccagatata cgcgttgaca ttgattattg actagttatt aatagtaatc    5340
aattacgggg tcattagttc atagcccata tatggagttc cgcgttacat aacttacggt    5400
aaatggcccg cctggctgac cgcccaacga ccccgcccca ttgacgtcaa taatgacgta    5460
tgttcccata gtaacgccaa tagggacttt ccattgacgt caatgggtgg actatttacg    5520
gtaaactgcc cacttggcag tacatcaagt gtatcatatg ccaagtacgc cccctattga    5580
cgtcaatgac ggtaaatggc ccgcctggca ttatgcccag tacatgacct tatgggactt    5640
tcctacttgg cagtacatct acgtattagt catcgctatt accatggtga tgcggttttg    5700
gcagtacatc aatgggcgtg gatagcggtt tgactcacgg ggatttccaa gtctccaccc    5760
cattgacgtc aatgggagtt tgttttggca ccaaaatcaa cgggactttc caaaatgtcg    5820
taacaactcc gccccattga cgcaaatggg cggtaggcgt gtacggtggg aggtctatat    5880
aagcagagct ctctggctaa ctagagaacc cactgcttac tggcttatcg aaattaatac    5940
gactcactat agggagaccc aagctggttt aaacttaagc ttggtaccga gctcactagt    6000
ccagtgtggt ggcagatatc cagcacagtg gcggccgctc gagtctagag ggcccgtttt    6060
gcctgtactg ggtctctctg gttagaccag atctgagcct gggagctctc tggctaacta    6120
gggaacccac tgcttaagcc tcaataaagc ttgccttgag tgcttcaagt agtgtgtgcc    6180
cgtctgttgt gtgactctgg taactagaga tccctcagac ccttttagtc agtgtggaaa    6240
atctctagca gtggcgcccg aacagggact tgaaagcgaa agggaaacca gaggagctct    6300
```

```
ctcgacgcag gactcggctt gctgaagcgc gcacggcaag aggcgagggg cggcgactgg      6360
tgagtacgcc aaaaattttg actagcggag gctagaagga gagagatggg tgcgagagcg      6420
tcagtattaa gcgggggaga attagatcgc gatgggaaaa aattcggtta aggccagggg      6480
gaaagaaaaa atataaatta aaacatatag tatgggcaag cagggagcta gaacgattcg      6540
cagttaatcc tggcctgtta gaaacatcag aaggctgtag acaaatactg ggacagctac      6600
aaccatccct tcagacagga tcagaagaac ttagatcatt atataataca gtagcaaccc      6660
tctattgtgt gcatcaaagg atagagataa aagacaccaa ggaagcttta gacaagatag      6720
aggaagagca aaacaaaagt aagaccaccg cacagcaagc ggccgctgat cttcagacct      6780
ggaggaggag atatgaggga caattggaga agtgaattat ataaatataa agtagtaaaa      6840
attgaaccat taggagtagc acccaccaag gcaaagagaa gagtggtgca gagagaaaaa      6900
agagcagtgg gaataggagc tttgttcctt gggttcttgg gagcagcagg aagcactatg      6960
ggcgcagcgt caatgacgct gacggtacag gccagacaat tattgtctgg tatagtgcag      7020
cagcagaaca atttgctgag ggctattgag gcgcaacagc atctgttgca actcacagtc      7080
tggggcatca agcagctcca ggcaagaatc ctggctgtgg aaagatacct aaaggatcaa      7140
cagctcctgg ggatttgggg ttgctctgga aaactcattt gcaccactgc tgtgccttgg      7200
aatgctagtt ggagtaataa atctctggaa cagatttgga atcacacgac ctggatggag      7260
tgggacagag aaattaacaa ttacacaagc ttaatacact ccttaattga agaatcgcaa      7320
aaccagcaag aaaagaatga acaagaatta ttggaattag ataaatgggc aagtttgtgg      7380
aattggttta acataacaaa ttggctgtgg tatataaaat tattcataat gatagtagga      7440
ggcttggtag gtttaagaat agttttttgct gtactttcta tagtgaatag agttaggcag      7500
ggatattcac cattatcgtt tcagacccac ctcccaaccc cgaggggacc cgacaggccc      7560
ttaattaatt ggctccggtg cccgtcagtg ggcagagcgc acatcgccca cagtccccga      7620
gaagttgggg ggagggggtcg gcaattgaac cggtgcctag agaaggtggc gcggggtaaa      7680 ctggaaagt gatgtcgtgt actggctccg ccttttttccc gagggtgggg gagaaccgta      7740
tataagtgca gtagtcgccg tgaagctagc aattgtgagc ggataacaat tccacagtcg      7800
accctaggtt gtgtcgcgag tgttggatcc cagctgacac caattgtgag cgctcacaat      7860
tgctagaaga atacaaccac gactatataa gaatacaacc acgactccgt tcttttttcgc      7920 aacgggtttg ccgccagaac acaggtaagt gccgtgtgtg gttcccgcgg gcctggcctc      7980
tttacgggtt atgcccttg cgtgccttga attacttcca cctggctgca gtacgtgatt      8040
cttgatcccg agcttcgggt tggaagtggg tgggagagtt cgaggccttg cgcttaagga      8100
gccccttcgc ctcgtgcttg agttgaggcc tggcctgggc gctggggccg ccgcgtgcga      8160
atctggtggc accttcgcgc ctgtctcgct gctttcgata agtctctagc catttaaaat      8220 tttgatgac ctgctgcgac gcttttttttc tggcaagata gtcttgtaaa tgcgggccaa      8280
gatctgcaca ctggtatttc ggtttttggg gccgcgggcg gcgacggggc ccgtgcgtcc      8340
cagcgcacat gttcggcgag gcggggcctg cgagcgcggc caccgagaat cggacggggg      8400
tagtctcaag ctggccggcc tgctctggtg cctggcctcg cgccgccgtg tatcgccccg      8460 ccctgggcg caaggctggc ccggtcggca ccagttgcgt gagcggaaag atggccgctt      8520
cccggccctg ctgcagggag ctcaaaatgg aggacgcggc gctcgggaga gcgggcgggt      8580
gagtcaccca cacaaaggaa aagggccttt ccgtcctcag ccgtcgcttc atgtgactcc      8640
acggagtacc gggcgccgtc caggcacctc gattagttct cgagcttttg gagtacgtcg      8700
```

```
tctttaggtt gggggagggg gttttatgcg atggagtttc cccacactga gtgggtggag    8760
actgaagtta ggccagcttg gcacttgatg taattctcct tggaatttgc ccttttgag    8820
tttggatctt ggttcattct caagcctcag acagtggttc aaagttttt tcttccattt    8880
caggtgaatt cggccattac ggcccgccac catggctaga ttagataaaa gtaaagtgat    8940
taacagcgca ttagagctgc ttaatgaggt cggaatcgaa ggtttaacaa cccgtaaact    9000
cgcccagaag ctaggtgtag agcagcctac attgtattgg catgtaaaaa ataagcgggc    9060
tttgctcgac gccttagcca ttgagatgtt agataggcac catactcact tttgcccttt    9120
agaaggggaa agctggcaag attttttacg taataacgct aaaagtttta gatgtgcttt    9180
actaagtcat cgcgatggag caaaagtaca tttaggtaca cggcctacag aaaaacagta    9240
tgaaactctc gaaaatcaat tagccttttt atgccaacaa ggttttttcac tagagaatgc    9300
attatatgca ctcagcgctg tggggcattt tactttaggt tgcgtattgg aagatcaaga    9360
gcatcaagtc gctaaagaag aaagggaaac acctactact gatagtatgc cgccattatt    9420
acgacaagct atcgaattat ttgatcacca aggtgcagag ccagccttct tattcggcct    9480
tgaattgatc atatgcggat tagaaaaaca acttaaatgt gaaagtgggt cgccaaaaaa    9540
gaagagaaag gtcgacggcg gtggtgcttt gtctcctcag cactctgctg tcactcaagg    9600
aagtatcatc aagaacaagg agggcatgga tgctaagtca ctaactgcct ggtcccggac    9660
actggtgacc ttcaaggatg tatttgtgga cttcaccagg gaggagtgga agctgctgga    9720
cactgctcag cagatcgtgt acagaaatgt gatgctggag aactataaga acctggtttc    9780
cttgggttat cagcttacta agccagatgt gatcctccgg ttggagaagg gagaagagcc    9840
ctggctggtg gagagagaaa ttcaccaaga gacccatcct gattcagaga ctgcatttga    9900
aatcaaatca tcagtttaag gccgcct                                        9927
```

<210> SEQ ID NO 20
<211> LENGTH: 8916
<212> TYPE: DNA
<213> ORGANISM: Artificial Sequence
<220> FEATURE:
<223> OTHER INFORMATION: Synthetic

<400> SEQUENCE: 20

```
agaattcgat atcaagctta tcgataatca acctctggat tacaaaattt gtgaaagatt      60
gactggtatt cttaactatg ttgctccttt tacgctatgt ggatacgctg ctttaatgcc     120
tttgtatcat gctattactt cccgtacggc tttcattttc cctccttgt ataaatcctg     180
gttgctgtct ctttatgagg agttgtggcc cgttgtcagg caacgtggcg tggtgtgcac     240
tgtgtttgct gacgcaaccc ccactggttg gggcattgcc accacctatc aactcctttc     300
cgggactttc gctttccccc tccctattgc cacggcggaa ctcattgccg cctgccttgc     360
ccgctgctgg acaggggctc ggctgttggg cactgacaat tccgtggtgt tgtcggggaa     420
gctgacgtcc tttccatggc tgctcgcctg tgttgccaac tggattctgc gcgggacgtc     480
cttctgctac gtcccttcgg ccctcaatcc agcggacctt ccttcccgcg gcctgctgcc     540
ggttctgcgg cctcttccgc gtcttcgcct tcgccctcag acgagtcgga tctccctttg     600
ggccgcctcc ccgcctgcct gcaggtttgt cgagacctag aaaaacatgg agcaatcaca     660
agtagcaata cagcagctac caatgctgat tgtgcctggc tagaagcaca agaggaggag     720
gaggtgggtt ttccagtcac acctcaggta ccttttaagac caatgactta caaggcagct     780
gtagatctta gccactttt aaaagaaaag ggggactgg aagggctaat tcactcccaa       840
```

```
cgaagacaag atctgctttt tgcttgtact gggtctctct ggttagacca gatctgagcc    900
tgggagctct ctggctaact agggaaccca ctgcttaagc ctcaataaag cttgccttga    960
gtgcttcaag tagtgtgtgc ccgtctgttg tgtgactctg gtaactagag atccctcaga   1020
ccctttagt cagtgtggaa aatctctagc agggcccgtt taaacccgct gatcagcctc    1080
gactgtgcct tctagttgcc agccatctgt tgtttgcccc tccccgtgc cttccttgac    1140
cctgaaggt gccactccca ctgtcctttc ctaataaaat gaggaaattg catcgcattg    1200
tctgagtagg tgtcattcta ttctgggggg tggggtgggg caggacagca aggggagga    1260
ttgggaagac aatagcaggc atgctgggga tgcggtgggc tctatggctt ctgaggcgga   1320
aagaaccagc tggggctcta ggggtatcc ccacgcgccc tgtagcggcg cattaagcgc    1380
ggcgggtgtg tgggtacgc gcagcgtgac cgctacactt gccagcgccc tagcgcccgc    1440
tcctttcgct ttcttccctt cctttctcgc cacgttcgcc ggctttcccc gtcaagctct   1500
aaatcggggc atccctttag ggttccgatt tagtgcttta cggcacctcg accccaaaaa   1560
acttgattag ggtgatggtt cacgtagtgg gccatcgccc tgatagacgg ttttccgccc   1620
tttgacgttg gagtccacgt tctttaatag tggactcttg ttccaaactg gaacaacact   1680
caaccctatc tcggtctatt cttttgattt ataagggatt ttggggatt cggcctattg    1740
gttaaaaaat gagctgattt aacaaaaatt taacgcgaat taattctgtg aatgtgtgt    1800
cagttagggt gtggaaagtc cccaggctcc ccaggcaggc agaagtatgc aaagcatgca   1860
tctcaattag tcagcaacca ggtgtggaaa gtccccaggc tccccagcag gcagaagtat   1920
gcaaagcatg catctcaatt agtcagcaac catagtcccg cccctaactc cgcccatccc   1980
gcccctaact ccgcccagtt ccgcccattc tccgccccat ggctgactaa ttttttttat   2040
ttatgcagag gccgaggccg cctctgcctc tgagctattc cagaagtagt gaggaggctt   2100
ttttggaggc ctaggctttt gcaaaaagct cccgggagct tgtatatcca ttttcggatc   2160
tgatcagcac gtgttgacaa ttaatcatcg gcatagtata tcggcatagt ataatacgac   2220
aaggtgagga actaaaccat ggccaagttg accagtgccg ttccggtgct caccgcgcgc   2280
gacgtcgccg gagcggtcga gttctggacc gaccggctcg ggttctcccg ggacttcgtg   2340
gaggacgact tcgccggtgt ggtccgggac gacgtgaccc tgttcatcag cgcggtccag   2400
gaccaggtgg tgccggacaa cacctggcc tgggtgtggg tgcgcggcct ggacgagctg    2460
tacgccgagt ggtcggaggt cgtgtccacg aacttccggg acgcctccgg gccggccatg   2520
accgagatcg cgagcagcc gtgggggcgg gagttcgccc tgcgcgaccc ggccggcaac   2580
tgcgtgcact tcgtggccga ggagcaggac tgacacgtgc tacgagattt cgattccacc   2640
gccgccttct atgaaaggtt gggcttcgga atcgttttcc gggacgccgg ctggatgatc   2700
ctccagcgcg ggatctcat gctggagttc ttcgcccacc ccaacttgtt tattgcagct    2760
tataatggtt acaaataaag caatagcatc acaaatttca caaataaagc atttttttca   2820
ctgcattcta gttgtggttt gtccaaactc atcaatgtat cttatcatgt ctgtataccg   2880
tcgacctcta gctagagctt ggcgtaatca tggtcatagc tgtttcctgt gtgaaattgt   2940
tatccgctca caattccaca acatacga gccggaagca taaagtgtaa agcctggggt    3000
gcctaatgag tgagctaact cacattaatt gcgttcgct cactgcccgc tttccagtcg    3060
ggaaacctgt cgtgccagct gcattaatga atcggccaac gcgcggggag aggcggttg    3120
cgtattgggc gctcttccgc ttcctcgctc actgactcgc tgcgctcggt cgttcggctg   3180
cggcgagcgg tatcagctca ctcaaaggcg gtaatacggt tatccacaga atcaggggat   3240
```

```
aacgcaggaa agaacatgtg agcaaaaggc cagcaaaagg ccaggaaccg taaaaaggcc    3300
gcgttgctgg cgttttttcca taggctccgc cccctgacg agcatcacaa aaatcgacgc    3360
tcaagtcaga ggtggcgaaa cccgacagga ctataaagat accaggcgtt tccccctgga    3420
agctccctcg tgcgctctcc tgttccgacc ctgccgctta ccggatacct gtccgccttt    3480
ctcccttcgg gaagcgtggc gctttctcaa tgctcacgct gtaggtatct cagttcggtg    3540
taggtcgttc gctccaagct gggctgtgtg cacgaacccc ccgttcagcc cgaccgctgc    3600
gccttatccg gtaactatcg tcttgagtcc aacccggtaa gacacgactt atcgccactg    3660
gcagcagcca ctggtaacag gattagcaga gcgaggtatg taggcggtgc tacagagttc    3720
ttgaagtggt ggcctaacta cggctacact agaaggacag tatttggtat ctgcgctctg    3780
ctgaagccag ttaccttcgg aaaaagagtt ggtagctctt gatccggcaa acaaaccacc    3840
gctggtagcg gtggtttttt tgtttgcaag cagcagatta cgcgcagaaa aaaggatct    3900
caagaagatc ctttgatctt ttctacgggg tctgacgctc agtggaacga aaactcacgt    3960
taagggattt tggtcatgag attatcaaaa aggatcttca cctagatcct tttaaattaa    4020
aaatgaagtt ttaaatcaat ctaaagtata tatgagtaaa cttggtctga cagttaccaa    4080
tgcttaatca gtgaggcacc tatctcagcg atctgtctat ttcgttcatc catagttgcc    4140
tgactcccccg tcgtgtagat aactacgata cgggagggct taccatctgg ccccagtgct    4200
gcaatgatac cgcgagaccc acgctcaccg gctccagatt tatcagcaat aaaccagcca    4260
gccggaaggg ccgagcgcag aagtggtcct gcaactttat ccgcctccat ccagtctatt    4320
aattgttgcc gggaagctag agtaagtagt tcgccagtta atagtttgcg caacgttgtt    4380
gccattgcta caggcatcgt ggtgtcacgc tcgtcgtttg gtatggcttc attcagctcc    4440
ggttcccaac gatcaaggcg agttacatga tccccccatgt tgtgcaaaaa agcggttagc    4500
tccttcggtc ctccgatcgt tgtcagaagt aagttggccg cagtgttatc actcatggtt    4560
atggcagcac tgcataattc tcttactgtc atgccatccg taagatgctt ttctgtgact    4620
ggtgagtact caaccaagtc attctgagaa tagtgtatgc ggcgaccgag ttgctcttgc    4680
ccggcgtcaa tacgggataa taccgcgcca catagcagaa ctttaaaagt gctcatcatt    4740
ggaaaacgtt cttcggggcg aaaactctca aggatcttac cgctgttgag atccagttcg    4800
atgtaaccca ctcgtgcacc caactgatct tcagcatctt ttactttcac cagcgtttct    4860
gggtgagcaa aaacaggaag gcaaaatgcc gcaaaaaagg gaataagggc gacacggaaa    4920
tgttgaatac tcatactctt ccttttcaa tattattgaa gcatttatca gggttattgt    4980
ctcatgagcg gatacatatt tgaatgtatt tagaaaaata acaaataggg gttccgcgc    5040
acatttcccc gaaaagtgcc acctgacgtc gacggatcgg gagatctccc gatcccctat    5100
ggtgcactct cagtacaatc tgctctgatg ccgcatagtt aagccagtat ctgctccctg    5160
cttgtgtgtt ggaggtcgct gagtagtgcg cgagcaaaat ttaagctaca acaaggcaag    5220
gcttgaccga caattgcatg aagaatctgc ttagggttag gcgttttgcg ctgcttcgcg    5280
atgtacgggc cagatatacg cgttgacatt gattattgac tagttattaa tagtaatcaa    5340
ttacggggtc attagttcat agcccatata tggagttccg cgttacataa cttacggtaa    5400
atggcccgcc tggctgaccg cccaacgacc cccgcccatt gacgtcaata atgacgtatg    5460
ttcccatagt aacgccaata gggactttcc attgacgtca atgggtggac tatttacggt    5520
aaactgccca cttggcagta catcaagtgt atcatatgcc aagtacgccc cctattgacg    5580
tcaatgacgg taaatggccc gcctggcatt atgcccagta catgacctta tgggactttc    5640
```

```
ctacttggca gtacatctac gtattagtca tcgctattac catggtgatg cggttttggc    5700
agtacatcaa tgggcgtgga tagcggtttg actcacgggg atttccaagt ctccacccca    5760
ttgacgtcaa tgggagtttg ttttggcacc aaaatcaacg ggactttcca aaatgtcgta    5820
acaactccgc cccattgacg caaatgggcg gtaggcgtgt acggtgggag gtctatataa    5880
gcagagctct ctggctaact agagaaccca ctgcttactg gcttatcgaa attaatacga    5940
ctcactatag ggagacccaa gctggtttaa acttaagctt ggtaccgagc tcactagtcc    6000
agtgtggtgg cagatatcca gcacagtggc ggccgctcga ggggcccgtt tgcctgtac     6060 tgggtctctc tggttagacc agatctgagc ctgggagctc tctggctaac tagggaaccc    6120
actgcttaag cctcaataaa gcttgccttg agtgcttcaa gtagtgtgtg cccgtctgtt    6180
gtgtgactct ggtaactaga tccctcag acccttttag tcagtgtgga aaatctctag      6240
cagtggcgcc cgaacaggga cttgaaagcg aaagggaaac cagaggagct ctctcgacgc    6300
aggactcggc ttgctgaagc gcgcacggca agaggcgagg ggcggcgact ggtgagtacg    6360
ccaaaaattt tgactagcgg aggctagaag gagagagatg ggtgcgagag cgtcagtatt    6420
aagcggggga gaattagatc gcgatgggaa aaaattcggt taaggccagg gggaaagaaa    6480
aaatataaat taaaacatat agtatgggca agcagggagc tagaacgatt cgcagttaat    6540
cctggcctgt tagaaacatc agaaggctgt agacaaatac tgggacagct acaaccatcc    6600
cttcagacag gatcagaaga acttagatca ttatataata cagtagcaac cctctattgt    6660
gtgcatcaaa ggatagagat aaaagacacc aaggaagctt tagacaagat agaggaagag    6720
caaaacaaaa gtaagaccac cgcacagcaa gcggccgctg atcttcagac ctggaggagg    6780
agatatgagg gacaattgga gaagtgaatt atataaatat aaagtagtaa aaattgaacc    6840
attaggagta gcacccacca aggcaaagag aagagtggtg cagagagaaa aaagagcagt    6900
gggaatagga gctttgttcc ttgggttctt gggagcagca ggaagcacta tgggcgcagc    6960
gtcaatgacg ctgacggtac aggccagaca attattgtct ggtatagtgc agcagcagaa    7020
caatttgctg agggctattg aggcgcaaca gcatctgttg caactcacag tctgggcat     7080 caagcagctc caggcaagaa tcctggctgt ggaaagatac ctaaaggatc aacagctcct    7140
ggggatttgg ggttgctctg gaaaactcat ttgcaccact gctgtgcctt ggaatgctag    7200
ttggagtaat aaatctctgg aacagatttg gaatcacacg acctggatgg agtgggacag    7260
agaaattaac aattacacaa gcttaataca ctccttaatt gaagaatcgc aaaaccagca    7320
agaaaagaat gaacaagaat tattggaatt agataaatgg gcaagtttgt ggaattggtt    7380
taacataaca aattggctgt ggtatataaa attattcata atgatagtag gaggcttggt    7440
aggtttaaga atagtttttg ctgtactttc tatagtgaat agagttaggc agggatattc    7500
accattatcg tttcagaccc acctcccaac cccgagggga cccgacaggc ccttaattaa    7560
tcccctgatt ctgtggataa ccgtattacc gcctttgagt gagctgcacc tagtacggat    7620
tagaagccgc cgagcgggtg acagccctcc gaaggaagac tctcctccgt gcgtcctcgt    7680
cttcaccggt cgcgttcctg aaacgcagat gtgcctcgcg ccgcactgct ccgaacaatg    7740
tcgactctag aggtaaactc gacctatata agcagagctc gtttagtgaa ccgtcagatc    7800
gcctggagac gccatccacg ctgttttgac ctccatagaa gacaccggga ccgatccagc    7860
ctccgcggcc ccgaattgaa ttcggccatt acggcctgcc accgtgccac catgctggag    7920
cccggcgaga agccctacaa gtgccccgag tgcggcaaga gcttcagcga ctgcagggac    7980
ctggccaggc accagaggac ccacaccggc gagaagccct acaagtgccc cgagtgcggc    8040
```

```
aagagcttca gcgaccccgg caacctggtg aggcaccaga ggacccacac cggcgagaag    8100 cccctacaagt gccccgagtg cggcaagagc ttcagccaga gcagcagcct ggtgaggcac    8160
cagaggaccc acaccggcga gaagccctac aagtgccccg agtgcggcaa gagcttcagc    8220
cagagggccc acctggagag caccagagg acccacaccg cgagaagcc ctacaagtgc      8280 cccgagtgcg gcaagagctt cagccagagc ggcgacctga ggaggcacca gaggacccac    8340
accggcgaga agccctacaa gtgccccgag tgcggcaaga gcttcagcca gagcagcaac    8400
ctggtgaggc accagaggac ccacaccggc aagaagacca gcggcccagg cggccgatgc    8460
taagtcactg actgcctggt cccggacact ggtgaccttc aaggatgtgt ttgtggactt    8520
caccagggag gagtggaagc tgctggacac tgctcagcag atcctgtaca gaaatgtgat    8580
gctggagaac tataagaacc tggttttcctt gggttatcag cttactaagc cagatgtgat    8640
cctccggttg gagaagggag aagagccctg gctggtggag agagaaattc accaagagac    8700
ccatcctgat tcagagactg catttgaaat caaatcatca gttgggcgcg ccgacgcgct    8760
ggacgatttc gatctcgaca tgctgggttc tgatgccctc gatgactttg acctggatat    8820
gttgggaagc gacgcattgg atgactttga tctggacatg ctcggctccg atgctctgga    8880
cgatttcgat ctcgatatgt taattaacta attaat                              8916
```

<210> SEQ ID NO 21
<211> LENGTH: 8916
<212> TYPE: DNA
<213> ORGANISM: Artificial Sequence
<220> FEATURE:
<223> OTHER INFORMATION: Synthetic

<400> SEQUENCE: 21

```
agaattcgat atcaagctta tcgataatca acctctggat tacaaaattt gtgaaagatt      60
gactggtatt cttaactatg ttgctccttt tacgctatgt ggatacgctg ctttaatgcc     120
tttgtatcat gctattactt cccgtacggc tttcattttc tcctccttgt ataaatcctg     180
gttgctgtct ctttatgagg agttgtggcc cgttgtcagg caacgtggcg tggtgtgcac     240
tgtgtttgct gacgcaaccc ccactggttg gggcattgcc accacctatc aactcctttc     300
cgggactttc gctttccccc tccctattgc cacggcggaa ctcattgccg cctgccttgc     360
ccgctgctgg acaggggctc ggctgttggg cactgacaat tccgtggtgt tgtcggggaa     420
gctgacgtcc tttccatggc tgctcgcctg tgttgccaac tggattctgc gcgggacgtc     480
cttctgctac gtcccttcgg ccctcaatcc agcggacctt ccttcccgcg gcctgctgcc     540
ggttctgcgg cctcttccgc gtcttcgcct tcgccctcag acgagtcgga tctcccttg     600 ggccgcctcc ccgcctgcct gcaggtttgt cgagacctag aaaaacatgg agcaatcaca     660
agtagcaata cagcagctac caatgctgat tgtgcctggc tagaagcaca agaggaggag     720
gaggtgggtt ttccagtcac acctcaggta ccttttaagac caatgactta caaggcagct     780
gtagatctta gccactttt aaaagaaaag ggggactgg aagggctaat tcactcccaa      840
cgaagacaag atctgctttt tgcttgtact gggtctctct ggttagacca gatctgagcc     900
tgggagctct ctggctaact agggaaccca ctgcttaagc ctcaataaag cttgccttga     960
gtgcttcaag tagtgtgtgc ccgtctgttg tgtgactctg gtaactagag atccctcaga    1020 ccctttagt cagtgtggaa aatctctagc agggcccgtt taaacccgct gatcagcctc    1080
gactgtgcct tctagttgcc agccatctgt tgtttgcccc tcccccgtgc cttccttgac    1140
cctggaaggt gccactccca ctgtcctttc ctaataaaat gaggaaattg catcgcattg    1200
```

-continued

```
tctgagtagg tgtcattcta ttctgggggg tggggtgggg caggacagca agggggagga      1260
ttgggaagac aatagcaggc atgctgggga tgcggtgggc tctatggctt ctgaggcgga      1320
aagaaccagc tggggctcta gggggtatcc ccacgcgccc tgtagcggcg cattaagcgc      1380
ggcgggtgtg gtggttacgc gcagcgtgac cgctacactt gccagcgccc tagcgcccgc      1440
tcctttcgct ttcttccctt cctttctcgc cacgttcgcc ggctttcccc gtcaagctct      1500
aaatcgggga atccctttag ggttccgatt tagtgcttta cggcacctcg accccaaaaa      1560
acttgattag ggtgatggtt cacgtagtgg gccatcgccc tgatagacgg ttttttcgccc     1620 tttgacgttg gagtccacgt tctttaatag tggactcttg ttccaaactg gaacaacact      1680
caaccctatc tcggtctatt cttttgattt ataagggatt ttggggatttt cggcctattg     1740 gttaaaaaat gagctgattt aacaaaaatt taacgcgaat taattctgtg gaatgtgtgt     1800
cagttagggt gtggaaagtc cccaggctcc ccaggcaggc agaagtatgc aaagcatgca      1860
tctcaattag tcagcaacca ggtgtggaaa gtccccaggc tccccagcag gcagaagtat     1920
gcaaagcatg catctcaatt agtcagcaac catagtcccg ccctaactc cgcccatccc      1980 gcccctaact ccgcccagtt ccgcccattc tccgcccat ggctgactaa ttttttttat      2040
ttatgcagag gccgaggccg cctctgcctc tgagctattc cagaagtagt gaggaggctt      2100
ttttggaggc ctaggctttt gcaaaaagct cccgggagct gtatatcca ttttcggatc      2160 tgatcagcac gtgttgacaa ttaatcatcg gcatagtata tcggcatagt ataatacgac      2220
aaggtgagga actaaaccat ggccaagttg accagtgccg ttccggtgct caccgcgcgc      2280
gacgtcgccg gagcggtcga gttctggacc gaccggctcg ggttctcccg ggacttcgtg      2340
gaggacgact tcgccggtgt ggtccgggac gacgtgaccc tgttcatcag cgcggtccag      2400
gaccaggtgg tgccggacaa caccctggcc tgggtgtggg tgcgcggcct ggacgagctg      2460
tacgccgagt ggtcggaggt cgtgtccacg aacttccggg acgcctccgg gccggccatg      2520
accgagatcg cgagcagcc gtgggggcgg gagttcgccc tgcgcgaccc ggccggcaac      2580
tgcgtgcact tcgtggccga ggagcaggac tgacacgtgc tacgagattt cgattccacc      2640
gccgccttct atgaaaggtt gggcttcgga atcgttttcc gggacgccgg ctggatgatc      2700
ctccagcgcg ggatctcat gctggagttc ttcgcccacc ccaacttgtt tattgcagct      2760
tataatggtt acaaataaag caatagcatc acaaatttca caaataaagc attttttca      2820 ctgcattcta gttgtggttt gtccaaactc atcaatgtat cttatcatgt ctgtataccg      2880
tcgacctcta gctagagctt ggcgtaatca tggtcatagc tgtttcctgt gtgaaattgt      2940
tatccgctca caattccaca acatacga gccggaagca taaagtgtaa agcctggggt      3000
gcctaatgag tgagctaact cacattaatt gcgttgcgct cactgcccgc tttccagtcg      3060
ggaaacctgt cgtgccagct gcattaatga atcggccaac gcgcgggggag aggcggtttg      3120 cgtattgggc gctcttccgc ttcctcgctc actgactcgc tgcgctcggt cgttcggctg      3180
cggcgagcgg tatcagctca ctcaaaggcg gtaatacggt tatccacaga atcaggggat      3240
aacgcaggaa agaacatgtg agcaaaaggc cagcaaaagg ccaggaaccg taaaaaggcc      3300
gcgttgctgg cgttttttcca taggctccgc ccccctgacg agcatcacaa aaatcgacgc      3360
tcaagtcaga ggtggcgaaa cccgacagga ctataaagat accaggcgtt ccccctggaa      3420
agctccctcg tgcgctctcc tgttccgacc ctgccgctta ccggatacct gtccgccttt      3480
ctcccttcgg gaagcgtggc gctttctcaa tgctcacgct gtaggtatct cagttcggtg      3540
taggtcgttc gctccaagct gggctgtgtg cacgaacccc ccgttcagcc cgaccgctgc      3600
```

```
gccttatccg gtaactatcg tcttgagtcc aacccggtaa gacacgactt atcgccactg    3660
gcagcagcca ctggtaacag gattagcaga gcgaggtatg taggcggtgc tacagagttc    3720
ttgaagtggt ggcctaacta cggctacact agaaggacag tatttggtat ctgcgctctg    3780
ctgaagccag ttaccttcgg aaaaagagtt ggtagctctt gatccggcaa acaaaccacc    3840
gctggtagcg gtggttttt tgtttgcaag cagcagatta cgcgcagaaa aaaggatct    3900
caagaagatc ctttgatctt ttctacgggg tctgacgctc agtggaacga aaactcacgt    3960
taagggattt tggtcatgag attatcaaaa aggatcttca cctagatcct tttaaattaa    4020
aaatgaagtt ttaaatcaat ctaaagtata tatgagtaaa cttggtctga cagttaccaa    4080
tgcttaatca gtgaggcacc tatctcagcg atctgtctat ttcgttcatc catagttgcc    4140
tgactccccg tcgtgtagat aactacgata cgggagggct taccatctgg ccccagtgct    4200
gcaatgatac cgcgagaccc acgctcaccg gctccagatt tatcagcaat aaaccagcca    4260
gccgaagggg ccgagcgcag aagtggtcct gcaactttat ccgcctccat ccagtctatt    4320
aattgttgcc gggaagctag agtaagtagt tcgccagtta atagtttgcg caacgttgtt    4380
gccattgcta caggcatcgt ggtgtcacgc tcgtcgtttg gtatggcttc attcagctcc    4440
ggttcccaac gatcaaggcg agttacatga tcccccatgt tgtgcaaaaa agcggttagc    4500
tccttcggtc ctccgatcgt tgtcagaagt aagttggccg cagtgttatc actcatggtt    4560
atggcagcac tgcataattc tcttactgtc atgccatccg taagatgctt ttctgtgact    4620
ggtgagtact caaccaagtc attctgagaa tagtgtatgc ggcgaccgag ttgctcttgc    4680
ccggcgtcaa tacgggataa taccgcgcca catagcagaa ctttaaaagt gctcatcatt    4740
ggaaaacgtt cttcggggcg aaaactctca aggatcttac cgctgttgag atccagttcg    4800
atgtaaccca ctcgtgcacc caactgatct tcagcatctt ttactttcac cagcgtttct    4860
gggtgagcaa aaacaggaag gcaaaatgcc gcaaaaaagg gaataagggc gacacggaaa    4920
tgttgaatac tcatactctt cctttttcaa tattattgaa gcatttatca gggttattgt    4980
ctcatgagcg gatacatatt tgaatgtatt tagaaaaata acaaataggg gttccgcgc    5040
acatttcccc gaaaagtgcc acctgacgtc gacggatcgg gagatctccc gatccctat    5100
ggtgcactct cagtacaatc tgctctgatg ccgcatagtt aagccagtat ctgctccctg    5160
cttgtgtgtt ggaggtcgct gagtagtgcg cgagcaaaat ttaagctaca acaaggcaag    5220
gcttgaccga caattgcatg aagaatctgc ttagggttag gcgttttgcg ctgcttcgcg    5280
atgtacgggc cagatatacg cgttgacatt gattattgac tagttattaa tagtaatcaa    5340
ttacggggtc attagttcat agcccatata tggagttccg cgttacataa cttacggtaa    5400
atggcccgcc tggctgaccg cccaacgacc cccgcccatt gacgtcaata atgacgtatg    5460
ttcccatagt aacgccaata gggactttcc attgacgtca atgggtggac tatttacggt    5520
aaactgccca cttggcagta catcaagtgt atcatatgcc aagtacgccc cctattgacg    5580
tcaatgacgg taaatggccc gcctggcatt atgcccagta catgacctta tgggactttc    5640
ctacttggca gtacatctac gtattagtca tcgctattac catggtgatg cggttttggc    5700
agtacatcaa tgggcgtgga tagcggtttg actcacgggg atttccaagt ctccacccca    5760
ttgacgtcaa tgggagtttg ttttggcacc aaaatcaacg ggactttcca aaatgtcgta    5820
acaactccgc cccattgacg caaatgggcg gtaggcgtgt acggtgggag gtctatataa    5880
gcagagctct ctggctaact agagaaccca ctgcttactg gcttatcgaa attaatacga    5940
ctcactatag ggagacccaa gctggtttaa acttaagctt ggtaccgagc tcactagtcc    6000
```

```
agtgtggtgg cagatatcca gcacagtggc ggccgctcga ggggcccgtt ttgcctgtac    6060
tgggtctctc tggttagacc agatctgagc ctgggagctc tctggctaac tagggaaccc    6120
actgcttaag cctcaataaa gcttgccttg agtgcttcaa gtagtgtgtg cccgtctgtt    6180
gtgtgactct ggtaactaga gatccctcag acccttttag tcagtgtgga aaatctctag    6240
cagtggcgcc cgaacaggga cttgaaagcg aaagggaaac cagaggagct ctctcgacgc    6300
aggactcggc ttgctgaagc gcgcacggca agaggcgagg ggcggcgact ggtgagtacg    6360
ccaaaaattt tgactagcgg aggctagaag gagagagatg ggtgcgagag cgtcagtatt    6420
aagcggggga gaattagatc gcgatgggaa aaaattcggt taaggccagg gggaaagaaa    6480
aaatataaat taaaacatat agtatgggca agcagggagc tagaacgatt cgcagttaat    6540
cctggcctgt tagaaacatc agaaggctgt agacaaatac tgggacagct acaaccatcc    6600
cttcagacag gatcagaaga acttagatca ttatataata cagtagcaac cctctattgt    6660
gtgcatcaaa ggatagagat aaaagacacc aaggaagctt tagacaagat agaggaagag    6720
caaaacaaaa gtaagaccac cgcacagcaa gcggccgctg atcttcagac ctggaggagg    6780
agatatgagg gacaattgga gaagtgaatt atataaatat aaagtagtaa aaattgaacc    6840
attaggagta gcacccacca aggcaaagag aagagtggtg cagagagaaa aaagagcagt    6900
gggaatagga gctttgttcc ttgggttctt gggagcagca ggaagcacta tgggcgcagc    6960
gtcaatgacg ctgacggtac aggccagaca attattgtct ggtatagtgc agcagcagaa    7020
caatttgctg agggctattg aggcgcaaca gcatctgttg caactcacag tctgggcat    7080
caagcagctc caggcaagaa tcctggctgt ggaaagatac ctaaaggatc aacagctcct    7140
ggggatttgg ggttgctctg gaaaactcat ttgcaccact gctgtgcctt ggaatgctag    7200
ttggagtaat aaatctctgg aacagatttg gaatcacacg acctggatgg agtgggacag    7260
agaaattaac aattacacaa gcttaataca ctccttaatt gaagaatcgc aaaaccagca    7320
agaaaagaat gaacaagaat tattggaatt agataaatgg gcaagtttgt ggaattggtt    7380
taacataaca aattggctgt ggtatataaa attattcata atgatagtag gaggcttggt    7440
aggtttaaga atagttttg ctgtactttc tatagtgaat agagttaggc agggatattc    7500
accattatcg tttcagaccc acctcccaac cccgagggga cccgacaggc ccttaattaa    7560
tccccctgatt ctgtggataa ccgtattacc gcctttgagt gagctgcacc tagtacggat    7620
tagaagccgc cgagcgggtg acagccctcc gaaggaagac tctcctccgt gcgtcctcgt    7680
cttcaccggt cgcgttcctg aaacgcagat gtgcctcgcg ccgcactgct ccgaacaatg    7740
tcgactctag aggtaaactc gacctatata agcagagctc gtttagtgaa ccgtcagatc    7800
gcctggagac gccatccacg ctgttttgac ctccatagaa gacaccggga ccgatccagc    7860
ctccgcggcc ccgaattgaa ttcggccatt acggcctgcc accgtgccac catgctggag    7920
cccggcgaga agccctacaa gtgccccgag tgcggcaaga gcttcagcag gagcgacgag    7980
ctggtgaggc accagaggac ccacaccggc gagaagccct acaagtgccc cgagtgcggc    8040
aagagcttca gcaggagcga caagctggtg aggcaccaga ggacccacac cggcgagaag    8100
ccctacaagt gccccgagtg cggcaagagc ttcagcagga gcgacgacct ggtgaggcac    8160
cagaggaccc acaccggcga gaagccctac aagtgccccg agtgcggcaa gagcttcagc    8220
aggagcgaca acctggtgag gcaccagagg acccacaccg gcgagaagcc ctacaagtgc    8280
cccgagtgcg gcaagagctt cagcgacccc ggcgccctgg tgaggcacca gaggacccac    8340
accggcgaga agccctacaa gtgccccgag tgcggcaaga gcttcagcga ccccggccac    8400
```

```
ctggtgaggc accagaggac ccacaccggc aagaagacca gcggcccagg cggccgatgc    8460
taagtcactg actgcctggt cccggacact ggtgaccttc aaggatgtgt tgtggactt    8520 caccagggag gagtggaagc tgctggacac tgctcagcag atcctgtaca gaaatgtgat    8580
gctggagaac tataagaacc tggtttcctt gggttatcag cttactaagc cagatgtgat    8640
cctccggttg gagaagggag aagagccctg gctggtggag agagaaattc accaagagac    8700
ccatcctgat tcagagactg catttgaaat caaatcatca gttgggcgcg ccgacgcgct    8760
ggacgatttc gatctcgaca tgctgggttc tgatgccctc gatgactttg acctggatat    8820
gttgggaagc gacgcattgg atgactttga tctggacatg ctcggctccg atgctctgga    8880
cgatttcgat ctcgatatgt taattaacta attaat                              8916

<210> SEQ ID NO 22
<211> LENGTH: 10562
<212> TYPE: DNA
<213> ORGANISM: Artificial Sequence
<220> FEATURE:
<223> OTHER INFORMATION: Synthetic

<400> SEQUENCE: 22
cgtgccacca tgctggagcc cggcgagaag ccctacaagt gccccgagtg cggcaagagc      60
ttcagcgaca cggcaacct gagggtgcac cagaggaccc acaccggcga aagccctac       120 aagtgccccg agtgcggcaa gagcttcagc cagagggcca acctgagggc ccaccagagg     180
acccacaccg gcgagaagcc ctacaagtgc cccgagtgcg gcaagagctt cagcaccagc     240
ggcagcctgg tgaggcacca gaggacccac accggcgaga agccctacaa gtgccccgag     300
tgcggcaaga gcttcagcac cagcggccac ctggtgaggc accagaggac ccacaccggc     360
gagaagccct acaagtgccc cgagtgcggc aagagcttca gcaccagcgg cgagctggtg     420
aggcaccaga ggacccacac cggcgagaag ccctacaagt gccccgagtg cggcaagagc     480
ttcagcacca gcgcaacct ggtgaggcac cagaggaccc acaccggcaa gaagaccagc      540
ggcccaggcg ccgatgcta agtcactgac tgcctggtcc cggacactgg tgaccttcaa     600
ggatgtgttt gtggacttca ccagggagga gtggaagctg ctggacactg ctcagcagat    660
cctgtacaga aatgtgatgc tggagaacta taagaacctg gtttccttgg gttatcagct    720
tactaagcca gatgtgatcc tccggttgga gaagggagaa gagccctggc tggtggagag    780
agaaattcac caagagaccc atcctgattc agagactgca tttgaaatca aatcatcagt    840
tgggcgcgcc gacgcgctgg acgatttcga tctcgacatg ctgggttctg atgccctcga    900
tgactttgac ctggatatgt tgggaagcga cgcattggat gactttgatc tggacatgct    960
cggctccgat gctctggacg atttcgatct cgatatgtta attaactaac gatcacatgg   1020
tcctgctgga gttcgtgacc gccgccggga tcactctcgg catggacgag ctgtacaagt   1080
aagcggccgc aatcaacctc tggattacaa aatttgtgaa agattgactg gtattcttaa   1140
ctatgttgct ccttttacgc tatgtggata cgctgcttta atgcctttgt atcatgctat   1200
tacttcccgt acggctttca ttttctcctc cttgtataaa tcctggttgc tgtctcttta   1260
tgaggagttg tggcccgttg tcaggcaacg tggcgtggtg tgcactgtgt ttgctgacgc   1320 aaccccact ggttggggca ttgccaccac ctatcaactc ctttccggga ctttcgcttt   1380
ccccctccct attgccacgg cggaactcat gccgcctgc cttgcccgct gctggacagg    1440
ggctcggctg tttgggcactg acaattccgt ggtgttgtcg gggaagctga cgtccttcc    1500 atggctgctc gcctgtgttg ccaactggat tctgcgcggg acgtccttct gctacgtccc    1560
```

-continued

```
ttcggccctc aatccagcgg accttccttc ccgcggcctg ctgccggttc tgcggcctct    1620
tccgcgtctt cgccttcgcc ctcagacgag tcggatctcc cttttgggccg cctcccccgcc    1680 tgcctgcagg tttgtcgaga cctagaaaaa catggagcaa tcacaagtag caatacagca    1740
gctaccaatg ctgattgtgc ctggctagaa gcacaagagg aggaggaggt gggttttcca    1800
gtcacacctc aggtaccttt aagaccaatg acttacaagg cagctgtaga tcttagccac    1860
tttttaaaag aaaagggggg actggaaggg ctaattcact cccaacgaag acaagatctg    1920 cttttttgctt gtactgggtc tctctggtta gaccagatct gagcctggga gctctctggc    1980
taactaggga acccactgct taagcctcaa taaagcttgc cttgagtgct tcaagtagtg    2040
tgtgcccgtc tgttgtgtga ctctggtaac tagagatccc tcagacccctt ttagtcagtg    2100 tggaaaatct ctagcagggc ccgtttaaac ccgctgatca gcctcgactg tgccttctag    2160
ttgccagcca tctgttgttt gcccctcccc cgtgccttcc ttgaccctgg aaggtgccac    2220
tcccactgtc ctttcctaat aaaatgagga aattgcatcg cattgtctga gtaggtgtca    2280
ttctattctg ggggtgggg tggggcagga cagcaagggg gaggattggg aagacaatag    2340
caggcatgct ggggatgcgg tgggctctat ggcttctgag gcggaaagaa ccagctgggg    2400 ctctagggg tatccccacg cgccctgtag cggcgcatta agcgcggcgg gtgtggtggt    2460
tacgcgcagc gtgaccgcta cacttgccag cgccctagcg cccgctcctt tcgctttctt    2520
cccttccttt ctcgccacgt tcgccggctt tccccgtcaa gctctaaatc ggggcatccc    2580
tttagggttc cgatttagtg ctttacggca cctcgacccc aaaaaacttg attagggtga    2640
tggttcacgt agtgggccat cgccctgata gacggttttt cgccctttga cgttggagtc    2700
cacgttcttt aatagtggac tcttgttcca aactggaaca acactcaacc ctatctcggt    2760
ctattctttt gatttataag ggattttggg gatttcggcc tattggttaa aaaatgagct    2820
gatttaacaa aaatttaacg cgaattaatt ctgtggaatg tgtgtcagtt agggtgtgga    2880
aagtccccag gctccccagg caggcagaag tatgcaaagc atgcatctca attagtcagc    2940
aaccaggtgt ggaaagtccc caggctcccc agcaggcaga agtatgcaaa gcatgcatct    3000
caattagtca gcaaccatag tcccgccccct aactccgccc atcccgcccc taactccgcc    3060
cagttccgcc cattctccgc cccatggctg actaattttt tttatttatg cagaggccga    3120
ggccgcctct gcctctgagc tattccagaa gtagtgagga ggcttttttg gaggcctagg    3180
cttttgcaaa aagctcccgg gagcttgtat atccattttc ggatctgatc agcacgtgtt    3240
gacaattaat catcggcata gtatatcggc atagtataat acgacaaggt gaggaactaa    3300
accatggcca agttgaccag tgccgttccg gtgctcaccg cgcgcgacgt cgccggagcg    3360
gtcgagttct ggaccgaccg gctcgggttc tcccgggact cgtggagga cgacttcgcc    3420 ggtgtggtcc gggacgacgt gaccctgttc atcagcgcgg tccaggacca ggtggtgccg    3480
gacaacaccc tggcctgggt gtgggtgcgc ggcctggacg agctgtacgc cgagtggtcg    3540
gaggtcgtgt ccacgaactt ccgggacgcc tccggccgg ccatgaccga gatcggcgag    3600
cagccgtggg ggcgggagtt cgccctgcgc gaccccgccg gcaactgcgt gcacttcgtg    3660
gccgaggagc aggactgaca cgtgctacga gatttcgatt ccaccgccgc cttctatgaa    3720
aggttgggct tcggaatcgt tttccgggac gccggctgga tgatcctcca gcgcggggat    3780
ctcatgctgg agttcttcgc ccaccccaac ttgtttattg cagcttataa tggttacaaa    3840
taaagcaata gcatcacaaa tttcacaaat aaagcatttt tttcactgca ttctagttgt    3900
ggtttgtcca aactcatcaa tgtatcttat catgtctgta taccgtcgac ctctagctag    3960
```

```
agcttggcgt aatcatggtc atagctgttt cctgtgtgaa attgttatcc gctcacaatt    4020
ccacacaaca tacgagccgg aagcataaag tgtaaagcct ggggtgccta atgagtgagc    4080
taactcacat taattgcgtt gcgctcactg cccgctttcc agtcgggaaa cctgtcgtgc    4140
cagctgcatt aatgaatcgg ccaacgcgcg gggagaggcg gtttgcgtat tgggcgctct    4200
tccgcttcct cgctcactga ctcgctgcgc tcggtcgttc ggctgcggcg agcggtatca    4260
gctcactcaa aggcggtaat acggttatcc acagaatcag gggataacgc aggaaagaac    4320
atgtgagcaa aaggccagca aaaggccagg aaccgtaaaa aggccgcgtt gctggcgttt    4380
ttccataggc tccgcccccc tgacgagcat cacaaaaatc gacgctcaag tcagaggtgg    4440
cgaaacccga caggactata aagataccag gcgtttcccc ctggaagctc cctcgtgcgc    4500
tctcctgttc cgaccctgcc gcttaccgga tacctgtccg cctttctccc ttcgggaagc    4560
gtggcgcttt ctcaatgctc acgctgtagg tatctcagtt cggtgtaggt cgttcgctcc    4620
aagctgggct gtgtgcacga accccccgtt cagcccgacc gctgcgcctt atccggtaac    4680
tatcgtcttg agtccaaccc ggtaagacac gacttatcgc cactggcagc agccactggt    4740
aacaggatta gcagagcgag gtatgtaggc ggtgctacag agttcttgaa gtggtggcct    4800
aactacggct acactagaag gacagtattt ggtatctgcg ctctgctgaa gccagttacc    4860
ttcggaaaaa gagttggtag ctcttgatcc ggcaaacaaa ccaccgctgg tagcggtggt    4920
ttttttgttt gcaagcagca gattacgcgc agaaaaaaag gatctcaaga agatcctttg    4980
atcttttcta cggggtctga cgctcagtgg aacgaaaact cacgttaagg gattttggtc    5040
atgagattat caaaaaggat cttcacctag atccttttaa attaaaaatg aagttttaaa    5100
tcaatctaaa gtatatatga gtaaacttgg tctgacagtt accaatgctt aatcagtgag    5160
gcacctatct cagcgatctg tctatttcgt tcatccatag ttgcctgact ccccgtcgtg    5220
tagataacta cgatacggga gggcttacca tctggcccca gtgctgcaat gataccgcga    5280
gacccacgct caccggctcc agatttatca gcaataaacc agccagccgg aagggccgag    5340
cgcagaagtg gtcctgcaac tttatccgcc tccatccagt ctattaattg ttgccgggaa    5400
gctagagtaa gtagttcgcc agttaatagt ttgcgcaacg ttgttgccat tgctacaggc    5460
atcgtggtgt cacgctcgtc gtttggtatg gcttcattca gctccggttc ccaacgatca    5520
aggcgagtta catgatcccc catgttgtgc aaaaaagcgg ttagctcctt cggtcctccg    5580
atcgttgtca gaagtaagtt ggccgcagtg ttatcactca tggttatggc agcactgcat    5640
aattctctta ctgtcatgcc atccgtaaga tgcttttctg tgactggtga gtactcaacc    5700
aagtcattct gagaatagtg tatgcggcga ccgagttgct cttgcccggc gtcaatacgg    5760
gataataccg cgccacatag cagaacttta aaagtgctca tcattggaaa acgttcttcg    5820
gggcgaaaac tctcaaggat cttaccgctg ttgagatcca gttcgatgta acccactcgt    5880
gcacccaact gatcttcagc atcttttact ttcaccagcg tttctgggtg agcaaaaaca    5940
ggaaggcaaa atgccgcaaa aaagggaata agggcgacac ggaaatgttg aatactcata    6000
ctcttccttt ttcaatatta ttgaagcatt tatcagggtt attgtctcat gagcggatac    6060
atatttgaat gtatttagaa aaataaacaa ataggggttc cgcgcacatt tccccgaaaa    6120
gtgccacctg acgtcgacgg atcgggagat ctcccgatcc cctatggtgc actctcagta    6180
caatctgctc tgatgccgca tagttaagcc agtatctgct ccctgcttgt gtgttggagg    6240
tcgctgagta gtgcgcgagc aaaatttaag ctacaacaag gcaaggcttg accgacaatt    6300
gcatgaagaa tctgcttagg gttaggcgtt ttgcgctgct tcgcgatgta cgggccagat    6360
```

```
atacgcgttg acattgatta ttgactagtt attaatagta atcaattacg gggtcattag   6420
ttcatagccc atatatggag ttccgcgtta cataacttac ggtaaatggc ccgcctggct   6480
gaccgcccaa cgacccccgc ccattgacgt caataatgac gtatgttccc atagtaacgc   6540
caatagggac tttccattga cgtcaatggg tggactattt acggtaaact gcccacttgg   6600
cagtacatca agtgtatcat atgccaagta cgccccctat tgacgtcaat gacggtaaat   6660
ggcccgcctg gcattatgcc cagtacatga ccttatggga cttttcctact tggcagtaca   6720 tctacgtatt agtcatcgct attaccatgg tgatgcggtt ttggcagtac atcaatgggc   6780
gtggatagcg gtttgactca cggggatttc caagtctcca ccccattgac gtcaatggga   6840
gtttgttttg gcaccaaaat caacgggact ttccaaaatg tcgtaacaac tccgcccat    6900 tgacgcaaat gggcggtagg cgtgtacggt gggaggtcta taagcaga gctctctggc    6960 taactagaga acccactgct tactggctta tcgaaattaa tacgactcac tatagggaga   7020
cccaagctgt tttaaactta agcttggtac cgagctcact agtccagtgt ggtggcagat   7080
atccagcaca gtggcggccg ctcgagtcta gagggcccgt tttgcctgta ctgggtctct   7140
ctggttagac cagatctgag cctgggagct ctctggctaa ctaggaacc cactgcttaa    7200 gcctcaataa agcttgcctt gagtgcttca agtagtgtgt gcccgtctgt tgtgtgactc   7260
tggtaactag agatccctca gacccttttta gtcagtgtgg aaaatctcta gcagtggcgc   7320
ccgaacaggg acttgaaagc gaaagggaaa ccagaggagc tctctcgacg caggactcgg   7380
cttgctgaag cgcgcacggc aagaggcgag gggcggcgac tggtgagtac gccaaaaatt   7440
ttgactagcg gaggctagaa ggagagagat gggtgcgaga gcgtcagtat taagcggggg   7500
agaattagat cgcgatggga aaaaattcgg ttaaggccag ggggaaagaa aaatataaa   7560 ttaaaacata tagtatgggc aagcagggag ctagaacgat tcgcagttaa tcctggcctg   7620
ttagaaacat cagaaggctg tagacaaata ctgggacagc tacaaccatc ccttcagaca   7680
ggatcagaag aacttagatc attatataat acagtagcaa ccctctattg tgtgcatcaa   7740
aggatagaga taaagacac caaggaagct ttagacaaga tagaggaaga gcaaaacaaa   7800
agtaagacca ccgcacagca agcggccgct gatcttcaga cctggaggag gagatatgag   7860
ggacaattgg agaagtgaat tatataaata taaagtagta aaaattgaac cattaggagt   7920
agcacccacc aaggcaaaga gaagagtggt gcagagagaa aaaagagcag tgggaatagg   7980
agctttgttc cttgggttct tgggagcagc aggaagcact atgggcgcag cgtcaatgac   8040
gctgacggta caggccagac aattattgtc tggtatagtg cagcagcaga acaatttgct   8100
gagggctatt gaggcgcaac agcatctgtt gcaactcaca gtctggggca tcaagcagct   8160
ccaggcaaga atcctggctg tggaaagata cctaaaggat caacagctcc tggggatttg   8220
gggttgctct ggaaaactca tttgcaccac tgctgtgcct tggaatgcta gttggagtaa   8280
taaatctctg gaacagattt ggaatcacac gacctggatg gagtgggaca gagaaattaa   8340
caattacaca agcttaatac actccttaat tgaagaatcg caaaaccagc aagaaaagaa   8400
tgaacaagaa ttattggaat tagataaatg ggcaagtttg tggaattggt ttaacataac   8460
aaattggctg tggtatatag aaattattca taatgatagt aggaggcttg gtaggtttaa   8520
gaatagtttt tgctgtactt tctatagtga atagagttag gcagggatat tcaccattat   8580
cgtttcagac ccacctccca accccgaggg gacccgacag gcccgaagga atagaagaag   8640
aaggtggaga gagagacaga gacagatcca ttcgattagt gaacggatcg cactgcgtg    8700 cgccaattct gcagacaaat ggcagtattc atccacaatt ttaaaagaaa agggggatt    8760
```

-continued

```
gggggggtaca gtgcagggga aagaatagta gacataatag caacagacat acaaactaaa      8820
gaattacaaa aacaaattac aaaaattcaa aattttcggg tttattacag ggacagcaga      8880
gatccagttt ggggttgctc tggaaaactc atttgcacca ctgctgtgcc ttggaatgct      8940
agttggagta ataaatctct ggaacagatt tggaatcaca cgacctggat ggagtgggac      9000
agagaaatta acaattacac aagcttaata cactccttaa ttgaagaatc gcaaaaccag      9060
caagaaaaga atgaacaaga attattggaa ttagataaat gggcaagttt gtggaattgg      9120
tttaacataa caaattggct gtggtatata aaattattca taatgatagt aggaggcttg      9180
gtaggtttaa gaatagtttt tgctgtactt tctatagtga atagagttag gcagggatat      9240
tcaccattat cgtttcagac ccacctccca accccgaggg gacccgacag gcccttaatt      9300
aattggctcc ggtgcccgtc agtgggcaga gcgcacatcg cccacagtcc ccgagaagtt      9360
ggggggaggg gtcggcaatt gaaccggtgc ctagagaagg tggcgcgggg taaactggga      9420
aagtgatgtc gtgtactggc tccgcctttt tcccgagggt gggggagaac cgtatataag      9480
tgcagtagtc gccgtgaagc tagcggcgtc gaggcggggg tgatatggcg tcgaggcggg      9540
ggtggctagc cgttctttt cgcaacgggt ttgccgccag aacacaggta agtgccgtgt      9600
gtggttcccg cgggcctggc ctctttacgg gttatggccc ttgcgtgcct tgaattactt      9660
ccacctggct gcagtacgtg attcttgatc ccgagcttcg ggttggaagt gggtgggaga      9720
gttcgaggcc ttgcgcttaa ggagcccctt cgcctcgtgc ttgagttgag gcctggcctg      9780
ggcgctgggg ccgccgcgtg cgaatctggt ggcaccttcg cgcctgtctc gctgctttcg      9840
ataagtctct agccatttaa aattttttgat gacctgctgc gacgcttttt ttctggcaag      9900
atagtcttgt aaatgcgggc caagatctgc acactggtat ttcggttttt ggggccgcgg      9960
gcggcgacgg ggcccgtgcg tcccagcgca catgttcggc gaggcgggc ctgcgagcgc     10020 ggccaccgag aatcggacgg gggtagtctc aagctggccg gcctgctctg gtgcctggcc     10080
tcgcgccgcc gtgtatcgcc ccgccctggg cggcaaggct ggcccggtcg gcaccagttg     10140
cgtgagcgga aagatggccg cttcccggcc ctgctgcagg gagctcaaaa tggaggacgc     10200
ggcgctcggg agagcgggcg ggtgagtcac ccacacaaag gaaaagggcc tttccgtcct     10260
cagccgtcgc ttcatgtgac tccacggagt accgggcgcc gtccaggcac ctcgattagt     10320
tctcgagctt ttggagtacg tcgtctttag gttgggggga ggggttttat gcgatggagt     10380
ttccccacac tgagtgggtg gagactgaag ttaggccagc ttggcacttg atgtaattct     10440
ccttggaatt tgccctttt gagtttggat cttggttcat tctcaagcct cagacagtgg     10500
ttcaaagttt ttttcttcca tttcaggtga attcggccat tacggcctcc caccggccgc     10560
ct                                                                   10562
```

<210> SEQ ID NO 23
<211> LENGTH: 9215
<212> TYPE: DNA
<213> ORGANISM: Artificial Sequence
<220> FEATURE:
<223> OTHER INFORMATION: Synthetic

<400> SEQUENCE: 23

```
ttgccaccat gctggagccc ggcgagaagc cctacaagtg ccccgagtgc ggcaagagct        60
tcagcaccca cctggacctg atcaggcacc agaggaccca caccggcgag aagccctaca       120
agtgccccga gtgcggcaag agcttcagca ggaccgacac cctgagggac accagagga       180 cccacaccgg cgagaagccc tacaagtgcc ccgagtgcgg caagagcttc agcgacaaga       240
```

```
aggacctgac caggcaccag aggacccaca ccggcgagaa gccctacaag tgccccgagt     300
gcggcaagag cttcagcagc cccgccgacc tgaccaggca ccagaggacc cacaccggcg     360
agaagcccta caagtgcccc gagtgcggca agagcttcag caccaccggc aacctgaccg     420
tgcaccagag gacccacacc ggcgagaagc cctacaagtg ccccgagtgc ggcaagagct     480
tcagcaggaa ggacaacctg aagaaccacc agaggaccca caccggcaag aagaccagcg     540
gcccaggcgg ccgatgctaa gtcactgact gcctggtccc ggacactggt gaccttcaag     600
gatgtgtttg tggacttcac cagggaggag tggaagctgc tggacactgc tcagcagatc     660
ctgtacagaa atgtgatgct ggagaactat aagaacctgg tttccttggg ttatcagctt     720
actaagccag atgtgatcct ccggttggag aagggagaag agccctggct ggtggagaga     780
gaaattcacc aagagaccca tcctgattca gagactgcat ttgaaatcaa atcatcagtt     840
gggcgcgccg acgcgctgga cgatttcgat ctcgacatgc tgggttctga tgccctcgat     900
gactttgacc tggatatgtt gggaagcgac gcattggatg actttgatct ggacatgctc     960
ggctccgatg ctctggacga tttcgatctc gatatgttaa ttaactaata tgtgtgggag    1020
ggctaagggc gcgccgttct agagaattcg atatcaagct tatcgataat caacctctgg    1080
attacaaaat ttgtgaaaga ttgactggta ttcttaacta tgttgctcct tttacgctat    1140
gtggatacgc tgctttaatg cctttgtatc atgctattac ttcccgtacg gctttcattt    1200
tctcctcctt gtataaatcc tggttgctgt ctctttatga ggagttgtgg cccgttgtca    1260
ggcaacgtgg cgtggtgtgc actgtgtttg ctgacgcaac ccccactggt tggggcattg    1320
ccaccaccta tcaactcctt tccgggactt tcgctttccc cctccctatt gccacggcgg    1380
aactcattgc cgcctgcctt gcccgctgct ggacagggc tcggctgttg ggcactgaca    1440
attccgtggt gttgtcgggg aagctgacgt cctttccatg gctgctcgcc tgtgttgcca    1500
actggattct gcgcgggacg tccttctgct acgtcccttc ggccctcaat ccagcggacc    1560
ttccttcccg cggcctgctg ccggttctgc ggcctcttcc gcgtcttcgc cttcgccctc    1620
agacgagtcg gatctccctt gggccgcct ccccgcctgc ctgcaggttt gtcgagacct    1680
agaaaaacat ggagcaatca caagtagcaa tacagcagct accaatgctg attgtgcctg    1740
gctagaagca caagaggagg aggaggtggg ttttccagtc acacctcagg tacctttaag    1800
accaatgact tacaaggcag ctgtagatct tagccacttt ttaaaagaaa agggggggact    1860 ggaagggcta attcactccc aacgaagaca agatctgctt tttgcttgta ctgggtctct    1920
ctggttagac cagatctgag cctgggagct ctctggctaa ctagggaacc cactgcttaa    1980
gcctcaataa agcttgcctt gagtgcttca agtagtgtgt gcccgtctgt tgtgtgactc    2040
tggtaactag agatccctca gacccttta gtcagtgtgg aaaatctcta gcagggcccg    2100
tttaaacccg ctgatcagcc tcgactgtgc cttctagttg ccagccatct gttgtttgcc    2160
cctcccccgt gccttccttg accctggaag gtgccactcc cactgtcctt tcctaataaa    2220
atgaggaaat tgcatcgcat tgtctgagta ggtgtcattc tattctgggg ggtggggtgg    2280
ggcaggacag caaggggag gattgggaag acaatagcag gcatgctggg gatgcggtgg    2340
gctctatggc ttctgaggcg gaaagaacca gctgggctc tagggggtat ccccacgcgc    2400
cctgtagcgg cgcattaagc gcggcggtg tggtggttac gcgcagcgtg accgctacac    2460
ttgccagcgc cctagcgccc gctccttcg ctttcttccc ttcctttctc gccacgttcg    2520
ccggctttcc ccgtcaagct ctaaatcggg gcatcccttt agggttccga tttagtgctt    2580
tacggcacct cgaccccaaa aaacttgatt agggtgatgg ttcacgtagt gggccatcgc    2640
```

```
cctgatagac ggttttcgc cctttgacgt tggagtccac gttctttaat agtggactct    2700
tgttccaaac tggaacaaca ctcaacccta tctcggtcta ttcttttgat ttataaggga    2760
ttttggggat tcggcctat tggttaaaaa atgagctgat ttaacaaaaa tttaacgcga     2820
attaattctg tggaatgtgt gtcagttagg gtgtggaaag tccccaggct ccccaggcag    2880
gcagaagtat gcaaagcatg catctcaatt agtcagcaac caggtgtgga aagtccccag    2940
gctccccagc aggcagaagt atgcaaagca tgcatctcaa ttagtcagca accatagtcc    3000
cgcccctaac tccgcccatc cgcccctaa ctccgcccag ttccgcccat tctccgcccc     3060
atggctgact aattttttt atttatgcag aggccgaggc cgcctctgcc tctgagctat     3120
tccagaagta gtgaggaggc ttttttggag gcctaggctt ttgcaaaaag ctcccgggag    3180
cttgtatatc cattttcgga tctgatcagc acgtgttgac aattaatcat cggcatagta    3240
tatcggcata gtaataacg acaaggtgag gaactaaacc atggccaagt tgaccagtgc     3300
cgttccggtg ctcaccgcgc gcgacgtcgc cggagcggtc gagttctgga ccgaccggct    3360
cgggttctcc cggacttcg tggaggacga cttcgccggt gtggtccggg acgacgtgac     3420
cctgttcatc agcgcggtcc aggaccaggt ggtgccggac aacaccctgg cctgggtgtg    3480
ggtgcgcggc ctggacgagc tgtacgccga gtggtcggag gtcgtgtcca cgaacttccg    3540
ggacgcctcc gggccggcca tgaccgagat cggcgagcag ccgtggggc gggagttcgc     3600
cctgcgcgac ccggccggca actgcgtgca cttcgtggcc gaggagcagg actgacacgt    3660
gctacgagat ttcgattcca ccgccgcctt ctatgaaagg ttgggcttcg gaatcgtttt    3720
ccgggacgcc ggctggatga tcctccagcg cggggatctc atgctggagt tcttcgccca    3780
ccccaacttg tttattgcag cttataatgg ttacaaataa agcaatagca tcacaaattt    3840
cacaaataaa gcattttttt cactgcattc tagttgtggt ttgtccaaac tcatcaatgt    3900
atcttatcat gtctgtatac cgtcgacctc tagctagagc ttggcgtaat catggtcata    3960
gctgtttcct gtgtgaaatt gttatccgct cacaattcca cacaacatac gagccggaag    4020
cataaagtgt aaagcctggg gtgcctaatg agtgagctaa ctcacattaa ttgcgttgcg    4080
ctcactgccc gctttccagt cgggaaacct gtcgtgccag ctgcattaat gaatcggcca    4140
acgcgcgggg agaggcggtt tgcgtattgg gcgctcttcc gcttcctcgc tcactgactc    4200
gctgcgctcg tcgttcggc tgcggcgagc ggtatcagct cactcaaagg cggtaatacg     4260
gttatccaca gaatcagggg ataacgcagg aaagaacatg tgagcaaaag gccagcaaaa    4320
ggccaggaac cgtaaaaagg ccgcgttgct ggcgtttttc cataggctcc gcccccctga    4380
cgagcatcac aaaaatcgac gctcaagtca gaggtggcga aacccgacag gactataaag    4440
ataccaggcg tttccccctg gaagctccct cgtgcgctct cctgttccga ccctgccgct    4500
taccggatac ctgtccgcct ttctcccttc gggaagcgtg gcgctttctc aatgctcacg    4560
ctgtaggtat ctcagttcgg tgtaggtcgt tcgctccaag ctgggctgtg tgcacgaacc    4620
ccccgttcag cccgaccgct gcgccttatc cggtaactat cgtcttgagt ccaacccggt    4680
aagacacgac ttatcgccac tggcagcagc cactggtaac aggattagca gagcgaggta    4740
tgtaggcggt gctacagagt tcttgaagtg gtggcctaac tacggctaca ctagaaggac    4800
agtatttggt atctgcgctc tgctgaagcc agttaccttc ggaaaaagag ttggtagctc    4860
ttgatccggc aaacaaacca ccgctggtag cggtggtttt tttgtttgca agcagcagat    4920
tacgcgcaga aaaaaggat ctcaagaaga tcctttgatc ttttctacgg ggtctgacgc     4980
tcagtggaac gaaaactcac gttaagggat tttggtcatg agattatcaa aaaggatctt    5040
```

```
cacctagatc cttttaaatt aaaaatgaag ttttaaatca atctaaagta tatatgagta    5100
aacttggtct gacagttacc aatgcttaat cagtgaggca cctatctcag cgatctgtct    5160
atttcgttca tccatagttg cctgactccc cgtcgtgtag ataactacga tacgggaggg    5220
cttaccatct ggccccagtg ctgcaatgat accgcgagac ccacgctcac cggctccaga    5280
tttatcagca ataaaccagc cagccggaag ggccgagcgc agaagtggtc ctgcaacttt    5340
atccgcctcc atccagtcta ttaattgttg ccgggaagct agagtaagta gttcgccagt    5400
taatagtttg cgcaacgttg ttgccattgc tacaggcatc gtggtgtcac gctcgtcgtt    5460
tggtatggct tcattcagct ccggttccca acgatcaagg cgagttacat gatcccccat    5520
gttgtgcaaa aaagcggtta gctccttcgg tcctccgatc gttgtcagaa gtaagttggc    5580
cgcagtgtta tcactcatgg ttatggcagc actgcataat tctcttactg tcatgccatc    5640
cgtaagatgc ttttctgtga ctggtgagta ctcaaccaag tcattctgag aatagtgtat    5700
gcggcgaccg agttgctctt gcccggcgtc aatacgggan aataccgcgc cacatagcag    5760
aactttaaaa gtgctcatca ttggaaaacg ttcttcgggg cgaaaactct caaggatctt    5820
accgctgttg agatccagtt cgatgtaacc cactcgtgca cccaactgat cttcagcatc    5880
ttttactttc accagcgttt ctgggtgagc aaaaacagga aggcaaaatg ccgcaaaaaa    5940
gggaataagg gcgacacgga aatgttgaat actcatactc ttccttttc aatattattg    6000 aagcatttat cagggttatt gtctcatgag cggatacata tttgaatgta tttagaaaaa    6060
taaacaaata ggggttccgc gcacatttcc ccgaaaagtg ccacctgacg tcgacggatc    6120
gggagatctc ccgatcccct atggtgcact ctcagtacaa tctgctctga tgccgcatag    6180
ttaagccagt atctgctccc tgcttgtgtg ttggaggtcg ctgagtagtg cgcgagcaaa    6240
atttaagcta caacaaggca aggcttgacc gacaattgca tgaagaatct gcttagggtt    6300
aggcgttttg cgctgcttcg cgatgtacgg gccagatata cgcgttgaca ttgattattg    6360
actagttatt aatagtaatc aattacgggg tcattagttc atagcccata tatggagttc    6420
cgcgttacat aacttacggt aaatggcccg cctggctgac cgcccaacga cccccgccca    6480
ttgacgtcaa taatgacgta tgttcccata gtaacgccaa tagggacttt ccattgacgt    6540
caatgggtgg actatttacg gtaaactgcc cacttggcag tacatcaagt gtatcatatg    6600
ccaagtacgc cccctattga cgtcaatgac ggtaaatggc ccgcctggca ttatgcccag    6660
tacatgacct tatgggactt tcctacttgg cagtacatct acgtattagt catcgctatt    6720
accatggtga tgcggttttg gcagtacatc aatgggcgtg atagcggttt gactcacgg    6780 ggatttccaa gtctccaccc cattgacgtc aatgggagtt tgttttggca ccaaaatcaa    6840
cgggactttc caaaatgtcg taacaactcc gccccattga cgcaaatggg cggtaggcgt    6900
gtacggtggg aggtctatat aagcagagct ctctggctaa ctagagaacc cactgcttac    6960
tggcttatcg aaattaatac gactcactat agggagaccc aagctggttt aaacttaagc    7020
ttggtaccga gctcactagt ccagtgtggt ggcagatatc cagcacagtg gcggccgctc    7080
gaggggcccg ttttgcctgt actgggtctc tctggttaga ccagatctga gcctgggagc    7140
tctctggcta actagggaac ccactgctta agcctcaata agcttgcct tgagtgcttc    7200 aagtagtgtg tgcccgtctg ttgtgtgact ctggtaacta gagatccctc agacccttt    7260 agtcagtgtg gaaaatctct agcagtggcg cccgaacagg gacttgaaag cgaaagggaa    7320
accagaggag ctctctcgac gcaggactcg gcttgctgaa gcgcgcacgg caagaggcga    7380
ggggcggcga ctggtgagta cgccaaaaat tttgactagc ggaggctaga aggagagaga    7440
```

-continued

```
tgggtgcgag agcgtcagta ttaagcgggg gagaattaga tcgcgatggg aaaaaattcg    7500
gttaaggcca gggggaaaga aaaaatataa attaaaacat atagtatggg caagcaggga    7560
gctagaacga ttcgcagtta atcctggcct gttagaaaca tcagaaggct gtagacaaat    7620
actgggacag ctacaaccat cccttcagac aggatcagaa gaacttagat cattatataa    7680
tacagtagca accctctatt gtgtgcatca aaggatagag ataaaagaca ccaaggaagc    7740
tttagacaag atagaggaag agcaaaacaa agtaagacc accgcacagc aagcggccgc     7800
tgatcttcag acctggagga ggagatatga gggacaattg gagaagtgaa ttatataaat    7860
ataaagtagt aaaaattgaa ccattaggag tagcacccac caaggcaaag agaagagtgg    7920
tgcagagaga aaaaagagca gtgggaatag gagctttgtt ccttgggttc ttgggagcag    7980
caggaagcac tatgggcgca gcgtcaatga cgctgacggt acaggccaga caattattgt    8040
ctggtatagt gcagcagcag aacaatttgc tgagggctat tgaggcgcaa cagcatctgt    8100
tgcaactcac agtctggggc atcaagcagc tccaggcaag aatcctggct gtggaaagat    8160
acctaaagga tcaacagctc ctggggattt ggggttgctc tggaaaactc atttgcacca    8220
ctgctgtgcc ttggaatgct agttggagta ataaatctct ggaacagatt tggaatcaca    8280
cgacctggat ggagtgggac agagaaatta acaattacac aagcttaata cactccttaa    8340
ttgaagaatc gcaaaaccag caagaaaaga atgaacaaga attattggaa ttagataaat    8400
gggcaagttt gtggaattgg tttaacataa caaattggct gtggtatata aaattattca    8460
taatgatagt aggaggcttg gtaggtttaa gaatagtttt tgctgtactt tctatagtga    8520
atagagttag gcagggatat tcaccattat cgtttcagac ccacctccca accccgaggg    8580
gacccgacag gccccttaatt aatccctga ttctgtggat aaccgtatta ccgcctttga    8640
gtgagctgca caaagaaaca aaccaacctg tctgtattat caaagtgaaa ggctacaata    8700
ggacaaagaa acaaaccaac ctgtctgtat tatcaaagtg aaaggctaca ataggacaaa    8760
gaaacaaacc aacctgtctg tattatcaaa gtgaaaggct acaataggac aaagaaacaa    8820
accaacctgt ctgtattatc aaagtgaaag gctacaatag gacaaagaaa caaaccaacc    8880
tgtctgtatt atcaaagtga aaggctacaa taggacaaag aaacaaacca acctgtctgt    8940
attatcaaag tgaaaggcta cataggaca agaaacaaa ccaacctgtc tgtattatca       9000
aagtgaaagg ctacaatagg acggtaaact cgacctatat aagcagagct cgtttagtga    9060
accgtcagat cgcctggaga cgccatccac gctgttttga cctccataga agacaccggg    9120
accgatccag cctccgcggc cccgaattga attctaacac cgtgcgtgtt gactatttta    9180
cctctggcgg tgataggcca ttacggcctg ccacc                                9215
```

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Ser Gly Tyr Gly Arg Lys Lys Arg Arg Gln Arg Arg Cys
1               5                   10

<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Ser Gly Arg Gln Ile Lys Ile Trp Phe Gln Asn Arg Arg Met Lys Trp
1               5                   10                  15

Lys Lys Cys

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Gly Arg Lys Lys Arg Arg Gln Arg Arg Arg Pro Pro Gln Gly
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Tyr Gly Arg Lys Lys Arg Arg Gln Arg Arg Pro Pro Gln
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Synthetic

<400> SEQUENCE: 28

Cys Arg Gln Ile Lys Ile Trp Phe Gln Asn Arg Arg Met Lys Trp Lys
1               5                   10                  15

Lys

<210> SEQ ID NO 29
<211> LENGTH: 54
<212> TYPE: DNA
<213> ORGANISM: Artificial Sequence
<220> FEATURE:
<223> OTHER INFORMATION: Synthetic

<400> SEQUENCE: 29
gatcccgtaa aaagcgtcgt cgagaaagcc gtaagaaacg tcgacgtgaa agca          54

<210> SEQ ID NO 30
<211> LENGTH: 54
<212> TYPE: DNA
<213> ORGANISM: Artificial Sequence
<220> FEATURE:
<223> OTHER INFORMATION: Synthetic

<400> SEQUENCE: 30
agcttgcttt cacgtcgacg tttcttacgg ctttctcgac gacgcttttt acgg          54

<210> SEQ ID NO 31
<211> LENGTH: 72
<212> TYPE: DNA
<213> ORGANISM: Artificial Sequence
<220> FEATURE:
<223> OTHER INFORMATION: Synthetic

```
<400> SEQUENCE: 31
gatccggtgc gtatgatctg cgtcgtcgag aacgtcagag ccgtctgcgt cgacgtgaaa      60
gacagagcag aa                                                         72

<210> SEQ ID NO 32
<211> LENGTH: 72
<212> TYPE: DNA
<213> ORGANISM: Artificial Sequence
<220> FEATURE:
<223> OTHER INFORMATION: Synthetic

<400> SEQUENCE: 32
agctttctgc tctgtctttc acgtcgacgc agacggctct gacgttctcg acgacgcaga     60
tcatacgcac cg                                                         72

<210> SEQ ID NO 33
<211> LENGTH: 60
<212> TYPE: DNA
<213> ORGANISM: Artificial Sequence
<220> FEATURE:
<223> OTHER INFORMATION: Synthetic

<400> SEQUENCE: 33
gatccgttaa acgtggactg aaacttcgtc atgttcgtcc gcgtgtgacc cgtgatgtga     60

<210> SEQ ID NO 34
<211> LENGTH: 60
<212> TYPE: DNA
<213> ORGANISM: Artificial Sequence
<220> FEATURE:
<223> OTHER INFORMATION: Synthetic

<400> SEQUENCE: 34
agcttcacat cacgggtcac acgcggacga acatgacgaa gtttcagtcc acgtttaacg     60
```

What is claimed is:

1. A composition comprising one or more mammalian vectors, wherein the one or more vectors comprise:
   a) a first nucleotide sequence comprising a promoter operably linked to a nucleic acid sequence encoding a first cell-cell communication molecule,
   b) a second nucleotide sequence comprising a promoter operably linked to a nucleic acid sequence encoding a second cell-cell communication molecule that binds with said first cell-cell communication molecule to produce a first binding molecule,
   c) a third nucleotide sequence comprising a promoter operably linked to a nucleic acid sequence encoding a first cell fate regulator protein that induces differentiation of a first cell type into a second cell type that expresses a marker protein of said second cell type,
   d) a fourth nucleotide sequence comprising a promoter operably linked to a nucleic acid sequence encoding a first repressor,
   e) a fifth nucleotide sequence comprising a promoter operably linked to a nucleic acid sequence encoding a first activator, wherein
      i) said first repressor represses expression of said first activator, and
      ii) said first activator activates expression of;
         1) said first repressor, and
         2) said first activator,
   f) a sixth nucleotide sequence comprising a promoter operably linked to a nucleic acid sequence encoding a second repressor,
   g) a seventh nucleotide sequence comprising a promoter operably linked to a nucleic acid sequence encoding a third repressor,
   h) a eight nucleotide sequence comprising a promoter operably linked to a nucleic acid sequence encoding a second activator,
   i) a ninth nucleotide sequence comprising a promoter operably linked to a nucleic acid sequence encoding a fourth repressor, wherein
      i) said second repressor represses expression of said third repressor,
      ii) said third repressor represses expression of said second activator,
      iii) said second activator activates expression of said fourth repressor, and
      iv) said first activator activates expression of said second repressor,
   j) a tenth nucleotide sequence comprising a promoter operably linked to a nucleic acid sequence encoding a fifth repressor,
   k) an eleventh nucleotide sequence comprising a promoter operably linked to a nucleic acid sequence encoding a sixth repressor, wherein
      i) said fifth repressor represses expression of said sixth repressor and of said first cell-cell communication molecule, ii) said sixth repressor represses expression of said fifth repressor, and iii) said fourth repressor represses expression of said fifth repressor, l) a twelfth nucleotide sequence comprising a promoter operably linked to a nucleic acid sequence encoding a seventh repressor wherein i) said first binding molecule induces expression of said seventh repressor, and ii) said seventh repressor represses expression of said fourth repressor, and m) a thirteenth nucleotide sequence comprising a promoter operably linked to a nucleic acid sequence encoding a second cell fate regulator protein that is operably linked to a cell type specific promoter of said second cell type, wherein the second regulator induces differentiation of said second cell type into a third cell type, wherein expression of said first cell fate regulator protein causes expression of said second cell fate regulator protein and differentiation of said second cell type into said third cell type wherein said fifth repressor represses expression of said twelfth nucleic acid sequence, and wherein said first cell-cell communication molecule and said second cell-cell communication molecule are selected from the group consisting of, (1) the first cell-cell communication molecule comprising LuxI and the second cell-cell communication molecule comprising LuxR, (2) the first cell-cell communication molecule comprising LuxR and the second cell-cell communication molecule comprising LuxI, (3) the first cell-cell communication molecule comprising CinI and the second cell-cell communication molecule comprising CinR, (4) the first cell-cell communication molecule comprising CinR and the second cell-cell communication molecule comprising CinI, (5) the first cell-cell communication molecule comprising RhlI and the second cell-cell communication molecule comprising RhlIR, and (6) the first cell-cell communication molecule comprising RhlIR and the second cell-cell communication molecule comprising RhlI.

2. The composition of claim 1, wherein said one or more vectors further comprises:

n) a fourteenth nucleic acid sequence encoding a third cell fate regulator protein that is operably linked to a cell type specific promoter of said second cell type, that induces differentiation of said second cell type into said third cell type, wherein expression of said first cell fate regulator protein causes expression of said second cell fate regulator protein and said third cell fate regulator protein.

3. The composition of claim 2, wherein said one or more vectors further comprises:

o) a fifteenth nucleic acid sequence encoding a third cell-cell communication molecule, wherein said sixth repressor represses expression of said third cell-cell communication molecule, and p) a sixteenth nucleic acid sequence encoding a fourth cell-cell communication molecule that is binds with said first cell-cell communication molecule to produce a second binding molecule.

4. The composition of claim 3, wherein said second binding molecule induces expression of said second activator.

5. The composition of claim 3, wherein said one or more vectors further comprises:

q) a seventeenth nucleic acid sequence encoding a protein that inhibits cell growth, wherein said second binding molecule induces expression of said protein that inhibits cell growth.

\* \* \* \* \*